US012752001B2

(12) United States Patent
Nachbagauer et al.

(10) Patent No.: US 12,752,001 B2
(45) Date of Patent: Oct. 6, 2026

(54) MUTANT INFLUENZA B/VICTORIA LINEAGE VIRUS HEMAGGLUTININ PROTEINS

(71) Applicant: ModernaTX, Inc., Cambridge, MA (US)

(72) Inventors: Raffael Nachbagauer, Rahway, NJ (US); Farbod Mahmoudinobar, Rahway, NJ (US); Elif Nihal Korkmaz, Brookline, MA (US)

(73) Assignee: ModernaTX, Inc., Cambridge, MA (US)

(*) Notice: Subject to any disclaimer, the term of this patent is extended or adjusted under 35 U.S.C. 154(b) by 0 days.

(21) Appl. No.: 19/398,368

(22) Filed: Nov. 24, 2025

(65) Prior Publication Data

US 2026/0158129 A1 Jun. 11, 2026

Related U.S. Application Data

(63) Continuation of application No. 19/320,264, filed on Sep. 5, 2025, which is a continuation of application No. PCT/US2024/019210, filed on Mar. 8, 2024.

(60) Provisional application No. 63/582,208, filed on Sep. 12, 2023, provisional application No. 63/518,923, filed on Aug. 11, 2023, provisional application No. 63/489,707, filed on Mar. 10, 2023.

(51) Int. Cl.

| | |
|---|---|
| ***A61K 39/145*** | (2006.01) |
| ***A61K 9/1271*** | (2025.01) |
| ***A61K 9/51*** | (2006.01) |
| ***A61P 31/16*** | (2006.01) |
| ***C07K 14/005*** | (2006.01) |
| ***C07K 14/11*** | (2006.01) |
| ***C12N 7/00*** | (2006.01) |
| *A61K 39/00* | (2006.01) |

(52) U.S. Cl.
CPC .......... *A61K 39/145* (2013.01); *A61K 9/1271* (2013.01); *A61K 9/5123* (2013.01); *A61P 31/16* (2018.01); *C07K 14/005* (2013.01); *C12N 7/00* (2013.01); *A61K 2039/53* (2013.01); *A61K 2039/55555* (2013.01); *A61K 2039/575* (2013.01); *C07K 14/11* (2013.01); *C12N 2760/16222* (2013.01); *C12N 2760/16234* (2013.01)

(58) Field of Classification Search
None
See application file for complete search history.

(56) References Cited

U.S. PATENT DOCUMENTS

| | | | |
|---|---|---|---|
| 3,906,092 | A | 9/1975 | Hilleman |
| 4,790,987 | A | 12/1988 | Compans et al. |
| 5,169,628 | A | 12/1992 | Wathen |
| 5,256,555 | A | 10/1993 | Milburn et al. |
| 5,427,782 | A | 6/1995 | Compans et al. |
| 5,756,264 | A | 5/1998 | Schwartz et al. |
| 5,824,497 | A | 10/1998 | Andrews et al. |
| 5,861,501 | A | 1/1999 | Benseler et al. |
| 5,989,911 | A | 11/1999 | Fournier et al. |
| 6,022,715 | A | 2/2000 | Merenkova et al. |
| 6,040,427 | A | 3/2000 | Locht et al. |
| 6,096,503 | A | 8/2000 | Sutcliffe et al. |
| 6,100,024 | A | 8/2000 | Hudson et al. |
| 6,225,091 | B1 | 5/2001 | Klein et al. |
| 6,500,419 | B1 | 12/2002 | Hone et al. |
| 6,514,948 | B1 | 2/2003 | Raz et al. |
| 6,528,262 | B1 | 3/2003 | Gilad et al. |
| 6,534,312 | B1 | 3/2003 | Shiver et al. |
| 6,610,044 | B2 | 8/2003 | Mathiesen |
| 6,652,886 | B2 | 11/2003 | Ahn et al. |
| 6,696,038 | B1 | 2/2004 | Mahato et al. |
| 6,924,365 | B1 | 8/2005 | Miller et al. |
| 7,001,890 | B1 | 2/2006 | Wagner et al. |
| 7,208,161 | B1 | 4/2007 | Murphy et al. |
| 7,316,925 | B2 | 1/2008 | Draghia-Akli et al. |
| 7,371,404 | B2 | 5/2008 | Panzner et al. |
| 7,449,324 | B2 | 11/2008 | Fouchier et al. |
| 7,531,342 | B2 | 5/2009 | Fouchier et al. |
| 7,566,454 | B2 | 7/2009 | Lu et al. |
| 7,671,186 | B2 | 3/2010 | Klein et al. |
| 7,704,720 | B2 | 4/2010 | Tang et al. |
| 7,776,523 | B2 | 8/2010 | Garcia et al. |
| 7,884,184 | B2 | 2/2011 | De Groot et al. |
| 7,943,168 | B2 | 5/2011 | Schlesinger et al. |
| 8,058,069 | B2 | 11/2011 | Yaworski et al. |
| 8,158,601 | B2 | 4/2012 | Chen et al. |
| 8,178,660 | B2 | 5/2012 | Weiner et al. |
| 8,217,016 | B2 | 7/2012 | Hoerr et al. |

(Continued)

FOREIGN PATENT DOCUMENTS

| | | | |
|---|---|---|---|
| AU | 652831 | B2 | 9/1994 |
| AU | 2015210364 | A1 | 8/2015 |

(Continued)

OTHER PUBLICATIONS

U.S. Appl. No. 18/335,949, filed Jun. 15, 2023, Nasir et al.

(Continued)

*Primary Examiner* — Nicole Kinsey White
(74) *Attorney, Agent, or Firm* — Foley & Lardner LLP

(57) ABSTRACT

Some aspects of the disclosure relate to vaccines (e.g., RNA vaccines (e.g., mRNA vaccines)) for seasonal influenza viruses as well as methods of using the vaccines. Also described are combination vaccines (e.g., RNA vaccines (e.g., mRNA vaccines)) for seasonal influenza viruses and other respiratory viruses (e.g., respiratory syncytial viruses and coronaviruses), as well as methods of using the vaccines.

9 Claims, 42 Drawing Sheets

Specification includes a Sequence Listing.

(56) References Cited

U.S. PATENT DOCUMENTS 8,252,289 B2 8/2012 Eleouet et al.
8,278,036 B2 10/2012 Kariko et al.
8,278,063 B2 10/2012 Pandey et al.
8,383,340 B2 2/2013 Ketterer et al.
8,470,771 B2 6/2013 Gao et al.
8,506,966 B2 8/2013 Podda et al.
8,569,256 B2 10/2013 Heyes et al.
8,609,142 B2 12/2013 Troiano et al.
8,613,954 B2 12/2013 Zale et al.
8,617,608 B2 12/2013 Zale et al.
8,628,801 B2 1/2014 Garreta et al.
8,642,076 B2 2/2014 Manoharan et al.
8,658,354 B2 2/2014 Kida et al.
8,663,599 B1 3/2014 Sung et al.
8,691,223 B2 4/2014 Van Den Brink et al.
8,691,750 B2 4/2014 Constien et al.
8,691,966 B2 4/2014 Kariko et al.
8,692,292 B2 4/2014 Umeda et al.
8,710,200 B2 4/2014 Schrum et al.
8,722,341 B2 5/2014 Fouchier et al.
8,734,832 B2 5/2014 O'Hagan et al.
8,734,853 B2 5/2014 Sood et al.
8,754,062 B2 6/2014 De Fougerolles et al.
8,822,663 B2 9/2014 Schrum et al.
8,841,433 B2 9/2014 Fouchier et al.
8,877,206 B2 11/2014 Chen et al.
8,883,202 B2 11/2014 Manoharan et al.
8,889,146 B2 11/2014 Blais et al.
8,927,206 B2 1/2015 De Jong et al.
8,927,692 B2 1/2015 Weiner et al.
8,980,864 B2 3/2015 Hoge et al.
8,999,380 B2 4/2015 Bancel et al.
9,008,142 B2 4/2015 Minneman et al.
9,012,219 B2 4/2015 Kariko et al.
9,018,089 B2 4/2015 Liniger et al.
9,139,554 B2 9/2015 Hope et al.
9,192,651 B2 11/2015 Chakraborty et al.
9,192,661 B2 11/2015 Jain et al.
9,220,683 B2 12/2015 Manoharan et al.
9,221,891 B2 12/2015 Bancel et al.
9,226,959 B2 1/2016 Kramps et al.
9,234,013 B2 1/2016 Thess et al.
9,271,996 B2 3/2016 De Fougerolles et al.
9,283,287 B2 3/2016 Chakraborty et al.
9,295,689 B2 3/2016 De Fougerolles et al.
9,303,079 B2 4/2016 Chakraborty et al.
9,376,726 B2 6/2016 Fouchier et al.
9,452,211 B2 9/2016 Meijberg et al.
9,464,124 B2 10/2016 Bancel et al.
9,512,456 B2 12/2016 Wang et al.
9,533,047 B2 1/2017 De Fougerolles et al.
9,567,653 B2 2/2017 Fouchier et al.
9,572,896 B2 2/2017 Bancel et al.
9,597,380 B2 3/2017 Chakraborty et al.
9,623,095 B2 4/2017 Kallen et al.
9,629,804 B2 4/2017 Heartlein et al.
9,669,089 B2 6/2017 Thess et al.
9,675,668 B2 6/2017 Bancel et al.
9,693,958 B2 7/2017 Zhu
9,790,531 B2 10/2017 Wang et al.
9,803,199 B2 10/2017 Koizumi et al.
9,868,691 B2 1/2018 Benenato
9,872,900 B2 1/2018 Ciaramella et al.
9,937,196 B2 4/2018 Samal et al.
10,022,435 B2 7/2018 Ciaramella et al.
10,023,626 B2 7/2018 Bolen et al.
10,064,934 B2 9/2018 Ciaramella et al.
10,064,935 B2 9/2018 Ciaramella et al.
10,124,055 B2 11/2018 Ciaramella et al.
10,207,010 B2 2/2019 Besin et al.
10,232,055 B2 3/2019 Kariko et al.
10,272,150 B2 4/2019 Ciaramella et al.
10,273,269 B2 4/2019 Ciaramella
10,286,086 B2 5/2019 Roy et al.
10,323,076 B2 6/2019 Ellsworth et al.
10,385,088 B2 8/2019 Fraley et al.
10,449,244 B2 10/2019 Ciaramella et al.
10,465,190 B1 11/2019 Chen et al.
10,493,143 B2 12/2019 Ciaramella et al.
10,526,629 B2 1/2020 Rabideau et al.
10,543,269 B2 1/2020 Ciaramella et al.
10,653,712 B2 5/2020 Hoge et al.
10,653,767 B2 5/2020 Ciaramella et al.
10,695,419 B2 6/2020 Ciaramella et al.
10,702,599 B2 7/2020 Ciaramella et al.
10,702,600 B1 7/2020 Ciaramella et al.
10,857,105 B2 12/2020 Benenato et al.
10,906,944 B2 2/2021 He et al.
10,912,826 B2 2/2021 Thess et al.
10,925,958 B2 2/2021 Ciaramella
10,933,127 B2 3/2021 Ciaramella et al.
10,953,089 B1 3/2021 Smith et al.
10,960,070 B2 3/2021 Graham et al.
11,027,025 B2 6/2021 Hoge et al.
11,045,540 B2 6/2021 Ciaramella
11,103,578 B2 8/2021 Ciaramella et al.
11,266,735 B2 3/2022 Kallen et al.
11,351,242 B1 6/2022 Panther et al.
11,384,352 B2 7/2022 Miracco
11,406,703 B2 8/2022 Kramarczyk et al.
11,464,848 B2 10/2022 Ciaramella et al.
11,485,960 B2 11/2022 Dousis et al.
11,497,807 B2 11/2022 Ciaramella et al.
11,547,673 B1 1/2023 Sahin et al.
11,564,893 B2 1/2023 Smith
11,566,051 B2 1/2023 Zhang et al.
11,576,961 B2 2/2023 Ciaramella et al.
11,638,693 B2 5/2023 Geall
11,638,694 B2 5/2023 Geall
11,643,441 B1 5/2023 Ciaramella et al.
11,666,534 B2 6/2023 Geall
11,696,946 B2 7/2023 Ciaramella
11,752,206 B2 9/2023 Ciaramella et al.
11,766,401 B2 9/2023 Geall
11,786,467 B2 10/2023 Geall
11,786,607 B2 10/2023 Hoge et al.
11,851,694 B1 12/2023 Mauger et al.
11,866,696 B2 1/2024 Issa et al.
11,872,278 B2 1/2024 Ciaramella et al.
11,905,525 B2 2/2024 Brito et al.
11,911,453 B2 2/2024 Ciaramella et al.
11,912,982 B2 2/2024 Issa et al.
11,918,644 B2 3/2024 Ciaramella
12,070,495 B2 8/2024 Lusso et al.
12,109,261 B1 10/2024 He et al.
12,133,899 B2 11/2024 Sahin et al.
12,151,029 B2 11/2024 Hennessy et al.
12,318,443 B2 6/2025 Ciaramella
12,329,811 B2 6/2025 Nachbagauer et al.
12,383,508 B2 8/2025 Almarsson et al.
12,403,335 B2 9/2025 Ciaramella et al.
12,453,766 B2 10/2025 Ciaramella et al.
12,491,260 B2 12/2025 Besin et al.
12,577,554 B2 3/2026 Derosa et al.
2001/0001066 A1 5/2001 Cezayirli et al.
2001/0005506 A1 6/2001 Cezayirli et al.
2002/0137720 A1 9/2002 Ertl et al.
2003/0032615 A1 2/2003 Felgner et al.
2003/0073619 A1 4/2003 Mahato et al.
2003/0083272 A1 5/2003 Wiederholt et al.
2003/0092653 A1 5/2003 Kisich et al.
2003/0135040 A1 7/2003 Eritja et al.
2003/0165849 A1 9/2003 Zhang et al.
2003/0232061 A1 12/2003 Fouchier et al.
2004/0005545 A1 1/2004 Fouchier et al.
2004/0096451 A1 5/2004 Young et al.
2004/0132683 A1 7/2004 Felgner et al.
2004/0167090 A1 8/2004 Monahan et al.
2005/0032730 A1 2/2005 Von Der Mulbe et al.
2005/0059624 A1 3/2005 Hoerr et al.
2005/0250723 A1 11/2005 Hoerr et al.
2005/0287540 A1 12/2005 Murphy et al.
2006/0002958 A1 1/2006 Naylor
2006/0024668 A1 2/2006 Hoek

(56) References Cited

U.S. PATENT DOCUMENTS

2006/0083780 A1 4/2006 Heyes et al.
2006/0172003 A1 8/2006 Meers et al.
2006/0172966 A1 8/2006 Lipford et al.
2006/0188490 A1 8/2006 Hoerr et al.
2006/0217338 A1 9/2006 Lu et al.
2006/0228367 A1 10/2006 Ulbrandt et al.
2006/0247195 A1 11/2006 Ray
2007/0141030 A1 6/2007 Yu et al.
2007/0252295 A1 11/2007 Panzner et al.
2007/0280929 A1 12/2007 Hoerr et al.
2007/0281336 A1 12/2007 Jendrisak et al.
2007/0292453 A1 12/2007 Dittmer et al.
2008/0025914 A1 1/2008 Bjork
2008/0025944 A1 1/2008 Hoerr et al.
2008/0057080 A1 3/2008 Luke et al.
2008/0076174 A1 3/2008 Selden et al.
2008/0171079 A1 7/2008 Hanon et al.
2008/0171711 A1 7/2008 Hoerr et al.
2008/0220471 A1 9/2008 Davis et al.
2008/0267873 A1 10/2008 Hoerr et al.
2008/0274463 A1 11/2008 Chen et al.
2009/0042825 A1 2/2009 Matar et al.
2009/0093433 A1 4/2009 Woolf et al.
2009/0104226 A1 4/2009 Perri et al.
2009/0123529 A1 5/2009 Li
2009/0148467 A1 6/2009 Friedman et al.
2009/0162395 A1 6/2009 Crowe et al.
2009/0286852 A1 11/2009 Kariko et al.
2010/0015232 A1 1/2010 Besenbacher et al.
2010/0028943 A1 2/2010 Thomas et al.
2010/0047261 A1 2/2010 Hoerr et al.
2010/0048883 A1 2/2010 Ketterer et al.
2010/0068226 A1 3/2010 Taylor et al.
2010/0112042 A1 5/2010 Polisky et al.
2010/0129877 A1 5/2010 Sahin et al.
2010/0130588 A1 5/2010 Yaworski et al.
2010/0189729 A1 7/2010 Hoerr et al.
2010/0203076 A1 8/2010 Fotin-Mleczek et al.
2010/0239608 A1 9/2010 Mulbe et al.
2010/0260817 A1 10/2010 Slobodkin et al.
2010/0272747 A1 10/2010 Chow et al.
2010/0273220 A1 10/2010 Yanik et al.
2010/0285135 A1 11/2010 Wendorf et al.
2010/0291156 A1 11/2010 Barner et al.
2010/0303851 A1 12/2010 Hoerr et al.
2010/0305196 A1 12/2010 Probst et al.
2011/0045022 A1 2/2011 Tsai
2011/0053829 A1 3/2011 Baumhof et al.
2011/0065095 A1 3/2011 Kida et al.
2011/0077287 A1 3/2011 Mãœlbe et al.
2011/0086904 A1 4/2011 Russell
2011/0135645 A1 6/2011 Williamson et al.
2011/0143397 A1 6/2011 Kariko et al.
2011/0143436 A1 6/2011 Dahl et al.
2011/0184160 A1 7/2011 Weiner et al.
2011/0200582 A1 8/2011 Baryza et al.
2011/0244026 A1 10/2011 Guild et al.
2011/0250225 A1 10/2011 Fotin-Mleczek et al.
2011/0256175 A1 10/2011 Hope et al.
2011/0269950 A1 11/2011 Mulbe et al.
2011/0300205 A1 12/2011 Geall et al.
2011/0311472 A1 12/2011 Hoerr et al.
2012/0009221 A1 1/2012 Hoerr et al.
2012/0021042 A1 1/2012 Panzner et al.
2012/0027813 A1 2/2012 Podda et al.
2012/0045471 A1 2/2012 Haller et al.
2012/0046346 A1 2/2012 Rossi et al.
2012/0053333 A1 3/2012 Mauro et al.
2012/0058153 A1 3/2012 Ilyinskii et al.
2012/0069014 A1 3/2012 Wong et al.
2012/0101148 A1 4/2012 Aking et al.
2012/0177701 A1 7/2012 Ilyinskii et al.
2012/0177724 A1 7/2012 Irvine et al.
2012/0178702 A1 7/2012 Huang et al.
2012/0189700 A1 7/2012 Aguilar et al.
2012/0195917 A1 8/2012 Sahin et al.
2012/0195936 A1 8/2012 Rudolph et al.
2012/0213812 A1 8/2012 Lipford et al.
2012/0213818 A1 8/2012 Hoerr et al.
2012/0219573 A1 8/2012 Baumhof et al.
2012/0237975 A1 9/2012 Schrum et al.
2012/0252117 A1 10/2012 Selden et al.
2012/0258046 A1 10/2012 Mutzke
2012/0263648 A1 10/2012 Shapiro et al.
2012/0276209 A1 11/2012 Cullis et al.
2012/0295832 A1 11/2012 Constien et al.
2012/0301955 A1 11/2012 Thomas et al.
2013/0007828 A1 1/2013 Kister et al.
2013/0017223 A1 1/2013 Hope et al.
2013/0022538 A1 1/2013 Rossi et al.
2013/0064894 A1 3/2013 Martin et al.
2013/0065942 A1 3/2013 Matar et al.
2013/0078281 A1 3/2013 He et al.
2013/0090372 A1 4/2013 Budzik et al.
2013/0102034 A1 4/2013 Schrum
2013/0111615 A1 5/2013 Kariko et al.
2013/0115274 A1 5/2013 Knopov et al.
2013/0116307 A1 5/2013 Heyes et al.
2013/0121988 A1 5/2013 Hoerr et al.
2013/0123338 A1 5/2013 Heyes et al.
2013/0129785 A1 5/2013 Manoharan et al.
2013/0142818 A1 6/2013 Baumhof et al.
2013/0149375 A1 6/2013 Geall
2013/0150625 A1 6/2013 Budzik et al.
2013/0156845 A1 6/2013 Manoharan et al.
2013/0158021 A1 6/2013 Dong et al.
2013/0164400 A1 6/2013 Knopov et al.
2013/0171241 A1 7/2013 Geall
2013/0177587 A1 7/2013 Robinson et al.
2013/0177639 A1 7/2013 Geall et al.
2013/0177640 A1 7/2013 Geall et al.
2013/0178541 A1 7/2013 Stanton et al.
2013/0183355 A1 7/2013 Jain et al.
2013/0189351 A1 7/2013 Geall
2013/0195867 A1 8/2013 Hoerr et al.
2013/0195967 A1 8/2013 Guild et al.
2013/0195968 A1 8/2013 Geall et al.
2013/0195969 A1 8/2013 Geall et al.
2013/0197068 A1 8/2013 Kariko et al.
2013/0202645 A1 8/2013 Barner et al.
2013/0202684 A1 8/2013 Geall et al.
2013/0236533 A1 9/2013 Von Andrian et al.
2013/0236974 A1 9/2013 De Fougerolles
2013/0243848 A1 9/2013 Lobovkina et al.
2013/0245103 A1 9/2013 De Fougerolles et al.
2013/0245104 A1 9/2013 De Fougerolles et al.
2013/0245107 A1 9/2013 De Fougerolles et al.
2013/0259923 A1 10/2013 Chakraborty et al.
2013/0266640 A1 10/2013 De Fougerolles et al.
2013/0274504 A1 10/2013 Colletti et al.
2013/0274523 A1 10/2013 Bawiec et al.
2013/0280283 A1 10/2013 Lorenz et al.
2013/0287832 A1 10/2013 O'Hagan et al.
2013/0295043 A1 11/2013 Kallen et al.
2013/0330401 A1 12/2013 Payne et al.
2013/0336998 A1 12/2013 Kallen et al.
2014/0024076 A1 1/2014 Tang et al.
2014/0037660 A1 2/2014 Folin-Mleczek et al.
2014/0039032 A1 2/2014 Kuboyama et al.
2014/0044772 A1 2/2014 Maclachlan et al.
2014/0044791 A1 2/2014 Basilion et al.
2014/0045913 A1 2/2014 Kuboyama et al.
2014/0050759 A1 2/2014 Falkner et al.
2014/0065204 A1 3/2014 Hayes et al.
2014/0065228 A1 3/2014 Yaworski et al.
2014/0105966 A1 4/2014 Bancel et al.
2014/0112950 A1 4/2014 Singh et al.
2014/0121393 A1 5/2014 Manoharan et al.
2014/0127248 A1 5/2014 Ross et al.
2014/0134129 A1 5/2014 Thalhamer et al.
2014/0134201 A1 5/2014 Tureci et al.
2014/0141042 A1 5/2014 Vitelli et al.
2014/0141070 A1 5/2014 Geall et al.
2014/0142290 A1 5/2014 Madden et al.

(56) References Cited

U.S. PATENT DOCUMENTS

2014/0147432 A1 5/2014 Chakraborty et al.
2014/0147454 A1 5/2014 Chakraborty et al.
2014/0148502 A1 5/2014 Bancel et al.
2014/0193482 A1 7/2014 Chakraborty et al.
2014/0193484 A1 7/2014 Bertholet Girardin et al.
2014/0200257 A1 7/2014 Rajeev et al.
2014/0206752 A1 7/2014 Afeyan et al.
2014/0206753 A1 7/2014 Guild et al.
2014/0212498 A1 7/2014 Brito et al.
2014/0220083 A1 8/2014 Brito et al.
2014/0227346 A1 8/2014 Geall et al.
2014/0242152 A1 8/2014 Geall et al.
2014/0248314 A1 9/2014 Swanson et al.
2014/0248320 A1 9/2014 Tsai
2014/0255472 A1 9/2014 Geall et al.
2014/0271699 A1 9/2014 Kwong et al.
2014/0271829 A1 9/2014 Lilja et al.
2014/0275227 A1 9/2014 Hoge et al.
2014/0302079 A1 10/2014 Nabel et al.
2014/0308304 A1 10/2014 Manoharan et al.
2014/0328825 A1 11/2014 Meis et al.
2014/0348924 A1 11/2014 Pascolo
2014/0370497 A1 12/2014 Fouchier et al.
2014/0378538 A1 12/2014 Bancel
2015/0030622 A1 1/2015 Marshall et al.
2015/0030669 A1 1/2015 Platscher et al.
2015/0051268 A1 2/2015 Bancel et al.
2015/0056253 A1 2/2015 Bancel et al.
2015/0064233 A1 3/2015 Shih et al.
2015/0079121 A1 3/2015 Weiner et al.
2015/0086612 A1 3/2015 Sahin et al.
2015/0086613 A1 3/2015 Derosa et al.
2015/0093413 A1 4/2015 Thess et al.
2015/0118183 A1 4/2015 Baumhof
2015/0118264 A1 4/2015 Baumhof et al.
2015/0126589 A1 5/2015 Geiger et al.
2015/0140027 A1 5/2015 Cardosa et al.
2015/0141499 A1 5/2015 Bancel et al.
2015/0184195 A1 7/2015 Thess et al.
2015/0202153 A1 7/2015 Frank et al.
2015/0203446 A1 7/2015 Manoharan et al.
2015/0307542 A1 10/2015 Roy et al.
2015/0315541 A1 11/2015 Bancel et al.
2015/0335728 A1 11/2015 Wong et al.
2015/0376115 A1 12/2015 Ansell et al.
2016/0022580 A1 1/2016 Ramsay et al.
2016/0022806 A1 1/2016 Weiner et al.
2016/0024139 A1 1/2016 Berlanda Scorza et al.
2016/0024140 A1 1/2016 Issa et al.
2016/0024141 A1 1/2016 Issa et al.
2016/0032273 A1 2/2016 Shahrokh et al.
2016/0032284 A1 2/2016 Chen et al.
2016/0032316 A1 2/2016 Weissman et al.
2016/0038612 A1 2/2016 Hoge et al.
2016/0039884 A1 2/2016 Li et al.
2016/0046675 A1 2/2016 Kwong et al.
2016/0151284 A1 6/2016 Heyes et al.
2016/0151474 A1 6/2016 Kallen et al.
2016/0166678 A1 6/2016 Kallen et al.
2016/0194368 A1 7/2016 Hoge et al.
2016/0194625 A1 7/2016 Hoge et al.
2016/0243221 A1 8/2016 Hoge et al.
2016/0271272 A1 9/2016 Bancel et al.
2016/0317647 A1 11/2016 Ciaramella et al.
2016/0331828 A1 11/2016 Ciaramella et al.
2016/0331844 A1 11/2016 Fotin-Mleczek et al.
2016/0361411 A1 12/2016 Gindy et al.
2016/0376224 A1 12/2016 Du et al.
2017/0002041 A1 1/2017 Hauser et al.
2017/0009244 A1 1/2017 Sahin et al.
2017/0016026 A1 1/2017 Florkiewicz
2017/0043037 A1 2/2017 Kariko et al.
2017/0065675 A1 3/2017 Bancel et al.
2017/0130255 A1 5/2017 Wang et al.
2017/0202979 A1 7/2017 Chakraborty et al.
2017/0204152 A1 7/2017 Nelson et al.
2017/0210697 A1 7/2017 Benenato
2017/0210698 A1 7/2017 Benenato
2017/0224844 A1 8/2017 Benenato
2017/0239371 A1 8/2017 Guild et al.
2017/0340724 A1 11/2017 Ciaramella et al.
2017/0340725 A1 11/2017 Ciaramella et al.
2018/0000953 A1 1/2018 Almarsson et al.
2018/0002393 A1 1/2018 Fougerolles et al.
2018/0008694 A1 1/2018 Ciaramella et al.
2018/0021258 A1 1/2018 Graham et al.
2018/0028645 A1 2/2018 Ciaramella et al.
2018/0028664 A1 2/2018 Besin et al.
2018/0147298 A1 5/2018 Besin et al.
2018/0161422 A1 6/2018 Thess et al.
2018/0237849 A1 8/2018 Thompson
2018/0243225 A1 8/2018 Ciaramella
2018/0243230 A1 8/2018 Smith
2018/0256628 A1 9/2018 Hoge et al.
2018/0271795 A1 9/2018 Martini et al.
2018/0271970 A1 9/2018 Ciaramella et al.
2018/0273977 A1 9/2018 Mousavi et al.
2018/0274009 A1 9/2018 Marquardt et al.
2018/0280496 A1 10/2018 Ciaramella et al.
2018/0289792 A1 10/2018 Ciaramella et al.
2018/0296663 A1 10/2018 Hipp et al.
2018/0303925 A1 10/2018 Weissman et al.
2018/0303929 A1 10/2018 Ciaramella et al.
2018/0311336 A1 11/2018 Ciaramella et al.
2018/0311343 A1 11/2018 Huang et al.
2018/0312549 A1 11/2018 Ciaramella
2018/0318409 A1 11/2018 Valiante et al.
2018/0326039 A1 11/2018 Haruta
2018/0351057 A1 12/2018 Seo et al.
2018/0351843 A1 12/2018 Sharma et al.
2018/0363019 A1 12/2018 Hoge et al.
2018/0369374 A1 12/2018 Frederick et al.
2018/0371047 A1 12/2018 Ticho et al.
2019/0002890 A1 1/2019 Martini et al.
2019/0008938 A1 1/2019 Ciaramella et al.
2019/0008948 A1 1/2019 Ciaramella et al.
2019/0015501 A1 1/2019 Ciaramella et al.
2019/0085368 A1 3/2019 Bancel et al.
2019/0099481 A1 4/2019 Ciaramella et al.
2019/0125839 A1 5/2019 Frederick et al.
2019/0167811 A1 6/2019 Benenato et al.
2019/0175517 A1 6/2019 Martini et al.
2019/0175727 A1 6/2019 Huang et al.
2019/0192646 A1 6/2019 Cohen et al.
2019/0192653 A1 6/2019 Hoge et al.
2019/0240317 A1 8/2019 Ciaramella et al.
2019/0241633 A1 8/2019 Fotin-Mleczek et al.
2019/0274968 A1 9/2019 Weissman et al.
2019/0275170 A1 9/2019 Benenato et al.
2019/0298657 A1 10/2019 Martini et al.
2019/0298658 A1 10/2019 Benenato et al.
2019/0300906 A1 10/2019 Martini et al.
2019/0309337 A1 10/2019 Rabideau et al.
2019/0314292 A1 10/2019 Benenato et al.
2019/0314493 A1 10/2019 Ciaramella et al.
2019/0336452 A1 11/2019 Brader
2019/0336595 A1 11/2019 Ciaramella
2019/0351040 A1 11/2019 Valiante et al.
2019/0351047 A1 11/2019 Jasny et al.
2019/0351048 A1 11/2019 Rauch
2019/0382774 A1 12/2019 Hoge et al.
2019/0390181 A1 12/2019 Benenato et al.
2020/0030432 A1 1/2020 Ciaramella et al.
2020/0032274 A1 1/2020 Mauger et al.
2020/0038499 A1 2/2020 Narayanan et al.
2020/0054737 A1 2/2020 Ciaramella et al.
2020/0061185 A1 2/2020 Graham et al.
2020/0069599 A1 3/2020 Smith et al.
2020/0069793 A1 3/2020 Ciaramella
2020/0069794 A1 3/2020 Ciaramella et al.
2020/0071689 A1 3/2020 Miracco
2020/0085916 A1 3/2020 Martini et al.
2020/0109420 A1 4/2020 Brito et al.
2020/0129445 A1 4/2020 Patel et al.

(56) References Cited

U.S. PATENT DOCUMENTS

| | | | |
|---|---|---|---|
| 2020/0129608 | A1 | 4/2020 | Ciaramella et al. |
| 2020/0129615 | A1 | 4/2020 | Ciaramella et al. |
| 2020/0163878 | A1 | 5/2020 | Baumhof et al. |
| 2020/0239869 | A1 | 7/2020 | Issa et al. |
| 2020/0254086 | A1 | 8/2020 | Hoge et al. |
| 2020/0282046 | A1 | 9/2020 | Ciaramella et al. |
| 2020/0282047 | A1 | 9/2020 | Ciaramella et al. |
| 2020/0297634 | A1 | 9/2020 | Karmali et al. |
| 2020/0306191 | A1 | 10/2020 | Schariter et al. |
| 2020/0338004 | A1 | 10/2020 | Hansson et al. |
| 2020/0368162 | A1 | 11/2020 | Martini |
| 2020/0368343 | A1 | 11/2020 | Ciaramella et al. |
| 2020/0399322 | A1 | 12/2020 | Baumhof et al. |
| 2020/0405844 | A1 | 12/2020 | Ciaramella et al. |
| 2020/0407402 | A1 | 12/2020 | He et al. |
| 2021/0023199 | A1 | 1/2021 | Kallen et al. |
| 2021/0030866 | A1 | 2/2021 | Kallen et al. |
| 2021/0046173 | A1 | 2/2021 | Ciaramella et al. |
| 2021/0060175 | A1 | 3/2021 | Fotin-Mleczek et al. |
| 2021/0087135 | A1 | 3/2021 | Benenato et al. |
| 2021/0128716 | A1 | 5/2021 | Thess et al. |
| 2021/0139543 | A1 | 5/2021 | He et al. |
| 2021/0145982 | A1 | 5/2021 | Hoge et al. |
| 2021/0162037 | A1 | 6/2021 | Jasny et al. |
| 2021/0163919 | A1 | 6/2021 | Issa et al. |
| 2021/0187097 | A1 | 6/2021 | Ciaramella et al. |
| 2021/0206818 | A1 | 7/2021 | Huang et al. |
| 2021/0217484 | A1 | 7/2021 | Giessel et al. |
| 2021/0220467 | A1 | 7/2021 | Ciaramella et al. |
| 2021/0228707 | A1 | 7/2021 | Metkar et al. |
| 2021/0228708 | A1 | 7/2021 | Smith et al. |
| 2021/0268086 | A1 | 9/2021 | Zhong et al. |
| 2021/0309976 | A1 | 10/2021 | Dousis et al. |
| 2021/0378980 | A1 | 12/2021 | Horhota et al. |
| 2022/0031631 | A1 | 2/2022 | Almarsson et al. |
| 2022/0047518 | A1 | 2/2022 | Hennessy et al. |
| 2022/0054653 | A1 | 2/2022 | Martini et al. |
| 2022/0062175 | A1 | 3/2022 | Smith et al. |
| 2022/0062408 | A1 | 3/2022 | Kramarczyk et al. |
| 2022/0125899 | A1 | 4/2022 | Ashburn et al. |
| 2022/0145381 | A1 | 5/2022 | Elich et al. |
| 2022/0175906 | A1 | 6/2022 | Ciaramella et al. |
| 2022/0193223 | A1 | 6/2022 | Ciaramella et al. |
| 2022/0211838 | A1 | 7/2022 | Oostvogels et al. |
| 2022/0236253 | A1 | 7/2022 | Hopson |
| 2022/0241399 | A1 | 8/2022 | Lusso et al. |
| 2022/0257746 | A1 | 8/2022 | Ciaramella et al. |
| 2022/0347292 | A1 | 11/2022 | Panther et al. |
| 2022/0348900 | A1 | 11/2022 | Shamashkin et al. |
| 2022/0349006 | A1 | 11/2022 | Amato et al. |
| 2022/0370616 | A1 | 11/2022 | Hennessy |
| 2022/0378904 | A1 | 12/2022 | Panther et al. |
| 2022/0401551 | A1 | 12/2022 | Kramarczyk et al. |
| 2022/0409720 | A1 | 12/2022 | Ciaramella |
| 2023/0000970 | A1 | 1/2023 | Nachbagauer et al. |
| 2023/0020362 | A1 | 1/2023 | Ciaramella et al. |
| 2023/0044692 | A1 | 2/2023 | Ciaramella et al. |
| 2023/0113170 | A1 | 4/2023 | Graham et al. |
| 2023/0114180 | A1 | 4/2023 | Ciaramella et al. |
| 2023/0116376 | A1 | 4/2023 | Ciaramella et al. |
| 2023/0141153 | A1 | 5/2023 | Zhang et al. |
| 2023/0142529 | A1 | 5/2023 | White et al. |
| 2023/0173060 | A1 | 6/2023 | Benmohamed |
| 2023/0181481 | A1 | 6/2023 | White et al. |
| 2023/0190761 | A1 | 6/2023 | Brader et al. |
| 2023/0212645 | A1 | 7/2023 | Marquardt et al. |
| 2023/0242594 | A1 | 8/2023 | Mclellan et al. |
| 2023/0270836 | A1 | 8/2023 | Ciaramella et al. |
| 2023/0285539 | A1 | 9/2023 | Joyce et al. |
| 2023/0287437 | A1 | 9/2023 | Smith et al. |
| 2023/0303632 | A1 | 9/2023 | Ciaramella et al. |
| 2023/0310576 | A1 | 10/2023 | Ciaramella et al. |
| 2023/0338506 | A1 | 10/2023 | Shaw et al. |
| 2023/0338512 | A1 | 10/2023 | Muik et al. |
| 2023/0346907 | A1 | 11/2023 | Ciaramella et al. |
| 2023/0346914 | A1 | 11/2023 | Stewart-Jones et al. |
| 2023/0355743 | A1 | 11/2023 | Stewart-Jones et al. |
| 2023/0374079 | A1 | 11/2023 | Ciaramella et al. |
| 2023/0381301 | A1 | 11/2023 | Ciaramella et al. |
| 2023/0390379 | A1 | 12/2023 | Ciaramella et al. |
| 2024/0000917 | A1 | 1/2024 | Ciaramella |
| 2024/0100145 | A1 | 3/2024 | Bollman et al. |
| 2024/0100151 | A1 | 3/2024 | Carfi et al. |
| 2024/0139309 | A1 | 5/2024 | Carfi et al. |
| 2024/0156952 | A1 | 5/2024 | Ciaramella et al. |
| 2024/0173400 | A1 | 5/2024 | Ciaramella et al. |
| 2024/0181030 | A1 | 6/2024 | Himansu et al. |
| 2024/0207392 | A1 | 6/2024 | Chandramouli et al. |
| 2024/0209068 | A1 | 6/2024 | Deal et al. |
| 2024/0216500 | A1 | 7/2024 | Nachbagauer et al. |
| 2024/0226028 | A1 | 7/2024 | Goldman et al. |
| 2024/0226277 | A1 | 7/2024 | Nachbagauer et al. |
| 2024/0229109 | A1 | 7/2024 | Rabideau et al. |
| 2024/0238211 | A1 | 7/2024 | Brader et al. |
| 2024/0263226 | A1 | 8/2024 | Schmitt |
| 2024/0285754 | A1 | 8/2024 | Stewart-Jones |
| 2024/0293534 | A1 | 9/2024 | Stewart-Jones |
| 2024/0299525 | A1 | 9/2024 | Ciaramella et al. |
| 2024/0299531 | A1 | 9/2024 | Stewart-Jones |
| 2024/0335526 | A1 | 10/2024 | Ciaramella et al. |
| 2024/0358819 | A1 | 10/2024 | Stewart-Jones |
| 2024/0366745 | A1 | 11/2024 | Ciaramella et al. |
| 2024/0382581 | A1 | 11/2024 | Stewart-Jones |
| 2024/0398927 | A9 | 12/2024 | Ciaramella et al. |
| 2025/0041407 | A1 | 2/2025 | Ciaramella |
| 2025/0067729 | A1 | 2/2025 | Brader |
| 2025/0073327 | A1 | 3/2025 | Lusso et al. |
| 2025/0082748 | A1 | 3/2025 | Ciaramella et al. |
| 2025/0099569 | A1 | 3/2025 | Ciaramella et al. |
| 2025/0121220 | A1 | 4/2025 | Ciaramella et al. |
| 2025/0121221 | A1 | 4/2025 | Ciaramella et al. |
| 2025/0281418 | A1 | 9/2025 | Smith |
| 2025/0360194 | A1 | 11/2025 | Bahl et al. |

FOREIGN PATENT DOCUMENTS

| | | | |
|---|---|---|---|
| CA | 2473135 | A1 | 6/2003 |
| CA | 3178344 | A1 | 10/2021 |
| CA | 3194325 | A1 | 5/2022 |
| CN | 102076847 | A | 5/2011 |
| CN | 102177236 | A | 9/2011 |
| CN | 102573901 | A | 7/2012 |
| CN | 106244608 | A | 12/2016 |
| CN | 108366604 | A | 8/2018 |
| CN | 110951756 | A | 4/2020 |
| CN | 110974950 | A | 4/2020 |
| CN | 110974954 | A | 4/2020 |
| CN | 111032863 | A | 4/2020 |
| CN | 111088283 | A | 5/2020 |
| CN | 111218458 | A | 6/2020 |
| CN | 111218459 | A | 6/2020 |
| CN | 111303254 | A | 6/2020 |
| CN | 111518175 | A | 8/2020 |
| CN | 111592602 | A | 8/2020 |
| CN | 111848753 | A | 10/2020 |
| CN | 111939250 | A | 11/2020 |
| CN | 111978377 | A | 11/2020 |
| CN | 112023035 | A | 12/2020 |
| CN | 112028976 | A | 12/2020 |
| CN | 112043825 | A | 12/2020 |
| CN | 112048005 | A | 12/2020 |
| CN | 112094327 | A | 12/2020 |
| CN | 112220920 | A | 1/2021 |
| CN | 112226445 | A | 1/2021 |
| CN | 112266411 | A | 1/2021 |
| CN | 112321688 | A | 2/2021 |
| CN | 112358533 | A | 2/2021 |
| CN | 112480217 | A | 3/2021 |
| CN | 112546211 | A | 3/2021 |
| CN | 112626089 | A | 4/2021 |
| CN | 112794884 | A | 5/2021 |
| CN | 113999128 | A | 2/2022 |
| EP | 0 204 401 | A1 | 12/1986 |
| EP | 1 026 253 | A2 | 8/2000 |

(56) References Cited

FOREIGN PATENT DOCUMENTS

| | | | |
|---|---|---|---|
| EP | 1 083 232 | A1 | 3/2001 |
| EP | 1 301 614 | B1 | 4/2003 |
| EP | 1 383 556 | A1 | 1/2004 |
| EP | 1 026 253 | B2 | 9/2004 |
| EP | 1 083 232 | B1 | 2/2005 |
| EP | 1 619 254 | A1 | 1/2006 |
| EP | 1 383 556 | B1 | 10/2007 |
| EP | 1 905 844 | A2 | 4/2008 |
| EP | 2 092 064 | B1 | 9/2010 |
| EP | 1 619 254 | B1 | 12/2010 |
| EP | 2 188 379 | B1 | 1/2013 |
| EP | 2 548 960 | A1 | 1/2013 |
| EP | 3 083 578 | A1 | 10/2016 |
| EP | 2 548 960 | B1 | 1/2018 |
| EP | 3 452 101 | A2 | 3/2019 |
| EP | 3 608 308 | A1 | 2/2020 |
| EP | 3 901 261 | A1 | 10/2021 |
| EP | 4 008 357 | B1 | 12/2022 |
| JP | 2015-518472 | A | 7/2015 |
| JP | 2016-515815 | A | 6/2016 |
| JP | 2016-539944 | A | 12/2016 |
| JP | 2017-513956 | A | 6/2017 |
| JP | 7443608 | B2 | 10/2023 |
| JP | 7438604 | B2 | 2/2024 |
| WO | WO-87/05326 | A1 | 9/1987 |
| WO | WO-90/11092 | A1 | 10/1990 |
| WO | WO-92/19752 | A1 | 11/1992 |
| WO | WO-93/14778 | A1 | 8/1993 |
| WO | WO-95/08626 | A1 | 3/1995 |
| WO | WO-95/24485 | A2 | 9/1995 |
| WO | WO-95/26204 | A1 | 10/1995 |
| WO | WO-95/33835 | A1 | 12/1995 |
| WO | WO-96/40945 | A2 | 12/1996 |
| WO | WO-97/48370 | A2 | 12/1997 |
| WO | WO-98/00547 | A1 | 1/1998 |
| WO | WO-98/12207 | A1 | 3/1998 |
| WO | WO-98/58956 | A2 | 12/1998 |
| WO | WO-99/14346 | A2 | 3/1999 |
| WO | WO-99/33982 | A2 | 7/1999 |
| WO | WO-99/52503 | A2 | 10/1999 |
| WO | WO-00/29561 | A2 | 5/2000 |
| WO | WO-00/50586 | A2 | 8/2000 |
| WO | WO-01/21810 | A1 | 3/2001 |
| WO | WO-01/93836 | A2 | 12/2001 |
| WO | WO-02/48310 | A2 | 6/2002 |
| WO | WO-02/064799 | A2 | 8/2002 |
| WO | WO-03/059381 | A2 | 7/2003 |
| WO | WO-03/072720 | A2 | 9/2003 |
| WO | WO-2004/058166 | A2 | 7/2004 |
| WO | WO-2004/076645 | A2 | 9/2004 |
| WO | WO-2005/000235 | A2 | 1/2005 |
| WO | WO-2005/007689 | A1 | 1/2005 |
| WO | WO-2005/009346 | A2 | 2/2005 |
| WO | WO-2005/027825 | A2 | 3/2005 |
| WO | WO-2005/027936 | A2 | 3/2005 |
| WO | WO-2005/027963 | A2 | 3/2005 |
| WO | WO-2005/034992 | A2 | 4/2005 |
| WO | WO-2005/118813 | A2 | 12/2005 |
| WO | WO-2005/118857 | A2 | 12/2005 |
| WO | WO-2005/120152 | A2 | 12/2005 |
| WO | WO-2006/020071 | A2 | 2/2006 |
| WO | WO-2006/050280 | A2 | 5/2006 |
| WO | WO-2006/056027 | A1 | 6/2006 |
| WO | WO-2006/071255 | A2 | 7/2006 |
| WO | WO-2006/071903 | A2 | 7/2006 |
| WO | WO-2006/074341 | A2 | 7/2006 |
| WO | WO-2006/095259 | A2 | 9/2006 |
| WO | WO-2007/024708 | A2 | 3/2007 |
| WO | WO-2007/038862 | A1 | 4/2007 |
| WO | WO-2007/051303 | A1 | 5/2007 |
| WO | WO-2007/064952 | A2 | 6/2007 |
| WO | WO-2007/094854 | A2 | 8/2007 |
| WO | WO-2007/095976 | A2 | 8/2007 |
| WO | WO-2008/011609 | A2 | 1/2008 |
| WO | WO-2008/014979 | A3 | 2/2008 |
| WO | WO-2008/043052 | A2 | 4/2008 |
| WO | WO-2008/052770 | A2 | 5/2008 |
| WO | WO-2008/077592 | A1 | 7/2008 |
| WO | WO-2008/083949 | A2 | 7/2008 |
| WO | WO-2008/103276 | A2 | 8/2008 |
| WO | WO-2008/143640 | A1 | 11/2008 |
| WO | WO-2008/145129 | A2 | 12/2008 |
| WO | WO-2008/151049 | A2 | 12/2008 |
| WO | WO-2009/030254 | A1 | 3/2009 |
| WO | WO-2009/030481 | A1 | 3/2009 |
| WO | WO-2009/046738 | A1 | 4/2009 |
| WO | WO-2009/046739 | A1 | 4/2009 |
| WO | WO-2009/095226 | A2 | 8/2009 |
| WO | WO-2009/127060 | A1 | 10/2009 |
| WO | WO-2009/127230 | A1 | 10/2009 |
| WO | WO-2010/037408 | A1 | 4/2010 |
| WO | WO-2010/037539 | A1 | 4/2010 |
| WO | WO-2010/042877 | A1 | 4/2010 |
| WO | WO-2010/053572 | A2 | 5/2010 |
| WO | WO-2010/054401 | A1 | 5/2010 |
| WO | WO-2010/054406 | A1 | 5/2010 |
| WO | WO-2010/060430 | A2 | 6/2010 |
| WO | WO-2010/077717 | A1 | 7/2010 |
| WO | WO-2010/088537 | A3 | 8/2010 |
| WO | WO-2010/088927 | A1 | 8/2010 |
| WO | WO-2010/115046 | A2 | 10/2010 |
| WO | WO-2010/129709 | A1 | 11/2010 |
| WO | WO-2010/144740 | A1 | 12/2010 |
| WO | WO-2010/148013 | A2 | 12/2010 |
| WO | WO-2010/149743 | A2 | 12/2010 |
| WO | WO-2011/005799 | A2 | 1/2011 |
| WO | WO-2011/017548 | A1 | 2/2011 |
| WO | WO-2011/026641 | A9 | 3/2011 |
| WO | WO-2011/068810 | A1 | 6/2011 |
| WO | WO-2011/069529 | A1 | 6/2011 |
| WO | WO-2011/069586 | A1 | 6/2011 |
| WO | WO-2011/071931 | A2 | 6/2011 |
| WO | WO-2011/106607 | A2 | 9/2011 |
| WO | WO-2011/127255 | A1 | 10/2011 |
| WO | WO-2011/130624 | A2 | 10/2011 |
| WO | WO-2011/140627 | A1 | 11/2011 |
| WO | WO-2011/144358 | A1 | 11/2011 |
| WO | WO-2011/150264 | A2 | 1/2012 |
| WO | WO-2012/006359 | A1 | 1/2012 |
| WO | WO-2012/006369 | A2 | 1/2012 |
| WO | WO-2012/006372 | A1 | 1/2012 |
| WO | WO-2012/006376 | A2 | 1/2012 |
| WO | WO-2012/006377 | A2 | 1/2012 |
| WO | WO-2012/006378 | A1 | 1/2012 |
| WO | WO-2012/006380 | A2 | 1/2012 |
| WO | WO-2012/019630 | A1 | 2/2012 |
| WO | WO-2012/019780 | A1 | 2/2012 |
| WO | WO-2012/024629 | A1 | 2/2012 |
| WO | WO-2012/030683 | A2 | 3/2012 |
| WO | WO-2012/030901 | A1 | 3/2012 |
| WO | WO-2012/031043 | A1 | 3/2012 |
| WO | WO-2012/031046 | A2 | 3/2012 |
| WO | WO-2012/038450 | A1 | 3/2012 |
| WO | WO-2012/045075 | A1 | 4/2012 |
| WO | WO-2012/045082 | A2 | 4/2012 |
| WO | WO-2012/051211 | A2 | 4/2012 |
| WO | WO-2012/068295 | A1 | 5/2012 |
| WO | WO-2012/072269 | A1 | 6/2012 |
| WO | WO-2012/075040 | A2 | 6/2012 |
| WO | WO-2012/089225 | A1 | 7/2012 |
| WO | WO-2012/092569 | A2 | 7/2012 |
| WO | WO-2012/099805 | A2 | 7/2012 |
| WO | WO-2012/113413 | A1 | 8/2012 |
| WO | WO-2012/113513 | A1 | 8/2012 |
| WO | WO-2012/116714 | A1 | 9/2012 |
| WO | WO-2012/116715 | A1 | 9/2012 |
| WO | WO-2012/116810 | A1 | 9/2012 |
| WO | WO-2012/116811 | A1 | 9/2012 |
| WO | WO-2012/135805 | A2 | 10/2012 |
| WO | WO-2012/138453 | A1 | 10/2012 |
| WO | WO-2012/149045 | A2 | 11/2012 |
| WO | WO-2012/149376 | A2 | 11/2012 |
| WO | WO-2012/159754 | A2 | 11/2012 |
| WO | WO-2012/170889 | A1 | 12/2012 |

(56) References Cited

FOREIGN PATENT DOCUMENTS

WO WO-2012/170930 A1 12/2012
WO WO-2012/177760 A1 12/2012
WO WO-2013/006825 A1 1/2013
WO WO-2013/006834 A1 1/2013
WO WO-2013/006837 A1 1/2013
WO WO-2013/006838 A1 1/2013
WO WO-2013/006842 A2 1/2013
WO WO-2013/024865 A1 2/2013
WO WO-2013/030778 A2 3/2013
WO WO-2013/052167 A2 4/2013
WO WO-2013/052523 A1 4/2013
WO WO-2013/055905 A1 4/2013
WO WO-2013/056132 A2 4/2013
WO WO-2013/059496 A1 4/2013
WO WO-2013/075266 A1 5/2013
WO WO-2013/078199 A2 5/2013
WO WO-2013/079473 A1 6/2013
WO WO-2013/090186 A1 6/2013
WO WO-2013/090648 A1 6/2013
WO WO-2013/093648 A2 6/2013
WO WO-2013/102203 A1 7/2013
WO WO-2013/113326 A1 8/2013
WO WO-2013/113502 A1 8/2013
WO WO-2013/120498 A1 8/2013
WO WO-2013/120628 A1 8/2013
WO WO-2013/120629 A1 8/2013
WO WO-2013/143555 A1 10/2013
WO WO-2013/151663 A1 10/2013
WO WO-2013/151736 A2 10/2013
WO WO-2013/174409 A1 11/2013
WO WO-2013/177444 A2 11/2013
WO WO-2013/182683 A1 12/2013
WO WO-2013/185069 A1 12/2013
WO WO-2014/028487 A1 2/2014
WO WO-2014/028763 A1 2/2014
WO WO-2014/035457 A1 3/2014
WO WO-2014/071219 A1 5/2014
WO WO-2014/071963 A1 5/2014
WO WO-2014/072061 A1 5/2014
WO WO-2014/074912 A1 5/2014
WO WO-2014/081507 A1 5/2014
WO WO-2014/089239 A1 6/2014
WO WO-2014/089486 A1 6/2014
WO WO-2014/093574 A1 6/2014
WO WO-2014/108515 A1 7/2014
WO WO-2014/127917 A1 8/2014
WO WO-2014/136086 A1 9/2014
WO WO-2014/140211 A1 9/2014
WO WO-2014/144196 A1 9/2014
WO WO-2014/144711 A1 9/2014
WO WO-2014/145038 A1 9/2014
WO WO-2014/151488 A1 9/2014
WO WO-2014/152027 A1 9/2014
WO WO-2014/152030 A1 9/2014
WO WO-2014/152200 A1 9/2014
WO WO-2014/152211 A1 9/2014
WO WO-2014/152540 A1 9/2014
WO WO-2014/152774 A1 9/2014
WO WO-2014/152940 A1 9/2014
WO WO-2014/152966 A1 9/2014
WO WO-2014/159813 A1 10/2014
WO WO-2014/160243 A1 10/2014
WO WO-2014/160463 A1 10/2014
WO WO-2014/174018 A1 10/2014
WO WO-2014/182661 A2 11/2014
WO WO-2014/202570 A1 12/2014
WO WO-2014/210356 A1 12/2014
WO WO-2015/005253 A1 1/2015
WO WO-2015/006747 A2 1/2015
WO WO-2015/013551 A1 1/2015
WO WO-2015/023461 A2 2/2015
WO WO-2015/024667 A1 2/2015
WO WO-2015/024668 A2 2/2015
WO WO-2015/024669 A1 2/2015
WO WO-2015/048744 A2 4/2015
WO WO-2015/061467 A1 4/2015
WO WO-2015/062738 A1 5/2015
WO WO-2015/081155 A1 6/2015
WO WO-2015/085318 A2 6/2015
WO WO-2015/095340 A1 6/2015
WO WO-2015/095346 A1 6/2015
WO WO-2015/101414 A2 7/2015
WO WO-2015/101415 A1 7/2015
WO WO-2015/130584 A2 9/2015
WO WO-2015/135558 A1 9/2015
WO WO-2015/143335 A1 9/2015
WO WO-2015/149944 A2 10/2015
WO WO-2015/164674 A1 10/2015
WO WO-2015/177312 A1 11/2015
WO WO-2015/183969 A1 12/2015
WO WO-2015/188933 A1 12/2015
WO WO-2015/189425 A1 12/2015
WO WO-2015/199952 A1 12/2015
WO WO-2016/005480 A1 1/2016
WO WO-2016/012800 A1 1/2016
WO WO-2016/031986 A1 3/2016
WO WO-2016/037053 A1 3/2016
WO WO-2016/103238 A1 6/2016
WO WO-2016/123864 A1 8/2016
WO WO-2016/128376 A1 8/2016
WO WO-2016/138160 A1 9/2016
WO WO-2016/164762 A1 10/2016
WO WO-2016/174227 A1 11/2016
WO WO-2016/176330 A1 11/2016
WO WO-2016/184822 A1 11/2016
WO WO-2016/201377 A1 12/2016
WO WO-2016/203025 A1 12/2016
WO WO-2017/011773 A2 1/2017
WO WO-2017/015457 A1 1/2017
WO WO-2017/015463 A2 1/2017
WO WO-2017/019935 A1 2/2017
WO WO-2017/020026 A1 2/2017
WO WO-2017/031232 A1 2/2017
WO WO-2017/031241 A1 2/2017
WO WO-2017/049245 A2 3/2017
WO WO-2017/053297 A1 3/2017
WO WO-2017/062513 A1 4/2017
WO WO-2017/066789 A1 4/2017
WO WO-2017/070601 A1 4/2017
WO WO-2017/070616 A2 4/2017
WO WO-2017/070618 A1 4/2017
WO WO-2017/070620 A1 4/2017
WO WO-2017/070620 A2 4/2017
WO WO-2017/070622 A1 4/2017
WO WO-2017/070623 A1 4/2017
WO WO-2017/070626 A2 4/2017
WO WO-2017/075038 A1 5/2017
WO WO-2017/075531 A1 5/2017
WO WO-2017/081082 A1 5/2017
WO WO-2017/112865 A1 6/2017
WO WO-2017/127750 A1 7/2017
WO WO-2017/153936 A1 9/2017
WO WO-2017/174564 A1 10/2017
WO WO-2017/182524 A1 10/2017
WO WO-2017/191258 A1 11/2017
WO WO-2017/191274 A2 11/2017
WO WO-2017/201333 A1 11/2017
WO WO-2017/201340 A2 11/2017
WO WO-2017/201342 A1 11/2017
WO WO-2017/201347 A1 11/2017
WO WO-2017/201349 A1 11/2017
WO WO-2018/006052 A1 1/2018
WO WO-2018/053209 A1 3/2018
WO WO-2018/075592 A1 4/2018
WO WO-2018/075980 A1 4/2018
WO WO-2018/078053 A1 5/2018
WO WO-2018/081318 A1 5/2018
WO WO-2018/081459 A1 5/2018
WO WO-2018/081462 A1 5/2018
WO WO-2018/081638 A1 5/2018
WO WO-2018/089801 A1 5/2018
WO WO-2018/089851 A2 5/2018
WO WO-2018/107088 A2 6/2018
WO WO-2018/111967 A1 6/2018

(56) References Cited

FOREIGN PATENT DOCUMENTS

| | | | |
|---|---|---|---|
| WO | WO-2018/115527 | A2 | 6/2018 |
| WO | WO-2018/140826 | A1 | 8/2018 |
| WO | WO-2018/140826 | A9 | 8/2018 |
| WO | WO-2018/144082 | A1 | 8/2018 |
| WO | WO-2018/144778 | A1 | 8/2018 |
| WO | WO-2018/151816 | A1 | 8/2018 |
| WO | WO-2018/157009 | A1 | 8/2018 |
| WO | WO-2018/170245 | A1 | 9/2018 |
| WO | WO-2018/170256 | A1 | 9/2018 |
| WO | WO-2018/170260 | A1 | 9/2018 |
| WO | WO-2018/170270 | A1 | 9/2018 |
| WO | WO-2018/170347 | A1 | 9/2018 |
| WO | WO-2018/175783 | A1 | 9/2018 |
| WO | WO-2018/187590 | A1 | 10/2018 |
| WO | WO-2018/200737 | A1 | 11/2018 |
| WO | WO-2018/232355 | A1 | 12/2018 |
| WO | WO-2018/232357 | A1 | 12/2018 |
| WO | WO-2019/018765 | A1 | 1/2019 |
| WO | WO-2019/036670 | A2 | 2/2019 |
| WO | WO-2019/036682 | A1 | 2/2019 |
| WO | WO-2019/036683 | A1 | 2/2019 |
| WO | WO-2019/036685 | A1 | 2/2019 |
| WO | WO-2019/055807 | A1 | 3/2019 |
| WO | WO-2019/081750 | A1 | 5/2019 |
| WO | WO-2019/092153 | A1 | 5/2019 |
| WO | WO-2019/103993 | A1 | 5/2019 |
| WO | WO-2019/145310 | A1 | 8/2019 |
| WO | WO-2019/148101 | A1 | 8/2019 |
| WO | WO-2019/202035 | A1 | 10/2019 |
| WO | WO-2020/006242 | A1 | 1/2020 |
| WO | WO-2020/056370 | A1 | 3/2020 |
| WO | WO-2020/061284 | A1 | 3/2020 |
| WO | WO-2020/061295 | A1 | 3/2020 |
| WO | WO-2020/061367 | A1 | 3/2020 |
| WO | WO-2020/097291 | A1 | 5/2020 |
| WO | WO-2020/163719 | A2 | 8/2020 |
| WO | WO-2020/172239 | A1 | 8/2020 |
| WO | WO-2020/185811 | A1 | 9/2020 |
| WO | WO-2020/190750 | A1 | 9/2020 |
| WO | WO-2020/243561 | A1 | 12/2020 |
| WO | WO-2021/016430 | A1 | 1/2021 |
| WO | WO-2021/030533 | A1 | 2/2021 |
| WO | WO-2021/050864 | A1 | 3/2021 |
| WO | WO-2021/055811 | A1 | 3/2021 |
| WO | WO-2021/138447 | A1 | 7/2021 |
| WO | WO-2021/147025 | A1 | 7/2021 |
| WO | WO-2021/154763 | A1 | 8/2021 |
| WO | WO-2021/154812 | A1 | 8/2021 |
| WO | WO-2021/155243 | A1 | 8/2021 |
| WO | WO-2021/155274 | A1 | 8/2021 |
| WO | WO-2021/155733 | A1 | 8/2021 |
| WO | WO-2021/156267 | A1 | 8/2021 |
| WO | WO-2021/159040 | A2 | 8/2021 |
| WO | WO-2021/159040 | A9 | 8/2021 |
| WO | WO-2021/159118 | A2 | 8/2021 |
| WO | WO-2021/159130 | A2 | 8/2021 |
| WO | WO-2021/160346 | A1 | 8/2021 |
| WO | WO-2021/163365 | A1 | 8/2021 |
| WO | WO-2021/178971 | A1 | 9/2021 |
| WO | WO-2021/198706 | A2 | 10/2021 |
| WO | WO-2021/204175 | A1 | 10/2021 |
| WO | WO-2021/211343 | A1 | 10/2021 |
| WO | WO-2021/213924 | A1 | 10/2021 |
| WO | WO-2021/213945 | A1 | 10/2021 |
| WO | WO-2021/222304 | A1 | 11/2021 |
| WO | WO-2021/226436 | A1 | 11/2021 |
| WO | WO-2021/231901 | A1 | 11/2021 |
| WO | WO-2021/231929 | A1 | 11/2021 |
| WO | WO-2021/231963 | A1 | 11/2021 |
| WO | WO-2021/237084 | A1 | 11/2021 |
| WO | WO-2021/237174 | A1 | 11/2021 |
| WO | WO-2021/239880 | A1 | 12/2021 |
| WO | WO-2021/247817 | A1 | 12/2021 |
| WO | WO-2021/262672 | A1 | 12/2021 |
| WO | WO-2022/009121 | A1 | 1/2022 |
| WO | WO-2022/032154 | A2 | 2/2022 |
| WO | WO-2022/043551 | A2 | 3/2022 |
| WO | WO-2022/046898 | A1 | 3/2022 |
| WO | WO-2022/067010 | A1 | 3/2022 |
| WO | WO-2022/076562 | A1 | 4/2022 |
| WO | WO-2022/081544 | A1 | 5/2022 |
| WO | WO-2022/099003 | A1 | 5/2022 |
| WO | WO-2022/101469 | A1 | 5/2022 |
| WO | WO-2022/104265 | A1 | 5/2022 |
| WO | WO-2022/137133 | A1 | 6/2022 |
| WO | WO-2022/150717 | A1 | 7/2022 |
| WO | WO-2022/155524 | A1 | 7/2022 |
| WO | WO-2022/155530 | A1 | 7/2022 |
| WO | WO-2022/162027 | A2 | 8/2022 |
| WO | WO-2022/187698 | A1 | 9/2022 |
| WO | WO-2022/197624 | A1 | 9/2022 |
| WO | WO-2022/204491 | A1 | 9/2022 |
| WO | WO-2022/212191 | A1 | 10/2022 |
| WO | WO-2022/212442 | A1 | 10/2022 |
| WO | WO-2022/212711 | A1 | 10/2022 |
| WO | WO-2022/212711 | A2 | 10/2022 |
| WO | WO-2022/221335 | A1 | 10/2022 |
| WO | WO-2022/221336 | A1 | 10/2022 |
| WO | WO-2022/221359 | A1 | 10/2022 |
| WO | WO-2022/221440 | A1 | 10/2022 |
| WO | WO-2022/226277 | A1 | 10/2022 |
| WO | WO-2022/226318 | A1 | 10/2022 |
| WO | WO-2022/232585 | A1 | 11/2022 |
| WO | WO-2022/233629 | A1 | 11/2022 |
| WO | WO-2022/241103 | A1 | 11/2022 |
| WO | WO-2022/245888 | A1 | 11/2022 |
| WO | WO-2022/266010 | A1 | 12/2022 |
| WO | WO-2022/266012 | A1 | 12/2022 |
| WO | WO-2022/266389 | A1 | 12/2022 |
| WO | WO-2023/274860 | A1 | 1/2023 |
| WO | WO-2023/283642 | A1 | 1/2023 |
| WO | WO-2023/283642 | A2 | 1/2023 |
| WO | WO-2023/283645 | A1 | 1/2023 |
| WO | WO-2023/283651 | A1 | 1/2023 |
| WO | WO-2023/006920 | A1 | 2/2023 |
| WO | WO-2023/014649 | A1 | 2/2023 |
| WO | WO-2023/018773 | A1 | 2/2023 |
| WO | WO-2023/018923 | A1 | 2/2023 |
| WO | WO-2023/019181 | A1 | 2/2023 |
| WO | WO-2023/056401 | A1 | 4/2023 |
| WO | WO-2023/069625 | A1 | 4/2023 |
| WO | WO-2023/069895 | A1 | 4/2023 |
| WO | WO-2023/069900 | A1 | 4/2023 |
| WO | WO-2023/076358 | A1 | 5/2023 |
| WO | WO-2023/076658 | A1 | 5/2023 |
| WO | WO-2023/081311 | A1 | 5/2023 |
| WO | WO-2023/092069 | A1 | 5/2023 |
| WO | WO-2023/094713 | A2 | 6/2023 |
| WO | WO-2023/107999 | A2 | 6/2023 |
| WO | WO-2023/114307 | A1 | 6/2023 |
| WO | WO-2023/132885 | A1 | 7/2023 |
| WO | WO-2023/135333 | A1 | 7/2023 |
| WO | WO-2023/137149 | A1 | 7/2023 |
| WO | WO-2023/147091 | A1 | 8/2023 |
| WO | WO-2023/150256 | A1 | 8/2023 |
| WO | WO-2023/154818 | A1 | 8/2023 |
| WO | WO-2023/196914 | A1 | 10/2023 |
| WO | WO-2023/201204 | A1 | 10/2023 |
| WO | WO-2023/201294 | A1 | 10/2023 |
| WO | WO-2023/201296 | A1 | 10/2023 |
| WO | WO-2023/212696 | A1 | 11/2023 |
| WO | WO-2023/225524 | A1 | 11/2023 |
| WO | WO-2023/239836 | A1 | 12/2023 |
| WO | WO-2023/250119 | A1 | 12/2023 |
| WO | WO-2024/010993 | A1 | 1/2024 |
| WO | WO-2024/015890 | A1 | 1/2024 |
| WO | WO-2024/026005 | A1 | 2/2024 |
| WO | WO-2024/030369 | A1 | 2/2024 |
| WO | WO-2024/050483 | A1 | 3/2024 |
| WO | WO-2024/097874 | A1 | 5/2024 |
| WO | WO-2024/104947 | A2 | 5/2024 |
| WO | WO-2024/123978 | A1 | 6/2024 |
| WO | WO-2024/151811 | A1 | 7/2024 |

(56) References Cited

FOREIGN PATENT DOCUMENTS

WO WO-2024/163465 A1 8/2024
WO WO-2024/191860 A2 9/2024
WO WO-2024/206835 A1 10/2024

OTHER PUBLICATIONS

U.S. Appl. No. 18/351,057, filed Jul. 12, 2023, Bollman et al.
U.S. Appl. No. 18/351,843, filed Jul. 13, 2023, Bollman et al.
U.S. Appl. No. 18/494,666, filed Oct. 25, 2023, Nasir et al.
U.S. Appl. No. 18/605,658, filed Mar. 14, 2024, Nasir et al.
U.S. Appl. No. 62/972,886, filed Feb. 11, 2020, Graham et al.
U.S. Appl. No. 63/032,502, filed May 29, 2020, Mclellan et al.
"Katalin Kariko and Drew Weissman awarded Horwitz Prize for pioneering research on COVID-19 vaccines," Columbia University Irving Medical Center, Aug. 16, 2021, (available at https://www.cuimc.columbia.edu/ news/horwitz-prize-2021).
'Heroes of Chemistry' recognized for contributions to health, medicine and more, American Chemical Society, 2022 pp. 1-2.
[IPR-2023-01358] Patent Owner's Preliminary Response in IPR2023-01358 dated Dec. 8, 2023.
[IPR-2023-01358] Patent Owner's Preliminary Statement Regarding Petitioner's Inconsistent Positions in IPR2023-01358 dated Jan. 16, 2024.
[IPR-2023-01358] Patent Owner's Response in IPR2023-01358 dated May 31, 2024.
[IPR-2023-01358] Patent Owner's Sur-Reply in IPR2023-01358 dated Oct. 16, 2024.
[IPR-2023-01358] Patent Owner's Sur-Reply in Support of Preliminary Response in IPR2023-01358 dated Jan. 25, 2024.
[IPR-2023-01358] Petitioner's Preliminary Statement Regarding Patent Owner's Inconsistent Positions in IPR-2023-01358 dated Jan. 23, 2024.
[IPR-2023-01358] Petitioner's Reply to Patent Owner's Preliminary Response in IPR2023-01358 dated Jan. 12, 2024.
[IPR-2023-01358] Petitioner's Reply to Patent Owner's Response in IPR2023-01358 dated Aug. 30, 2024.
[IPR2023-01359] Patent Owner's Preliminary Response in IPR2023-01359 dated Dec. 7, 2023.
[IPR2023-01359] Patent Owner's Preliminary Statement Regarding Alleged Inconsistent Positions in IPR2023-01359 dated Jan. 16, 2024.
[IPR2023-01359] Patent Owner's Response in IPR2023-01359 dated May 31, 2024.
[IPR2023-01359] Patent Owner's Sur-Reply in IPR2023-01359 dated Oct. 16, 2024.
[IPR2023-01359] Patent Owner's Sur-Reply in Support of Preliminary Response in IPR2023-01359 dated Jan. 25, 2024.
[IPR2023-01359] Petitioner's Reply to Patent Owner's Preliminary Response in IPR2024-01359 dated Jan. 12, 2024.
[IPR2023-01359] Petitioner's Reply to Patent Owner's Response in IPR2023-01359 dated Aug. 30, 2024.
[No Author Listed] Lineage list. Last accessed Oct. 17, 2023 at https://cov-lineages.org/lineage_list.html. 77 pages.
[No Author Listed], "BioNTech Expands Clinical Oncology Portfolio with First Patient Dosed in Phase 2 Trial of mRNA-based Individualized Immunotherapy BNT122 in Colorectal Cancer Patients," Press Release, BioNTech, Oct. 1, 2021, 2 pages.
[No Author Listed], "Coronavirus (COVID-19) Update: FDA Authorizes Changes to Simplify Use of Bivalent mRNA COVID-19 Vaccines," FDA News Release, Apr. 18, 2023, 3 pages.
[No Author Listed], "European Commission Authorizes COVID 19 Vaccine Moderna in Europe," Jan. 6, 2021, Accessed from https://www.drugs.com/clinical_trials/european-commission-authorizes-covid-19-vaccine-moderna-europe-19152.html, 5 pages.
[No Author Listed], "Messenger RNA" definition. The Penguin Dictionary of Science. 2009: 3 pages.
[No Author Listed], "Messenger RNA" definition. Webster's New World Medical Dictionary. 2008;3:271.
[No Author Listed], "Messenger RNA", Internet: Wikipedia. Jun. 19, 2013, XP002699196, Retrieved from the Internet: URL: http://en.wikipedia.org/wiki/Messenger RNA.
[No Author Listed], "Moderna has noplans to share its COVID-19 vaccine recipe," Associated Press, Oct. 11, 2021, 2 pages.
[No Author Listed], "Moderna Receives FDA Authorization for Emergency Use of Omicron-Targeting Bivalent COVID-19 Booster Vaccine for Adults 18 Years and Older," News Release, Moderna, Aug. 31, 2022, 5 page.
[No Author Listed], "Moderna Reports Fourth Quarter and Fiscal Year 2020 Financial Results and Provides Business Updates," Press Release, Feb. 25, 2021, retrieved from URL <https://s29.q4cdn.com/435878511/files/doc_news/2021/02/25/moderna-reports-fourth-quarter-and-fiscal-year-2020-financial.pdf>, 9 pages.
[No Author Listed], "Modified mRNA Vaccines, 2021 Lasker-DeBakey Clinical Medical Research Award," 2021, retrieved on Nov. 14, 2022, retrieved from URL <https://laskerfoundation.org/winners/modified-mrna-vaccines/>, 17 pages.
[No Author Listed], "Pfizer and BioNTech Choose Lead mRNA Vaccine Candidate Against COVID-19 and Commence Pivotal Phase 2/3 Global Study," Press Release, Jul. 27, 2020, 7 pages.
[No Author Listed], "Pfizer/BioNTech COVID-19 mRNA vaccine (BNT162, PF-07302048)," TGA Pre-Submission Meeting, Sep. 18, 2020, retrieved on Oct. 3, 2024, retrieved from URL https://www.tga.gov.au/sites/default/files/foi-2389-03-1.pdf, 180 pages.
[No Author Listed], "The species Severe acute respiratory syndrome-related coronavirus: classifying 2019-nCoV and naming it SARS-CoV-2: Classifying 2019-nCoV and Naming it SARS-CoV-2, 5," Nature Microbiology, Mar. 2020, 5(4):536-544.
[No Author Listed], 2022 Breakthrough Prize in Life Sciences Awarded to Penn Medicine mRNA Pioneers Drew Weissman and Katalin Kariko. Press Release. Sep. 9, 2021: 3 pages.
[No Author Listed], 3rd International mRNA Health Conference Program. mRNA Conference. Nov. 11, 2015: 28 pages.
[No Author Listed], A Phase 3, Randomized, Stratified, Observer-Blind, Placebo-Controlled Study to Evaluate the Efficacy, Safety, and Immunogenicity ofmRNA-1273 SARSCoV-2 Vaccine in Adults Aged 18 Years and Older. ModernaTX, Inc. Protocol mRNA-1273-P301, Amendment 3. Aug. 20, 2020. 135 pages.
[No Author Listed], AIVC recommendation for the composition of influenza vaccine for Australia in 2021. Australian Government Therapeutic Goods Administration (TGA). Published Oct. 9, 2020. Retrieved from Internet Jul. 29, 2022. 2 pages.
[No Author Listed], An Audience with Moncef Slaoui. Nat Rev Drug Discov Jul. 1, 2015; vol. 14, pp. 452-453. https://doi.org/10.1038/nrd4669.
[No Author Listed], Background document on the mRNA-1273 vaccine (Moderna) against COVID-19. World Health Organization. Feb. 3, 2021. Accessed from <https://www.who.int/publications/i/item/background-document-on-the-mrna-1273-vaccine-(moderna)-against-covid-19>. 41 pages.
[No Author Listed], BioNTech Fourth Quarter and Full-Year 2019 Results. BioNTech. Mar. 31, 2020: 15 pages.
[No Author Listed], BioNTech SE Annual Report (Form 20-F) 179, F-12. United States Securities and Exchange Commission. Mar. 30, 2021: 739 pages.
[No Author Listed], BioNTech SE Annual Report (Form 20-F) 81. United States Securities and Exchange Commission. Mar. 30, 2022: 700 pages.
[No Author Listed], BioNTech Signs Collaboration Agreement with Pfizer to Develop mRNA-based Vaccines for Prevention of Influenza. Press Release. Aug. 16, 2018: 3 pages.
[No Author Listed], BNT162 COVID-19 Vaccine Program Update. BioNTech. Apr. 23, 2020: 15 pages.
[No Author Listed], Canada Exercises Increased Option for 20 Million Doses of mRNA Vaccine Against COVID-19 (mRNA-1273). Moderna Press Release. Sep. 22, 2020. 2 pages.
[No Author Listed], Cdc. SARS-CoV-2 Variant Classifications and Definitions. https://www.cdc.gov/corona virus/2019-ncov /variants/variant-classifications .html. Updated Sep. 1, 2023. 5 pages.
[No Author Listed], Comirnaty (mRNA-1273) EMA SmPC (summary of product characteristics);. Published Dec. 1, 2021. 276 pages.

(56) References Cited

OTHER PUBLICATIONS

[No Author Listed], Comirnaty Dosing Schedule for People 12 Years of Age & Older (2023-2024 Formula). Oct. 2023: 2 pages.
[No Author Listed], Coronavirus (COVID-19) Update: FDA Issues Policies to Guide Medical Product Developers Addressing Virus Variants. FDA News Release. Feb. 22, 2021. 5 pages.
[No Author Listed], Could COVID-19 vaccines be tweaked to cover new coronavirus variants? I Gavi, the Vaccine Alliance. Published Jan. 14, 2021. URL:https://www.gavi.org/vaccineswork/could-covid-19-vaccines-be-tweaked-cover-new-coronavirus-variants: Last accessed Apr. 26, 2022. 5 pages.
[No Author Listed], COVID-19 Vaccine Development Program. Pfizer. Jul. 1, 2020: 18 pages.
[No Author Listed], DARPA Awards Moderna Therapeutics a Grant for up to $25 Million to Develop Messenger RNA Therapeutics. News Release. Moderna. Oct. 2, 2013: 1 page.
[No Author Listed], Dosing Schedule for Ages 12 Years of Age and Older with Pfizer-BioNTech COVID-19 Vaccine, Bivalent (Original and Omicron BA.4/BA.5). Apr. 2023: 7-9.
[No Author Listed], *E. coli* ColEl origin of replication polynucleotide SEQ: 2. EBI Accession No. GSN:BDO77990. Geneseq. Apr. 20, 2017.
[No Author Listed], Experimental COVID-19 Vaccine Protects Upper and Lower Airways in Nonhuman Primates. NIH News Release. Jul. 28, 2020. 4 pages.
[No Author Listed], Experimental COVID-19 Vaccine Safe, Generates Immune Response. NIH News Release. Jul. 14, 2020. 4 pages.
[No Author Listed], Fact Sheet for Healthcare Providers Administering Vaccine: Emergency Use Authorization of Pfizer-BioNTech COVID-19 Vaccine (2023-2024 Formula) for 6 Months through 11 Years of Age. Pfizer-BioNTech. Sep. 2023: 59 pages.
[No Author Listed], Geneseq Accession No. BC153556. First entry: Jan. 14, 2016. 3 pages.
[No Author Listed], Geneseq Accession No. BGP67180. First entry: Sep. 19, 2019. 3 pages.
[No Author Listed], Goldman Sachs Virtual 41st Annual Global Healthcare Conference. Pfizer Inc. Jun. 9, 2020: 13 pages.
[No Author Listed], History of Changes for Study: NCT04283461, Safety and Immunogenicity Study of 2019-nCoV Vaccine (mRNA-1273) for Prophylaxis of SARS-CoV-2 Infection (COVID-19). Version submitted Dec. 8, 2022. 8 pages.
[No Author Listed], History of Changes for Study: NCT04283461, Safety and Immunogenicity Study of 2019-nCoV Vaccine (mRNA-1273) for Prophylaxis of SARS-CoV-2 Infection (COVID-19). Version submitted Mar. 11, 2021. 10 pages.
[No Author Listed], History of Changes for Study: NCT04405076, Dose-Confirmation Study to Evaluate the Safety, Reactogenicity, and Immunogenicity of mRNA-1273 COVID-19 Vaccine in Adults Aged 18 Years and Older. Version submitted Dec. 6, 2022. 6 pages.
[No Author Listed], Influenza A virus A/Jiangxi/1PB13/2013(H10N8) hemagglutinin protein. UniProtKB Accession: A0A059T4Al. Sep. 3, 2014. 1 p. 1.
[No Author Listed], Katalin Kariko Laureate de la Grande Medaille 2021 de L'Academie des Sciences. Press Release. De L'Academie des Sciences. Sep. 28, 2021: 2 pages.
[No Author Listed], List of past and pending litigations. Prepared Oct. 24, 2023. 1 page.
[No Author Listed], Messenger RNA Pioneer Katalin Kariko Receives European Inventor Award 2022 for Lifetime Achievement. Press Release. European Patent Office. Jun. 21, 2022: 4 pages.
[No Author Listed], Moderna Advances Late-Stage Development of its Vaccine (mRNA-1273) Against COVID-19. Moderna Press Release. Jun. 11, 2020. 3 pages.
[No Author Listed], Moderna and Lonza Announce Worldwide Strategic Collaboration to Manufacture Moderna's Vaccine (mRNA-1273) Against Novel Coronavirus. Moderna Press Release. May 1, 2020. 3 pages.
[No Author Listed], Moderna Announces Award from U.S. Government Agency BARDA for up to $483 Million to Accelerate Development of mRNA Vaccine (mRNA-1273) Against Novel Coronavirus. Moderna Press Release. Apr. 16, 2020. 3 pages.
[No Author Listed], Moderna Announces Expansion of BARDA Agreement to Support Larger Phase 3 Program for Vaccine (mRNA-1273) Against COVID-19. Moderna Press Release. Jul. 26, 2020. 3 pages.
[No Author Listed], Moderna Announces First Participant Dosed in NIH-led Phase 1 Study of mRNA Vaccine (mRNA-1273) Against Novel Coronavirus Moderna Press Release. Mar. 16, 2020. 2 pages.
[No Author Listed], Moderna Announces First Participant Dosed in Phase 2 Study of Omicron-Specific Booster Candidate and Publication of Data on Booster Durability Against Omicron Variant. News Release. Moderna. Jan. 26, 2022: 4 pages.
[No Author Listed], Moderna Announces First Participant Dosed in Phase 2 Study of Omicron-Specific Booster Candidate. News Release. Mar. 10, 2022: 3 pages.
[No Author Listed], Moderna Announces First Participants in Each Age Cohort Dosed in Phase 2 Study of mRNA Vaccine (mRNA-1273) Against Novel Coronavirus. Moderna Press Release. May 29, 2020. 2 pages.
[No Author Listed], Moderna Announces Funding Award from CEPI to Accelerate Development of Messenger RNA (mRNA) Vaccine Against Novel Coronavirus. News Release, Moderna. Jan. 23, 2020: 2 pages.
[No Author Listed], Moderna Announces IND Submitted to U.S. FDA for Phase 2 Study of mRNA Vaccine (mRNA-1273) Against Novel Coronavirus. Moderna Press Release. Apr. 27, 2020. 3 pages.
[No Author Listed], Moderna Announces it has Shipped Variant-Specific Vaccine Candidate, mRNA-1273.351, to NIH for Clinical Study. Moderna Press Release. Feb. 24, 2021. 3 pages.
[No Author Listed], Moderna Announces Phase 3 COVE Study of mRNA Vaccine Against COVID-19 (mRNA-1273) Begins. Moderna Press Release. Jul. 27, 2020. 3 pages.
[No Author Listed], Moderna Announces Positive Interim Phase 1 Data for its mRNA Vaccine (mRNA-1273) Against Novel Coronavirus. Moderna Press Release. May 18, 2020. 3 pages.
[No Author Listed], Moderna Announces Progress Across Broad Portfolio and all Three Clinical Stage Therapeutic Areas at 2020 R&D Day. Moderna Press Release. Sep. 17, 2020. 4 pages.
[No Author Listed], Moderna Announces Publication in The New England Journal of Medicine of Interim Results From Phase 1 Study of Its mRNA Vaccine Against COVID-19 (mRNA-1273). Moderna Press Release. Jul. 14, 2020. 5 pages.
[No Author Listed], Moderna Announces Publication in The New England Journal of Medicine of Non-Human Primate Preclinical Viral Challenge Study of its mRNA Vaccine Against COVID-19 (mRNA-1273). Moderna Press Release. Jul. 28, 2020. 3 pages.
[No Author Listed], Moderna Announces Strategy to Address Omicron (B.1.1.529) SARSCoV-2 Variant. Press Release. Moderna. Nov. 26, 2021: 2 pages.
[No Author Listed], Moderna Announces Supply Agreement with U.S. Government for Initial 100 Million Doses of mRNA Vaccine Against COVID-19 (mRNA-1273). Moderna Press Release. Aug. 11, 2020. 3 pages.
[No Author Listed], Moderna Completes Enrollment of Phase 2 Study of its mRNA Vaccine Against COVID-19 (mRNA-1273). Moderna Press Release. Jul. 8, 2020. 2 pages.
[No Author Listed], Moderna Confirms Advanced Discussions with European Commission to Supply Europe with 80 Million Doses of mRNA Vaccine Against COVID-19 (mRNA-1273). Moderna Press Release. Aug. 24, 2020. 3 pages.
[No Author Listed], Moderna Confirms Discussions with the Ministry of Health, Labour and Welfare to Supply Japan with 40 Million Doses of mRNA Vaccine Against COVID-19 (mRNA-1273). Moderna Press Release. Aug. 28, 2020. 2 pages.
[No Author Listed], Moderna Inc to Discuss Updates on Respiratory Syncytial Virus (RSV) Vaccine Program Call. Edited Transcript. Refinitiv. Oct. 8, 2020: 14 pages.
[No Author Listed], Moderna Patents, retrieved on Jul. 1, 2024, retrieved from URL <https://www.modernatx.com/en-US/patents>, 1 page.

(56) References Cited

OTHER PUBLICATIONS

[No Author Listed], Moderna Provides Business Update and Announces Three New Development Programs in Infectious Disease Vaccines. Press Release. Jan. 11, 2021. 5 pages.
[No Author Listed], Moderna Receives FDA Fast Track Designation for mRNA Vaccine (mRNA-1273) Against Novel Coronavirus. Moderna Press Release. May 12, 2020. 2 pages.
[No Author Listed], Moderna Ships mRNA Vaccine Against Novel Coronavirus (mRNA-1273) for Phase 1 Study. Moderna Press Release. Feb. 24, 2020. 2 pages.
[No Author Listed], Moderna's COVID-19 Vaccine Candidate Meets its Primary Efficacy Endpoint in the First Interim Analysis of the Phase 3 COVE Study. Press Release. Nov. 16, 2020. 3 pages.
[No Author Listed], Moderna's Update Patent Pledge. Press Release. Moderna. Mar. 7, 2022: 2 pages.
[No Author Listed], Nih Clinical Trial of Investigational Vaccine for COVID-19 begins. NIH News Release. Mar. 16, 2020. 3 pages.
[No Author Listed], NIH-Moderna Investigational COVID-19 Vaccine Shows Promise in Mouse Studies. NIH News Release. Aug. 5, 2020. 4 pages.
[No Author Listed], Penn mRNA Scientists Drew Weissman and Katalin Kariko Receive 2021 Lasker Award, America's Top Biomedical Research Prize. Penn News Release. Sep. 24, 2021: 6 pages.
[No Author Listed], Pfizer and BioNTech Announce Early Positive Data from an Ongoing Phase 1/2 Study of mRNA-based Vaccine Candidate against SARS-CoV-2. Press Release. Jul. 1, 2020: 5 pages.
[No Author Listed], Pfizer and BioNTech Announce Early Positive Update from German Phase 1/2 Study of COVID-19 Vaccine Study, Including First T Cell Response Data. Press Release. Jul. 20, 2020: 6 pages.
[No Author Listed], Pfizer and BioNTech Announce Phase 3 Trial Data Showing High Efficacy of a Booster Dose of Their COVID-19 Vaccine. Press Release. Pfizer. Oct. 21, 2021: 10 pages.
[No Author Listed], Pfizer and BioNTech Granted FDA Emergency Use Authorization of OmicronBA.4/BA.5-Adapted Bivalent COVID-19 Vaccine Booster for Ages 12 Years and Older. Pfizer. Aug. 31, 2022: 12 pages.
[No Author Listed], Pfizer and BioNTech Receive Expanded U.S. Emergency Use Authorization for an Additional COVID-19 Vaccine Booster in Individuals Aged 50 Years and Older. Press Release. Pfizer. Mar. 29, 2022: 12 pages.
[No Author Listed], Pfizer and BioNTech Submit Applications to U.S. FDA for Omicron XBB. 1.5-Adapted Monovalent COVID-19 Vaccine. Pfizer. Jun. 23, 2023: 8 pages.
[No Author Listed], Pfizer and BioNTech Submit Supplemental Biologics License Application for U.S. FDA Approval of Omicron BA.4/BA.5-Adapted Bivalent COVID-19 Vaccine for Ages 12 Years and Older as Primary Series or Booster. Pfizer. Feb. 24, 2023: 9 pages.
[No Author Listed], Pfizer Inc to discuss data from an ongoing phase 1/2 study of mRNA-based vaccine candidate against SARS_CoV-2 Call. Edited Transcript. Thomson Reuters. Jul. 1, 2020: 15 pages.
[No Author Listed], Pfizer reports fourth-quarter and full-year 2021 results. Pfizer. Feb. 8, 2022: 41 pages.
[No Author Listed], Pfizer-BioNTech COVID-19 Vaccine Information Sheet. 3 pages.
[No Author Listed], Phase 3 Clinical Trial of investigational Vaccine for COVID-19 Begins. NIH News Release. Jul. 27, 2020. 3 pages.
[No Author Listed], Pioneering Scientists Awarded the Albany Prize, America's Most Distinguished Prize in Medicine, for Research Leading to Covid-19 Vaccines. The Albany Prize. Aug. 26, 2021: 4 pages.
[No Author Listed], Press release, Moderna, "Moderna Announces Publication in The New England Journal of Medicine of Interim Results From Older Adult Age Cohorts in Phase 1 Study of its mRNA Vaccine Against COVID-19 (mRNA-1273)", Sep. 29, 2020. 7 pages.
[No Author Listed], Q2 2020 Earnings Call. BioNTech SE. Aug. 11, 2020 :26 pages.
[No Author Listed], RBC capital Markets Global Healthcare Conference. Pfizer Inc. May 19, 2020: 9 pages.
[No Author Listed], Remarks by President Trump and Members of the Coronavirus Task Force in Meeting with Pharmaceutical Companies. The White House. Mar. 2, 2020: 31 pages.
[No Author Listed], SARS-Co V-2 variants of concern as of May 4, 2023. European Centre for Disease Prevention and Control. Last accessed May 16, 2023 at https://www.ecdc.europa.eu/en/covid-I 9/variants-concern. 7 pages.
[No Author Listed], Severe acute respiratory syndrome coronavirus 2 isolate Wuhan-Hu-I, complete genome. GenBank Accession No. 045512, published on Jul. 18, 2020. 15 pages.
[No Author Listed], Severe acute respiratory syndrome coronavirus 2 isolate Wuhan-Hu-I, complete genome. Genbank Accession No. MN908947.3. Jan. 13, 2020. 15 pages.
[No Author Listed], Spike glycoprotein [Middle East respiratory syndrome coronavirus]. GenBank Accession No. AGN52936.1. Published Jun. 10, 2013. 2 pages.
[No Author Listed], SPIKE_CVHSA. UniProtKB Accession No. P59594. Published Oct. 14, 2015. 1 page.
[No Author Listed], Spikevax (mRNA-1273) EMA SmPC (summary of product characteristics). Published Jan. 20, 2021. 137 pages.
[No Author Listed], Statement by Moderna on Intellectual Property Matters during the COVID-19 Pandemic. Press Release. Moderna. Oct. 8, 2020: 1 page.
[No Author Listed], Statement from NIH and BARDA on the FDA Emergency Use Authorization of the Moderna COVID-19 Vaccines. COVID.gov. Dec. 18, 2020: 3 pages.
[No Author Listed], T7RNAP [Cloning vector pTara:500*]. GenBank Accession No. ATP60600. Nov. 4, 2017. Retrieved on Jan. 19, 2024 from <https:/ /www .ncbi.nlm.nih.gov/protein/ A TP60600. 1?report= genbank&log$=protalign&blast_rank=8&RID=UM61 W 4MM0 16>.
[No Author Listed], Two Pioneering RNA Scientists Win the 2021 Dr. Paul Janssen Award for Biomedical Research. Press Release. Johnson & Johnson. Sep. 28, 2021: 2 pages.
[No Author Listed], User Guide for mMessage mMachine T7 Kit from Ambion. 2012. p. 1-36.
[No Author Listed], Vaccine information fact sheet for recipients and caregivers about Comirnaty (COVID-19 Vaccine, mRNA) and the Pfizer-BioNTech COVID-19 vaccine to prevent coronavirus disease 2019 (COVID-19) for use in individuals 12 years of age and older. Jul. 8, 2022: 9 pages.
[No Author Listed], Who Drug Information, vol. 35, No. 2, 2021, 341 pages.
[No Author Listed], Who Drug Information. 2021;35(2):578-9.
[No Author Listed], World Health Organization. 2021. Classification of Omicron(B.1.1.529): SARS-Co-V-2 Variant of Concern. Nov. 26, 2021. 3 pages.
[No Author Listed]. Reflection paper on the regulatory requirements for vaccines intended to provide protection against variant strain(s) of SARS-CoV-2. European Medicines Agency. EMA/117973/2021. Feb. 23, 2021. 7 pages.
Aartse et al., Influenza A Virus Hemagglutinin Trimer, Head and Stem Proteins Identify and Quantify Different Hemagglutinin-Specific B Cell Subsets in Humans. Vaccines (Basel). Jul. 2, 2021;9(7):717. doi: 10.3390/vaccines9070717.
Abbasi, COVID-19 and mRNA Vaccines-First Large Test for a New Approach. JAMA. Sep. 22, 2020;324(12):1125-1127. doi: 10.1001/jama.2020.16866.
Adney et al., Efficacy of an Adjuvanted Middle East Respiratory Syndrome Coronavirus Spike Protein Vaccine in Dromedary Camels and Alpacas. Viruses. Mar. 2, 2019;11(3). pii: E212. doi: 10.3390/vl 1030212.
Agnihothram, S., Review Committee Chair, Summary Basis for Regulatory Action, 2022, STN 125752/0 (30 Pages).
Agrawal et al., "Immunization with inactivated Middle East Respiratory Syndrome coronavirus vaccine leads to lung immunopathology on challenge with live virus," Human Vaccine Immunotherapy, Sep. 2016, vol. 12, No. 9 (pp. 2351-2356).

(56) References Cited

OTHER PUBLICATIONS

Ahmad et al., "New multivalent cationic lipids reveal bell curve for transfection efficiency versus membrane charge density: lipid-DNA complexes for gene delivery," 2005, J. Gene Med., pp. 739-748.
Ahmed et al., Biochemistry, Lipids, Statpearls Publishing (2023) (available at https://www.ncbi.nlm.nih.gov/books/NBK525952/).
Akinc et al., "Targeted Delivery of RNAi Therapeutics With Endogenous and Exogenous Ligand-Based Mechanisms," Molecular Therapy, Jul. 2010, vol. 18, No. 7 (1357-1364).
Akinc, et al., "A combinatorial library of lipid-like materials for delivery of RNAi therapeutics," Nature Biotechnology, Apr. 27, 2008, vol. 26, pp. 561-569 (with supplemental content).
Al Kahlout et al., Comparative Serological Study for the Prevalence of Anti-MERS Coronavirus Antibodies in High- and Low-Risk Groups in Qatar. J Immunol Res. Feb. 18, 2019;2019: 1386740. doi: 10.1155/2019/1386740. eCollection 2019.
Alberer et al., "Safety and immunogenicity of a mRNA rabies vaccine in healthy adults: an open-label, non-randomised, prospective, first-in-human phase 1 clinical trial," Lancet, Sep. 23, 2017, 390:1511-1520.
Aleku, M., et al., Atu027, a liposomal small interfering RNA formulation targeting protein kinase N3, inhibits cancer progression. Cancer Res. 2008; 68: 9788-9798.
Alfonso et al., An Anti-Idiotype Vaccine Elicits a Specific Response to N-Glycolyl Sialic Acid Residues of Glycoconjugates in Melanoma Patients, The Journal of Immunology, 2002, vol. 168, pp. 3523-2529.
Aliprantis et al., "A phase 1, randomized, placebo-controlled study to evaluate the safety and immunogenicity of an mRNA-based RSV prefusion F protein vaccine in healthy younger and older adults," Hum Vaccin Immunother. May 4, 2021, vol. 17, No. 5 (pp. 1248-1261).
Allen et al., "Liposomal drug delivery systems: From concept to clinical applications," Advanced Drug Delivery Reviews, Jan. 2013, vol. 65 (pp. 36-48).
*Alnylam Pharmaceuticals, Inc.* v. *Moderna, Inc.* (Fed. Circ. 2023-2357) D.I. 8—Docketing Statement. Sep. 21, 2023. 2 pages.
*Alnylam Pharmaceuticals, Inc.* v. *Moderna, Inc. et al* (D. Del. 23-cv-580-CFC) D.I. 1—Complaint for Patent Infringement, May 26, 2023. 28 pages.
*Alnylam Pharmaceuticals, Inc.* v. *Moderna, Inc. et al* (D. Del. 23-cv-580-CFC) D.I. 12—Answer to the Complaint, Jul. 17, 2023. 37 pages.
*Alnylam Pharmaceuticals, Inc.* v. *Moderna, Inc. et al.* (D. Del. 22-cv-335-CFC) D.I. 1—Complaint for Patent Infringement, Mar. 17, 2022. 14 pages.
*Alnylam Pharmaceuticals, Inc.* v. *Moderna, Inc. et al.* (D. Del. 22-cv-335-CFC) D.I. 128—Final Judgement, Aug. 30, 2023. 2 pages.
*Alnylam Pharmaceuticals, Inc.* v. *Moderna, Inc. et al.* (D. Del. 22-cv-335-CFC) D.I. 130—Notice of Appeal to the U.S. Court of Appeals for the Federal Circuit, Aug. 31, 2023. 3 pages.
*Alnylam Pharmaceuticals, Inc.* v. *Moderna, Inc. et al.* (D. Del. 22-cv-335-CFC) D.I. 87—Answer to the Complaint, May 10, 2023. 44 pages.
Altieri et al., The influence of 4-thiouridine labeling on pre-mRNA splicing outcomes. PLoS One. Dec. 13, 2021;16(12):e0257503. doi: 10.1371/journal.pone.0257503. eCollection2021.
Anderson et al. The Bridge, National Academy Of Engineering of the National Academies, Fall 2006, vol. 36., No. 3, pp. 1-60.
Anderson et al., "Incorporation of pseudouridine into mRNA enhances translation by diminishing PKR activation," Nucleic Acids Research, 2010, vol. 38, No. 17., pp. 5884-5892.
Anderson et al., "Safety and Immunogenicity of SARS-COV-2 mRNA-1273 Vaccine in Older Adults," The New England Journal of Medicine, vol. 38, Issue 25, pp. 2427-2438 (2020) doi: 10.1056/NEJMoa2028436.
Anderson et al., Nucleoside modifications in RNA limit activation of 2'-5'-oligoadenylate synthetase and increase resistance to cleavage by Rnase L. Nucleic Acids Res. 2011; 39(21), pp. 1-10.
Anderson, D.M. et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.
Andrews-Pfannkoch, C. et al., Hydroxyapatite-mediated separation of double-stranded DNA, single-stranded DNA, and RNA genomes from natural viral assemblages. Appl Environ Microbiol. Aug. 2010;76(15):5039-45. Epub Jun. 11, 2010.
Andries et al., "N(1)-methylpseudouridine-incorporated mRNA outperforms pseudouridine-incorporated mRNA by providing enhanced protein expression and reduced immunogenicity in mammalian cell lines and mice," Journal of Controlled Release, Nov. 10, 2015, vol. 217 (pp. 337-344).
Andries, O., et al., Comparison of the gene transfer efficiency of mRNA/GL67 and pDNA/GL67 complexes in respiratory cells. Mol Pharmaceutics. 2012; 9: 2136-2145.
Apostolopoulos, V. et al., Cellular mucins: targets for immunotherapy. Crit Rev Immunol. 1994; 14(3-4):293-309.
*Arbutus BioPharma Corp. et al.* v. *Moderna, Inc. et al.* (D. Del. 22-cv-252-MSG) D.I. 1—Complaint for Patent Infringement, Feb. 28, 2022. 51 pages.
*Arbutus BioPharma Corp. et al.* v. *Moderna, Inc. et al.* (D. Del. 22-cv-252-MSG) D.I. 31—District Court Memorandum, Nov. 2, 2022. 16 pages.
*Arbutus BioPharma Corp. et al.* v. *Moderna, Inc. et al.* (D. Del. 22-cv-252-MSG) D.I. 35—Answer to the Complaint, Nov. 30, 2022. 83 pages.
*Arbutus BioPharma Corp. et al.* v. *Moderna, Inc. et al.* (D. Del. 22-cv-252-MSG) D.I. 64—District Court Memorandum, Mar. 10, 2023. 4 pages.
Archer, S.J., Induction of a T-cell specific antigen on bone marrow lymphocytes with thymus RNA. Immunology. Jan. 1978;34(1):123-39.
Arthur, Pfizer predicts $54bn in 2022 revenue from Comirnaty and Paxlovid. BioPharmaReporter. Feb. 8, 2022: 2 pages.
Ashley, D.M. et al., "Bone marrow-generated dendritic cells pulsed with tumor extracts or tumor RNA induce antitumor immunity against central nervous system tumors." J. Exp. Med. Oct. 6, 1997; 186(7): 1177-82.
Ast, "How did alternative splicing evolve?" Nat Rev Genet. Oct. 2004;S(10):773-82.
Atkins et al., "The molecular pathogenesis of Semliki Forest virus: a model virus made useful?," Journal of General Virology 2287, 1999 (11 Pages).
Atsmon et al., Safety and immunogenicity of multimeric-001—a novel universal influenza vaccine. J Clin Immunol. Jun. 2012;32(3):595-603. doi: 10.1007/s10875-011-9632-5. Epub Feb. 9, 2012.
Aurup et al. "Translation of 2'-modified mRNA in vitro and in vivo," Nucleic Acids Research, 1994, vol. 22, No. 23 (pp. 4963-4968).
Ausar et al., High-throughput screening of stabilizers for respiratory syncytial virus: identification of stabilizers and their effects on the conformational thermostability of viral particles. Hum Vaccin. May-Jun. 2007:3(3):94-103. Epub May 15, 2007.
Austin et al., Split-Dose Administration Enhances Immune Responses Elicited by a mRNA/Lipid Nanoparticle Vaccine Expressing Respiratory Syncytial Virus F Protein. Mol. Pharm. Jan. 2, 2023;20(1):279-289. doi: 10.1021/acs.molpharmaceut.2c00635. Epub Oct. 17, 2022.
Baars et al., A Phase II Study of Active Specific Immunotherapy and 5-FU/Leucovorin as Adjuvant Therapy For Stage III Colon Carcinoma, British Journal of Cancer, 2002, vol. 86, No. 8, pp. 1230-1234.
Baden et al., "Efficacy and safety of the mRNA-1273 SARS-CoV-2 vaccine," N. Engl. J. Med, vol. 384, No. 5, 403-416 (2021).
Badis et al., A snoRNA that guides the two most conserved pseudouridine modifications, within rRNA confers a growth advantage in yeast. RNA. Jul. 2003; 9(7): 771-779.
Bahl, et al., "Preclinical and clinical demonstration of immunogenicity by mRNA vaccines against H10N8 and H7N9 influenza viruses," Molecular Therapy, American Society of Gene & Cell Therapy, Jun. 2017, vol. 25, No. 6 (pp. 1316-1327).

(56) References Cited

OTHER PUBLICATIONS

Baker et al., RNA-guided RNA-modification: functional organization of the archaeal H/ACA RNP. Genes Dev. May 15, 2005;19(10):1238-48. Epub May 3, 2005.
Bancel, Our Global Commitment to Vaccine Access. Moderna. Oct. 8, 2021: 1 page.
Bangham et al., Diffusion of univalent ions across the lamellae of swollen phospholipids. J Mol. Biol. Aug. 1965; 13(1):238-52. doi: 10.1016/s0022-2836(65)80093-6.
Barbier et al., "The clinical progress of mRNA vaccines and irnrnunotherapies," Nat Biotechnol. Jun. 2022;40(6):840-854. doi: 10.1038/s41587-022-01294-2. Epub May 9, 2022. Article XP03789781.
Barbier et al., "The clinical progress of mRNA vaccines and immunotherapies," Nature Biotechnology, Jun. 2022, 40(6):840-54.
Barr et al., "Epidemiological, antigen and genetic characteristics of seasonal influenza A(H1N1), A(H3N2) and B influenza viruses: basis for the WHO recommendation on the competition of influenza vaccines for using in the 2009-2010 northern hemisphere season." 2010, Vaccine, 28(5), 1156-1167. https://doi.org/10.1016/j.vaccine.2009.11.043.
Basarkar et al., "Nanoparticulate systems for polynucleotide delivery." International journal of nanomedicine, 2(3), 353-360.
Basha et al., "Influence of cationic lipid composition on gene silencing properties of lipid nanoparticle formulations of siRNA in antigen-presenting cells," Molecular Therapy, Dec. 2011, vol. 19, No. 12 (pp. 2186-2200).
Bauman et al., "Safety, tolerability, and immunogenicity of mRNA-4157 in combination with pembrolizumab in subjects with unresectable solid tumors (KEYNOTE-603): An update." J Immunother Cancer. 2020;8(Suppl 3):A477. https:/ /jitc.bmj.com/content/8/Suppl_3/A477.1.
Bear, "Gene expression and regulation," Lewin's Cells, 2011, Chapter 4:105-68.
Belliveau, N.M., et al., Microfluidic synthesis of highly potent limit-size lipid nanoparticles for in vivo delivery of siRNA. Mol Ther Nucleic Acids. Aug. 20, I2; I(8): e37.
Bennett et al., Cholesterol enhances cationic liposome-mediated DNA transfection of human respiratory epithelial cells. Biosci. Rep. Feb. 1995; 15(1):47-53. doi: 10.1007/BF01200214.
Bentebibel et al., "ICOS(+)PD-1(+)CXCR3(+) T follicular helper cells contribute to the generation of high-avidity antibodies following influenza vaccination." 2016, Scientific Reports, 6, 26494. https://doi.org/10.1038/srep26494.
Berkeley Lovelace Jr. & Noah Higgins-Dunn, Dr. Anthony Fauci says chance of coronavirus vaccine being highly effective is 'not great', CNBC.com (last updated Aug. 8, 2020), https://www.cnbc.com/2020/08/07/coronavirus-vaccine-dr-fauci-says-chances-of-it-being-highly-effective-is-not-great.html.
Bermudez, "We decided not to enforce our patent during the pandemic": Noubar Afeyan, cofounder of Moderna. BBC News World. May 6, 2021: 11 pages.
Bernstein, P. et al., Poly(A), poly(A) binding protein and the regulation of mRNA stability. Trends Biochem Sci. Sep. 1988;14(9):373-7.
Bettinger, T. et al, Peptide-mediated RNA delivery: a novel approach for enhanced transfection of primary and past-mitotic cells. Nucleic Acids Res. Sep. 15, 2001;29(18):3882-91.
Bevilacqua, A. et al., Post-transcriptional regulation of gene expression by degradation of messenger RNAs. J Cell Physiol. Jun. 2003;195(3):356-72.
Bharali et al., "Nanoparticles and cancer therapy: A concise review with emphasis on dendrimers," 2009, Int J Nanomedicine, 2009; 4: 1-7.
Bhavana et al., "COVID-19: Pathophysiology, treatment options, nanotechnology approaches, and research agenda to combating the SARS-CoV2 pandemic" Life Sci., 2020, vol. 261, Article 118336. doi: 10.1016/j.lfs.2020.118336.
Biopharma, Palivizumab—Synagis; MEDI-493; respiratory syncytial virus (RSV) monoclonal antibody, recombinant, Sample Synagis, Medlmmnune, Inc., 2013, No. vol. pp. 1-19.
Bisht et al., "Severe acute respiratory syndrome coronavirus spike protein expressed by attenuated vaccinia virus protectively immunizes mice," 2004, Biological Sciences (6 Pages).
Bloom et al., Self-amplifying RNA vaccines for infectious diseases. Gene Ther. Apr. 2021;28(3-4): 117-129. doi: 10.1038/s41434-020-00204-y. Epub Oct. 22, 2020.
Blumenthal et al., Q beta replicase template specificity: different templates require different GTP concentrations for initiation. Proc Natl Acad Sci US A. May 1980;77(5):2601-5. doi: 10.1073/pnas.77.5.2601.
Boczkowski et al., "Induction of Tumor Immunity and Cytotoxic T Lymphocyte Responses Using Dendritic Cells Transfected with Messenger RNA Amplified from Tumor Cells," Cancer Research, Feb. 15, 2000, vol. 60 (pp. 1028-1034).
Boehm et al., "Programmed emergence of a domain of gene expression in a bacterial population," 2016, GenBank: ATP60600.1, https://www.ncbi.nlm.nih.gov/protein/ATP60600.1?report=genbank&log$=protalign&blast_rank=8&RID=UM61W4MM016.
Bogers et al., Potent immune responses in rhesus macaques induced by nonviral delivery of a self-amplifying RNA vaccine expressing HIV type 1 envelope with a cationic nanoemulsion. J. Infect. Dis. Mar. 15, 2015; 211(6):947-55. doi: 10.1093/infdis/jiu522. Epub Sep. 18, 2014.
Boheemen et al., "Genomic characterization of a newly discovered coronavirus associated with acute respiratory distress syndrome in humans," 2012, MBIO, Article e00473.
Bolhassani et al., Improvement of Different Vaccine Delivery Systems for Cancer Therapy, Molecular Cancer, Biomed Central, London, GB, 2011 vol. 10, No. 3, pp. 1-20.
Bommakanti et al., "Design of an HA2-based *Escherichia coli* expressed influenza immunogen that protects mice from pathogenic challenge." Proc Natl Acad Sci US A. Aug. 3, 2010;107(31):13701-6. doi: 10.1073/pnas.1007465107. Epub Jul. 6, 2010.
Bonehill, A., et al., Single-step antigen loading and activation of dendritic cells by mRNA electroporation for the purpose of therapeutic vaccination in melanoma patients. Clin. Cancer. Res. May 2009; 15(10): 3366-3375.
Bose et al., Influence of cationic lipid concentration on properties of lipid-polymer hybrid nanospheres for gene delivery. Int J Nanomedicine. Sep. 2, 2015:10:5367-82. doi: 10.2147;1JN.S87120. eCollection 2015.
Bose et al., "Role of nucleolin in human parainfluenza virus type 3 infection of human lung epithelial cells," Journal of Virology, Aug. 2004, vol. 78, No. 15 (pp. 8146-8158).
Bouloy, M., et al., "Both the 7-methyl and the 2'-O-methyl groups in the cap of mRNA strongly influence its ability to act as primer for influenza virus RNA transcription." Proceedings of the National Academy of Sciences of the United States of America, vol. 77, Issue 7, 3952-3956. https://doi.org/10.1073/pnas.77.7.3952.
Bourla, "An Open Letter from Pfizer Chairman and CEO to Colleagues," 2021, Pfizer (3 Pages).
Bowie et al., "Deciphering the Message in Protein Sequences: Tolerance to Amino Acid Substitutions", Science, vol. 247, No. 4948, Mar. 16, 1990, pp. 1306-1310.
Brandenburg et al., Mechanisms of Hemagglutinin Targeted Influenza Virus Neutralization, PLOS One, 2013, vol. 8, Issue 12, pp. 1-14.
Brennan, Ribonucleoside triphosphate concentration-dependent termination of bacteriophage SP01 transcription in vitro by Bacillus subtilis RNA polymerase. Virology Jun. 1984;135(2):555-60. doi: 10.1016/0042-6822(84)90211-3.
Brito et al, Self-Amplifying mRNA Vaccines, Adv Genet, vol. 89, 2014, p. 179-233.
Brito et al., "A Cationic Nanoemulsion for the Delivery of Next-generation RNA Vaccines," Molecular Therapy, vol. 22, No. 12, 2118-2129, Dec. 2014.
Brown, Genomes. 2002. 2nd Edition. Oxford: Wiley-Liss. p. 1-20.
Bruxvoort et al., "Real-world effectiveness of the mRNA-1273 vaccine against COVID-19: Interim results from a prospective observational cohort study," 2022, Lancet Reg Health Am, Article 100134 doi: 10.1016/j.lana.2021.100134.

(56) References Cited

OTHER PUBLICATIONS

Buchholz et al., "Contributions of the structural proteins of severe acute respiratory syndrome coronavirus to protective immunity," 2004, vol. 101, Issue 26, Biological Sciences.
Burke et al., Formulation, stability, and delivery of live attenuated vaccines for human use. Crit Rev Ther Dmg Carrier Syst. 1999; 16(1):1-83.
Buschmann et al., "Nanomaterial Delivery Systems for mRNA Vaccines," 2021, Vaccines, vol. 9, Issue 1, p. 65. doi: 10.3390/vaccines9010065.
Buschmann et al., "Chitosans for Delivery of Nucleic Acids," 2013, Advanced Drug Delivery Reviews, pp. 1234-1270.
Callaway, "Omicron likely to weaken COVID vaccine protection," 2021, Nature, vol. 600, Issue 7889, pp. 367-368. doi: 10.1038/d41586-021-03672-3.
Cannon, G. et al., RNA based vaccines. DNA Cell Biol. Dec. 2002;21(12):953-61.
Carralot, J.P. et al., Polarization of immunity induced by direct injection of naked sequence-stabilized MRNA vaccines. Cell Mal Life Sci. Sep. 2004;61 (18):2418-24.
Carvalho et al., The first 12 months of COVID-19: a timeline of immunological insights. Nat Rev Immunol. Apr. 2021;21(4):245-256. doi: 10.1038/s41577-021-00522-1. Epub Mar. 15, 2021.
Cassimeris et al., "Lewin's Cells, Second Edition" 2011, Jones and Bartlett Publishers, 109 Pages.
Cele et al., "SARS-Co V-2 Omicron has extensive but incomplete escape of Pfizer BNT162b2 elicited neutralization and requires ACE2 for infection," 2021, medRxiv, doi: 10.1101/2021.12.08.21267417. 2021.12.08.21267417. 15 pages.
Center for Drug Evaluation and Research Approval Package for New Drug Application No. 50-718/S-50 for Doxil, Approved Dec. 28, 2015 (97 Pages).
Cerutti et al., Potent SARS-Co V-2 neutralizing antibodies directed against spike N-terminal domain target a single supersite. Cell Host Microbe. May 12, 2021;29(5):819-833.e7. doi: 10.1016/j.chom.2021.03.005. Epub Mar. 12, 2021.
Chalkias et al., "Safety, immunogenicity and antibody persistence of a bivalent Beta-containing booster vaccine against COVID-19: a phase 2/3 trial," 2022, Nature Medicine, pp. 2388-2397.
Chan et al., "Genomic characterization of the 2019 novel human-pathogenic coronavirus isolated from a patient with atypical pneumonia after visiting Wuhan," 2020, Emerg Microbes Infect, vol. 9, Issue 1, pp. 221-236. doi: 10.1080/22221751.2020.1719902.
Chang et al., Recent Insights into the Developments of Therapeutics Against Coronavirus Disease by Targeting N Protein, 2016, Drug Discovery Today, No. 4, pp. 562-572.
Charette, M. et al., Pseudouridine in RNA: what, where, how, and why. IUBMB Life. 2000, May:49(5):341-51.
Chaudhary et al., "mRNA vaccines for infectious diseases: principles, delivery and clinical translation." Nat Rev Drug Discov. Nov. 2021;20(11):817-838. doi: 10.1038/s41573-021-00283-5. Epub Aug. 25, 2021. Erratum in: Nat Rev Drug Discov. Sep. 21, 2021.
Chen et al., "A flexible RNA backbone within the polypyrimidine tract is required for U2AF65 binding and pre-mRNA splicing in vivo." 2010, Molecular and cellular biology, 30(17), 4108-4119. https://doi.org/10.1128/MCB.00531-10.
Chen et al., "A novel neutralizing monoclonal antibody targeting the N-terminal domain of the MERS-Co V spike protein," 2017, Emerg Microbes Infect, vol. 6, Issue 6, Article e6, doi: 10.1038/emi.2017.50.
Chen et al., "Emerging coronaviruses: Genome structure, replication, and pathogenesis," 2020, J Med Virol., vol. 92, Issue 4, pp. 418-423. doi: 10.1002/jmv.25681.
Chen et al., "Human monoclonal antibodies targeting the haemagglutinin glycoprotein can neutralize H7N9 influenza virus." 2015, Nature communications, 6, 6714. https://doi.org/10.1038/ncomms7714.
Chen et al., "Influence of particle size on the in vivo potency of lipid nanoparticle formulations of siRNA," 2016, Journal of Controlled Release, Elsevier, vol. 235, pp. 236-244, XP029633339, ISSN: 0168-3659, DOI: 10.1016/J.JCONREL.2016.05.059.
Chen et al., "Receptor-binding domain of SARS-Cov spike protein: Soluble expression in *E. coli*, purification and functional characterization," World J. Gastroenterol., Oct. 21, 2005, 11(39):6159-6164.
Chen et al., "Vaccination of Monoglycosylated Hemagglutinin Induces Cross-Strain Protection Against Influenza Virus Infection," PNAS, 2013, vol. 111, No. 7, pp. 1-6.
Chen et al., "Vaccine design of hemagglutinin glycoprotein against influenza," 2011, Trends Biotechnol, vol. 9, pp. 426-434, doi: 10.1016/j.tibtech.2011.04.007.
Chen et al., Clinical and epidemiological characteristics of a fatal case of avian influenza A HI0N8 virus infection: a descriptive study. Lancet. Feb. 22, 2014;383(9918):714-21. doi: 10.1016/S0140-6736(14)601 11-2.
Chen et al., Gold-loading magnetic core-shell organic/inorganic nanocomposites: Facile preparation and multiple properties. Polymers for Advanced Technologies. Jun. 17, 2014;25(9): 1069-76.
Chen, Z. et al., Enhanced protection against a lethal influenza virus challenge by immunization with both hemagglutinin- and neuraminidase-expressing DNAs. Vaccine. Feb. 26, 1999; 17(7-8):653-9.
Cheng et al., "Selective Organ Targeting (SORT) nanoparticles for tissue specific mRNA delivery and CRISPR/Cas gene editing," 2020, Nat Nanotechnol., vol. 15 Issue 4, pp. 313-320.
Cheng, C., et al., Multifunctional triblock copolymers for intracellular messenger RNA delivery. 2012, Biomaterials, 33(28), 6868-6876. https://doi.org/10.1016/j.biomaterials.2012.06.020.
Cheng, W.F. et al., Enhancement of sindbis virus self-replicating RNA vaccine potency by linkage of herpes simplex virus type 1 VP22 protein to antigen. Journal of virology, 75(5), 2368-2376. https://doi.org/10.1128/JVI.75.5.2368-2376.2001.
Cherry et al., "SARS: The First Pandemic of the 21st Century," 2004, Pediatric Research, vol. 56, Issue 1, pp. 1-5.
Chi et al., "A neutralizing human antibody binds to the N-terminal domain of the Spike protein of SARS-CoV-2," 2020, Science, vol. 369, Issue 6504, pp. 650-655. doi: 10.1126/science.abc6952.
Chinnakannan et al., The Design and Development of a Multi-HBV Antigen Encoded in Chimpanzee Adenoviral and Modified Vaccinia Ankara Viral Vectors; A Novel Therapeutic Vaccine Strategy against HBV. Vaccines (Basel). Apr. 14, 2020;8(2):184. doi: 10.3390/vaccines8020184.
Cho et al., The PurR regulon in *Escherichia coli* K-12 MG1655. Nucleic Acids Res. Aug. 2011;39(15):6456-64. doi: 10.1093/nar/gkr307. Epub May 13, 2011.
Choi et al., "2'-O-methylation in mRNA disrupts tRNA decoding during translation elongation," Nature Structural & Molecular Biology, Mar. 2018, vol. 25, No. 3 (pp. 208-216).
Choi et al., Safety and immunogenicity of SARS-CoV-2 variant mRNA vaccine boosters in healthy adults: an interim analysis. Nat Med. Nov. 2021;27(11):2025-2031. doi: 10.1038/s41591-021-01527-y. Epub Sep. 15, 2021.
Choi et al., Serum Neutralizing Activity of mRNA-1273 against SARS-CoV-2 Variants, J. Virol. Nov. 9, 2021;95(23):e0131321. doi: 10.1128/JVI.01313-21. Epub Sep. 22, 2021.
Chu et al., "Immune Memory Response After a Booster Injection of mRNA-1273 for Severe Acute Respiratory Syndrome Coronavirus-2 (SARS-CoV-2)," 2021, MedRxiv, doi: https://doi.org/10.1101/2021.09.29.21264089 (52 Pages).
Clancy et al., "Translation: DNA to mRNA to Protein," 2008, Nature Education 2008, vol. 1, Issue 1, p. 101 (https://www.nature.com/scitable/topicpage/translation-dna-to-mrna-to-protein-393/).
Clinical trial NCT04528719: A Dose Escalation Study to Evaluate Safety, Reactogenicity, and Immunogenicity of mRNA-1345 in Healthy Adults and in Children Who Are Respiratory Syncytial Virus Seropositive (ModernaTX, Inc.) First Posted Aug. 27, 2020. Retrieved online on Mar. 15, 2021 at https://www.clinicaltrials.gov/ct2/show/NCT04528719=term=NCT04528719&draw=2&rank=1.
Cobb, M., "Who discovered messenger RNA?," 2015, Curr. Biol. Jun. 29, 2015;25(13): R526-32. doi: 10.1016/j.cub.2015.05.032.
Coelho et al., "Safety and Efficacy of RNAi Therapy for Transthyretin Amyloidosis," 2013, vol. 369, Issue 9, New England J. Med. (11 Pages).

(56) References Cited

OTHER PUBLICATIONS

Cohen, New crop of mRNA vaccines aim for accessibility. Science. Apr. 8, 2022;376(6589):120-121. doi: 10.1126/science.abq3935. Epub Apr. 7, 2022.
Cohen, Scientists are moving at record speed to create new coronavirus vaccines—but they may come too late. Science Insider. Jan. 27, 2020. 6 pages.
Cohen, Scientists question Moderna invention claim in COVID-19 vaccine dispute. Science Insider. Aug. 29, 2022: 3 pages.
Colter J.S., et al., "Infectivity of ribonucleic acid isolated from virus-infected tissues." Virology. 1957: 4(3): 522-532.
Comirnaty, "Highlights of Prescribing Information," FDA Label, Jul. 2022, 27 pages.
Comirnaty, "Highlights of Prescribing Information," FDA Label, Oct. 2023, 36 pages.
Comirnaty, "Highlights of Prescribing Information," FDA Label, Oct. 2024, 37 pages.
Condon, C., et al., DNA-based immunization by in vivo transfection of dendritic cells. Nature medicine, 2(10), 1122-1128. https://doi.org/10.1038/nm1096-1122.
Conry et al., Characterization of a messenger RNA polynucleotide vaccine vector. Cancer Res. Apr. 1, 1995 ;55 (7):1397-1400.
Corbett et al., Evaluation of the mRNA-1273 Vaccine against SARS-CoV-2 in Nonhuman Primates. N Engl J Med 2020; 383: 1544-55. doi: 10.1056/NEJMoa2024671.
Corbett et al., SARS-CoV-2 mRNA vaccine design enabled by prototype pathogen preparedness. Nature. Oct. 2020;586(7830):567-571. doi: 10.1038/s41586-020-2622-0. Epub Aug. 5, 2020.
Cosman et al., "ULBPs, Novel MHC class I-Related Molecules, Bind to CMV glycoprotein UL16 and Stimulate NK Cytotoxicity through the NKG2D Receptor." 2001, Immunity, 14(2), 123-133. https://doi.org/10.1016/s1074-7613(01)00095-4.
Cowling V. H. (2009). Regulation of mRNA cap methylation. The Biochemical journal, 425(2), 295-302. https://doi.org/10.1042/BJ20091352.
Cox et al., "FluBlok, a recombinant hemagglutinin influenza vaccine," Protein Sciences Corp, Journal Compilation, Influenza and Other Respiratory Viruses, 2, 211-219, 2008.
Cross et al., Can mRNA disrupt the drug industry? C&EN, 2018: 96(35);35-40.
Cross, "Without these lipid shells, there would be no mRNA vaccines for COVID-19," Chem Eng News. Mar. 6, 2021; 99(8). 8 pages.
Cu et al., Enhanced Delivery and Potency of Self-Amplifying mRNA Vaccines by Electroporation in Situ, Vaccines, 2013, 1, 367-383. Abstract Only.
Cuburu. N. et al., Intravaginal immunization with HPV vectors induces tissue-resident CDS+ T cell responses. J Clin In vest. Dec. 3, 2012; 122(12): 4606-4620.
Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.
Cunningham et al., The cycle of human herpes simplex virus infection: virus transport and immune control. J Infect Dis. Sep. 15, 2006; 194 Suppl 1:SI 1-8. doi: 10.1086/505359.
Curriculum Vitae of Daniel O. Griffin, M.D., Ph.D., 2023, 22 pages.
Curriculum Vitae of Deborah Fuller (Deposition Exhibit), filed in IPR2023-01359 on Aug. 30, 2024, 2 pages.
Curriculum Vitae of James J. Moon, Ph.D., filed in IPR2023-01359 on Aug. 28, 2023, 28 pages.
Dahlman et al., "In vivo endothelial siRNA delivery using polymeric nanoparticles with low molecular weight," Nature Nanotechnology, 2014, vol. 9 (pp. 648-655).
Dai et al., "Viral targets for vaccines against COVID-19," Nat Rev Immunol., 2021, vol. 21, Issue 2, pp. 73-82, doi: 10.1038/s41577-020-00480-0. Epub Dec. 18, 2020.
Dai et al., Viral targets for vaccines against COVID-19. Nat Rev Immunol. Feb. 2021;21(2):73-82. doi: 10.1038/s41577-020-00480-0. Epub Dec. 18, 2020.
Daniels et al., Influenza Virus Characterisation, Surveillance report, Summary Europe, Jul. 2012 (11 pages).
Dankova et al., Synthesis of the alkaloid arecoline, the active constituent of betel nuts. CAPLUS Database. Database Accession No. 1943:2081. Jan. 1, 1941. 1 page.
Davis, D.R. Stabilization of RNA stacking by pseudouridine. Nucleic Acids Res. 1995; 23(24): 5020-5026.
De Jong et al., Drug delivery and nanoparticles: applications and hazards. Int J Nanomedicine. 2008;3(2): 133-49.
De Marco, D., et al., "A non-VH1-69 heterosubtypic neutralizing human monoclonal antibody protects mice against H1N1 and H5N1 viruses." 2012, PloS one, 7(4), e34415. https://doi.org/10.1371/journal.pone.0034415.
De Pooter et al., mRNA Therapeutic Vaccine for Hepatitis B Demonstrates Immunogenicity and Efficacy in the AA V-HBV Mouse Model. Vaccines (Basel). Feb. 25, 2024;12(3):237. doi: 10.3390/vaccines 12030237.
Dean et al., Rapid amplification of plasmid and phage DNA using Phi29 DNA polymerase and multiply-primed rolling circle amplification, Genome Research, 2001, vol. 11 (pp. 1095-1099).
Decision of the Regional Court of Dusseldorf concerning EP 3718565 B1 decided on Oct. 31, 2022.
Declaration of Daniel O. Griffin, M.D., Ph.D. in IPR2023-01358 dated Aug. 27, 2023.
Declaration of Daniel O. Griffin, M.D., Ph.D. in IPR2023-01359 dated Aug. 27, 2023.
Declaration of Deborah H. Fuller, Ph.D., in IPR2023-01358 dated May 30, 2024 (public redacted version of Ex. 2199).
Declaration of Deborah H. Fuller, Ph.D., in IPR2023-01359 dated May 30, 2024. (public redacted version of Ex. 2199).
Declaration of Douglas L. Sawyer in IPR2023-01358 dated Jul. 17, 2024.
Declaration of Douglas L. Sawyer in IPR2023-01359 dated Jul. 17, 2024.
Declaration of Gabrielle Landes in IPR2023-01358 dated Apr. 25, 2024.
Declaration of Gabrielle Landes in IPR2023-01359 dated Apr. 25, 2024.
Declaration of James E. Malackowski in IPR2023-01358 dated May 29, 2024.
Declaration of James E. Malackowski in IPR2023-01359 dated May 29, 2024.
Declaration of James J. Moon, Ph.D. in IPR2023-01358 dated Apr. 25, 2023.
Declaration of James J. Moon, Ph.D. in IPR2023-01359 dated Apr. 25, 2023.
Declaration of Kathryn S. Kayali in IPR2023-01358 dated Apr. 16, 2024.
Declaration of Kathryn S. Kayali in IPR2023-01359 dated Apr. 26, 2024.
Declaration of L. Ross Pierce in IPR2023-01358 dated Aug. 30, 2024 (Redacted public version).
Declaration of L. Ross Pierce in IPR2023-01359 dated Aug. 30, 2024. (Redacted public version).
Declaration of M. Ryan Meuth in IPR2023-01358 dated Apr. 25, 2024.
Declaration of M. Ryan Meuth in IPR2023-01359 dated Apr. 25, 2024.
Declaration of Philp Krause, M.D., in IPR2023-01359 dated May 28, 2024. (public redacted version of Ex. 2200).
Declaration of Philp Krause, M.D., in IPR2023-01358 dated May 28, 2024. (public redacted version of Ex. 2200).
Declaration of Thomas H. L. Selby in IPR2023-01359 dated Apr. 26, 2024.
Declaration of W. Christopher Bakewell in IPR2023-01358 dated Aug. 30, 2024.
Declaration of W. Christopher Bakewell in IPR2023-01359 dated Aug. 30, 2024.
Declaration of Warren C.W. Chan, Ph.D. in IPR2023-01358 dated May 29, 2024, 136 pages.
Declaration of Warren C.W. Chan, Ph.D. in IPR2023-01359 dated May 29, 2024.

(56) References Cited

OTHER PUBLICATIONS

Deering et al., "Nucleic acid vaccines: prospects for non-viral delivery of mRNA vaccines," Expert Opinion on Drug Delivery, 11:6, 885-899, 2014.
Defendants' Supplemental Patent-Related Disclosures, Exhibit C—Invalidity Contentions of U.S. Pat. No. 10,702,600 (Jun. 27, 2023)(Excerpts).
Defendants' Patent-Related Disclosures, Exhibit D—Invalidity Contentions of U.S. Pat. No. 10,933,127, 2023, pp. 1-5 (Excerpts).
Defendants' Patent-Related Disclosures, Exhibit C—Invalidity Contentions of U.S. Pat. No. 10,702,600 (Mar. 31, 2023) (Excerpts).
Defendants' Supplemental Patent-Related Disclosures, Exhibit D—Invalidity Contentions of U.S. Pat. No. 10,933,127, 2023, pp. 1-110 (Excerpts).
Defrancesco, "The 'anti-hype' vaccine," Nat. Biotechnol., vol. 35, Issue 3, pp. 193-197, doi: 10.1038/nbt.3812. Epub Feb. 27, 2017.
Degroot et al., Part II—The Positive Sense Single Stranded RNA Viruses, Family Coronaviridae, in Virus Taxonomy: Ninth report of the International Committee on Taxonomy of Virus 806 (2012). 25 pages.
Dejnirattisai et al., Reduced neutralisation of SARS-CoV-2 omicron B.1.1.529 variant by post-immunisation serum. Lancet. Jan. 15, 2022;399(10321):234-236. doi: 10.1016/S0140-6736(21)02844-0. Epub Dec. 20, 2021.
Del Pozo-Rodriguez et al., Lipid nanoparticles as vehicles for macromolecules: nucleic acids and peptides. Recent Pat Drug Deliv Formul. Sep. 2011;5(3):214-26. doi: 10.2174/187221111797200515.
Delehanty Peptides for Specific Intracellular Delivery and Targeting of Nanoparticles: Implications for Developing Nanoparticle-Mediated Drug Delivery, Future Science, Therapeutic Delivery, 2010 vol. 1, No. 3 pp. 411-433.
Delivery means to avoid degradation of RNA preparations: Lipid nanoparticles (LNPs) for RNA delivery. CosmoBio. English-Language Machine Translation. Published: Oct. 23, 2022. Retrieved from the Internet: https://www.cosmobio.co.jp/product/detail/lipid-nanoparticles-for-rna-deliveryecl.asp?entry_id=43081. Last Accessed: Oct. 23, 2023. 10 pages.
Deming et al, "Vaccine Efficacy in Senescent Mice Challenged with Recombinant SARS-CoV Bearing Epidemic and Zoonotic Spike Variants," 2006, vol. 3, Issue 12, PLOS Medicine.
Deposition of Daniel O. Griffin, M.D., Ph.D. (May 22, 2024), in *BioNTech SE and Pfizer Inc.* v. *Moderna TX, Inc.*, in IPR2023-01358 and -01359.
Deposition of Daniel O. Griffin, M.D., Ph.D. (Sep. 20, 2024) in *BioNTech SE and Pfizer Inc.* v. *Moderna TX, Inc.*, in IPR2023-01358 and -01359.
Deposition of Deborah Fuller, Ph.D., dated Aug. 2, 2024.
Deposition of James E. Malackowski dated Jul. 22, 2024 and Errata Sheet dated Aug. 27, 2024.
Deposition of James J. Moon, Ph.D. (May 10, 2024), in *BioNTech SE and Pfizer Inc.* v. *Moderna TX, Inc.*, in IPR2023-01358 and -01359.
Deposition of James J. Moon, Ph.D. (Sep. 13, 2024) in *BioNTech SE and Pfizer Inc.* v. *Moderna TX, Inc.*, in IPR2023-01358 and -01359.
Deposition of L. Ross Pierce, M.D., in *BioNTech SE and Pfizer Inc.* v. *Moderna TX, Inc.*, in IPR2023-01358 and IPR2023-01359, Oct. 4, 2024 (redacted version of Ex. 2256), 56 pages.
Deposition of Philip Krause, M.D., dated Aug. 14, 2024 (redacted).
Deposition of W. Christopher Bakewell (Oct. 3, 2024) in *BioNTech SE and Pfizer Inc.* v. *Moderna TX, Inc.*, in IPR2023-01358 and -01359.
Deposition of Warren C.W. Chan Ph.D. in *BioNTech SE and Pfizer Inc.* v. *Moderna TX, Inc.*, in IPR2023-01358 and IPR2023-01359, Jul. 30, 2024, 375 pages.
Devoldere et al., Evading innate immunity in nonviral mRNA delivery: don't shoot the messenger. Drug Discov Today. Jan. 2016;21(1):I 1-25. doi: 10.1016/j.drudis.2015.07.009. Epub Jul. 23, 2015.
Dicaro et al., In Vivo Delivery of Nucleic Acid-Formulated Microparticles as a Potential Tolerogenic Vaccine for Type 1 Diabetes. Rev Diabet Stud. 2012 Winter;9(4):348-56.
Diebold, Sandra S. et al, "Innate Antiviral Responses by Means of TLR7-Mediated Recognition of Single-Stranded RNA," Science, vol. 303, (Mar. 5, 2004), pp. 1529-1531.
Diken et al., Current Developments in Actively Personalized Cancer Vaccination with a Focus on RNA as the Drug Format. Prag Tumor Res. 2015;42:44-54. doi: 10.1159/000437184. Epub Sep. 4, 2015.
Dimitriadis et al., "Translation of rabbit globin mRNA introduced by liposomes into mouse lymphocytes," 1978, Nature, vol. 274, Issue 5674, pp. 923-924, doi: 10.1038/274923a0.
Disbrow, G. L., et al., "Codon optimization of the HPV-16 E5 gene enhances protein expression." 2003, Virology, 311(1), 105-114. https://doi.org/10.1016/s0042-6822(03)00129-6.
Division of Microbiology and Infectious Diseases (DMID) Protocol, "Phase I, Open-Label, Dose-Ranging Study of the Safety and Immunogenicity of 2019-nCoV Vaccine (mRNA-1273) in Healthy Adults," 2020, pp. 1-12 (Excerpts).
Division of Microbiology and Infectious Diseases (DMID) Protocol No. 20-0003—mRMA-1273, Version 1.0 (Excerpts—Exhibit No. 2150 in IPR2023-01359), dated Feb. 14, 2020, 14 pages.
Division of Microbiology and Infectious Diseases (DMID) Protocol No. 20-0003—mRMA-1273, Version 3.0 (Excerpts—Exhibit No. 2149 in IPR2023-01358), dated Mar. 30, 2020, 13 pages.
Division of Microbiology and Infectious Diseases (DMID) Protocol No. 20-0003—mRMA-1273, Version 4.0 (Excerpts—Exhibit No. 2151 in IPR2023-01359), dated May 20, 2020, 16 pages.
Division of Microbiology and Infectious Diseases (DMID) Protocol, "Phase I, Open-Label, Dose-Ranging Study of the Safety and Immunogenicity of 2019-nCoV Vaccine (mRNA-1273) in Healthy Adults (Excerpts—Exhibit No. 2054 in IPR2023-01359)," dated Feb. 14, 2020, 10 pages.
Division of Microbiology and Infectious Diseases (DMID) Protocol, "Phase I, Open-Label, Dose-Ranging Study of the Safety and Immunogenicity of 2019-nCoV Vaccine (mRNA-1273) in Healthy Adults," 2020, pp. 1-8 (Excerpts).
Dolgin, Business: The billion-dollar biotech. Nature. Jun. 4, 2015;522(7554):26-8. doi: 10.1038/522026a.
Dolgin, mRNA flu shots move into trials. Nature Reviews Drug Discovery 20, 801-803 (2021).
Dormitzer, Synthetic Vaccinology at Novartis, Presentation at The National Academy of Sciences Forum on Synthetic Biology. Oct. 21, 2013, The Keck Center, Washington, DC. 12 pages.
Drummond et al., "The Evolutionary Consequences of Erroneous Protein Synthesis," 2009, Nature Reviews Genetics (10 Pages).
Du et al., "Recombinant adeno-associated virus expressing the receptor-binding domain of severe acute respiratory syndrome coronavirus S protein elicits neutralizing antibodies: Implication for developing SARS vaccines," 2006, Virology, vol. 353, Issue 1, p. 6-16.
Du et al., The spike protein of SARS-Co V—a target for vaccine and therapeutic development. Nat Rev Microbial. Mar. 2009; 7(3):226-36. doi: 10.1038/nrmicro2090. Epub Feb. 9, 2009.
Ducani, C., et al., (2014). Rolling circle replication requires single-stranded DNA binding protein to avoid termination and production of double-stranded DNA. Nucleic acids research, 42(16), 10596-10604. https://doi.org/10.1093/nar/gku737.
Dufourc, E., "Sterols and membrane dynamics," 2008, J. Chem. Biol. (15 Pages).
Dunham, S.P. et al., "The application of nucleic acid vaccines in veterinary medicine," Research in Veterinary Science, 2002, 73, 9-16.
Easton, LE. et al., Rapid, nondenaturing RNA purification using weak anion-exchange fast performance liquid chromatography. RNA. Mar. 2010;16(3):647-53. Epub Jan. 25, 2010.
Edelheit, S., et al., Transcriptome-wide mapping of 5-methylcytidine RNA modifications in bacteria, archaea, and yeast reveals m5C within archaeal mRNAs. 2013, PLoS genetics, 9(6), e1003602. https://doi.org/10.1371/journal.pgen.1003602.
El Ouahabi, A., et al., Double long-chain amidine liposome-mediated self replicating RNA transfection. 1996, FEBS letters, 380(1-2), 108-112. https://doi.org/10.1016/0014-5793(96)00038-5.

(56) References Cited

OTHER PUBLICATIONS

El Sahly et al., "Efficacy of the mRNA-1273 SARS-CoV-2 Vaccine at Completion of Blinded Phase," 2021, N Engl J Med. vol. 385, 1774-1785.
Ellebedy et al., Influenza Vaccines. Vaccine. Nov. 5, 2009; 27(Suppl 4): D65-D68.
Engler et al., "Half-vs full-dose trivalent inactivated influenza vaccine (2004-2005): age, dose, and sex effects on immune responses," 2008, Arch Intern Med., vol. 168, Issue 22, pp. 2405-2414. doi: 10.1001/archintemmed.2008.513.
Erasmus et al., A Nanostructured Lipid Carrier for Delivery of a Replicating Viral RNA Provides Single, Low-Dose Protection against Zika. Mol Ther. Oct. 3, 2018;26(10):2507-2522. With Supplemental Information. doi: 10.1016/j.ymthe.2018.07.010. Epub Aug. 2, 2018.
Ernsting et al., "Factors controlling the pharmacokinetics, biodistribution and intratumoral penetration of nanoparticles. J Control Release," Dec. 28, 2013;172(3):782-94. doi: 10.1016/j.jconrel.2013.09.013. Epub Sep. 25, 2013.
Escriou et al., Protection from SARS coronavirus conferred by live measles vaccine expressing the spike glycoprotein. Virology. Mar. 2014;452-453:32-41. doi: 10.1016/j.virol.2014.01.002.
Espeseth et al., Modified mRNA/lipid nanoparticle-based vaccines expressing respiratory syncytial virus F protein variants are immunogenic and protective in rodent models of RSV infection. NPJ Vaccines. Feb. 14, 2020:5:16. doi: I0.1038/s41541-020-0163-z. eCollection 2020.
European Medicines Agency, "Assessment Report for COVID-19 Vaccine Moderna," dated Mar. 11, 2021, 169 pages.
European Medicines Agency, Assessment Report for Spikevax (Sep. 14, 2023).
European Medicines Agency, Nuvaxovid (available at https://www.ema.europa.eu/en/medicines/human/EPAR/nuvaxovid).
Ewert et al., Cationic liposome-nucleic acid complexes for gene delivery and silencing: pathways and mechanisms for plasmid DNA and siRNA. Top Curr Chem. 2010;296:191-226.
Fang et al., Development of lipid-shell and polymer core nanoparticles with water-soluble salidroside for anti-cancer therapy. Int J Mol Sci. Feb. 25, 2014;15(3):3373-88. doi: 10.3390/ijms 15033373.
Fauquet, Taxonomy, Classification and Nomenclature of Viruses. Encyclopedia of Virology. 2008:9-23. doi: 10.1016/B978-012374410-4.00509-4.
FDA, "E6(R2) Good Clinical Practice: Integrated Addendum to ICH E6(R1—Guidance for Industry," U.S. Department of Health and Human Services, Mar. 2018, 68 pages.
FDA, Guidance for Industry E6 Good Clinical Practice: Consolidated Guidance (Apr. 1996).
Feldman et al, "mRNA vaccines against H10N8 and H7N9 influenza viruses of pandemic potential are immunogenic and well tolerated in healthy adults in phase 1 randomized clinical trials," Vaccine, vol. 37, No. 25, pp. 3326-3334, XP085695609, ISSN: 0264-410X, DOI: 10.1016/J.VACCINE.2019.04.074.
Felgner, PL, Cationic lipid/polynucleotide condensates for in vitro and in vivo polynucleotide delivery-the cytofoctins. J. of Liposome Research. 1993; 3(1): 3-16.
Felgner, PL, et al., Lipofection: a highly efficient, lipid-mediated DNA-transfection procedure. Proc Natl Acad Sci USA. Nov. 1987;84(21):7413-7.
Felgner, PL, et al., Particulate systems and polymers for in vitro and in vivo delivery of polynucleotides. Adv, Drug Delivery Rev. 1990; 5(3): 163-187.
Fernandez et al., "Unusual base pairing during the decoding of a stop codon by the ribosome." 2013, Nature, 500(7460), 107-110. https://doi.org/10.1038/nature12302.
Final Written Decision in *BioNTech SE and Pfizer Inc*. v. *Moderna TX, Inc*., IPR2023-01358, dated Mar. 5, 2025, 124 pages.
Fleeton et al., "Self-replicative RNA vaccines elicit protection against influenza a virus, respiratory syncytial virus, and a tickborne encephalitis virus," J. Infectious Dis., May 1, 2001, vol. 183, No. 9, pp. 1395-1398. (Epub Mar. 30, 2001).
Fotakis et al., Computational cancer neoantigen prediction: current status and recent advances. Immunooncol Technol. Nov. 20, 2021:12:100052. doi: 10.1016/j.iotech.2021.100052. eCollection Dec. 2021.
Fraiser Kansteiner, It's the end of the line for J&J's COVID shot in the US, CDC says, Fiercepharma (May 16, 2023).
Fujimori, How this Once Little-Known Molecule is Disrupting Medicine, 2022, Pfizer (7 Pages).
Fuke et al., Role of poly (A) tail as an identity element for mRNA nuclear export, Nucleic Acids Research, 2008, vol. 36 No. 3, on. 1037-1049.
Fuller, Deborah, The Conversation, "How mRNA and DNA vaccines could soon treat cancers, HIV, autoimmune disorders and genetic diseases," 2022, pp. 1-5.
Furuichi et al., Viral and cellular mRNA capping: past and prospects. Adv Virus Res. 2000;55:135-84. doi: 10.1016/s0065-3527(00)55003-9.
Furuichi, Caps on Eukaryotic mRNAs. eLS. John Wiley & Sons. Jul. 1-12, 2014.
Fynan et al., "DNA vaccines: protective immunizations by parenteral, mucosal, and gene-gun inoculations." 1993, Proceedings of the National Academy of Sciences of the United States of America, 90(24), 11478-11482. https://doi.org/10.1073/pnas.90.24.11478.
Gainor et al., T-cell Responses to Individualized Neoantigen Therapy mRNA-4157 (V940) as Monotherapy or in Combination With Pembrolizumab. Presented at the Society for Immunotherapy of Cancer. Nov. 3-5, 2023. San Diego, CA, USA. Poster. 1 page.
Gallie, D., "The cap and poly(A) tail function synergistically to regulate mRNA translational efficiency," Genes & Development, 1991, vol. 5 (pp. 2108-2116).
Gandhi et al., "Immunization of HIV-1-Infected Persons with Autologous Dendritic Cells Transfected with mRNA Encoding HIV-1 Gag and Nef: Results of a Randomized, Placebo-Controlled Clinical Trial, 71 J," 2016, Acquired Immune Deficiency Syndrome, Basic Translational Science.
Gao et al., "Nonviral gene delivery: What we know and what is next," 2007, The AAPS Journal (13 Pages).
Gao R, et al., "Human infection with a novel avian-origin influenza A (H7N9) virus," 2013, N. Engl. J. vol. 368 (20), pp. 1888-1897 doi: 10.1056/NEJMoal.304459. Epub Apr. 11, 2013.
Garde et al., "The story of mRNA: How a once-dismissed idea became a leading technology in the Covid vaccine race," 2020, STAT News (23 Pages).
Geall et al., "Nonviral delivery of self-amplifying RNA vaccines," PNAS, 14604-14609, Sep. 4, 2012, vol. 109, No. 36.
Geall et al., "Using self-amplifying mRNA vaccines to facilitate a rapid response to pandemic influenza," 2014, Eur Pharm Rev. vol. 3 (8 pages).
Geall et al., RNA: the new revolution in nucleic acid vaccines. Semin Immunol. Apr. 2013; 25(2):152-9. doi: 10.1016/j.smim.2013.05.001. Epub Jun. 2, 2013.
GenBank Accession No. BAS30426.1 Submitted to NCBI on Sep. 2, 2015. 2 pages.
Geoffrey M. Cooper & Robert E. Hausman, Chapters 1, 7, and 8 in the Cell: A Molecular Approach, 5th Ed. (2009) (Excerpts).
Georgopoulos et al., Use of high-performance liquid chromatographic fractionation of large RNA molecules in the assay of group I intron ribozyme activity. J Chromatogr A. Jan. 28, 2000;868(1):109-14.
Gilboa, E. et al., Cancer immunotherapy with mRNA-transfected dendritic cells. Immunol Rev. Jun. 2004;199:251-63.
Gilleron et al., "Image-Based Analysis of Lipid Nanoparticle-Mediated siRNA Delivery, Intracellular Trafficking and Endosomal Escape," 2013, Nature Biotech. 638.
Ginn et al., "Gene Therapy Clinical Trials Worldwide to 2017: An Update," 2018, 20 J, Gene Med, Article e3015.
GISAID Accession No. EPI457621, pub. Jun. 16, 2013.
GISAID Accession No. EPI508781 Mar. 9, 2014.
Gjetting et al., "In vitro and in vivo effects of polyethylene glycol (PEG)-modified lipid in DOTAP/cholesterol-mediated gene transfection," International Journal of Nanomedicine, 2010, vol. 5 (pp. 371-383).

(56) References Cited

OTHER PUBLICATIONS

Glenn et al., Safety and immunogenicity of a Sf9 insect cell-derived respiratory syncytial virus fusion protein nanoparticle vaccine. Vaccine. Jan. 7, 2013;31(3):524-32. doi: 10.1016 j.vaccine.2012. I 1.009.
Gorbalenya et al, "The species Severe acute respiratory syndrome related coronavirus: classifying 2019-nCoV and naming it SARS-CoV-2," Nature Microbiology, Mar. 2020, 5(4):536-544.
Govind et al., Primer-independent initiation of RNA synthesis by SeMV recombinant RNA-dependent RNA polymerase. Virology. Jun. 5, 2010;401(2):280-92. doi: 10.1016/j.virol.2010.02.025. Epub Mar. 23, 2010.
Graf, M. et al., Codon-optimized genes that enable increased heterologous expression in mammalian cells and elicit efficient immune responses in mice after vaccination of naked DNA. Methods Mol Med. 2004; 94:197-210.
Graham et al., Novel antigens for RSV vaccines. Curr Opin Immunol. Aug. 2015;35:30-8. doi: 10.1016 j.coi.2015.0 . . . J . . . 005. Epub Jun. 10, 2015.
Graham et al., Novel Vaccine Technologies: Essential Components of an Adequate Response to Emerging Viral Diseases. JAMA. Apr. 10, 2018;319(14):1431-1432.
Granstein, R.D., Induction of anti-tumor immunity with epidermal cells pulsed with tumor-derived RNA or intradermal administration of RNA. The Journal of investigative dermatology, 2000, 114(4), 632-636.
Greer et al., Long-term protection in hamsters against human parainfluenza virus type 3 following mucosal or combinations of mucosal and systemic immunizations with chimeric alphavirus-based replicon particles. Scand J Immunol. Dec. 2007;66(6):645-53. Epub Oct. 17, 2007.
Griffin et al., "Co-infection with Hepatitis C Virus Increases Mortality in HIV-1 Infected Patients Through Increased Liver-Related Deaths Rather Than By Increasing Malignancy Related Deaths," 2016, vol. 7, Issue 4, J. Aids and Clin. Res. (3 Pages).
Griffin et al., "Cytokine storm of a different flavour: the different cytokine signature of SARS-CoV-2 the cause of COVID-19 from the original SARS outbreak," Journal of Global Antimicrobial Resistance, pp. 1-3.
Griffin et al., "Human B1 cells in umbilical cord and adult peripheral blood express the novel phenotype CD20 CD27 CD43 CD70-," 2011, vol. 208, Issue 1, J. Exp. Med. (14 Pages).
Griffin et al., A small CD11b human B1 cell subpopulation stimulates T cells and is expanded in lupus, 2011, vol. 208, Issue 13, J. Exp. Med (8 Pages).
Grosjean, H., Modification and editing of RNA: historical overview and important facts to remember. Fine-tuning of RNA functions by modification and editing. Topics Curr Gen. Jan. 2005; 12: 1-22.
Gruegelsiepe et al., Handbook of RNA Biochemistry, ed. R.K. Harmann, Part LI, pp. 3-21, 2005.
Guevara et al., "Advances in lipid nanoparticles for mRNA-based cancer immunotherapy," Front Chem. 8, 589959 (2020).
Guimaraes et al., Ionizable lipid nanoparticles encapsulating barcoded mRNA for accelerated in vivo delivery screening. J Control Release. Dec. 28, 2019; 316:404-417. doi: 10.1016/i.iconrel.2019.10.028. Epub Oct. 31, 2019. Author Manuscript, 30 pages.
Guimaraes, Pedro PG, et al. "Ionizable lipid nanoparticles encapsulating barcoded mRNA for accelerated in vivo delivery screening." Journal of Controlled Release 316 (2019): 404-417. (Year: 2019).
Guo et al., "Nanoparticles escaping RES and endosome: Challenges for siRNA delivery for cancer therapy," 2011 Journal of Nanomaterials (12 Pages).
Guo et al., An Engineered Receptor-Binding Domain Improves the Immunogenicity of Multivalent SARS-CoV-2 Vaccines. mBio. May-Jun. 2021; 12(3): e00930-21.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/i.eipb.2013.07.002. Epub Jul. 17, 2013.
Hajj et al., "Tools for translation: non-viral materials for therapeutic mRNA delivery," Nature Reviews Materials, Sep. 12, 2017, 2(10):1-17.
Halford et al., Herpes simplex virus 2 ICP0 mutant viruses are avirulent and immunogenic: implications for a genital herpes vaccine. PLoS One. Aug. 17, 2010;5(8):e12251. doi: 10.1371/journal.pone.0012251.
Harenberg et al., Persistence of Th1/Tc1 responses one year after tetravalent dengue vaccination in adults and adolescents in Singapore. Hum Vaccin Immunother. Nov. 2013;9(11):2317-25. doi: 10.4161/hv.25562. Epub Jul. 9, 2013.
Harris, J. et al., An improved RNA amplification procedure results in increased yield of autologous RNA transfected dendritic cell-based vaccine. Biochim Biophys Acta. Jun. 20, 2005;1724(1-2):127-36. Epub Apr. 7, 2005.
Hartmann et al., Handbook of RNA Biochemistry, Second Edition, "Part I RNA Synthesis and Detection." 2014. p. 3-27.
Hashiba et al., The use of design of experiments with multiple responses to determine optimal formulations for in vivo hepatic mRNA delivery. J Control Release. Nov. 10, 2020;327:467-476. doi: 10.1016/j.jconrel.2020.08.031.
Hassett et al., Optimization of Lipid Nanoparticles for Intramuscular Administration of mRNA Vaccines. Mol Ther Nucleic Acids. Apr. 15, 2019;15:1-11. Epub Feb. 7, 2019.
Hattinger, E., et al. "Prophylactic mRNA Vaccination against Allergy Confers Long-Term Memory Responses and Persistent Protection in Mice," 2015, Journal of Immunology Research 2015, Article 797421.
Hatziantoniou et al., Anaphylactic reactions to mRNA COVID-19 vaccines: A call for further study. Vaccine. May 6, 2021;39(19):2605-2607. doi: 10.1016/j.vaccine.2021.03.073. Epub Apr. 6, 2021. PMID: 33846043; PMCID: PMC8023205.
He et al., "Single-component, self-assembling, protein nanoparticles presenting the receptor binding domain and stabilized spike as SARS-CoV-2 vaccine candidates," 2021, Sci Adv. vol. 7, Issue 12, doi: 10.1126/sciadv.abf1591.
He et al., Low molecular weight protamine (LMWP): a nontoxic protamine substitute and an effective cell-penetrating peptide. J Control Release. Nov. 10, 2014; 193:63-73. doi: I0.1016/j.jconrel.2014.05.056. Epub Jun. 3, 2014.
He et al., Receptor-binding domain of SARS-CoV spike protein induces highly potent neutralizing antibodies: implication for developing subunit vaccine. Biochem Biophys Res Commun. Nov. 12, 2004;324(2):773-81. doi: 10.1016/j.bbrc.2004.09.106.
Hecker et al., "Non-Viral DNA and mRNA Gene Delivery to the CNS Pre-Operatively for Neuroprotection and Following Neurotrauma," Molecular Therapy, 2004, vol. 9. (pp. S258-S258).
Hecker J. G. (2013). Nonviral, cationic lipid-mediated delivery of mRNA. Methods Molecular Biology, 969, 73-88. https://doi.org/10.1007/978-1-62703-260-5_5.
Heidenreich, O. et al., Chemically modified RNA: approaches and applications. FASEEB J. Jan. 1993;7(1):90-6.
Heilman, KL et al., Internal 6-methyladenine residues increase the in vitro translation efficiency of dihydrofolate reductase messenger RNA. Int J Biochem Cell Biol. Jul. 1996; 28(7): 823-829.
Heinz et al., Distinguishing features of current COVID-19 vaccines: knowns and unknowns of antigen presentation and modes of action. NPJ Vaccines. Aug. 16, 2021;6(1):104. doi: 10.1038/s41541-021-00369-6.
Heiser, A. et al., Autologous dendritic cells transfected with prostate-specific antigen RNA stimulate CTL responses against metastatic prostate tumors. J Clin Invest. Feb. 2002; 109(3):409-17.
Heiser, A. et al., Induction of polyclonal prostate cancer-specific CTL using dendritic cells transfected with amplified tumor RNA. J Immunol. Mar. 1, 2001; 166(5):2953-60.
Hekele et al., "Rapidly produced SAM(®) vaccine against H7N9 influenza is immunogenic in mice," Emerg Microbes Infect. Aug. 2013;2(8):e52. doi: 10.1038/emi.2013.54. Epub Aug. 14, 2013. PMID: 26038486; PMCID: PMC3821287.
Hemagglutinin [Influenza A virus (A/mallard/Sweden/4/2002(H10N2)], GenBank Accession No. ADE75192, pub. Apr. 8, 2010.

(56) References Cited

OTHER PUBLICATIONS

Hemmer et al., Minimal peptide length requirements for CD4(+) T cell clones—implications for molecular mimicry and T cell survival. Int Immunol. Mar. 2000;I2(3):375-83. doi: 10.1093/intimm/12.3.375.
Heyes et al., "Cationic lipid saturation influences intracellular delivery of encapsulated nucleic acids," Journal of Controlled Release, Jul. 28, 2005, vol. 107 (pp. 276-287).
Hoernes et al., Nucleotide modifications within bacterial messenger RNAs regulate their translation and are able to rewire the genetic code. Nucleic Acids Res. Jan. 29, 2016; 44(2): 852-862.
Hoerr et al., "In vivo application of RNA leads to induction of specific cytotoxic T lymphocytes and antibodies," 2000, Eur. J. Immunol. 30: 1-7.
Hoerr, I. et al., Stabilized Messenger RNA (RNActiveTM) as a Tool for Innovative Gene Delivery. Tissue Engineering. Apr. 2007; 13(4): 865-925.
Hoerr, More than a messenger: A new class of drugs-mRNA-based therapeutics. Genetic Engineering & Biotechnology News. Jun. 18, 2013. http://www.genengnews.com/genarticles/more-than-a-messenger-a-new-class-of-drugs-mrna-based-therapeutics/ 4916/ Epub Aug. 20, 2005.
Holtkamp et al., "Modification of antigen-encoding RNA increases stability, translational efficacy, and T-cell stimulatory capacity of dendritic cells," 2006, vol. 108, Issue 13, Gene Therapy.
Hope et al., Reduction of Liposome Size and Preparation of Unilamellar Vesicles by Extrusion Techniques. In: Liposome Technology. 1993. Gregoriadis et al., Ed. vol. 1: 123.
Hori et al., "Antitumor Activity of Cationic Liposome-Mediated Bax mRNA Transfer in HOSM-1 Mandibular Osteoosarcoma Cells: A Comparative Study of Local Administration and Systemic Administration." Journal of Oral and Maxillofacial Surgery, 2014, vol. 72, No. 9, SUPPL. 1, p. e107, Abstract No. 98.
Hörr, RNA vaccine for the induction of specific cytotoxic T lymphocytes (CTL) and antibodies. Eberhard Karls University of Tubingen. Dissertation. English-Language Translation. 1999. 138 Pages.
Hou et al., "Lipid nanoparticles for mRNA delivery," Nature Reviews Materials vol. 6, pp. 1078-1094 (2021).
Houser et al., Influenza Vaccines: Challenges and Solutions. Cell Host Microbe. Mar. 11, 2015; 17(3): 295-300. doi: 10.1016/j.chom.2015.02.012.
Hsu et al., Cationic lipid nanoparticles for therapeutic delivery of siRNA and miRNA to murine liver tumor. Nanomedicine. Nov. 2013;9(8): 1169-80. doi: 10.1016/j.nano.2013.05.007. Epub May 30, 2013.
Hu et al., "Cytosolic delivery mediated via electrostatic surface binding of protein, virus, or siRNA cargos to pH-responsive core-shell gel particles," 2009, vol. 10, Issue 4, Biomacromolecules (10 Pages).
Huang et al. "Asymmetric 1-alkyl-2-acyl phosphatidylcholine: A helper lipid for enhanced non-viral gene delivery," 2012, (Author Manuscript), Int. J. Pharm., pp. 64-70.
Huang et al., Construction and biological characterisation of recombinant porcine circovirus type 2 expressing the V5 epitope tag. Vims Res. Nov. 2011;I61(2):115-23. doi: 10.1016/j.vimsres.2011.05.015. Epub May 27, 2011.
Huang, "In Vivo Delivery of RNAi with Lipid-Based Nanoparticles," 2011, 13 Ann. Rev. Biomed. Eng'g.
Huang, et al., "Structural and functional properties of SARS-CoV-2 spike protein: potential antivirus drug development for COVID-19," Acta Pharmacologica Sinica, 2020, vol. 41 (pp. 1141-1149).
Huang, et al., "Clinical features of patients infected with 2019 novel coronavirus in Wuhan, China," Lancet. 395, 497-506 (2020).
Huddleston, J.A. et al., The sequence of the nucleoprotein gene of human influenza A virus, strain A/NT/60/68. Nucleic Acids Res. 1982, Feb. 11;10(3): 1029-38.
Human Metapneumovirus (HM PV) Clinical Features, CDC Website, https://www.cdc.gov/surveillance/nrevss/hmpv/clinical.html, Sep. 5, 2019. (Year: 2019).
Imamura, Tadatsugu, and Hitoshi Oshitani. "Global reemergence of enterovirus D68 as an important pathogen for acute respiratory infections." Reviews in medical virology 25.2 (2015): 102-114. (Year: 2015).
Impagliazzo et al., A stable trimeric influenza hemagglutinin stem as a broadly protective immunogen. Science. Sep. 18, 2015;349(6254): 1301-6. doi: 10. I 126/science.aac7263. Epub Aug. 24, 2015.
Institution Decision in IPR2023-01358, dated Mar. 19, 2024, 97 pages.
Institution Decision in IPR2023-01359, dated Mar. 19, 2024, 96 pages.
Ivanovska et al., Immunization with a DNA chimeric molecule encoding a hemagglutinin peptide and a scFv CD21-specific antibody fragment induces long-lasting IgM and CTL responses to influenza virus. 2006, Vaccine, 24(11), 1830-1837. https://doi.org/10.1016/j.vaccine.2005.10.029.
Iwasaki, A. et al., Enhanced CTL responses mediated by plasmid DNA immunogens encoding costimulatorv molecules and cytokines. J Immunol. May 15, 1997: 158(10):4591-601.
Jackson et al., An mRNA Vaccine against SARS-CoV-2—Preliminary Report. N Engl J Med. Jul. 14, 2020; NEJMoa2022483. doi: 10.1056/NEJMoa2022483. Online ahead of print.
Jaishankar et al., Strong synthetic stationary phase promoter-based gene expression system for *Escherichia coli*. Plasmid. May 2020; 109: 102491. doi: 10.1016/j.plasmid.2020.102491. Epub Feb. 5, 2020.
Japanese Package Insert for Spikevax Intramuscular Injection (Monovalent: Omicron XBB.1.5), Oct. 2023, 17 pages (with English translation).
Jaume et al., "Anti-Severe Acute Respiratory Syndrome Coronavirus Spike Antibodies Trigger Infection of Human Immune Cells via a pH- and Cysteine Protease-Independent FcyR Pathway," 2011, Journal of Virology, pp. 10582-10597.
Javier et al., "Phylogenetic Analysis and Structural Modeling of SARS-CoV-2 Spike Protein Reveals an Evolutionary Distinct and Proteolytically Sensitive Activation Loop", Journal of Molecular Biology, vol. 432, 2020, pp. 3309-3325 (18 pages).
Jayaraman et al., "Maximizing the potency of siRNA lipid nanoparticles for hepatic gene silencing in vivo," Angewandte Chemie, 2012, vol. 51, Issue 34, pp. 8657-8661.
Jeffs et al., "A Scalable, Extrusion-Free Method for Efficient Liposomal Encapsulation of Plasmid DNA," 2005, 22 Pharmaceutical Research (11 Pages).
Jesse H. Erasmus et al., "An Alphavirus-derived replicon RNA vaccine induces SARS-CoV-2 neutralizing antibody and T cell responses in mice and nonhuman primates," 2020, Sci. Transl. Med. (11 Pages).
Jia et al., Kinetic mechanism of GTP binding and RNA synthesis during transcription initiation by bacteriophage T7 RNA polymerase. J Biol Chem. Nov. 28, 1997;272(48):30147-53. doi: 10.1074/jbc.272.48.30147.
Jiaming et al., The recombinant N-terminal domain of spike proteins is a potential vaccine against Middle East respiratory syndrome coronavirus (MERS-Co V) infection. Vaccine. Jan. 3, 2017;35(1):10-18. doi: 10.1016/j.vaccine.2016.11.064. Epub Nov. 26, 2016.
Jiang et al., The Variation of SARS-CoV-2 and Advanced Research on Current Vaccines. Front Med (Lausanne). Jan. 18, 2022:8:806641. doi: 10.3389/fmed.2021.806641.
Jirikowski, G.F., et al., Reversal of diabetes insipidus in Brattleboro Rats: Intrahypothalamic injection of vasopressin mRNA. Science. Feb. 1992; 255(5047): 996-998.
Johanning et al., A Sindbis virus mRNA polynucleotide vector achieves prolonged and high level heterologous gene expression in vivo. Nucleic Acids Res. May 11, 1995; 23(9): 1495-1501.
Johansson et al., "Intradermal Electroporation of Naked Replicon RNA Elicits Strong Immune Responses," 2012, PLoSONE, Article e29732.
John et al., Multi-antigenic human cytomegalovirus mRNA vaccines that elicit potent humoral and cell-mediated immunity. Vaccine. Mar. 14, 2018;36(12):1689-1699. doi:10.1016/j.vaccine.2018.01.029. Epub Feb. 15, 2018.
Jorquera et al., Nanoparticle vaccines encompassing the respiratory syncytial virus (RSV) G protein CX3C chemokine motif induce

(56) References Cited

OTHER PUBLICATIONS robust immunity protecting from challenge and disease. PLoS One. Sep. 2013 I 0;8(9):e74905. doi: 10.137 I/journal.pone.0074905. eCollection 2013.
Kabanov, A.V. et al., "A new class of antivirals: antisense oligonucleotides combined with a hydrophobic substituent effectively inhibit influenza virus reproduction and synthesis of virus specific proteins in MOCK cells." FEBS Lett. Jan. 1, 1990 ;259(2):327-30.
Kallen et al., "A development that may evolve into a revolution in medicine: mRNA as the basis for novel, nucleotide-based vaccines and drugs," Ther. Adv. Vaccines. Jan. 2014;2(1):10-31. doi: 10.1177/2051013613508729.
Kallen et al., "A novel, disruptive vaccination technology: self-adjuvanted RNActive(RTM) vaccines," Hum. Vaccine Immunother. Oct. 2013;9(10):2263-76. doi: 10.4161/hv.25181. Epub Jun. 4, 2013.
Kalra et al., Virosomes: As a Drug Delivery Carrier. American Journal of Advanced Drug Delivery. 2013;1:29-35.
Kam et al., "Antibodies against trimeric S glycoprotein protect hamsters against SARS-CoV challenge despite their capacity to mediate Fc[gamma]RII-dependent entry into B cells in vitro," 2007, Vaccine (13 Pages).
Kanapathipillai et al., "Nanoparticle targeting of anti-cancer drugs that alter intracellular signaling or influence the tumor microenvironment," Advanced Drug Delivery Reviews, Dec. 15, 2014 (pp. 107-118).
Kanasty et al., "Delivery materials for siRNA therapeutics," 2013, Nature Materials, pp. 967-977.
Kanaya, S. et al., Codon usage and tRNA genes in eukaryotes: correlation of codon usage diversity with translation efficiency and with CG-dinucleotide usage as assessed by multivariate analysis. J Mol Evol. Oct.-Nov. 2001;53(4-5):290-8.
Kansensho.or.jp [online], "Novel Coronavirus Infection," The Japanese Association for Infectious Diseases, last updated on May 23, 2024, retrieved on Jun. 4, 2025, retrieved from URL https://www.kansensho.or.jp/modules/topics/index.php?content_id=31, 16 pages (with English Translation).
Kansensho.or.jp [online], "Response to Novel Coronavirus (2019-nCoV) Infection (as of Jan. 28, 2020)," General incorporated foundation Japanese Association for Infectious Diseases, Jan. 28, 2020, retrieved on Jun. 4, 2025, retrieved from URL https://www.kansensho.or.jp/uploads/files/topics/2019ncov/2019ncov_taiou_200128.pdf, 6 pages (with English Translation).
Karijolich et al., Modifying the genetic code: Converting nonsense codons into sense codons by targeted pseudouridylation. Nature. Jun. 15, 2011:474(7351):395-8. doi: 10.1038/nature10165.
Kariko et al., "Generating the optimal mRNA for therapy: HPLC purification eliminates immune activation and improves translation of nucleoside-modified, protein-encoding mRNA," 2011, Nucleic Acids Research, vol. 39, No. 21, e142 (10 pages).
Kariko et al., "Impacts of Nucleoside Modification on RNA-mediated activation of toll-like receptors," 2008, Nucleic Acids in Innate Immunity, pp. 171-188.
Kariko et al., "Modified Uridines are the Key to A Successful Message," Nat Rev Immunol. 21 :619 (2021).
Kariko et al., "Naturally occurring nucleoside modifications suppress the immunostimulatory activity of RNA: Implication for therapeutic RNA development," Curr. Opin. Drug Discov. Devel., pp. 523-532.
Kariko et al., "Incorporation of Pseudouridine Into mRNA Yields Superior Nonimmunogenic Vector With Increased Translational Capacity and Biological Stability," Molecular Therapy, Nov. 2008, vol. 16, No. 11 (pp. 1833-1844).
Kariko et al., In vivo protein expression from mRNA delivered into adult rat brain. J. Neuroscience Methods. Jan. 2001; 105(1): 77-86.
Kariko et al., Increased erythropoiesis in mice injected with submicrogram quantities of pseudouridine-containing mRNA encoding erythropoietin. Mol. Ther. May 2012; 20(5): 948-953.
Kariko et al., Increased eythropoiesis in mice injected with submicrogram quantities of pseudouridine-containing mRNA encoding erythropoietin, 2012, vol. 20, Issue 5, Molecular Therapy, 948-953.
Kariko et al., Phosphate-enhanced transfection of cationic lipid-complexed mRNA and plasmid DNA. Biochim Biophys Acta. Mar. 2, 1998; 1369(2):320-34.
Kariko, et al., "Suppression of RNA recognition by Toll-like receptors: the impact of nucleoside modification and the evolutionary origin of RNA," Immunity, Aug. 2005, vol. 23 (pp. 165-175).
Karin Bok, Accelerated COVID-19 vaccine development: milestones, lessons, and prospects, 54 Immunity 1636 (2021).
Kauffman et al., "Optimization of Lipid Nanoparticle Formulations for mRNA Delivery in Vivo with Fractional Factorial and Definitive Screening Designs." Nano Lett. Nov. 11, 2015; 15(11): 7300-6.
Kauffman et al., Efficacy and immunogenicity of unmodified and pseudouridine-modified mRNA delivered systemically with lipid nanoparticles in vivo. Biomaterials. Dec. 2016;109:78-87. doi: 10.1016/j.biomaterials.2016.09.006. Epub Sep. 25, 2016.
Kauffman et al., Materials for non-viral intracellular delivery of messenger RNA therapeutics. J Control Release. Oct. 28, 2016;240:227-234. doi: 10.1016/j.jconrel.2015.12.032.
Kaukinen et al., The reactivity of phosphodiester bonds within linear single-stranded oligoribonucleotides is strongly dependent on the base sequence. Nucleic Acids Res. Jan. 15, 2002;30(2):468-74. doi: 10.1093/nar/30.2.468.
Keegan, The Lasker Awards: A History of "America's Nobels". Cell Mentor. Sep. 11, 2018: 7 pages.
Kenneth Murphy, Janeway's Immunobiology, 8th Ed. (2012) (Excerpts).
Kern et al., Application of a Fed-Batch System to Produce RNA by in Vitro Transcription. Biotechnol Prog. Mar.-Apr. 1999; 15(2): 174-84. doi: 10.1021/bp990008g.
Keshwara et al., Rabies-based vaccine induces potent immune responses against Nipah virus. NPJ Vaccines. Apr. 15, 2019;4:15. Erratum in: NPJ Vaccines. May 13, 2019;4:18.
Khoury et al., Neutralizing antibody levels are highly predictive of immune protection from symptomatic SARS-CoV-2 infection. Nat Med. Jul. 2021;27(7):1205-1211. doi: 10.1038/s41591-021-01377-8. Epub May 17, 2021.
Khurana et al., Recombinant HA1 produced in *E.coli* forms functional oligomers and generates strain-specific SRID potency antibodies for pandemic influenza vaccines. Vaccine. Aug. 5, 2011;29(34):5657-65. doi: 10.1016/j.vaccine.2011.06.014. Epub Jun. 23, 2011.
Kierzek et al., The contribution of pseudouridine to stabilities and structure of RNAs. Nucleic Acids Res. Mar. 2014;42(5):3492-501. doi: 10.1093/nar/gktl330. Epub Dec. 24, 2013.
Kim et al., "Generation and Characterization of DNA Vaccines Targeting the Nucleocapsid Protein of Severe Acute Respiratory Syndrome Coronavirus," 2004, vol. 78 J, Issue 9, Virology, pp. 4638-4645.
Kim et al., GenBank Accession No. ACF25291.1, pub. Jul. 13, 2008.
Kim et al., GenBank Accession No. FJ750874.1 pub. Mar. 5, 2010.
Kim et al., GenBank Accession No. JN817576.1, pub. Dec. 20, 2012.
Kim, Jin Hee et al.; "High Cleavage Efficiency of a 2A Peptide Derived from Porcine Teschovirus-1 in Human Cell Lines, Zebrafish and Mice"; PLoS One, vol. 6, issue 4; Apr. 29, 2011; 8 pages.
King et al., "Virus Taxonomy: Classification and Nomenclature of Viruses," 2012, Elsevier Academic Press (50 Pages).
Kirchdoerfer et al., "Stabilized coronavirus spikes are resistant to conformational changes induced by receptor recognition or proteolysis. ," Scientific Reports, (2018); 8(1):15701. doi: 10.1038/s41598-018-34171-7.
Kisich et al., Antimycobacterial agent based on mRNA encoding human beta-defensin 2 enables primary macrophages to restrict growth of *My co bacterium tuberculosis*. Infect Immun. Apr. 2001;69(4):2692-9.
Klinman, D.M. et al., DNA vaccines: safety and efficacy issues. Springer Semin Immunopathol. 1997;19(2):245-56.

(56) References Cited

OTHER PUBLICATIONS

Knepper et al., The novel human influenza A(H7N9) virus is naturally adapted to efficient growth in human lung tissue. MBio. Oct. 8, 2013;4(5):e00601-13.
Knowles et al., "Cloning and Expression of a Yieldin-Like Gene in Pea," GenBank Accession No. EF051125. Submitted to NCBI on Oct. 7, 2006.
Koch, G., et al., Quantitative Studies on the Infectivity of ribonucleic acid from partially purified and highly purified poliovirus preparations. Virology. Mar. 1960; 10(3): 329-343.
Kolata, Kati Kariko Helped Shield the World from the Coronavirus. New York Times. Sep. 24, 2021: 5 pages.
Kon et al., A single-dose FI-based mRNA-LNP vaccine provides protection against the lethal plague bacterium. Sci Adv. Mar. 10, 2023;9(10):eadg1036. doi: 10.1126/sciadv.adg1036. Epub Mar. 8, 2023.
Konwarh, "Nanobodies: Prospects of Expanding the Gamut of Neutralizing Antibodies Against the Novel Coronavirus, SARS-CoV-2," Frontiers in immunology, Jun. 23, 2020, 11:1531, 6 pages.
Kopera et al., Expression, purification and characterization of glycosylated influenza H5NI hemagglutinin produced in Pichia pastoris. Acta Biochim Pol. 2014;61(3):597-602. Epub Sep. 12, 2014.
Kore et al., "Synthesis and biological validation of N7-(4-chlorophenoxyethyl) substituted dinucleotide cap analogs for mRNA translation," Bioorganic & Medicinal Chemistry, Jun. 2013, vol. 21, No. 15 (pp. 4570-4574).
Kormann et al., "Expression of therapeutic proteins after delivery of chemically modified mRNA in mice," Nature Biotechnology, Feb. 2011, vol. 29, No. 2 (pp. 154-157).
Kowalski, et al., "Delivering the Messenger: Advances in Technologies for Therapeutic mRNA Delivery," Molecular Therapy, Apr. 2019, vol. 27, No. 4 (pp. 1-19).
Koyama et al., Analysis on GENIE reveals novel recurrent variants that affect molecular diagnosis of sizable number of cancer patients. BMC Cancer. Feb. 1, 2019;19(1):114. doi: 10. I 186/sI2885-019-5313-I.
Koyama et al., Emergence of Drift Variants That May Affect COVID-19 Vaccine Development and Antibody Treatment. Pathogens. Apr. 26, 2020;9(5):324. doi: 10.3390/pathogens9050324.
Kozak, "Regulation of translation via mRNA structure in prokaryotes and eukaryotes", GENE (2005), pp. 13-37.
Kozielski et al., "Bioreducible Cationic Polymer-Based Nanoparticles for Efficient and Environmentally Triggered Cytoplasmic siRNA Delivery to Primary Human Brain Cancer Cells," ACS Nano, 2014, vol. 8, No. 4 (pp. 3232-3241).
Krammer et al., "Chimeric Hemagglutinin Influenza Virus Vaccine Constructs Elicit Broadly Protective Stalk-Specific Antibodies," Journal of Virology, Jun. 2013, 87(12):6542-6550.
Kramps et al., Messenger RNA-based vaccines: progress, challenges, applications. Wiley Interdiscip Rev RNA. Nov.-Dec. 2013;4(6):737-49.
Kranz et al., "Systemic RNA Delivery to Dendritic Cells Exploits Antiviral Defense for Cancer Immunotherapy," 2016, Nature, vol. 534, pp. 396-411.
Kreiter et al., "Intranodal Vaccination with Naked Antigen-Encoding RNA Elicits Potent Prophylactic and Therapeutic Antitumoral Immunity," 2010, Cancer Research, pp. 9031-9040.
Kreiter, S., et al., Tumor vaccination using messenger RNA: prospects of a future therapy. Curr Opinion in Immun. Jun. 2011; 23(3): 399-406.
Kresge, The messenger RNA pioneers everyone ignored. Bloomberg, Nov. 23, 2021, https://www.bloomberg.com/news/newsletters/2021-11-23/themessenger-rna-pioneers-everyone-ignored (last accessed Aug. 24, 2023). 8 pages.
Kudla et al., "High Guanine and Cytosine Content Increases mRNA Levels in Mammalian Cells," PLOS Biology, Jun. 2006, vol. 4, No. 6, e180 (pp. 1-10).
Kuhn, A.N., et al., mRNA as a versatile tool for exogenous protein expression. Current Gene Therapy. Oct. 2012; 12 (5): 347-361.
Kulkarni et al., Lipid Nanoparticles Enabling Gene Therapies: From Concepts to Clinical Utility. Nucleic Acid Ther. Jun. 2018;28(3):146-157. doi: 10.1089/nat.2018.0721. Epub Apr. 23, 2018.
Kumar et al., Shielding of Lipid Nanoparticles for siRNA Delivery: Impact on Physicochemical Properties, Cytokine Induction, and Efficacy. Mol Ther Nucleic Acids. Nov. 18, 2014;3(11):e210. doi: 10.1038/mtna.2014.61.
Kurimoto et al., PEG-OligoRNA Hybridization of mRNA for Developing Sterically Stable Lipid Nanoparticles toward In Vivo Administration. Molecules. Apr. 3, 2019;24(7): 1303.
Kusakabe, K. et al., The timing of GM-CSF expression plasmid administration influences the Th1/Th2 response induced by an HIV-1-specific DNA vaccine. J Immunol. Mar 2000 I5;164(6):3102-11.
Kutikuppala et al., Prospects and Challenges in Developing mRNA Vaccines for Infectious Diseases and Oncogenic Viruses. Med Sci (Basel). May 22, 2024;12(2):28. doi: 10.3390/medsci12020028.
Kutzler et al., "DNA Vaccines: Ready for Prime Time?," 2008, Nature Reviews Genetics, vol. 9, pp. 776-788.
Kwong, P. et al., Broadly Neutralizing Antibodies and the Search for an HIV-1 Vaccine: The End of the Beginning, Nature Reviews, immunology, vol. 13, Sep. 2013, pp. 693-701.
Langer, "New Methods of Drug Delivery," Science, Sep. 1990, vol. 249, No. 4976 (pp. 1527-1533).
Laursen et al., Broadly Neutralizing Antibodies Against Influenza Viruses, Antiviral Research, 2013, vol. 98, pp. 476-483.
Leal et al., "Phase I clinical trial of an intranodally administered mRNA-based therapeutic vaccine against HIV-1 infection," 2018, AIDS, vol. 32, Issue 17, Pages.
Lee et al., Lipid Nanoparticle siRNA Systems for Silencing the Androgen Receptor in Human Prostate Cancer in Vivo, International Journal of Cancer, 2012, vol. 131, pp. 781-790.
Leitner, W.W. et al., DNA and RNA-based vaccines: principles, progress and prospects. Vaccine. Dec. 10, 1999;18 (9-10):765-77.
Leroueil et al., Wide varieties of cationic nanoparticles induce defects in supported lipid bilayers. Nano Lett. Feb. 2008;8(2):420-4. doi: 10.1021/nl0722929. Epub Jan. 25, 2008.
Leung et al., "Chapter Four—Lipid nanoparticles for short interfering RNA delivery," 2014, in Advances in Genetic, vol. 88 (40 Pages).
Leung et al., Lipid nanoparticles for short interfering RNA delivery. Adv Genet. 2014;88:71-110. doi: 10.1016/B978-0-12-800148-6.00004-3.
Leuschner, et al., "Therapeutic siRNA silencing in inflammatory monocytes in mice," Nature Biotechnology, Oct. 9, 2011, vol. 29, No. 11 (pp. 1005-1010).
Lewandowski, L.J. et al., Separation of the infectious ribonucleic acid of potato spindle tuber virus from double-stranded ribonucleic acid of plant tissue extracts. J Virol. Nov. 1971;8(5):809-12.
Lewis, Dynamic Polyconjugates (DPC) Technology: An elegant solution to the siRNA delivery problem. Arrowhead Research Corp (NASDAQ: ARWR). Nov. 2011.
Li et al., "Application of ultra-high performance liquid chromatography for chemical characterization of liposome-based therapeutic small-interfering RNA," 13 American Pharmaceutical Review 102 (2010). 13 pages.
Li et al., "Cell Attachment Domains of the Porcine Epidemic Diarrhea Virus Spike Protein Are Key Targets of Neutralizing Antibodies," J Virol. May 26, 2017;91(12):e00273-17. doi: 10.1128/JVI.00273-17. Print-pub: Jun. 15, 2017.
Li et al., "Overcoming obstacles to develop effective and safe siRNA therapeutics," Expert Opinion on Biological Therapy, May 2009, vol. 9, No. 5 (pp. 609-619).
Li et al., Developing lipid nanoparticle-based siRNA therapeutics for hepatocellular carcinoma using an integrated approach. Mol Cancer Ther. Nov. 2013;12(11):2308-18. doi: 10.1158/1535-7163.MCT-12-0983-T. Epub Aug. 13, 2013.
Li et al., Effects of local structural transformation of lipid-like compounds on delivery of messenger RNA. Sci Rep. Feb. 26, 2016;6:22137. doi: 10.1038/srep22137.

(56) References Cited

OTHER PUBLICATIONS

Li et al., Environmental connections of novel avian-origin H&N9 influenza virus infection and virus adaptation to the human, Science China, Life Sciences, vol. 56, No. 6 GISAID Accession No. EPI443651, pub. Dec. 11, 2013.
Li et al., Lipid-based nanoparticles for nucleic acid delivery. Pharm Res. Mar. 2007;24(3):438-49. doi: 10.1007/sl1095-006-9180-5.
Li et al., Prophylactic, therapeutic and immune enhancement effect of liposome-encapsulated PolyICLC on highly pathogenic H5NI influenza infection. J Gene Med. Jan. 2011;13(1):60-72. doi: 10.1002/jgm.1536.
Li, "Receptor recognition mechanisms of coronaviruses: a decade of structural studies," J Virol., Feb. 2015, 89(4):1954-64.
Li, L. et al., Preparation and gene delivery of alkaline amino acids-based cationic liposomes. Arch Pham Res. Jul. 2008;31(7):924-31. Epub Aug. 14, 2008.
Li, Structure, Function, and Evolution of Corona virus Spike Proteins. Annu Rev Viral. Sep. 29, 2016;3(1):237-261. doi: 10.1146/annurev-virology-110615-042301. Epub Aug. 25, 2016.
Lian, et al., Trends and developments in liposome drug delivery systems. J Pharm Sci. Jun. 2001;90(6):667-80.
Liang et al., "Efficient Targeting and Activation of Antigen-Presenting Cells In Vivo after Modified mRNA Vaccine Administration in Rhesus Macaques," 2017, vol. 25, No. 12, Molecular Therapy, American Society of Gene & Cell Therapy, pp. 2635-2647.
Liang et al., Enhanced Neutralizing Antibody Response Induced by Respiratory Syncytial Virus Prefusion F Protein Expressed by a Vaccine Candidate. J Virol. Sep. 2015;89(18):9499-510.
Limberis, Met al., Intranasal Antibody Gene Transfer in Mice and Ferrets Elicits Broad Protection Against Pandemic Influenza, Science Transl Med vol. 5, Issue 187, 99. 1-8.
Lin et al., "Lipid-based nanoparticles in the systemic delivery of siRNA," Nanomedicine, 2014, vol. 9, No. 1 (pp. 105-120).
Lin et al., "Three-dimensional imaging of lipid gene-carriers: Membrane charge density controls universal transfection behavior in lamellar cationic liposome-DNA complexes," 2003, vol. 84, Biophysical Journal, pp. 3307-3316.
Lin et al., Glycan Masking of Epitopes in the NTD and RBD of the Spike Protein Elicits Broadly Neutralizing Antibodies Against SARS-CoV-2 Variants. Front Immunol. Dec. 2, 2021: 12:795741. doi: 10.3389/fimmu.2021.795741.
Lin et al., Progress and challenges of mRNA vaccines. Interdisc Med. Dec. 22, 2022;1(1).
Lin et al., The herpes simplex virus ICP0 RING finger domain inhibits IRF3- and IRF7-mediated activation of interferon-stimulated genes. J Viral. Feb. 2004;78(4 ): 1675-84. doi: 10.1128/jvi.78.4.1675-1684.2004.
Lindgren et al., "Induction of Robust B Cell Responses after Influenza mRNA Vaccination Is Accompanied by Circulating Hemagglutinin-Specific ICOS+ PD-1+ CXCR3+ T Follicular Helper Cells." Front Immunol. Nov. 13, 2017, vol. 8, Article 1539. doi: 10.3389/fimmu.2017.01539. eCollection 2017.
Liu et al., "Influence of polyethylene glycol density and surface lipid on pharmacokinetics and biodistribution of lipid-calcium-phosphate nanoparticles," 2014, (Author Manuscript), published in final edited form as 35 Biomaterials 3027.
Liu et al., "The Membrane Protein of Severe Acute Respiratory Syndrome Coronavirus Acts as a Dominant Immunogen Revealed by a Clustering Region of Novel Functionally and Structurally Defined Cytotoxic T-Lymphocyte Epitopes," 2010, vol. 202 J, Infectious Diseases, pp. 1171-1180.
Liu et al., Chimeric severe acute respiratory syndrome coronavirus (SARS-CoV)S glycoprotein and influenza matrix 1 efficiently form virus-like particles (VLPs) that protect mice against challenge with SARS-CoV. Vaccine. Sep. 2, 2011;29(38):6606-13. doi: 10.1016/j.vaccine.2011.06.111. Epub Jul. 14, 2011.
Liu et al., Potent neutralizing antibodies against multiple epitopes on SARS-CoV-2 spike. Nature. Aug. 2020;584(7821):450-456. doi: 10.1038/s41586-020-2571-7. Epub Jul. 22, 2020.
Liu, "AstraZeneca withdraws US COVID vaccine application, shifts focus to antibody treatments," Fierce Pharma, Nov. 10, 2022, 2 pages.
Loftus, Moderna Signals It May Enforce Covid-19 Vaccine Patents in Wealthy Nations. Wall Street Journal. Mar. 7, 2022. https://www.wsj.com/articles/moderna-signals-it-may-enforcecovid-I 9-vaccine-patents-in-wealthy-nations-11646699609.
Lorenzi, J.C., et al., Intranasal vaccination with messenger RNA as a new approach in gene therapy: Use against tuberculosis. BMC Biotechnol. Oct. 2010; 10(77): 1-11.
Love, et al., "Lipid-like materials for low-dose, in vivo gene silencing," Proceedings of the National Academy of Sciences, Feb. 2, 2010, vol. 107, No. 5 (pp. 1864-1869).
Lu et al., "Genomic characterisation and epidemiology of 2019 novel coronavirus: implications for virus origins and receptor binding", Lancet, 2020, vol. 395, pp. 565-574, epub 2020.
Lu et al., "Immunogenicity of DNA Vaccines Expressing Human Immunodeficiency Virus Type 1 Envelope Glycoprotein With and Without Deletions in the V1/2 and V3 Regions," AIDS Research & Human Retroviruses, pp. 151-155.
Lu et al., Bat-to-human: spike features determining 'host jump' of coronaviruses SARS-CoV, Mers-CoV, and beyond. Trends Microbiol. Aug. 2015;23(8):468-78. doi:10.1016 j.tim.2015.06.003. Epub Jul. 21, 2015.
Luo et al., "Synthetic DNA Delivery Systems," Nature Biotechnology, 18:33-37 (2008).
Lutz et al., Unmodified mRNA in LNPs constitutes a competitive technology for prophylactic vaccines. NPJ Vaccines. Oct. 19, 2017:2:29. doi: 10.1038/s41541-017-0032-6.
Ma et al., Intranasal vaccination with recombinant receptor-binding domain of MERS-Co V spike protein induces much stronger local mucosal immune responses than subcutaneous immunization: Implication for designing novel mucosal MERS vaccines. Vaccine. Apr. 11, 2014;32(18):2100-8. doi: 10.1016/j.vaccine.2014.02.004.
Ma, B. et al . . . HPV pseudovirions as DNA delivery vehicles. Ther Deliv. Apr. 2, 2011(4): 427-430.
Maclachlan, "Lipid Nanoparticle-mediated delivery of messenger RNA Presentation," 1st International mRNA Health Conference. Tubingen, Germany. Oct. 24, 2013. http://files.shareholder.com/downloads/ ABEA-50QJTB/262824 I 206x0x699789/47-543dl2-db34-4e6e-88a9-f3ae5d97bld2/MacLachlan mRNA Conf 2013 .pdf. Last accessed Dec. 22, 2016.
Madden et al., Systemic delivery of mRNA therapeutics using lipid nanoparticles (LNP): improved potency for novel LNP and influence of route of administration on protein expression. 2nd International mRNA Health Conference. Nov. 12, 2014.https://acuitastx.com/wpcontent/uploads/2015/0I/Poster-Second-International- mRNA-Health-Conference.pdf. 1 page.
Magee, W.E. et al, Marked stimulation of lymphocyte-mediated attack on tumor cells by target-directed liposomes containing immune RNA, Cancer Res., 1978, 38(4):1173-6.
Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8).
Maier, et al., Biodegradable lipids enabling rapidly eliminated lipid nanoparticles for systemic delivery of RNAi therapeutics, Molecular Therapy, Aug. 1, 2013, vol. 21, No. 8, pp. 1570-1578.
Malone et al., "Cationic liposome-mediated RNA transfection," Proceedings of the National Academy of Sciences, USA, Aug. 1989, vol. 86, No. 16 (pp. 6077-6081).
Mandal et al., Reprogramming human fibroblasts to pluripotency using modified mRNA. Nat Protoc. Mar. 2013;8(3):568-82. doi: 10.1038/nprot.2013.019. Epub Feb. 21, 2013.
Marc et al., Nucleic acid vaccination strategies against infectious diseases. Expert Opin Drug Deliv. 2015:12(12):1851-65. doi:10.1517/17425247.2015.1077559. Epub Sep. 12, 2015.
Marshall et al., "Ch. 79: Regulation and Testing of Vaccines," Plotkin's Vaccines, 7th edition, 2018, pp. 1547-1565.
Martin et al., "A SARS DNA Vaccine Induces Neutralizing Antibody and Cellular Immune Responses in Healthy Adults in a Phase I Clinical Trial," 2008, Vaccine (6 Pages).

(56) References Cited

OTHER PUBLICATIONS

Martinez-Flores et al., SARS-CoV-2 Vaccines Based on the Spike Glycoprotein and Implications of New Viral Variants. Front Immunol. Jul. 12, 2021;12:701501. doi: 10.3389/fimmu.2021.701501. eCollection 2021.
Martinon et al., "Induction of virus-specific cytotoxic T lymphocytes in vivo by liposome-entrapped mRNA," European Journal of Immunology, Jul. 1993, vol. 23, No. 7 (pp. 1719-1722).
Maruggi et al., mRNA as a Transformative Technology for Vaccine Development to Control Infectious Diseases. Mol Ther. Apr. 10, 2019;27(4):757-772. doi: 10.1016/j.ymthe.2019.01.020. Epub Feb. 7, 2019.
Marzi et al, Vaccines. An Ebola whole-virus vaccine is protective in nonhuman primates. Science. Apr. 24, 2015;348(6233):439-42. doi: 10.1126/science.aaa49 I 9. Epub Mar. 26, 2015.
Mas et al., Engineering, Structure and Immunogenicity of the Human Metapneumovirus F Protein in the Postfusion Conformation. PLoS Pathog. Sep. 9, 2016;12(9).
Matray et al., "Synthesis and properties of RNA analogs—oligoribonucleotide N3' ---> P5' phosphoramidates," Nucleic Acids Research, 1999, 27(20):3976-3985.
Matsuda et al., Determinants of initiation Codon Selection During Translation in Mammalian Cells, PLOS One, 2010, vol. 5, Issue 11, un. 1-13.
Matthew G. Stanton & Kerry E. Murphy-Benenato, "Messenger RNA as a Novel Therapeutic Approach," 2017, Topics in Medicinal Chemistry RNA Therapeutics, pp. 1-2 (Excerpts).
Maurer et al., "Spontaneous Entrapment of Polynucleotides upon Electrostatic Interaction with Ethanol-Destabilized Cationic Liposomes," Biophys. J., 80:2310-2326 (2001).
Mccallum et al., "N-terminal domain antigenic mapping reveals a site of vulnerability for SARS-CoV-2," Cell, 2021, vol. 184, Issue 9, pp. 2332-2347.
Mckay et al., Self-amplifying RNA SARS-CoV-2 lipid nanoparticle vaccine candidate induces high neutralizing antibody titers in mice. Nat Commun. Jul. 9, 2020;11(1):3523. doi: 10.1038/s41467-020-I 7409-9.
Mckenzie et al., Nucleic acid vaccines: tasks and tactics. Immunol Res. 2001; 24(3):225-44.
Mclellan et al., Structure and function of RSV surface glycoproteins. Curr Top Microbiol Immunol. 2013;372:83-104. doi: 10.1007 /978-3-642-38919-I _ 4.
Mclellan et al., Structure of respiratory syncytial virus fusion glycoprotein in the postfusion conformation reveals preservation of neutralizing epitopes. J Virol. Aug. 2011;85(15):7788-96.
Mclellan et al., Structure-based design of a fusion glycoprotein vaccine for respiratory syncytial virus. Science. Nov. 1, 2013;342(6158):592-8.
MEGAscript Kit Product Manual, Oct. 27, 2009. Ambion/ Invitrogen website: http://lools.invitrogen.com/contenl/sfs/ manuals/ cms_072987.pdf, (last accessed Mar. 17, 2013), 29 pages.
Mellits et al., Removal of double-stranded contaminants from RNA transcripts: synthesis of adenovirus VA RNAI from a T7 vector. 1990. Nucleic acids research, 18(18), 5401-5406. https://doi.org/ 10.1093/nar/18.18.5401.
Mendonca et al., Design of lipid-based nanoparticles for delivery of therapeutic nucleic acids. Drug Discov Today. Mar. 2023;28(3): 103505. doi: 10.1016/j.drudis.2023.103505. Epub Jan. 25, 2023.
Miao et al., Delivery of mRNA vaccines with heterocyclic lipids increases anti-tumor efficacy by STING-mediated immune cell activation. Nat Biotechnol 37, 117 4-1185 (2019). https://doi.org/ 10.1038/s41587-019-024 7-3.
Michel et al., Cationic Nanoliposomes Meet mRNA: Efficient Delivery of Modified mRNA Using Hemocompatible and Stable Vectors for Therapeutic Applications. Mol Ther Nucleic Acids. Sep. 15, 2017;8:459-468. doi: 10.1016/j.omtn.2017.07.013. Epub Jul. 25, 2017.
Middleton et al., Hendra virus vaccine, a one health approach to protecting horse, human, and environmental health. Emerg Infect Dis. Mar. 2014;20(3):372-9. doi: 10.3201/eid2003.13 I 159.
Midoux et al., "Lipid-based mRNA vaccine delivery systems," Expert Review Vaccines, Feb. 2015, vol. 14, No. 2 (pp. 221-234).
Midoux et al., Lipid-based mRNA vaccine delivery systems. Expert Rev Vaccines. Feb. 2015;I4(2):221-34. doi: 10.1586/14760584.2015. 986104. Epub Dec. 26, 2014. Review.
Mignone, F., et al., "Untranslated regions of mRNAs," Genome Biology, vol. 3, No. 3, pp. 1-10, BioMed Central Ltd (2002).
Mitchell, DA et al., RNA transfected dendritic cells as cancer vaccines. Curr Opin Mol Ther. Apr. 2000;2(2):176-81.
Mitchell, DA et al., RNA-transfected dendritic cells in cancer immunotherapy. J Clin Invest. Nov. 2000;I06 (9):1065-9.
Mochida et al., Exogenous mRNA encoding tetanus or botulinum neurotoxins expressed in Aplysia neurons. Proc Natl Acad Sci US A. Oct. 1990;87(20):7844-8. doi: 10.1073/pnas.87.20.7844.
Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Moderna Form 10-K for the fiscal year ended Dec. 31, 2018.
Moderna Form 10-K for the fiscal year ended Dec. 31, 2022.
Moderna Form 10-Q for the quarterly period ended Jun. 30, 2024.
Moderna Form 8-K, Mar. 16, 2020.
Moderna, Inc. 2020 Form 10-K.
Moderna, Inc. 2023 Form 10-K.
Moderna, Inc., Patents, https://www.modernatx.com/patents (3 Pages).
Moderna, Science & Technology Day dated May 17, 2022.
Moderna, Vaccines and Related Biological Products Advisory Committee Presentation: Moderna COVID-19 Variant Vaccines; MOD_ 000767652-MOD_000767686, dated Jun. 15, 2023, 35 pages.
*ModernaTX, Inc. et al* v. *Pfizer Inc.et al*. (D. Mass. 22-11378-RGS) D.I. 105—District Court Memorandum and Order on Claim Construction, Aug. 1, 2023. 15 pages.
*ModernaTX, Inc. et al*.v. *Pfizer Inc.et al*. (D. Mass. 22-11378-RGS) D.I. 1—Complaint for Patent Infringement, Aug. 26, 2022. 39 pages.
*ModernaTX, Inc. et al*.v. *Pfizer Inc.et al*. (D. Mass. 22-11378-RGS) D.I. 45—Answer to the Complaint, Dec. 5, 2022. 81 pages.
Modjarrad., MERS-CoV vaccine candidates in development: The current landscape. Vaccine. Jun. 3, 2016;34(26):2982-2987. doi: 10.1016/j.vaccine.2016.03.104. Epub Apr. 12, 2016.
Moffat et al., "Functions of the C-Terminal Domain of Varicella-Zoster Virus Glycoprotein E in Viral Replication In Vitro and Skin and T-Cell Tropism In Vivo," Journal of Virology, Nov. 2004, 78(22):12406-12415.
Mok et al., "Fusion Protein [Human metapneumovirus]," 2006, J. Virol. vol. 81, No. 24, GenBank Accession No. ABM67072. 1 page.
Mok et al., An Alphavirus Replicon-Based Human Metapneumovirus Vaccine Is Immunogenic and Protective in Mice and Cotton Rats. J Virol. Nov. 2008; 82(22): 11410-11418.
Monika Kumari et al., A critical overview of current progress for COVID-19: development of vaccines, antiviral drugs, and therapeutic antibodies, J. Biomed Sci 29(68) (2022).
Mullard, COVID-19 vaccine success enables a bolder vision for mRNA cancer vaccines, says BioNTech CEO. Nat Rev Drug Discov. Jul. 2021;20(7):500-501. doi: 10.1038/d41573-021-00110-x.
Mullen et al., Mapping of intracellular localization domains and evidence for colocalization interactions between the IE110 and IE175 nuclear transactivator proteins of herpes simplex virus. J Viral. May 1994;68(5):3250-66. doi: 10.1128/JVI.68.5.3250-3266. 1994.
Muller, M.R. et al., Transfection of dendritic cells with RNA induces CD4- and CD8-mediated T cell immunity against breast carcinomas and reveals the immunodominance of presented T cell epitopes. J Immunol. Jun. 15, 2003;170(12):5892-6.
Mulligan et al., Phase I/II study of COVID-19 RNA vaccine BNT162b1 in adults. Nature. Oct. 2020; 586(7830):589-593. doi: 10.1038/s41586-020-2639-4. Epub Aug. 12, 2020.
Munster et al., Hemagglutinin [Influenza A virus (A/mallard/Sweden/ 91/2002(H7N9))]. GenBank: AAY46211.1. Dep. Sep. 30, 2005.
Muthumani et al., A synthetic consensus anti-spike protein DNA vaccine induces protective immunity against Middle East respira-

(56) References Cited

OTHER PUBLICATIONS tory syndrome coronavirus in nonhuman primates. Sci Transl Med. Aug. 19, 2015;7(301):30Iral32. doi: 10.1126/scitranslmed.aac7462.
Nagata, Synthesis and Biological Activity of Artificial mRNA Prepared, with Novel Phosphorylating Reagents, Nucleic Acids Research, 2010, vol. 38, No. 21, pp. 7845-7857.
Nagata, T. et al., Codon optimization effect on translational efficiency of DNA vaccine in mammalian cells: analysis of plasmid DNA encoding a CTL epitope derived from microorganisms. Biochem Biophys Res Commun. Aug. 2, 1999;261 (2):445-51.
Nair, S. et al., Soluble proteins delivered to dendritic cells via pH-sensitive liposomes induce primary cytotoxic T lymphocyte responses in vitro. J Exp Med. Feb. 1, 1992;175(2):609-12.
Nakayama et al., "Comparison of Current Regulatory Status for Gene-Based Vaccines in the U.S., Europe and Japan," 2015, Vaccines, pp. 186-202.
Nance et al.,Modifications in an Emergency: The Role of NI-Methylpseudouridine in COVID-19 Vaccines. ACS Cent Sci. May 26, 2021;7(5):748-756. doi: 10.1021/acscentsci.Ic00197. Epub Apr. 6, 2021.
Narayanan et al., Interplay between viruses and host mRNA degradation. Biochim Biophys Acta. Jun.-Jul. 2013;1829(6-7):732-41.
National Human Genome Research Institute, "Double Helix," 2023, NIH, https://www.genome.gov/geneticsglossary/Double-Helix (2 Pages).
National Human Genome Research Institute, Central Dogma, 2023, NIH, https://www.genome.gov/geneticsglossary/Central-Dogma (4 Pages).
Nedialkov et al., NTP-driven translocation by human RNA polymerase II. J Biol Chem. May 16, 2003;278(20):18303-12. doi: 10.1074/jbc.M301103200. Epub Mar. 13, 2003.
No Author Listed], "Messenger RNA" definition. Collins Dictionary of Science. 2005:514.
No Author Listed], Moderna Announces FDA Authorization of Moderna COVID 19 Vaccine in U.S. Press Release. Dec. 19, 2020. 3 pages.
No Author Listed], Moderna Announces Positive Interim Phase I Clinical Data Demonstrating First mRNA Vaccine Candidate, mRNA-1440, Induces High Levels of Immunogenicity. Moderna Press Release. Apr. 27, 2017. 5 pages.
Onpattro, "Highlights of Prescribing Information," FDA Prescribing Label, Aug. 2018, 14 pages.
Oostvogels et al., Phase 1 Assessment of the Safety and Immunogenicity of an mRNA-Lipid Nanoparticle Vaccine Candidate Against SARS-Co V-2 in Human Volunteers. medRxiv Nov. 9, 2020. 20228551;1-38. doi: https://doi.org/10.1101/2020.11.09.20228551.
Openshaw et al., "Immune Responses and Disease Enhancement During Respiratory Syncytial Virus Infection," 2005, Clinical Microbiology Reviews, vol. 18, Issue 13, pp. 541-555.
Opposition against European Patent No. 3324979 B 1, filed by BioNTech SE (Opponent) against ModernaTX, Inc. (Patentee) on Jul. 10, 2023. 86 pages.
Ostro et al., "Evidence for translation of rabbit globin mRNA after liposome-mediated insertion into a human cell line," 1978, Nature, pp. 921-923.
Ouranidis et al., Pharma 4.0 Continuous mRNA Drug Products Manufacturing. Pharmaceutics. Aug. 31, 2021;13(9):1371. doi: 10.3390/pharmaceutics13091371.
Painter, H., et al., 494. Topical delivery of mRNA to the murine lung and nasal epithelium. Mol Ther. 2004: 9: S187.
Palese, P., Making Better influenza Virus Vaccines?, Emerging Infectious Diseases, vol. 12, No. 1, Jan. 2006, pp. 61-65.
Pallesen et al., "Immunogenicity and structures of a rationally designed prefusion MERS-CoV spike antigen," 2017, Proc Natl. Acad. Sci. USA, Article E7348.
Paoletti, E., "Applications of pox virus vectors to vaccination: an update," Proceedings of the National Academy of Sciences, Oct. 1996, vol. 93 (pp. 11349-11353).
Paramasivam et al., "Endosomal Escape of Delivered mRNA from Endosomal Recycling Tubules Visualized at the Nanoscale," 221 J. Cell Biology e202110137.
Pardi et al., Developing an influenza vaccine using lipid nanoparticle-encapsulated nucleoside-modified mRNA. Eur. J. Immunol. Aug. 2016;46(SI):1232-1233. Abstract 1349.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/i.iconrel. 2015.08.007. Epub Aug. 8, 2015.
Pardi et al., mRNA vaccines—a new era in vaccinology. Nat Rev Drug Discov. Apr. 2018;17(4):261-279.
Pardi et al., Nucleoside-modified mRNA vaccines induce potent T follicular helper and germinal center B cell responses. J Exp Med. Jun. 4, 2018;215(6):1571-1588. doi: 10.1084/jem.20171450. Epub May 8, 2018.
Pardi et al., Zika virus protection by a single low-dose nucleoside-modified mRNA vaccination. Nature. Mar. 9, 2017;543(7644):248-251. doi: 10.1038/nature21428. Epub Feb. 2, 2017.
Parisien et al., Rationalization and prediction of selective decoding of pseudouridine-modified nonsense and sense codons. RNA. Mar. 2012;I8(3):355-67. doi: 10.1261/rna.031351.111. Epub Jan. 26, 2012.
Park et al., "Non-Viral COVID-19 Vaccine Delivery Systems," Advanced Drug Delivery Reviews, pp. 137-151.
Park et al., The Miracle Workers. Heroes of the Year. TIME Magazine. 2021: 17 pages.
Pascolo, S., "Vaccination with Messenger RNA (mRNA)," 2008, Handbook of Experimental Pharmacology, pp. 221-235.
Pascolo., Messenger RNA-based vaccines. Expert Opin Biol Ther. Aug. 2004;4(8): 1285-94. doi: 10.1517/14712598.4.8.1285.
Patel et al., Naturally-occurring cholesterol analogues in lipid nanoparticles induce polymorphic shape and enhance intracellular delivery of mRNA. Nat Commun. Feb. 20, 2020;11(1):983. doi: 10.1038/s41467-020-14527-2.
Patent Sublicense Agreement Between Cellscript, LLC and ModernaTx, Inc., dated Jun. 26, 2017.
Pathak et al., Intra-host variability in global SARS-CoV-2 genomes as signatures of RNA editing: implications in viral and host response outcomes. bioRxiv Dec. 9, 2020; 2020. 12.09.417519; doi: https://doi.org/10.1101/2020.12.09.417519. 32 pages.
Peabody et al., Termination-reinitiation occurs in the translation of mammalian cell mRNAs. Mol Cell Biol. Jul. 1986;6(7):2695-703. doi: 10.1128/mcb.6.7.2695-2703.1986.
Peculis, B. RNA processing: pocket guides to ribosomal RNA. Curr Biol. Aug. 1, 1997; 7(8):R480-2.
Peek et al., "Nanotechnology in vaccine delivery," 2008, Adv. Drug Deliv. Rev., pp. 915-928.
Pegu et al., "Durability of mRNA-1273 vaccine-induced antibodies against SARSCoV-2 variants," 2021, Science, pp. 1-5.
Petition For Inter Partes Review of U.S. Pat. No. 10,702,600. *BioNTech SE and Pfizer Inc.* (Petitioners) v. *ModernaTX, Inc.* (Patent Owner). Filed Aug. 28, 2023. 87 pages.
Petition For Inter Partes Review of U.S. Pat. No. 10,933,127. *BioNTech SE and Pfizer Inc.* (Petitioners) v. *ModernaTX, Inc.* (Patent Owner). Filed Aug. 28, 2023. 89 pages.
Petition For Inter Partes Review of U.S. Pat. No. 8,058,069 (IPR2019-00554). *Moderna Therapeutics, Inc.* (Petitioner) v. *Arbutus Biopharma Corporation* (Patent Owner). Filed Nov. 15, 2011. 81 pages.
Petsch et al., "Protective efficacy of in vitro synthesized, specific mRNA vaccines against influenza A virus infection," 2012, Nature Biotechnology, vol. 30, No. 12, pp. 1210-1216.
Pfoh et al., Crystal Structure of USP7 Ubiquitin-like Domains with an ICPO Peptide Reveals a Novel Mechanism Used by Viral and Cellular Proteins to Target USP7. PLoS Pathog. Jun. 5, 2015; I 1(6):e1004950. doi: 10.137 I/journal.ppat.1004950.
Phua et al., Mesenger RNA (mRNA) nanoparticle tumour vaccination. Nanoscale. Jul. 21, 2014:6(14):7715-29. dsoi: 10.1039/c4nr01346h.
Phue et al., Modified *Escherichia coli* B (BL21), a superior producer of plasmid DNA compared with *Escherichia coli* K (DH5alpha). Biotechnol Bioeng. Nov. 1, 2008;101(4):831-6. doi: 10.1002/bit. 21973.
Pine et al., Development of an mRNA-lipid nanoparticle vaccine against Lyme disease. Mol Ther. Sep. 6, 2023;31(9):2702-2714. doi: 10.1016/j.ymthe.2023.07.022. Epub Aug. 2, 2023.

(56) References Cited

OTHER PUBLICATIONS

Plotkin, S., A., "Vaccines: Past, Present and Future, 11 Nature Medicine Supplement 55," 2005, Historical Perspective, Nature Medicine, pp. S5-S11.
Polack, Fernando P., et al. "Safety and efficacy of the BNT162b2 mRNA Covid-19 vaccine." New England journal of medicine 383.27 (2020): 2603-2615. (Year: 2020).
Pollard et al., Type I IFN counteracts the induction of antigen-specific immune responses by lipid-based delivery of mRNA vaccines. Mol Ther. Jan. 2013; 21 (1): 251-259.
Poveda et al., Establishing Preferred Product Characterization for the Evaluation of RNA Vaccine Antigens. Vaccines (Basel). Sep. 27, 2019;7(4):131. doi: 10.3390/vaccines7040131.
Press Release, Novavax, U.S. FDA Grants Emergency Use Authorization for Novavax COVID-19 Vaccine, Adjuvanted for Individuals Aged 18 and Over (Jul. 13, 2022).
Pro Hac Vice Declaration of Amy K. Wigmore in IPR2023-01358 dated Apr. 16, 2024.
Pro Hac Vice Declaration of Amy K. Wigmore in IPR2023-01359 dated Apr. 16, 2024.
Pro Hac Vice Declaration of Andrew J. Danford in IPR2023-01358 dated Jul. 1, 2024.
Pro Hac Vice Declaration of Joshua L. Stern in IPR2023-01358 dated Apr. 17, 2024.
Pro Hac Vice Declaration of Kevin S. Prussia in IPR2023-01358 dated Apr. 17, 2024.
Pro Hac Vice Declaration of Kevin S. Prussia in IPR2023-01359 dated Apr. 17, 2024.
Probst et al., Characterization of the ribonuclease activity on the skin surface. Genet Vaccines Ther. May 29, 2006;4:4. doi: 10.1186/1479-0556-4-4.
Probst, I, et al., Spontaneous cellular uptake of exogenous messenger RNA in vivo is nucleic acid-specific, saturable and ion dependent. Gene Therapy. 2007; 14: 1175-1180.
Programme of the 1st International mRNA Health Conference, Germany; Oct. 2013. 32 pages.
*Promosome, LLC* v. *Moderna, Inc.* (S.D. Cal. 23-cv-1047-JES-DDL) D.I. 1—Complaint for Patent Infringement, Jun. 6, 2023. 51 pages.
*Promosome, LLC* v. *Moderna, Inc.* (S.D. Cal. 23-cv-1047-JES-DDL) D.I. 30—Notice of Dismissal, Sep. 19, 2023. 4 pages.
Pulford, B., et al., Liposome-siRNA-peptide complexes cross the blood-brain barrier and significantly decrease PrP'C on neuronal cells and PrP'RES in infected cell cultures. PLoS ONE. 201 O; 5(6): e11085.
Pulliam et al., Increased risk of SARS-CoV-2 reinfection associated with emergence of the Omicron variant in South Africa. medRxiv 2021. doi:10.1101/2021.I I.I I.21266068:2021.I I.I I.21266068. 42 pages.
Qu et al., Design, synthesis and biological evaluation of multivalent glucosides with high affinity as ligands for brain targeting liposomes. Eur J Med Chem. Jan. 24, 2014;72: 110-8. doi: 10.1016/j.ejmech.2013.10.007. Epub Nov. 20, 2013.
Rabinovich, P.M., et al., Synthetic messenger RNA as a tool for gene therapy. Hum. Gene Ther. Oct. 2006; 17: 1027-1035.
Raj et al., "Dipeptidyl peptidase 4 is a functional receptor for the emerging human coronavirus—EMC," Nature, vol. 495, 6 pages (Mar. 13, 2013).
Ramamoorth et al., Non Viral vectors in gene therapy—an overview. J Clin Diagn Res. Jan. 2015; 9(1) GE01-GE06.
Ramamoorth et al., Nonviral vectors in gene therapy—an overview. J Clin Diagn Res. Jan. 2015; 9(I ): GE01-GE06.
Rammensee et al., Peptides naturally presented by MHC class I molecules. Annu Rev Immunol. 1993; 11 :213-44.
Read M, et al. (2005) A versatile reducible polycation-based system for efficient delivery of a broad range of nucleic acids. Nucleic Acids Research, 33(9): 1-16.
Regalado, Don't panic about the latest coronavirus mutations say drug companies. MIT Technology Review. Dec. 23, 2020. 5 pages.
Regalado, Moderna believes it could update its coronavirus vaccine without a big new trial. MIT Technology Review. Jan. 13, 2021. 4 pages.
Regla-Nava et al., "Severe Acute Respiratory Syndrome Coronaviruses with Mutations in the E Protein Are Attenuated and Promising Vaccine Candidates," 2015, vol. 89, Journal of Virology (18 Pages).
Reichmuth et al., "mRNA Vaccine Delivery Using Lipid Nanoparticles." Ther. Deliv. 2016;7(5):319-34. doi: 10.4155/tde-2016-0006.
Reichmuth, et al., "mRNA Vaccine Delivery Using Lipid Nanoparticles," Therapeutic Delivery, Apr. 2016, vol. 7, No. 5 (pp. 319-334).
Rejman et al., mRNA transfection of cervical carcinoma and mesenchymal stem cells mediated bv cationic carriers. J Controlled Rel. Nov. 2010; 147(3): 385-391.
Ren et al., Full genome of influenza A (H7N9) virus derived by direct sequencing without culture. Emerg Infect Dis. Nov. 2013;19(11):1881-4. doi: 10.3201/eidl 911.130664.
Ren et al., Recent vaccine development for human metapneumovirus. J Gen Virol. Jul. 2015;96(Pt 7):1515-20.
Reply Declaration of Daniel Griffin in IPR2023-01358 dated Aug. 30, 2024. (Redacted public version).
Reply Declaration of Daniel Griffin in IPR2023-01359 dated Aug. 30, 2024. (Redacted public version).
Reply Declaration of James Moon in IPR2023-01358 dated Aug. 30, 2024. (Redacted public version).
Reply Declaration of James Moon in IPR2023-01359 dated Aug. 30, 2024. (Redacted public version).
Reyes-Sandoval, A et al., DNA Vaccines. Curr Mol Med. May 2001; 1(2):217-43.
Richner, et al., "Modified mRNA vaccines protect against Zika virus infection," Cell, Mar. 9, 2017, vol. 168 No. 6 (pp. 1114-1125).
Rittig et al., Intradermal vaccinations with RNA coding for TAA generate CD8+ and CD4+ immune responses and induce clinical benefit in vaccinated patients. Mol Ther. May 2011;I9(5):990-9. doi: 10.1038/mt.2010.289. Epub Dec. 28, 2010.
Robbins et al., Moderna Backs down in its Vaccine Patent Fight with the NIH. New York Times. Dec. 17, 2021: 1 page.
Robbins, et al., 2'-O-methyl-modified RNAs Act as TLR7 Antagonists, Molecular Therapy, 2007, vol. 15, No. 9, on. 1663-1669.
Robinson, F. et al., "Expression of human nPTB is limited by extreme suboptimal codon content." PLoS One. Mar. 12, 2008;3(3):el801.
Robinson, H.L. et al., Protection against a lethal influenza virus challenge by immunization with a haemagglutinin-expressing plasmid DNA. Vaccine. 1993;11(9):957-60.
Rock, KL et al., A new foreign policy: MHC class I molecules monitor the outside world. Immunol Today. Mar. 1996;17(3): 131-7.
Rockoff, Startup Moderna Shows Promise in Vaccine Trial. The Wall Street Journal. Apr. 27, 2017. 2 pages.
Rod Daniels, "Surveillance Report: Influenza virus characterisation," 2012, ECOC (11 Pages).
Rodriguez-Gascon et al., Development of nucleic acid vaccines: use of self-amplifying RNA in lipid nanoparticles. Int J Nanomedicine. 2014; 9: 1833-1843.
Rongbao et al., GISAID Accession No. EPI497477, Dec. 20, 2013.
Rosa et al., mRNA vaccines manufacturing: Challenges and bottlenecks. Vaccine. Apr. 15, 2021;39(16):2190-2200. doi: 10.1016/j.vaccine.2021.03.038. Epub Mar. 24, 2021.
Ross, J. Control of messenger RNA stability in higher eukaryotes. Trends Genet. 1996. May 12(5):171-5.
Rossi et al., IRES-based Venezuelan equine encephalitis vaccine candidate elicits protective immunity in mice. Virology. Mar. 15, 2013;437(2):81-8. doi: 10.1016/j.virol.2012.11.013. Epub Jan. 22, 2013.
Rozenski et al., The RNA Modification Database: 1999 update. Nucleic Acids Res. Jan. 1, 1999;27(1):196-7.
Sabnis et al., "A novel amino lipid series for mRNA delivery: improved endosomal escape and sustained pharmacology and safety in non-human primates," Mol. Ther. 26, 1509-1519 (2018).
Saenz-Badillos et al., RNA as a tumor vaccine: a review of the literature. Exp Dermatol. Jun. 2001;10(3):143-54.
Sahdev et al., Biomaterials for Nanoparticle Vaccine Delivery Systems, Pharmaceutical Research, 2014, pp. 2563-2582.

(56) References Cited

OTHER PUBLICATIONS

Sahin et al., An RNA vaccine drives immunity in checkpoint-inhibitor-treated melanoma. Nature. Sep. 2020;585(7823):107-112. doi: 10.1038/s41586-020-2537-9. Epub Jul. 29, 2020.
Sahin et al., mRNA-based therapeutics—developing a new class of drugs. Nat Rev Drug Discov. Oct. 2014;13(10):759-80. doi: 10.1038/nrd4278. Epub Sep. 19, 2014.
Sahin et al., Personalized RNA mutanome vaccines mobilize poly-specific therapeutic immunity against cancer. Nature. Jul. 13, 2017;547(7662):222-226. doi: 10.1038/nature23003. Epub Jul. 5, 2017.
Salomon et al., A liposomal RNA vaccine inducing neoantigen-specific CD4 T cells augments the anti tumor activity of local radiotherapy in mice. Oncoimmunology. Jun. 22, 2020;9(1):1771925. doi: 10.1080/2162402X.2020.1771925.
Santoro et al., An efficient system for the evolution of aminoacyl-tRNA synthetase specificity. NatBiotechnol. Oct. 2002;20(10):1044-8. doi: 10.1038/nbt742.
Sarkar et al., S glycoprotein diversity of the Omicron variant. medRxiv 2021. doi: 10.1101/2021.12.04.21267284:2021.12.04.21267284. 30 pages.
Satz et al., Mechanism of immune transfer by RNA extracts. Immune RNA induces the synthesis of idiotype-bearing antigen receptors in noncommitted cells. Mol Cell Biochem. Dec. 16, 1980;33(3): 105-13.
Sayour et al., "RNA nanoparticle vaccines facilitate and sustain adoptive cellular therapy targeting pediatric intracranial malignancies," Pediatric Blood and Cancer, Jun. 2015, vol. 62, Supp. Supplement 2, pp. S24, Abstract No. 4012.
Scheel et al., Immunostimulating capacities of stabilized RNA molecules. Eur J Immunol. Feb. 2004;34(2):537-47.
Schirmacher et al., Intra-pinna anti-tumor vaccination with self-replicating infectious RNA or with DNA encoding a model tumor antigen and a cytokine. Gene Ther. 2000 Ju1;7(13):1137-47.
Schlake et al., "Developing mRNA-vaccine technologies," 2012, RNA Biology. vol. 9. Issue 11. pp. 1319-1330.
Schmidt et al., Fast and Flexible mRNA Vaccine Manufacturing as a Solution to Pandemic Situations by Adopting Chemical Engineering Good Practice-Continuous Autonomous Operation in Stainless Steel Equipment Concepts. Processes. 2021 ;9(11): 1874-93.
Schmidt et al., Progress in the development of human parainfluenza virus vaccines. Expert Rev. Respir Med. Aug. 2011:5(4): pp. 515-526.
Schmitt, W.E. et al., In vitro induction of a bladder cancer-specific T-cell response by mRNA-transfected dendritic cells. J Cancer Res Clin Oneal. 2001 ;127(3):203-6.
Schneider et al., Measuring control of transcription initiation by changing concentrations of nucleotides and their derivatives. Methods Enzymol. 2003:370:606-17. doi: 10.1016/S0076-6879(03)70051-2.
Schoenmaker et al., mRNA-lipid nanoparticle COVID-19 vaccines: Structure and stability. Int J Pharm. May 15, 2021;601:120586. doi: 10.1016/j.ijpharm.2021.120586. Epub Apr. 9, 2021.
Schott et al., "Viral and non-viral approaches for transient delivery of mRNA and proteins," Current Gene Therapy, Oct. 2011, vol. 11, No. 5 (pp. 382-398).
Schumann et al., Multiple links between 5-methylcytosine content of mRNA and translation. BMC Biol. Apr. 15, 2020;18(1):40. doi: 10.I 186/s12915-020-00769-5.
Schuurhuis et al., Ins and outs of dendritic cells. Int Arch Allergy Immunol. 2006;140(1):53-72. doi: 10.1159/000092002. Epub Mar. 13, 2006.
Schwendener, Liposomes as vaccine delivery systems: a review of the recent advances. Ther Adv Vaccines. Nov. 2014;2(6):159-82. doi: 10. 1177/2051013614541440.
Segura, J., et al., Monitoring gene therapy by external imaging of mRNA: Pilot study on murine erythropoietin. Ther Drug Monit. Oct. 2007; 29(5): 612-8.
Semple et al., "Efficient encapsulation of antisense oligonucleotides in lipid vesicles using ionizable aminolipids: Formation of novel small multilamellar vesicle structures," 2001, Biochimica Et Biophysica Acta, pp. 152-166.
Semple et al., "Rational design of cationic lipids for siRNA delivery," 2010, Nature Biotechnology, pp. 172-178.
Shamriz et al., "Effect of linker length and residues on the structure and stability of a fusion protein with malaria vaccine application," Comput Biol Med., Sep. 2016, 76:24-29.
Sharp, J.S. et al., Effect of translational signals on mRNA decay in Bacillus subtilis. J Bacteriol. Sep. 2003; 185 (18):5372-9.
Shaw et al., "The Path to an RSV Vaccine," 2013, Current Opinion in Virology, pp. 332-342.
Shidhadye et al., Solid lipid nanoparticles and nanostructured lipid carriers—innovative generations of solid lipid carriers. Curr Drug Deliv. Oct. 2008; 5(4):324-3 I. doi: 10.2174/156720108785915087.
Shim et al., "Intranasal immunization with plasmid DNA encoding spike protein of SARS-coronavirus/polyethylenimine nanoparticles elicits antigen-specific humoral and cellular immune responses," BMC Immunology, vol. 11, No. 65 (9 pages).
Shin et al., Recent Advances in RNA Therapeutics and RNA Delivery Systems Based on Nanoparticles. Adv. Therap., Nov. 2018;I0):1800065. Review.
Sirin et al. AB-Bind: Antibody binding mutational database for computational affinity predictions. Protein Sci. Feb. 2016;25(2):393-409. doi: 10.1002/pro.2829. Epub Nov. 6, 2015.
Skidmore et al.,Genomic Sequencing of SARS-CoV-2 E484K Variant B.1.243.1, Arizona, USA. Emerg Infect Dis. Oct. 2021;27(10):2718-2720. doi: 10.3201/eid2710.211189.
Slimko et al., "Codon optimization of Caenorhabditis elegans GluCI ion channel genes for mammalian cells dramatically improves expression levels," 2003, Journal of Neuroscience Methods, 7 pages.
Smits, E., et al., RNA-based gene transfer for adult stem cells and T cells. Leukemia. 2004; 18: 1898-1902.
Sohn, R.L., et al., In-vivo particle mediated delivery of mRNA to mammalian tissues: ballistic and biological effects. Wound Rep and Regen. Jul.-Aug. 2001; 287-296.
Song et al., "Middle East Respiratory Syndrome Coronavirus Spike Protein Delivered by Modified Vaccinia Virus Ankara Efficiently Induces Virus-Neutralizing Antibodies," 2013, 87 J. of Virology, pp. 1-5.
Spikevax (COVID-19 Vaccine, mRNA), "Highlights of Prescribing Information," FDA Label, Apr. 2024, 45 pages.
Spikevax (COVID-19 Vaccine, mRNA), "Highlights of Prescribing Information," FDA Label, Jan. 2025, 43 pages.
Spikevax (COVID-19 Vaccine, mRNA), "Highlights of Prescribing Information," FDA Label, Sep. 2023, 45 pages.
Spiro et al., Hemgagglutinin [Influenza A Virus (A/turkey/Italy/4426/2000(H7N1)] GenBank Accession No. ABO77067.1, pub. Apr. 2, 2007.
Spiro et al., The NIAID, Influenza Genome Sequencing Project, Hemagglutinin [Influenza A Virus (A/duck/Italy/4692-9/2004(H7)], GenBank Accession No. AEK65976, pub. Aug. 2, 2011.
Squires, et al., Widespread occurrence of 5-methylcytosine in human coding an non-coding RNC, Nucleic Acids Research. 2012. vol. 40, No. 11. DP. 5023-5033.
Stab et al., "Protective efficacy and immunogenicity of a combinatory DNA vaccine against Influenza A Virus and the Respiratory Syncytial Virus." PLoS One. Aug. 14, 2013;8(8):e72217 doi: 10.1371/journal.pone.0072217. eCollection 2013.
Stanekova et al., Conserved epitopes of influenza A virus inducing protective immunity and their prospects for universal vaccine development. Virol J. Nov. 30, 2010:7:351.
Steel et al., "Influenza Virus Vaccine Based on the Conserved Hemagglutinin Stalk Domain," mBio, May 18, 2010, 1(1):e00018-10, 9 pages.
Steinle et al., Concise Review: Application of In Vitro Transcribed Messenger RNA for Cellular Engineering and Reprogramming: Progress and Challenges. Stem Cells. Jan. 2017;35(1):68-79. doi: 10.1002/stem.2402. Epub Jun. 20, 2016.

(56) References Cited

OTHER PUBLICATIONS

Steitz et al., "Effective Induction of Anti-Melanoma Immunity Following Genetic Vaccination with Synthetic mRNA Coding for the Fusion Protein EGFP.TRP2," Cancer Immunology, Mar. 2006, 55(3):246-253.
Stenler et al., "Safety and efficacy of DNA vaccines: Plasmids vs. minicircles," 2014, vol. 10, Issue 5, Human Vaccines & Immunotherapeutics.
Stephenson et al., Cross-reactivity to highly pathogenic avian influenza H5N1 viruses after vaccination with nonadjuvanted and MF59-adjuvanted influenza A/Duck/Singapore/97 (H5N3) vaccine: a potential priming strategy. J infect Dis. Apr. 15, 2005;191(8): 1210-1215. doi: 10.1086/428948.
Stewart-Jones et al., "Domain-based mRNA vaccines encoding spike protein N-terminal and receptor binding domains confer protection against SARS-CoV-2," Science Translational Medicine, Sep. 13, 2023, 15(713):eadf4100, 16 pages.
Strobel, I., et al., Human dendritic cells transfected with either RNA or DNA encoding influenza matrix protein M1 differ in their ability to stimulate cytotoxic T lymphocytes. Gene Ther. Dec. 2000; 7(23): 2028-2035.
Strong, V.T. et al., Incorporation of beta-globin untranslated regions into a Sindbis virus vector for augmentation of heterologous mRNA expression. Gene Ther. Jun. 1997;4(6):624-7.
Sullenger et al., Emerging clinical applications of RNA. Nature. Jul. 11, 2002;418(6894):252-8.
Szebeni et al., "Activation of complement by therapeutic liposomes and other lipid excipient-based therapeutic products: prediction and prevention," 2011, Adv Drug Deliv Rev., Sep. 16;63(12):1020-30. doi: 10.1016/j.addr.2011.06.017. Epub Jul. 14, 2011.
Szebeni et al., "Complement activation as a bioequivalence issue relevant to the development of generic liposomes and other nanoparticulate drugs," Biochem Biophys Res Commun. Dec. 18, 2015;468(3):490-7. doi: 10.1016/j.bbrc.2015.06.177. Epub Jul. 14, 2015. PMID: 26182876.
Szebeni, J. Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014.
Tai et al., "Characterization of the receptor-binding domain (RBD) of 2019 novel coronavirus: implication for development of RBD protein as a viral attachment inhibitor and vaccine", Cellular & Molecular Immunology, vol. 17, Mar. 19, 2020, pp. 613-620.
Tam et al., Advances in Lipid Nanoparticles for siRNA Delivery. Pharmaceutics. Sep. 18, 2013; vol. 5, Issue 3, pp. 498-507. doi: 10.3390/pharmaceutics5030498.
Tang et al., A host-range restricted parainfluenza virus type 3 (PIV3) expressing the human metapneumovirus (hMPV) fusion protein elicits protective immunity in African green monkeys. Vaccine. Feb. 25, 2005;23(14):1657-67.
Tavernier et al., "mRNA as gene therapeutic: How to control protein expression," Journal of Controlled Release, Mar. 2011, vol. 150, No. 3 (pp. 238-247).
Tegally al., Emergence and rapid spread of a new severe acute respiratory syndrome related coronavirus 2 (SARS-Co V-2) lineage with multiple spike mutations in South Africa. medRxIV. 2020. 19 Pages. doi: 10.1101/2020.12.21.20248640.
Tenchov et al., "Lipid Nanoparticles—From Liposomes to mRNA Vaccine Delivery, a Landscape of Research Diversity and Advancement," ACS Nano, Jun. 28, 2021, 15(11):16982-17015.
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.
Teufel, R. et al., Human peripheral blood mononuclear cells transfected with messenger RNA stimulate antigen-specific cytotoxic T-lymphocytes in vitro. Cell Mol Life Sci. Aug. 2005;62(15):1755-62.
Tews et al., Chapter 2: Self-Replicating RNA. RNA Vaccines. 2017; 1499: 15-35. Published online Jun. 11, 2016. doi: 10.1007/978-1-4939-6481-9_2.
Thery et al., The cell biology of antigen presentation in dendritic cells. Curr Opin Immunol. Feb. 2001;I3(1):45-51. doi: 10.1016/s0952-7915(00)00180-1.
Thess et al., "Sequence-engineered mRNA Without Chemical Nucleoside Modifications Enables an Effective Protein Therapy in Large Animals.," Molecular Therapy, Sep. 2015, vol. 23, No. 9, pp. 1456-1464 (Epub Jun. 8, 2015 doi: 10.1038/mt.2015.103).
To et al., An overview of rational design of mRNA-based therapeutics and vaccines. Expert Opin Drug Discov. Nov. 2021;I6(11):1307-1317. doi: 10.1080/17460441.2021.1935859. Epub Jul. 19, 2021.
Torchilin, V. el al., Multifunctional and Stimuli-Sensitive Pharmaceutical Nanocarriers, Eur J. Pharm Biopharm, 2009, vol. 71, No. 3, pp. 431-444.
Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 12, 2014.
Tracy, M., "Progress in the Development of LNP Delivery for siRNA Advancing LNPs to the Clinic" International Liposome Research Days Meeting, Vancouver, Canada. Aug. 2010, pp. 1-52.
Triana-Alonso et al., Self-coded 3'-extension of run-off transcripts produces aberrant products during in vitro transcription with T7 RNA polymerase. J Biol Chem. Mar. 17, 1995;270(11):6298-307. doi: 10.1074/jbc.270.11.6298.
Trojan et al., Immune reactivity against a novel HLA-A3-restricted influenza virus peptide identified by predictive algorithms and interferon-gamma quantitative PCR. (2003) Journal of immunotherapy, 26(1), 41-46. https://doi.org/10.1097/00002371-200301000-00005.
Ueda, et al., Phosphorothioate-containing RNAs show mRNA activity in the prokaryotic translation systems in vitro. (1991). Nucleic acids research, 19(3), 547-552. https://doi.org/10.1093/nar/19.3.547.
Ulmer et al., "Heterologous Protection Against Influenza by Injection of DNA Encoding a Viral Proten," Science, (Mar. 19, 1993), vol. 259, No. 5102, pp. 1745-1749.
Ulmer et al., RNA-based vaccines. Vaccine. Jun. 22, 2012;30(30):4414-8. doi: 10.1016/j.vaccine.2012.04.060. Epub Apr. 28, 2012.
Updated Curriculum Vitae of Daniel O. Griffin, Ph.D.
Uzgun et al, PEGylation improves nanoparticle formation and transfection efficiency of messenger RNA. Pharm Res. Sep. 2011; 28(9); 2223-2232.
Valich, L., "COVID-19 Vaccine: What's RNA research got to do with it?" 2020, 18 pages.
Van Tendeloo, V.F., et al., mRNA-based gene transfer as a tool for gene and cell therapy. Curr Opin Mol Therapeutics. 2007: 9(5): 423-431.
Vardi et al., Moderna's Mysterious Medicines. Forbes. Dec. 14, 2016: 5 pages.
Vardi, Moderna's Mysterious Coronavirus Vaccine Delivery System. Forbes. Jul. 29, 2020: 9 pages.
Vassilev, V.B. et al., Microparticle-mediated RNA immunization against bovine viral diarrhea virus. Vaccine. Feb. 28, 2001;19(15-16):2012-9.
Vennema et al., "Early death after feline Infectious Peritonitis Virus Challenge due to Recombinant Vaccinia Virus Immunization," Journal of Virology, Mar. 1990, 64(3):1407-1409.
Vergati et al., "Strategies for Cancer Vaccine Development," 2010, Journal of Biomedicine and Biotechnology, (13 Pages).
Verma et al., Double-headed nucleosides: Synthesis and applications. Beilstein J Org Chem. Jun. 8, 2021;17:1392-1439. doi: 10.3762/bjoc.I 7.98.
Vogel et al., BNT162b vaccines protect rhesus macaques from SARS-CoV-2. Nature. Apr. 2021; 592(7853):283-289. doi: 10.1038/s41586-021-03275-y.
Von Niessen et al., Improving mRNA-Based Therapeutic Gene Delivery by Expression-Augmenting 3' UTRs Identified by Cellular Library Screening. Mol Ther. Apr. 10, 2019;27(4):824-836. doi: 10.1016/j.ymthe.2018.12.0II.
W. Michael McDonnell & Frederick K. Asari, Molecular medicine—DNA vaccines, 334 N. Engl. J. Med. 42 (1996).
W.R. Pearson et al., "Improved tools for biological sequence comparison", Proc. Natl. Acad. Sci. USA, Apr. 1988, pp. 2444-2448, vol. 85.

(56) References Cited

OTHER PUBLICATIONS

Walls et al., Crucial steps in the structure determination of a coronavirus spike glycoprotein using cryo-electron microscopy. Protein Sci. Jan. 2017;26(1): 113-121. doi: 10.1002/pro.3048.
Walls et al., Tectonic conformational changes of a coronavirus spike glycoprotein promote membrane fusion. Proc Natl Acad Sci US A. Oct. 17, 2017;II4(42):III57-11162. doi: 10.1073/pnas.1708727114.
Walsh et al., Safety and Immunogenicity of Two RNA-Based Covid-19 Vaccine Candidates. N Engl J Med. Oct. 14, 2020;NEJMoa2027906: 1-13. doi: 10.1056/NEJMoa2027906.
Walter et al., "Evaluation of the BNT162b2 COVID-19 Vaccine in Children 5 to 11 Years of Age," New England J. Med., 2022; 386: 35-46 (published online Nov. 9, 2021).
Wan et al., "Comparison of Immunogenicity Between Codon Optimized HIV-1 Thailand Subtype B gp140 and gp145 Vaccines," 2007, Vaccine, vol. 25, pp. 4949-4959.
Wan et al., Lipid nanoparticle delivery systems for siRNA-based therapeutics. Drug Deliv Transl Res. Feb. 2014; 4(1):74-83. doi:10.1007/s13346-013-0161-z.
Wang et al., "Evaluation of candidate vaccine approaches for MERS-CoV," Nature Communications, Jul. 2015, 6(1):7712, 11 pages.
Wang et al., "Structure-based development of human antibody cocktails against SARS-CoV-2," Cell Research, Jan. 2021, 31(1):101-103.
Wang et al., "Systemic delivery of modified mRNA encoding herpes simplex virus 1 thymidine kinase for targeted cancer gene therapy," Molecular Therapy, Feb. 2013, vol. 21, No. 2, pp. 358-367.
Wang et al., An Evidence Based Perspective on mRNA-SARS-Co V-2 Vaccine Development. Med Sci Monit. May 5, 2020;26: e924700. doi: 10.12659/MSM.924700.
Wang et al., Chapter 3: Lipid Nanoparticles for the Delivery of Nucleic Acids. Book: Nanoparticulate Drug Delivery Systems: Strategies, Technologies, and Applications. 2013. 29 pages.
Wang et al., Delivery of oligonucleotides with lipid nanoparticles. Adv Drug Deliv Rev. Jun. 29, 2015;87:68-80. doi: 10.1016/j.addr.2015.02.007. Epub Feb. 27, 2015.
Wang et al., Enhanced bioavailability and efficiency of curcumin for the treatment of asthma by its formulation in solid lipid nanoparticles. Int J Nanomedicine. 2012:7:3667-77. doi: 10.2147:1JN.S30428. Epub Jul. 17, 2012.
Wang et al., Hemagglutinin (HA) proteins from H1 and H3 serotypes of influenza A viruses require different antigen designs for the induction of optimal protective antibody responses as studied by codon-optimized HA DNA vaccines. J Virol. Dec. 2006;80(23): 11628-37. Epub Sep. 20, 2006.
Wang et al., Increased Resistance of SARS-CoV-2 Variants B. 1.351 and B.1.1.7 to Antibody Neutralization. bioRxiv. Jan. 26, 2021; 23 pages. doi: 10.II0I /2021.01.25.428137.
Wang et al., Lymphatic-targeted cationic liposomes: a robust vaccine adjuvant for promoting long-term immunological memory. Vaccine. Sep. 22, 2014;32(42):5475-83. doi: 10.1016/j.vaccine.2014.07.081. Epub Aug. 7, 2014.
Wang et al., mRNA vaccine-elicited antibodies to SARS-Co V-2 and circulating variants. Nature. Apr. 2021;592(7855):616-622. doi: 10.1038/s41586-021-03324-6. Epub Feb. 10, 2021. PMID: 33567448; PMCID: PMC8503938.
Wang et al., Purification of the messenger ribonucleic acid for the lipoprotein of the *Escherichia coli* outer membrane. Biochemistry. Oct. 2, 1979;18(20):4270-7.
Wang et al., Structural Definition of a Neutralization-sensitive Epitope on the MERS-CoV S1-NTD. Cell Rep. Sep. 24, 2019;28(13):3395-3405.e6. doi: 10.1016/j.celrep.2019.08.052. Author's Manuscript, 29 pages.
Wang, et al., "Antibody resistance of SARS-CoV-2 variants B. 1.351 and B.1.1.7," Nature, 593(7857):130-135 (Epub Mar. 8, 2021).
Weaver., "Post-Transcriptional Events II: Capping and Polyadenylation," Molecular Biology. 1999. WCB/McGraw-Hill. Chapter 15:456. 5 pages.
Weber et al, "Individualised neoantigen therapy mRNA-4157 (V940) plus pembrolizumab versus pembrolizumab monotherapy in resected melanoma (KEYNOTE-942): a randomised, phase 2b study", The Lancet, Elsevier, 2024 vol. 403, Issue 10427, pp. 632-644, Article XP087469992.
Weber, J., "mRNA-4157 (V940) individualized neoantigen therapy + pembrolizumab versus pembrolizumab in high-risk resected melanoma: clinical efficacy and correlates of response", 2023, 18 pages.
Wei et al., "Induction of Broadly Neutralizing H1N1 Influenza Antibodies by Vaccination," Science, Aug. 27, 2010, 329:1060-1064.
Weide et al., "Direct Injection of Protamine-protected mRNA: Results of a Phase 1/2 Vaccination Trial in Metastatic Melanoma Patients," 2009, Immunotherapy (11 Pages).
Weide et al., "Results of the First Phase I/II Clinical Vaccination Trial with Direct Injection of mRNA," 2008, J. Immunotherapy, pp. 180-188.
Weilhammer et al., The use of nanolipoprotein particles to enhance the immunostimulatory properties of innate immune agonists against lethal influenza challenge. Biomaterials. Dec. 2013; 34(38):10305-18. doi: 10.1016/j_biomaterials. Sep. 2013 038. Epub Sep. 27, 2013.
Weissman et al., HPLC purification of in vitro transcribed long RNA. Methods Mol Biol. 2013;969:43-54. doi: 10.1007/978-1-62703-260-5 3.
Weissman, mRNA transcript therapy. Expert Rev Vaccines. Feb. 2015;I4(2):265-81. doi: 10.1586/14760584.2015.973859. Epub Oct. 31, 2014.
Wen et al., New Approaches for Immunization and Therapy against Human Metapneumovirus. Clin Vaccine Immunol. Aug. 2015;22(8):858-66.
Wentworth et al., Fusion glycoprotein FO [human respirovirus 3], 2014, GenBank Accession No. AHX22069.1.
Wentworth et al., Hemagglutinin [Influenza A virus (A/Anhui1DEWH72-01/2013(H7N9))]. Gen Bank: AHZ39686.1. Dep. May 9, 2014.
Whitehead et al., "Knocking down barriers: Advances in siRNA delivery," 2009, Nature Reviews Drug Discovery, pp. 129-138.
Whitt, "Generation of VSV pseudotypes using recombinant ?G-VSV for studies on virus entry, identification of entry inhibitors, and immune responses to vaccines," J Virol Methods., Nov. 2010, 169(2):365-374.
Wilhelm et al., Reduced Neutralization of SARS-CoV-2 Omicron Variant by Vaccine Sera and Monoclonal Antibodies. medRxiv. 2021. doi:10.1101/2021.12.07.21267432:2021.12.07.21267432. 9 pages.
Williams et al., Human metapneumovirus isolate TN/92-4 fusion protein gene, complete eds. GenBank: EF051124.1. Nov. 29, 2007.
Wilson et al., "Real Time Measurement of PEG Shedding from Lipid Nanoparticles in Serum via Spectroscopy," Molecular Pharmaceutics, 2015 12(2):386-392.
Winkler, et al., "Changing the antigen binding specificity by single point mutations of an anti-p24 (HIV-1) antibody," J Immunol 165(8):4505-4514 (2000).
Withoff et al., "Replication-defective Recombinant Semliki Forest Virus Encoding GM-CSF as a Vector System for Rapid and Facile Generation of Autologous Human Tumor Cell Vaccines," 2001, Gene Therapy, pp. 1515-1523.
Wohlbold et al., "An H10N8 influenza virus vaccine strain and mouse challenge model based on the human isolate A/Jiangxi-Donghu/346/13." Vaccine. Feb. 25, 2015;.33(9): 1102-6. doi: 10.1016/i.vaccine.2015.01.026. Epub Jan. 17, 2015.
Wolff et al., "Direct gene transfer into mouse muscle in vivo," Science, Mar. 23, 1990, vol. 247 (pp. 1465-1468).
Wong et al., An mRNA vaccine for influenza. Nat Biotechnol. Dec. 2012;30(12):1202-4.
Woodle et al., Sterically stabilized liposomes. Biochim Biophys Acta. Aug. 14, 1992;1113(2): 171-99. doi: 10.1016/0304-4157(92)90038-c.
World Health Organization, Department of Communicable Disease Surveillance and Response, WHO/CSR 2006, pp. 1-90.
World Health Organization, Serological Diagnosis of influenza by Microneutralization Assay, 2010, No. Vol., pp. 1-25.

(56) References Cited

OTHER PUBLICATIONS

World Health Organization, WHO Manual on Animal Influenza Diagnosis and Surveillance, WHO Global Influenza Programme, CDS, CSR, NCS, 2002, vol. 5, pp. 1-99.
World Health Organization: "Recommended composition of influenza virus vaccines for use in the 2021 southern hemisphere influenza season", 2020, XP055900467, pp. 1-9.
Wrapp et al., Cryo-EM structure of the 2019-nCoV spike in the prefusion conformation. Science. Feb. 19, 2020. pii: eabb2507. doi: 10.1126/science.abb2507.
Wu et al., "A new coronavirus associated with human respiratory disease in China," Nature, Mar. 12, 2020 (online Feb. 3, 2020), 579:265-269, Methods, Extended Date fig. 1-9, Supplementary Information, Supplementary Tables 1-8, 35 pages.
Wu et al., "Fusion Protein Vectors to Increase Protein Production and Evaluate the Immunogenicity of Genetic Vaccines", Molecular Therapy, vol. 2, No. 3, Sep. 2000, pp. 288-297, DOI: 10.1006/mthe.2000.0126 (10 pages).
Wu et al., "Genetic Characterization of H7N9 avian influenza viruses in Zhejiang, China," Hemagglutinin [Influenza A Virus (A/Chicken/Zhejiang/C483/2013(H7N9)], AGN69400, pub. Jun. 11, 2014.
Wu et al., "Genetic characterization of H7N9 avian influenza viruses in Zhejiang, China," Influenza A Virus (A/chicken/Zhejiang/C483/2013(H7N9)) segment 4 hemagglutinin (HA) gene, complete cds, GenBank Accession No. KF042104, pub. Jun. 11, 2014.
Wu et al., A sequence that affects the copy number and stability of pSW200 and ColEl. J Bacterial. 2010 Jul; 192(14):3654-60. doi: 10.1128/JB.00095-10. Epub May 21, 2010.
Wu et al., mRNA-1273 vaccine induces neutralizing antibodies against spike mutants from global SARS-CoV-2 variants. bioRxiv preprint. Jan. 25, 2021. doi: 10.1101/2021.01.25.427948. 20 pages.
Wu et al., Serum Neutralizing Activity Elicited by mRNA-1273 Vaccine. N Engl J Med. Apr. 15, 2021;384(15):1468-1470. doi: 10.1056/NEJMc2102179. Epub Mar. 17, 2021.
Wu et al., Variant SARS-CoV-2 mRNA vaccines confer broad neutralization as primary or booster series in mice. bioRxiv [Preprint]. Oct. 7, 2021:2021.04.13.439482. doi: 10.1101/2021.04.13.439482. Update in: Vaccine. Dec. 17, 2021;39(51):7394-7400.
Xia, Detailed Dissection and Critical Evaluation of the Pfizer/BioNTech and Moderna mRNA Vaccines. Vaccines (Basel). Jul. 3, 2021;9(7):734. doi: 10.3390/vaccines9070734.
Xu et al., GISAID Accession No. EPI487905, pub. Nov. 23, 2011.
Xue et al., Lipid-Based Nanocarriers for RNA Delivery. Curr Pharm Des. 2015;21(22):3140-7.
Yamamoto et al., "Current prospects for mRNA gene delivery," European Journal of Pharmaceutics and Biopharmaceutics, Mar. 2009, vol. 7, No. 3 (pp. 484-489).
Yang et al., "A vaccine targeting the RBD of the S protein of SARS-CoV-2 induces protective immunity," Nature, Jul. 29, 2020, 586:572-577.
Yang et al., "Evasion of Antibody Neutralization in Emerging Severe Acute Respiratory Syndrome Coronaviruses," 2005, PNAS, vol. 102, Issue 3, pp. 797-801.
Yang et al., "Mutations of Novel Influenza A(H10N8) Virus in Chicken Eggs and MDCK Cells," NCBI, GenBank Accession No. KJ406543.1 dated Jun. 12, 2014.
Yang et al., A DNA vaccine induces SARS coronavirus neutralization and protective immunity in mice. Nature. Apr. 1, 2004;428(6982):561-4. doi: 10.1038/nature02463.
Yang et al., Mutations of Novel Influenza A*H10N8) Virus in Chicken Eggs and MOCK Cells, Hemagglutinin [Influenza A Virus (A/Jiangxi/IPB13/2013(H10N8)], GenBank Accession No. AHK10761.1, pub. Jun. 12, 2014.
Yang et al., The structure and functions of coronavirus genomic 3' and 5' ends. Virus Res. Aug. 3, 2015;206:120-33. doi: 10.1016/j.virusres.2015.02.025. Epub Feb. 28, 2015. PMID: 25736566; PMCID: PMC4476908.
Ye et al., Rational development of a combined mRNA vaccine against COVID-19 and influenza. NPJ Vaccines. Jul. 26, 2022;7(1):84. doi: 10.1038/s41541-022-00478-w.
Yildiz et al., Trans-Amplifying RNA: A Journey from Alphavirus Research to Future Vaccines. Viruses. Mar. 25, 2024;16(4):503. doi: 10.3390/v16040503.
Yin et al., "Non-viral vectors for gene-based therapy", Nature Reviews | Genetics, Aug. 2014, pp. 541-555, vol. 15, No. 8, 2014 Macmillan Publishers Limited.
Yin et al., Immunogenicity and protective efficacy of recombinant fusion proteins containing spike protein of infectious bronchitis virus and hemagglutinin of H3N2 influenza virus in chickens. Virus Res. Sep. 2, 2016;223:206-12. doi: 10.1016/j.virusres.2016.07.010. Epub Aug. 3, 2016.
Ying et al., "Cancer therapy using a self-replicating RNA vaccine", Nat. Med., Jul. 1999, vol. 5, No. 7, pp. 823-827.
Yoo et al., Synthesis and Processing of the Haemagglutinin-Esterase Glycoprotein of Bovine Coronavirus Encoded in the E3 Region of Adenovirus, vol. 73, J. Gen. Virology, pp. 2591-2600.
Youn et al., Modified mRNA as an alternative to plasmid DNA (pDNA) for transcript replacement and vaccination therapy. Expert Opin Biol Ther. 2015;15(9):1337-48.
Yuan et al., Cryo-EM structures of MERS-CoV and SARS-CoV spike glycoproteins reveal the dynamic receptor binding domains. Nat Commun. Apr. 10, 2017;8:15092.
Zacks Equity Research, "Moderna's (MRNA) Flu Vaccine Data Fails to Impress Investors", Dec. 13, 2021 (Dec. 13, 2021), pp. 1-6.
Zangi, et al., "Modified mRNA directs the fate of heart progenitor cells and induces vascular regeneration after myocardial infarction," Nature Biotechnol. Oct. 2013;31(10):898-907. doi: 10.1038/nbt.2682. Epub Sep. 8, 2013.
Zavitz et al., Dissecting the functional role of PriA protein-catalysed primosome assembly in *Escherichia coli* DNA replication. Mol Microbial. Dec. 1991;5(12):2869-73. doi: 10.1111/j.1365-2958.1991.tb01846.x.
Ze et al., Identification of effective constituents of influenza vaccine by immunization with plasmid DNAs encoding viral proteins. Jpn J Infect Dis. Dec. 2000;53(6):219-28.
Zeng et al., Formulation and Delivery Technologies for mRNA Vaccines. Curr Top Microbial Immunol. Jun. 2, 2020; 10.1007/82 2020 217. doi: 10.1007/822020.
Zerboni et al., Varicella-zoster virus glycoprotein E is a critical determinant of virulence in the SCID mouse-human model of neuropathogenesis. J Virol. Jan. 2011;85(1):98-111. doi: 10.1128/JVI.0 1902-10. Epub Oct. 20, 2010.
Zhang et al., A Thermostable mRNA Vaccine against COVID-19. Cell. Sep. 3, 2020;182(5):1271-1283.el6. doi: 10.1016/j.cell.2020.07.024. Epub Jul. 23, 2020.
Zhang et al., Construction of eukaryotic expressing plasmids encoding HA and HAI of influenza A virus and their transient expression in HEK293 cells. J Huazhong Univ Sci Technolog Med Sci. 2006;26(2):225-7, 230.
Zhang et al., Delivery of mRNA vaccine with a lipid-like material potentiates antitumor efficacy through Toll-like receptor 4 signaling. Proc Natl Acad Sci US A. Feb. 9, 2021; 118(6):e2005191118. doi: 10.1073/pnas.2005191118.
Zhang et al., Prefusion spike protein stabilization through computational mutagenesis. Proteins. Apr. 2021;89(4):399-408. doi: 10.1002/prot.26025. Epub Dec. 4, 2020.
Zhao et al., A therapeutic hepatitis B mRNA vaccine with strong immunogenicity and persistent virological suppression. NPJ Vaccines. Feb. 3, 2024;9(1):22. doi: 10.1038/s41541-024-00813-3.
Zhao et al., Chapter Two: Lipid Nanoparticles for Gene Delivery. Book: Advances in Genetics. Elsevier, 2014. 21 pages.
Zhao et al., Key Aspects of Coronavirus Avian Infectious Bronchitis Virus. Pathogens. May 2023 I 1;12(5):698. doi: 10.3390/pathogens12050698.
Zhao et al., Nanoparticle vaccines. Vaccine. Jan. 9, 2014;32(3):327-37. doi: 10.1016/i.vaccine.2013.11.069. Epub Dec. 2, 2013.
Zhou et al., "Current RNA-Based Therapeutics in Clinical Trials," 2019, Current Gene Therapy, pp. 172-196.

(56) References Cited

OTHER PUBLICATIONS

Zhou et al., Evidence of escape of SARS-Co V-2 variant B.1.351 from natural and vaccine induced sera. Cell. Apr. 29, 2021; 184(9): 2348-2361.e6.

Zhou, W.Z. et al., RNA melanoma vaccine: induction of antitumor immunity by human glycoprotein 100 mRNA immunization. Hum Gene Ther. Nov. 1, 1999;10(16):2719-24.

Zhu et al., "Receptor-binding domain as a target for developing SARS vaccines," Journal of Thoracic Disease, Aug. 2013, 5(Suppl 2):S142-S148.

Zhukovsky et al., Heterogeneity of early intermediates in cell-liposome fusion mediated by influenza hemagglutinin. Biophys J. Nov. 1, 2006;91(9):3349-58. doi: 10.1529/biophysj.106.088005. Epub Aug. 11, 2006.

Ziganshina et al., Antibody-Dependent Enhancement with a Focus on SARS-CoV-2 and Anti-Glycan Antibodies. Viruses. Jul. 20, 2023;15(7): 1584. doi: 10.3390/vI5071584.

Zohra et al., Drastic effect of nanoapatite particles on liposome-mediated mRNA delivery to mammalian cells. Analytical Biochem. Oct. 2005; 345(1):164-166.

Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010.

Zumla et al., Middle East respiratory syndrome. Lancet. Sep. 5, 2015;386(9997):995-1007. doi: I0.10 I 6/S0140-6736(15)60454-8. Epub 20 l5 Jun. 3.

[IPR-2023-01358] Final Written Decision: Judgement Final Written Decision Determining All Challenged Claims Unpatentable 35 U.S.C. § 318(a) Granting the Parties' Motions to Seal (Papers 41, 58, 71, 77) 37 C.F.R. § 42.14.

Byrd-Leotis et al., "Influenza hemagglutinin (HA) stem region mutations that stabilize or destabilize the structure of multiple HA subtypes," 2015, Journal of virology, 89(8), 4504-4516. https://doi.org/10.1128/JVI.00057-15.

Cotter et al., "A Single Amino Acid in the Stalk Region of the H1N1pdm Influenza Virus HA Protein Affects Viral Fusion, Stability and Infectivity," 2014, PLOS Pathogens, vol. 10, Issue 1, Article e1003831.

Dosey et al., "Stabilization of the H5 clade 2.3.4.4b hemagglutinin improves vaccine-elicited neutralizing antibody responses in mice," 2026, Science Translational Medicine, vol. 18, Issue 839, Article eaea8770.

Dreyfus et al., "Highly conserved protective epitopes on influenza B viruses," 2012, Science, vol. 337, No. 6100, pp. 1343-1348. https://doi.org/10.1126/science.1222908.

Freyn et al., "A Multi-Targeting, Nucleoside-Modified mRNA Influenza Virus Vaccine Provides Broad Protection in Mice," 2020, Mol Ther., vol. 28, Issue 7, pp. 1569-1584. doi: 10.1016/j.ymthe.2020.04.018. Epub Apr. 19, 2020.

Freyn et al., "Antigen modifications improve nucleoside-modified mRNA-based influenza virus vaccines in mice," 2021, Molecular Therapy. Methods & Clinical Development, vol. 22, No. 7, pp. 1569-1584.

Hanson et al., "Identification of Stabilizing Mutations in an H5 Hemagglutinin Influenza Virus Protein," 2016, Journal of Virology, 90(6), 2981-2992. https://doi.org/10.1128/JVI.02790-15.

Hsieh et al., "Structure-based design of prefusion-stabilized SARS-Co V-2 spikes," 2020, Science, Sep. 18;369(6510):1501-1505. doi: 10.1126/science.abd0826. Epub Jul. 23, 2020.

Hu et al., "Autographa californica Multiple Nucleopolyhedrovirus ac76 Is Involved in Intranuclear Microvesicle Formation," 2010, J Virol, vol. 84, Issue 15, https://doi.org/10.1128/jvi.02103-09.

Juraszek et al., "Engineering a cleaved, prefusion-stabilized influenza B virus hemagglutinin by identification and locking of all six pH switches," 2024, PNAS Nexus, 3(10), 13 pages. https://doi.org/10.1093/pnasnexus/pgae462.

Kalani et al., "Characterizing a histidine switch controlling pH-dependent conformational changes of the influenza virus hemagglutinin," 2013, Biophysical journal, 105(4), 993-1003. https://doi.org/10.1016/j.bpj.2013.06.047.

Krarup et al., "A highly stable prefusion RSV F vaccine derived from structural analysis of the fusion mechanism," 2015, Nature Communications, vol. 6, Article 8143.

Laporte et al., "Hemagglutinin Cleavability, Acid Stability, and Temperature Dependence Optimize Influenza B Virus for Replication in Human Airways," 2019, Journal of virology, 94(1), e01430-19. https://doi.org/10.1128/JVI.01430-19.

Lee et al.; "Design and Structure of an Engineered Disulfide-Stabilized Influenza Virus Hemagglutinin Trimer"; Journal of Virology, vol. 89, No. 14; Jul. 2015; pp. 7417-7420.

Lu et al., Production and stabilization of the trimeric influenza hemagglutinin stem domain for potentially broadly protective influenza vaccines. Proc Natl Acad Sci US A. Jan. 7, 2014; 111(1): 125-30. doi: 10.1073/pnas.1308701110. Epub Dec. 16, 2013.

Lugovtsev, Vladimir Y. et al.; "Generation of the influenza B viruses with improved growth phenotype by substitution of specific amino acids of hemagglutinin"; Virology, vol. 365, No. 2; May 8, 2007; pp. 315-323.

Mair et al, "A histidine residue of the influenza virus hemagglutinin controls the pH dependence of the conformational change mediating membrane fusion," 2014, Journal of Virology, 88(22), 13189-13200. https://doi.org/10.1128/JVI.01704-14.

Milder et al., "Universal stabilization of the influenza hemagglutinin by structure-based redesign of the pH switch regions," 2022, Proc. Natl. Acad. Sci. U.S.A., vol. 119, No. 6, Article e2115379119, https://doi.org/10.1073/pnas.

Ni et al., "Structural insights into the membrane fusion mechanism mediated by influenza virus hemagglutinin," 2014, Biochemistry, 53(5), 846-854. https://doi.org/10.1021/bi401525h.

Thornlow et al., "Altering the Immunogenicity of Hemagglutinin Immunogens by Hyperglycosylation and Disulfide Stabilization," 2021, Front. Immunol., vol. 12, Article 737973. doi: 10.3389/fimmu.2021.737973.

Wang et al., "Crystal structure of unliganded influenza B virus hemagglutinin," 2008, Journal of virology, 82(6), 3011-3020. https://doi.org/10.1128/JVI.02477-07.

Weldon et al., "Enhanced Immunogenicity of Stabilized Trimeric Soluble Influenza Hemagglutinin," 2010, PLoS ONE, vol. 5, Issue 9, Article e12466.

*Substitutions in FIG. 1A are numbered according to post-signal peptide cleavage form of HA protein.

*Substitutions in FIG. 1B are numbered according to post-signal peptide cleavage form of HA protein.

CR8059 - MFI x Freq - 72 Hours

| | Austria | | | | | | | | | Phuket | | | |
|---|---|---|---|---|---|---|---|---|---|---|---|---|---|
| WT | X | | | | | | | | | x | | | |
| H363Y | | X | | | | X | X | | X | | x | | |
| K388M | | | X | | | | | | | | | x | |
| K388L | | | | X | | | | | | | | | |
| H455W | | | | | X | | | X | | | | | x |
| A270V | | | | | | X | | | | | | | |
| S434A | | | | | | | X | | | | | | |
| D422N | | | | | | | | X | X | | | | |

*Substitutions in FIG. 1C are numbered according to post-signal peptide cleavage form of HA protein.

Polyclonal Sera - MFI x Freq - 72 Hours

| | Austria | | | | | | | | | Phuket | | | |
|---|---|---|---|---|---|---|---|---|---|---|---|---|---|
| WT | X | | | | | | | | | x | | | |
| H363Y | | X | | | | X | X | | X | | x | | |
| K388M | | | X | | | | | | | | | x | |
| K388L | | | | X | | | | | | | | | |
| H455W | | | | | X | | | X | | | | | x |
| A270V | | | | | | X | | | | | | | |
| S434A | | | | | | | X | | | | | | |
| D422N | | | | | | | | X | X | | | | |

*Substitutions in FIG. 1D are numbered according to post-signal peptide cleavage form of HA protein.

| Study | Exp. #1 | | | Exp. #2 | | | | |
|---|---|---|---|---|---|---|---|---|
| H363Y | x | | | | x | x | | x |
| H455W | | x | | | | | x | |
| K388M | | | x | | | | | |
| K368L | | | | x | | | | |
| A270V | | | | | x | | | |
| S434A | | | | | | x | | |
| D422N | | | | | | | x | x |

*Substitutions in FIG. 2A are numbered according to post-signal peptide cleavage form of HA protein.

| Study | Exp. #1 | | | Exp. #2 | | | | |
|---|---|---|---|---|---|---|---|---|
| H363Y | x | | | | x | x | | x |
| H455W | | x | | | | | x | |
| K388M | | | x | | | | | |
| K368L | | | | x | | | | |
| A270V | | | | | x | | | |
| S434A | | | | | | x | | |
| D422N | | | | | | | x | x |

*Substitutions in FIG. 2B are numbered according to post-signal peptide cleavage form of HA protein.

| Study | | Exp. #1 | | | | Exp. #2 | | | | | |
|---|---|---|---|---|---|---|---|---|---|---|---|
| PBS | x | | | | | | | | | | |
| WT | | x | | | | x | | | | | |
| H363Y | | | x | | | | | x | x | | x |
| H455W | | | | x | | | | | | x | |
| K388M | | | | | x | | | | | | |
| K388L | | | | | | | x | | | | |
| A270V | | | | | | | | x | | | |
| S434A | | | | | | | | | x | | |
| D422N | | | | | | | | | | x | x |

*Substitutions in FIG. 3A are numbered according to post-signal peptide cleavage form of HA protein.

| Study | | Exp. #1 | | | | Exp. #2 | | | | | |
|---|---|---|---|---|---|---|---|---|---|---|---|
| PBS | x | | | | | | | | | | |
| WT | | x | | | | x | | | | | |
| H363Y | | | x | | | | | x | x | | x |
| H455W | | | | x | | | | | | x | |
| K388M | | | | | x | | | | | | |
| K388L | | | | | | | x | | | | |
| A270V | | | | | | | | x | | | |
| S434A | | | | | | | | | x | | |
| D422N | | | | | | | | | | x | x |

*Substitutions in FIG. 3B are numbered according to post-signal peptide cleavage form of HA protein.

| Study | Exp. #1 | | | Exp. #2 | | | | |
|---|---|---|---|---|---|---|---|---|
| H363Y | x | | | | x | x | | X |
| H455W | | x | | | | | X | |
| K388M | | | x | | | | | |
| K388L | | | | x | | | | |
| A270Y | | | | | x | | | |
| S434A | | | | | | x | | |
| D422N | | | | | | | x | x |

*Substitutions in FIG. 4A are numbered according to post-signal peptide cleavage form of HA protein.

| Study | Exp. #1 | | | Exp. #2 | | | | |
|---|---|---|---|---|---|---|---|---|
| H363Y | x | | | | x | x | x | |
| H455W | | x | | | | | | x |
| K388M | | | x | | | | | |
| K388L | | | | x | | | | |
| A270V | | | | | x | | | |
| S434A | | | | | | x | | |
| D422N | | | | | | | x | x |

*Substitutions in FIG. 4B are numbered according to post-signal peptide cleavage form of HA protein.

| Study | | Exp. #1 | | | | Exp. #2 | | | | | |
|---|---|---|---|---|---|---|---|---|---|---|---|
| PBS | x | | | | | | | | | | |
| WT | | x | | | | x | | | | | |
| H363Y | | | x | | | | | x | x | | x |
| H455W | | | | x | | | | | | x | |
| K388M | | | | | x | | | | | | |
| K388L | | | | | | | x | | | | |
| A270V | | | | | | | | x | | | |
| S434A | | | | | | | | | x | | |
| D422N | | | | | | | | | | x | x |

*Substitutions in FIG. 5A are numbered according to post-signal peptide cleavage form of HA protein.

| Study | | Exp. #1 | | | | Exp. #2 | | | | | |
|---|---|---|---|---|---|---|---|---|---|---|---|
| PBS | x | | | | | | | | | | |
| WT | | x | | | | x | | | | | |
| H363Y | | | x | | | | | x | x | | x |
| H455W | | | | x | | | | | | x | |
| K388M | | | | | x | | | | | | |
| K388L | | | | | | | x | | | | |
| A270V | | | | | | | | x | | | |
| S434A | | | | | | | | | x | | |
| D422N | | | | | | | | | | x | x |

*Substitutions in FIG. 5B are numbered according to post-signal peptide cleavage form of HA protein.

| Study | | Exp. #1 | | | | Exp. #2 | | | | | |
|---|---|---|---|---|---|---|---|---|---|---|---|
| PBS | x | | | | | | | | | | |
| WT | | x | | | | x | | | | | |
| H363Y | | | x | | | | | x | x | | x |
| H455W | | | | x | | | | | | x | |
| K388M | | | | | x | | | | | | |
| K388L | | | | | | | x | | | | |
| A270V | | | | | | | | x | | | |
| S434A | | | | | | | | | x | | |
| D422N | | | | | | | | | | x | x |

*Substitutions in FIG. 6A are numbered according to post-signal peptide cleavage form of HA protein.

| Study | | Exp. #1 | | | | Exp. #2 | | | | | |
|---|---|---|---|---|---|---|---|---|---|---|---|
| PBS | x | | | | | | | | | | |
| WT | | x | | | | x | | | | | |
| H363Y | | | x | | | | | x | x | | x |
| H455W | | | | x | | | | | | x | |
| K388M | | | | | x | | | | | | |
| K388L | | | | | | | x | | | | |
| A270V | | | | | | | | x | | | |
| S434A | | | | | | | | | x | | |
| D422N | | | | | | | | | | x | x |

*Substitutions in FIG. 6B are numbered according to post-signal peptide cleavage form of HA protein.

| Study | | Exp. #1 | | | | Exp. #2 | | | | | |
|---|---|---|---|---|---|---|---|---|---|---|---|
| PBS | x | | | | | | | | | | |
| WT | | x | | | | x | | | | | |
| H363Y | | | x | | | | | x | x | | x |
| H455W | | | | x | | | | | | x | |
| K388M | | | | | x | | | | | | |
| K388L | | | | | | | x | | | | |
| A270V | | | | | | | | x | | | |
| S434A | | | | | | | | | x | | |
| D422N | | | | | | | | | | x | x |

*Substitutions in FIG. 7A are numbered according to post-signal peptide cleavage form of HA protein.

| Study | | Exp. #1 | | | | Exp. #2 | | | | | |
|---|---|---|---|---|---|---|---|---|---|---|---|
| PBS | x | | | | | | | | | | |
| WT | | x | | | | x | | | | | |
| H363Y | | | x | | | | | x | x | | x |
| H455W | | | | x | | | | | | x | |
| K388M | | | | | x | | | | | | |
| K388L | | | | | | | x | | | | |
| A270V | | | | | | | | x | | | |
| S434A | | | | | | | | | x | | |
| D422N | | | | | | | | | | x | x |

*Substitutions in FIG. 7B are numbered according to post-signal peptide cleavage form of HA protein.

*Substitutions in FIG. 8 are numbered according to post-signal peptide cleavage form of HA protein.

*Substitutions in FIG. 9 are numbered according to post-signal peptide cleavage form of HA protein.

```
SEQ_ID_122    MKAKLLVLLCTFTATYADTICIGYHANNSTDTVDTVLEKNVTVTHSVNLLEDSHNGKLCL  60
SEQ_ID_123    MKAKLLVLLCTFTATYADTICIGYHANNSTDTVDTVLEKNVTVTHSVNLLEDSHNGKLCL  60
SEQ_ID_124    MKVKLLVLLCTFTATYADTICIGYHANNSTDTVDTVLEKNVTVTHSVNLLEDSHNGKLCL  60
SEQ_ID_125    MKVKLLVLLCTFTATYADTICIGYHANNSTDTVDTVLEKNVTVTHSVNLLENSHNGKLCL  60
SEQ_ID_127    MKAILVVLLYTFATANADTLCIGYHANNSTDTVDTVLEKNVTVTHSVNLLEDKHNGKLCK  60
SEQ_ID_128    MKAILVVLLYTFTTANADTLCIGYHANNSTDTVDTVLEKNVTVTHSVNLLEDKHNGKLCK  60
SEQ_ID_129    MKAILVVLLYTFTTANADTLCIGYHANNSTDTVDTVLEKNVTVTHSVNLLEDKHNGKLCK  60
SEQ_ID_130    MKAILVVLLYTFTTANADTLCIGYHANNSTDTVDTVLEKNVTVTHSVNLLEDKHNGKLCK  60
SEQ_ID_131    MKAILVVLLYTFTTANADTLCIGYHANNSTDTVDTVLEKNVTVTHSVNLLEDKHNGKLCK  60
SEQ_ID_132    MKAILVVMLYTFTTANADTLCIGYHANNSTDTVDTVLEKNVTVTHSVNLLEDKHNGKLCK  60
SEQ_ID_133    MKAILVVMLYTFTTANADTLCIGYHANNSTDTVDTVLEKNVTVTHSVNLLEDKHNGKLCK  60
SEQ_ID_134    MKAILVVMLYTFTTANADTLCIGYHANNSTDTVDTVLEKNVTVTHSVNLLEDKHNGKLCK  60
SEQ_ID_135    MKAILVVMLYTFTTANADTLCIGYHANNSTDTVDTVLEKNVTVTHSVNLLEDKHNGKLCK  60
              **. *:*:* **::: ***:*******************************:.******

SEQ_ID_122    LKGIAPLQLGNCSVAGWILGNPECESLISKESWSYIVETPNPENGTCYPGYFADYEELRE  120
SEQ_ID_123    LKGIAPLQLGNCSVAGWILGNPECELLISKESWSYIVETPNPENGTCYPGYFADYEELRE  120
SEQ_ID_124    LKGIAPLQLGNCSVAGWILGNPECELLISRESWSYIVEKPNPENGTCYPGHFADYEELRE  120
SEQ_ID_125    LKGIAPLQLGNCSVAGWILGNPECELLISKESWSYIVEKPNPENGTCYPGHFADYEELRE  120
SEQ_ID_127    LRGVAPLHLGKCNIAGWILGNPECESLSTASSWSYIVETPSSDNGTCYPGDFIDYEELRE  120
SEQ_ID_128    LRGVAPLHLGKCNIAGWILGNPECESLSTASSWSYIVETSNSDNGTCYPGDFINYEELRE  120
SEQ_ID_129    LGGVAPLHLGKCNIAGWILGNPECESLSTARSWSYIVETSNSDNGTCYPGDFINYEELRE  120
SEQ_ID_130    LRGVAPLHLGKCNIAGWILGNPECESLSTARSWSYIVETSNSDNGTCYPGDFINYEELRE  120
SEQ_ID_131    LRGVAPLHLGKCNIAGWILGNPECESLSTARSWSYIVETSNSDNGTCYPGDFINYEELRE  120
SEQ_ID_132    LRGVAPLHLGQCNIAGWILGNPECESLSTARSWSYIVETSNSDNGTCYPGDFINYEELRE  120
SEQ_ID_133    LRGVAPLHLGKCNIAGWILGNPECESLSTARSWSYIVETSNSDNGTCYPGDFINYEELRE  120
SEQ_ID_134    LRGVAPLHLGQCNIAGWILGNPECESLSTARSWSYIVETSNSDNGTCYPGDFINYEELRE  120
SEQ_ID_135    LRGVAPLHLGQCNIAGWILGNPECESLSTARSWSYIVETSNSDNGTCYPGDFINYEELRE  120
              * *:***:**:*.:*********** * :  *******. . :******* * :******

SEQ_ID_122    QLSSVSSFERFEIFPKESSWPNHTV-TGVTASCSHNGKSSFYRNLLWLTEKNGLYPNLSN  179
SEQ_ID_123    QLSSVSSFERFEIFPKESSWPNHTV-TGVSASCSHNGKSSFYRNLLWLTGKNGLYPNLSK  179
SEQ_ID_124    QLSSVSSFERFEIFPKESSWPNHTT-TGVSASCSHNGESSFYKNLLWLTGKNGLYPNLSK  179
SEQ_ID_125    QLSSVSSFERFEIFPKESSWPNHTV-TGVSASCSHNGESSFYRNLLWLTGKNGLYPNLSK  179
SEQ_ID_127    QLSSVSSFERFEIFPKTSSWPNHDSNKGVTAACPHAGAKSFYKNLIWLVKKGXSYPKLSK  180
SEQ_ID_128    QLSSVSSFERFEIFPKTSSWPNHDSNKGVTAACPHAGAKSFYKNLIWLVKKGNSYPKLNQ  180
SEQ_ID_129    QLSSVSSFERFEIFPKTSSWPNHDSNKGVTAACPHAGAKSFYKNLIWLVKKGNSYPKLNQ  180
SEQ_ID_130    QLSSVSSFERFEIFPKTSSWPNHDSDKGVTAACPHAGAKSFYKNLIWLVKKGNSYPKLNQ  180
SEQ_ID_131    QLSSVSSFERFEIFPKTSSWPNHDSDKGVTAACPHAGAKSFYKNLIWLVKKGNSYPKLNQ  180
SEQ_ID_132    QLSSVSSFERFEIFPKTSSWPNHDSDNGVTAACSHAGARSFYKNLIWLVKKGKSYPKINQ  180
SEQ_ID_133    QLSSVSSFERFEIFPKTSSWPNHDSDNGVTAACPHAGAKSFYKNLIWLVKKGKSYPKINQ  180
SEQ_ID_134    QLSSVSSFERFEIFPKTSSWPNHDSDNGVTAACSHAGAKSFYKNLIWLVKKGKSYPKINQ  180
SEQ_ID_135    QLSSVSSFERFEIFPKTSSWPNHDSDNGVTAACSHAGARSFYKNLIWLVKKGKSYPKINQ  180
              **************** ******    .**:*:* * *  ***:**:**. *.  **::.:

SEQ_ID_122    SYVNNKEKEVLVLWGVHHPSNIRDQRAIYHTENAYVSVVSSHYSRRFTPEIAKRPKVRGQ  239
SEQ_ID_123    SYVNNKEKEVLVLWGVHHPPNIGNQRALYHTENAYVSVVSSHYSRRFTPEIAKRPKVRDQ  239
SEQ_ID_124    SYANNKEKEVLVLWGVHHPPNIGDQRALYHTENAYVSVVSSHYSRKFTPEIAKRPKVRDR  239
SEQ_ID_125    SYANNKEKEVLVLWGVHHPPNIGNQKALYHTENAYVSVVSSHYSRKFTPEIAKRPKVRDQ  239
SEQ_ID_127    SYINDKGKEVLVLWGIHHPSTSADQQSLYQNADAYVFVGSSRYSKKFKPEIAIRPKVRXX  240
SEQ_ID_128    SYINDKGKEVLVLWGIHHPSTTADQQSLYQNADAYVFVGTSRYSKKFKPEIATRPKVRDR  240
SEQ_ID_129    TYINDKGKEVLVLWGIHHPPTTADQQSLYQNADAYVFVGTSRYSKKFKPEIATRPKVRDQ  240
SEQ_ID_130    TYINDKGKEVLVLWGIHHPPTIAAQESLYQNADAYVFVGTSRYSKKFKPEIATRPKVRDQ  240
SEQ_ID_131    TYINDKGKEVLVLWGIHHPPTIAAQESLYQNADAYVFVGTSRYSKKFKPEIATRPKVRDQ  240
SEQ_ID_132    TYINDKGKEVLVLWGIHHPPTITDQESLYQNADAYVFVGTSRYSKKFKPEIAARPKVRDQ  240
SEQ_ID_133    TYINDKGKEVLVLWGIHHPPTIADQQSLYQNADAYVFVGTSRYSKKFKPEIATRPKVRDQ  240
SEQ_ID_134    TYINDKGKEVLVLWGIHHPPTITDQESLYQNADAYVFVGTSRYSKKFKPEIAARPKVRDR  240
SEQ_ID_135    TYINDKGKEVLVLWGIHHPPTITDQESLYQNADAYVFVGTSRYSKKFKPEIATRPKVRDQ  240
              :* *:* ********:*** .    *.::*:. :*** * :*:**::*.**** *****
```

FIG. 19A

```
SEQ_ID_122     EGRINYYWTLLEPGDTIIFEANGNLIAPWYAFALSRGFGSGIITSNAPMNECDAKCQTPQ  299
SEQ_ID_123     EGRINYYWTLLEPGDTIIFEANGNLIAPWYAFALSRGFGSGIITSNAPMDECDAKCQTPQ  299
SEQ_ID_124     EGRINYYWTLLEPGDTIIFEANGNLIAPRYAFALSRGFGSGIINSNAPMDECDAKCQTPQ  299
SEQ_ID_125     EGRINYYWTLLEPGDTIIFEANGNLIAPRYAFALSRGFGSGIINSNAPMDKCDAKCQTPQ  299
SEQ_ID_127     EGRMNYYWTLVEPGDKITFEATGNLVVPRYAFAMERNAGSGIIISDTPVHDCNTTCQTPK  300
SEQ_ID_128     EGRMNYYWTLVEPGDKITFEATGNLVVPRYAFTMERNAGSGIIISDTPVHDCNTTCQTPE  300
SEQ_ID_129     EGRMNYYWTLVEPGDKITFEATGNLVVPRYAFTMERNAGSGIIISDTPVHDCNTTCQTAE  300
SEQ_ID_130     EGRMNYYWTLVEPGDKITFEATGNLVVPRYAFTMERDAGSGIIISDTPVHDCNTTCQTPE  300
SEQ_ID_131     EGRMNYYWTLVEPGDKITFEATGNLVVPRYAFTMERDAGSGIIISDTPVHDCNTTCQTPE  300
SEQ_ID_132     AGRMNYYWTLVEPGDKITFEATGNLVAPRYAFTMEKEAGSGIIISDTPVHDCNATCQTPE  300
SEQ_ID_133     EGRMNYYWTLVEPGDKITFEATGNLVAPRYAFTMERDAGSGIIISDTPVHDCNTTCQTPE  300
SEQ_ID_134     AGRMNYYWTLVEPGDKITFEATGNLVAPRYAFTMEKEAGSGIIISDTPVHDCNATCQTPE  300
SEQ_ID_135     AGRMNYYWTLVEPGDKITFEATGNLVAPRYAFTMEKEAGSGIIISDTPVHDCNATCQTPE  300
                **:******:****.* ***.***:.* ***::.:  ***** *::*:..*::.*** :

SEQ_ID_122     GAINSSLPFQNVHPVTIGECPKYVRSTKLRMVTGLRNIPSIQSRGLFGAIAGFIEGGWTG  359
SEQ_ID_123     GAINSSLPFQNVHPVTIGECPKYVRSAKLRMVTGLRNIPSIQSRGLFGAIAGFIEGGWTG  359
SEQ_ID_124     GAINSSLPFQNVHPVTIGECPKYVRSAKLRMVTGLRNIPSIQSRGLFGAIAGFIEGGWTG  359
SEQ_ID_125     GAINSSLPFQNVHPVTIGECPKYVRSAKLRMVTGLRNIPSIQSRGLFGAIAGFIEGGWTG  359
SEQ_ID_127     GAINTSLPFQNIHPITIGKCPKYVKSTKLRLATGLRNIPSIQSRGLFGAIAGFIEGGWTG  360
SEQ_ID_128     GAINTSLPFQNIHPITIGKCPKYVKSTKLRLATGLRNVPSIQSRGLFGAIAGFIEGGWTG  360
SEQ_ID_129     GAINTSLPFQNVHPVTIGKCPKYVKSTKLRLATGLRNVPSIQSRGLFGAIAGFIEGGWTG  360
SEQ_ID_130     GAINTSLPFQNVHPITIGKCPKYVKSTKLRLATGLRNVPSIQSRGLFGAIAGFIEGGWTG  360
SEQ_ID_131     GAINTSLPFQNVHPITIGKCPKYVKSTKLRLATGLRNVPSIQSRGLFGAIAGFIEGGWTG  360
SEQ_ID_132     GAINTSLPFQNVHPITIGKCPKYVRSTKLRLATGLRNVPSIQSRGLFGAIAGFIEGGWTG  360
SEQ_ID_133     GAINTSLPFQNVHPITIGKCPKYVKSTKLRLATGLRNVPSIQSRGLFGAIAGFIEGGWTG  360
SEQ_ID_134     GAINTSLPFQNVHPITIGKCPKYVRSTKLRLATGLRNVPSIQSRGLFGAIAGFIEGGWTG  360
SEQ_ID_135     GAINTSLPFQNVHPITIGKCPKYVRSTKLRLATGLRNVPSIQSRGLFGAIAGFIEGGWTG  360
               ****:******:**:***:*****:*:***:.*****:**********************

SEQ_ID_122     MMDGWYGYHHQNEQGSGYAADQKSTQNAINGITNKVNSVIEKMNTQFTAVGKEFNKLERR  419
SEQ_ID_123     MVDGWYGYHHQNEQGSGYAADQKSTQNAINGITNKVNSVIEKMNTQFTAVGKEFNKLERR  419
SEQ_ID_124     MVDGWYGYHHQNEQGSGYAADQKSTQNAINGITNKVNSVIEKMNTQFTAVGKEFNKLERR  419
SEQ_ID_125     MVDGWYGYHHQNEQGSGYAADQKSTQNAINGITNKVNSVIEKMNTQFTAVGKEFNKLERR  419
SEQ_ID_127     MVDGWYGYHHQNEQGSGYAADLKSTQNAIDEITNKVNSVIEKMNTQFTAVGKEFNHLEKR  420
SEQ_ID_128     MVDGWYGYHHQNEQGSGYAADLKSTQNAIDKITNKVNSVIEKMNTQFTAVGKEFNHLEKR  420
SEQ_ID_129     MVDGWYGYHHQNEQGSGYAADLKSTQNAIDKITNKVNSVIEKMNTQFTAVGKEFNHLEKR  420
SEQ_ID_130     MVDGWYGYHHQNEQGSGYAADLKSTQNAIDKITNKVNSVIEKMNTQFTAVGKEFNHLEKR  420
SEQ_ID_131     MVDGWYGYHHQNEQGSGYAADLKSTQNAIDKITNKVNSVIEKMNTQFTAVGKEFNHLEKR  420
SEQ_ID_132     MVDGWYGYHHQNDQGSGYAADLKSTQNAIDKITNKVNSVIEKMNTQFTAVGKEFNHLEKR  420
SEQ_ID_133     MVDGWYGYHHQNEQGSGYAADLKSTQNAIDKITNKVNSVIEKMNTQFTAVGKEFNHLEKR  420
SEQ_ID_134     MVDGWYGYHHQNDQGSGYAADLKSTQNAIDKITNKVNSVIEKMNTQFTAVGKEFNHLEKR  420
SEQ_ID_135     MVDGWYGYHHQNDQGSGYAADLKSTQNAIDKITNKVNSVIEKMNTQFTAVGKEFNHLEKR  420
               *:**********:******** *******: ************************:**:*

SEQ_ID_122     MENLNKKVDDGFLDIWTYNAELLVLLENERTLDFHDSNVKNLYEKVKSQLKNNAKEIGNG  479
SEQ_ID_123     MENLNKKVDDGFLDIWTYNAELLVLLENERTLDFHDSNVKNLYEKVKSQLKNNAKEIGNG  479
SEQ_ID_124     MENLNKKVDDGFIDIWTYNAELLVLLENERTLDFHDSNVKNLYEKVKSQLKNNAKEIGNG  479
SEQ_ID_125     MENLNKKVDDGFIDIWTYNAELLVLLENERTLDFHDSNVKNLYEKVKSQLKNNAKEIGNG  479
SEQ_ID_127     IENLNKKVDDGFLDIWTYNAELLVLLENERTLDYHDSNVKNLYEKVRSQLKNNAKEIGNG  480
SEQ_ID_128     IENLNKKVDDGFLDIWTYNAELLVLLENERTLDYHDSNVKNLYEKVRNQLKNNAKEIGNG  480
SEQ_ID_129     IENLNKKVDDGFLDIWTYNAELLVLLENERTLDYHDSNVKNLYEKVRNQLKNNAKEIGNG  480
SEQ_ID_130     IENLNKKVDDGFLDIWTYNAELLVLLENERTLDYHDSNVKNLYEKVRNQLKNNAKEIGNG  480
SEQ_ID_131     IENLNKKVDDGFLDIWTYNAELLVLLENERTLDYHDSNVKNLYEKVRNQLKNNAKEIGNG  480
SEQ_ID_132     IENLNKKVDDGFLDVWTYNAELLVLLENERTLDYHDSNVKNLYEKVRHQLKNNAKEIGNG  480
SEQ_ID_133     IENLNKKVDDGFLDIWTYNAELLVLLENERTLDYHDSNVKNLYEKVRNQLKNNAKEIGNG  480
SEQ_ID_134     IENLNKKVDDGFLDVWTYNAELLVLLENERTLDYHDSNVKNLYEKVRHQLKNNAKEIGNG  480
SEQ_ID_135     IENLNKKVDDGFLDVWTYNAELLVLLENERTLDYHDSNVKNLYEKVRHQLKNNAKEIGNG  480
               :***********:*:******************:************: ************
```

FIG. 19A (continued)

```
SEQ_ID_122      CFEFYHKCNNECMESVKNGTYDYPKYSEESKLNREKIDGVKLESMGVYQILAIYSTVASS  539
SEQ_ID_123      CFEFYHKCNNECMESVKNGTYDYPKYSEESKLNREKIDGVKLESMGVYQILAIYSTVASS  539
SEQ_ID_124      CFEFYHKCNDECMESVKNGTYDYPKYSEESKLNREKIDGVKLESMGVYQILAIYSTVASS  539
SEQ_ID_125      CFEFYHKCNDECMESVKNGTYDYPKYSEESKLNREKIDGVKLESMGVYQILAIYSTVASS  539
SEQ_ID_127      CFEFYHKCDNTCMESVKNGTYDYPKYSEEAKLNREEIDGVKLESTRIYQILAIYSTVASS  540
SEQ_ID_128      CFEFYHKCDNTCMESVKNGTYDYPKYSEEAKLNREKIDGVKLESTRIYQILAIYSTVASS  540
SEQ_ID_129      CFEFYHKCDNTCMESVKNGTYDYPKYSEEAKLNREKIDGVKLESTRIYQILAIYSTVASS  540
SEQ_ID_130      CFEFYHKCDNTCMESVKNGTYDYPKYSEEAKLNREKIDGVKLESTRIYQILAIYSTVASS  540
SEQ_ID_131      CFEFYHKCDNTCMESVKNGTYDYPKYSEEAKLNREKIDGVKLESTRIYQILAIYSTVASS  540
SEQ_ID_132      CFEFYHKCDNTCMESVKNGTYDYPKYSEEAKLNREKIDGVKLDSTRIYQILAIYSTVASS  540
SEQ_ID_133      CFEFYHKCDNTCMESVKNGTYDYPKYSEEAKLNREKIDGVKLDSTRIYQILAIYSTVASS  540
SEQ_ID_134      CFEFYHKCDNTCMESVKNGTYDYPKYSEEAKLNREKIDGVKLDSTRIYQILAIYSTVASS  540
SEQ_ID_135      CFEFYHKCDNTCMESVKNGTYDYPKYSEEAKLNREKIDGVKLDSTRIYQILAIYSTVASS  540
                ********:: ******************:*****:******:*  :*************

SEQ_ID_122      LVLLVSLGAISFWMCSNGSLQCRICI      565
SEQ_ID_123      LVLLVSLGAISFWMCSNGSLQCRICI      565
SEQ_ID_124      LVLLVSLGAISFWMCSNGSLQCRICI      565
SEQ_ID_125      LVLLVSLGAISFWMCSNGSLQCRICI      565
SEQ_ID_127      LVLVVSLGAISFWMCSNGSLQCRICI      566
SEQ_ID_128      LVLVVSLGAISFWMCSNGSLQCRICI      566
SEQ_ID_129      LVLVVSLGAISFWMCSNGSLQCRICI      566
SEQ_ID_130      LVLVVSLGAISFWMCSNGSLQCRICI      566
SEQ_ID_131      LVLVVSLGAISFWMCSNGSLQCRICI      566
SEQ_ID_132      LVLVVSLGAISFWMCSNGSLQCRICI      566
SEQ_ID_133      LVLVVSLGAISFWMCSNGSLQCRICI      566
SEQ_ID_134      LVLVVSLGAISFWMCSNGSLQCRICI      566
SEQ_ID_135      LVLVVSLGAISFWMCSNGSLQCRICI      566
                ***:**********************
Signal peptides indicated by underlining (amino acids 1-17)
```

FIG. 19A (continued)

```
SEQ_ID_136    MKTIIALSYILCLVFAQKIPGNDNSTATLCLGHHAVPNGTLVKTITNDQIEVTNATELVQ  60
SEQ_ID_137    MKTIIALSYILCLVFAQKLPGNDNSTATLCLGHHAVPNGTLVKTITNDQIEVTNATELVQ  60
SEQ_ID_138    MKTIIALSYILCLVFAQKLPGNDNSTATLCLGHHAVPNGTIVKTITNDQIEVTNATELVQ  60
SEQ_ID_139    MKTIIALSYILCLVFAQKLPGNDNSTATLCLGHHAVPNGTIVKTITNDQIEVTNATELVQ  60
SEQ_ID_140    MKTIIALSYILCLVFAQKLPGNDDSTATLCLGHHAVPNGTIVKTITNDQIEVTNATELVQ  60
SEQ_ID_141    MKTIIALSYILCLVFTQKLPGNDNSTATLCLGHHAVPNGTIVKTITNDQIEVTNATELVQ  60
SEQ_ID_142    MKTIIALSYILCLVFAQKLPGNDNSTATLCLGHHAVPNGTIVKTITNDQIEVTNATELVQ  60
SEQ_ID_143    MKTIIALSHILCLVFAQKLPGNDNSTATLCLGHHAVPNGTIVKTITNDQIEVTNATELVQ  60
SEQ_ID_144    MKTIIALSYILCLVFAQKLPGNDNSTATLCLGHHAVPNGTIVKTITNDRIEVTNATELVQ  60
SEQ_ID_145    MKTIIALSYILCLVFAQKLPGNDNSTATLCLGHHAVPNGTIVKTITNDRIEVTNATELVQ  60
SEQ_ID_146    MKTIIALSYILCLVFAQKIPGNDNSTATLCLGHHAVPNGTIVKTITNDRIEVTNATELVQ  60
SEQ_ID_147    MKTIIALSYILCLVFAQKIPGNDNSTATLCLGHHAVPNGTIVKTITNDRIEVTNATELVQ  60
SEQ_ID_148    MKTIIALSCILCLVFAQKIPGNDNSTATLCLGHHAVPNGTIVKTITNDRIEVTNATELVQ  60
SEQ_ID_149    MKTIIALSYILCLVFTQKIPGNDNSTATLCLGHHAVPNGTIVKTITNDRIEVTNATELVQ  60
SEQ_ID_150    MKTIIALSYILCLGFTQKIPGNDNSTATLCLGHHAVPNGTIVKTITNDRIEVTNATELVQ  60
SEQ_ID_151    MKTIIALSYILCLVFAQKIPGNDNSTATLCLGHHAVPNGTIVKTITNDRIEVTNATELVQ  60
SEQ_ID_152    MKTIIALSNILCLVFAQKIPGNDNSTATLCLGHHAVPNGTIVKTITNDRIEVTNATELVQ  60
SEQ_ID_153    MKTIIALSNILCLVFAQKIPGNDNSTATLCLGHHAVPNGTIVKTITNDRIEVTNATELVQ  60
              ******** **** *:**:****:****************:*******:***********

SEQ_ID_136    SSSTGRICDSPHRILDGENCTLIDALLGDPHCDGFQNKEWDLFVERSKAYSNCYPYDVPD  120
SEQ_ID_137    SSSTGRICDSPHQILDGENCTLIDALLGDPHCDGFQNKEWDLFVERSKAYSNCYPYDVPD  120
SEQ_ID_138    SSSTGGICDSPHQILDGENCTLIDALLGDPQCDGFQNKKWDLFVERSKAYSNCYPYDVPD  120
SEQ_ID_139    SSSTGGICDSPHQILDGENCTLIDALLGDPQCDGFQNKKWDLFVERSKAYSNCYPYDVPD  120
SEQ_ID_140    SSSTGGICDSPHQILDGENCTLIDALLGDPQCDGFQNKKWDLFVERSKAYSNCYPYDVPD  120
SEQ_ID_141    SSSTGEICDSPHQILDGENCTLIDALLGDPQCDGFQNKKWDLFVERSKAYSNCYPYDVPD  120
SEQ_ID_142    SSSTGEICDSPHQILDGKNCTLIDALLGDPQCDGFQNKKWDLFVERSKAYSNCYPYDVPD  120
SEQ_ID_143    NSSIGEICDSPHQILDGENCTLIDALLGDPQCDGFQNKKWDLFVERSKAYSNCYPYDVPD  120
SEQ_ID_144    NSSIGEICDSPHQILDGENCTLIDALLGDPQCDGFQNKKWDLFVERSKAYSNCYPYDVPD  120
SEQ_ID_145    NSSIGEICDSPHQILDGENCTLIDALLGDPQCDGFQNKKWDLFVERSKAYSNCYPYDVPD  120
SEQ_ID_146    NSSIGEICDSPHQILDGENCTLIDALLGDPQCDGFQNKKWDLFVERSKAYSNCYPYDVPD  120
SEQ_ID_147    NSSIGEICDSPHQILDGENCTLIDALLGDPQCDGFQNKKWDLFVERSKAYSNCYPYDVPD  120
SEQ_ID_148    NSSIGEICDSPHQILDGENCTLIDALLGDPQCDGFQNKKWDLFVERNKAYSNCYPYDVPD  120
SEQ_ID_149    NSSIGEICDSPHQILDGGNCTLIDALLGDPQCDGFQNKKWDLFVERSRAYSNCYPYDVPD  120
SEQ_ID_150    NSSIGEICDSPHQILDGGNCTLIDALLGDPQCDGFQNKKWDLFVERSRAYSNCYPYDVPD  120
SEQ_ID_151    NSSIGEICDSPHQILDGGNCTLIDALLGDPQCDGFQNKEWDLFVERSRANSNCYPYDVPD  120
SEQ_ID_152    NSSIGEICDSPHQILDGGNCTLIDALLGDPQCDGFQNKEWDLFVERSRANSNCYPYDVPD  120
SEQ_ID_153    NSSIGEICDSPHQILDGGNCTLIDALLGDPQCDGFQNKEWDLFVERSRANSNCYPYDVPD  120
              .** * ******:**** ************:*******:*******.:* **********

SEQ_ID_136    YASLRSLVASSGTLEFNNESFNWTGVAQNGTSYACKRSSIKSFFSRLNWLHQLKYKYPAL  180
SEQ_ID_137    YASLRSLVASSGTLEFNNESFNWTGVAQNGTSSACKRRSINSFFSRLNWLHQLKYRYPAL  180
SEQ_ID_138    YASLRSLVASSGTLEFNNESFNWTGVTQNGTSSACKRRSNKSFFSRLNWLTHLKYKYPAL  180
SEQ_ID_139    YASLRSLVASSGTLEFNNESFNWTGVTQNGTSSSCKRRSNNSFFSRLNWLTHLKFKYPAL  180
SEQ_ID_140    YASLRSLVASSGTLEFNDESFNWTGVTQNGTSSSCKRRSNNSFFSRLNWLTHLKFKYPAL  180
SEQ_ID_141    YASLRSLVASSGTLEFNNESFNWTGVTQNGTSSACIRRSNNSFFSRLNWLTHLKFKYPAL  180
SEQ_ID_142    YASLRSLVASSGTLEFNNESFNWTGVTQNGTSSACIRRSKNSFFSRLNWLTHLNFKYPAL  180
SEQ_ID_143    YASLRSLVASSGTLEFNNESFNWTGVTQNGTSSACIRRSNNSFFSRLNWLTHLNFKYPAL  180
SEQ_ID_144    YASLRSLVASSGTLEFNNESFNWNGVTQNGTSSACIRRSNNSFFSRLNWLTHLNFKYPAL  180
SEQ_ID_145    YASLRSLVASSGTLEFNNESFNWAGVTQNGTSSSCIRGSNSSFFSRLNWLTHLNSKYPAL  180
SEQ_ID_146    YASLRSLVASSGTLEFNNESFNWTGVTQNGTSSACIRRSSSSFFSRLNWLTHLNYTYPAL  180
SEQ_ID_147    YASLRSLVASSGTLEFKNESFNWTGVTQNGTSSACIRGSSSSFFSRLNWLTHLNYTYPAL  180
SEQ_ID_148    YASLRSLVASSGTLEFNNESFNWAGVTQNGTSSSCIRGSKSSFFSRLNWLTHLNSKYPAL  180
SEQ_ID_149    YASLRSLVASSGTLEFKNESFNWAGVTQNGKSFSCIRGSSSSFFSRLNWLTHLNYTYPAL  180
SEQ_ID_150    YASLRSLVASSGTLEFKNESFNWAGVTQNGKSFSCIRGSSSSFFSRLNWLTHLNYTYPAL  180
SEQ_ID_151    YASLRSLVASSGTLEFKNESFNWTGVKQNGTSSACIRGSSSSFFSRLNWLTHLNYTYPAL  180
SEQ_ID_152    YASLRSLVASSGTLEFKNESFNWTGVKQNGTSSACIRGSSSSFFSRLNWLTSLNNIYPAQ  180
SEQ_ID_153    YASLRSLVASSGTLEFKNESFNWTGVKQNGTSSACIRGSSSSFFSRLNWLTHLNNIYPAQ  180
              ****************::***** ** ***.* :* * * .*********  *:  ***
```

FIG. 19B (continued)

```
SEQ_ID_136      NVTMPNNDKFDKLYIWGVHHPSTDSDQTSIYAQASGRVTVSTKRSQQTVIPNIGSRPWVR  240
SEQ_ID_137      NVTMPNNDKFDKLYIWGVHHPSTDSDQTSLYTQASGRVTVSTKRSQQTVIPNIGSRPWVR  240
SEQ_ID_138      NVTMPNNEKFDKLYIWGVLHPGTDSDQISLYAQASGRITVSTKRSQQTVIPNIGSRPRVR  240
SEQ_ID_139      NVTMPNNEKFDKLYIWGVHHPGTNNDQISLYTQASGRITVSTKRSQQTVIPNIGSRPRVR  240
SEQ_ID_140      NVTMPNNEKFDKLYIWGVHHPVTDNDQIFLYAQASGRITVSTKRSQQTVIPNIGSRPRIR  240
SEQ_ID_141      NVTMPNNEKFDKLYIWGVHHPGTDNDQIFLYAQASGRITVSTKRSQQTVIPNIGSRPRVR  240
SEQ_ID_142      NVTMPNNEQFDKLYIWGVHHPGTDKDQIFLYAQASGRITVSTKRSQQTVSPNIGSRPRVR  240
SEQ_ID_143      NVTMPNNEQFDKLYIWGVHHPGTDKDQIFLYAQSSGRITVSTKRSQQAVIPNIGSRPRIR  240
SEQ_ID_144      NVTMPNNEQFDKLYIWGVHHPGTDKDQIFLYAQPSGRITVSTKRSQQAVIPNIGSRPRIR  240
SEQ_ID_145      NVTMPNNEQFDKLYIWGVHHPGTDKDQIFLYAQSSGRITVSTKRSQQAVIPNIGSRPRIR  240
SEQ_ID_146      NVTMPNNEQFDKLYIWGVHHPGTDKDQIFLYAQSSGRITVSTKRSQQAVIPNIGSRPRIR  240
SEQ_ID_147      NVTMPNKEQFDKLYIWGVHHPGTDKDQIFLYAQSSGRITVSTKRSQQAVIPNIGSRPRIR  240
SEQ_ID_148      NVTMPNNEQFDKLYIWGVHHPGTDKDQISLYAQSSGRITVSTKRSQQAVIPNIGSRPRIR  240
SEQ_ID_149      NVTMPNKEQFDKLYIWGVHHPGTDKDQISLYAQSSGRITVSTKRSQQAVIPNIGSRPRIR  240
SEQ_ID_150      NVTMPNKEQFDKLYIWGVHHPGTDKDQISLYAQSSGRITVSTKRSQQAVIPNIGSRPRIR  240
SEQ_ID_151      NVTMPNNEQFDKLYIWGVHHPSTDKDQISLFAQPSGRITVSTKRSQQAVIPNIGSRPRIR  240
SEQ_ID_152      NVTMPNKEQFDKLYIWGVHHPDTDKNQISLFAQSSGRITVSTKRSQQAVIPNIGSRPRIR  240
SEQ_ID_153      NVTMPNKEQFDKLYIWGVHHPDTDKNQISLFAQSSGRITVSTKRSQQAVIPNIGSRPRIR  240
                ******:::********* ** *:.:*  :::* ***:*********:* ******* :*

SEQ_ID_136      GISSRISIHWTIVKPGDILLINSKGNLIAPRGYFKIRSGKSSIMRSDAPIGKCNSECITP  300
SEQ_ID_137      GISSRISIYWTIVKPGDILLINSTGNLIAPRGYFKIRSGKSSIMRSDAPIGKCNSECITP  300
SEQ_ID_138      GVSSRISIYWTIVKPGDILLINSTGNLIAPRGYFKIRSGKSSIMRSDAPIGKCNSECITP  300
SEQ_ID_139      DIPSRISIYWTIVKPGDILLINSTGNLIAPRGYFKIRSGKSSIMRSDAPIGKCNSECITP  300
SEQ_ID_140      NIPSRISIYWTIVKPGDILLINSTGNLIAPRGYFKIRSGKSSIMRSDAPIGKCNSECITP  300
SEQ_ID_141      NIPSRISIYWTIVKPGDILLINSTGNLIAPRGYFKIRSGKSSIMRSDAPIGKCNSECITP  300
SEQ_ID_142      NIPSRISIYWTIVKPGDILLINSTGNLIAPRGYFKIRSGKSSIMRSDAPIGKCNSECITP  300
SEQ_ID_143      NIPSRISIYWTIVKPGDILLINSTGNLIAPRGYFKIRSGKSSIMRSDAPIGKCNSECITP  300
SEQ_ID_144      NIPSRISIYWTIVKPGDILLINSTGNLIAPRGYFKIRSGKSSIMRSDAPIGKCKSECITP  300
SEQ_ID_145      DIPSRISIYWTIVKPGDILLINSTGNLIAPRGYFKIRSGKSSIMRSDAPIGKCKSECITP  300
SEQ_ID_146      DIPSRISIYWTIVKPGDILLINSTGNLIAPRGYFKIRSGKSSIMRSDAPIGKCKSECITP  300
SEQ_ID_147      DIPSRISIYWTIVKPGDILLINSTGNLIAPRGYFKIRSGKSSIMRSDAPIGKCKSECITP  300
SEQ_ID_148      DIPSRISIYWTIVKPGDILLINSTGNLIAPRGYFKIRSGKSSIMRSDAPIGKCKSECITP  300
SEQ_ID_149      DIPSRISIYWTIVKPGDILLINSTGNLIAPRGYFKIRSGKSSIMRSDAPIGKCKSECITP  300
SEQ_ID_150      DIPSRISIYWTIVKPGDILLINSTGNLIAPRGYFKIRSGKSSIMRSDAPIGKCKSECITP  300
SEQ_ID_151      DIPSRISIYWTIVKPGDILLINSTGNLIAPRGYFKIRSGKSSIMRSDAPIGKCKSECITP  300
SEQ_ID_152      DIPSRISIYWTIVKPGDILLINSTGNLIAPRGYFKIRSGKSSIMRSDAPIGKCKSECITP  300
SEQ_ID_153      DIPSRISIYWTIVKPGDILLINSTGNLIAPRGYFKIRSGKSSIMRSDAPIGKCKSECITP  300
                .: *****:**************.*****************************:******

SEQ_ID_136      NGSIPNDKPFQNVNRITYGACPRYVKQNTLKLATGMRNVPEKQTRGIFGAIAGFIENGWE  360
SEQ_ID_137      NGSIPNDKPFQNVNRITYGACPRYVKQNTLKLATGMRNVPEKQTRGIFGAIAGFIENGWE  360
SEQ_ID_138      NGSIPNDKPFQNVNRITYGACPRYIKQNTLKLATGMRNVPEKQTRGIFGAIAGFIENGWE  360
SEQ_ID_139      NGSIPNDKPFQNVNRITYGACPRYVKQNTLKLATGMRNVPEKQTRGIFGAIAGFIENGWE  360
SEQ_ID_140      NGSIPNDKPFQNVNRITYGACPRYVKQNTLKLATGMRNVPEKQTRGIFGAIAGFIENGWE  360
SEQ_ID_141      NGSIPNDKPFQNVNRITYGACPRYVKQNTLKLATGMRNVPEKQTRGIFGAIAGFIENGWE  360
SEQ_ID_142      NGSIPNDKPFQNVNRITYGACPRYVKQNTLKLATGMRNVPEKQTRGIFGAIAGFIENGWE  360
SEQ_ID_143      NGSIPNDKPFQNVNRITYGACPRYVKQSTLKLATGMRNVPEKQTRGIFGAIAGFIENGWE  360
SEQ_ID_144      NGSIPNDKPFQNVNRITYGACPRYVKQSTLKLATGMRNVPEKQTRGIFGAIAGFIENGWE  360
SEQ_ID_145      NGSIPNDKPFQNVNRITYGACPRYVKQSTLKLATGMRNVPERQTRGIFGAIAGFIENGWE  360
SEQ_ID_146      NGSIPNDKPFQNVNRITYGACPRYVKHSTLKLATGMRNVPEKQTRGIFGAIAGFIENGWE  360
SEQ_ID_147      NGSIPNDKPFQNVNRITYGACPRYVKHSTLKLATGMRNVPEKQTRGIFGAIAGFIENGWE  360
SEQ_ID_148      NGSIPNDKPFQNVNRITYGACPRYVKQSTLKLATGMRNVPERQTRGIFGAIAGFIENGWE  360
SEQ_ID_149      NGSIPNDKPFQNVNRITYGACPRYVKQSTLKLATGMRNVPEKQTRGIFGAIAGFIENGWE  360
SEQ_ID_150      NGSIPNDKPFQNVNRITYGACPRYVKQNTLKLATGMRNVPEKQTRGIFGAIAGFIENGWE  360
SEQ_ID_151      NGSIPNDKPFQNVNRITYGACPRYVKQSTLKLATGMRNVPEKQTRGIFGAIAGFIENGWE  360
SEQ_ID_152      NGSIPNDKPFQNVNRITYGACPRYVKQSTLKLATGMRNVPEKQTRGIFGAIAGFIENGWE  360
SEQ_ID_153      NGSIPNDKPFQNVNRITYGACPRYVKQSTLKLATGMRNVPEKQTRGIFGAIAGFIENGWE  360
                ************************:*:.*************:******************
```

FIG. 19B (continued)

```
SEQ_ID_136     GMVDGWYGFRHQNSEGTGQAADLKSTQAAINQINGKLNRLIEKTNEKFHQIEKEFSEVEG  420
SEQ_ID_137     GMMDGWYGFRHQNSEGTGQAADLKSTQAAINQINGKLNRLIEKTNEKFHQIEKEFSEVEG  420
SEQ_ID_138     GMVDGWYGFRHQNSEGTGQAADLKSTQAAINQINGKLNRLIGKTNEKFHQIEKEFSEVEG  420
SEQ_ID_139     GMVDGWYGFRHQNSEGIGQAADLKSTQAAINQINGKLNRLIGKTNEKFHQIEKEFSEVEG  420
SEQ_ID_140     GMVDGWYGFRHQNSEGIGQAADLKSTQAAINQINGKLNRLIGKTNEKFHQIEKEFSEVEG  420
SEQ_ID_141     GMVDGWYGFRHQNSEGIGQAADLKSTQAAIDQINGKLNRLIGKTNEKFHQIEKEFSEVEG  420
SEQ_ID_142     GMVDGWYGFRHQNSEGRGQAADLKSTQAAIDQINGKLNRLIGKTNEKFHQIEKEFSEVEG  420
SEQ_ID_143     GMVDGWYGFRHQNSEGRGQAADLKSTQAAIDQINGKLNRLIGKTNEKFHQIEKEFSEVEG  420
SEQ_ID_144     GMVDGWYGFRHQNSEGRGQAADLKSTQAAIDQINGKLNRLIGKTNEKFHQIEKEFSEVEG  420
SEQ_ID_145     GMVDGWYGFRHQNSEGRGQAADLKSTQAAIDQINGKLNRLIGKTNEKFHQIEKEFSEVEG  420
SEQ_ID_146     GMVDGWYGFRHQNSEGRGQAADLKSTQAAIDQINGKLNRLIGKTNEKFHQIEKEFSEVEG  420
SEQ_ID_147     GMVDGWYGFRHQNSEGRGQAADLKSTQAAIDQINGKLNRLIGKTNEKFHQIEKEFSEVEG  420
SEQ_ID_148     GMVDGWYGFRHQNSEGRGQAADLKSTQAAIDQINGKLNRLIGKTNEKFHQIEKEFSEVEG  420
SEQ_ID_149     GMVDGWYGFRHQNSEGRGQAADLKSTQAAIDQINGKLNRLIGKTNEKFHQIEKEFSEVEG  420
SEQ_ID_150     GMVDGWYGFRHQNSEGRGQAADLKSTQAAIDQINGKLNRLIGKTNEKFHQIEKEFSEVEG  420
SEQ_ID_151     GMVDGWYGFRHQNSEGRGQAADLKSTQAAIDQINGKLNRLIGKTNEKFHQIEKEFSEVEG  420
SEQ_ID_152     GMVDGWYGFRHQNSEGRGQAADLKSTQAAIDQINGKLNRLIGKTNEKFHQIEKEFSEVEG  420
SEQ_ID_153     GMVDGWYGFRHQNSEGRGQAADLKSTQAAIDQINGKLNRLIGKTNEKFHQIEKEFSEVEG  420
               **:************** *************:********** *****************

SEQ_ID_136     RIQDLEKYVEDTKIDLWSYNAELLVALENQHTIDLTDSEMNKLFERTRKQLRENAEDMGN  480
SEQ_ID_137     RIQDLEKYVEDTKIDLWSYNAELLVALENQHTIDLTDSEMNKLFERTRKQLRENAEDMGN  480
SEQ_ID_138     RIQDLEKYVEDTKIDLWSYNAELLVALENQHTIDLTDSEMNKLFERTKKQLRENAEDMGN  480
SEQ_ID_139     RIQDLEKYVEDTKIDLWSYNAELLVALENQHTIDLTDSEMNKLFERTKKQLRENAEDMGN  480
SEQ_ID_140     RIQDLEKYVEDTKIDLWSYNAELLVALENQHTIDLTDSEMNKLFERTKKQLRENAEDMGN  480
SEQ_ID_141     RIQDLEKYVEDTKIDLWSYNAELLVALENQHTIDLTDSEMNKLFEKTKKQLRENAEDMGN  480
SEQ_ID_142     RIQDLEKYVEDTKIDLWSYNAELLVALENQHTIDLTDSEMNKLFEKTKKQLRENAEDMGN  480
SEQ_ID_143     RIQDLEKYVEDTKIDLWSYNAELLVALENQHTIDLTDSEMNKLFEKTKKQLRENAEDMGN  480
SEQ_ID_144     RIQDLEKYVEDTKIDLWSYNAELLVALENQHTIDLTDSEMNKLFEKTKKQLRENAEDMGN  480
SEQ_ID_145     RIQDLEKYVEDTKIDLWSYNAELLVALENQHTIDLTDSEMNKLFEKTKKQLRENAEDMGN  480
SEQ_ID_146     RIQDLEKYVEDTKIDLWSYNAELLVALENQHTIDLTDSEMNKLFEKTKKQLRENAEDMGN  480
SEQ_ID_147     RVQDLEKYVEDTKIDLWSYNAELLVALENQHTIDLTDSEMNKLFEKTKKQLRENAEDMGN  480
SEQ_ID_148     RIQDLEKYVEDTKIDLWSYNAELLVALENQHTIDLTDSEMNKLFEKTKKQLRENAEDMGN  480
SEQ_ID_149     RVQDLEKYVEDTKIDLWSYNAELLVALENQHTIDLTDSEMNKLFEKTKKQLRENAEDMGN  480
SEQ_ID_150     RVQDLEKYVEDTKIDLWSYNAELLVALENQHTIDLTDSEMNKLFEKTKKQLRENAEDMGN  480
SEQ_ID_151     RVQDLEKYVEDTKIDLWSYNAELLVALENQHTIDLTDSEMNKLFEKTKKQLRENAEDMGN  480
SEQ_ID_152     RVQDLEKYVEDTKIDLWSYNAELLVALENQHTIDLTDSEMNKLFEKTKKQLRENAEDMGN  480
SEQ_ID_153     RVQDLEKYVEDTKIDLWSYNAELLVALENQHTIDLTDSEMNKLFEKTKKQLRENAEDMGN  480
               *:*******************************************:*:************

SEQ_ID_136     GCFKIYHKCDNACIGSIRNGTYDHDVYRDEALNNRFQIKGVELKSGYKDWILWISFAISC  540
SEQ_ID_137     GCFKIYHKCDNACIGSIRNGTYDHDVYRDEALNNRFQIKGVELKSGYKDWILWISFAISC  540
SEQ_ID_138     GCFKIYHKCDNACIGSIRNGTYDHDVYRDEALNNRFQIKGVELKSGYKDWILWISFAISC  540
SEQ_ID_139     GCFKIYHKCDNACIGSIRNGTYDHDVYRDEALNNRFQIKGVELKSGYKDWILWISFAISC  540
SEQ_ID_140     GCFKIYHKCDNACIGSIRNGTYDHDVYRDEALNNRFQIKGVELKSGYKDWILWISFAISC  540
SEQ_ID_141     GCFKIYHKCDNACIGSIRNGTYDHDVYRDEALNNRFQIKGVELKSGYKDWILWISFAISC  540
SEQ_ID_142     GCFKIYHKCDNACIGSIRNGTYDHDVYRDEALNNRFQIKGVELKSGYKDWILWISFAISC  540
SEQ_ID_143     GCFKIYHKCDNACIGSIRNGTYDHDVYRDEALNNRFQIKGVELKSGYKDWILWISFAISC  540
SEQ_ID_144     GCFKIYHKCDNACIGSIRNGTYDHDVYRDEALNNRFQIKGVELKSGYKDWILWISFAISC  540
SEQ_ID_145     GCFKIYHKCDNACIGSIRNGTYDHDVYRDEALNNRFQIKGVELKSGYKDWILWISFAISC  540
SEQ_ID_146     GCFKIYHKCDNACIGSIRNGTYDHNVYRDEALNNRFQIKGVELKSGYKDWILWISFAISC  540
SEQ_ID_147     GCFKIYHKCDNACIESIRNETYDHNVYRDEALNNRFQIKGVELKSGYKDWILWISFAISC  540
SEQ_ID_148     GCFKIYHKCDNACMGSIRNGTYDHNVYRDEALNNRFQIKGVELKSGYKDWILWISFAISC  540
SEQ_ID_149     GCFKIYHKCDNACIGSIRNETYDHNVYRDEALNNRFQIKGVELKSGYKDWILWISFAISC  540
SEQ_ID_150     GCFKIYHKCDNACIGSIRNETYDHNVYRDEALNNRFQIKGVELKSGYKDWILWISFAISC  540
SEQ_ID_151     GCFKIYHKCDNACIGSIRNETYDHNVYRDEALNNRFQIKGVELKSGYKDWILWISFAMSC  540
SEQ_ID_152     GCFKIYHKCDNACIGSIRNETYDHNVYRDEALNNRFQIKGVELKSGYKDWILWISFAMSC  540
SEQ_ID_153     GCFKIYHKCDNACIGSIRNETYDHNVYRDEALNNRFQIKGVELKSGYKDWILWISFAMSC  540
               *************: **** ****:********************************:**
```

FIG. 19B (continued)

```
SEQ_ID_136      FLLCVVLLGFIMWACQKGNIRCNICI      566
SEQ_ID_137      FLLCVVLLGFIMWACQKGNIRCNICI      566
SEQ_ID_138      FLLCVALLGFIMWACQKGNIRCNICI      566
SEQ_ID_139      FLLCVALLGFIMWACQKGNIRCNICI      566
SEQ_ID_140      FLLCVALLGFIMWACQKGNIRCNICI      566
SEQ_ID_141      FLLCVALLGFIMWACQKGNIRCNICI      566
SEQ_ID_142      FLLCVALLGFIMWACQKGNIRCNICI      566
SEQ_ID_143      FLLCVALLGFIMWACQKGNIRCNICI      566
SEQ_ID_144      FLLCVALLGFIMWACQKGNIRCNICI      566
SEQ_ID_145      FLLCVALLGFIMWACQKGNIRCNICI      566
SEQ_ID_146      FLLCVALLGFIMWACQKGNIRCNICI      566
SEQ_ID_147      FLLCVALLGFIMWACQKGNIRCNICI      566
SEQ_ID_148      FLLCVALLGFIMWACQKGNIRCNICI      566
SEQ_ID_149      FLLCVALLGFIMWACQKGNIRCNICI      566
SEQ_ID_150      FLLCVALLGFIMWACQKGNIRCNICI      566
SEQ_ID_151      FLLCIALLGFIMWACQKGNIRCNICI      566
SEQ_ID_152      FLLCIALLGFIMWACQKGNIRCNICI      566
SEQ_ID_153      FLLCIALLGFIMWACQKGNIRCNICI      566
                ****:.********************
Signal peptides indicated by underlining (amino acids 1-16)
```

FIG. 19B (continued)

```
SEQ_ID_154    MKAIIVLLMVVTSNADRICTGITSSNSPHVVKTATQGEVNVTGVIPLTTTPTKSHFANLK  60
SEQ_ID_155    MKAIIVLLMVVTSNADRICTGITSSNSPHVVKTATQGEVNVTGVIPLTTTPTKSHFANLK  60
SEQ_ID_156    MKAIIVLLMVVTSNADRICTGITSSNSPHVVKTATQGEVNVTGVIPLTTTPTKSHFANLK  60
SEQ_ID_157    MKAIIVLLMVVTSNADRICTGITSSNSPHVVKTATQGEVNVTGVIPLTTTPTKSHFANLK  60
SEQ_ID_158    MKAIIVLLMVVTSSADRICTGITSSNSPHVVKTATQGEVNVTGVIPLTTTPTKSHFANLK  60
SEQ_ID_159    MKAIIVLLMVVTSNADRICTGITSSNSPHVVKTATQGEVNVTGVIPLTTTPTKSHFANLK  60
SEQ_ID_160    MKAIIVLLMVVTSNADRICTGITSSNSPHVVKTATQGEVNVTGVIPLTTTPTKSHFANLK  60
              *************.**********************************************

SEQ_ID_154    GTKTRGKLCPKCLNCTDLDVALGRPKCTGNIPSAKVSILHEVRPVTSGCFPIMHDRTKIR  120
SEQ_ID_155    GTKTRGKLCPKCLNCTDLDVALGRPKCTGNIPSAKVSILHEVRPVTSGCFPIMHDRTKIR  120
SEQ_ID_156    GTETRGKLCPKCLNCTDLDVALGRPKCTGNIPSARVSILHEVRPVTSGCFPIMHDRTKIR  120
SEQ_ID_157    GTETRGKLCPKCLNCTDLDVALGRPKCTGKIPSARVSILHEVRPVTSGCFPIMHDRTKIR  120
SEQ_ID_158    GTETRGKLCPKCLNCTDLDVALGRPKCTGKIPSARVSILHEVRPVTSGCFPIMHDRTKIR  120
SEQ_ID_159    GTETRGKLCPKCLNCTDLDVALGRPKCTGKIPSARVSILHEVRPVTSGCFPIMHDRTKIR  120
SEQ_ID_160    GTETRGKLCPKCLNCTDLDVALGRPKCTGKIPSARVSILHEVRPVTSGCFPIMHDRTKIR  120
              **:**************************:****:*************************

SEQ_ID_154    QLPNLLRGYEHIRLSIHNVINAEKAPGGPYKIGTSGSCPNVTNGNGFFATMAWAVPKNDN  180
SEQ_ID_155    QLPNLLRGYERIRLSNHNVINAEKAPGGPYKIGTSGSCPNVTNGNGFFATMAWAVPKNEN  180
SEQ_ID_156    QLPNLLRGYEHIRLSTHNVINAENAPGGPYKIGTSGSCPNVTNGNGFFATMAWAVPKNDN  180
SEQ_ID_157    QLPNLLRGYEHIRLSTHNVINAENAPGGPYKIGTSGSCPNITNGNGFFATMAWAVPKNDK  180
SEQ_ID_158    QLPNLLRGYEHVRLSTHNVINAEGAPGGPYKIGTSGSCPNITNGNGFFATMAWAVPD--K  178
SEQ_ID_159    QLPNLLRGYEHVRLSTHNVINAEDAPGRPYEIGTSGSCPNITNGNGFFATMAWAVPK---  177
SEQ_ID_160    QLPNLLRGYEHVRLSTHNVINTEDAPGGPYEIGTSGSCLNITNGKGFFATMAWAVPK---  177
              **********:.*** *****:* *** **:******* *:***:***********.

SEQ_ID_154    NKTATNSLTIEVPYICTEGEDQITVWGFHSDNENQMAKLYGDSKPQKFTSSANGVTTHYV  240
SEQ_ID_155    NKTATNSLTIEVPYICTEGEDQITVWGFHSDSETQMAKLYGDSKPQKFTSSANGVTTHYV  240
SEQ_ID_156    NKTATNSLTIEVPYICTEGEDQITVWGFHSDNEIQMAKLYGDSKPQKFTSSANGVTTHYV  240
SEQ_ID_157    NKTATNPLTIEVPYICTEGEDQITVWGFHSDNETQMAKLYGDSKPQKFTSSANGVTTHYV  240
SEQ_ID_158    NKTATNPLTIEVPYVCTEGEDQITVWGFHSDNETQMAKLYGDSKPQKFTSSANGVTTHYV  238
SEQ_ID_159    NKTATNPLTIEVPYICTEGEDQITVWGFHSDSETQMAKLYGDSKPQKFTSSANGVTTHYV  237
SEQ_ID_160    NKTATNPLTIEVPYICTEEEDQITVWGFHSDDETQMARLYGDSKPQKFTSSANGVTTHYV  237
              ****** *******:*** ************.* ***:**********************

SEQ_ID_154    SQIGGFPNQTEDGGLPQSGRIVVDYMVQKSGKTGTITYQRGILLPQKVWCASGRSKVIKG  300
SEQ_ID_155    SQIGGFPNQTEDGGLPQSGRIVVDYMVQKSGKTGTITYQRGILLPQKVWCASGRSKVIKG  300
SEQ_ID_156    SQIGGFPNQTEDGGLPQSGRIVVDYMVQKSGKTGTITYQRGILLPQKVWCASGRSKVIKG  300
SEQ_ID_157    SQIGGFPNQTEDGGLPQSGRIVVDYMVQKSGKTGTITYQRGILLPQKVWCASGRSKVIKG  300
SEQ_ID_158    SQIGGFPNQTEDGGLPQSGRIVVDYMVQKSGKTGTITYQRGILLPQKVWCASGRSKVIKG  298
SEQ_ID_159    SQIGGFPNQTEDGGLPQSGRIVVDYMVQKSGKTGTITYQRGILLPQKVWCASGRSKVIKG  297
SEQ_ID_160    SQIGGFPNQTEDGGLPQSGRIVVDYMVQKSGKTGTITYQRGILLPQKVWCASGKSKVIKG  297
              ************************************ ****************:******

SEQ_ID_154    SLPLIGEADCLHEKYGGLNKSKPYYTGEHAKAIGNCPIWVKTPLKLANGTKYRPPAKLLK  360
SEQ_ID_155    SLPLIGEADCLHEKYGGLNKSKPYYTGEHAKAIGNCPIWVKTPLKLANGTKYRPPAKLLK  360
SEQ_ID_156    SLPLIGEADCLHEKYGGLNKSKPYYTGEHAKAIGNCPIWVKTPLKLANGTKYRPPAKLLK  360
SEQ_ID_157    SLPLIGEADCLHEKYGGLNKSKPYYTGEHAKAIGNCPIWVKTPLKLANGTKYRPPAKLLK  360
SEQ_ID_158    SLPLIGEADCLHEKYGGLNKSKPYYTGEHAKAIGNCPIWVKTPLKLANGTKYRPPAKLLK  358
SEQ_ID_159    SLPLIGEADCLHEKYGGLNKSKPYYTGEHAKAIGNCPIWVKTPLKLANGTKYRPPAKLLK  357
SEQ_ID_160    SLPLIGEADCLHEKYGGLNKSKPYYTGEHAKAIGNCPIWVKTPLKLANGTKYRPPAKLLK  357
              ************************************************************
```

FIG. 19C

```
SEQ_ID_154      ERGFFGAIAGFLEGGWEGMIAGWHGYTSHGAHGVAVAADLKSTQEAINKITKNLNSLSEL  420
SEQ_ID_155      ERGFFGAIAGFLEGGWEGMIAGWHGYTSHGAHGVAVAADLKSTQEAINKITKNLNSLSEL  420
SEQ_ID_156      ERGFFGAIAGFLEGGWEGMIAGWHGYTSHGAHGVAVAADLKSTQEAINKITKNLNSLSEL  420
SEQ_ID_157      ERGFFGAIAGFLEGGWEGMIAGWHGYTSHGAHGVAVAADLKSTQEAINKITKNLNSLSEL  420
SEQ_ID_158      ERGFFGAIAGFLEGGWEGMIAGWHGYTSHGAHGVAVAADLKSTQEAINKITKNLNSLSEL  418
SEQ_ID_159      ERGFFGAIAGFLEGGWEGMIAGWHGYTSHGAHGVAVAADLKSTQEAINKITKNLNSLSEL  417
SEQ_ID_160      ERGFFGAIAGFLEGGWEGMIAGWHGYTSHGAHGVAVAADLKSTQEAINKITKNLNSLSEL  417
                ************************************************************

SEQ_ID_154      EVKNLQRLSGAMDELHNEILELDEKVDDLRADTISSQIELAVLLSNEGIINSEDEHLLAL  480
SEQ_ID_155      EVKNLQRLSGAMDELHNEILELDEKVDDLRADTISSQIELAVLLSNEGIINSEDEHLLAL  480
SEQ_ID_156      EVKNLQRLSGAMDELHNEILELDEKVDDLRADTISSQIELAVLLSNEGIINSEDEHLLAL  480
SEQ_ID_157      EVKNLQRLSGAMDELHNEILELDEKVDDLRADTISSQIELAVLLSNEGIINSEDEHLLAL  480
SEQ_ID_158      EVKNLQRLSGAMDELHNEILELDEKVDDLRADTISSQIELAVLLSNEGIINSEDEHLLAL  478
SEQ_ID_159      EVKNLQRLSGAMDELHNEILELDEKVDDLRADTISSQIELAVLLSNEGIINSEDEHLLAL  477
SEQ_ID_160      EVKNLQRLSGAMDELHNEILELDEKVDDLRADTISSQIELAVLLSNEGIINSEDEHLLAL  477
                ************************************************************

SEQ_ID_154      ERKLKKMLGPSAVEIGNGCFETKHKCNQTCLDRIAAGTFNAGEFSLPTFDSLNITAASLN  540
SEQ_ID_155      ERKLKKMLGPSAVEIGNGCFETKHKCNQTCLDRIAAGTFNAGEFSLPTFDSLNITAASLN  540
SEQ_ID_156      ERKLKKMLGPSAVEIGNGCFETKHKCNQTCLDRIAAGTFDAGEFSLPTFDSLNITAASLN  540
SEQ_ID_157      ERKLKKMLGPSAVEIGNGCFETKHKCNQTCLDRIAAGTFDAGEFSLPTFDSLNITAASLN  540
SEQ_ID_158      ERKLKKMLGPSAVEIGNGCFETKHKCNQTCLDKIAAGTFDAGEFSLPTFDSLNITAASLN  538
SEQ_ID_159      ERKLKKMLGPSAVEIGNGCFETKHKCNQTCLDRIAAGTFDAGEFSLPTFDSLNITAASLN  537
SEQ_ID_160      ERKLKKMLGPSAVEIGNGCFETKHKCNQTCLDRIAAGTFDAGEFSLPTFDSLNITAASLN  537
                ********************************:******:********************

SEQ_ID_154      DDGLDNHTILLYYSTAASSLAVTLMIAIFIVYMVSRDNVSCSICL      585
SEQ_ID_155      DDGLDNHTILLYYSTAASSLAVTLMIAIFVVYMVSRDNVSCSICL      585
SEQ_ID_156      DDGLDNHTILLYYSTAASSLAVTLMIAIFVVYMVSRDNVSCSICL      585
SEQ_ID_157      DDGLDNHTILLYYSTAASSLAVTLMIAIFVVYMVSRDNVSCSICL      585
SEQ_ID_158      DDGLDNHTILLYYSTAASSLAVTLMIAIFVVYMVSRDNVSCSICL      583
SEQ_ID_159      DDGLDNHTILLYYSTAASSLAVTLMIAIFVVYMVSRDNVSCSICL      582
SEQ_ID_160      DDGLDNHTILLYYSTAASSLAVTLMIAIFVVYMVSRDNVSCSICL      582
                *****************************:***************
Signal peptides indicated by underlining (amino acids 1-15)
```

FIG. 19C (continued)

```
SEQ_ID_164    MKAIIVLLMVVTSNADRICTGITSSNSPHVVKTATQGEVNVTGVIPLTTTPTKSYFANLK   60
SEQ_ID_165    MKAIIVLLMVVTSNADRICTGITSSNSPHVVKTATQGEVNVTGVIPLTTTPTKSYFANLK   60
SEQ_ID_166    MKAIIVLLMVVTSNADRICTGITSSNSPHVVKTATQGEVNVTGVIPLTTTPTKSYFANLK   60
SEQ_ID_167    MKAIIVLLMVVTSNADRICTGITSSNSPHVVKTATQGEVNVTGVIPLTTTPTKSYFANLK   60
              ************************************************************

SEQ_ID_164    GTRTRGKLCPDCLNCTDLDVALGRPMCVGTTPSAKASILHEVKPVTSGCFPIMHDRTKIR   120
SEQ_ID_165    GTRTRGKLCPDCLNCTDLDVALGRPMCVGTTPSAKASILHEVRPVTSGCFPIMHDRTKIR   120
SEQ_ID_166    GTKTRGKLCPDCLNCTDLDVALGRPMCVGTTPSAKASILHEVRPVTSGCFPIMHDRTKIR   120
SEQ_ID_167    GTRTRGKLCPDCLNCTDLDVALGRPMCVGTTPSAKASILHEVRPVTSGCFPIMHDRTKIR   120
              **:***************************************:*****************

SEQ_ID_164    QLPNLLRGYENIRLSTQNVIDAEKAPGGPYRLGTSGSCPNATSKSGFFATMAWAVPKDNN   180
SEQ_ID_165    QLPNLLRGYENIRLSTQNVIDAEKAPGGPYRLGTSGSCPNATSKIGFFATMAWAVPKDNY   180
SEQ_ID_166    QLANLLRGYENIRLSTQNVIDAEKAPGGPYRLGTSGSCPNATSKSGFFATMAWAVPKDNN   180
SEQ_ID_167    QLPNLLRGYEKIRLSTQNVIDAEKAPGGPYRLGTSGSCPNATSKIGFFATMAWAVPKDNY   180
              ** *******:********************************* ************** 

SEQ_ID_164    KNATNPLTVEVPYICTEGEDQITVWGFHSDDKTQMKNLYGDSNPQKFTSSANGVTTHYVS   240
SEQ_ID_165    KNATNPLTVEVPYICTEGEDQITVWGFHSDNKTQMKSLYGDSNPQKFTSSANGVTTHYVS   240
SEQ_ID_166    KNATNPLTVEVPYICAEGEDQITVWGFHSDDKTQMKNLYGDSNPQKFTSSANGVTTHYVS   240
SEQ_ID_167    KNATNPLTVEVPYICTEGEDQITVWGFHSDNKTQMKSLYGDSNPQKFTSSANGVTTHYVS   240
              ***************:**************:*****.***********************

SEQ_ID_164    QIGSFPDQTEDGGLPQSGRIVVDYMMQKPGKTGTIVYQRGVLLPQKVWCASGRSKVIKGS   300
SEQ_ID_165    QIGDFPDQTEDGGLPQSGRIVVDYMMQKPGKTGTIVYQRGVLLPQKVWCASGRSKVIKGS   300
SEQ_ID_166    QIGGFPDQTEDGGLPQSGRIVVDYMMQKPGKTGTIVYQRGVLLPQKVWCASGRSKVIKGS   300
SEQ_ID_167    QIGDFPDQTEDGGLPQSGRIVVDYMMQKPGKTGTIVYQRGVLLPQKVWCASGRSKVIKGS   300
              ***.********************************************************

SEQ_ID_164    LPLIGEADCLHEKYGGLNKSKPYYTGEHAKAIGNCPIWVKTPLKLANGTKYRPPAKLLKE   360
SEQ_ID_165    LPLIGEADCLHEKYGGLNKSKPYYTGEHAKAIGNCPIWVKTPLKLANGTKYRPPAKLLKE   360
SEQ_ID_166    LPLIGEADCLHEKYGGLNKSKPYYTGEHAKAIGNCPIWVKTPLKLANGTKYRPPAKLLKE   360
SEQ_ID_167    LPLIGEADCLHEEYGGLNKSKPYYTGKHAKAIGNCPIWVKTPLKLANGTKYRPPAKLLKE   360
              ************:*************:*********************************

SEQ_ID_164    RGFFGAIAGFLEGGWEGMIAGWHGYTSHGAHGVAVAADLKSTQEAINKITKNLNSLSELE   420
SEQ_ID_165    RGFFGAIAGFLEGGWEGMIAGWHGYTSHGAHGVAVAADLKSTQEAINKITKNLNSLSELE   420
SEQ_ID_166    RGFFGAIAGFLEGGWEGMIAGWHGYTSHGAHGVAVAADLKSTQEAINKITKNLNSLSELE   420
SEQ_ID_167    RGFFGAIAGFLEGGWEGMIAGWHGYTSHGAHGVAVAADLKSTQEAINKITKNLNSLSELE   420
              ************************************************************

SEQ_ID_164    VKNLQRLSGAMDELHNEILELDEKVDDLRADTISSQIELAVLLSNEGIINSEDEHLLALE   480
SEQ_ID_165    VKNLQRLSGAMDELHNEILELDEKVDDLRADTISSQIELAVLLSNEGIINSEDEHLLALE   480
SEQ_ID_166    VKNLQRLSGAMDELHNEILELDEKVDDLRADTISSQIELAVLLSNEGIINSEDEHLLALE   480
SEQ_ID_167    VKNLQRLSGAMDELHNEILELDEKVDDLRADTISSQIELAVLLSNEGIINSEDEHLLALE   480
              ************************************************************

SEQ_ID_164    RKLKKMLGPSAVEIGNGCFETKHKCNQTCLDRIAAGTFNAGEFSLPTFDSLNITAASLND   540
SEQ_ID_165    RKLKKMLGPSAVDIGNGCFETKHKCNQTCLDRIAAGTFNAGEFSLPTFDSLNITAASLND   540
SEQ_ID_166    RKLKKMLGPSAVDIGNGCFETKHKCNQTCLDRIAAGTFNAGEFSLPTFDSLNITAASLND   540
SEQ_ID_167    RKLKKMLGPSAVDIGNGCFETKHKCNQTCLDRIAAGTFNAGEFSLPTFDSLNITAASLND   540
              ************:***********************************************

SEQ_ID_164    DGLDNHTILLYYSTAASSLAVTLMLAIFIVYMVSRDNVSCSICL       584
SEQ_ID_165    DGLDNHTILLYYSTAASSLAVTLMLAIFIVYMVSRDNVSCSICL       584
SEQ_ID_166    DGLDNHTILLYYSTAASSLAVTLMLAIFIVYMVSRDNVSCSICL       584
SEQ_ID_167    DGLDNHTILLYYSTAASSLAVTLMLAIFIVYMVSRDNVSCSICL       584
              ********************************************
```

FIG. 19D

```
Brisbane_2008     1 MKAIIVLLMVVTSNADRICTGITSSNSPHVVKTATQGEVNVTGVIPLTTT    50
                    ||||||||||||||||||||||||||||||||||||||||||||||||||
Austria_2021      1 MKAIIVLLMVVTSNADRICTGITSSNSPHVVKTATQGEVNVTGVIPLTTT    50

Brisbane_2008    51 PTKSHFANLKGTETRGKLCPKCLNCTDLDVALGRPKCTGKIPSARVSILH   100
                    ||||||||||||||||||||||||||||||||||||||||||||||||||
Austria_2021     51 PTKSHFANLKGTETRGKLCPKCLNCTDLDVALGRPKCTGKIPSARVSILH   100

Brisbane_2008   101 EVRPVTSGCFPIMHDRTKIRQLPNLLRGYEHIRLSTHNVINAENAPGGPY   150
                    |||||||||||||||||||||||||||||||:|||||||||.|:||||||
Austria_2021    101 EVRPVTSGCFPIMHDRTKIRQLPNLLRGYEHVRLSTHNVINTEDAPGGPY   150

Brisbane_2008   151 KIGTSGSCPNITNGNGFFATMAWAVPKNDKNKTATNPLTIEVPYICTEGE   200
                    :|||||||.|||||.|||||||||||   |||||||||||||||||||.|
Austria_2021    151 EIGTSGSCLNITNGKGFFATMAWAVP---KNKTATNPLTIEVPYICTEEE   197

Brisbane_2008   201 DQITVWGFHSDNETQMAKLYGDSKPQKFTSSANGVTTHYVSQIGGFPNQT   250
                    |||||||||||:|||||:||||||||||||||||||||||||||||||||
Austria_2021    198 DQITVWGFHSDDETQMARLYGDSKPQKFTSSANGVTTHYVSQIGGFPNQT   247

Brisbane_2008   251 EDGGLPQSGRIVVDYMVQKSGKTGTITYQRGILLPQKVWCASGRSKVIKG   300
                    |||||||||||||||||||||||||||||||||||||||||||:||||||
Austria_2021    248 EDGGLPQSGRIVVDYMVQKSGKTGTITYQRGILLPQKVWCASGKSKVIKG   297

Brisbane_2008   301 SLPLIGEADCLHEKYGGLNKSKPYYTGEHAKAIGNCPIWVKTPLKLANGT   350
                    ||||||||||||||||||||||||||||||||||||||||||||||||||
Austria_2021    298 SLPLIGEADCLHEKYGGLNKSKPYYTGEHAKAIGNCPIWVKTPLKLANGT   347

Brisbane_2008   351 KYRPPAKLLKERGFFGAIAGFLEGGWEGMIAGWHGYTSHGAHGVAVAADL   400
                    ||||||||||||||||||||||||||||||||||||||||||||||||||
Austria_2021    348 KYRPPAKLLKERGFFGAIAGFLEGGWEGMIAGWHGYTSHGAHGVAVAADL   397

Brisbane_2008   401 KSTQEAINKITKNLNSLSELEVKNLQRLSGAMDELHNEILELDEKVDDLR   450
                    ||||||||||||||||||||||||||||||||||||||||||||||||||
Austria_2021    398 KSTQEAINKITKNLNSLSELEVKNLQRLSGAMDELHNEILELDEKVDDLR   447

Brisbane_2008   451 ADTISSQIELAVLLSNEGIINSEDEHLLALERKLKKMLGPSAVEIGNGCF   500
                    ||||||||||||||||||||||||||||||||||||||||||||||||||
Austria_2021    448 ADTISSQIELAVLLSNEGIINSEDEHLLALERKLKKMLGPSAVEIGNGCF   497

Brisbane_2008   501 ETKHKCNQTCLDRIAAGTFDAGEFSLPTFDSLNITAASLNDDGLDNHTIL   550
                    ||||||||||||||||||||||||||||||||||||||||||||||||||
Austria_2021    498 ETKHKCNQTCLDRIAAGTFDAGEFSLPTFDSLNITAASLNDDGLDNHTIL   547

Brisbane_2008   551 LYYSTAASSLAVTLMIAIFVVYMVSRDNVSCSICL    585   (SEQ ID NO: 157)
                    |||||||||||||||||||||||||||||||||||
Austria_2021    548 LYYSTAASSLAVTLMIAIFVVYMVSRDNVSCSICL    582   (SEQ ID NO: 71)
```

SEQ ID NO: 157 = B/Brisbane/60/2008 (B/Victoria lineage) HA protein
SEQ ID NO: 71 = B/Austria/1359417/2021 (B/Victoria lineage) HA protein

572 matches to SEQ ID NO: 71 / 585 residues (including gaps in SEQ ID NO: 71) = 97.8% identity

FIG. 19E

```
Beijing_1995        1 MKAKLLVLLCTFTATYADTICIGYHANNSTDTVDTVLEKNVTVTHSVNLL    50
                      |||.|:|:|.|||...|||:||||||||||||||||||||||||||||||
Wisconsin_2022      1 MKAILVVMLYTFTTANADTLCIGYHANNSTDTVDTVLEKNVTVTHSVNLL    50

Beijing_1995       51 EDSHNGKLCLLKGIAPLQLGNCSVAGWILGNPECESLISKESWSYIVETP   100
                      ||.||||||.|:|:|||.||.|::|||||||||||||.:..||||||||.
Wisconsin_2022     51 EDKHNGKLCKLRGVAPLHLGQCNIAGWILGNPECESLSTARSWSYIVETS   100

Beijing_1995      101 NPENGTCYPGYFADYEELREQLSSVSSFERFEIFPKESSWPNH-TVTGVT   149
                      |.:|||||||.|.:||||||||||||||||||||||.|||||| :..|||
Wisconsin_2022    101 NSDNGTCYPGDFINYEELREQLSSVSSFERFEIFPKTSSWPNHDSDNGVT   150

Beijing_1995      150 ASCSHNGKSSFYRNLLWLTEKNGLYPNLSNSYVNNKEKEVLVLWGVHHPS   199
                      |:|||.|..|||:||:||.:|...||.::.:|:|:|.||||||||:|||.
Wisconsin_2022    151 AACSHAGARSFYKNLIWLVKKGKSYPKINQTYINDKGKEVLVLWGIHHPP   200

Beijing_1995      200 NIRDQRAIYHTENAYVSVVSSHYSRRFTPEIAKRPKVRGQEGRINYYWTL   249
                      .|.||.::|...:|||.|.:|.||::|.||||.|||||.|.||:||||||
Wisconsin_2022    201 TITDQESLYQNADAYVFVGTSRYSKKFKPEIATRPKVRDQAGRMNYYWTL   250

Beijing_1995      250 LEPGDTIIFEANGNLIAPWYAFALSRGFGSGIITSNAPMNECDAKCQTPQ   299
                      :||||.|.|||.|||:||.|||.:.:..|||||.|:.|:::|:|.||||:
Wisconsin_2022    251 VEPGDKITFEATGNLVAPRYAFTMEKEAGSGIIISDTPVHDCNATCQTPE   300

Beijing_1995      300 GAINSSLPFQNVHPVTIGECPKYVRSTKLRMVTGLRNIPSIQSRGLFGAI   349
                      ||||:|||||||||:|||:|||||||||||:.|||||:||||||||||||
Wisconsin_2022    301 GAINTSLPFQNVHPITIGKCPKYVRSTKLRLATGLRNVPSIQSRGLFGAI   350

Beijing_1995      350 AGFIEGGWTGMMDGWYGYHHQNEQGSGYAADQKSTQNAINGITNKVNSVI   399
                      |||||||||||:||||||||||:||||||||.|||||||:.|||||||||
Wisconsin_2022    351 AGFIEGGWTGMVDGWYGYHHQNDQGSGYAADLKSTQNAIDKITNKVNSVI   400

Beijing_1995      400 EKMNTQFTAVGKEFNKLERRMENLNKKVDDGFLDIWTYNAELLVLLENER   449
                      |||||||||||||||.||:|:|||||||||||||:|||||||||||||||
Wisconsin_2022    401 EKMNTQFTAVGKEFNHLEKRIENLNKKVDDGFLDVWTYNAELLVLLENER   450

Beijing_1995      450 TLDFHDSNVKNLYEKVKSQLKNNAKEIGNGCFEFYHKCNNECMESVKNGT   499
                      |||:||||||||||||:.||||||||||||||||||||:|.|||||||||
Wisconsin_2022    451 TLDYHDSNVKNLYEKVRHQLKNNAKEIGNGCFEFYHKCDNTCMESVKNGT   500

Beijing_1995      500 YDYPKYSEESKLNREKIDGVKLESMGVYQILAIYSTVASSLVLLVSLGAI   549
                      |||||||||:||||||||||||:|..:||||||||||||||||:||||||
Wisconsin_2022    501 YDYPKYSEEAKLNREKIDGVKLDSTRIYQILAIYSTVASSLVLVVSLGAI   550

Beijing_1995      550 SFWMCSNGSLQCRICI    565    (SEQ ID NO: 123)
                      ||||||||||||||||
Wisconsin_2022    551 SFWMCSNGSLQCRICI    566    (SEQ ID NO: 83)

SEQ ID NO: 123 = A/Beijing/262/1995(H1N1) virus HA protein
SEQ ID NO: 83 = A/Wisconsin/67/2022(H1N1)pdm09 virus HA protein
```

FIG. 19F

```
Austria_w_SP       1 MKAIIVLLMVVTSNADRICTGITSSNSPHVVKTATQGEVNVTGVIPLTTT     50
                                    |||||||||||||||||||||||||||||||||||
Austria_no_SP      1 ---------------DRICTGITSSNSPHVVKTATQGEVNVTGVIPLTTT     35

Austria_w_SP      51 PTKSHFANLKGTETRGKLCPKCLNCTDLDVALGRPKCTGKIPSARVSILH    100
                     ||||||||||||||||||||||||||||||||||||||||||||||||||
Austria_no_SP     36 PTKSHFANLKGTETRGKLCPKCLNCTDLDVALGRPKCTGKIPSARVSILH     85

Austria_w_SP     101 EVRPVTSGCFPIMHDRTKIRQLPNLLRGYEHVRLSTHNVINTEDAPGGPY    150
                     ||||||||||||||||||||||||||||||||||||||||||||||||||
Austria_no_SP     86 EVRPVTSGCFPIMHDRTKIRQLPNLLRGYEHVRLSTHNVINTEDAPGGPY    135

Austria_w_SP     151 EIGTSGSCLNITNGKGFFATMAWAVPKNKTATNPLTIEVPYICTEEEDQI    200
                     ||||||||||||||||||||||||||||||||||||||||||||||||||
Austria_no_SP    136 EIGTSGSCLNITNGKGFFATMAWAVPKNKTATNPLTIEVPYICTEEEDQI    185

Austria_w_SP     201 TVWGFHSDDETQMARLYGDSKPQKFTSSANGVTTHYVSQIGGFPNQTEDG    250
                     ||||||||||||||||||||||||||||||||||||||||||||||||||
Austria_no_SP    186 TVWGFHSDDETQMARLYGDSKPQKFTSSANGVTTHYVSQIGGFPNQTEDG    235

Austria_w_SP     251 GLPQSGRIVVDYMVQKSGKTGTITYQRGILLPQKVWCASGKSKVIKGSLP    300
                     ||||||||||||||||||||||||||||||||||||||||||||||||||
Austria_no_SP    236 GLPQSGRIVVDYMVQKSGKTGTITYQRGILLPQKVWCASGKSKVIKGSLP    285

Austria_w_SP     301 LIGEADCLHEKYGGLNKSKPYYTGEHAKAIGNCPIWVKTPLKLANGTKYR    350
                     ||||||||||||||||||||||||||||||||||||||||||||||||||
Austria_no_SP    286 LIGEADCLHEKYGGLNKSKPYYTGEHAKAIGNCPIWVKTPLKLANGTKYR    335

Austria_w_SP     351 PPAKLLKERGFFGAIAGFLEGGWEGMIAGWHGYTSHGAHGVAVAADLKST    400
                     ||||||||||||||||||||||||||||||||||||||||||||||||||
Austria_no_SP    336 PPAKLLKERGFFGAIAGFLEGGWEGMIAGWHGYTSHGAHGVAVAADLKST    385

Austria_w_SP     401 QEAINKITKNLNSLSELEVKNLQRLSGAMDELHNEILELDEKVDDLRADT    450
                     ||||||||||||||||||||||||||||||||||||||||||||||||||
Austria_no_SP    386 QEAINKITKNLNSLSELEVKNLQRLSGAMDELHNEILELDEKVDDLRADT    435

Austria_w_SP     451 ISSQIELAVLLSNEGIINSEDEHLLALERKLKKMLGPSAVEIGNGCFETK    500
                     ||||||||||||||||||||||||||||||||||||||||||||||||||
Austria_no_SP    436 ISSQIELAVLLSNEGIINSEDEHLLALERKLKKMLGPSAVEIGNGCFETK    485

Austria_w_SP     501 HKCNQTCLDRIAAGTFDAGEFSLPTFDSLNITAASLNDDGLDNHTILLYY    550
                     ||||||||||||||||||||||||||||||||||||||||||||||||||
Austria_no_SP    486 HKCNQTCLDRIAAGTFDAGEFSLPTFDSLNITAASLNDDGLDNHTILLYY    535

Austria_w_SP     551 STAASSLAVTLMIAIFVVYMVSRDNVSCSICL    582      (SEQ ID NO: 71)
                     ||||||||||||||||||||||||||||||||
Austria_no_SP    536 STAASSLAVTLMIAIFVVYMVSRDNVSCSICL    567      (SEQ ID NO: 174)
```

SEQ ID NO: 71 = B/Austria/1359417/2021 (B/Victoria lineage) HA protein including signal peptide
SEQ ID NO: 174 = B/Austria/1359417/2021 (B/Victoria lineage) HA protein after SP cleavage

SEQ ID NO: 71 comprises an amino acid sequence (aa 16-582 of SEQ ID NO: 71) with 100% identity to SEQ ID NO: 174

FIG. 19G

```
SEQ_ID_87    1 MKAIIVLLMVVTSNADRICTGITSSNSPHVVKTATQGEVNVTGVIPLTTT  50
               ||||||||||||||||||||||||||||||||||||||||||||||||||
SEQ_ID_71    1 MKAIIVLLMVVTSNADRICTGITSSNSPHVVKTATQGEVNVTGVIPLTTT  50

SEQ_ID_87   51 PTKSHFANLKGTETRGKLCPKCLNCTDLDVALGRPKCTGKIPSARVSILH  100
               ||||||||||||||||||||||||||||||||||||||||||||||||||
SEQ_ID_71   51 PTKSHFANLKGTETRGKLCPKCLNCTDLDVALGRPKCTGKIPSARVSILH  100

SEQ_ID_87  101 EVRPVTSGCFPIMHDRTKIRQLPNLLRGYEHVRLSTHNVINTEDAPGGPY  150
               ||||||||||||||||||||||||||||||||||||||||||||||||||
SEQ_ID_71  101 EVRPVTSGCFPIMHDRTKIRQLPNLLRGYEHVRLSTHNVINTEDAPGGPY  150

SEQ_ID_87  151 EIGTSGSCLNITNGKGFFATMAWAVPKNKTATNPLTIEVPYICTEEEDQI  200
               ||||||||||||||||||||||||||||||||||||||||||||||||||
SEQ_ID_71  151 EIGTSGSCLNITNGKGFFATMAWAVPKNKTATNPLTIEVPYICTEEEDQI  200

SEQ_ID_87  201 TVWGFHSDDETQMARLYGDSKPQKFTSSANGVTTHYVSQIGGFPNQTEDG  250
               ||||||||||||||||||||||||||||||||||||||||||||||||||
SEQ_ID_71  201 TVWGFHSDDETQMARLYGDSKPQKFTSSANGVTTHYVSQIGGFPNQTEDG  250

SEQ_ID_87  251 GLPQSGRIVVDYMVQKSGKTGTITYQRGILLPQKVWCVSGKSKVIKGSLP  300
               ||||||||||||||||||||||||||||||||||.|||||||||||||||
SEQ_ID_71  251 GLPQSGRIVVDYMVQKSGKTGTITYQRGILLPQKVWCASGKSKVIKGSLP  300

SEQ_ID_87  301 LIGEADCLHEKYGGLNKSKPYYTGEHAKAIGNCPIWVKTPLKLANGTKYR  350
               ||||||||||||||||||||||||||||||||||||||||||||||||||
SEQ_ID_71  301 LIGEADCLHEKYGGLNKSKPYYTGEHAKAIGNCPIWVKTPLKLANGTKYR  350

SEQ_ID_87  351 PPAKLLKERGFFGAIAGFLEGGWEGMIAGWYGYTSHGAHGVAVAADLKST  400
               ||||||||||||||||||||||||||||||||:|||||||||||||||||
SEQ_ID_71  351 PPAKLLKERGFFGAIAGFLEGGWEGMIAGWHGYTSHGAHGVAVAADLKST  400

SEQ_ID_87  401 QEAINKITKNLNSLSELEVKNLQRLSGAMDELHNEILELDEKVDDLRADT  450
               ||||||||||||||||||||||||||||||||||||||||||||||||||
SEQ_ID_71  401 QEAINKITKNLNSLSELEVKNLQRLSGAMDELHNEILELDEKVDDLRADT  450

SEQ_ID_87  451 ISSQIELAVLLSNEGIINSEDEHLLALERKLKCMLGPSAVEIGCGCFETK  500
               ||||||||||||||||||||||||||||||||||.||||||||||.||||
SEQ_ID_71  451 ISSQIELAVLLSNEGIINSEDEHLLALERKLKKMLGPSAVEIGNGCFETK  500

SEQ_ID_87  501 HKCNQTCLDRIAAGTFDAGEFSLPTFDSLNITAASLNDDGLDNHTILLYY  550
               ||||||||||||||||||||||||||||||||||||||||||||||||||
SEQ_ID_71  501 HKCNQTCLDRIAAGTFDAGEFSLPTFDSLNITAASLNDDGLDNHTILLYY  550

SEQ_ID_87  551 STAASSLAVTLMIAIFVVYMVSRDNVSCSICL  582
               ||||||||||||||||||||||||||||||||
SEQ_ID_71  551 STAASSLAVTLMIAIFVVYMVSRDNVSCSICL  582
```

FIG. 19H

```
SEQ_ID_85      1 MKAIIVLLMVVTSNADRICTGITSSNSPHVVKTATQGEVNVTGVIPLTTT    50
                 ||||||||||||||||||||||||||||||||||||||||||||||||||
SEQ_ID_70      1 MKAIIVLLMVVTSNADRICTGITSSNSPHVVKTATQGEVNVTGVIPLTTT    50

SEQ_ID_85     51 PTKSYFANLKGTRTRGKLCPDCLNCTDLDVALGRPMCVGTTPSAKASILH   100
                 ||||||||||||||||||||||||||||||||||||||||||||||||||
SEQ_ID_70     51 PTKSYFANLKGTRTRGKLCPDCLNCTDLDVALGRPMCVGTTPSAKASILH   100

SEQ_ID_85    101 EVRPVTSGCFPIMHDRTKIRQLPNLLRGYEKIRLSTQNVIDAEKAPGGPY   150
                 ||||||||||||||||||||||||||||||||||||||||||||||||||
SEQ_ID_70    101 EVRPVTSGCFPIMHDRTKIRQLPNLLRGYEKIRLSTQNVIDAEKAPGGPY   150

SEQ_ID_85    151 RLGTSGSCPNATSKIGFFATMAWAVPKDNYKNATNPLTVEVPYICTEGED   200
                 ||||||||||||||||||||||||||||||||||||||||||||||||||
SEQ_ID_70    151 RLGTSGSCPNATSKIGFFATMAWAVPKDNYKNATNPLTVEVPYICTEGED   200

SEQ_ID_85    201 QITVWGFHSDNKTQMKSLYGDSNPQKFTSSANGVTTHYCSQIGDFPDQTE   250
                 |||||||||||||||||||||||||||||||||||||||||||||.||||
SEQ_ID_70    201 QITVWGFHSDNKTQMKSLYGDSNPQKFTSSANGVTTHYVSQIGDFPDQTE   250

SEQ_ID_85    251 DGGLPQSGRIVVDYMMQKPGKTGTICYQRGVLLPQKVWCASGRSKVIKGS   300
                 ||||||||||||||||||||||||.|||||||||||||||||||||||||
SEQ_ID_70    251 DGGLPQSGRIVVDYMMQKPGKTGTIVYQRGVLLPQKVWCASGRSKVIKGS   300

SEQ_ID_85    301 LPLIGEADCLHEEYGGLNKSKPYYTGKHAKAIGNCPIWVKTPLKLANGTK   350
                 ||||||||||||||||||||||||||||||||||||||||||||||||||
SEQ_ID_70    301 LPLIGEADCLHEEYGGLNKSKPYYTGKHAKAIGNCPIWVKTPLKLANGTK   350

SEQ_ID_85    351 YRPPAKLLKERGFFGAIAGFLEGGWEGMIAGWHGYTSHGAHGVAVAADLK   400
                 ||||||||||||||||||||||||||||||||||||||||||||||||||
SEQ_ID_70    351 YRPPAKLLKERGFFGAIAGFLEGGWEGMIAGWHGYTSHGAHGVAVAADLK   400

SEQ_ID_85    401 STQEAINKITKNLNSLSELEVCNLQRLSGAMDELHNEILELDEKVDDLRA   450
                 ||||||||||||||||||||||.|||||||||||||||||||||||||||
SEQ_ID_70    401 STQEAINKITKNLNSLSELEVKNLQRLSGAMDELHNEILELDEKVDDLRA   450

SEQ_ID_85    451 CTISSQIELAVLLSNEGIINSEDEHLLALERKLKKMLGPSAVDIGNGCFE   500
                 .|||||||||||||||||||||||||||||||||||||||||||||||||
SEQ_ID_70    451 DTISSQIELAVLLSNEGIINSEDEHLLALERKLKKMLGPSAVDIGNGCFE   500

SEQ_ID_85    501 TKHKCNQTCLDRIAAGTFNAGEFSLPTFDSLNITAASLNDDGLDNHTILL   550
                 ||||||||||||||||||||||||||||||||||||||||||||||||||
SEQ_ID_70    501 TKHKCNQTCLDRIAAGTFNAGEFSLPTFDSLNITAASLNDDGLDNHTILL   550

SEQ_ID_85    551 YYSTAASSLAVTLMLAIFIVYMVSRDNVSCSICL   584
                 ||||||||||||||||||||||||||||||||||
SEQ_ID_70    551 YYSTAASSLAVTLMLAIFIVYMVSRDNVSCSICL   584
```

FIG. 19I

```
SEQ_ID_94     1 MKAILVVMLYTFTTANADTLCIGYHANNSTDTVDTVCEKNVTVTHSVNLL   50
                |||||||||||||||||||||||||||||||||||| |||||||||||||
SEQ_ID_83     1 MKAILVVMLYTFTTANADTLCIGYHANNSTDTVDTVLEKNVTVTHSVNLL   50

SEQ_ID_94    51 EDKHNGKLCKLRGVAPLHLGQCNIAGWILGNPECESLSTARSWSYIVETS  100
                ||||||||||||||||||||||||||||||||||||||||||||||||||
SEQ_ID_83    51 EDKHNGKLCKLRGVAPLHLGQCNIAGWILGNPECESLSTARSWSYIVETS  100

SEQ_ID_94   101 NSDNGTCYPGDFINYEELREQLSSVSSFERFEIFPKTSSWPNHDSDNGVT  150
                ||||||||||||||||||||||||||||||||||||||||||||||||||
SEQ_ID_83   101 NSDNGTCYPGDFINYEELREQLSSVSSFERFEIFPKTSSWPNHDSDNGVT  150

SEQ_ID_94   151 AACSHAGARSFYKNLIWLVKKGKSYPKINQTYINDKGKEVLVLWGIHHPP  200
                ||||||||||||||||||||||||||||||||||||||||||||||||||
SEQ_ID_83   151 AACSHAGARSFYKNLIWLVKKGKSYPKINQTYINDKGKEVLVLWGIHHPP  200

SEQ_ID_94   201 TITDQESLYQNADAYVFVGTSRYSKKFKPEIATRPKVRDQAGRMNYYWTL  250
                ||||||||||||||||||||||||||||||||||||||||||||||||||
SEQ_ID_83   201 TITDQESLYQNADAYVFVGTSRYSKKFKPEIATRPKVRDQAGRMNYYWTL  250

SEQ_ID_94   251 VEPGDKITFEATGNLVAPRYAFTMEKEAGSGIIISDTPVHDCNATCQTPE  300
                ||||||||||||||||||||||||||||||||||||||||||||||||||
SEQ_ID_83   251 VEPGDKITFEATGNLVAPRYAFTMEKEAGSGIIISDTPVHDCNATCQTPE  300

SEQ_ID_94   301 GAINTSLPFQNVHPITIGKCPKYVRSTKLRLATGLRNVPSIQSRGLFGAI  350
                ||||||||||||||||||||||||||||||||||||||||||||||||||
SEQ_ID_83   301 GAINTSLPFQNVHPITIGKCPKYVRSTKLRLATGLRNVPSIQSRGLFGAI  350

SEQ_ID_94   351 AGFIEGGWTGMVDGWYGYHHQNDQGSGYAADLKSTQNAIDCITNKVNSVI  400
                |||||||||||||||||||||||||||||||||||||||| |||||||||
SEQ_ID_83   351 AGFIEGGWTGMVDGWYGYHHQNDQGSGYAADLKSTQNAIDKITNKVNSVI  400

SEQ_ID_94   401 EKMNTQFTAVGKEFNHLEKRIENLNKKVDDGFLDVWTYNAELLVLLENER  450
                ||||||||||||||||||||||||||||||||||||||||||||||||||
SEQ_ID_83   401 EKMNTQFTAVGKEFNHLEKRIENLNKKVDDGFLDVWTYNAELLVLLENER  450

SEQ_ID_94   451 TLDYHDSNVKNLYEKVRHQLKNNAKEIGNGCFEFYHKCDNTCMESVKNGT  500
                ||||||||||||||||||||||||||||||||||||||||||||||||||
SEQ_ID_83   451 TLDYHDSNVKNLYEKVRHQLKNNAKEIGNGCFEFYHKCDNTCMESVKNGT  500

SEQ_ID_94   501 YDYPKYSEEAKLNREKIDGVKLDSTRIYQILAIYSTVASSLVLVVSLGAI  550
                ||||||||||||||||||||||||||||||||||||||||||||||||||
SEQ_ID_83   501 YDYPKYSEEAKLNREKIDGVKLDSTRIYQILAIYSTVASSLVLVVSLGAI  550

SEQ_ID_94   551 SFWMCSNGSLQCRICI    566
                ||||||||||||||||
SEQ_ID_83   551 SFWMCSNGSLQCRICI    566
```

FIG. 19J

```
SEQ_ID_91      1 MKTIIALSNILCLVFAQKIPGNDNSTATLCLGHHAVPNGTIVKTITNDRI   50
                 ||||||||||||||||||||||||||||||||||||||||||||||||||
SEQ_ID_82      1 MKTIIALSNILCLVFAQKIPGNDNSTATLCLGHHAVPNGTIVKTITNDRI   50

SEQ_ID_91     51 EVTNATELVQNSSIGEICGSPHQILDGGNCTLIDALLGDPQCDGFQNKEW  100
                 ||||||||||||||||||||||||||||||||||||||||||||||||||
SEQ_ID_82     51 EVTNATELVQNSSIGEICGSPHQILDGGNCTLIDALLGDPQCDGFQNKEW  100

SEQ_ID_91    101 DLFVERSRANSNCYPYDVPDYASLRSLVASSGTLEFKNESFNWTGVKQNG  150
                 ||||||||||||||||||||||||||||||||||||||||||||||||||
SEQ_ID_82    101 DLFVERSRANSNCYPYDVPDYASLRSLVASSGTLEFKNESFNWTGVKQNG  150

SEQ_ID_91    151 TSSACIRGSSSSFFSRLNWLTSLNNIYPAQNVTMPNKEQFDKLYIWGVHH  200
                 ||||||||||||||||||||||||||||||||||||||||||||||||||
SEQ_ID_82    151 TSSACIRGSSSSFFSRLNWLTSLNNIYPAQNVTMPNKEQFDKLYIWGVHH  200

SEQ_ID_91    201 PDTDKNQISLFAQSSGRITVSTKRSQQAVIPNIGSRPRIRGIPSRISIYW  250
                 ||||||||||||||||||||||||||||||||||||||||||||||||||
SEQ_ID_82    201 PDTDKNQISLFAQSSGRITVSTKRSQQAVIPNIGSRPRIRGIPSRISIYW  250

SEQ_ID_91    251 TIVKPGDILLINSTGNLIAPRGYFKIRSGKSSIMRSDAPIGKCKSECITP  300
                 ||||||||||||||||||||||||||||||||||||||||||||||||||
SEQ_ID_82    251 TIVKPGDILLINSTGNLIAPRGYFKIRSGKSSIMRSDAPIGKCKSECITP  300

SEQ_ID_91    301 NGSIPNDKPFQNVNRITYGACPRYVKQSTLKLATGMRNVPEKQTRGIFGA  350
                 ||||||||||||||||||||||||||||||||||||||||||||||||||
SEQ_ID_82    301 NGSIPNDKPFQNVNRITYGACPRYVKQSTLKLATGMRNVPEKQTRGIFGA  350

SEQ_ID_91    351 IAGFIENGWEGMVDGWYGFRHQNSEGRGQAADLKSTQAAIDQINGKLNRL  400
                 ||||||||||||||||||||||||||||||||||||||||||||||||||
SEQ_ID_82    351 IAGFIENGWEGMVDGWYGFRHQNSEGRGQAADLKSTQAAIDQINGKLNRL  400

SEQ_ID_91    401 IPKTNEKFHQIEKPFSEVEGPVQDLEKYVEDTKIDLWSYNAELLVALENQ  450
                 | ||||||||||| |||||| |||||||||||||||||||||||||||||
SEQ_ID_82    401 IGKTNEKFHQIEKEFSEVEGRVQDLEKYVEDTKIDLWSYNAELLVALENQ  450

SEQ_ID_91    451 HTIDLTDSEMNKLFEKTKKQLRENAEDMGNGCFKIYHKCDNACIGSIRNE  500
                 ||||||||||||||||||||||||||||||||||||||||||||||||||
SEQ_ID_82    451 HTIDLTDSEMNKLFEKTKKQLRENAEDMGNGCFKIYHKCDNACIGSIRNE  500

SEQ_ID_91    501 TYDHNVYRDEALNNRFQIKGVELKSGYKDWILWISFAMSCFLLCIALLGF  550
                 ||||||||||||||||||||||||||||||||||||||||||||||||||
SEQ_ID_82    501 TYDHNVYRDEALNNRFQIKGVELKSGYKDWILWISFAMSCFLLCIALLGF  550

SEQ_ID_91    551 IMWACQKGNIRCNICI    566
                 ||||||||||||||||
SEQ_ID_82    551 IMWACQKGNIRCNICI    566
```

FIG. 19K

SEQUENCE LISTING

```
Sequence total quantity: 233
SEQ ID NO: 1            moltype = RNA  length = 47
FEATURE                 Location/Qualifiers
source                  1..47
                        mol_type = other RNA
                        organism = synthetic construct
5'UTR                   1..47
SEQUENCE: 1
gggaaataag agagaaaaga agagtaagaa gaaatataag agccacc                47

SEQ ID NO: 2            moltype = RNA  length = 57
FEATURE                 Location/Qualifiers
source                  1..57
                        mol_type = other RNA
                        organism = synthetic construct
5'UTR                   1..57
SEQUENCE: 2
gggaaataag agagaaaaga agagtaagaa gaaatataag accccggcgc cgccacc     57

SEQ ID NO: 3            moltype = RNA  length = 119
FEATURE                 Location/Qualifiers
source                  1..119
                        mol_type = other RNA
                        organism = synthetic construct
5'UTR                   1..119
SEQUENCE: 3
tgataatagg ctggagcctc ggtggccatg cttcttgccc cttgggcctc cccccagccc  60
ctcctcccct tcctgcaccc gtacccccgt ggtctttgaa taaagtctga gtgggcggc   119

SEQ ID NO: 4            moltype = RNA  length = 119
FEATURE                 Location/Qualifiers
source                  1..119
                        mol_type = other RNA
                        organism = synthetic construct
5'UTR                   1..119
SEQUENCE: 4
tgataatagg ctggagcctc ggtggcctag cttcttgccc cttgggcctc cccccagccc  60
ctcctcccct tcctgcaccc gtacccccgt ggtctttgaa taaagtctga gtgggcggc   119

SEQ ID NO: 5            moltype = RNA  length = 75
FEATURE                 Location/Qualifiers
source                  1..75
                        mol_type = other RNA
                        organism = synthetic construct
5'UTR                   1..75
SEQUENCE: 5
ggaaatcgca aaatttgctc ttcgcgttag atttctttta gttttctcgc aactagcaag  60
ctttttgttc tcgcc                                                   75
```

-continued

```
SEQ ID NO: 6            moltype = RNA  length = 203
FEATURE                 Location/Qualifiers
source                  1..203
                        mol_type = other RNA
                        organism = synthetic construct
5'UTR                   1..203
SEQUENCE: 6
ggaaatcccc acaaccgcct catatccagg ctcaagaata gagctcagtg ttttgttgtt  60
taatcattcc gacgtgtttt gcgatattcg cgcaaagcag ccagtcgcgc gcttgctttt  120
aagtagagtt gtttttccac ccgtttgcca ggcatcttta atttaacata tttttatttt  180
tcaggctaac ctacgccgcc acc                                          203

SEQ ID NO: 7            moltype = RNA  length = 76
FEATURE                 Location/Qualifiers
source                  1..76
                        mol_type = other RNA
                        organism = synthetic construct
5'UTR                   1..76
SEQUENCE: 7
ggaaataaga gagaaaagaa gagtaagaag aaatataaga tctccctgag cttcagggag  60
ccccggcgcc gccacc                                                  76

SEQ ID NO: 8            moltype = RNA  length = 89
FEATURE                 Location/Qualifiers
source                  1..89
                        mol_type = other RNA
                        organism = synthetic construct
5'UTR                   1..89
SEQUENCE: 8
ggaaacccc caccccccgta agagagaaaa gaagagtaag aagaaatata agatctccct  60
gagcttcagg gagccccggc gccgccacc                                    89

SEQ ID NO: 9            moltype = RNA  length = 59
FEATURE                 Location/Qualifiers
source                  1..59
                        mol_type = other RNA
                        organism = synthetic construct
5'UTR                   1..59
SEQUENCE: 9
ggagaacttc cgcttccgtt ggcgcaagcg ctttcatttt ttctgctacc gtgactaag   59

SEQ ID NO: 10           moltype = RNA  length = 46
FEATURE                 Location/Qualifiers
source                  1..46
                        mol_type = other RNA
                        organism = synthetic construct
5'UTR                   1..46
SEQUENCE: 10
ggaaataaga gagaaaagaa gagtaagaag aaatataaga gccacc                 46

SEQ ID NO: 11           moltype = RNA  length = 56
FEATURE                 Location/Qualifiers
source                  1..56
                        mol_type = other RNA
                        organism = synthetic construct
5'UTR                   1..56
SEQUENCE: 11
ggaaataaga gagaaaagaa gagtaagaag aaatataaga ccccggcgcc gccacc      56

SEQ ID NO: 12           moltype = RNA  length = 81
FEATURE                 Location/Qualifiers
source                  1..81
                        mol_type = other RNA
                        organism = synthetic construct
5'UTR                   1..81
SEQUENCE: 12
ggaaatcgca aaatttgctc ttcgcgttag atttctttta gttttctcgc aactagcaag  60
ctttttgttc tcgccgccgc c                                            81

SEQ ID NO: 13           moltype = RNA  length = 81
FEATURE                 Location/Qualifiers
source                  1..81
                        mol_type = other RNA
                        organism = synthetic construct
5'UTR                   1..81
SEQUENCE: 13
ggaaatcgca aaattttctt ttcgcgttag atttctttta gttttctttc aactagcaag  60
ctttttgttc tcgccgccgc c                                            81
```

```
SEQ ID NO: 14           moltype = RNA  length = 75
FEATURE                 Location/Qualifiers
source                  1..75
                        mol_type = other RNA
                        organism = synthetic construct
5'UTR                   1..75
SEQUENCE: 14
ggaaatcgca aaatgctctc gcgttagatt tcttttagtt ttctykcaac tagcaagctt  60
tttgttctcg ccrcc                                                   75

SEQ ID NO: 15           moltype = RNA  length = 79
FEATURE                 Location/Qualifiers
source                  1..79
                        mol_type = other RNA
                        organism = synthetic construct
5'UTR                   1..79
SEQUENCE: 15
ggaaaatttt agcctggaac gttagataac tgtcctgttg tctttatata cttggtcccc  60
aagtagtttg tcttccaaa                                               79

SEQ ID NO: 16           moltype = RNA  length = 79
FEATURE                 Location/Qualifiers
source                  1..79
                        mol_type = other RNA
                        organism = synthetic construct
5'UTR                   1..79
SEQUENCE: 16
ggaaacttta tttagtgtta ctttattttc tgtttatttg tgtttcttca gtgggtttgt  60
tctaatttcc ttggccgcc                                               79

SEQ ID NO: 17           moltype = RNA  length = 79
FEATURE                 Location/Qualifiers
source                  1..79
                        mol_type = other RNA
                        organism = synthetic construct
5'UTR                   1..79
SEQUENCE: 17
ggaaaatctg tattaggttg gcgtgttctt tggtcggttg ttagtattgt tgttgattcg  60
tttgtggtcg gttgccgcc                                               79

SEQ ID NO: 18           moltype = RNA  length = 79
FEATURE                 Location/Qualifiers
source                  1..79
                        mol_type = other RNA
                        organism = synthetic construct
5'UTR                   1..79
SEQUENCE: 18
ggaaaattat taacatcttg gtattctcga taaccattcg ttggatttta ttgtattcgt  60
agtttgggtt cctgccgcc                                               79

SEQ ID NO: 19           moltype = RNA  length = 79
FEATURE                 Location/Qualifiers
source                  1..79
                        mol_type = other RNA
                        organism = synthetic construct
5'UTR                   1..79
SEQUENCE: 19
ggaaattatt attatttcta gctacaattt atcattgtat tattttagct attcatcatt  60
atttacttgg tgatcaaca                                               79

SEQ ID NO: 20           moltype = RNA  length = 79
FEATURE                 Location/Qualifiers
source                  1..79
                        mol_type = other RNA
                        organism = synthetic construct
5'UTR                   1..79
SEQUENCE: 20
ggaaataggt tgttaaccaa gttcaagcct aataagcttg gattctggtg acttgcttca  60
ccgttggcgg gcaccgatc                                               79

SEQ ID NO: 21           moltype = RNA  length = 74
FEATURE                 Location/Qualifiers
source                  1..74
                        mol_type = other RNA
                        organism = synthetic construct
5'UTR                   1..74
SEQUENCE: 21
ggaaatcgta gagagtcgta cttagtacat atcgactatc ggtggacacc atcaagatta  60
taaaccaggc caga                                                    74
```

```
SEQ ID NO: 22          moltype = RNA  length = 79
FEATURE                Location/Qualifiers
source                 1..79
                       mol_type = other RNA
                       organism = synthetic construct
5'UTR                  1..79
SEQUENCE: 22
ggaaacccgc ccaagcgacc ccaacatatc agcagttgcc caatcccaac tcccaacaca  60
atccccaagc aacgccgcc                                               79

SEQ ID NO: 23          moltype = RNA  length = 79
FEATURE                Location/Qualifiers
source                 1..79
                       mol_type = other RNA
                       organism = synthetic construct
5'UTR                  1..79
SEQUENCE: 23
ggaaagcgat tgaaggcgtc ttttcaacta ctcgattaag gttgggtatc gtcgtgggac  60
ttggaaattt gttgtttcc                                               79

SEQ ID NO: 24          moltype = RNA  length = 79
FEATURE                Location/Qualifiers
source                 1..79
                       mol_type = other RNA
                       organism = synthetic construct
5'UTR                  1..79
SEQUENCE: 24
ggaaactaat cgaaataaaa gagccccgta ctcttttatt tctattaggt taggagcctt  60
agcatttgta tcttaggta                                               79

SEQ ID NO: 25          moltype = RNA  length = 79
FEATURE                Location/Qualifiers
source                 1..79
                       mol_type = other RNA
                       organism = synthetic construct
5'UTR                  1..79
SEQUENCE: 25
ggaaatgtga tttccagcaa cttcttttga atatattgaa ttcctaattc aaagcgaaca  60
aatctacaag ccatatacc                                               79

SEQ ID NO: 26          moltype = RNA  length = 74
FEATURE                Location/Qualifiers
source                 1..74
                       mol_type = other RNA
                       organism = synthetic construct
5'UTR                  1..74
SEQUENCE: 26
ggaaatcgta gagagtcgta cttacgtggt cgccattgca tagcgcgcga aagcaacagg  60
aacaagaacg cgcc                                                    74

SEQ ID NO: 27          moltype = RNA  length = 74
FEATURE                Location/Qualifiers
source                 1..74
                       mol_type = other RNA
                       organism = synthetic construct
5'UTR                  1..74
SEQUENCE: 27
ggaaatcgta gagagtcgta cttagaataa acagagtcgg gtcgacttgt ctctgatact  60
acgacgtcac aatc                                                    74

SEQ ID NO: 28          moltype = RNA  length = 79
FEATURE                Location/Qualifiers
source                 1..79
                       mol_type = other RNA
                       organism = synthetic construct
5'UTR                  1..79
SEQUENCE: 28
ggaaaatttg ccttcggagt tgcgtatcct gaactgccca gcctcctgat atacaactgt  60
tccgcttatt cgggccgcc                                               79

SEQ ID NO: 29          moltype = RNA  length = 79
FEATURE                Location/Qualifiers
source                 1..79
                       mol_type = other RNA
                       organism = synthetic construct
5'UTR                  1..79
SEQUENCE: 29
ggaaatctga gcaggaatcc tttgtgcatt gaagacttta gattcctctc tgcggtagac  60
```

```
gtgcacttat aagtatttg                                              79

SEQ ID NO: 30           moltype = RNA  length = 79
FEATURE                 Location/Qualifiers
source                  1..79
                        mol_type = other RNA
                        organism = synthetic construct
5'UTR                   1..79
SEQUENCE: 30
ggaaagcgat tgaaggcgtc ttttcaacta ctcgattaag gttgggtatc gtcgtgggac  60
ttggaaattt gttgccacc                                              79

SEQ ID NO: 31           moltype = RNA  length = 104
FEATURE                 Location/Qualifiers
source                  1..104
                        mol_type = other RNA
                        organism = synthetic construct
5'UTR                   1..104
SEQUENCE: 31
ggaaattttt ttttgatatt ataagagttt ttttttgata ttaagaaaat tttttttga  60
tattagaaga gtaagaagaa atataagacc ccggcgccgc cacc                  104

SEQ ID NO: 32           moltype = RNA  length = 57
FEATURE                 Location/Qualifiers
source                  1..57
                        mol_type = other RNA
                        organism = synthetic construct
5'UTR                   1..57
SEQUENCE: 32
ggaaataaga gagaaaagaa gagtaagaag aaatataaga gccaaaaaaa aaaaacc     57

SEQ ID NO: 33           moltype = RNA  length = 76
FEATURE                 Location/Qualifiers
source                  1..76
                        mol_type = other RNA
                        organism = synthetic construct
5'UTR                   1..76
SEQUENCE: 33
ggaaatctcc ctgagcttca gggagtaaga gagaaaagaa gagtaagaag aaatataaga  60
ccccggcgcc gccacc                                                 76

SEQ ID NO: 34           moltype =   length =
SEQUENCE: 34
000

SEQ ID NO: 35           moltype = RNA  length = 36
FEATURE                 Location/Qualifiers
source                  1..36
                        mol_type = other RNA
                        organism = synthetic construct
3'UTR                   1..36
SEQUENCE: 35
ggactcacta tttgttttcg cgcccagttg caaaaa                           36

SEQ ID NO: 36           moltype = RNA  length = 119
FEATURE                 Location/Qualifiers
source                  1..119
                        mol_type = other RNA
                        organism = synthetic construct
3'UTR                   1..119
SEQUENCE: 36
taaagctccc cgggggcctc ggtggcctag cttcttgccc cttgggcctc cccccagccc  60
ctcctcccct tcctgcaccc gtacccccgt ggtctttgaa taaagtctga gtgggcggc   119

SEQ ID NO: 37           moltype = RNA  length = 119
FEATURE                 Location/Qualifiers
source                  1..119
                        mol_type = other RNA
                        organism = synthetic construct
3'UTR                   1..119
SEQUENCE: 37
taagtctaag ctggagcctc ctgagagacc tgtgtgaact attgagaaga tcggaacagc  60
tccttactct gaggaagttg gtacccccgt ggtctttgaa taaagtctga gtgggcggc   119

SEQ ID NO: 38           moltype = RNA  length = 185
FEATURE                 Location/Qualifiers
source                  1..185
                        mol_type = other RNA
                        organism = synthetic construct
```

```
3'UTR                  1..185
SEQUENCE: 38
taaagctccc cggggcaaac accattgtca cactccagcc tcggtggcct agcttcttgc  60
cccttgggcc caaacaccat tgtcacactc catcccccca gcccctcctc cccttcctgc  120
acccgtaccc cccaaacacc attgtcacac tccagtggtc tttgaataaa gtctgagtgg  180
gcggc                                                              185

SEQ ID NO: 39          moltype = RNA  length = 170
FEATURE                Location/Qualifiers
source                 1..170
                       mol_type = other RNA
                       organism = synthetic construct
3'UTR                  1..170
SEQUENCE: 39
taaagctccc cggggtccat aaagtaggaa acactacagc tggagcctcg gtggcctagc  60
ttcttgcccc ttgggcccaa acaccattgt cacactccat ccccccagcc cctcctcccc  120
ttcctgcacc cgtacccccg tggtctttga ataaagtctg agtgggcggc            170

SEQ ID NO: 40          moltype = RNA  length = 141
FEATURE                Location/Qualifiers
source                 1..141
                       mol_type = other RNA
                       organism = synthetic construct
3'UTR                  1..141
SEQUENCE: 40
taaagctccc cgggggcctc ggtggcctag cttcttgccc cttgggcctc cccccagccc  60
ctcctcccct tcctgcaccc gtacccccca aacaccattg tcacactcca gtggtctttg  120
aataaagtct gagtgggcgg c                                            141

SEQ ID NO: 41          moltype = RNA  length = 185
FEATURE                Location/Qualifiers
source                 1..185
                       mol_type = other RNA
                       organism = synthetic construct
3'UTR                  1..185
SEQUENCE: 41
taagcccctc cggggcaaac accattgtca cactccagcc tcggtggcct agcttcttgc  60
cccttgggcc caaacaccat tgtcacactc catcccccca gcccctcctc cccttcctgc  120
acccgtaccc cccaaacacc attgtcacac tccagtggtc tttgaataaa gtctgagtgg  180
gcggc                                                              185

SEQ ID NO: 42          moltype = RNA  length = 187
FEATURE                Location/Qualifiers
source                 1..187
                       mol_type = other RNA
                       organism = synthetic construct
3'UTR                  1..187
SEQUENCE: 42
taagcccctc cggggtccat aaagtaggaa acactacagc ctcggtggcc tagcttcttg  60
ccccttgggc ctccataaag taggaaacac tacatccccc cagcccctcc tccccttcct  120
gcacccgtac cccccgcatt attactcacg gtacgagtgg tctttgaata aagtctgagt  180
gggcggc                                                            187

SEQ ID NO: 43          moltype = RNA  length = 170
FEATURE                Location/Qualifiers
source                 1..170
                       mol_type = other RNA
                       organism = synthetic construct
3'UTR                  1..170
SEQUENCE: 43
taagcccctc cggggtccat aaagtaggaa acactacagc tggagcctcg gtggcctagc  60
ttcttgcccc ttgggcccaa acaccattgt cacactccat ccccccagcc cctcctcccc  120
ttcctgcacc cgtacccccg tggtctttga ataaagtctg agtgggcggc            170

SEQ ID NO: 44          moltype = RNA  length = 141
FEATURE                Location/Qualifiers
source                 1..141
                       mol_type = other RNA
                       organism = synthetic construct
3'UTR                  1..141
SEQUENCE: 44
taagcccctc cgggggcctc ggtggcctag cttcttgccc cttgggcctc cccccagccc  60
ctcctcccct tcctgcaccc gtacccccca aacaccattg tcacactcca gtggtctttg  120
aataaagtct gagtgggcgg c                                            141

SEQ ID NO: 45          moltype = RNA  length = 76
FEATURE                Location/Qualifiers
source                 1..76
                       mol_type = other RNA
```

```
                        organism = synthetic construct
5'UTR                   1..76
                        note = H1_Wisconsin_2019_WT_V2
SEQUENCE: 45
aggaaatcgc aaaatttgct cttcgcgtta gatttctttt agttttctcg caactagcaa  60
gctttttgtt ctcgcc                                                  76

SEQ ID NO: 46           moltype = RNA  length = 1698
FEATURE                 Location/Qualifiers
source                  1..1698
                        mol_type = other RNA
                        organism = synthetic construct
misc_feature            1..1698
                        note = H1_Wisconsin_2019_WT_V2 ORF
SEQUENCE: 46
atgaaggcca tcctggtcgt gatgctgtac accttcacca ccgccaacgc cgacaccctg  60
tgcatcggct accacgccaa caacagcacc gacaccgtgg acaccgtgct ggagaagaac  120
gtgaccgtga cccacagcgt gaacctgctg gaggacaagc acaacggcaa gctgtgcaag  180
ctgaggggag tggcacccct gcacctgggc aagtgcaaca tcgccggctg gatcctgggc  240
aaccccgagt gcgagagcct gagcacagcc cggagctgga gctacatcgt ggagaccagc  300
aacagcgaca acggcacctg ttaccccggc gacttcatca actacgagga gctgcgggag  360
cagctgagca gcgtgagcag cttcgagcgg ttcgagatct tccccaagac cagcagctgg  420
cccaaccacg acagcgacaa cggcgtgaca gcagcctgtc cacacgccgg agccaagagc  480
ttctacaaga acctgatctg gctggtgaag aagggcaaga gctaccccaa gatcaaccag  540
acctacatca acgacaaggg caaggaggtg ctggtgctgt ggggcatcca ccacccacct  600
accatcgccg accagcagag cctgtaccag aacgccgacg cctacgtgtt cgtgggcacc  660
agccggtaca gcaagaagtt caagccagag atcgccaccc ggcccaaggt gagagaccag  720
gagggccgga tgaactacta ctggaccctg gtggagcccg gagacaagat taccttcgag  780
gccaccggca acctggtggc cctcggtac gccttcacca tggaacggga cgctggcagc  840
ggcatcatca tcagcgacac tcccgtgcac gactgcaaca ccacctgcca gactcccgag  900
ggcgctatca acaccagcct gcccttccag aacgtgcacc ccatcaccat cggcaagtgc  960
cccaagtacg taaagagcac caaattgcgg ctggccaccg gactcaggaa cgtgcccagc  1020
atccaaagcc ggggcctgtt tggcgcaatc gccggcttca tcgagggcgg ctggactggc  1080
atggtggacg gctggtacgg ctaccaccac cagaacgaac aggggagcgg ctacgcagct  1140
gacctgaaga gcacccagaa cgccatcgac aagatcacca acaaggtgaa cagcgtgatc  1200
gagaagatga acacccagtt caccgccgtg ggcaaggagt tcaaccacct ggagaagcgg  1260
atcgagaacc tgaacaagaa ggtggacgac ggcttcctgg acatctggac ctacaacgcc  1320
gagctgctgg ttctgctgga gaacgagcgg accctggact atcacgacag caacgtgaag  1380
aacctgtacg agaaggtgcg gaaccagctg aagaacaacg ccaaggagat cggcaacggc  1440
tgcttcgagt tctaccacaa gtgcgacaac acctgcatgg agagcgtgaa gaacggcacc  1500
tacgactacc ccaagtacag cgaggaggcc aagctgaacc gggagaagat cgacggcgtg  1560
aagctggaca gcacccggat ctaccagatc ctggccatct acagcaccgt ggccagcagc  1620
ctggtgctgg tggtgagcct gggcgccatc agcttctgga tgtgcagcaa cggcagcctg  1680
cagtgccgga tctgcatc                                                1698

SEQ ID NO: 47           moltype = RNA  length = 115
FEATURE                 Location/Qualifiers
source                  1..115
                        mol_type = other RNA
                        organism = synthetic construct
3'UTR                   1..115
                        note = H1_Wisconsin_2019_WT_V2
SEQUENCE: 47
taaagctccc cgggggcctc ggtggccctc caccgaagca gccatcagca cccccagccc  60
ctcctcccct tcctgcaggt caaagtggtc tttgaataaa gtctgagtgg gcggc       115

SEQ ID NO: 48           moltype = AA  length = 566
FEATURE                 Location/Qualifiers
source                  1..566
                        mol_type = protein
                        note = Influenza A virus
                        organism = unidentified
REGION                  1..566
                        note = H1_Wisconsin_2019_WT_V2 AA
SEQUENCE: 48
MKAILVVMLY TFTTANADTL CIGYHANNST DTVDTVLEKN VTVTHSVNLL EDKHNGKLCK  60
LRGVAPLHLG KCNIAGWILG NPECESLSTA RSWSYIVETS NSDNGTCYPG DFINYEELRE  120
QLSSVSSFER FEIFPKTSSW PNHDSDNGVT AACPHAGAKS FYKNLIWLVK KGKSYPKINQ  180
TYINDKGKEV LVLWGIHHPP TIADQQSLYQ NADAYVFVGT SRYSKKFKPE IATRPKVRDQ  240
EGRMNYYWTL VEPGDKITFE ATGNLVAPRY AFTMERDAGS GIIISDTPVH DCNTTCQTPE  300
GAINTSLPFQ NVHPITIGKC PKYVKSTKLR LATGLRNVPS IQSRGLFGAI AGFIEGGWTG  360
MVDGWYGYHH QNEQGSGYAA DLKSTQNAID KITNKVNSVI EKMNTQFTAV GKEFNHLEKR  420
IENLNKKVDD GFLDIWTYNA ELLVLLENER TLDYHDSNVK NLYEKVRNQL KNNAKEIGNG  480
CFEFYHKCDN TCMESVKNGT YDYPKYSEEA KLNREKIDGV KLDSTRIYQI LAIYSTVASS  540
LVLVVSLGAI SFWMCSNGSL QCRICI                                       566

SEQ ID NO: 49           moltype = RNA  length = 1698
FEATURE                 Location/Qualifiers
source                  1..1698
```

-continued

```
                         mol_type = other RNA
                         organism = synthetic construct
misc_feature             1..1698
                         note = H3_A/Darwin/6/2021_G53D_V2 ORF
SEQUENCE: 49
atgaagacca tcatcgccct gagcaacatc ctgtgcctgg tgttcgccca gaagatcccc  60
ggcaacgata acagcaccgc caccctgtgt ctgggacacc acgccgtgcc caacggcacc  120
atcgtgaaga ctatcaccaa cgaccggatc gaggtgacca acgccaccga gctggtgcag  180
aacagcagca tcggcgagat ctgcgacagc cctcaccaga tcctggacgg cggcaactgc  240
accctgatcg acgcactgct gggcgaccct cagtgcgacg gctttcagaa caaggagtgg  300
gacctgttcg tggagagatc gcgggccaac agcaactgct acccctacga cgtccccgac  360
tacgcaagcc tgagaagcct cgtggcctca agcggcaccc tggagttcaa gaacgagagc  420
ttcaactgga ccggcgtgaa gcagaacggc acctcaagcg cctgcatccg gggctccagc  480
agcagcttct tctcacggct gaactggctg acccacctga acaacatcta ccccgcccag  540
aacgtgacca tgcccaacaa ggagcagttc gacaagctgt acatctgggg agtgcaccat  600
cccgacaccg acaagaacca gattagcctg ttcgcccaga gcagcggccg gatcaccgtg  660
agcaccaagc ggagccagca ggccgtgatc cccaacatcg gctctcggcc cagaatccgg  720
gacatcccca gccggatcag catctactgg accattgtga agcccggcga catcctgctg  780
atcaactcca ccggcaacct gatcgcccct cggggctatt tcaagatccg gagcggcaag  840
agcagcatca tgcggagcga cgcccctatc ggcaagtgca agagcgagtg catcacaccc  900
aacggaagca tccccaacga caagcccttc cagaacgtga accggataac ctacggcgcc  960
tgccctagat acgtgaagca gagcaccctg aagctggcca ccggcatgcg gaacgtgccc  1020
gagaagcaga ctcggggcat cttcggcgcc atcgccggct tcatcgagaa cggctgggag  1080
ggcatggtgg acggctggta cggcttccgg caccagaact ctgagggcag aggacaggcc  1140
gcagacctga agagcaccca ggccgccatc gaccagatca acggcaagct gaaccggctg  1200
atcggcaaga ccaacgagaa gttccaccag atcgagaagg agttcagcga ggtggagggc  1260
agggtacagg acctggagaa gtacgtggag gacaccaaga tcgacctgtg gagctacaac  1320
gccgagctgc tggtagccct ggagaaccag cacaccatcg acctgaccga cagcgagatg  1380
aacaagctgt tcgagaagac caagaagcag ctgcgggaga acgccgagga catgggcaac  1440
ggctgcttca agatctacca caagtgcgac aacgcctgca tcggcagcat ccggaacgag  1500
acctacgacc acaacgtgta ccgggacgag gccctgaaca accggttcca gatcaagggc  1560
gtggagctga agagcggcta caaggactgg atcctgtgga tcagcttcgc catgtcctgc  1620
ttcctgctgt gcatcgccct gctgggtttc atcatgtggg cctgccagaa gggcaacatc  1680
cggtgcaaca tctgcatc                                                1698

SEQ ID NO: 50            moltype = RNA  length = 117
FEATURE                  Location/Qualifiers
source                   1..117
                         mol_type = other RNA
                         organism = synthetic construct
3'UTR                    1..117
                         note = H3_A/Darwin/6/2021_G53D_V2
SEQUENCE: 50
taaagctccc cgggggcctc ggtggccctc cgcatcagac caacggcaca cccccagccc  60
ctcctcccct tcctgcaggt caaggagtgg tctttgaata aagtctgagt gggcggc     117

SEQ ID NO: 51            moltype = AA  length = 566
FEATURE                  Location/Qualifiers
source                   1..566
                         mol_type = protein
                         note = Influenza A virus
                         organism = unidentified
REGION                   1..566
                         note = H3_A/Darwin/6/2021_G53D_V2 AA
SEQUENCE: 51
MKTIIALSNI LCLVFAQKIP GNDNSTATLC LGHHAVPNGT IVKTITNDRI EVTNATELVQ  60
NSSIGEICDS PHQILDGGNC TLIDALLGDP QCDGFQNKEW DLFVERSRAN SNCYPYDVPD  120
YASLRSLVAS SGTLEFKNES FNWTGVKQNG TSSACIRGSS SSFFSRLNWL THLNNIYPAQ  180
NVTMPNKEQF DKLYIWGVHH PDTDKNQISL FAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                       566

SEQ ID NO: 52            moltype = RNA  length = 1746
FEATURE                  Location/Qualifiers
source                   1..1746
                         mol_type = other RNA
                         organism = synthetic construct
misc_feature             1..1746
                         note = B/Austria/1359417/2021 H363Y A270V HA_SEv4.5 ORF
SEQUENCE: 52
atgaaggcta tcatcgtgct gttaatggtg gtgaccagca acgccgaccg gatctgcaca  60
ggcatcacct ctagcaacag ccctcacgtg gtcaagaccg ccacacaggg cgaggtgaac  120
gtgaccggcg tgattcccct gaccaccacc cctaccaaga gccacttcgc caacctgaag  180
ggaaccgaga cccggggcaa gctgtgtcca aagtgcctga actgtaccga cctggacgtg  240
gctctgggca gacccaagtg caccggcaag atccccagcg cccgggtgtc tatcttgcac  300
```

-continued

```
gaagtgcggc ccgtgactag cggttgcttc cccatcatgc acgaccggac caagatcaga  360
cagctgccca acctgctgcg gggctacgag cacgtgcggc tgtccaccca taacgtgatc  420
aacaccgaag acgcacccgg cggcccatac gagatcggca ccagcggctc ttgcctgaat  480
atcaccaacg gcaagggatt ctttgctacc atggcctggg ccgtgccaaa gaacaagact  540
gccaccaacc ctctgaccat cgaggtgccc tacatctgca ccgaggagga ggaccagatc  600
accgtgtggg gcttccacag cgacgacgag acacagatgg ccagactgta cggcgacagc  660
aaaccccaga agttcaccag cagcgccaac ggcgtgacca cccactacgt gagccagatt  720
ggcggcttcc ctaaccaaac cgaggacggc ggcttacccc agagcggccg gatcgtggtg  780
gactacatgg ttcagaagag cggcaagacc ggcaccatca cctaccagcg gggcatcctg  840
ttaccacaga aggtgtggtg cgtgtcaggg aaatcaaagg tcatcaaggg ctccctgcca  900
ctgattggcg aggccgactg cctgcacgag aagtacggcg gcctgaacaa gagcaagccc  960
tactacaccg gcgagcacgc caaggcaatc ggcaactgcc ccatctgggt gaagacaccc  1020
ctgaagctgg caaacggcac caagtaccgg ccacccgcca aactgctgaa ggagcggggc  1080
ttcttcggcg ccattgccgg cttcctcgaa ggcggttggg agggcatgat cgcaggctgg  1140
tacggctaca ctagccacgg cgcacacgga gtagcagtgg ccgccgacct gaagagcacc  1200
caggaggcca tcaacaagat caccaagaac ctgaacagcc tgagcgagct ggaggtgaag  1260
aatctgcaga ggctgtctgg cgctatggac gagctgcaca acgagatcct ggagctggac  1320
gagaaggtgg acgacttacg ggccgacacc atcagcagcc agatcgagct ggcagtgctg  1380
ctgagcaacg agggcatcat caacagcgag gacgagcacc tgctggccct ggagcggaag  1440
ctgaagaaga tgctgggccc ttctgccgtg gagatcggta acggctgctt cgagaccaag  1500
cacaagtgca accagacctg cctggatcgg atcgcagccg gcacctttga cgccggggag  1560
ttcagcctgc ccaccttcga cagcttgaac atcaccgccg ccagcctgaa cgacgacggc  1620
ctggacaacc acaccatcct gctgtactac tctacagccg ctagcagcct ggccgtgacc  1680
ctgatgatcg ccatcttcgt ggtgtacatg gtgagccggg acaacgtgag ctgcagcatc  1740
tgcctg                                                             1746

SEQ ID NO: 53           moltype = RNA  length = 116
FEATURE                 Location/Qualifiers
source                  1..116
                        mol_type = other RNA
                        organism = synthetic construct
3'UTR                   1..116
                        note = B/Austria/1359417/2021 H363Y A270V HA_SEv4.5
SEQUENCE: 53
taaagctccc cgggggcctc ggtggccctc aacctacgcc gaagaccacg cccccagccc  60
ctcctcccct tcctgcaggt caagagtggt ctttgaataa agtctgagtg ggcggc      116

SEQ ID NO: 54           moltype = AA  length = 582
FEATURE                 Location/Qualifiers
source                  1..582
                        mol_type = protein
                        organism = synthetic construct
REGION                  1..582
                        note = B/Austria/1359417/2021 H363Y A270V HA_SEv4.5 AA
SEQUENCE: 54
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NTEDAPGGPY EIGTSGSCLN ITNGKGFFAT MAWAVPKNKT  180
ATNPLTIEVP YICTEEEDQI TVWGFHSDDE TQMARLYGDS KPQKFTSSAN GVTTHYVSQI  240
GGFPNQTEDG GLPQSGRIVV DYMVQKSGKT GTITYQRGIL LPQKVWCVSG KSKVIKGSLP  300
LIGEADCLHE KYGGLNKSKP YYTGEHAKAI GNCPIWVKTP LKLANGTKYR PPAKLLKERG  360
FFGAIAGFLE GGWEGMIAGW YGYTSHGAHG VAVAADLKST QEAINKITKN LNSLSELEVK  420
NLQRLSGAMD ELHNEILELD EKVDDLRADT ISSQIELAVL LSNEGIINSE DEHLLALERK  480
LKKMLGPSAV EIGNGCFETK HKCNQTCLDR IAAGTFDAGE FSLPTFDSLN ITAASLNDDG  540
LDNHTILLYY STAASSLAVT LMIAIFVVYM VSRDNVSCSI CL                    582

SEQ ID NO: 55           moltype = RNA  length = 1752
FEATURE                 Location/Qualifiers
source                  1..1752
                        mol_type = other RNA
                        organism = synthetic construct
misc_feature            1..1752
                        note = B/Phuket/3073/2013 H363Y A270V HA ORF
SEQUENCE: 55
atgaaggcta tcatcgtgct actcatggtg gtaaccagca acgccgaccg gatctgcacc  60
ggcatcacca gcagcaacag cccgcacgtt gtgaagaccg ccacccaagg cgaggtgaac  120
gtgaccggcg tgatcccact gaccaccact cccaccaaga gctacttcgc caacctgaag  180
ggcactcgga ctcggggcaa gctctgcccc gactgcctga actgcaccga cctggacgtg  240
gctctgggca gacccatgtg cgtggggacc acccccttctg ccaaggcctc aatcctgcac  300
gaggtcaggc ccgtgaccag cgggtgcttc cccatcatgc acgaccggac caagatcaga  360
cagctgccca acctgctgcg gggctacgag aagatccggc tgagcacaca gaacgtgatc  420
gacgccgaga aggcccctgg aggtccctac cggctgggca ccagcggaag ctgccccaac  480
gccacgagca agatcggctt cttcgccacc atggcctggg ctgtgcccaa ggacaactac  540
aagaacgcca ccaatcccct gaccgtggag gtgccctaca tttgtaccga gggcgaggac  600
cagatcaccg tgtggggctt ccacagcgac aacaagaccc aaatgaagag cctgtacggc  660
gacagcaatc cccagaagtt cacaagcagc gccaacggtg tgaccaccca ctacgtgagc  720
cagattggcg acttccccga ccagaccgag gacggagggc tgccgcagag tggccggatc  780
gtggtggact acatgatgca gaagcccggc aagaccggca ccatagtgta tcagcggggc  840
gtgctgttgc ctcagaaagt ttggtgtgtg agcggcagga gcaaggtgat caagggcagc  900
```

```
cttcccctga tcggcgaggc agactgcctc cacgaggagt acggcggcct gaacaagagc  960
aagccctact acaccggcaa gcacgccaag gcaatcggga actgccccat ctgggtcaag  1020
acccctctga agctggccaa cggcaccaag taccggccac cagccaagct gctgaaggag  1080
cggggcttct ttggcgccat tgccggcttc ctcgagggag gctgggaggg catgatcgcc  1140
ggctggtacg gctacacaag ccacggcgca cacggagtgg ctgtggctgc cgacctgaag  1200
agcacccagg aggccatcaa caagatcacc aagaatctga acagcctgag cgagctggag  1260
gtgaagaacc tgcagcggct gtcaggcgcc atggacgagc tgcacaacga gatcctggag  1320
ctggacgaga aggtggacga cctgcgtgcc gacaccatca gcagccagat cgagctggcc  1380
gtactgctga gcaacgaggg catcatcaac agcgaggacg agcacctgct ggccctggag  1440
cggaaactga agaagatgct gggaccctct gccgtggaca tcggcaacgg ctgcttcgag  1500
actaagcaca agtgcaacca gacctgcctg gatcggatcg ccgccggaac cttcaacgcc  1560
ggcgagttca gcctgcccac cttcgacagc ttaaacatca ccgccgccag cctgaacgac  1620
gacggcctgg acaaccacac catcctgctg tactacagca ctgccgcctc aagcctggcc  1680
gtgaccctga tgctggccat cttcatcgtg tacatggtga gccgggacaa cgtgagctgc  1740
agcatctgcc tg                                                      1752
```

```
SEQ ID NO: 56           moltype = RNA  length = 114
FEATURE                 Location/Qualifiers
source                  1..114
                        mol_type = other RNA
                        organism = synthetic construct
3'UTR                   1..114
                        note = B/Phuket/3073/2013 H363Y A270V HA
SEQUENCE: 56
taaagctccc cgggggcctc ggtggccctc aacgaccctg ccgcagcaaa cccccagccc  60
ctcctcccct tcctgcagga tcagtggtct ttgaataaag tctgagtggg cggc        114
```

```
SEQ ID NO: 57           moltype = AA  length = 584
FEATURE                 Location/Qualifiers
source                  1..584
                        mol_type = protein
                        organism = synthetic construct
REGION                  1..584
                        note = B/Phuket/3073/2013 H363Y A270V HA AA
SEQUENCE: 57
MKAIIVLLMV VTSNADRICT GITSSNSPHV VKTATQGEVN VTGVIPLTTT PTKSYFANLK  60
GTRTRGKLCP DCLNCTDLDV ALGRPMCVGT TPSAKASILH EVRPVTSGCF PIMHDRTKIR  120
QLPNLLRGYE KIRLSTQNVI DAEKAPGGPY RLGTSGSCPN ATSKIGFFAT MAWAVPKDNY  180
KNATNPLTVE VPYICTEGED QITVWGFHSD NKTQMKSLYG DSNPQKFTSS ANGVTTHYVS  240
QIGDFPDQTE DGGLPQSGRI VVDYMMQKPG KTGTIVYQRG VLLPQKVWCV SGRSKVIKGS  300
LPLIGEADCL HEEYGGLNKS KPYYTGKHAK AIGNCPIWVK TPLKLANGTK YRPPAKLLKE  360
RGFFGAIAGF LEGGWEGMIA GWYGYTSHGA HGVAVAADLK STQEAINKIT KNLNSLSELE  420
VKNLQRLSGA MDELHNEILE LDEKVDDLRA DTISSQIELA VLLSNEGIIN SEDEHLLALE  480
RKLKKMLGPS AVDIGNGCFE TKHKCNQTCL DRIAAGTFNA GEFSLPTFDS LNITAASLND  540
DGLDNHTILL YYSTAASSLA VTLMLAIFIV YMVSRDNVSC SICL                   584
```

```
SEQ ID NO: 58           moltype = RNA  length = 1572
FEATURE                 Location/Qualifiers
source                  1..1572
                        mol_type = other RNA
                        organism = synthetic construct
misc_feature            1..1572
                        note = NTD-RBD-HATM_V2 ORF
SEQUENCE: 58
atgttcgtgt tcctggtgct gctgcccctg gtgagcagcc agtgcgtgaa cctgaccacc  60
cggacccagc tgccaccagc ctacaccaac agcttcaccc ggggcgtcta ctaccccgac  120
aaggtgttcc ggagcagcgt cctgcacagc acccaggacc tgttcctgcc cttcttcagc  180
aacgtgacct ggttccacgc catccacgtg agcggcacca acggcaccaa gcggttcgac  240
aaccccgtgc tgcccttcaa cgacggcgtg tacttcgcca gcaccgagaa gagcaacatc  300
atccggggct ggatcttcgg caccaccctg gacagcaaga cccagagcct gctgatcgtg  360
aataacgcca ccaacgtggt gatcaaggtg tgcgagttcc agttctgcaa cgaccccttc  420
ctgggcgtgt actaccacaa gaacaacaag agctggatgg agagcgagtt ccgggtgtac  480
agcagcgcca acaactgcac cttcgagtac gtgagccagc ccttcctgat ggacctggag  540
ggcaagcagg gcaacttcaa gaacctgcgg gagttcgtgt tcaagaacat cgacggctac  600
ttcaagatct acagcaagca caccccaatc aacctggtgc gggatctgcc ccagggcttc  660
tcagccctgg agcccctggt ggacctgccc atcggcatca acatcacccg gttccagacc  720
ctgctggccc tgcaccggag ctacctgacc ccaggcgaca gcagcagcgg gtggacagca  780
ggcgcggctg cttactacgt gggctacctg cagccccgga ccttcctgct gaagtacaac  840
gagaacggca ccatcaccga cgccgtggac ggaggcggat cgggaggcgg acccaacatc  900
accaacctgt gccccttcgg cgaggtgttc aacgccaccc ggttcgccag cgtgtacgcc  960
tggaaccgga agcggatcag caactgcgtg gccgactaca gcgtgctgta caacagcgcc  1020
agcttcagca ccttcaagtg ctacggcgtg agccccacca agctgaacga cctgtgcttc  1080
accaacgtgt acgccgacag cttcgtgatc cgtggcgacg aggtgcggca gatcgcaccc  1140
ggccagacag gcaagatcgc cgactacaac tacaagctgc ccgacgactt caccggctgc  1200
gtgatcgcct ggaacagcaa caacctcgac agcaaggtgg gcggcaacta caactacctg  1260
taccggctgt tccggaagag caacctgaag cccttcgagc gggacatcag caccgagatc  1320
taccaagccg gctccacccc ttgcaacggc gtggagggct tcaactgcta cttccctctg  1380
cagagctacg gcttccagcc caccaacggc gtgggctacc agccctaccg ggtggtggtg  1440
ctgagcttcg agctgctgca cgccccagcc accgtgtgtg gccccaagtc tggcggaggc  1500
```

```
agcatcctgg ccatctacag caccgtggcc agcagcctgg tgctgctggt gagcctgggc  1560
gccatcagct tc                                                      1572

SEQ ID NO: 59           moltype = RNA  length = 119
FEATURE                 Location/Qualifiers
source                  1..119
                        mol_type = other RNA
                        organism = synthetic construct
3'UTR                   1..119
                        note = NTD-RBD-HATM_V2
SEQUENCE: 59
taaagctccc cgggggcctc ggtggcctag cttcttgccc cttgggcctc cccccagccc  60
ctcctcccct tcctgcacct gtacttccgt ggtctttgaa taaagtctga gtgggcggc   119

SEQ ID NO: 60           moltype = AA  length = 524
FEATURE                 Location/Qualifiers
source                  1..524
                        mol_type = protein
                        organism = synthetic construct
REGION                  1..524
                        note = NTD-RBD-HATM_V2 AA
SEQUENCE: 60
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD GGGSGGGPNI  300
TNLCPFGEVF NATRFASVYA WNRKRISNCV ADYSVLYNSA SFSTFKCYGV SPTKLNDLCF  360
TNVYADSFVI RGDEVRQIAP GQTGKIADYN YKLPDDFTGC VIAWNSNNLD SKVGGNYNYL  420
YRLFRKSNLK PFERDISTEI YQAGSTPCNG VEGFNCYFPL QSYGFQPTNG VGYQPYRVVV  480
LSFELLHAPA TVCGPKSGGG SILAIYSTVA SSLVLLVSLG AISF                   524

SEQ ID NO: 61           moltype = RNA  length = 1557
FEATURE                 Location/Qualifiers
source                  1..1557
                        mol_type = other RNA
                        organism = synthetic construct
misc_feature            1..1557
                        note = BA.4.BA.5-NTD-RBD-HATM ORF
SEQUENCE: 61
atgttcgtgt tcctggtgct gctgcccctg gtgagcagcc agtgcgtgaa cctgatcacc  60
cggacccaga gctacaccaa cagcttcacc cggggcgtct actaccccga caaggtgttc  120
cggagcagcg tcctgcacag cacccaggac ctgttcctgc ccttcttcag caacgtgacc  180
tggttccacg ccatcagcgg caccaacggc accaagcggt tcgacaaccc cgtgctgccc  240
ttcaacgacg gcgtgtactt cgccagcacc gagaagagca acatcatccg gggctggatc  300
ttcggcacca ccctggacag caagacccag agcctgctga tcgtgaataa cgccaccaac  360
gtggtgatca aggtgtgcga gttccagttc tgcaacgacc ccttcctgga cgtgtactac  420
cacaagaaca acaagagctg gatggagagc gagttccggg tgtacagcag cgccaacaac  480
tgcaccttcg agtacgtgag ccagcccttc ctgatggacc tggagggcaa gcagggcaac  540
ttcaagaacc tgcgggagtt cgtgttcaag aacatcgacg gctacttcaa gatctacagc  600
aagcacaccc caatcaacct gggccgggat ctgccccagg gcttctcagc cctggagccc  660
ctggtggacc tgcccatcgg catcaacatc acccggttcc agaccctgct ggccctgcac  720
cggagctacc tgaccccagg cgacagcagc agcgggtgga cagcaggcgc ggctgcttac  780
tacgtgggct acctgcagcc ccggaccttc ctgctgaagt acaacgagaa cggcaccatc  840
accgacgccg tggacggcgg aggctctgga ggcggcccca acatcaccaa cctgtgcccc  900
ttcgacgagg tgttcaacgc cacccggttc gccagcgtgt acgcctggaa ccggaagcgg  960
atcagcaact gcgtggccga ctacagcgtg ctgtacaact tcgccccatt cttcgccttc  1020
aagtgctacg gcgtgagccc caccaagctg aacgacctgt gcttcaccaa cgtgtacgcc  1080
gacagcttcg tgatccgtgg caacgaggtg agccagatcg cacccggcca gacaggcaac  1140
atcgccgact acaactacaa gctgcccgac gacttcaccg gctgcgtgat cgcctggaac  1200
agcaacaagc tcgacagcaa ggtgggcggc aactacaact accggtaccg gctgttccgg  1260
aagagcaacc tgaagccctt cgagcgggac atcagcaccg agatctacca agccggcaac  1320
aagccttgca acggcgtggc cggcgtgaac tgctacttcc ctctgcagag ctacggcttc  1380
cggcccacct acggcgtggg ccaccagccc taccgggtgg tggtgctgag cttcgagctg  1440
ctgcacgccc cagccaccgt gtgtggcccc aagagcggcg gcggcagcat cctggccatc  1500
tacagcaccg tggccagcag cctggtgctg ctggtgagcc tgggcgccat cagcttt     1557

SEQ ID NO: 62           moltype = RNA  length = 122
FEATURE                 Location/Qualifiers
source                  1..122
                        mol_type = other RNA
                        organism = synthetic construct
3'UTR                   1..122
                        note = BA.4.BA.5-NTD-RBD-HATM
SEQUENCE: 62
taaagctccc cgggggcctc ggtggcctag cttcttgccc cttgggcctc cccccagccc  60
ctcctcccct tcctgcattt gcctgtgagc agtggtcttt gaataaagtc tgagtgggcg  120
gc                                                                 122
```

```
SEQ ID NO: 63           moltype = AA  length = 519
FEATURE                 Location/Qualifiers
source                  1..519
                        mol_type = protein
                        organism = synthetic construct
REGION                  1..519
                        note = BA.4.BA.5-NTD-RBD-HATM AA
SEQUENCE: 63
MFVFLVLLPL VSSQCVNLIT RTQSYTNSFT RGVYYPDKVF RSSVLHSTQD LFLPFFSNVT  60
WFHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDGGGSG GGPNITNLCP  300
FDEVFNATRF ASVYAWNRKR ISNCVADYSV LYNFAPFFAF KCYGVSPTKL NDLCFTNVYA  360
DSFVIRGNEV SQIAPGQTGN IADYNYKLPD DFTGCVIAWN SNKLDSKVGG NYNYRYRLFR  420
KSNLKPFERD ISTEIYQAGN KPCNGVAGVN CYFPLQSYGF RPTYGVGHQP YRVVVLSFEL  480
LHAPATVCGP KSGGGSILAI YSTVASSLVL LVSLGAISF                        519

SEQ ID NO: 64           moltype = RNA  length = 1889
FEATURE                 Location/Qualifiers
source                  1..1889
                        mol_type = other RNA
                        organism = synthetic construct
misc_feature            1..1889
                        note = H1_Wisconsin_2019_WT_V2
SEQUENCE: 64
aggaaatcgc aaaatttgct cttcgcgtta gatttctttt agttttctcg caactagcaa  60
gctttttgtt ctcgccatga aggccatcct ggtcgtgatg ctgtacacct tcaccaccgc  120
caacgccgac accctgtgca tcggctacca cgccaacaac agcaccgaca ccgtggacac  180
cgtgctggag aagaacgtga ccgtgaccca cagcgtgaac ctgctggagg acaagcacaa  240
cggcaagctg tgcaagctga ggggagtggc acccctgcac ctgggcaagt gcaacatcgc  300
cggctggatc ctgggcaacc ccgagtgcga gagcctgagc acagcccgga gctggagcta  360
catcgtggag accagcaaca gcgacaacgg cacctgttac cccggcgact tcatcaacta  420
cgaggagctg cgggagcagc tgagcagcgt gagcagcttc gagcggttcg agatcttccc  480
caagaccagc agctggccca accacgacag cgacaacggc gtgacagcag cctgtccaca  540
cgccggagcc aagagcttct acaagaacct gatctggctg gtgaagaagg gcaagagcta  600
ccccaagatc aaccagacct acatcaacga caagggcaag gaggtgctgg tgctgtgggg  660
catccaccac ccacctacca tcgccgacca gcagagcctg taccagaacg ccgacgccta  720
cgtgttcgtg ggcaccagcc ggtacagcaa gaagttcaag ccagagatcg ccacccggcc  780
caaggtgaga gaccaggagg gccggatgaa ctactactgg accctggtgg agcccggaga  840
caagattacc ttcgaggcca ccggcaacct ggtggcccct cggtacgcct tcaccatgga  900
acgggacgct ggcagcggca tcatcatcag cgacactccc gtgcacgact gcaacaccac  960
ctgccagact cccgagggcg ctatcaacac cagcctgccc ttccagaacg tgcaccccat  1020
caccatcggc aagtgcccca agtacgtaaa gagcaccaaa ttgcggctgg ccaccggact  1080
caggaacgtg cccagcatcc aaagccgggg cctgtttggc gcaatcgccg gcttcatcga  1140
gggcggctgg actggcatgg tggacggctg gtacggctac caccaccaga acgaacaggg  1200
gagcggctac gcagctgacc tgaagagcac ccagaacgcc atcgacaaga tcaccaacaa  1260
ggtgaacagc gtgatcgaga agatgaacac ccagttcacc gccgtgggca aggagttcaa  1320
ccacctggag aagcggatcg agaacctgaa caagaaggtg gacgacggct tcctggacat  1380
ctggacctac aacgccgagc tgctggttct gctggagaac gagcggaccc tggactatca  1440
cgacagcaac gtgaagaacc tgtacgagaa ggtgcggaac cagctgaaga acaacgccaa  1500
ggagatcggc aacggctgct tcgagttcta ccacaagtgc gacaacacct gcatggagag  1560
cgtgaagaac ggcacctacg actaccccaa gtacagcgag gaggccaagc tgaaccggga  1620
gaagatcgac ggcgtgaagc tggacagcac ccggatctac cagatcctgg ccatctacag  1680
caccgtggcc agcagcctgg tgctggtggt gagcctgggc gccatcagct tctggatgtg  1740
cagcaacggc agcctgcagt gccggatctg catctaaagc tccccggggg cctcggtggc  1800
cctccaccga agcagccatc agcaccccca gcccctcctc cccttcctgc aggtcaaagt  1860
ggtctttgaa taaagtctga gtgggcggc                                   1889

SEQ ID NO: 65           moltype = RNA  length = 1891
FEATURE                 Location/Qualifiers
source                  1..1891
                        mol_type = other RNA
                        organism = synthetic construct
misc_feature            1..1891
                        note = H3_A/Darwin/6/2021_G53D_V2
SEQUENCE: 65
aggaaatcgc aaaatttgct cttcgcgtta gatttctttt agttttctcg caactagcaa  60
gctttttgtt ctcgccatga agaccatcat cgccctgagc aacatcctgt gcctggtgtt  120
cgcccagaag atccccggca acgataacag caccgccacc ctgtgtctgg gacaccacgc  180
cgtgcccaac ggcaccatcg tgaagactat caccaacgac cggatcgagg tgaccaacgc  240
caccgagctg gtgcagaaca gcagcatcgg cgagatctgc gacagccctc accagatcct  300
ggacggcggc aactgcaccc tgatcgacgc actgctgggc gaccctcagt gcgacggctt  360
tcagaacaag gagtgggacc tgttcgtgga gagatcgcgg gccaacagca actgctaccc  420
ctacgacgtc cccgactacg caagcctgag aagcctcgtg gcctcaagcg gcaccctgga  480
gttcaagaac gagagcttca actggaccgg cgtgaagcag aacggcacct caagcgcctg  540
catccggggc tccagcagca gcttcttctc acggctgaac tggctgaccc acctgaacaa  600
catctacccc gcccagaacg tgaccatgcc caacaaggag cagttcgaca agctgtacat  660
ctggggagtg caccatcccg acaccgacaa gaaccagatt agcctgttcg cccagagcag  720
```

-continued

```
cggccggatc accgtgagca ccaagcggag ccagcaggcc gtgatcccca acatcggctc  780
tcggcccaga atccgggaca tccccagccg gatcagcatc tactggacca ttgtgaagcc  840
cggcgacatc ctgctgatca actccaccgg caacctgatc gcccctcggg gctatttcaa  900
gatccggagc ggcaagagca gcatcatgcg gagcgacgcc cctatcggca agtgcaagag  960
cgagtgcatc acacccaacg gaagcatccc caacgacaag cccttccaga acgtgaaccg  1020
gataacctac ggcgcctgcc ctagatacgt gaagcagagc accctgaagc tggccaccgg  1080
catgcggaac gtgcccgaga agcagactcg gggcatcttc ggcgccatcg ccggcttcat  1140
cgagaacggc tgggagggca tggtggacgg ctggtacggc ttccggcacc agaactctga  1200
gggcagagga caggccgcag acctgaagag cacccaggcc gccatcgacc agatcaacgg  1260
caagctgaac cggctgatcg gcaagaccaa cgagaagttc caccagatcg agaaggagtt  1320
cagcgaggtg gagggcaggg tacaggacct ggagaagtac gtggaggaca ccaagatcga  1380
cctgtggagc tacaacgccg agctgctggt agccctggag aaccagcaca ccatcgacct  1440
gaccgacagc gagatgaaca agctgttcga gaagaccaag aagcagctgc gggagaacgc  1500
cgaggacatg ggcaacggct gcttcaagat ctaccacaag tgcgacaacg cctgcatcgg  1560
cagcatccgg aacgagacct acgaccacaa cgtgtaccgg gacgaggccc tgaacaaccg  1620
gttccagatc aagggcgtgg agctgaagag cggctacaag gactggatcc tgtggatcag  1680
cttcgccatg tcctgcttcc tgctgtgcat cgccctgctg ggtttcatca tgtgggcctg  1740
ccagaagggc aacatccggt gcaacatctg catctaaagc tccccggggg cctcggtggc  1800
cctccgcatc agaccaacgg cacacccccca gcccctcctc cccttcctgc aggtcaagga  1860
gtggtctttg aataaagtct gagtgggcgg c                                 1891
```

```
SEQ ID NO: 66          moltype = RNA  length = 1938
FEATURE                Location/Qualifiers
source                 1..1938
                       mol_type = other RNA
                       organism = synthetic construct
misc_feature           1..1938
                       note = B/Austria/1359417/2021 H363Y A270V HA_SEv4.5
SEQUENCE: 66
aggaaatcgc aaaatttgct cttcgcgtta gatttctttt agttttctcg caactagcaa  60
gctttttgtt ctcgccatga aggctatcat cgtgctgtta atggtggtga ccagcaacgc  120
cgaccggatc tgcacaggca tcacctctag caacagccct cacgtggtca agaccgccac  180
acagggcgag gtgaacgtga ccggcgtgat tcccctgacc accaccccta ccaagagcca  240
cttcgccaac ctgaagggaa ccgagacccg gggcaagctg tgtccaaagt gcctgaactg  300
taccgacctg gacgtggctc tgggcagacc caagtgcacc ggcaagatcc ccagcgcccg  360
ggtgtctatc ttgcacgaag tgcggcccgt gactagcggt tgcttcccca tcatgcacga  420
ccggaccaag atcagacagc tgcccaacct gctgcggggc tacgagcacg tgcggctgtc  480
cacccataac gtgatcaaca ccgaagacgc acccggcggc ccatacgaga tcggcaccag  540
cggctcttgc ctgaatatca ccaacggcaa gggattcttt gctaccatgg cctgggccgt  600
gccaaagaac aagactgcca ccaaccctct gaccatcgag gtgccctaca tctgcaccga  660
ggaggaggac cagatcaccg tgtggggctt ccacagcgac gacgagacac agatggccag  720
actgtacggc gacagcaaac cccagaagtt caccagcagc gccaacggcg tgaccaccca  780
ctacgtgagc cagattggcg gcttccctaa ccaaaccgag gacggcggct taccccagag  840
cggccggatc gtggtggact acatggttca gaagagcggc aagaccggca ccatcaccta  900
ccagcggggc atcctgttac cacagaaggt gtggtgcgtg tcagggaaat caaaggtcat  960
caagggctcc ctgccactga ttggcgaggc cgactgcctg cacgagaagt acggcggcct  1020
gaacaagagc aagccctact acaccggcga gcacgccaag gcaatcggca actgccccat  1080
ctgggtgaag acacccctga agctggcaaa cggcaccaag taccggccac ccgccaaact  1140
gctgaaggag cggggcttct tcggcgccat tgccggcttc ctcgaaggcg gttgggaggg  1200
catgatcgca ggctggtacg gctacactag ccacggcgca cacggagtag cagtggccgc  1260
cgacctgaag agcacccagg aggccatcaa caagatcacc aagaacctga acagcctgag  1320
cgagctggag gtgaagaatc tgcagaggct gtctggcgct atggacgagc tgcacaacga  1380
gatcctggag ctggacgaga aggtggacga cttacgggcc gacaccatca gcagccagat  1440
cgagctggca gtgctgctga gcaacgaggg catcatcaac agcgaggacg agcacctgct  1500
ggccctggag cggaagctga agaagatgct gggcccttct gccgtggaga tcggtaacgg  1560
ctgcttcgag accaagcaca agtgcaacca gacctgcctg gatcggatcg cagccggcac  1620
ctttgacgcc ggggagttca gcctgcccac cttcgacagc ttgaacatca ccgccgccag  1680
cctgaacgac gacggcctgg acaaccacac catcctgctg tactactcta cagccgctag  1740
cagcctggcc gtgaccctga tgatcgccat cttcgtggtg tacatggtga gccgggacaa  1800
cgtgagctgc agcatctgcc tgtaaagctc cccgggggcc tcggtggccc tcaacctacg  1860
ccgaagacca cgcccccagc ccctcctccc cttcctgcag gtcaagagtg gtctttgaat  1920
aaagtctgag tgggcggc                                                1938
```

```
SEQ ID NO: 67          moltype = RNA  length = 1942
FEATURE                Location/Qualifiers
source                 1..1942
                       mol_type = other RNA
                       organism = synthetic construct
misc_feature           1..1942
                       note = B/Phuket/3073/2013 H363Y A270V HA
SEQUENCE: 67
aggaaatcgc aaaatttgct cttcgcgtta gatttctttt agttttctcg caactagcaa  60
gctttttgtt ctcgccatga aggctatcat cgtgctactc atggtggtaa ccagcaacgc  120
cgaccggatc tgcaccggca tcaccagcag caacagcccg cacgttgtga agaccgccac  180
ccaaggcgag gtgaacgtga ccggcgtgat cccactgacc accactccca ccaagagcta  240
cttcgccaac ctgaagggca ctcggactcg gggcaagctc tgccccgact gcctgaactg  300
caccgacctg gacgtggctc tgggcagacc catgtgcgtg gggaccaccc cttctgccaa  360
ggcctcaatc ctgcacgagg tcaggcccgt gaccagcggg tgcttcccca tcatgcacga  420
ccggaccaag atcagacagc tgcccaacct gctgcggggc tacgagaaga tccggctgag  480
```

```
cacacagaac gtgatcgacg ccgagaaggc ccctggaggt ccctaccggc tgggcaccag  540
cggaagctgc cccaacgcca cgagcaagat cggcttcttc gccaccatgg cctgggctgt  600
gcccaaggac aactacaaga acgccaccaa tcccctgacc gtggaggtgc cctacatttg  660
taccgagggc gaggaccaga tcaccgtgtg gggcttccac agcgacaaca agacccaaat  720
gaagagcctg tacggcgaca gcaatcccca gaagttcaca agcagcgcca acggtgtgac  780
cacccactac gtgagccaga ttggcgactt ccccgaccag accgaggacg gagggctgcc  840
gcagagtggc cggatcgtgg tggactacat gatgcagaag cccggcaaga ccggcaccat  900
agtgtatcag cggggcgtgc tgttgcctca gaaagtttgg tgtgtgagcg gcaggagcaa  960
ggtgatcaag ggcagccttc ccctgatcgg cgaggcagac tgcctccacg aggagtacgg  1020
cggcctgaac aagagcaagc cctactacac cggcaagcac gccaaggcaa tcgggaactg  1080
ccccatctgg gtcaagaccc ctctgaagct ggccaacggc accaagtacc ggccaccagc  1140
caagctgctg aaggagcggg gcttctttgg cgccattgcc ggcttcctcg agggaggctg  1200
ggagggcatg atcgccggct ggtacggcta cacaagccac ggcgcacacg gagtggctgt  1260
ggctgccgac ctgaagagca cccaggaggc catcaacaag atcaccaaga atctgaacag  1320
cctgagcgag ctggaggtga agaacctgca gcggctgtca ggcgccatgg acgagctgca  1380
caacgagatc ctggagctgg acgagaaggt ggacgacctg cgtgccgaca ccatcagcag  1440
ccagatcgag ctggccgtac tgctgagcaa cgagggcatc atcaacagcg aggacgagca  1500
cctgctggcc ctggagcgga aactgaagaa gatgctggga ccctctgccg tggacatcgg  1560
caacggctgc ttcgagacta agcacaagtg caaccagacc tgcctggatc ggatcgccgc  1620
cggaaccttc aacgccggcg agttcagcct gcccaccttc gacagcttaa acatcaccgc  1680
cgccagcctg aacgacgacg gcctggacaa ccacaccatc ctgctgtact acagcactgc  1740
cgcctcaagc ctggccgtga ccctgatgct ggccatcttc atcgtgtaca tggtgagccg  1800
ggacaacgtg agctgcagca tctgcctgta aagctccccg gggggcctcgg tggccctcaa  1860
cgaccctgcc gcagcaaacc cccagcccct cctccccttc ctgcaggatc agtggtcttt  1920
gaataaagtc tgagtgggcg gc                                          1942
```

```
SEQ ID NO: 68           moltype = RNA  length = 1767
FEATURE                 Location/Qualifiers
source                  1..1767
                        mol_type = other RNA
                        organism = synthetic construct
misc_feature            1..1767
                        note = NTD-RBD-HATM_V2
SEQUENCE: 68
aggaaatcgc aaaatttgct cttcgcgtta gatttctttt agttttctcg caactagcaa  60
gctttttgtt ctcgccatgt tcgtgttcct ggtgctgctg cccctggtga gcagccagtg  120
cgtgaacctg accacccgga cccagctgcc accagcctac accaacagct tcacccgggg  180
cgtctactac cccgacaagg tgttccggag cagcgtcctg cacagcaccc aggacctgtt  240
cctgcccttc ttcagcaacg tgacctggtt ccacgccatc cacgtgagcg gcaccaacgg  300
caccaagcgg ttcgacaacc ccgtgctgcc cttcaacgac ggcgtgtact tcgccagcac  360
cgagaagagc aacatcatcc ggggctggat cttcggcacc accctggaca gcaagaccca  420
gagcctgctg atcgtgaata acgccaccaa cgtggtgatc aaggtgtgcg agttccagtt  480
ctgcaacgac cccttcctgg gcgtgtacta ccacaagaac aacaagagct ggatggagag  540
cgagttccgg gtgtacagca gcgccaacaa ctgcaccttc gagtacgtga gccagccctt  600
cctgatggac ctggagggca agcagggcaa cttcaagaac ctgcgggagt tcgtgttcaa  660
gaacatcgac ggctacttca agatctacag caagcacacc ccaatcaacc tggtgcggga  720
tctgccccag ggcttctcag ccctggagcc cctggtggac ctgcccatcg gcatcaacat  780
cacccggttc cagaccctgc tggccctgca ccggagctac ctgaccccag gcgacagcag  840
cagcgggtgg acagcaggcg cggctgctta ctacgtgggc tacctgcagc cccggacctt  900
cctgctgaag tacaacgaga acggcaccat caccgacgcc gtggacggag gcggatcggg  960
aggcggaccc aacatcacca acctgtgccc cttcggcgag gtgttcaacg ccacccggtt  1020
cgccagcgtg tacgcctgga accggaagcg gatcagcaac tgcgtggccg actacagcgt  1080
gctgtacaac agcgccagct tcagcacctt caagtgctac ggcgtgagcc ccaccaagct  1140
gaacgacctg tgcttcacca acgtgtacgc cgacagcttc gtgatccgtg gcgacgaggt  1200
gcggcagatc gcacccggcc agacaggcaa gatcgccgac tacaactaca agctgcccga  1260
cgacttcacc ggctgcgtga tcgcctggaa cagcaacaac ctcgacagca aggtgggcgg  1320
caactacaac tacctgtacc ggctgttccg gaagagcaac ctgaagccct tcgagcggga  1380
catcagcacc gagatctacc aagccggctc caccccttgc aacggcgtgg agggcttcaa  1440
ctgctacttc cctctgcaga gctacggctt ccagcccacc aacggcgtgg gctaccagcc  1500
ctaccgggtg gtggtgctga gcttcgagct gctgcacgcc ccagccaccg tgtgtggccc  1560
caagtctggc ggaggcagca tcctggccat ctacagcacc gtggccagca gcctggtgct  1620
gctggtgagc ctgggcgcca tcagcttcta aagctccccg gggggcctcgg tggcctagct  1680
tcttgcccct tgggcctccc cccagcccct cctccccttc ctgcacctgt acttccgtgg  1740
tctttgaata aagtctgagt gggcggc                                     1767
```

```
SEQ ID NO: 69           moltype = RNA  length = 1755
FEATURE                 Location/Qualifiers
source                  1..1755
                        mol_type = other RNA
                        organism = synthetic construct
misc_feature            1..1755
                        note = BA.4.BA.5-NTD-RBD-HATM
SEQUENCE: 69
aggaaatcgc aaaatttgct cttcgcgtta gatttctttt agttttctcg caactagcaa  60
gctttttgtt ctcgccatgt tcgtgttcct ggtgctgctg cccctggtga gcagccagtg  120
cgtgaacctg atcacccgga cccagagcta caccaacagc ttcacccggg gcgtctacta  180
ccccgacaag gtgttccgga gcagcgtcct gcacagcacc caggacctgt tcctgccctt  240
cttcagcaac gtgacctggt tccacgccat cagcggcacc aacggcacca agcggttcga  300
caaccccgtg ctgcccttca acgacggcgt gtacttcgcc agcaccgaga agagcaacat  360
```

-continued

```
catccggggc tggatcttcg gcaccaccct ggacagcaag acccagagcc tgctgatcgt  420
gaataacgcc accaacgtgg tgatcaaggt gtgcgagttc cagttctgca acgacccctt  480
cctggacgtg tactaccaca agaacaacaa gagctggatg gagagcgagt tccgggtgta  540
cagcagcgcc aacaactgca ccttcgagta cgtgagccag cccttcctga tggacctgga  600
gggcaagcag ggcaacttca agaacctgcg ggagttcgtg ttcaagaaca tcgacggcta  660
cttcaagatc tacagcaagc acaccccaat caacctgggc cgggatctgc cccagggctt  720
ctcagccctg gagcccctgg tggacctgcc catcggcatc aacatcaccc ggttccagac  780
cctgctggcc ctgcaccgga gctacctgac cccaggcgac agcagcagcg ggtggacagc  840
aggcgcggct gcttactacg tgggctacct gcagccccgg accttcctgc tgaagtacaa  900
cgagaacggc accatcaccg acgccgtgga cggcggaggc tctggaggcg gccccaacat  960
caccaacctg tgccccttcg acgaggtgtt caacgccacc cggttcgcca gcgtgtacgc  1020
ctggaaccgg aagcggatca gcaactgcgt ggccgactac agcgtgctgt acaacttcgc  1080
cccattcttc gccttcaagt gctacggcgt gagccccacc aagctgaacg acctgtgctt  1140
caccaacgtg tacgccgaca gcttcgtgat ccgtggcaac gaggtgagcc agatcgcacc  1200
cggccagaca ggcaacatcg ccgactacaa ctacaagctg cccgacgact tcaccggctg  1260
cgtgatcgcc tggaacagca acaagctcga cagcaaggtg ggcggcaact acaactaccg  1320
gtaccggctg ttccggaaga gcaacctgaa gcccttcgag cgggacatca gcaccgagat  1380
ctaccaagcc ggcaacaagc cttgcaacgg cgtggccggc gtgaactgct acttccctct  1440
gcagagctac ggcttccggc ccacctacgg cgtgggccac cagccctacc gggtggtggt  1500
gctgagcttc gagctgctgc acgccccagc caccgtgtgt ggccccaaga gcggcggcgg  1560
cagcatcctg gccatctaca gcaccgtggc cagcagcctg gtgctgctgg tgagcctggg  1620
cgccatcagc ttttaaagct ccccgggggc ctcggtggcc tagcttcttg ccccttgggc  1680
ctccccccag cccctcctcc ccttcctgca tttgcctgtg agcagtggtc tttgaataaa  1740
gtctgagtgg gcggc                                                   1755
```

```
SEQ ID NO: 70           moltype = AA  length = 584
FEATURE                 Location/Qualifiers
source                  1..584
                        mol_type = protein
                        note = Influenza B virus
                        organism = unidentified
REGION                  1..584
                        note = B/Phuket/3073/2013 (B/Yamagata lineage) HA: wild-type
SEQUENCE: 70
MKAIIVLLMV VTSNADRICT GITSSNSPHV VKTATQGEVN VTGVIPLTTT PTKSYFANLK  60
GTRTRGKLCP DCLNCTDLDV ALGRPMCVGT TPSAKASILH EVRPVTSGCF PIMHDRTKIR  120
QLPNLLRGYE KIRLSTQNVI DAEKAPGGPY RLGTSGSCPN ATSKIGFFAT MAWAVPKDNY  180
KNATNPLTVE VPYICTEGED QITVWGFHSD NKTQMKSLYG DSNPQKFTSS ANGVTTHYVS  240
QIGDFPDQTE DGGLPQSGRI VVDYMMQKPG KTGTIVYQRG VLLPQKVWCA SGRSKVIKGS  300
LPLIGEADCL HEEYGGLNKS KPYYTGKHAK AIGNCPIWVK TPLKLANGTK YRPPAKLLKE  360
RGFFGAIAGF LEGGWEGMIA GWHGYTSHGA HGVAVAADLK STQEAINKIT KNLNSLSELE  420
VKNLQRLSGA MDELHNEILE LDEKVDDLRA DTISSQIELA VLLSNEGIIN SEDEHLLALE  480
RKLKKMLGPS AVDIGNGCFE TKHKCNQTCL DRIAAGTFNA GEFSLPTFDS LNITAASLND  540
DGLDNHTILL YYSTAASSLA VTLMLAIFIV YMVSRDNVSC SICL                  584

SEQ ID NO: 71           moltype = AA  length = 582
FEATURE                 Location/Qualifiers
source                  1..582
                        mol_type = protein
                        note = Influenza B virus
                        organism = unidentified
REGION                  1..582
                        note = B/Austria/1359417/2021 (B/Victoria lineage) HA:
                         wild-type
SEQUENCE: 71
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NTEDAPGGPY EIGTSGSCLN ITNGKGFFAT MAWAVPKNKT  180
ATNPLTIEVP YICTEEEDQI TVWGFHSDDE TQMARLYGDS KPQKFTSSAN GVTTHYVSQI  240
GGFPNQTEDG GLPQSGRIVV DYMVQKSGKT GTITYQRGIL LPQKVWCASG KSKVIKGSLP  300
LIGEADCLHE KYGGLNKSKP YYTGEHAKAI GNCPIWVKTP LKLANGTKYR PPAKLLKERG  360
FFGAIAGFLE GGWEGMIAGW HGYTSHGAHG VAVAADLKST QEAINKITKN LNSLSELEVK  420
NLQRLSGAMD ELHNEILELD EKVDDLRADT ISSQIELAVL LSNEGIINSE DEHLLALERK  480
LKKMLGPSAV EIGNGCFETK HKCNQTCLDR IAAGTFDAGE FSLPTFDSLN ITAASLNDDG  540
LDNHTILLYY STAASSLAVT LMIAIFVVYM VSRDNVSCSI CL                    582

SEQ ID NO: 72           moltype = AA  length = 584
FEATURE                 Location/Qualifiers
source                  1..584
                        mol_type = protein
                        organism = synthetic construct
REGION                  1..584
                        note = B_Phuket_HA: Q267L
SEQUENCE: 72
MKAIIVLLMV VTSNADRICT GITSSNSPHV VKTATQGEVN VTGVIPLTTT PTKSYFANLK  60
GTRTRGKLCP DCLNCTDLDV ALGRPMCVGT TPSAKASILH EVRPVTSGCF PIMHDRTKIR  120
QLPNLLRGYE KIRLSTQNVI DAEKAPGGPY RLGTSGSCPN ATSKIGFFAT MAWAVPKDNY  180
KNATNPLTVE VPYICTEGED QITVWGFHSD NKTQMKSLYG DSNPQKFTSS ANGVTTHYVS  240
QIGDFPDQTE DGGLPQSGRI VVDYMMLKPG KTGTIVYQRG VLLPQKVWCA SGRSKVIKGS  300
```

-continued

```
LPLIGEADCL HEEYGGLNKS KPYYTGKHAK AIGNCPIWVK TPLKLANGTK YRPPAKLLKE  360
RGFFGAIAGF LEGGWEGMIA GWHGYTSHGA HGVAVAADLK STQEAINKIT KNLNSLSELE  420
VKNLQRLSGA MDELHNEILE LDEKVDDLRA DTISSQIELA VLLSNEGIIN SEDEHLLALE  480
RKLKKMLGPS AVDIGNGCFE TKHKCNQTCL DRIAAGTFNA GEFSLPTFDS LNITAASLND  540
DGLDNHTILL YYSTAASSLA VTLMLAIFIV YMVSRDNVSC SICL                  584

SEQ ID NO: 73          moltype = AA  length = 584
FEATURE                Location/Qualifiers
source                 1..584
                       mol_type = protein
                       organism = synthetic construct
REGION                 1..584
                       note = B_Phuket_HA: G273A
SEQUENCE: 73
MKAIIVLLMV VTSNADRICT GITSSNSPHV VKTATQGEVN VTGVIPLTTT PTKSYFANLK  60
GTRTRGKLCP DCLNCTDLDV ALGRPMCVGT TPSAKASILH EVRPVTSGCF PIMHDRTKIR  120
QLPNLLRGYE KIRLSTQNVI DAEKAPGGPY RLGTSGSCPN ATSKIGFFAT MAWAVPKDNY  180
KNATNPLTVE VPYICTEGED QITVWGFHSD NKTQMKSLYG DSNPQKFTSS ANGVTTHYVS  240
QIGDFPDQTE DGGLPQSGRI VVDYMMQKPG KTATIVYQRG VLLPQKVWCA SGRSKVIKGS  300
LPLIGEADCL HEEYGGLNKS KPYYTGKHAK AIGNCPIWVK TPLKLANGTK YRPPAKLLKE  360
RGFFGAIAGF LEGGWEGMIA GWHGYTSHGA HGVAVAADLK STQEAINKIT KNLNSLSELE  420
VKNLQRLSGA MDELHNEILE LDEKVDDLRA DTISSQIELA VLLSNEGIIN SEDEHLLALE  480
RKLKKMLGPS AVDIGNGCFE TKHKCNQTCL DRIAAGTFNA GEFSLPTFDS LNITAASLND  540
DGLDNHTILL YYSTAASSLA VTLMLAIFIV YMVSRDNVSC SICL                  584

SEQ ID NO: 74          moltype = AA  length = 584
FEATURE                Location/Qualifiers
source                 1..584
                       mol_type = protein
                       organism = synthetic construct
REGION                 1..584
                       note = B_Phuket_HA: H435L
SEQUENCE: 74
MKAIIVLLMV VTSNADRICT GITSSNSPHV VKTATQGEVN VTGVIPLTTT PTKSYFANLK  60
GTRTRGKLCP DCLNCTDLDV ALGRPMCVGT TPSAKASILH EVRPVTSGCF PIMHDRTKIR  120
QLPNLLRGYE KIRLSTQNVI DAEKAPGGPY RLGTSGSCPN ATSKIGFFAT MAWAVPKDNY  180
KNATNPLTVE VPYICTEGED QITVWGFHSD NKTQMKSLYG DSNPQKFTSS ANGVTTHYVS  240
QIGDFPDQTE DGGLPQSGRI VVDYMMQKPG KTGTIVYQRG VLLPQKVWCA SGRSKVIKGS  300
LPLIGEADCL HEEYGGLNKS KPYYTGKHAK AIGNCPIWVK TPLKLANGTK YRPPAKLLKE  360
RGFFGAIAGF LEGGWEGMIA GWHGYTSHGA HGVAVAADLK STQEAINKIT KNLNSLSELE  420
VKNLQRLSGA MDELLNEILE LDEKVDDLRA DTISSQIELA VLLSNEGIIN SEDEHLLALE  480
RKLKKMLGPS AVDIGNGCFE TKHKCNQTCL DRIAAGTFNA GEFSLPTFDS LNITAASLND  540
DGLDNHTILL YYSTAASSLA VTLMLAIFIV YMVSRDNVSC SICL                  584

SEQ ID NO: 75          moltype = AA  length = 584
FEATURE                Location/Qualifiers
source                 1..584
                       mol_type = protein
                       organism = synthetic construct
REGION                 1..584
                       note = B_Phuket_HA:  Q267L-G273A-H435L
SEQUENCE: 75
MKAIIVLLMV VTSNADRICT GITSSNSPHV VKTATQGEVN VTGVIPLTTT PTKSYFANLK  60
GTRTRGKLCP DCLNCTDLDV ALGRPMCVGT TPSAKASILH EVRPVTSGCF PIMHDRTKIR  120
QLPNLLRGYE KIRLSTQNVI DAEKAPGGPY RLGTSGSCPN ATSKIGFFAT MAWAVPKDNY  180
KNATNPLTVE VPYICTEGED QITVWGFHSD NKTQMKSLYG DSNPQKFTSS ANGVTTHYVS  240
QIGDFPDQTE DGGLPQSGRI VVDYMMLKPG KTATIVYQRG VLLPQKVWCA SGRSKVIKGS  300
LPLIGEADCL HEEYGGLNKS KPYYTGKHAK AIGNCPIWVK TPLKLANGTK YRPPAKLLKE  360
RGFFGAIAGF LEGGWEGMIA GWHGYTSHGA HGVAVAADLK STQEAINKIT KNLNSLSELE  420
VKNLQRLSGA MDELLNEILE LDEKVDDLRA DTISSQIELA VLLSNEGIIN SEDEHLLALE  480
RKLKKMLGPS AVDIGNGCFE TKHKCNQTCL DRIAAGTFNA GEFSLPTFDS LNITAASLND  540
DGLDNHTILL YYSTAASSLA VTLMLAIFIV YMVSRDNVSC SICL                  584

SEQ ID NO: 76          moltype = AA  length = 582
FEATURE                Location/Qualifiers
source                 1..582
                       mol_type = protein
                       organism = synthetic construct
REGION                 1..582
                       note = B_Austria_HA: H383Y
SEQUENCE: 76
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NTEDAPGGPY EIGTSGSCLN ITNGKGFFAT MAWAVPKNKT  180
ATNPLTIEVP YICTEEEDQI TVWGFHSDDE TQMARLYGDS KPQKFTSSAN GVTTHYVSQI  240
GGFPNQTEDG GLPQSGRIVV DYMVQKSGKT GTITYQRGIL LPQKVWCASG KSKVIKGSLP  300
LIGEADCLHE KYGGLNKSKP YYTGEHAKAI GNCPIWVKTP LKLANGTKYR PPAKLLKERG  360
FFGAIAGFLE GGWEGMIAGW YGYTSHGAHG VAVAADLKST QEAINKITKN LNSLSELEVK  420
NLQRLSGAMD ELHNEILELD EKVDDLRADT ISSQIELAVL LSNEGIINSE DEHLLALERK  480
```

-continued

```
LKKMLGPSAV EIGNGCFETK HKCNQTCLDR IAAGTFDAGE FSLPTFDSLN ITAASLNDDG  540
LDNHTILLYY STAASSLAVT LMIAIFVVYM VSRDNVSCSI CL                     582

SEQ ID NO: 77          moltype = AA  length = 582
FEATURE                Location/Qualifiers
source                 1..582
                       mol_type = protein
                       organism = synthetic construct
REGION                 1..582
                       note = B_Austria_HA: A290V
SEQUENCE: 77
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NTEDAPGGPY EIGTSGSCLN ITNGKGFFAT MAWAVPKNKT  180
ATNPLTIEVP YICTEEEDQI TVWGFHSDDE TQMARLYGDS KPQKFTSSAN GVTTHYVSQI  240
GGFPNQTEDG GLPQSGRIVV DYMVQKSGKT GTITYQRGIL LPQKVWCVSG KSKVIKGSLP  300
LIGEADCLHE KYGGLNKSKP YYTGEHAKAI GNCPIWVKTP LKLANGTKYR PPAKLLKERG  360
FFGAIAGFLE GGWEGMIAGW YGYTSHGAHG VAVAADLKST QEAINKITKN LNSLSELEVK  420
NLQRLSGAMD ELHNEILELD EKVDDLRADT ISSQIELAVL LSNEGIINSE DEHLLALERK  480
LKKMLGPSAV EIGNGCFETK HKCNQTCLDR IAAGTFDAGE FSLPTFDSLN ITAASLNDDG  540
LDNHTILLYY STAASSLAVT LMIAIFVVYM VSRDNVSCSI CL                     582

SEQ ID NO: 78          moltype = AA  length = 1273
FEATURE                Location/Qualifiers
source                 1..1273
                       mol_type = protein
                       organism = synthetic construct
REGION                 1..1273
                       note = Wild-Type Wuhan-Hu-1; USA-WA1/2020 isolate S protein
SEQUENCE: 78
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 79          moltype =   length =
SEQUENCE: 79
000

SEQ ID NO: 80          moltype = RNA  length = 11
FEATURE                Location/Qualifiers
source                 1..11
                       mol_type = other RNA
                       organism = synthetic construct
SEQUENCE: 80
gggatcctac c                                                       11

SEQ ID NO: 81          moltype = AA  length = 883
FEATURE                Location/Qualifiers
source                 1..883
                       mol_type = protein
                       note = Bacteriophage T7
                       organism = unidentified
REGION                 1..883
                       note = WT T7 RNA polymerase
SEQUENCE: 81
MNTINIAKND FSDIELAAIP FNTLADHYGE RLAREQLALE HESYEMGEAR FRKMFERQLK  60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
```

```
SKKALMRYED VYMPEVYKAI NIAQNTAWKI NKKVLAVANV ITKWKHCPVE DIPAIEREEL  360
PMKPEDIDMN PEALTAWKRA AAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA                   883

SEQ ID NO: 82           moltype = AA  length = 566
FEATURE                 Location/Qualifiers
source                  1..566
                        mol_type = protein
                        note = Influenza A virus
                        organism = unidentified
REGION                  1..566
                        note = A/Darwin/6/2021(H3N2) HA: wild-type
SEQUENCE: 82
MKTIIALSNI LCLVFAQKIP GNDNSTATLC LGHHAVPNGT IVKTITNDRI EVTNATELVQ  60
NSSIGEICGS PHQILDGGNC TLIDALLGDP QCDGFQNKEW DLFVERSRAN SNCYPYDVPD  120
YASLRSLVAS SGTLEFKNES FNWTGVKQNG TSSACIRGSS SSFFSRLNWL TSLNNIYPAQ  180
NVTMPNKEQF DKLYIWGVHH PDTDKNQISL FAQSSGRITV STKRSQQAVI PNIGSRPRIR  240
GIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                      566

SEQ ID NO: 83           moltype = AA  length = 566
FEATURE                 Location/Qualifiers
source                  1..566
                        mol_type = protein
                        note = Influenza A virus
                        organism = unidentified
REGION                  1..566
                        note = A/Wisconsin/67/2022(H1N1) HA: wild-type
SEQUENCE: 83
MKAILVVMLY TFTTANADTL CIGYHANNST DTVDTVLEKN VTVTHSVNLL EDKHNGKLCK  60
LRGVAPLHLG QCNIAGWILG NPECESLSTA RSWSYIVETS NSDNGTCYPG DFINYEELRE  120
QLSSVSSFER FEIFPKTSSW PNHDSDNGVT AACSHAGARS FYKNLIWLVK KGKSYPKINQ  180
TYINDKGKEV LVLWGIHHPP TITDQESLYQ NADAYVFVGT SRYSKKFKPE IATRPKVRDQ  240
AGRMNYYWTL VEPGDKITFE ATGNLVAPRY AFTMEKEAGS GIIISDTPVH DCNATCQTPE  300
GAINTSLPFQ NVHPITIGKC PKYVRSTKLR LATGLRNVPS IQSRGLFGAI AGFIEGGWTG  360
MVDGWYGYHH QNDQGSGYAA DLKSTQNAID KITNKVNSVI EKMNTQFTAV GKEFNHLEKR  420
IENLNKKVDD GFLDVWTYNA ELLVLLENER TLDYHDSNVK NLYEKVRHQL KNNAKEIGNG  480
CFEFYHKCDN TCMESVKNGT YDYPKYSEEA KLNREKIDGV KLDSTRIYQI LAIYSTVASS  540
LVLVVSLGAI SFWMCSNGSL QCRICI                                      566

SEQ ID NO: 84           moltype = AA  length = 566
FEATURE                 Location/Qualifiers
source                  1..566
                        mol_type = protein
                        organism = synthetic construct
REGION                  1..566
                        note = A_Wisconsin_H1 HA: K395C-V36C
SEQUENCE: 84
MKAILVVMLY TFTTANADTL CIGYHANNST DTVDTCLEKN VTVTHSVNLL EDKHNGKLCK  60
LRGVAPLHLG QCNIAGWILG NPECESLSTA RSWSYIVETS NSDNGTCYPG DFINYEELRE  120
QLSSVSSFER FEIFPKTSSW PNHDSDNGVT AACSHAGARS FYKNLIWLVK KGKSYPKINQ  180
TYINDKGKEV LVLWGIHHPP TITDQESLYQ NADAYVFVGT SRYSKKFKPE IATRPKVRDQ  240
AGRMNYYWTL VEPGDKITFE ATGNLVAPRY AFTMEKEAGS GIIISDTPVH DCNATCQTPE  300
GAINTSLPFQ NVHPITIGKC PKYVRSTKLR LATGLRNVPS IQSRGLFGAI AGFIEGGWTG  360
MVDGWYGYHH QNDQGSGYAA DLKSTQNAID KITNCVNSVI EKMNTQFTAV GKEFNHLEKR  420
IENLNKKVDD GFLDVWTYNA ELLVLLENER TLDYHDSNVK NLYEKVRHQL KNNAKEIGNG  480
CFEFYHKCDN TCMESVKNGT YDYPKYSEEA KLNREKIDGV KLDSTRIYQI LAIYSTVASS  540
LVLVVSLGAI SFWMCSNGSL QCRICI                                      566

SEQ ID NO: 85           moltype = AA  length = 584
FEATURE                 Location/Qualifiers
source                  1..584
                        mol_type = protein
                        organism = synthetic construct
REGION                  1..584
                        note = B_Phuket_HA: V239C-V276C-D451C-K422C
SEQUENCE: 85
MKAIIVLLMV VTSNADRICT GITSSNSPHV VKTATQGEVN VTGVIPLTTT PTKSYFANLK  60
```

-continued

```
GTRTRGKLCP DCLNCTDLDV ALGRPMCVGT TPSAKASILH EVRPVTSGCF PIMHDRTKIR  120
QLPNLLRGYE KIRLSTQNVI DAEKAPGGPY RLGTSGSCPN ATSKIGFFAT MAWAVPKDNY  180
KNATNPLTVE VPYICTEGED QITVWGFHSD NKTQMKSLYG DSNPQKFTSS ANGVTTHYCS  240
QIGDFPDQTE DGGLPQSGRI VVDYMMQKPG KTGTICYQRG VLLPQKVWCA SGRSKVIKGS  300
LPLIGEADCL HEEYGGLNKS KPYYTGKHAK AIGNCPIWVK TPLKLANGTK YRPPAKLLKE  360
RGFFGAIAGF LEGGWEGMIA GWHGYTSHGA HGVAVAADLK STQEAINKIT KNLNSLSELE  420
VCNLQRLSGA MDELHNEILE LDEKVDDLRA CTISSQIELA VLLSNEGIIN SEDEHLLALE  480
RKLKKMLGPS AVDIGNGCFE TKHKCNQTCL DRIAAGTFNA GEFSLPTFDS LNITAASLND  540
DGLDNHTILL YYSTAASSLA VTLMLAIFIV YMVSRDNVSC SICL                  584
```

```
SEQ ID NO: 86          moltype = AA  length = 584
FEATURE                Location/Qualifiers
source                 1..584
                       mol_type = protein
                       organism = synthetic construct
REGION                 1..584
                       note = B_Phuket_HA: I367C-S401C-D451C-K422C
SEQUENCE: 86
MKAIIVLLMV VTSNADRICT GITSSNSPHV VKTATQGEVN VTGVIPLTTT PTKSYFANLK  60
GTRTRGKLCP DCLNCTDLDV ALGRPMCVGT TPSAKASILH EVRPVTSGCF PIMHDRTKIR  120
QLPNLLRGYE KIRLSTQNVI DAEKAPGGPY RLGTSGSCPN ATSKIGFFAT MAWAVPKDNY  180
KNATNPLTVE VPYICTEGED QITVWGFHSD NKTQMKSLYG DSNPQKFTSS ANGVTTHYVS  240
QIGDFPDQTE DGGLPQSGRI VVDYMMQKPG KTGTIVYQRG VLLPQKVWCA SGRSKVIKGS  300
LPLIGEADCL HEEYGGLNKS KPYYTGKHAK AIGNCPIWVK TPLKLANGTK YRPPAKLLKE  360
RGFFGACAGF LEGGWEGMIA GWHGYTSHGA HGVAVAADLK CTQEAINKIT KNLNSLSELE  420
VCNLQRLSGA MDELHNEILE LDEKVDDLRA CTISSQIELA VLLSNEGIIN SEDEHLLALE  480
RKLKKMLGPS AVDIGNGCFE TKHKCNQTCL DRIAAGTFNA GEFSLPTFDS LNITAASLND  540
DGLDNHTILL YYSTAASSLA VTLMLAIFIV YMVSRDNVSC SICL                  584
```

```
SEQ ID NO: 87          moltype = AA  length = 582
FEATURE                Location/Qualifiers
source                 1..582
                       mol_type = protein
                       organism = synthetic construct
REGION                 1..582
                       note = B_Austria_HA: H381Y-A288V-N494C-K483C
SEQUENCE: 87
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NTEDAPGGPY EIGTSGSCLN ITNGKGFFAT MAWAVPKNKT  180
ATNPLTIEVP YICTEEEDQI TVWGFHSDDE TQMARLYGDS KPQKFTSSAN GVTTHYVSQI  240
GGFPNQTEDG GLPQSGRIVV DYMVQKSGKT GTITYQRGIL LPQKVWCVSG KSKVIKGSLP  300
LIGEADCLHE KYGGLNKSKP YYTGEHAKAI GNCPIWVKTP LKLANGTKYR PPAKLLKERG  360
FFGAIAGFLE GGWEGMIAGW YGYTSHGAHG VAVAADLKST QEAINKITKN LNSLSELEVK  420
NLQRLSGAMD ELHNEILELD EKVDDLRADT ISSQIELAVL LSNEGIINSE DEHLLALERK  480
LKCMLGPSAV EIGCGCFETK HKCNQTCLDR IAAGTFDAGE FSLPTFDSLN ITAASLNDDG  540
LDNHTILLYY STAASSLAVT LMIAIFVVYM VSRDNVSCSI CL                    582
```

```
SEQ ID NO: 88          moltype = AA  length = 582
FEATURE                Location/Qualifiers
source                 1..582
                       mol_type = protein
                       organism = synthetic construct
REGION                 1..582
                       note = B_Austria_HA: H381Y-A288V-L422C-D444C
SEQUENCE: 88
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NTEDAPGGPY EIGTSGSCLN ITNGKGFFAT MAWAVPKNKT  180
ATNPLTIEVP YICTEEEDQI TVWGFHSDDE TQMARLYGDS KPQKFTSSAN GVTTHYVSQI  240
GGFPNQTEDG GLPQSGRIVV DYMVQKSGKT GTITYQRGIL LPQKVWCVSG KSKVIKGSLP  300
LIGEADCLHE KYGGLNKSKP YYTGEHAKAI GNCPIWVKTP LKLANGTKYR PPAKLLKERG  360
FFGAIAGFLE GGWEGMIAGW YGYTSHGAHG VAVAADLKST QEAINKITKN LNSLSELEVK  420
NCQRLSGAMD ELHNEILELD EKVCDLRADT ISSQIELAVL LSNEGIINSE DEHLLALERK  480
LKKMLGPSAV EIGNGCFETK HKCNQTCLDR IAAGTFDAGE FSLPTFDSLN ITAASLNDDG  540
LDNHTILLYY STAASSLAVT LMIAIFVVYM VSRDNVSCSI CL                    582
```

```
SEQ ID NO: 89          moltype = AA  length = 582
FEATURE                Location/Qualifiers
source                 1..582
                       mol_type = protein
                       organism = synthetic construct
REGION                 1..582
                       note = B_Austria_HA: H381Y-A288V-A364C-K483C
SEQUENCE: 89
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NTEDAPGGPY EIGTSGSCLN ITNGKGFFAT MAWAVPKNKT  180
ATNPLTIEVP YICTEEEDQI TVWGFHSDDE TQMARLYGDS KPQKFTSSAN GVTTHYVSQI  240
```

-continued

```
GGFPNQTEDG GLPQSGRIVV DYMVQKSGKT GTITYQRGIL LPQKVWCVSG KSKVIKGSLP  300
LIGEADCLHE KYGGLNKSKP YYTGEHAKAI GNCPIWVKTP LKLANGTKYR PPAKLLKERG  360
FFGCIAGFLE GGWEGMIAGW YGYTSHGAHG VAVAADLKST QEAINKITKN LNSLSELEVK  420
NLQRLSGAMD ELHNEILELD EKVDDLRADT ISSQIELAVL LSNEGIINSE DEHLLALERK  480
LKCMLGPSAV EIGNGCFETK HKCNQTCLDR IAAGTFDAGE FSLPTFDSLN ITAASLNDDG  540
LDNHTILLYY STAASSLAVT LMIAIFVVYM VSRDNVSCSI CL                    582

SEQ ID NO: 90          moltype = AA  length = 582
FEATURE                Location/Qualifiers
source                 1..582
                       mol_type = protein
                       organism = synthetic construct
REGION                 1..582
                       note = B_Austria_HA: H381Y-A288V-G367C-K483C
SEQUENCE: 90
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NTEDAPGGPY EIGTSGSCLN ITNGKGFFAT MAWAVPKNKT  180
ATNPLTIEVP YICTEEEDQI TVWGFHSDDE TQMARLYGDS KPQKFTSSAN GVTTHYVSQI  240
GGFPNQTEDG GLPQSGRIVV DYMVQKSGKT GTITYQRGIL LPQKVWCVSG KSKVIKGSLP  300
LIGEADCLHE KYGGLNKSKP YYTGEHAKAI GNCPIWVKTP LKLANGTKYR PPAKLLKERG  360
FFGAIACFLE GGWEGMIAGW YGYTSHGAHG VAVAADLKST QEAINKITKN LNSLSELEVK  420
NLQRLSGAMD ELHNEILELD EKVDDLRADT ISSQIELAVL LSNEGIINSE DEHLLALERK  480
LKCMLGPSAV EIGNGCFETK HKCNQTCLDR IAAGTFDAGE FSLPTFDSLN ITAASLNDDG  540
LDNHTILLYY STAASSLAVT LMIAIFVVYM VSRDNVSCSI CL                    582

SEQ ID NO: 91          moltype = AA  length = 566
FEATURE                Location/Qualifiers
source                 1..566
                       mol_type = protein
                       organism = synthetic construct
REGION                 1..566
                       note = A_Darwin_H3 HA: G402P-R421P-E414P
SEQUENCE: 91
MKTIIALSNI LCLVFAQKIP GNDNSTATLC LGHHAVPNGT IVKTITNDRI EVTNATELVQ  60
NSSIGEICGS PHQILDGGNC TLIDALLGDP QCDGFQNKEW DLFVERSRAN SNCYPYDVPD  120
YASLRSLVAS SGTLEFKNES FNWTGVKQNG TSSACIRGSS SSFFSRLNWL TSLNNIYPAQ  180
NVTMPNKEQF DKLYIWGVHH PDTDKNQISL FAQSSGRITV STKRSQQAVI PNIGSRPRIR  240
GIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IPKTNEKFHQ IEKPFSEVEG  420
PVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                      566

SEQ ID NO: 92          moltype = AA  length = 566
FEATURE                Location/Qualifiers
source                 1..566
                       mol_type = protein
                       organism = synthetic construct
REGION                 1..566
                       note = A_Darwin_H3 HA: S123C-R421C
SEQUENCE: 92
MKTIIALSNI LCLVFAQKIP GNDNSTATLC LGHHAVPNGT IVKTITNDRI EVTNATELVQ  60
NSSIGEICGS PHQILDGGNC TLIDALLGDP QCDGFQNKEW DLFVERSRAN SNCYPYDVPD  120
YACLRSLVAS SGTLEFKNES FNWTGVKQNG TSSACIRGSS SSFFSRLNWL TSLNNIYPAQ  180
NVTMPNKEQF DKLYIWGVHH PDTDKNQISL FAQSSGRITV STKRSQQAVI PNIGSRPRIR  240
GIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
CVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                      566

SEQ ID NO: 93          moltype = AA  length = 566
FEATURE                Location/Qualifiers
source                 1..566
                       mol_type = protein
                       organism = synthetic construct
REGION                 1..566
                       note = A_Darwin_H3 HA: Q392C-T46C
SEQUENCE: 93
MKTIIALSNI LCLVFAQKIP GNDNSTATLC LGHHAVPNGT IVKTICNDRI EVTNATELVQ  60
NSSIGEICGS PHQILDGGNC TLIDALLGDP QCDGFQNKEW DLFVERSRAN SNCYPYDVPD  120
YASLRSLVAS SGTLEFKNES FNWTGVKQNG TSSACIRGSS SSFFSRLNWL TSLNNIYPAQ  180
NVTMPNKEQF DKLYIWGVHH PDTDKNQISL FAQSSGRITV STKRSQQAVI PNIGSRPRIR  240
GIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DCINGKLNRL IGKTNEKFHQ IEKEFSEVEG  420
```

-continued

```
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                       566

SEQ ID NO: 94          moltype = AA  length = 566
FEATURE                Location/Qualifiers
source                 1..566
                       mol_type = protein
                       organism = synthetic construct
REGION                 1..566
                       note = A_Wisconsin_H1 HA: K391C-L37C
SEQUENCE: 94
MKAILVVMLY TFTTANADTL CIGYHANNST DTVDTVCEKN VTVTHSVNLL EDKHNGKLCK  60
LRGVAPLHLG QCNIAGWILG NPECESLSTA RSWSYIVETS NSDNGTCYPG DFINYEELRE  120
QLSSVSSFER FEIFPKTSSW PNHDSDNGVT AACSHAGARS FYKNLIWLVK KGKSYPKINQ  180
TYINDKGKEV LVLWGIHHPP TITDQESLYQ NADAYVFVGT SRYSKKFKPE IATRPKVRDQ  240
AGRMNYYWTL VEPGDKITFE ATGNLVAPRY AFTMEKEAGS GIIISDTPVH DCNATCQTPE  300
GAINTSLPFQ NVHPITIGKC PKYVRSTKLR LATGLRNVPS IQSRGLFGAI AGFIEGGWTG  360
MVDGWYGYHH QNDQGSGYAA DLKSTQNAID CITNKVNSVI EKMNTQFTAV GKEFNHLEKR  420
IENLNKKVDD GFLDVWTYNA ELLVLLENER TLDYHDSNVK NLYEKVRHQL KNNAKEIGNG  480
CFEFYHKCDN TCMESVKNGT YDYPKYSEEA KLNREKIDGV KLDSTRIYQI LAIYSTVASS  540
LVLVVSLGAI SFWMCSNGSL QCRICI                                       566

SEQ ID NO: 95          moltype = AA  length = 566
FEATURE                Location/Qualifiers
source                 1..566
                       mol_type = protein
                       note = Influenza A virus
                       organism = unidentified
REGION                 1..566
                       note = A/Sydney/5/2021(H1N1) HA: wild-type
SEQUENCE: 95
MKAILVVMLY TFTTANADTL CIGYHANNST DTVDTVLEKN VTVTHSVNLL EDKHNGKLCK  60
LRGVAPLHLG QCNIAGWILG NPECESLSTA RSWSYIVETS NSDNGTCYPG NFINYEELRE  120
QLSSVSSFER FEIFPKTSSW PNHDSDNGVT AACPHAGAKS FYKNLIWLVK KGKSYPKINQ  180
TYINDKGKEV LVLWGIHHPP TITDQESLYQ NADAYVFVGT SRYSKKFKPE IAARPKVRDR  240
AGRMNYYWTL VEPGDKITFE ATGNLVAPRY AFTMEKDAGS GIIISDTPVH DCNTTCQTPE  300
GAINTSLPFQ NVHPITIGKC PKYVRSTKLR LATGLRNVPS IQSRGLFGAI AGFIEGGWTG  360
MVDGWYGYHH QNEQGSGYAA DLKSTQNAID KITNKVNSVI EKMNTQFTAV GKEFNHLEKR  420
IENLNKKVDD GFLDIWTYNA ELLVLLENER TLDYHDSNVK NLYEKVRNQL KNNAKEIGNG  480
CFEFYHKCDN TCMESVKNGT YDYPKYSEEA KLNREKIDGV KLDSTRIYQI LAIYSTVASS  540
LVLVVSLGAI SFWMCSNGSL QCRICI                                       566

SEQ ID NO: 96          moltype = AA  length = 566
FEATURE                Location/Qualifiers
source                 1..566
                       mol_type = protein
                       organism = synthetic construct
REGION                 1..566
                       note = A_Sydney_H1 HA: K391C-L37C
SEQUENCE: 96
MKAILVVMLY TFTTANADTL CIGYHANNST DTVDTVCEKN VTVTHSVNLL EDKHNGKLCK  60
LRGVAPLHLG QCNIAGWILG NPECESLSTA RSWSYIVETS NSDNGTCYPG NFINYEELRE  120
QLSSVSSFER FEIFPKTSSW PNHDSDNGVT AACPHAGAKS FYKNLIWLVK KGKSYPKINQ  180
TYINDKGKEV LVLWGIHHPP TITDQESLYQ NADAYVFVGT SRYSKKFKPE IAARPKVRDR  240
AGRMNYYWTL VEPGDKITFE ATGNLVAPRY AFTMEKDAGS GIIISDTPVH DCNTTCQTPE  300
GAINTSLPFQ NVHPITIGKC PKYVRSTKLR LATGLRNVPS IQSRGLFGAI AGFIEGGWTG  360
MVDGWYGYHH QNEQGSGYAA DLKSTQNAID CITNKVNSVI EKMNTQFTAV GKEFNHLEKR  420
IENLNKKVDD GFLDIWTYNA ELLVLLENER TLDYHDSNVK NLYEKVRNQL KNNAKEIGNG  480
CFEFYHKCDN TCMESVKNGT YDYPKYSEEA KLNREKIDGV KLDSTRIYQI LAIYSTVASS  540
LVLVVSLGAI SFWMCSNGSL QCRICI                                       566

SEQ ID NO: 97          moltype = AA  length = 566
FEATURE                Location/Qualifiers
source                 1..566
                       mol_type = protein
                       organism = synthetic construct
REGION                 1..566
                       note = A_Sydney_H1 HA: K395C-V36C
SEQUENCE: 97
MKAILVVMLY TFTTANADTL CIGYHANNST DTVDTCLEKN VTVTHSVNLL EDKHNGKLCK  60
LRGVAPLHLG QCNIAGWILG NPECESLSTA RSWSYIVETS NSDNGTCYPG NFINYEELRE  120
QLSSVSSFER FEIFPKTSSW PNHDSDNGVT AACPHAGAKS FYKNLIWLVK KGKSYPKINQ  180
TYINDKGKEV LVLWGIHHPP TITDQESLYQ NADAYVFVGT SRYSKKFKPE IAARPKVRDR  240
AGRMNYYWTL VEPGDKITFE ATGNLVAPRY AFTMEKDAGS GIIISDTPVH DCNTTCQTPE  300
GAINTSLPFQ NVHPITIGKC PKYVRSTKLR LATGLRNVPS IQSRGLFGAI AGFIEGGWTG  360
MVDGWYGYHH QNEQGSGYAA DLKSTQNAID KITNCVNSVI EKMNTQFTAV GKEFNHLEKR  420
IENLNKKVDD GFLDIWTYNA ELLVLLENER TLDYHDSNVK NLYEKVRNQL KNNAKEIGNG  480
CFEFYHKCDN TCMESVKNGT YDYPKYSEEA KLNREKIDGV KLDSTRIYQI LAIYSTVASS  540
```

```
LVLVVSLGAI SFWMCSNGSL QCRICI                                    566

SEQ ID NO: 98           moltype = AA  length = 574
FEATURE                 Location/Qualifiers
source                  1..574
                        mol_type = protein
                        note = Human respiratory syncytial virus
                        organism = unidentified
REGION                  1..574
                        note = Wild-Type RSV F Glycoprotein
SEQUENCE: 98
MELLIHRSSA IFLTLAINTL YLTSSQNITE EFYQSTCSAV SRGYFSALRT GWYTSVITIE  60
LSNIKETKCN GTDTKVKLIK QELDKYKNAV TELQLLMQNT PAANNRARRE APQYMNYTIN  120
TTKNLNVSIS KKRKRRFLGF LLGVGSAIAS GIAVSKVLHL EGEVNKIKNA LLSTNKAVVS  180
LSNGVSVLTS KVLDLKNYIN NQLLPIVNQQ SCRISNIETV IEFQQKNSRL LEITREFSVN  240
AGVTTPLSTY MLTNSELLSL INDMPITNDQ KKLMSSNVQI VRQQSYSIMS IIKEEVLAYV  300
VQLPIYGVID TPCWKLHTSP LCTTNIKEGS NICLTRTDRG WYCDNAGSVS FFPQADTCKV  360
QSNRVFCDTM NSLTLPSEVS LCNTDIFNSK YDCKIMTSKT DISSSVITSL GAIVSCYGKT  420
KCTASNKNRG IIKTFSNGCD YVSNKGVDTV SVGNTLYYVN KLEGKNLYVK GEPIINYYDP  480
LVFPSDEFDA SISQVNEKIN QSLAFIRRSD ELLHNVNTGK STTNIMITAI IIVIIVVLLS  540
LIAIGLLLYC KAKNTPVTLS KDQLSGINNI AFSK                            574

SEQ ID NO: 99           moltype = AA  length = 510
FEATURE                 Location/Qualifiers
source                  1..510
                        mol_type = protein
                        organism = synthetic construct
REGION                  1..510
                        note = Prefusion RSV F Glycoprotein
SEQUENCE: 99
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATGSGSAIC SGVAVCKVLH  120
LEGEVNKIKS ALLSTNKAVV SLSNGVSVLT FKVLDLKNYI DKQLLPILNK QSCSISNIET  180
VIEFQQKNNR LLEITREFSV NAGVTTPVST YMLTNSELLS LINDMPITND QKKLMSNNVQ  240
IVRQQSYSIM CIIKEEVLAY VVQLPLYGVI DTPCWKLHTS PLCTTNTKEG SNICLTRTDR  300
GWYCDNAGSV SFFPQAETCK VQSNRVFCDT MNSRTLPSEV NLCNVDIFNP KYDCKIMTSK  360
TDVSSSVITS LGAIVSCYGK TKCTASNKNR GIIKTFSNGC DYVSNKGVDT VSVGNTLYCV  420
NKQEGKSLYV KGEPIINFYD PLVFPSDEFD ASISQVNEKI NQSLAFIRKS DELLHNVNAG  480
KSTTNIMITT IIIVIIVILL SLIAVGLLLY                                510

SEQ ID NO: 100          moltype = AA  length = 25
FEATURE                 Location/Qualifiers
source                  1..25
                        mol_type = protein
                        note = Human respiratory syncytial virus
                        organism = unidentified
REGION                  1..25
                        note = RSV F C-terminal 25 amino acids
SEQUENCE: 100
CKARSTPVTL SKDQLSGINN IAFSN                                     25

SEQ ID NO: 101          moltype = AA  length = 20
FEATURE                 Location/Qualifiers
source                  1..20
                        mol_type = protein
                        note = Human respiratory syncytial virus
                        organism = unidentified
REGION                  1..20
                        note = RSV F C-terminal 20 amino acids
SEQUENCE: 101
TPVTLSKDQL SGINNIAFSN                                           20

SEQ ID NO: 102          moltype = AA  length = 15
FEATURE                 Location/Qualifiers
source                  1..15
                        mol_type = protein
                        note = Human respiratory syncytial virus
                        organism = unidentified
REGION                  1..15
                        note = RSV-F C-terminal 15 amino acids
SEQUENCE: 102
SKDQLSGINN IAFSN                                                15

SEQ ID NO: 103          moltype = AA  length = 10
FEATURE                 Location/Qualifiers
source                  1..10
                        mol_type = protein
                        note = Human respiratory syncytial virus
                        organism = unidentified
```

```
REGION                  1..10
                        note = RSV-F C-terminal 10 amino acids
SEQUENCE: 103
SGINNIAFSN                                                         10

SEQ ID NO: 104          moltype = AA  length = 1273
FEATURE                 Location/Qualifiers
source                  1..1273
                        mol_type = protein
                        note = SARS-CoV-2
                        organism = unidentified
REGION                  1..1273
                        note = Wild-type SARS-CoV-2 S protein
SEQUENCE: 104
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 105          moltype = AA  length = 1273
FEATURE                 Location/Qualifiers
source                  1..1273
                        mol_type = protein
                        organism = synthetic construct
REGION                  1..1273
                        note = Prefusion SARS-CoV-2 S protein
SEQUENCE: 105
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 106          moltype = AA  length = 84
FEATURE                 Location/Qualifiers
source                  1..84
                        mol_type = protein
                        organism = synthetic construct
REGION                  1..84
                        note = RSV F1 subunit
SEQUENCE: 106
QNITEEFYQS TCSAVSKGYL SALRTGWYTS VITIELSNIK ENKCNGTDAK VKLIKQELDK  60
YKNAVTELQL LMQSTPACNS RARR                                         84
```

-continued

```
SEQ ID NO: 107          moltype = AA  length = 377
FEATURE                 Location/Qualifiers
source                  1..377
                        mol_type = protein
                        organism = synthetic construct
REGION                  1..377
                        note = RSV F2 subunit
SEQUENCE: 107
FLGFLLGVGS ACASGIAVSK VLHLEGEVNK IKSALLSTNK AVVSLSNGVS VLTIKVLDLK  60
NYIDKQLLPI VNKQSCSISN IETVIEFQQK NNRLLEITRE FSVNAGVTTP VSTYMLTNSE  120
LLSLINDMPI TNDQKKLMSS NVQIVRQQSY SIMSIIKEEV LAYVVQLPLY GVIDTPCWKL  180
HTSPLCTTNT KEGSNICLTR TDRGWYCDNA GSVSFFPQAE TCKVQSNRVF CDTMNSLTLP  240
SEVNLCNIDI FNPKYDCKIM TSKTDVSSSV ITSLGAIVSC YGKTKCTASN KNRGIIKTFS  300
NGCDYVSNKG VDTVSVGNTL YYVNKQEGKS LYVKGEPIIN FYDPLVFPSS EFDASISQVN  360
EKINQSLAFI RKSDELL                                                377

SEQ ID NO: 108          moltype = AA  length = 461
FEATURE                 Location/Qualifiers
source                  1..461
                        mol_type = protein
                        organism = synthetic construct
REGION                  1..461
                        note = RSV F protein
SEQUENCE: 108
QNITEEFYQS TCSAVSKGYL SALRTGWYTS VITIELSNIK ENKCNGTDAK VKLIKQELDK  60
YKNAVTELQL LMQSTPACNS RARRFLGFLL GVGSACASGI AVSKVLHLEG EVNKIKSALL  120
STNKAVVSLS NGVSVLTIKV LDLKNYIDKQ LLPIVNKQSC SISNIETVIE FQQKNNRLLE  180
ITREFSVNAG VTTPVSTYML TNSELLSLIN DMPITNDQKK LMSSNVQIVR QQSYSIMSII  240
KEEVLAYVVQ LPLYGVIDTP CWKLHTSPLC TTNTKEGSNI CLTRTDRGWY CDNAGSVSFF  300
PQAETCKVQS NRVFCDTMNS LTLPSEVNLC NIDIFNPKYD CKIMTSKTDV SSSVITSLGA  360
IVSCYGKTKC TASNKNRGII KTFSNGCDYV SNKGVDTVSV GNTLYYVNKQ EGKSLYVKGE  420
PIINFYDPLV FPSSEFDASI SQVNEKINQS LAFIRKSDEL L                     461

SEQ ID NO: 109          moltype = AA  length = 84
FEATURE                 Location/Qualifiers
source                  1..84
                        mol_type = protein
                        organism = synthetic construct
REGION                  1..84
                        note = RSV F1 subunit
SEQUENCE: 109
QNITEEFYQS TCSAVSRGYF SALRTGWYTS VITIELSNIK ETKCNGTDTK VKLIKQELDK  60
YKNAVTELQL LMQNTPACNN RARR                                        84

SEQ ID NO: 110          moltype = AA  length = 377
FEATURE                 Location/Qualifiers
source                  1..377
                        mol_type = protein
                        organism = synthetic construct
REGION                  1..377
                        note = RSV F2 subunit
SEQUENCE: 110
FLGFLLGVGS ACASGIAVSK VLHLEGEVNK IKNALLSTNK AVVSLSNGVS VLTIKVLDLK  60
NYINNQLLPI VNQQSCRISN IETVIEFQQK NSRLLEITRE FSVNAGVTTP LSTYMLTNSE  120
LLSLINDMPI TNDQKKLMSS NVQIVRQQSY SIMSIIKEEV LAYVVQLPIY GVIDTPCWKL  180
HTSPLCTTNI KEGSNICLTR TDRGWYCDNA GSVSFFPQAD TCKVQSNRVF CDTMNSLTLP  240
SEVSLCNTDI FNSKYDCKIM TSKTDISSSV ITSLGAIVSC YGKTKCTASN KNRGIIKTFS  300
NGCDYVSNKG VDTVSVGNTL YYVNKLEGKN LYVKGEPIIN YYDPLVFPSS EFDASISQVN  360
EKINQSLAFI RRSDELL                                                377

SEQ ID NO: 111          moltype = AA  length = 461
FEATURE                 Location/Qualifiers
source                  1..461
                        mol_type = protein
                        organism = synthetic construct
REGION                  1..461
                        note = RSV F protein
SEQUENCE: 111
QNITEEFYQS TCSAVSRGYF SALRTGWYTS VITIELSNIK ETKCNGTDTK VKLIKQELDK  60
YKNAVTELQL LMQNTPACNN RARRFLGFLL GVGSACASGI AVSKVLHLEG EVNKIKNALL  120
STNKAVVSLS NGVSVLTIKV LDLKNYINNQ LLPIVNQQSC RISNIETVIE FQQKNSRLLE  180
ITREFSVNAG VTTPLSTYML TNSELLSLIN DMPITNDQKK LMSSNVQIVR QQSYSIMSII  240
KEEVLAYVVQ LPIYGVIDTP CWKLHTSPLC TTNIKEGSNI CLTRTDRGWY CDNAGSVSFF  300
PQADTCKVQS NRVFCDTMNS LTLPSEVSLC NTDIFNSKYD CKIMTSKTDI SSSVITSLGA  360
IVSCYGKTKC TASNKNRGII KTFSNGCDYV SNKGVDTVSV GNTLYYVNKL EGKNLYVKGE  420
PIINYYDPLV FPSSEFDASI SQVNEKINQS LAFIRRSDEL L                     461

SEQ ID NO: 112          moltype = AA  length = 517
FEATURE                 Location/Qualifiers
```

```
source                  1..517
                        mol_type = protein
                        organism = synthetic construct
REGION                  1..517
                        note = RSV F protein
SEQUENCE: 112
MELLILKANA ITTILTAVTF CFASGQNITE EFYQSTCSAV SKGYLSALRT GWYTSVITIE  60
LSNIKENKCN GTDAKVKLIK QELDKYKNAV TELQLLMQST PATNNRARRF LGFLLGVGSA  120
IASGVAVCKV LHLEGEVNKI KSALLSTNKA VVSLSNGVSV LTFKVLDLKN YIDKQLLPIL  180
NKQSCSISNI ETVIEFQQKN NRLLEITREF SVNAGVTTPV STYMLTNSEL LSLINDMPIT  240
NDQKKLMSNN VQIVRQQSYS IMCIIKEEVL AYVVQLPLYG VIDTPCWKLH TSPLCTTNTK  300
EGSNICLTRT DRGWYCDNAG SVSFFPQAET CKVQSNRVFC DTMNSLTLPS EVNLCNVDIF  360
NPKYDCKIMT SKTDVSSSVI TSLGAIVSCY GKTKCTASNK NRGIIKTFSN GCDYVSNKGV  420
DTVSVGNTLY YVNKQEGKSL YVKGEPIINF YDPLVFPSDE FDASISQVNE KINQSLAFIR  480
KSDELLSAIG GYIPEAPRDG QAYVRKDGEW VLLSTFL                         517

SEQ ID NO: 113          moltype = DNA  length = 1530
FEATURE                 Location/Qualifiers
source                  1..1530
                        mol_type = other DNA
                        organism = synthetic construct
misc_feature            1..1530
                        note = Prefusion RSV F protein ORF
SEQUENCE: 113
atggagctgc tgatcctgaa ggccaacgcc atcacgacca tcctgaccgc cgtgaccttc  60
tgcttcgcca gcgggcagaa catcaccgag gagttctacc agtccacctg ctccgccgtg  120
agcaagggct acctgtctgc cctgagaacc ggctggtaca ccagcgtgat caccatcgag  180
ctgtccaaca tcaaggagaa caagtgcaac ggcaccgacg ccaaggtgaa gctgatcaag  240
caggagctgg acaagtacaa gaacgcagtg accgagctgc agctgctgat gcagagcaca  300
ccagccaccg gtagcgggtc cgccatttgc tccggcgtgg ccgtgtgcaa ggtgctgcac  360
ctggagggcg aggtgaacaa gatcaagagc gccctgctct ccaccaacaa ggccgtggtg  420
agcctgagca acggggtgag cgtgctgacc ttcaaggtgc tggacctgaa gaactacatc  480
gacaagcagc tgctgcctat cctgaacaag cagagctgca gcatcagcaa catcgagacc  540
gtgatcgagt tccagcagaa gaacaaccgg ctgctggaga tcaccaggga gttcagcgtg  600
aacgcagggg tgaccacacc cgtgtccacc tacatgctga ccaactccga gctgctgagc  660
ctgatcaacg atatgcccat caccaacgac cagaagaagc tgatgagcaa caacgtgcag  720
atcgtgcggc agcagtccta ctccatcatg tgcatcatca aggaggaggt gctggcctac  780
gtggtgcagc tgcccctgta cggcgtgatc gacacccctt gctggaagct gcacaccagc  840
cctctgtgca ccaccaacac gaaggagggc agcaatatct gcctgacccg gaccgacagg  900
ggctggtact gcgacaacgc cggcagcgtg tccttctttc cccaggccga gacctgcaag  960
gtgcagtcca acagggtgtt ctgcgacacc atgaactctc gcaccctgcc cagcgaggtg  1020
aacctgtgca acgtggacat cttcaacccc aagtacgact gcaagatcat gacctccaag  1080
accgacgtgt cctctagcgt tatcacctcc ctgggcgcca tcgtgagctg ctacggcaag  1140
accaagtgca ccgccagcaa caagaacagg ggcatcatca agaccttcag caacgggtgc  1200
gactacgtgt ccaacaaggg cgtggacacc gtgtccgtgg gcaacaccct gtactgcgtg  1260
aacaagcagg agggcaagag cctgtacgtg aagggcgagc ccatcatcaa cttctacgac  1320
cctctggtgt tccccagcga cgagttcgac gccagcatct cccaggtgaa cgagaagatc  1380
aaccagagcc tggccttcat ccgcaagagc gacgagctgc tgcacaacgt gaacgccggc  1440
aagagcacca caaacatcat gatcaccacc atcatcatcg tgataatcgt gatcctgctg  1500
tccctgatcg ctgtgggcct gctgctgtac                                 1530

SEQ ID NO: 114          moltype = AA  length = 15
FEATURE                 Location/Qualifiers
source                  1..15
                        mol_type = protein
                        organism = synthetic construct
REGION                  1..15
                        note = Linker
SEQUENCE: 114
GGSGGSGGSG GSGGG                                                 15

SEQ ID NO: 115          moltype = AA  length = 8
FEATURE                 Location/Qualifiers
source                  1..8
                        mol_type = protein
                        organism = synthetic construct
REGION                  1..8
                        note = Linker
SEQUENCE: 115
GGGSGGGS                                                         8

SEQ ID NO: 116          moltype = AA  length = 7
FEATURE                 Location/Qualifiers
source                  1..7
                        mol_type = protein
                        organism = synthetic construct
REGION                  1..7
                        note = Linker
SEQUENCE: 116
```

```
GGGSGGG                                                                    7

SEQ ID NO: 117          moltype = AA  length = 6
FEATURE                 Location/Qualifiers
source                  1..6
                        mol_type = protein
                        organism = synthetic construct
REGION                  1..6
                        note = Linker
SEQUENCE: 117
GGGSGG                                                                     6

SEQ ID NO: 118          moltype = AA  length = 4
FEATURE                 Location/Qualifiers
source                  1..4
                        mol_type = protein
                        organism = synthetic construct
REGION                  1..4
                        note = Linker
SEQUENCE: 118
GGGS                                                                       4

SEQ ID NO: 119          moltype = AA  length = 4
FEATURE                 Location/Qualifiers
source                  1..4
                        mol_type = protein
                        organism = synthetic construct
REGION                  1..4
                        note = Linker
SEQUENCE: 119
GSGG                                                                       4

SEQ ID NO: 120          moltype = AA  length = 4
FEATURE                 Location/Qualifiers
source                  1..4
                        mol_type = protein
                        note = Influenza A virus
                        organism = unidentified
REGION                  1..4
                        note = Polybasic cleavage site
SEQUENCE: 120
RKTR                                                                       4

SEQ ID NO: 121          moltype = AA  length = 4
FEATURE                 Location/Qualifiers
source                  1..4
                        mol_type = protein
                        note = Influenza A virus
                        organism = unidentified
REGION                  1..4
                        note = Polybasic cleavage site
SEQUENCE: 121
RKKR                                                                       4

SEQ ID NO: 122          moltype = AA  length = 565
FEATURE                 Location/Qualifiers
source                  1..565
                        mol_type = protein
                        note = Influenza A virus
                        organism = unidentified
REGION                  1..565
                        note = A/Beijing/262/1995 (H1N1) HA
SEQUENCE: 122
MKAKLLVLLC TFTATYADTI CIGYHANNST DTVDTVLEKN VTVTHSVNLL EDSHNGKLCL  60
LKGIAPLQLG NCSVAGWILG NPECESLISK ESWSYIVETP NPENGTCYPG YFADYEELRE  120
QLSSVSSFER FEIFPKESSW PNHTVTGVTA SCSHNGKSSF YRNLLWLTEK NGLYPNLSNS  180
YVNNKEKEVL VLWGVHHPSN IRDQRAIYHT ENAYVSVVSS HYSRRFTPEI AKRPKVRGQE  240
GRINYYWTLL EPGDTIIFEA NGNLIAPWYA FALSRGFGSG IITSNAPMNE CDAKCQTPQG  300
AINSSLPFQN VHPVTIGECP KYVRSTKLRM VTGLRNIPSI QSRGLFGAIA GFIEGGWTGM  360
MDGWYGYHHQ NEQGSGYAAD QKSTQNAING ITNKVNSVIE KMNTQFTAVG KEFNKLERRM  420
ENLNKKVDDG FLDIWTYNAE LLVLLENERT LDFHDSNVKN LYEKVKSQLK NNAKEIGNGC  480
FEFYHKCNNE CMESVKNGTY DYPKYSEESK LNREKIDGVK LESMGVYQIL AIYSTVASSL  540
VLLVSLGAIS FWMCSNGSLQ CRICI                                        565

SEQ ID NO: 123          moltype = AA  length = 565
FEATURE                 Location/Qualifiers
source                  1..565
                        mol_type = protein
                        note = Influenza A virus
```

```
                         organism = unidentified
REGION                   1..565
                         note = A/New Caledonia/20/1999 (H1N1) HA
SEQUENCE: 123
MKAKLLVLLC TFTATYADTI CIGYHANNST DTVDTVLEKN VTVTHSVNLL EDSHNGKLCL  60
LKGIAPLQLG NCSVAGWILG NPECELLISK ESWSYIVETP NPENGTCYPG YFADYEELRE  120
QLSSVSSFER FEIFPKESSW PNHTVTGVSA SCSHNGKSSF YRNLLWLTGK NGLYPNLSKS  180
YVNNKEKEVL VLWGVHHPPN IGNQRALYHT ENAYVSVVSS HYSRRFTPEI AKRPKVRDQE  240
GRINYYWTLL EPGDTIIFEA NGNLIAPWYA FALSRGFGSG IITSNAPMDE CDAKCQTPQG  300
AINSSLPFQN VHPVTIGECP KYVRSAKLRM VTGLRNIPSI QSRGLFGAIA GFIEGGWTGM  360
VDGWYGYHHQ NEQGSGYAAD QKSTQNAING ITNKVNSVIE KMNTQFTAVG KEFNKLERRM  420
ENLNKKVDDG FLDIWTYNAE LLVLLENERT LDFHDSNVKN LYEKVKSQLK NNAKEIGNGC  480
FEFYHKCNNE CMESVKNGTY DYPKYSEESK LNREKIDGVK LESMGVYQIL AIYSTVASSL  540
VLLVSLGAIS FWMCSNGSLQ CRICI                                       565

SEQ ID NO: 124           moltype = AA  length = 565
FEATURE                  Location/Qualifiers
source                   1..565
                         mol_type = protein
                         note = Influenza A virus
                         organism = unidentified
REGION                   1..565
                         note = A/Solomon Islands/3/2006 (H1N1) HA
SEQUENCE: 124
MKVKLLVLLC TFTATYADTI CIGYHANNST DTVDTVLEKN VTVTHSVNLL EDSHNGKLCL  60
LKGIAPLQLG NCSVAGWILG NPECELLISR ESWSYIVEKP NPENGTCYPG HFADYEELRE  120
QLSSVSSFER FEIFPKESSW PNHTTTGVSA SCSHNGESSF YKNLLWLTGK NGLYPNLSKS  180
YANNKEKEVL VLWGVHHPPN IGDQRALYHT ENAYVSVVSS HYSRKFTPEI AKRPKVRDRE  240
GRINYYWTLL EPGDTIIFEA NGNLIAPRYA FALSRGFGSG IINSNAPMDE CDAKCQTPQG  300
AINSSLPFQN VHPVTIGECP KYVRSAKLRM VTGLRNIPSI QSRGLFGAIA GFIEGGWTGM  360
VDGWYGYHHQ NEQGSGYAAD QKSTQNAING ITNKVNSVIE KMNTQFTAVG KEFNKLERRM  420
ENLNKKVDDG FIDIWTYNAE LLVLLENERT LDFHDSNVKN LYEKVKSQLK NNAKEIGNGC  480
FEFYHKCNDE CMESVKNGTY DYPKYSEESK LNREKIDGVK LESMGVYQIL AIYSTVASSL  540
VLLVSLGAIS FWMCSNGSLQ CRICI                                       565

SEQ ID NO: 125           moltype = AA  length = 565
FEATURE                  Location/Qualifiers
source                   1..565
                         mol_type = protein
                         note = Influenza A virus
                         organism = unidentified
REGION                   1..565
                         note = A/Brisbane/59/2007 (H1N1) HA
SEQUENCE: 125
MKVKLLVLLC TFTATYADTI CIGYHANNST DTVDTVLEKN VTVTHSVNLL ENSHNGKLCL  60
LKGIAPLQLG NCSVAGWILG NPECELLISK ESWSYIVEKP NPENGTCYPG HFADYEELRE  120
QLSSVSSFER FEIFPKESSW PNHTVTGVSA SCSHNGESSF YRNLLWLTGK NGLYPNLSKS  180
YANNKEKEVL VLWGVHHPPN IGNQKALYHT ENAYVSVVSS HYSRKFTPEI AKRPKVRDQE  240
GRINYYWTLL EPGDTIIFEA NGNLIAPRYA FALSRGFGSG IINSNAPMDK CDAKCQTPQG  300
AINSSLPFQN VHPVTIGECP KYVRSAKLRM VTGLRNIPSI QSRGLFGAIA GFIEGGWTGM  360
VDGWYGYHHQ NEQGSGYAAD QKSTQNAING ITNKVNSVIE KMNTQFTAVG KEFNKLERRM  420
ENLNKKVDDG FIDIWTYNAE LLVLLENERT LDFHDSNVKN LYEKVKSQLK NNAKEIGNGC  480
FEFYHKCNDE CMESVKNGTY DYPKYSEESK LNREKIDGVK LESMGVYQIL AIYSTVASSL  540
VLLVSLGAIS FWMCSNGSLQ CRICI                                       565

SEQ ID NO: 126           moltype =   length =
SEQUENCE: 126
000

SEQ ID NO: 127           moltype = AA  length = 566
FEATURE                  Location/Qualifiers
source                   1..566
                         mol_type = protein
                         note = Influenza A virus
                         organism = unidentified
REGION                   1..566
                         note = A/California/7/2009 (H1N1)pdm09 HA
SEQUENCE: 127
MKAILVVLLY TFATANADTL CIGYHANNST DTVDTVLEKN VTVTHSVNLL EDKHNGKLCK  60
LRGVAPLHLG KCNIAGWILG NPECESLSTA SSWSYIVETP SSDNGTCYPG DFIDYEELRE  120
QLSSVSSFER FEIFPKTSSW PNHDSNKGVT AACPHAGAKS FYKNLIWLVK KGXSYPKLSK  180
SYINDKGKEV LVLWGIHHPS TSADQQSLYQ NADAYVFVGS SRYSKKFKPE IAIRPKVRXX  240
EGRMNYYWTL VEPGDKITFE ATGNLVVPRY AFAMERNAGS GIIISDTPVH DCNTTCQTPK  300
GAINTSLPFQ NIHPITIGKC PKYVKSTKLR LATGLRNIPS IQSRGLFGAI AGFIEGGWTG  360
MVDGWYGYHH QNEQGSGYAA DLKSTQNAID EITNKVNSVI EKMNTQFTAV GKEFNHLEKR  420
IENLNKKVDD GFLDIWTYNA ELLVLLENER TLDYHDSNVK NLYEKVRSQL KNNAKEIGNG  480
CFEFYHKCDN TCMESVKNGT YDYPKYSEEA KLNREEIDGV KLESTRIYQI LAIYSTVASS  540
LVLVVSLGAI SFWMCSNGSL QCRICI                                      566
```

```
SEQ ID NO: 128          moltype = AA  length = 566
FEATURE                 Location/Qualifiers
source                  1..566
                        mol_type = protein
                        note = Influenza A virus
                        organism = unidentified
REGION                  1..566
                        note = A/Michigan/45/2015 (H1N1)pdm09 HA
SEQUENCE: 128
MKAILVVLLY TFTTANADTL CIGYHANNST DTVDTVLEKN VTVTHSVNLL EDKHNGKLCK  60
LRGVAPLHLG KCNIAGWILG NPECESLSTA SSWSYIVETS NSDNGTCYPG DFINYEELRE  120
QLSSVSSFER FEIFPKTSSW PNHDSNKGVT AACPHAGAKS FYKNLIWLVK KGNSYPKLNQ  180
SYINDKGKEV LVLWGIHHPS TTADQQSLYQ NADAYVFVGT SRYSKKFKPE IATRPKVRDR  240
EGRMNYYWTL VEPGDKITFE ATGNLVVPRY AFTMERNAGS GIIISDTPVH DCNTTCQTPE  300
GAINTSLPFQ NIHPITIGKC PKYVKSTKLR LATGLRNVPS IQSRGLFGAI AGFIEGGWTG  360
MVDGWYGYHH QNEQGSGYAA DLKSTQNAID KITNKVNSVI EKMNTQFTAV GKEFNHLEKR  420
IENLNKKVDD GFLDIWTYNA ELLVLLENER TLDYHDSNVK NLYEKVRNQL KNNAKEIGNG  480
CFEFYHKCDN TCMESVKNGT YDYPKYSEEA KLNREKIDGV KLESTRIYQI LAIYSTVASS  540
LVLVVSLGAI SFWMCSNGSL QCRICI                                      566

SEQ ID NO: 129          moltype = AA  length = 566
FEATURE                 Location/Qualifiers
source                  1..566
                        mol_type = protein
                        note = Influenza A virus
                        organism = unidentified
REGION                  1..566
                        note = A/Brisbane/02/2018 (H1N1)pdm09 HA
SEQUENCE: 129
MKAILVVLLY TFTTANADTL CIGYHANNST DTVDTVLEKN VTVTHSVNLL EDKHNGKLCK  60
LGGVAPLHLG KCNIAGWILG NPECESLSTA RSWSYIVETS NSDNGTCYPG DFINYEELRE  120
QLSSVSSFER FEIFPKTSSW PNHDSNKGVT AACPHAGAKS FYKNLIWLVK KGNSYPKLNQ  180
TYINDKGKEV LVLWGIHHPP TTADQQSLYQ NADAYVFVGT SRYSKKFKPE IATRPKVRDQ  240
EGRMNYYWTL VEPGDKITFE ATGNLVVPRY AFTMERNAGS GIIISDTPVH DCNTTCQTAE  300
GAINTSLPFQ NVHPVTIGKC PKYVKSTKLR LATGLRNVPS IQSRGLFGAI AGFIEGGWTG  360
MVDGWYGYHH QNEQGSGYAA DLKSTQNAID KITNKVNSVI EKMNTQFTAV GKEFNHLEKR  420
IENLNKKVDD GFLDIWTYNA ELLVLLENER TLDYHDSNVK NLYEKVRNQL KNNAKEIGNG  480
CFEFYHKCDN TCMESVKNGT YDYPKYSEEA KLNREKIDGV KLESTRIYQI LAIYSTVASS  540
LVLVVSLGAI SFWMCSNGSL QCRICI                                      566

SEQ ID NO: 130          moltype = AA  length = 566
FEATURE                 Location/Qualifiers
source                  1..566
                        mol_type = protein
                        note = Influenza A virus
                        organism = unidentified
REGION                  1..566
                        note = A/Guangdong-Maonan/SWL1536/2019 (H1N1)pdm09 HA
SEQUENCE: 130
MKAILVVLLY TFTTANADTL CIGYHANNST DTVDTVLEKN VTVTHSVNLL EDKHNGKLCK  60
LRGVAPLHLG KCNIAGWILG NPECESLSTA RSWSYIVETS NSDNGTCYPG DFINYEELRE  120
QLSSVSSFER FEIFPKTSSW PNHDSDKGVT AACPHAGAKS FYKNLIWLVK KGNSYPKLNQ  180
TYINDKGKEV LVLWGIHHPP TIAAQESLYQ NADAYVFVGT SRYSKKFKPE IATRPKVRDQ  240
EGRMNYYWTL VEPGDKITFE ATGNLVVPRY AFTMERDAGS GIIISDTPVH DCNTTCQTPE  300
GAINTSLPFQ NVHPITIGKC PKYVKSTKLR LATGLRNVPS IQSRGLFGAI AGFIEGGWTG  360
MVDGWYGYHH QNEQGSGYAA DLKSTQNAID KITNKVNSVI EKMNTQFTAV GKEFNHLEKR  420
IENLNKKVDD GFLDIWTYNA ELLVLLENER TLDYHDSNVK NLYEKVRNQL KNNAKEIGNG  480
CFEFYHKCDN TCMESVKNGT YDYPKYSEEA KLNREKIDGV KLESTRIYQI LAIYSTVASS  540
LVLVVSLGAI SFWMCSNGSL QCRICI                                      566

SEQ ID NO: 131          moltype = AA  length = 566
FEATURE                 Location/Qualifiers
source                  1..566
                        mol_type = protein
                        note = Influenza A virus
                        organism = unidentified
REGION                  1..566
                        note = A/Hawaii/70/2019 (H1N1)pdm09 HA
SEQUENCE: 131
MKAILVVLLY TFTTANADTL CIGYHANNST DTVDTVLEKN VTVTHSVNLL EDKHNGKLCK  60
LRGVAPLHLG KCNIAGWILG NPECESLSTA RSWSYIVETS NSDNGTCYPG DFINYEELRE  120
QLSSVSSFER FEIFPKTSSW PNHDSDKGVT AACPHAGAKS FYKNLIWLVK KGNSYPKLNQ  180
TYINDKGKEV LVLWGIHHPP TIAAQESLYQ NADAYVFVGT SRYSKKFKPE IATRPKVRDQ  240
EGRMNYYWTL VEPGDKITFE ATGNLVVPRY AFTMERDAGS GIIISDTPVH DCNTTCQTPE  300
GAINTSLPFQ NVHPITIGKC PKYVKSTKLR LATGLRNVPS IQSRGLFGAI AGFIEGGWTG  360
MVDGWYGYHH QNEQGSGYAA DLKSTQNAID KITNKVNSVI EKMNTQFTAV GKEFNHLEKR  420
IENLNKKVDD GFLDIWTYNA ELLVLLENER TLDYHDSNVK NLYEKVRNQL KNNAKEIGNG  480
CFEFYHKCDN TCMESVKNGT YDYPKYSEEA KLNREKIDGV KLESTRIYQI LAIYSTVASS  540
LVLVVSLGAI SFWMCSNGSL QCRICI                                      566
```

```
SEQ ID NO: 132          moltype = AA  length = 566
FEATURE                 Location/Qualifiers
source                  1..566
                        mol_type = protein
                        note = Influenza A virus
                        organism = unidentified
REGION                  1..566
                        note = A/Victoria/2570/2019 (H1N1)pdm09 HA
SEQUENCE: 132
MKAILVVMLY TFTTANADTL CIGYHANNST DTVDTVLEKN VTVTHSVNLL EDKHNGKLCK  60
LRGVAPLHLG QCNIAGWILG NPECESLSTA RSWSYIVETS NSDNGTCYPG DFINYEELRE  120
QLSSVSSFER FEIFPKTSSW PNHDSDNGVT AACSHAGARS FYKNLIWLVK KGKSYPKINQ  180
TYINDKGKEV LVLWGIHHPP TITDQESLYQ NADAYVFVGT SRYSKKFKPE IAARPKVRDQ  240
AGRMNYYWTL VEPGDKITFE ATGNLVAPRY AFTMEKEAGS GIIISDTPVH DCNATCQTPE  300
GAINTSLPFQ NVHPITIGKC PKYVRSTKLR LATGLRNVPS IQSRGLFGAI AGFIEGGWTG  360
MVDGWYGYHH QNDQGSGYAA DLKSTQNAID KITNKVNSVI EKMNTQFTAV GKEFNHLEKR  420
IENLNKKVDD GFLDVWTYNA ELLVLLENER TLDYHDSNVK NLYEKVRHQL KNNAKEIGNG  480
CFEFYHKCDN TCMESVKNGT YDYPKYSEEA KLNREKIDGV KLDSTRIYQI LAIYSTVASS  540
LVLVVSLGAI SFWMCSNGSL QCRICI                                      566

SEQ ID NO: 133          moltype = AA  length = 566
FEATURE                 Location/Qualifiers
source                  1..566
                        mol_type = protein
                        note = Influenza A virus
                        organism = unidentified
REGION                  1..566
                        note = A/Wisconsin/588/2019 (H1N1)pdm09 HA
SEQUENCE: 133
MKAILVVMLY TFTTANADTL CIGYHANNST DTVDTVLEKN VTVTHSVNLL EDKHNGKLCK  60
LRGVAPLHLG KCNIAGWILG NPECESLSTA RSWSYIVETS NSDNGTCYPG DFINYEELRE  120
QLSSVSSFER FEIFPKTSSW PNHDSDNGVT AACPHAGAKS FYKNLIWLVK KGKSYPKINQ  180
TYINDKGKEV LVLWGIHHPP TIADQQSLYQ NADAYVFVGT SRYSKKFKPE IATRPKVRDQ  240
EGRMNYYWTL VEPGDKITFE ATGNLVAPRY AFTMERDAGS GIIISDTPVH DCNTTCQTPE  300
GAINTSLPFQ NVHPITIGKC PKYVKSTKLR LATGLRNVPS IQSRGLFGAI AGFIEGGWTG  360
MVDGWYGYHH QNEQGSGYAA DLKSTQNAID KITNKVNSVI EKMNTQFTAV GKEFNHLEKR  420
IENLNKKVDD GFLDIWTYNA ELLVLLENER TLDYHDSNVK NLYEKVRNQL KNNAKEIGNG  480
CFEFYHKCDN TCMESVKNGT YDYPKYSEEA KLNREKIDGV KLDSTRIYQI LAIYSTVASS  540
LVLVVSLGAI SFWMCSNGSL QCRICI                                      566

SEQ ID NO: 134          moltype = AA  length = 566
FEATURE                 Location/Qualifiers
source                  1..566
                        mol_type = protein
                        note = Influenza A virus
                        organism = unidentified
REGION                  1..566
                        note = A/Victoria/4897/2022 (H1N1)pdm09 HA
SEQUENCE: 134
MKAILVVMLY TFTTANADTL CIGYHANNST DTVDTVLEKN VTVTHSVNLL EDKHNGKLCK  60
LRGVAPLHLG QCNIAGWILG NPECESLSTA RSWSYIVETS NSDNGTCYPG DFINYEELRE  120
QLSSVSSFER FEIFPKTSSW PNHDSDNGVT AACSHAGAKS FYKNLIWLVK KGKSYPKINQ  180
TYINDKGKEV LVLWGIHHPP TITDQESLYQ NADAYVFVGT SRYSKKFKPE IAARPKVRDR  240
AGRMNYYWTL VEPGDKITFE ATGNLVAPRY AFTMEKEAGS GIIISDTPVH DCNATCQTPE  300
GAINTSLPFQ NVHPITIGKC PKYVRSTKLR LATGLRNVPS IQSRGLFGAI AGFIEGGWTG  360
MVDGWYGYHH QNDQGSGYAA DLKSTQNAID KITNKVNSVI EKMNTQFTAV GKEFNHLEKR  420
IENLNKKVDD GFLDVWTYNA ELLVLLENER TLDYHDSNVK NLYEKVRHQL KNNAKEIGNG  480
CFEFYHKCDN TCMESVKNGT YDYPKYSEEA KLNREKIDGV KLDSTRIYQI LAIYSTVASS  540
LVLVVSLGAI SFWMCSNGSL QCRICI                                      566

SEQ ID NO: 135          moltype = AA  length = 566
FEATURE                 Location/Qualifiers
source                  1..566
                        mol_type = protein
                        note = Influenza A virus
                        organism = unidentified
REGION                  1..566
                        note = A/Wisconsin/67/2022 (H1N1)pdm09 HA
SEQUENCE: 135
MKAILVVMLY TFTTANADTL CIGYHANNST DTVDTVLEKN VTVTHSVNLL EDKHNGKLCK  60
LRGVAPLHLG QCNIAGWILG NPECESLSTA RSWSYIVETS NSDNGTCYPG DFINYEELRE  120
QLSSVSSFER FEIFPKTSSW PNHDSDNGVT AACSHAGARS FYKNLIWLVK KGKSYPKINQ  180
TYINDKGKEV LVLWGIHHPP TITDQESLYQ NADAYVFVGT SRYSKKFKPE IATRPKVRDQ  240
AGRMNYYWTL VEPGDKITFE ATGNLVAPRY AFTMEKEAGS GIIISDTPVH DCNATCQTPE  300
GAINTSLPFQ NVHPITIGKC PKYVRSTKLR LATGLRNVPS IQSRGLFGAI AGFIEGGWTG  360
MVDGWYGYHH QNDQGSGYAA DLKSTQNAID KITNKVNSVI EKMNTQFTAV GKEFNHLEKR  420
IENLNKKVDD GFLDVWTYNA ELLVLLENER TLDYHDSNVK NLYEKVRHQL KNNAKEIGNG  480
CFEFYHKCDN TCMESVKNGT YDYPKYSEEA KLNREKIDGV KLDSTRIYQI LAIYSTVASS  540
```

```
LVLVVSLGAI SFWMCSNGSL QCRICI                                      566

SEQ ID NO: 136         moltype = AA  length = 566
FEATURE                Location/Qualifiers
source                 1..566
                       mol_type = protein
                       note = Influenza A virus
                       organism = unidentified
REGION                 1..566
                       note = A/Sydney/5/97 (H3N2) HA
SEQUENCE: 136
MKTIIALSYI LCLVFAQKIP GNDNSTATLC LGHHAVPNGT LVKTITNDQI EVTNATELVQ  60
SSSTGRICDS PHRILDGENC TLIDALLGDP HCDGFQNKEW DLFVERSKAY SNCYPYDVPD  120
YASLRSLVAS SGTLEFNNES FNWTGVAQNG TSYACKRSSI KSFFSRLNWL HQLKYKYPAL  180
NVTMPNNDKF DKLYIWGVHH PSTDSDQTSI YAQASGRVTV STKRSQQTVI PNIGSRPWVR  240
GISSRISIHW TIVKPGDILL INSKGNLIAP RGYFKIRSGK SSIMRSDAPI GKCNSECITP  300
NGSIPNDKPF QNVNRITYGA CPRYVKQNTL KLATGMRNVP EKQTRGIFGA IAGFIENGWE  360
GMVDGWYGFR HQNSEGTGQA ADLKSTQAAI NQINGKLNRL IEKTNEKFHQ IEKEFSEVEG  420
RIQDLEKYVE DTKIDLWSYN AELLVALENQ HTIDLTDSEM NKLFERTRKQ LRENAEDMGN  480
GCFKIYHKCD NACIGSIRNG TYDHDVYRDE ALNNRFQIKG VELKSGYKDW ILWISFAISC  540
FLLCVVLLGF IMWACQKGNI RCNICI                                      566

SEQ ID NO: 137         moltype = AA  length = 566
FEATURE                Location/Qualifiers
source                 1..566
                       mol_type = protein
                       note = Influenza A virus
                       organism = unidentified
REGION                 1..566
                       note = A/Moscow/10/1999 (H3N2) HA
SEQUENCE: 137
MKTIIALSYI LCLVFAQKLP GNDNSTATLC LGHHAVPNGT LVKTITNDQI EVTNATELVQ  60
SSSTGRICDS PHQILDGENC TLIDALLGDP HCDGFQNKEW DLFVERSKAY SNCYPYDVPD  120
YASLRSLVAS SGTLEFNNES FNWTGVAQNG TSSACKRRSI NSFFSRLNWL HQLKYRYPAL  180
NVTMPNNDKF DKLYIWGVHH PSTDSDQTSL YTQASGRVTV STKRSQQTVI PNIGSRPWVR  240
GISSRISIYW TIVKPGDILL INSTGNLIAP RGYFKIRSGK SSIMRSDAPI GKCNSECITP  300
NGSIPNDKPF QNVNRITYGA CPRYVKQNTL KLATGMRNVP EKQTRGIFGA IAGFIENGWE  360
GMMDGWYGFR HQNSEGTGQA ADLKSTQAAI NQINGKLNRL IEKTNEKFHQ IEKEFSEVEG  420
RIQDLEKYVE DTKIDLWSYN AELLVALENQ HTIDLTDSEM NKLFERTRKQ LRENAEDMGN  480
GCFKIYHKCD NACIGSIRNG TYDHDVYRDE ALNNRFQIKG VELKSGYKDW ILWISFAISC  540
FLLCVVLLGF IMWACQKGNI RCNICI                                      566

SEQ ID NO: 138         moltype = AA  length = 566
FEATURE                Location/Qualifiers
source                 1..566
                       mol_type = protein
                       note = Influenza A virus
                       organism = unidentified
REGION                 1..566
                       note = A/Fujian/411/2002 (H3N2) HA
SEQUENCE: 138
MKTIIALSYI LCLVFAQKLP GNDNSTATLC LGHHAVPNGT IVKTITNDQI EVTNATELVQ  60
SSSTGGICDS PHQILDGENC TLIDALLGDP QCDGFQNKKW DLFVERSKAY SNCYPYDVPD  120
YASLRSLVAS SGTLEFNNES FNWTGVTQNG TSSACKRRSN KSFFSRLNWL THLKYKYPAL  180
NVTMPNNEKF DKLYIWGVLH PGTDSDQISL YAQASGRITV STKRSQQTVI PNIGSRPRVR  240
GVSSRISIYW TIVKPGDILL INSTGNLIAP RGYFKIRSGK SSIMRSDAPI GKCNSECITP  300
NGSIPNDKPF QNVNRITYGA CPRYIKQNTL KLATGMRNVP EKQTRGIFGA IAGFIENGWE  360
GMVDGWYGFR HQNSEGTGQA ADLKSTQAAI NQINGKLNRL IGKTNEKFHQ IEKEFSEVEG  420
RIQDLEKYVE DTKIDLWSYN AELLVALENQ HTIDLTDSEM NKLFERTKKQ LRENAEDMGN  480
GCFKIYHKCD NACIGSIRNG TYDHDVYRDE ALNNRFQIKG VELKSGYKDW ILWISFAISC  540
FLLCVALLGF IMWACQKGNI RCNICI                                      566

SEQ ID NO: 139         moltype = AA  length = 566
FEATURE                Location/Qualifiers
source                 1..566
                       mol_type = protein
                       note = Influenza A virus
                       organism = unidentified
REGION                 1..566
                       note = A/California/7/2004 (H3N2) HA
SEQUENCE: 139
MKTIIALSYI LCLVFAQKLP GNDNSTATLC LGHHAVPNGT IVKTITNDQI EVTNATELVQ  60
SSSTGGICDS PHQILDGENC TLIDALLGDP QCDGFQNKKW DLFVERSKAY SNCYPYDVPD  120
YASLRSLVAS SGTLEFNNES FNWTGVTQNG TSSSCKRRSN NSFFSRLNWL THLKFKYPAL  180
NVTMPNNEKF DKLYIWGVHH PGTNNDQISL YTQASGRITV STKRSQQTVI PNIGSRPRVR  240
DIPSRISIYW TIVKPGDILL INSTGNLIAP RGYFKIRSGK SSIMRSDAPI GKCNSECITP  300
NGSIPNDKPF QNVNRITYGA CPRYVKQNTL KLATGMRNVP EKQTRGIFGA IAGFIENGWE  360
GMVDGWYGFR HQNSEGIGQA ADLKSTQAAI NQINGKLNRL IGKTNEKFHQ IEKEFSEVEG  420
RIQDLEKYVE DTKIDLWSYN AELLVALENQ HTIDLTDSEM NKLFERTKKQ LRENAEDMGN  480
```

-continued

```
GCFKIYHKCD NACIGSIRNG TYDHDVYRDE ALNNRFQIKG VELKSGYKDW ILWISFAISC  540
FLLCVALLGF IMWACQKGNI RCNICI                                       566

SEQ ID NO: 140          moltype = AA  length = 566
FEATURE                 Location/Qualifiers
source                  1..566
                        mol_type = protein
                        note = Influenza A virus
                        organism = unidentified
REGION                  1..566
                        note = A/Wisconsin/67/2005 (H3N2) HA
SEQUENCE: 140
MKTIIALSYI LCLVFAQKLP GNDDSTATLC LGHHAVPNGT IVKTITNDQI EVTNATELVQ  60
SSSTGGICDS PHQILDGENC TLIDALLGDP QCDGFQNKKW DLFVERSKAY SNCYPYDVPD  120
YASLRSLVAS SGTLEFNDES FNWTGVTQNG TSSSCKRRSN NSFFSRLNWL THLKFKYPAL  180
NVTMPNNEKF DKLYIWGVHH PVTDNDQIFL YAQASGRITV STKRSQQTVI PNIGSRPRIR  240
NIPSRISIYW TIVKPGDILL INSTGNLIAP RGYFKIRSGK SSIMRSDAPI GKCNSECITP  300
NGSIPNDKPF QNVNRITYGA CPRYVKQNTL KLATGMRNVP EKQTRGIFGA IAGFIENGWE  360
GMVDGWYGFR HQNSEGIGQA ADLKSTQAAI NQINGKLNRL IGKTNEKFHQ IEKEFSEVEG  420
RIQDLEKYVE DTKIDLWSYN AELLVALENQ HTIDLTDSEM NKLFERTKKQ LRENAEDMGN  480
GCFKIYHKCD NACIGSIRNG TYDHDVYRDE ALNNRFQIKG VELKSGYKDW ILWISFAISC  540
FLLCVALLGF IMWACQKGNI RCNICI                                       566

SEQ ID NO: 141          moltype = AA  length = 566
FEATURE                 Location/Qualifiers
source                  1..566
                        mol_type = protein
                        note = Influenza A virus
                        organism = unidentified
REGION                  1..566
                        note = A/Brisbane/10/2007 (H3N2) HA
SEQUENCE: 141
MKTIIALSYI LCLVFTQKLP GNDNSTATLC LGHHAVPNGT IVKTITNDQI EVTNATELVQ  60
SSSTGEICDS PHQILDGENC TLIDALLGDP QCDGFQNKKW DLFVERSKAY SNCYPYDVPD  120
YASLRSLVAS SGTLEFNNES FNWTGVTQNG TSSACIRRSN NSFFSRLNWL THLKFKYPAL  180
NVTMPNNEKF DKLYIWGVHH PGTDNDQIFL YAQASGRITV STKRSQQTVI PNIGSRPRVR  240
NIPSRISIYW TIVKPGDILL INSTGNLIAP RGYFKIRSGK SSIMRSDAPI GKCNSECITP  300
NGSIPNDKPF QNVNRITYGA CPRYVKQNTL KLATGMRNVP EKQTRGIFGA IAGFIENGWE  360
GMVDGWYGFR HQNSEGIGQA ADLKSTQAAI DQINGKLNRL IGKTNEKFHQ IEKEFSEVEG  420
RIQDLEKYVE DTKIDLWSYN AELLVALENQ HTIDLTDSEM NKLFEKTKKQ LRENAEDMGN  480
GCFKIYHKCD NACIGSIRNG TYDHDVYRDE ALNNRFQIKG VELKSGYKDW ILWISFAISC  540
FLLCVALLGF IMWACQKGNI RCNICI                                       566

SEQ ID NO: 142          moltype = AA  length = 566
FEATURE                 Location/Qualifiers
source                  1..566
                        mol_type = protein
                        note = Influenza A virus
                        organism = unidentified
REGION                  1..566
                        note = A/Perth/16/2009 (H3N2) HA
SEQUENCE: 142
MKTIIALSYI LCLVFAQKLP GNDNSTATLC LGHHAVPNGT IVKTITNDQI EVTNATELVQ  60
SSSTGEICDS PHQILDGKNC TLIDALLGDP QCDGFQNKKW DLFVERSKAY SNCYPYDVPD  120
YASLRSLVAS SGTLEFNNES FNWTGVTQNG TSSACIRRSK NSFFSRLNWL THLNFKYPAL  180
NVTMPNNEQF DKLYIWGVHH PGTDKDQIFL YAQASGRITV STKRSQQTVS PNIGSRPRVR  240
NIPSRISIYW TIVKPGDILL INSTGNLIAP RGYFKIRSGK SSIMRSDAPI GKCNSECITP  300
NGSIPNDKPF QNVNRITYGA CPRYVKQNTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RIQDLEKYVE DTKIDLWSYN AELLVALENQ HTIDLTDSEM NKLFEKTKKQ LRENAEDMGN  480
GCFKIYHKCD NACIGSIRNG TYDHDVYRDE ALNNRFQIKG VELKSGYKDW ILWISFAISC  540
FLLCVALLGF IMWACQKGNI RCNICI                                       566

SEQ ID NO: 143          moltype = AA  length = 566
FEATURE                 Location/Qualifiers
source                  1..566
                        mol_type = protein
                        note = Influenza A virus
                        organism = unidentified
REGION                  1..566
                        note = A/Victoria/361/2011 (H3N2) HA
SEQUENCE: 143
MKTIIALSHI LCLVFAQKLP GNDNSTATLC LGHHAVPNGT IVKTITNDQI EVTNATELVQ  60
NSSIGEICDS PHQILDGENC TLIDALLGDP QCDGFQNKKW DLFVERSKAY SNCYPYDVPD  120
YASLRSLVAS SGTLEFNNES FNWTGVTQNG TSSACIRRSN NSFFSRLNWL THLNFKYPAL  180
NVTMPNNEQF DKLYIWGVHH PGTDKDQIFL YAQSSGRITV STKRSQQAVI PNIGSRPRIR  240
NIPSRISIYW TIVKPGDILL INSTGNLIAP RGYFKIRSGK SSIMRSDAPI GKCNSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
```

-continued

```
RIQDLEKYVE DTKIDLWSYN AELLVALENQ HTIDLTDSEM NKLFEKTKKQ LRENAEDMGN  480
GCFKIYHKCD NACIGSIRNG TYDHDVYRDE ALNNRFQIKG VELKSGYKDW ILWISFAISC  540
FLLCVALLGF IMWACQKGNI RCNICI                                       566

SEQ ID NO: 144          moltype = AA  length = 566
FEATURE                 Location/Qualifiers
source                  1..566
                        mol_type = protein
                        note = Influenza A virus
                        organism = unidentified
REGION                  1..566
                        note = A/Texas/50/2012 (H3N2) HA
SEQUENCE: 144
MKTIIALSYI LCLVFAQKLP GNDNSTATLC LGHHAVPNGT IVKTITNDRI EVTNATELVQ  60
NSSIGEICDS PHQILDGENC TLIDALLGDP QCDGFQNKKW DLFVERSKAY SNCYPYDVPD  120
YASLRSLVAS SGTLEFNNES FNWNGVTQNG TSSACIRRSN NSFFSRLNWL THLNFKYPAL  180
NVTMPNNEQF DKLYIWGVHH PGTDKDQIFL YAQPSGRITV STKRSQQAVI PNIGSRPRIR  240
NIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RIQDLEKYVE DTKIDLWSYN AELLVALENQ HTIDLTDSEM NKLFEKTKKQ LRENAEDMGN  480
GCFKIYHKCD NACIGSIRNG TYDHDVYRDE ALNNRFQIKG VELKSGYKDW ILWISFAISC  540
FLLCVALLGF IMWACQKGNI RCNICI                                       566

SEQ ID NO: 145          moltype = AA  length = 566
FEATURE                 Location/Qualifiers
source                  1..566
                        mol_type = protein
                        note = Influenza A virus
                        organism = unidentified
REGION                  1..566
                        note = A/Switzerland/9715293/2013 (H3N2) HA
SEQUENCE: 145
MKTIIALSYI LCLVFAQKLP GNDNSTATLC LGHHAVPNGT IVKTITNDRI EVTNATELVQ  60
NSSIGEICDS PHQILDGENC TLIDALLGDP QCDGFQNKKW DLFVERSKAY SNCYPYDVPD  120
YASLRSLVAS SGTLEFNNES FNWAGVTQNG TSSSCIRGSN SSFFSRLNWL THLNSKYPAL  180
NVTMPNNEQF DKLYIWGVHH PGTDKDQIFL YAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP ERQTRGIFGA IAGFIENGWE  360
GMVDGWYGFR HQNSEGRGQA ADLKSTQAAI DQINGKLNRL IGKTNEKFHQ IEKEFSEVEG  420
RIQDLEKYVE DTKIDLWSYN AELLVALENQ HTIDLTDSEM NKLFEKTKKQ LRENAEDMGN  480
GCFKIYHKCD NACIGSIRNG TYDHDVYRDE ALNNRFQIKG VELKSGYKDW ILWISFAISC  540
FLLCVALLGF IMWACQKGNI RCNICI                                       566

SEQ ID NO: 146          moltype = AA  length = 566
FEATURE                 Location/Qualifiers
source                  1..566
                        mol_type = protein
                        note = Influenza A virus
                        organism = unidentified
REGION                  1..566
                        note = A/Hong Kong/4801/2014 (H3N2) HA
SEQUENCE: 146
MKTIIALSYI LCLVFAQKIP GNDNSTATLC LGHHAVPNGT IVKTITNDRI EVTNATELVQ  60
NSSIGEICDS PHQILDGENC TLIDALLGDP QCDGFQNKKW DLFVERSKAY SNCYPYDVPD  120
YASLRSLVAS SGTLEFNNES FNWTGVTQNG TSSACIRRSS SSFFSRLNWL THLNYTYPAL  180
NVTMPNNEQF DKLYIWGVHH PGTDKDQIFL YAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKHSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RIQDLEKYVE DTKIDLWSYN AELLVALENQ HTIDLTDSEM NKLFEKTKKQ LRENAEDMGN  480
GCFKIYHKCD NACIGSIRNG TYDHNVYRDE ALNNRFQIKG VELKSGYKDW ILWISFAISC  540
FLLCVALLGF IMWACQKGNI RCNICI                                       566

SEQ ID NO: 147          moltype = AA  length = 566
FEATURE                 Location/Qualifiers
source                  1..566
                        mol_type = protein
                        note = Influenza A virus
                        organism = unidentified
REGION                  1..566
                        note = A/Singapore/INFIMH-16-0019/2016 (H3N2) HA
SEQUENCE: 147
MKTIIALSYI LCLVFAQKIP GNDNSTATLC LGHHAVPNGT IVKTITNDRI EVTNATELVQ  60
NSSIGEICDS PHQILDGENC TLIDALLGDP QCDGFQNKKW DLFVERSKAY SNCYPYDVPD  120
YASLRSLVAS SGTLEFKNES FNWTGVTQNG TSSACIRGSS SSFFSRLNWL THLNYTYPAL  180
NVTMPNKEQF DKLYIWGVHH PGTDKDQIFL YAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKHSTL KLATGMRNVP EKQTRGIFGA IAGFIENGWE  360
```

```
GMVDGWYGFR HQNSEGRGQA ADLKSTQAAI DQINGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIESIRNE TYDHNVYRDE ALNNRFQIKG VELKSGYKDW ILWISFAISC  540
FLLCVALLGF IMWACQKGNI RCNICI                                       566

SEQ ID NO: 148          moltype = AA  length = 566
FEATURE                 Location/Qualifiers
source                  1..566
                        mol_type = protein
                        note = Influenza A virus
                        organism = unidentified
REGION                  1..566
                        note = A/Kansas/14/2017 (H3N2) HA
SEQUENCE: 148
MKTIIALSCI LCLVFAQKIP GNDNSTATLC LGHHAVPNGT IVKTITNDRI EVTNATELVQ  60
NSSIGEICDS PHQILDGENC TLIDALLGDP QCDGFQNKKW DLFVERNKAY SNCYPYDVPD  120
YASLRSLVAS SGTLEFNNES FNWAGVTQNG TSSSCIRGSK SSFFSRLNWL THLNSKYPAL  180
NVTMPNNEQF DKLYIWGVHH PGTDKDQISL YAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP ERQTRGIFGA IAGFIENGWE  360
GMVDGWYGFR HQNSEGRGQA ADLKSTQAAI DQINGKLNRL IGKTNEKFHQ IEKEFSEVEG  420
RIQDLEKYVE DTKIDLWSYN AELLVALENQ HTIDLTDSEM NKLFEKTKKQ LRENAEDMGN  480
GCFKIYHKCD NACMGSIRNG TYDHNVYRDE ALNNRFQIKG VELKSGYKDW ILWISFAISC  540
FLLCVALLGF IMWACQKGNI RCNICI                                       566

SEQ ID NO: 149          moltype = AA  length = 566
FEATURE                 Location/Qualifiers
source                  1..566
                        mol_type = protein
                        note = Influenza A virus
                        organism = unidentified
REGION                  1..566
                        note = A/Hong Kong/2671/2019 (H3N2) HA
SEQUENCE: 149
MKTIIALSYI LCLVFTQKIP GNDNSTATLC LGHHAVPNGT IVKTITNDRI EVTNATELVQ  60
NSSIGEICDS PHQILDGGNC TLIDALLGDP QCDGFQNKKW DLFVERSRAY SNCYPYDVPD  120
YASLRSLVAS SGTLEFKNES FNWAGVTQNG KSFSCIRGSS SSFFSRLNWL THLNYTYPAL  180
NVTMPNKEQF DKLYIWGVHH PGTDKDQISL YAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAISC  540
FLLCVALLGF IMWACQKGNI RCNICI                                       566

SEQ ID NO: 150          moltype = AA  length = 566
FEATURE                 Location/Qualifiers
source                  1..566
                        mol_type = protein
                        note = Influenza A virus
                        organism = unidentified
REGION                  1..566
                        note = A/Hong Kong/45/2019 (H3N2) HA
SEQUENCE: 150
MKTIIALSYI LCLGFTQKIP GNDNSTATLC LGHHAVPNGT IVKTITNDRI EVTNATELVQ  60
NSSIGEICDS PHQILDGGNC TLIDALLGDP QCDGFQNKKW DLFVERSRAY SNCYPYDVPD  120
YASLRSLVAS SGTLEFKNES FNWAGVTQNG KSFSCIRGSS SSFFSRLNWL THLNYTYPAL  180
NVTMPNKEQF DKLYIWGVHH PGTDKDQISL YAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKQNTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAISC  540
FLLCVALLGF IMWACQKGNI RCNICI                                       566

SEQ ID NO: 151          moltype = AA  length = 566
FEATURE                 Location/Qualifiers
source                  1..566
                        mol_type = protein
                        note = Influenza A virus
                        organism = unidentified
REGION                  1..566
                        note = A/Cambodia/e0826360/2020 (H3N2) HA
SEQUENCE: 151
MKTIIALSYI LCLVFAQKIP GNDNSTATLC LGHHAVPNGT IVKTITNDRI EVTNATELVQ  60
NSSIGEICDS PHQILDGGNC TLIDALLGDP QCDGFQNKEW DLFVERSRAN SNCYPYDVPD  120
YASLRSLVAS SGTLEFKNES FNWTGVKQNG TSSACIRGSS SSFFSRLNWL THLNYTYPAL  180
NVTMPNNEQF DKLYIWGVHH PSTDKDQISL FAQPSGRITV STKRSQQAVI PNIGSRPRIR  240
DIPSRISIYW TIVKPGDILL INSTGNLIAP RGYFKIRSGK SSIMRSDAPI GKCKSECITP  300
```

```
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                       566

SEQ ID NO: 152         moltype = AA  length = 566
FEATURE                Location/Qualifiers
source                 1..566
                       mol_type = protein
                       note = Influenza A virus
                       organism = unidentified
REGION                 1..566
                       note = A/Darwin/9/2021 (H3N2) HA
SEQUENCE: 152
MKTIIALSNI LCLVFAQKIP GNDNSTATLC LGHHAVPNGT IVKTITNDRI EVTNATELVQ  60
NSSIGEICDS PHQILDGGNC TLIDALLGDP QCDGFQNKEW DLFVERSRAN SNCYPYDVPD  120
YASLRSLVAS SGTLEFKNES FNWTGVKQNG TSSACIRGSS SSFFSRLNWL TSLNNIYPAQ  180
NVTMPNKEQF DKLYIWGVHH PDTDKNQISL FAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                       566

SEQ ID NO: 153         moltype = AA  length = 566
FEATURE                Location/Qualifiers
source                 1..566
                       mol_type = protein
                       note = Influenza A virus
                       organism = unidentified
REGION                 1..566
                       note = A/Darwin/6/2021 (H3N2) HA
SEQUENCE: 153
MKTIIALSNI LCLVFAQKIP GNDNSTATLC LGHHAVPNGT IVKTITNDRI EVTNATELVQ  60
NSSIGEICDS PHQILDGGNC TLIDALLGDP QCDGFQNKEW DLFVERSRAN SNCYPYDVPD  120
YASLRSLVAS SGTLEFKNES FNWTGVKQNG TSSACIRGSS SSFFSRLNWL THLNNIYPAQ  180
NVTMPNKEQF DKLYIWGVHH PDTDKNQISL FAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP EKQTRGIFGA IAGFIENGWE  360
GMVDGWYGFR HQNSEGRGQA ADLKSTQAAI DQINGKLNRL IGKTNEKFHQ IEKEFSEVEG  420
RVQDLEKYVE DTKIDLWSYN AELLVALENQ HTIDLTDSEM NKLFEKTKKQ LRENAEDMGN  480
GCFKIYHKCD NACIGSIRNE TYDHNVYRDE ALNNRFQIKG VELKSGYKDW ILWISFAMSC  540
FLLCIALLGF IMWACQKGNI RCNICI                                       566

SEQ ID NO: 154         moltype = AA  length = 585
FEATURE                Location/Qualifiers
source                 1..585
                       mol_type = protein
                       note = Influenza B virus
                       organism = unidentified
REGION                 1..585
                       note = B/Shangdong/7/1997 HA
SEQUENCE: 154
MKAIIVLLMV VTSNADRICT GITSSNSPHV VKTATQGEVN VTGVIPLTTT PTKSHFANLK  60
GTKTRGKLCP KCLNCTDLDV ALGRPKCTGN IPSAKVSILH EVRPVTSGCF PIMHDRTKIR  120
QLPNLLRGYE HIRLSIHNVI NAEKAPGGPY KIGTSGSCPN VTNGNGFFAT MAWAVPKNDN  180
NKTATNSLTI EVPYICTEGE DQITVWGFHS DNENQMAKLY GDSKPQKFTS SANGVTTHYV  240
SQIGGFPNQT EDGGLPQSGR IVVDYMVQKS GKTGTITYQR GILLPQKVWC ASGRSKVIKG  300
SLPLIGEADC LHEKYGGLNK SKPYYTGEHA KAIGNCPIWV KTPLKLANGT KYRPPAKLLK  360
ERGFFGAIAG FLEGGWEGMI AGWHGYTSHG AHGVAVAADL KSTQEAINKI TKNLNSLSEL  420
EVKNLQRLSG AMDELHNEIL ELDEKVDDLR ADTISSQIEL AVLLSNEGII NSEDEHLLAL  480
ERKLKKMLGP SAVEIGNGCF ETKHKCNQTC LDRIAAGTFN AGEFSLPTFD SLNITAASLN  540
DDGLDNHTIL LYYSTAASSL AVTLMIAIFI VYMVSRDNVS CSICL                  585

SEQ ID NO: 155         moltype = AA  length = 585
FEATURE                Location/Qualifiers
source                 1..585
                       mol_type = protein
                       note = Influenza B virus
                       organism = unidentified
REGION                 1..585
                       note = B/Hong Kong/330/2001 HA
SEQUENCE: 155
MKAIIVLLMV VTSNADRICT GITSSNSPHV VKTATQGEVN VTGVIPLTTT PTKSHFANLK  60
GTKTRGKLCP KCLNCTDLDV ALGRPKCTGN IPSAKVSILH EVRPVTSGCF PIMHDRTKIR  120
QLPNLLRGYE RIRLSNHNVI NAEKAPGGPY KIGTSGSCPN VTNGNGFFAT MAWAVPKNEN  180
NKTATNSLTI EVPYICTEGE DQITVWGFHS DSETQMAKLY GDSKPQKFTS SANGVTTHYV  240
```

-continued

```
SQIGGFPNQT EDGGLPQSGR IVVDYMVQKS GKTGTITYQR GILLPQKVWC ASGRSKVIKG  300
SLPLIGEADC LHEKYGGLNK SKPYYTGEHA KAIGNCPIWV KTPLKLANGT KYRPPAKLLK  360
ERGFFGAIAG FLEGGWEGMI AGWHGYTSHG AHGVAVAADL KSTQEAINKI TKNLNSLSEL  420
EVKNLQRLSG AMDELHNEIL ELDEKVDDLR ADTISSQIEL AVLLSNEGII NSEDEHLLAL  480
ERKLKKMLGP SAVEIGNGCF ETKHKCNQTC LDRIAAGTFN AGEFSLPTFD SLNITAASLN  540
DDGLDNHTIL LYYSTAASSL AVTLMIAIFV VYMVSRDNVS CSICL                  585

SEQ ID NO: 156         moltype = AA  length = 585
FEATURE                Location/Qualifiers
source                 1..585
                       mol_type = protein
                       note = Influenza B virus
                       organism = unidentified
REGION                 1..585
                       note = B/Malaysia/2506/2004 HA
SEQUENCE: 156
MKAIIVLLMV VTSNADRICT GITSSNSPHV VKTATQGEVN VTGVIPLTTT PTKSHFANLK  60
GTETRGKLCP KCLNCTDLDV ALGRPKCTGN IPSARVSILH EVRPVTSGCF PIMHDRTKIR  120
QLPNLLRGYE HIRLSTHNVI NAENAPGGPY KIGTSGSCPN VTNGNGFFAT MAWAVPKNDN  180
NKTATNSLTI EVPYICTEGE DQITVWGFHS DNEIQMAKLY GDSKPQKFTS SANGVTTHYV  240
SQIGGFPNQT EDGGLPQSGR IVVDYMVQKS GKTGTITYQR GILLPQKVWC ASGRSKVIKG  300
SLPLIGEADC LHEKYGGLNK SKPYYTGEHA KAIGNCPIWV KTPLKLANGT KYRPPAKLLK  360
ERGFFGAIAG FLEGGWEGMI AGWHGYTSHG AHGVAVAADL KSTQEAINKI TKNLNSLSEL  420
EVKNLQRLSG AMDELHNEIL ELDEKVDDLR ADTISSQIEL AVLLSNEGII NSEDEHLLAL  480
ERKLKKMLGP SAVEIGNGCF ETKHKCNQTC LDRIAAGTFD AGEFSLPTFD SLNITAASLN  540
DDGLDNHTIL LYYSTAASSL AVTLMIAIFV VYMVSRDNVS CSICL                  585

SEQ ID NO: 157         moltype = AA  length = 585
FEATURE                Location/Qualifiers
source                 1..585
                       mol_type = protein
                       note = Influenza B virus
                       organism = unidentified
REGION                 1..585
                       note = B/Brisbane/60/2008 HA
SEQUENCE: 157
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HIRLSTHNVI NAENAPGGPY KIGTSGSCPN ITNGNGFFAT MAWAVPKNDK  180
NKTATNPLTI EVPYICTEGE DQITVWGFHS DNETQMAKLY GDSKPQKFTS SANGVTTHYV  240
SQIGGFPNQT EDGGLPQSGR IVVDYMVQKS GKTGTITYQR GILLPQKVWC ASGRSKVIKG  300
SLPLIGEADC LHEKYGGLNK SKPYYTGEHA KAIGNCPIWV KTPLKLANGT KYRPPAKLLK  360
ERGFFGAIAG FLEGGWEGMI AGWHGYTSHG AHGVAVAADL KSTQEAINKI TKNLNSLSEL  420
EVKNLQRLSG AMDELHNEIL ELDEKVDDLR ADTISSQIEL AVLLSNEGII NSEDEHLLAL  480
ERKLKKMLGP SAVEIGNGCF ETKHKCNQTC LDRIAAGTFD AGEFSLPTFD SLNITAASLN  540
DDGLDNHTIL LYYSTAASSL AVTLMIAIFV VYMVSRDNVS CSICL                  585

SEQ ID NO: 158         moltype = AA  length = 583
FEATURE                Location/Qualifiers
source                 1..583
                       mol_type = protein
                       note = Influenza B virus
                       organism = unidentified
REGION                 1..583
                       note = B/Colorado/06/2017 HA
SEQUENCE: 158
MKAIIVLLMV VTSSADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NAEGAPGGPY KIGTSGSCPN ITNGNGFFAT MAWAVPDKNK  180
TATNPLTIEV PYVCTEGEDQ ITVWGFHSDN ETQMAKLYGD SKPQKFTSSA NGVTTHYVSQ  240
IGGFPNQTED GGLPQSGRIV VDYMVQKSGK TGTITYQRGI LLPQKVWCAS GRSKVIKGSL  300
PLIGEADCLH EKYGGLNKSK PYYTGEHAKA IGNCPIWVKT PLKLANGTKY RPPAKLLKER  360
GFFGAIAGFL EGGWEGMIAG WHGYTSHGAH GVAVAADLKS TQEAINKITK NLNSLSELEV  420
KNLQRLSGAM DELHNEILEL DEKVDDLRAD TISSQIELAV LLSNEGIINS EDEHLLALER  480
KLKKMLGPSA VEIGNGCFET KHKCNQTCLD KIAAGTFDAG EFSLPTFDSL NITAASLNDD  540
GLDNHTILLY YSTAASSLAV TLMIAIFVVY MVSRDNVSCS ICL                    583

SEQ ID NO: 159         moltype = AA  length = 582
FEATURE                Location/Qualifiers
source                 1..582
                       mol_type = protein
                       note = Influenza B virus
                       organism = unidentified
REGION                 1..582
                       note = B/Washington/02/2019 HA
SEQUENCE: 159
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NAEDAPGRPY EIGTSGSCPN ITNGNGFFAT MAWAVPKNKT  180
```

```
ATNPLTIEVP YICTEGEDQI TVWGFHSDSE TQMAKLYGDS KPQKFTSSAN GVTTHYVSQI  240
GGFPNQTEDG GLPQSGRIVV DYMVQKSGKT GTITYQRGIL LPQKVWCASG RSKVIKGSLP  300
LIGEADCLHE KYGGLNKSKP YYTGEHAKAI GNCPIWVKTP LKLANGTKYR PPAKLLKERG  360
FFGAIAGFLE GGWEGMIAGW HGYTSHGAHG VAVAADLKST QEAINKITKN LNSLSELEVK  420
NLQRLSGAMD ELHNEILELD EKVDDLRADT ISSQIELAVL LSNEGIINSE DEHLLALERK  480
LKKMLGPSAV EIGNGCFETK HKCNQTCLDR IAAGTFDAGE FSLPTFDSLN ITAASLNDDG  540
LDNHTILLYY STAASSLAVT LMIAIFVVYM VSRDNVSCSI CL                     582

SEQ ID NO: 160         moltype = AA  length = 582
FEATURE                Location/Qualifiers
source                 1..582
                       mol_type = protein
                       note = Influenza B virus
                       organism = unidentified
REGION                 1..582
                       note = B/Austria/1359417/2021 HA
SEQUENCE: 160
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HVRLSTHNVI NTEDAPGGPY EIGTSGSCLN ITNGKGFFAT MAWAVPKNKT  180
ATNPLTIEVP YICTEEEDQI TVWGFHSDDE TQMARLYGDS KPQKFTSSAN GVTTHYVSQI  240
GGFPNQTEDG GLPQSGRIVV DYMVQKSGKT GTITYQRGIL LPQKVWCASG KSKVIKGSLP  300
LIGEADCLHE KYGGLNKSKP YYTGEHAKAI GNCPIWVKTP LKLANGTKYR PPAKLLKERG  360
FFGAIAGFLE GGWEGMIAGW HGYTSHGAHG VAVAADLKST QEAINKITKN LNSLSELEVK  420
NLQRLSGAMD ELHNEILELD EKVDDLRADT ISSQIELAVL LSNEGIINSE DEHLLALERK  480
LKKMLGPSAV EIGNGCFETK HKCNQTCLDR IAAGTFDAGE FSLPTFDSLN ITAASLNDDG  540
LDNHTILLYY STAASSLAVT LMIAIFVVYM VSRDNVSCSI CL                     582

SEQ ID NO: 161         moltype =   length =
SEQUENCE: 161
000

SEQ ID NO: 162         moltype =   length =
SEQUENCE: 162
000

SEQ ID NO: 163         moltype =   length =
SEQUENCE: 163
000

SEQ ID NO: 164         moltype = AA  length = 584
FEATURE                Location/Qualifiers
source                 1..584
                       mol_type = protein
                       note = Influenza B virus
                       organism = unidentified
REGION                 1..584
                       note = B/Florida/4/2006 HA
SEQUENCE: 164
MKAIIVLLMV VTSNADRICT GITSSNSPHV VKTATQGEVN VTGVIPLTTT PTKSYFANLK  60
GTRTRGKLCP DCLNCTDLDV ALGRPMCVGT TPSAKASILH EVKPVTSGCF PIMHDRTKIR  120
QLPNLLRGYE NIRLSTQNVI DAEKAPGGPY RLGTSGSCPN ATSKSGFFAT MAWAVPKDNN  180
KNATNPLTVE VPYICTEGED QITVWGFHSD DKTQMKNLYG DSNPQKFTSS ANGVTTHYVS  240
QIGSFPDQTE DGGLPQSGRI VVDYMMQKPG KTGTIVYQRG VLLPQKVWCA SGRSKVIKGS  300
LPLIGEADCL HEKYGGLNKS KPYYTGEHAK AIGNCPIWVK TPLKLANGTK YRPPAKLLKE  360
RGFFGAIAGF LEGGWEGMIA GWHGYTSHGA HGVAVAADLK STQEAINKIT KNLNSLSELE  420
VKNLQRLSGA MDELHNEILE LDEKVDDLRA DTISSQIELA VLLSNEGIIN SEDEHLLALE  480
RKLKKMLGPS AVEIGNGCFE TKHKCNQTCL DRIAAGTFNA GEFSLPTFDS LNITAASLND  540
DGLDNHTILL YYSTAASSLA VTLMLAIFIV YMVSRDNVSC SICL                   584

SEQ ID NO: 165         moltype = AA  length = 584
FEATURE                Location/Qualifiers
source                 1..584
                       mol_type = protein
                       note = Influenza B virus
                       organism = unidentified
REGION                 1..584
                       note = B/Wisconsin/1/2010 HA
SEQUENCE: 165
MKAIIVLLMV VTSNADRICT GITSSNSPHV VKTATQGEVN VTGVIPLTTT PTKSYFANLK  60
GTRTRGKLCP DCLNCTDLDV ALGRPMCVGT TPSAKASILH EVRPVTSGCF PIMHDRTKIR  120
QLPNLLRGYE NIRLSTQNVI DAEKAPGGPY RLGTSGSCPN ATSKIGFFAT MAWAVPKDNY  180
KNATNPLTVE VPYICTEGED QITVWGFHSD NKTQMKSLYG DSNPQKFTSS ANGVTTHYVS  240
QIGDFPDQTE DGGLPQSGRI VVDYMMQKPG KTGTIVYQRG VLLPQKVWCA SGRSKVIKGS  300
LPLIGEADCL HEKYGGLNKS KPYYTGEHAK AIGNCPIWVK TPLKLANGTK YRPPAKLLKE  360
RGFFGAIAGF LEGGWEGMIA GWHGYTSHGA HGVAVAADLK STQEAINKIT KNLNSLSELE  420
VKNLQRLSGA MDELHNEILE LDEKVDDLRA DTISSQIELA VLLSNEGIIN SEDEHLLALE  480
RKLKKMLGPS AVDIGNGCFE TKHKCNQTCL DRIAAGTFNA GEFSLPTFDS LNITAASLND  540
DGLDNHTILL YYSTAASSLA VTLMLAIFIV YMVSRDNVSC SICL                   584
```

```
SEQ ID NO: 166          moltype = AA  length = 584
FEATURE                 Location/Qualifiers
source                  1..584
                        mol_type = protein
                        note = Influenza B virus
                        organism = unidentified
REGION                  1..584
                        note = B/Massachusetts/2/2012 HA
SEQUENCE: 166
MKAIIVLLMV VTSNADRICT GITSSNSPHV VKTATQGEVN VTGVIPLTTT PTKSYFANLK  60
GTKTRGKLCP DCLNCTDLDV ALGRPMCVGT TPSAKASILH EVRPVTSGCF PIMHDRTKIR  120
QLANLLRGYE NIRLSTQNVI DAEKAPGGPY RLGTSGSCPN ATSKSGFFAT MAWAVPKDNN  180
KNATNPLTVE VPYICAEGED QITVWGFHSD DKTQMKNLYG DSNPQKFTSS ANGVTTHYVS  240
QIGGFPDQTE DGGLPQSGRI VVDYMMQKPG KTGTIVYQRG VLLPQKVWCA SGRSKVIKGS  300
LPLIGEADCL HEKYGGLNKS KPYYTGEHAK AIGNCPIWVK TPLKLANGTK YRPPAKLLKE  360
RGFFGAIAGF LEGGWEGMIA GWHGYTSHGA HGVAVAADLK STQEAINKIT KNLNSLSELE  420
VKNLQRLSGA MDELHNEILE LDEKVDDLRA DTISSQIELA VLLSNEGIIN SEDEHLLALE  480
RKLKKMLGPS AVDIGNGCFE TKHKCNQTCL DRIAAGTFNA GEFSLPTFDS LNITAASLND  540
DGLDNHTILL YYSTAASSLA VTLMLAIFIV YMVSRDNVSC SICL                  584

SEQ ID NO: 167          moltype = AA  length = 584
FEATURE                 Location/Qualifiers
source                  1..584
                        mol_type = protein
                        note = Influenza B virus
                        organism = unidentified
REGION                  1..584
                        note = B/Phuket/3073/2013 HA
SEQUENCE: 167
MKAIIVLLMV VTSNADRICT GITSSNSPHV VKTATQGEVN VTGVIPLTTT PTKSYFANLK  60
GTRTRGKLCP DCLNCTDLDV ALGRPMCVGT TPSAKASILH EVRPVTSGCF PIMHDRTKIR  120
QLPNLLRGYE KIRLSTQNVI DAEKAPGGPY RLGTSGSCPN ATSKIGFFAT MAWAVPKDNY  180
KNATNPLTVE VPYICTEGED QITVWGFHSD NKTQMKSLYG DSNPQKFTSS ANGVTTHYVS  240
QIGDFPDQTE DGGLPQSGRI VVDYMMQKPG KTGTIVYQRG VLLPQKVWCA SGRSKVIKGS  300
LPLIGEADCL HEEYGGLNKS KPYYTGKHAK AIGNCPIWVK TPLKLANGTK YRPPAKLLKE  360
RGFFGAIAGF LEGGWEGMIA GWHGYTSHGA HGVAVAADLK STQEAINKIT KNLNSLSELE  420
VKNLQRLSGA MDELHNEILE LDEKVDDLRA DTISSQIELA VLLSNEGIIN SEDEHLLALE  480
RKLKKMLGPS AVDIGNGCFE TKHKCNQTCL DRIAAGTFNA GEFSLPTFDS LNITAASLND  540
DGLDNHTILL YYSTAASSLA VTLMLAIFIV YMVSRDNVSC SICL                  584

SEQ ID NO: 168          moltype = AA  length = 17
FEATURE                 Location/Qualifiers
source                  1..17
                        mol_type = protein
                        note = Influenza A virus
                        organism = unidentified
REGION                  1..17
                        note = A/Wisconsin/67/2022 (H1N1)pdm09 H1 HA Signal Peptide
SEQUENCE: 168
MKAILVVMLY TFTTANA                                                17

SEQ ID NO: 169          moltype = AA  length = 16
FEATURE                 Location/Qualifiers
source                  1..16
                        mol_type = protein
                        note = Influenza A virus
                        organism = unidentified
REGION                  1..16
                        note = A/Darwin/6/2021 (H3N2) H3 HA Signal Peptide
SEQUENCE: 169
MKTIIALSNI LCLVFA                                                 16

SEQ ID NO: 170          moltype = AA  length = 15
FEATURE                 Location/Qualifiers
source                  1..15
                        mol_type = protein
                        note = Influenza B virus
                        organism = unidentified
REGION                  1..15
                        note = B/Austria/1359417/2021 B/Victoria lineage HA Signal
                         Peptide
SEQUENCE: 170
MKAIIVLLMV VTSNA                                                  15

SEQ ID NO: 171          moltype = AA  length = 15
FEATURE                 Location/Qualifiers
source                  1..15
                        mol_type = protein
```

-continued

```
                        note = Influenza B virus
                        organism = unidentified
REGION                  1..15
                        note = B/Phuket/3073/2013 B/Yamagata lineage HA Signal
                         Peptide
SEQUENCE: 171
MKAIIVLLMV VTSNA                                                   15

SEQ ID NO: 172          moltype = AA  length = 549
FEATURE                 Location/Qualifiers
source                  1..549
                        mol_type = protein
                        note = Influenza A virus
                        organism = unidentified
REGION                  1..549
                        note = A/Wisconsin/67/2022 (H1N1)pdm09 H1 HA without SP
SEQUENCE: 172
DTLCIGYHAN NSTDTVDTVL EKNVTVTHSV NLLEDKHNGK LCKLRGVAPL HLGQCNIAGW  60
ILGNPECESL STARSWSYIV ETSNSDNGTC YPGDFINYEE LREQLSSVSS FERFEIFPKT  120
SSWPNHDSDN GVTAACSHAG ARSFYKNLIW LVKKGKSYPK INQTYINDKG KEVLVLWGIH  180
HPPTITDQES LYQNADAYVF VGTSRYSKKF KPEIATRPKV RDQAGRMNYY WTLVEPGDKI  240
TFEATGNLVA PRYAFTMEKE AGSGIIISDT PVHDCNATCQ TPEGAINTSL PFQNVHPITI  300
GKCPKYVRST KLRLATGLRN VPSIQSRGLF GAIAGFIEGG WTGMVDGWYG YHHQNDQGSG  360
YAADLKSTQN AIDKITNKVN SVIEKMNTQF TAVGKEFNHL EKRIENLNKK VDDGFLDVWT  420
YNAELLVLLE NERTLDYHDS NVKNLYEKVR HQLKNNAKEI GNGCFEFYHK CDNTCMESVK  480
NGTYDYPKYS EEAKLNREKI DGVKLDSTRI YQILAIYSTV ASSLVLVVSL GAISFWMCSN  540
GSLQCRICI                                                          549

SEQ ID NO: 173          moltype = AA  length = 550
FEATURE                 Location/Qualifiers
source                  1..550
                        mol_type = protein
                        note = Influenza A virus
                        organism = unidentified
REGION                  1..550
                        note = A/Darwin/6/2021 (H3N2) H3 HA without SP
SEQUENCE: 173
QKIPGNDNST ATLCLGHHAV PNGTIVKTIT NDRIEVTNAT ELVQNSSIGE ICGSPHQILD  60
GGNCTLIDAL LGDPQCDGFQ NKEWDLFVER SRANSNCYPY DVPDYASLRS LVASSGTLEF  120
KNESFNWTGV KQNGTSSACI RGSSSSFFSR LNWLTSLNNI YPAQNVTMPN KEQFDKLYIW  180
GVHHPDTDKN QISLFAQSSG RITVSTKRSQ QAVIPNIGSR PRIRGIPSRI SIYWTIVKPG  240
DILLINSTGN LIAPRGYFKI RSGKSSIMRS DAPIGKCKSE CITPNGSIPN DKPFQNVNRI  300
TYGACPRYVK QSTLKLATGM RNVPEKQTRG IFGAIAGFIE NGWEGMVDGW YGFRHQNSEG  360
RGQAADLKST QAAIDQINGK LNRLIGKTNE KFHQIEKEFS EVEGRVQDLE KYVEDTKIDL  420
WSYNAELLVA LENQHTIDLT DSEMNKLFEK TKKQLRENAE DMGNGCFKIY HKCDNACIGS  480
IRNETYDHNV YRDEALNNRF QIKGVELKSG YKDWILWISF AMSCFLLCIA LLGFIMWACQ  540
KGNIRCNICI                                                         550

SEQ ID NO: 174          moltype = AA  length = 567
FEATURE                 Location/Qualifiers
source                  1..567
                        mol_type = protein
                        note = Influenza B virus
                        organism = unidentified
REGION                  1..567
                        note = B/Austria/1359417/2021 B/Victoria lineage HA without
                         SP
SEQUENCE: 174
DRICTGITSS NSPHVVKTAT QGEVNVTGVI PLTTTPTKSH FANLKGTETR GKLCPKCLNC  60
TDLDVALGRP KCTGKIPSAR VSILHEVRPV TSGCFPIMHD RTKIRQLPNL LRGYEHVRLS  120
THNVINTEDA PGGPYEIGTS GSCLNITNGK GFFATMAWAV PKNKTATNPL TIEVPYICTE  180
EEDQITVWGF HSDDETQMAR LYGDSKPQKF TSSANGVTTH YVSQIGGFPN QTEDGGLPQS  240
GRIVVDYMVQ KSGKTGTITY QRGILLPQKV WCASGKSKVI KGSLPLIGEA DCLHEKYGGL  300
NKSKPYYTGE HAKAIGNCPI WVKTPLKLAN GTKYRPPAKL LKERGFFGAI AGFLEGGWEG  360
MIAGWHGYTS HGAHGVAVAA DLKSTQEAIN KITKNLNSLS ELEVKNLQRL SGAMDELHNE  420
ILELDEKVDD LRADTISSQI ELAVLLSNEG IINSEDEHLL ALERKLKKML GPSAVEIGNG  480
CFETKHKCNQ TCLDRIAAGT FDAGEFSLPT FDSLNITAAS LNDDGLDNHT ILLYYSTAAS  540
SLAVTLMIAI FVVYMVSRDN VSCSICL                                      567

SEQ ID NO: 175          moltype = AA  length = 569
FEATURE                 Location/Qualifiers
source                  1..569
                        mol_type = protein
                        note = Influenza B virus
                        organism = unidentified
REGION                  1..569
                        note = B/Austria/1359417/2021 B/Yamagata lineage HA without
                         SP
SEQUENCE: 175
```

```
DRICTGITSS NSPHVVKTAT QGEVNVTGVI PLTTTPTKSY FANLKGTRTR GKLCPDCLNC  60
TDLDVALGRP MCVGTTPSAK ASILHEVRPV TSGCFPIMHD RTKIRQLPNL LRGYEKIRLS 120
TQNVIDAEKA PGGPYRLGTS GSCPNATSKI GFFATMAWAV PKDNYKNATN PLTVEVPYIC 180
TEGEDQITVW GFHSDNKTQM KSLYGDSNPQ KFTSSANGVT THYVSQIGDF PDQTEDGGLP 240
QSGRIVVDYM MQKPGKTGTI VYQRGVLLPQ KVWCASGRSK VIKGSLPLIG EADCLHEEYG 300
GLNKSKPYYT GKHAKAIGNC PIWVKTPLKL ANGTKYRPPA KLLKERGFFG AIAGFLEGGW 360
EGMIAGWHGY TSHGAHGVAV AADLKSTQEA INKITKNLNS LSELEVKNLQ RLSGAMDELH 420
NEILELDEKV DDLRADTISS QIELAVLLSN EGIINSEDEH LLALERKLKK MLGPSAVDIG 480
NGCFETKHKC NQTCLDRIAA GTFNAGEFSL PTFDSLNITA ASLNDDGLDN HTILLYYSTA 540
ASSLAVTLML AIFIVYMVSR DNVSCSICL                                  569

SEQ ID NO: 176         moltype = AA  length = 884
FEATURE                Location/Qualifiers
source                 1..884
                       mol_type = protein
                       organism = synthetic construct
REGION                 1..884
                       note = T7 RNA Polymerase Variant 1
SEQUENCE: 176
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVE DIPAIEREEL 360
PMKPEDIDMN PEALTAWKRA AAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KRSVMTLAYG SKEFGFRQQV LEDTIQPAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFAG                 884

SEQ ID NO: 177         moltype = AA  length = 884
FEATURE                Location/Qualifiers
source                 1..884
                       mol_type = protein
                       organism = synthetic construct
REGION                 1..884
                       note = T7 RNA Polymerase Variant 2
SEQUENCE: 177
MNTINIAKND FSDIELAAIP FNTLADHYGE RLAREQLALE HESYEMAEAR FRKMFERQLK  60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVW VIPAIEREEL 360
PMKPEDIDMN PEALTAWKRA AAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KRSVMTLAYG SKEFGFRQQV LEDTIQPAID 660
SGKGLMFTQP NQAAGYMAKL IWESVSVTVV AAVEAMNWLK SAAKLLAAEV KDKKTGEILR 720
KRCAVHWVTP DGFPVWQEYK KPIQTRLNLM FLGQFRLQPT INTNKDSEID AHKQESGIAP 780
NFVHSQDGSH LRKTVVWAHE KYGIESFALI HDSFGTIPAD AANLFKAVRE TMVDTYESCD 840
VLADFYDQFA DQLHESQLDK MPALPAKGNL NLRDILESDF AFAG                 884

SEQ ID NO: 178         moltype = AA  length = 883
FEATURE                Location/Qualifiers
source                 1..883
                       mol_type = protein
                       organism = synthetic construct
REGION                 1..883
                       note = T7 RNA Polymerase Variant 3
SEQUENCE: 178
MNTINIAKND FSDIELAAIP FNTLADHYGE RLAREQLALE HESYEMGEAR FRKMFERQLK  60
AGEVADNAAA KPLITTLLPK MIARINDWFE EVKAKRGKRP TAFQFLQEIK PEAVAYITIK 120
TTLACLTSAD NTTVQAVASA IGRAIEDEAR FGRIRDLEAK HFKKNVEEQL NKRVGHVYKK 180
AFMQVVEADM LSKGLLGGEA WSSWHKEDSI HVGVRCIEML IESTGMVSLH RQNAGVVGQD 240
SETIELAPEY AEAIATRAGA LAGISPMFQP CVVPPKPWTG ITGGGYWANG RRPLALVRTH 300
SKKALMRYED VYMPEVYKAI NIAQNTAWKI NKKVLAVANV ITKWKHCPVW VIPAIEREEL 360
PMKPEDIDMN PEALTAWKRA AAVYRKDKA RKSRRISLEF MLEQANKFAN HKAIWFPYNM 420
DWRGRVYAVS MFNPQGNDMT KGLLTLAKGK PIGKEGYYWL KIHGANCAGV DKVPFPERIK 480
FIEENHENIM ACAKSPLENT WWAEQDSPFC FLAFCFEYAG VQHHGLSYNC SLPLAFDGSC 540
SGIQHFSAML RDEVGGRAVN LLPSETVQDI YGIVAKKVNE ILQADAINGT DNEVVTVTDE 600
NTGEISEKVK LGTKALAGQW LAYGVTRSVT KRSVMTLAYG SKEFGFRQQV LEDTIQPAID 660
SGKGLMFTQP NQAAGYMAKL IWESVSVTVV AAVEAMNWLK SAAKLLAAEV KDKKTGEILR 720
```

-continued

```
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA                    883

SEQ ID NO: 179         moltype = AA  length = 883
FEATURE                Location/Qualifiers
source                 1..883
                       mol_type = protein
                       organism = synthetic construct
REGION                 1..883
                       note = T7 RNA Polymerase Variant 4
SEQUENCE: 179
MNTINIAKND FSDIELAAIP FNTLADHYGE RLAREQLALE HESYEMGEAR FRKMFERQLK  60
AGEVADNAAA KPLITTLLPK MIARINDWFE EVKAKRGKRP TAFQFLQEIK PEAVAYITIK  120
TTLACLTSAD NTTVQAVASA IGRAIEDEAR FGRIRDLEAK HFKKNVEEQL NKRVGHVYKK  180
AFMQVVEADM LSKGLLGGEA WSSWHKEDSI HVGVRCIEML IESTGMVSLH RQNAGVVGQD  240
SETIELAPEY AEAIATRAGA LAGISPMFQP CVVPPKPWTG ITGGGYWANG RRPLALVRTH  300
SKKALMRYED VYMPEVYKAI NIAQNTAWKI NKKVLAVANV ITKWKHCPVW VIPAIEREEL  360
PMKPEDIDMN PEALTAWKRA AAAVYRKDKA RKSRRISLEF MLEQANKFAN HKAIWFPYNM  420
DWRGRVYAVS MFNPQGNDMT KGLLTLAKGK PIGKEGYYWL KIHGANCAGV DKVPFPERIK  480
FIEENHENIM ACAKSPLENT WWAEQDSPFC FLAFCFEYAG VQHHGLSYNC SLPLAFDGSC  540
SGIQHFSAML RDEVGGRAVN LLPSETVQDI YGIVAKKVNE ILQADAINGT DNEVVTVTDE  600
NTGEISEKVK LGTKALAGQW LAYGVTRSVT KRSVMTLAYG SKEFGFRQQV LEDTIQPAID  660
SGKGLMFTQP NQAAGYMAKL IWESVSVTVV AAVEAMNWLK SAAKLLAAEV KDKKTGEILR  720
KRCAVHWVTP DGFPVWQEYK KPIQTRLNLM FLGQFRLQPT INTNKDSEID AHKQESGIAP  780
NFVHSQDGSH LRKTVVWAHE KYGIESFALI HDSFGTIPAD AANLFKAVRE TMVDTYESCD  840
VLADFYDQFA DQLHESQLDK MPALPAKGNL NLRDILESDF AFA                    883

SEQ ID NO: 180         moltype = AA  length = 470
FEATURE                Location/Qualifiers
source                 1..470
                       mol_type = protein
                       note = Influenza A virus
                       organism = unidentified
REGION                 1..470
                       note = A/Beijing/262/1995 (H1N1) NA
SEQUENCE: 180
MNPNQKIITI GSISIVIGII SLMLQIGNII SIWASHSIQT GSQNHTGICN QRIITYENST  60
WVNHTYVNIN NTNVVAGKDK TSVTLAGNSS LCSISGWAIY TKDNSIRIGS KGDVFVIREP  120
FISCSHLECR TFFLTQGALL NDKHSNGTVK DRSPYRALMS CPLGEAPSPY NSKFESVAWS  180
ASACHDGMGW LTIGISGPDN GAVAVLKYNG IITETIKSWK KRILRTQESE CVCVNGSCFT  240
IMTDGPSNGA ASYKIFKIEK GKVTKSIELN APNSHYEECS CYPDTGTVMC VCRDNWHGSN  300
RPWVSFNQNL DYQIGYICSG VFGDNPRPKD GEGSCNPVTV DGADGVKGFS YRYGNGVWIG  360
RTKSNRLRKG FEMIWDPNGW TDTDSDFSVK QDVVAMTDWS GYSGSFVQHP ELTGLDCIRP  420
CFWVELVRGR PRENTTIWTS GSSISFCGVN SDTANWSWPD GAELPFTIDK             470

SEQ ID NO: 181         moltype = AA  length = 470
FEATURE                Location/Qualifiers
source                 1..470
                       mol_type = protein
                       note = Influenza A virus
                       organism = unidentified
REGION                 1..470
                       note = A/New Caledonia/20/1999 (H1N1) NA
SEQUENCE: 181
MNPNQKIITI GSISIAIGII SLMLQIGNII SIWASHSIQT GSQNHTGVCN QRIITYENST  60
WVNHTYVNIN NTNVVAGKDK TSVTLAGNSS LCSISGWAIY TKDNSIRIGS KGDVFVIREP  120
FISCSHLECR TFFLTQGALL NDKHSNGTVK DRSPYRALMS CPLGEAPSPY NSKFESVAWS  180
ASACHDGMGW LTIGISGPDN GAVAVLKYNG IITETIKSWK KRILRTQESE CVCVNGSCFT  240
IMTDGPSNGA ASYKIFKIEK GKVTKSIELN APNFHYEECS CYPDTGTVMC VCRDNWHGSN  300
RPWVSFNQNL DYQIGYICSG VFGDNPRPKD GEGSCNPVTV DGADGVKGFS YKYGNGVWIG  360
RTKSNRLRKG FEMIWDPNGW TDTDSDFSVK QDVVAITDWS GYSGSFVQHP ELTGLDCIRP  420
CFWVELVRGL PRENTTIWTS GSSISFCGVN SDTANWSWPD GAELPFTIDK             470

SEQ ID NO: 182         moltype = AA  length = 470
FEATURE                Location/Qualifiers
source                 1..470
                       mol_type = protein
                       note = Influenza A virus
                       organism = unidentified
REGION                 1..470
                       note = A/Solomon Islands/3/2006 (H1N1) NA
SEQUENCE: 182
MNPNQKIITI GSISIAIGII SLILQIGNII SIWASHSIQT GSQNHTGICN QRIITYENST  60
WVNNTYVNIN NTNVVAEKDK TSVTLAGNSS LCSISGWAIY TKDNSIRIGS KGDVFVIREP  120
FISCSHLECR TFFLTQGALL NDKHSNGTVK DRSPYRALMS CPLGEAPSPY NSRFESVAWS  180
ASACHDGMGW LTIGISGPDN GAVAVLKYNG IITETIKSWK KRILRTQESE CVCMNGSCFT  240
IMTDGPSNGA ASYKIFKIEK GKVTKTIELN APNFHYEECS CYPDTGTVMC VCRDNWHGSN  300
RPWVSFNQNL DYQIGYICSG VFGDNPRPKD GEGSCNPVTV DGADGVKGFS YKYGNGVWIG  360
```

-continued

```
RTKSNRLRKG FEMIWDPNGW TNTDSDFSVK QDVVAITDWS GYSGSFVQHP ELTGLDCIRP  420
CFWVELVRGL PRENTTIWTS GSSISFCGVN SGTANWSWPD GAELPFTIDK             470

SEQ ID NO: 183          moltype = AA  length = 470
FEATURE                 Location/Qualifiers
source                  1..470
                        mol_type = protein
                        note = Influenza A virus
                        organism = unidentified
REGION                  1..470
                        note = A/Brisbane/59/2007 (H1N1) NA
SEQUENCE: 183
MNPNQKIITI GSISIAIGII SLMLQIGNII SIWASHSIQT GSQNNTGICN QRIITYENST  60
WVNHTYVNIN NTNVVAGEDK TSVTLAGNSS LCSISGWAIY TKDNSIRIGS KGDVFVIREP  120
FISCSHLECR TFFLTQGALL NDKHSNGTVK DRSPYRALMS CPLGEAPSPY NSKFESVAWS  180
ASACHDGMGW LTIGISGPDN GAVAVLKYNG IITGTIKSWK KQILRTQESE CVCMNGSCFT  240
IMTDGPSNKA ASYKIFKIEK GKVTKSIELN APNFHYEECS CYPDTGIVMC VCRDNWHGSN  300
RPWVSFNQNL DYQIGYICSG VFGDNPRPED GEGSCNPVTV DGANGVKGFS YKYDNGVWIG  360
RTKSNRLRKG FEMIWDPNGW TNTDSDFSVK QDVVAITDWS GYSGSFVQHP ELTGLDCIRP  420
CFWVELVRGL PRENTTIWTS GSSISFCGVN SDTANWSWPD GAELPFTIDK             470

SEQ ID NO: 184          moltype =   length =
SEQUENCE: 184
000

SEQ ID NO: 185          moltype = AA  length = 469
FEATURE                 Location/Qualifiers
source                  1..469
                        mol_type = protein
                        note = Influenza A virus
                        organism = unidentified
REGION                  1..469
                        note = A/California/7/2009 (H1N1)pdm09 NA
SEQUENCE: 185
MNPNQKIITI GSVCMTIGMA NLILQIGNII SIWISHSIQL GNQNQIETCN QSVITYENNT  60
WVNQTYVNIS NTNFAAGQSV VSVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGINW LTIGISGPDN GAVAVLKYNG IITDTIKSWR NNILRTQESE CACVNGSCFT  240
VMTDGPSNGQ ASYKIFRIEK GKIVKSVEMN APNYHYEECS CYPDSSEITC VCRDNWHGSN  300
RPWVSFNQNL EYQIGYICSG IFGDNPRPND KTGSCGPVSS NGANGVKGFS FKYGNGVWIG  360
RTKSISSRNG FEMIWDPNGW TGTDNNFSIK QDIVGINEWS GYSGSFVQHP ELTGLDCIRP  420
CFWVELIRGR PKENTIWTSG SSISFCGVNS DTVGWSWPDG AELPFTIDK              469

SEQ ID NO: 186          moltype = AA  length = 469
FEATURE                 Location/Qualifiers
source                  1..469
                        mol_type = protein
                        note = Influenza A virus
                        organism = unidentified
REGION                  1..469
                        note = A/Michigan/45/2015 (H1N1)pdm09 NA
SEQUENCE: 186
MNPNQKIITI GSICMTIGMA NLILQIGNII SIWVSHSIQI GNQSQIETCN QSVITYENNT  60
WVNQTYVNIS NTNFAAGQSV VSVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGINW LTIGISGPDS GAVAVLKYNG IITDTIKSWR NNILRTQESE CACVNGSCFT  240
IMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVSS NGANGVKGFS FKYGNGVWIG  360
RTKSISSRKG FEMIWDPNGW TGTDNKFSIK QDIVGINEWS GYSGSFVQHP ELTGLDCIRP  420
CFWVELIRGR PEENTIWTSG SSISFCGVNS DTVGWSWPDG AELPFTIDK              469

SEQ ID NO: 187          moltype = AA  length = 469
FEATURE                 Location/Qualifiers
source                  1..469
                        mol_type = protein
                        note = Influenza A virus
                        organism = unidentified
REGION                  1..469
                        note = A/Brisbane/02/2018 (H1N1)pdm09 NA
SEQUENCE: 187
MNPNQKIITI GSTCMTIGMA NLILQIGNII SIWVSHSIQI GNQSQIETCN QSVITYENNT  60
WVNQTYVNIS NTNFAARQSV ASVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGTNW LTIGISGPDS GAVAVLKYNG IITDTIKSWR NNILRTQESE CACVNGSCFT  240
IMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVSS NGANGVKGFS FKYGNGVWIG  360
RTKSISSRKG FEMIWDPNGW TGTDNKFSIK QDIVGINEWS GYSGSFVQHP ELTGLDCIRP  420
CFWVELIRGR PEENTIWTSG SSISFCGVDS DTVGWSWPDG AELPFTIDK              469
```

```
SEQ ID NO: 188          moltype = AA  length = 469
FEATURE                 Location/Qualifiers
source                  1..469
                        mol_type = protein
                        note = Influenza A virus
                        organism = unidentified
REGION                  1..469
                        note = A/Guangdong-Maonan/SWL1536/2019 (H1N1)pdm09 NA
SEQUENCE: 188
MNPNQKIITI GSICMTIGMA NLILQIGNII SIWVSHSIQI GNQSQIETCN KNVITYENNT  60
WVNQTYVNIS NTNSAARQSV ASVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGTNW LTIGISGPDS GAVAVLKYNG IITDTIKSWR NNILRTQESE CACVNGSCFT  240
IMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVSS NGANGVKGFS FKYGNGVWIG  360
RTKSISSRKG FEMIWDPNGW TGTDNKFSKK QDIVGINEWS GYSGSFVQHP ELTGLNCIRP  420
CFWVELIRGR PEENTIWTSG SSISFCGVDS DIVGWSWPDG AELPFTIDK             469

SEQ ID NO: 189          moltype = AA  length = 469
FEATURE                 Location/Qualifiers
source                  1..469
                        mol_type = protein
                        note = Influenza A virus
                        organism = unidentified
REGION                  1..469
                        note = A/Hawaii/70/2019 (H1N1)pdm09 NA
SEQUENCE: 189
MNPNQKIITI GSICMTIGMA NLILQIGNII SIWVSHSIQI GNQSQIETCN KNVITYENNT  60
WVNQTYVNIS NTNSAARQSV ASVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGTNW LTIGISGPDS GAVAVLKYNG IITDTIKSWR NNILRTQESE CACVNGSCFT  240
IMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVSS NGANGVKGFS FKYGNGVWIG  360
RTKSISSRKG FEMIWDPNGW TGTDNKFSKK QDIVGINEWS GYSGSFVQHP ELTGLNCIRP  420
CFWVELIRGR PEENTIWTSG SSISFCGVDS DIVGWSWPDG AELPFTIDK             469

SEQ ID NO: 190          moltype = AA  length = 469
FEATURE                 Location/Qualifiers
source                  1..469
                        mol_type = protein
                        note = Influenza A virus
                        organism = unidentified
REGION                  1..469
                        note = A/Victoria/2570/2019 (H1N1)pdm09 NA
SEQUENCE: 190
MNPNQKIITI GSICMTIGTA NLILQIGNII SIWVSHSIQI GNQSQIETCD KSVITYENNT  60
WVNQTFVNIS NTNSAARQSV ASVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGTNW LTIGISGPDS GAVAVLKYNG IITDTIKSWR NKILRTQESE CACVNGSCFT  240
IMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVSS NGANGVKGFS FKYGNGVWIG  360
RTKSISSRKG FEMIWDPNGW TETDNKFSKK QDIVGINEWS GYSGSFVQHP ELTGLNCIRP  420
CFWVELIRGR PEENTIWTSG SSISFCGVDS DIMGWSWPDG AELPFTIDN             469

SEQ ID NO: 191          moltype = AA  length = 469
FEATURE                 Location/Qualifiers
source                  1..469
                        mol_type = protein
                        note = Influenza A virus
                        organism = unidentified
REGION                  1..469
                        note = A/Wisconsin/588/2019 (H1N1)pdm09 NA
SEQUENCE: 191
MNPNQKIITI GSICMTIGTA NLILQIGNII SIWVSHSIQI GNQSQIETCN KSVITYENNT  60
WVNQTFVNIS NTNSAARQSV ASVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGTNW LTIGISGPDS GAVAVLKYNG IITDTIKSWR NKILRTQESE CACVNGSCFT  240
IMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVSS NGANGVKGFS FKYGNGVWIG  360
RTKSISSRKG FEMIWDPNGW TGTDNKFSKK QDIVGINEWS GYSGSFVQHP ELTGLNCIRP  420
CFWVELIRGR PEENTIWTSG SSISFCGVDS DIVGWSWPDG AELPFTIDK             469

SEQ ID NO: 192          moltype = AA  length = 469
FEATURE                 Location/Qualifiers
source                  1..469
                        mol_type = protein
                        note = Influenza A virus
                        organism = unidentified
REGION                  1..469
```

-continued

```
                     note = A/Victoria/4897/2022 (H1N1)pdm09 NA
SEQUENCE: 192
MNPNQKIITI GSICMTIGTA NLILQIGNII SIWVSHSIQI GNQSQIETCD KSVITYENNT  60
WVNQTFVNIS NTNSAARQSV ASVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGTNW LTIGISGPDS GAVAVLKYNG IITDTIKSWR NKILRTQESE CACVNGSCFT  240
IMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVSS NGANGVKGFS FKYGNGVWIG  360
RTKSISSRKG FEMIWDPNGW TETDNKFSKK QDIVGINEWS GYSGSFVQHP ELTGLNCIRP  420
CFWVELIRGR PEENTIWTSG SSISFCGVDS DIMGWSWPDG AELPFTIDN             469

SEQ ID NO: 193          moltype = AA  length = 469
FEATURE                 Location/Qualifiers
source                  1..469
                        mol_type = protein
                        note = Influenza A virus
                        organism = unidentified
REGION                  1..469
                        note = A/Wisconsin/67/2022 (H1N1)pdm09 NA
SEQUENCE: 193
MNPNQKIITI GSVCMTIGTA NLILQIGNII SIWVSHSIQI GNQSQIETCN KSVITYENNT  60
WVNQTFVNIS NTNSAARQSV ASVKLAGNSS LCPVSGWAIY SKDNSVRIGS KGDVFVIREP  120
FISCSPLECR TFFLTQGALL NDKHSNGTIK DRSPYRTLMS CPIGEVPSPY NSRFESVAWS  180
ASACHDGTNW LTIGISGPDS GAVAVLKYNG IITDTIKSWR NKILRTQESE CACVNGSCFT  240
IMTDGPSDGQ ASYKIFRIEK GKIIKSVEMK APNYHYEECS CYPDSSEITC VCRDNWHGSN  300
RPWVSFNQNL EYQMGYICSG VFGDNPRPND KTGSCGPVLS NGANGVKGFS FKYGNGVWIG  360
RTKSISSRKG FEMIWDPNGW TGTDNKFSKK QDIVGINEWS GYSGSFVQHP ELTGLNCIRP  420
CFWVELIRGR PEENTIWTSG SSISFCGVDS DIMGWSWPDG AELPFTIDN             469

SEQ ID NO: 194          moltype = AA  length = 469
FEATURE                 Location/Qualifiers
source                  1..469
                        mol_type = protein
                        note = Influenza A virus
                        organism = unidentified
REGION                  1..469
                        note = A/Sydney/5/97 (H3N2) NA
SEQUENCE: 194
MNPNQKIITI GSVSLTIATI CFLMQIAILV TTVTLHFKQY ECSSPPNNQV MLCEPTIIER  60
NITEIVYLTN TTIEKEICPK LAEYRNWSKP QCKITGFAPF SKDNSIRLSA GGDIWVTREP  120
YVSCDPDKCY QFALGQGTTL NNRHSNDTVH DRTPYRTLLM NELGVPFHLG TKQVCIAWSS  180
SSCHDGKAWL HVCVTGHDEN ATASFIYDGR LVDSIGSWSK KILRTQESEC VCINGTCTVV  240
MTDGSASGRA DTKILFIEEG KIVHISPLSG SAQHVEECSC YPRYPGVRCV CRDNWKGSNR  300
PIVDINVKDY SIVSSYVCSG LVGDTPRKND SSSSSHCLNP NNEEGGHGVK GWAFDDGNDV  360
WMGRTISEKF RSGYETFKVI EGWSKPNSKL QINRQVIVDR GNRSGYSGIF SVEGKSCINR  420
CFYVELIRGR KQETEVWWTS NSIVVFCGTS GTYGTGSWPD GADINLMPI             469

SEQ ID NO: 195          moltype = AA  length = 469
FEATURE                 Location/Qualifiers
source                  1..469
                        mol_type = protein
                        note = Influenza A virus
                        organism = unidentified
REGION                  1..469
                        note = A/Moscow/10/1999 (H3N2) NA
SEQUENCE: 195
MNPNQKIITI GSVSLTIATI CFLMQIAILV TTVTLHFKQY ECNSPPNNQV MLCEPTIIER  60
NITEIVYLTN TTIEKEICPK LAEYRNWSKP QCNITGFAPF SKDNSIRLSA GGDIWVTREP  120
YVSCDPDKCY QFALGQGTTL NNGHSNDTVH DRTPYRTLLM NELGVPFHLG TKQVCIAWSS  180
SSCHDGKAWL HVCVTGDDEN ATASFIYNGR LVDSIGSWSK KILRTQESEC VCINGTCTVV  240
MTDGSASGKA DTKILFIEEG KIVHTSPLSG SAQHVEECSC YPRYPGVRCV CRDNWKGSNR  300
PIVDINVKDY SIVSSYVCSG LVGDTPRKND SSSSSHCLDP NNEEGGHGVK GWAFDDGNDV  360
WMGRTISEKL RSGYETFKVI EGWSKPNSKL QINRQVIVDR GNRSGYSGIF SVEGKSCINR  420
CFYVELIRGR KQETEVLWTS NSIVVFCGTS GTYGTGSWPD GADINLMPI             469

SEQ ID NO: 196          moltype = AA  length = 469
FEATURE                 Location/Qualifiers
source                  1..469
                        mol_type = protein
                        note = Influenza A virus
                        organism = unidentified
REGION                  1..469
                        note = A/Fujian/411/2002 (H3N2) NA
SEQUENCE: 196
MNPNQKIITI GSVSLTISTI CFFMQIAILI TTVTLHFKQY EFNSPPNNQV MLCEPTIIER  60
NITEIVYLTN TTIEKEICPK LAEYRNWSKP QCNITGFAPF SKDNSIRLSA GGDIWVTREP  120
YVSCDPDKCY QFALGQGTTL NNVHSNDTVH DRTPYRTLLM NELGVPFHLG TKQVCIAWSS  180
SSCHDGKAWL HVCVTGDDEN ATASFIYNGR LVDSIVSWSK KILRTQESEC VCINGTCTVV  240
MTDGSASGKA DTKILFIEEG KIVHTSTLSG SAQHVEECSC YPRYPGVRCV CRDNWKGSNR  300
```

-continued

```
PIVDINIKDY SIVSSYVCSG LVGDTPRKND SSSSSHCLDP NNEEGGHGVK GWAFDDGNDV  360
WMGRTISEKL RSGYETFKVI EGWSNPNSKL QINRQVIVDR GNRSGYSGIF SVEGKSCINR  420
CFYVELIRGR KQETEVLWTS NSIVVFCGTS GTYGTGSWPD GADINLMPI             469

SEQ ID NO: 197          moltype = AA  length = 469
FEATURE                 Location/Qualifiers
source                  1..469
                        mol_type = protein
                        note = Influenza A virus
                        organism = unidentified
REGION                  1..469
                        note = A/California/7/2004 (H3N2) NA
SEQUENCE: 197
MNPNQKIITI GSVSLTISTI CFFMQIAILI TTVTLHFKQY EFNSPPNNQV MLCEPTIIER  60
NITEIVYLTN TTIEKEICPK LAEYRNWSKP QCDITGFAPF SKDNSIRLSA GGDIWVTREP  120
YVSCDPDKCY QFALGQGTTL NNVHSNDTVH DRTPYRTLLM NELGVPFHLG TKQVCIAWSS  180
SSCHDGKAWL HVCVTGDDKN ATASFIYNGR LVDSIVSWSK EILRTQESEC VCINGTCTVV  240
MTDGSASGKA DTKILFIEEG KIVHTSTLSG SAQHVEECSC YPRYPGVRCV CRDNWKGSNR  300
PIVDINIKDY SIVSSYVCSG LVGDTPRKND SSSSSHCLDP NNEEGGHGVK GWAFDDGNDV  360
WMGRTISEKL RSGYETFKVI EGWSNPNSKL QINRQVIVDR GNRSGYSGIF SVEGKSCINR  420
CFYVELIRGR KEETEVLWTS NSIVVFCGTS GTYGTGSWPD GADINLMPI             469

SEQ ID NO: 198          moltype = AA  length = 469
FEATURE                 Location/Qualifiers
source                  1..469
                        mol_type = protein
                        note = Influenza A virus
                        organism = unidentified
REGION                  1..469
                        note = A/Wisconsin/67/2005 (H3N2) NA
SEQUENCE: 198
MNPNQKIITI GSVSLTISTI CFFMQIAILI TTVTLHFKQY EFNSPPNNQV MLCEPTIIER  60
NITEIVYLTN TTIEKEICPK LAEYRNWSKP QCNITGFAPF SKDNSIRLSA GGDIWVTREP  120
YVSCDPDKCY QFALGQGTTL NNVHSNDTVH DRTPYRTLLM NELGVPFHLG TKQVCIAWSS  180
SSCHDGKAWL HVCVTGDDKN ATASFIYNGR LVDSIVSWSK EILRTQESEC VCINGTCTVV  240
MTDGSASGKA DTKILFIEEG KIVHTSTLSG SAQHVEECSC YPRYLGVRCV CRDNWKGSNR  300
PIVDINIKDY SIVSSYVCSG LVGDTPRKND SSSSSHCLDP NNEEGGHGVK GWAFDDGNDV  360
WMGRTISEKL RSGYETFKVI EGWSNPNSKL QINRQVIVDR GNRSGYSGIF SVEGKSCINR  420
CFYVELIRGR KEETEVLWTS NSIVVFCGTS GTYGTGSWPD GADINLMPI             469

SEQ ID NO: 199          moltype = AA  length = 469
FEATURE                 Location/Qualifiers
source                  1..469
                        mol_type = protein
                        note = Influenza A virus
                        organism = unidentified
REGION                  1..469
                        note = A/Brisbane/10/2007 (H3N2) NA
SEQUENCE: 199
MNPNQKIITI GSVSLTISTI CFFMQIAILI TTVTLHFKQY EFNSPPNNQV MLCEPTIIER  60
NITEIVYLTN TTIEKEICPK LAEYRNWSKP QCDITGFAPF SKDNSIRLSA GGDIWVTREP  120
YVSCDPDKCY QFALGQGTTL NNVHSNDTVR DRTPYRTLLM NELGVPFHLG TKQVCIAWSS  180
SSCHDGKAWL HVCITGDDKN ATASFIYNGR LVDSIVSWSK EILRTQESEC VCINGTCTVV  240
MTDGSASGKA DTKILFIEEG KIVHTSTLSG SAQHVEECSC YPRYPGVRCV CRDNWKGSNR  300
PIVDINIKDH STVSSYVCSG LVGDTPRKND SSSSSHCLDP NNEEGGHGVK GWAFDDGNDV  360
WMGRTISEKS RLGYETFKVI EGWSNPKSKL QINRQVIVDR GNRSGYSGIF SVEGKSCINR  420
CFYVELIRGR KEETEVLWTS NSIVVFCGTS GTYGTGSWPD GADINLMPI             469

SEQ ID NO: 200          moltype = AA  length = 469
FEATURE                 Location/Qualifiers
source                  1..469
                        mol_type = protein
                        note = Influenza A virus
                        organism = unidentified
REGION                  1..469
                        note = A/Perth/16/2009 (H3N2) NA
SEQUENCE: 200
MNPNQKIITI GSVSLTISTI CFFMQIAILI TTVTLHFKQY EFNSPPNNQV MLCEPTIIER  60
NITEIVYLTN TTIEKEICPK LAEYRNWSKP QCDITGFAPF SKDNSIRLSA GGDIWVTREP  120
YVSCDPDKCY QFALGQGTTL NNVHSNNTVR DRTPYRTLLM NELGVPFHLG TKQVCIAWSS  180
SSCHDGKAWL HVCITGDDKN ATASFIYNGR LVDSVVSWSK EILRTQESEC VCINGTCTVV  240
MTDGSASGKA DTKILFIEEG KIVHTSTLSG SAQHVEECSC YPRYPGVRCV CRDNWKGSNR  300
PIVDINIKDH SIVSSYVCSG LVGDTPRKND SSSSSHCLDP NNEEGGHGVK GWAFDDGNDV  360
WMGRTISEKS RLGYETFKVI EGWSNPKSKL QINRQVIVDR GNRSGYSGIF SVEGKSCINR  420
CFYVELIRGR KEETEVLWTS NSIVVFCGTS GTYGTGSWPD GADINLMPI             469

SEQ ID NO: 201          moltype = AA  length = 469
FEATURE                 Location/Qualifiers
source                  1..469
```

```
                        mol_type = protein
                        note = Influenza A virus
                        organism = unidentified
REGION                  1..469
                        note = A/Victoria/361/2011 (H3N2) NA
SEQUENCE: 201
MNPNQKIITI GSVSLTISTI CFFMQIAILI TTVTLHFKQY EFNSPPNNQV MLCEPTIIER  60
NITEIVYLTN TTIEKEICPK PAEYRNWSKP QCGITGFAPF SKDNSIRLSA GGDIWVTREP  120
YVSCDPDKCY QFALGQGTTL NNVHSNNTVR DRTPYRTLLM NELGVPFHLG TKQVCIAWSS  180
SSCHDGKAWL HVCITGDDKN ATASFIYNGR LVDSVVSWSK EILRTQESEC VCINGTCTVV  240
MTDGSASGKA DTKILFIKEG KIVHTSTLSG SAQHVEECSC YPRYPGVRCV CRDNWKGSNR  300
PIVDINIKDH SIVSSYVCSG LVGDTPRKTD SSSSSHCLDP NNEEGGHGVK GWAFDDGNDV  360
WMGRTINETS RLGYETFKVI EGWSNPKSKL QINRQVIVDR GDRSGYSGIF SVEGKSCINR  420
CFYVELIRGR KEETEVLWTS NSIVVFCGTS GTYGTGSWPD GADLNLMPI             469

SEQ ID NO: 202          moltype = AA  length = 469
FEATURE                 Location/Qualifiers
source                  1..469
                        mol_type = protein
                        note = Influenza A virus
                        organism = unidentified
REGION                  1..469
                        note = A/Texas/50/2012 (H3N2) NA
SEQUENCE: 202
MNPNQKIITI GSVSLTISTI CFFMQIAILI TTVTLHFKQY EFNSPPNNQV MLCEPTIIER  60
NITEIVYLTN TTIEKEICPK PAEYRNWSKP QCGITGFAPF SKDNSIRLSA GGDIWVTREP  120
YVSCDPDKCY QFALGQGTTL NNVHSNNTVH DRTPYRTLLM NELGVPFHLG TKQVCIAWSS  180
SSCHDGKAWL HVCITGDDKN ATASFIYNGR LVDSVVSWSK EILRTQESEC VCINGTCTVV  240
MTDGSASGKA DTKILFIEEG KIVHTSTLSG SAQHVEECSC YPRYPGVRCV CRDNWKGSNR  300
PIVDINIKDH SIVSSYVCSG LVGDTPRKND SSSSSHCLDP NNEEGGHGVK GWAFDDGNDV  360
WMGRTINETS RLGYETFKVI EGWSNPKSKL QINRQVIVDR GDRSGYSGIF SVEGKSCINR  420
CFYVELIRGR KEETEVLWTS NSIVVFCGTS GTYGTGSWPD GADLNLMPI             469

SEQ ID NO: 203          moltype = AA  length = 469
FEATURE                 Location/Qualifiers
source                  1..469
                        mol_type = protein
                        note = Influenza A virus
                        organism = unidentified
REGION                  1..469
                        note = A/Switzerland/9715293/2013 (H3N2) NA
SEQUENCE: 203
MNPNQKIITI GSVSLTISTI CFFMQIAILI TTVTLHFKQY EFNSPPNNQV MLCEPTIIER  60
NITEIVYLTN TTIEKEICPK PAEYRNWSKP QCGITGFAPF SKDNSIRLSA GGDIWVTREP  120
YVSCDPDKCY QFALGQGTTL NNVHSNNTVR DRTPYRTLLM NELGVPFHLG TKQVCIAWSS  180
SSCHDGKAWL HVCITGDDKN ATASFIYNGR LVDSVVSWSK DILRTQESEC VCINGTCTVV  240
MTDGSASGKA DTKILFIEEG KIVHTSTLSG SAQHVEECSC YPRYPGVRCV CRDNWKGSNR  300
PIVDINIKDH SIVSSYVCSG LVGDTPRKND SSSSSHCLDP NNEEGGHGVK GWAFDDGNDV  360
WMGRTINETS RLGYETFKVI EGWSNPKSKL QTNRQVIVDR GDRSGYSGIF SVEGKSCINR  420
CFYVELIRGR KEETEVLWTS NSIVVFCGTS GTYGTGSWPD GADLNLMPI             469

SEQ ID NO: 204          moltype = AA  length = 469
FEATURE                 Location/Qualifiers
source                  1..469
                        mol_type = protein
                        note = Influenza A virus
                        organism = unidentified
REGION                  1..469
                        note = A/Hong Kong/4801/2014 (H3N2) NA
SEQUENCE: 204
MNPNQKIITI GSVSLTISTI CFFMQIAILI TTVTLHFKQY EFNSPPNNQV MLCEPTIIER  60
NITEIVYLTN TTIEKEICPK PAEYRNWSKP QCGITGFAPF SKDNSIRLSA GGDIWVTREP  120
YVSCDPDKCY QFALGQGTTL NNVHSNNTVR DRTPYRTLLM NELGVPFHLG TKQVCIAWSS  180
SSCHDGKAWL HVCITGDDKN ATASFIYNGR LVDSVVSWSK DILRTQESEC ICINGTCTVV  240
MTDGSASGKA DTKILFIEEG KIVHTSTLSG SAQHVEECSC YPRYPGVRCV CRDNWKGSNR  300
PIVDINIKDH SIVSSYVCSG LVGDTPRKND SSSSSHCLDP NNEEGGHGVK GWAFDDGNDV  360
WMGRTINETS RLGYETFKVI EGWSNPKSKL QTNRQVIVDR GDRSGYSGIF SVEGKSCINR  420
CFYVELIRGR KEETEVLWTS NSIVVFCGTS GTYGTGSWPD GADLNLMPI             469

SEQ ID NO: 205          moltype = AA  length = 469
FEATURE                 Location/Qualifiers
source                  1..469
                        mol_type = protein
                        note = Influenza A virus
                        organism = unidentified
REGION                  1..469
                        note = A/Singapore/INFIMH-16-0019/2016 (H3N2) NA
SEQUENCE: 205
MNPNQKIITI GSVSLTISTI CFFMQIAILI TTVTLHFKQY EFNSPPNNQV MLCEPTIIER  60
```

-continued

```
NITEIVYLTN TTIEKEICPK PAEYRNWSKP QCGITGFAPF SKDNSIRLSA GGDIWVTREP  120
YVSCDPDKCY QFALGQGTTL NNVHSNNTVR DRTPYRTLLM NELGVPFHLG TKQVCIAWSS  180
SSCHDGKAWL HVCITGDDKN ATASFIYNGR LIDSVVSWSK DILRTQESEC VCINGTCTVV  240
MTDGNATGKA DTKILFIEEG KIVHTSKLSG SAQHVEECSC YPRYPGVRCV CRDNWKGSNR  300
PIVDINIKDH SIVSSYVCSG LVGDTPRKND SSSSSHCLNP NNEEGGHGVK GWAFDDGNDV  360
WMGRTINETS RLGYETFKVV EGWSNPKSKL QINRQVIVDR GDRSGYSGIF SVEGKSCINR  420
CFYVELIRGR KEETEVLWTS NSIVVFCGTS GTYGTGSWPD GADLNLMHI             469

SEQ ID NO: 206         moltype = AA  length = 469
FEATURE                Location/Qualifiers
source                 1..469
                       mol_type = protein
                       note = Influenza A virus
                       organism = unidentified
REGION                 1..469
                       note = A/Kansas/14/2017 (H3N2) NA
SEQUENCE: 206
MNPNQKIITI GSVSLTISTI CFFMQIAILI TTVTLHFKQY EFNSPPNNQV MLCEPTIIER  60
NITEIVYLTN TTIEREICPK PAEYRNWSKP QCGITGFAPF SKDNSIRLSA GGDIWVTREP  120
YVSCDPDKCY QFALGQGTTI NNVHSNNTAR DRTPHRTLLM NELGVPFHLG TKQVCIAWSS  180
SSCHDGKAWL HVCITGDDKN ATASFIYNGR LVDSVVSWSK DILRTQESEC VCINGTCTVV  240
MTDGNATGKA DTKILFIEEG KIVHTSKLSG SAQHVEECSC YPRYPGVRCV CRDNWKGSNR  300
PIVDINIKDH SIVSSYVCSG LVGDTPRKTD SSSSSHCLNP NNEKGGHGVK GWAFDDGNDV  360
WMGRTINETS RLGYETFKVV EGWSNPKSKL QINRQVIVDR GDRSGYSGIF SVEGKSCINR  420
CFYVELIRGR KEETEVLWTS NSIVVFCGTS GTYGTGSWPD GADLNLMHI             469

SEQ ID NO: 207         moltype = AA  length = 469
FEATURE                Location/Qualifiers
source                 1..469
                       mol_type = protein
                       note = Influenza A virus
                       organism = unidentified
REGION                 1..469
                       note = A/Hong Kong/2671/2019 (H3N2) NA
SEQUENCE: 207
MNPNQKIITI GSVSLTISTI CFFMQIAILI TTVTLHFKQY EFNSPPNNQV MLCEPTIIER  60
NITEIVYLTN TTIEKEICPK PAEYRNWSKP QCGITGFAPF SKDNSIRLSA GGDIWVTREP  120
YVSCDLDKCY QFALGQGTTL NNVHSNNTVR DRTPYRTLLM NELGVPFHLG TKQVCIAWSS  180
SSCHDGKAWL HVCITGDDKN ATASFIYNGR LVDSVVSWSN DILRTQESEC VCINGTCTVV  240
MTDGNATGKA DTKILFIEEG KIVHTSKLSG SAQHVEECSC YPRYPGVRCV CRDNWKGSNR  300
PIIDINIKDH SIVSSYVCSG LVGDTPRKSD SSSSSHCLNP NNEEGGHGVK GWAFDDGNDV  360
WMGRTINETS RLGYETFKVV EGWSNPKSKL QINRQVIVDR GDRSGYSGIF SVEGKSCINR  420
CFYVELIRGR KEETEVLWTS NSIVVFCGTS GTYGTGSWPD GADLNLMHT             469

SEQ ID NO: 208         moltype = AA  length = 469
FEATURE                Location/Qualifiers
source                 1..469
                       mol_type = protein
                       note = Influenza A virus
                       organism = unidentified
REGION                 1..469
                       note = A/Hong Kong/45/2019 (H3N2) NA
SEQUENCE: 208
MNPNQKIITI GSVSLTISTI CFFMQIAILI TTVTLHFKQY EFNSLPNNQV MLCEPTIIER  60
NITEIVYLTN TTIEKEICPK PAEYRNWSKP QCGITGFAPF SKDNSIRLSA GGDIWVTREP  120
YVSCDLDKCY QFALGQGTTL NNVHSNNTVR DRTPYRTLLM NELGVPFHLG TKQVCIAWSS  180
SSCHDGKAWL HVCITGDDKN ATASFIYNGR LVDSVVSWSN DILRTQESEC VCINGTCTVV  240
MTDGNATGKA DTKILFIEEG KIVHTSKLSG SAQHVEECSC YPRYPGVRCV CRDNWKGSNR  300
PIIDINIKDH SIVSSYVCSG LVGDTPRKSD SSSSSHCLNP NNEEGGHGVK GWAFDDGNDV  360
WMGRTINETS RLGYETFKVV EGWSNPKSKL QINRQVIVDR GDRSGYSGIF SVEGKSCINR  420
CFYVELIRGR KEETEVLWTS NSIVVFCGTS GTYGTGSWPD GADLNLMHI             469

SEQ ID NO: 209         moltype = AA  length = 469
FEATURE                Location/Qualifiers
source                 1..469
                       mol_type = protein
                       note = Influenza A virus
                       organism = unidentified
REGION                 1..469
                       note = A/Cambodia/e0826360/2020 (H3N2) NA
SEQUENCE: 209
MNPNQKIITI GSVSLTISTI CFFMQIAILI TTVTLHFKQY EFNSPPNNQV MLCEPTIIER  60
NMTEIVYLTN TTIEKEICPK PAEYRNWSKP QCGITGFAPF SKDNSIRLSA GGDIWVTREP  120
YVSCDLDKCY QFALGQGTTL NNVHSNNTVR DRTPYRTLLM NELGVPFHLG TKQVCIAWSS  180
SSCHDGKAWL HVCITGDDKN ATASFIYNGR LVDSVVSWSN DILRTQESEC VCINGTCTVV  240
MTDGNATGKA DTKILFIEEG KIVHTSKLSG SAQHVEECSC YPRYPGVRCV CRDNWKGSNR  300
PIIDINIKDH SIVSRYVCSG LVGDTPRKSD SSSSSHCLNP NNEKGDHGVK GWAFDDGNDV  360
WMGRTINETS RLGYETFKVV EGWSNPKSKL QINRQVIVDR GDRSGYSGIF SVEGKSCINR  420
CFYVELIRGR KEETEVLWTS NSIVVFCGTS GTYGTGSWPD GANLSLMHI             469
```

```
SEQ ID NO: 210          moltype = AA  length = 469
FEATURE                 Location/Qualifiers
source                  1..469
                        mol_type = protein
                        note = Influenza A virus
                        organism = unidentified
REGION                  1..469
                        note = A/Darwin/9/2021 (H3N2) NA
SEQUENCE: 210
MNPNQKIITI GSVSLTISTI CFFMQIAILI TTVTLHFKQY EFNSPPNNQV MLCEPTIIER  60
NITEIVYLTN TTIEKEICPK PAEYRNWSKP QCGITGFAPF SKDNSIRLSA GGDIWVTREP  120
YVSCDLDKCY QFALGQGTTL NNVHSNNTVS DRTPYRTLLM NELGVPFHLG TKQVCIAWSS  180
SSCHDGKAWL HVCITGDDKN ATASFIYNGR LVDSVVSWSN DILRTQESEC VCINGTCTVV  240
MTDGNATGKA DTKILFIEEG KIVHTSKLSG SAQHVEECSC YPRYPGVRCV CRDNWKGSNR  300
PIIDINIKDH SIVSRYVCSG LVGDTPRKSD SSSSSHCLNP NNEKGDHGVK GWAFDDGNDV  360
WMGRTINETS RLGYETFKVV EGWSNPKSKL QINRQVIVDR GDRSGYSGIF SVEGKSCINR  420
CFYVELIRGR KEETEVLWTS NSIVVFCGTS GTYGTGSWPD GANLSLMHI             469

SEQ ID NO: 211          moltype = AA  length = 469
FEATURE                 Location/Qualifiers
source                  1..469
                        mol_type = protein
                        note = Influenza A virus
                        organism = unidentified
REGION                  1..469
                        note = A/Darwin/6/2021 (H3N2) NA
SEQUENCE: 211
MNPNQKIITI GSVSLTISTI CFFMQIAILI TTVTLHFKQY EFNSPPNNQV MLCEPTIIER  60
NITEIVYLTN TTIEKEICPK PAEYRNWSKP QCGITGFAPF SKDNSIRLSA GGDIWVTREP  120
YVSCDLDKCY QFALGQGTTL NNVHSNNTVR DRTPYRTLLM NELGVPFHLG TKQVCIAWSS  180
SSCHDGKAWL HVCITGDDKN ATASFIYNGR LVDSVVSWSN DILRTQESEC VCINGTCTVV  240
MTDGNATGKA DTKILFIEEG KIVHTSKLSG SAQHVEECSC YPRYPGVRCV CRDNWKGSNR  300
PIIDINIKDH SIVSRYVCSG LVGDTPRKSD SSSSSHCLNP NNEKGDHGVK GWAFDDGNDV  360
WMGRTINETS RLGYETFKVV EGWSNPKSKL QINRQVIVDR GDRSGYSGIF SVEGKSCINR  420
CFYVELIRGR KEETEVLWTS NSIVVFCGTS GTYGTGSWPD GANLSLMHI             469

SEQ ID NO: 212          moltype = AA  length = 466
FEATURE                 Location/Qualifiers
source                  1..466
                        mol_type = protein
                        note = Influenza B virus
                        organism = unidentified
REGION                  1..466
                        note = B/Shangdong/7/1997 NA
SEQUENCE: 212
MLPSTIQTLT LFLTSGGVLL SLYVSALLSY LLYSDILLKF SPTKVIAPTM SLDCANASNV  60
QAVNHSATEE MTFLLPEPEW TYPRLSCQGS TFQKALLISP HRFGEAKGNS APLIIREPFI  120
ACGPKECKHF ALTHYAAQPG GYYNGTREDR NKLRHLISVN LGKIPTVENS IFHMAAWSGS  180
ACHDGREWTY IGVDGPDSNA LIKIKYGEAY TDTYHSYANN ILRTQESACN CIGGDCYLMI  240
TDGSASGISR CRFLKIREGR IIKEIFPTGR VEHTEECTCG FASNKTIECA CRDNSYTAKR  300
PFVKLNVETD TAEIRLMCTE TYLDTPRPDD GSITGPCESN GDKGNGGIKG GFVHQRMASR  360
IGRWYSRTMS KTKRMGMELY VKYDGDPWTD SDALAPSGVM VSIEEPGWYS FGFEIKDKKC  420
DVPCIGIEMV HDGGKKTWHS AATAIYCLMG SGQLLWDTVT GVDMAL                466

SEQ ID NO: 213          moltype = AA  length = 466
FEATURE                 Location/Qualifiers
source                  1..466
                        mol_type = protein
                        note = Influenza B virus
                        organism = unidentified
REGION                  1..466
                        note = B/Hong Kong/330/2001 NA
SEQUENCE: 213
MLPSTIQTLT LFLTSGGVLL SLYVSALLSY LLYSDILLKF SPTKIIAPTT SLDSANASNF  60
QAVNHSATKE MTFLLPEPEW TYPRLSCQGS TFQKALLISP HRFGEAKGNS APLIIREPFI  120
ACGPKECKHF ALTHYAAQPG GYYNGTREDR NKLRHLISVN LGKIPTVENS IFHMAAWSGS  180
ACHDGREWTY IGVDGPDSNA LIKIKYGEAY TDTYHSYANN ILRTQESACN CIGGDCYLMI  240
TDGSASGISK CRFLKIREGR IVKEIFPTGR VEHTEECTCG FASNKTIECA CRDNSYTAKR  300
PFVKLNVETD TAEIRLMCTE TYLDTPRPDD GSITGPCESN GDKGSGGIKG GFVHQRMASK  360
IGRWYSRTMS KTKRMGMELY VKYDGDPWTD SDALAPSGVM VSIEEPGWYS FGFEIKDKKC  420
DVPCIGIEMV HDGGKTTWHS AATAIYCLMG SGQLLWDTIT GVDMAL                466

SEQ ID NO: 214          moltype = AA  length = 466
FEATURE                 Location/Qualifiers
source                  1..466
                        mol_type = protein
                        note = Influenza B virus
                        organism = unidentified
```

```
REGION                  1..466
                        note = B/Malaysia/2506/2004 NA
SEQUENCE: 214
MLPSTIQTLT LFLTSGGVLL SLYVSASLSY LPYSDILLKF PSTEITAPTM PLDCANASNV  60
QAVNRSATKG VTLLLPEPEW TYPRLSCPGS TFQKALLISP HRFGETKGNS APLIIREPFI  120
ACGPKECKHF ALTHYAAQPG GYYNGTRGDR NKLRHLISVK LGKIPTVENS IFHMAAWSGS  180
ACHDGKEWTY IGVDGPDNNA LLKIKYGEAY TDTYHSYANN ILRTQESACN CIGGNCYLMI  240
TDGSASGVSE CRFLKIREGR IIKEIFPTGR IKHTEECTCG FASNKTIECA CRDNSYTAKR  300
PFVKLNVETD TAEIRLMCTE TYLDTPRPDD GSITGPCESN GDKGSGGIKG GFVHQRMASK  360
IGRWYSRTMS KTKRMGMGLY VKYDGDPWAD SDALAFSGVM VSMEEPGWYS FGFEIKDKKC  420
DVPCIGIEMV HDGGKETWHS AATAIYCLMG SGQLLWDTVT GVNMAL                466

SEQ ID NO: 215          moltype = AA  length = 466
FEATURE                 Location/Qualifiers
source                  1..466
                        mol_type = protein
                        note = Influenza B virus
                        organism = unidentified
REGION                  1..466
                        note = B/Brisbane/60/2008 NA
SEQUENCE: 215
MLPSTIQTLT LFLTSGGVLL SLYVSASLSY LLYSDILLKF SPTEITAPTM PLDCANASNV  60
QAVNRSATKG VTLLLPEPEW TYPRLSCPGS TFQKALLISP HRFGETKGNS APLIIREPFI  120
ACGPNECKHF ALTHYAAQPG GYYNGTRGDR NKLRHLISVK LGKIPTVENS IFHMAAWSGS  180
ACHDGKEWTY IGVDGPDNNA LLKVKYGEAY TDTYHSYANK ILRTQESACN CIGGNCYLMI  240
TDGSASGVSE CRFLKIREGR IIKEIFPTGR VKHTEECTCG FASNKTIECA CRDNSYTAKR  300
PFVKLNVETD TAEIRLMCTD TYLDTPRPND GSITGPCESN GDKGSGGIKG GFVHQRMESK  360
IGRWYSRTMS KTERMGMGLY VKYDGDPWAD SDALAFSGVM VSMKEPGWYS FGFEIKDKKC  420
DVPCIGIEMV HDGGKETWHS AATAIYCLMG SGQLLWDTVT GVDMAL                466

SEQ ID NO: 216          moltype = AA  length = 466
FEATURE                 Location/Qualifiers
source                  1..466
                        mol_type = protein
                        note = Influenza B virus
                        organism = unidentified
REGION                  1..466
                        note = B/Colorado/06/2017 NA
SEQUENCE: 216
MLPSTIQTLT LFLTSGGVLL SLYVSASLSY LLYSDILLKF SPTEITAPTM PLDCANASNV  60
QAVNRSATKG VTLLLPEPEW TYPRLSCPGS TFQKALLISP HRFGETKGNS APLIIREPFV  120
ACGPNECKHF ALTHYAAQPG GYYNGTRGDR NKLRHLISVK LGKIPTVENS IFHMAAWSGS  180
ACHDGKEWTY IGVDGPDNNA LLKVKYGEAY TDTYHSYANN ILRTQESACN CIGGNCYLMI  240
TDGSASGVSE CRFLKIREGR IIKEIFPTGR VKHTEECTCG FASNKTIECA CRDNRYTAKR  300
PFVKLNVETD TAEIRLMCTD TYLDTPRPND GSITGPCESD GDKGSGGIKG GFVHQRMKSK  360
IGRWYSRTMS QTERMGMGLY VKYGGDPWAD SDALAFSGVM VSMKEPGWYS FGFEIKDKKC  420
DVPCIGIEMV HDGGKETWHS AATAIYCLMG SGQLLWDTVT GVDMAL                466

SEQ ID NO: 217          moltype = AA  length = 466
FEATURE                 Location/Qualifiers
source                  1..466
                        mol_type = protein
                        note = Influenza B virus
                        organism = unidentified
REGION                  1..466
                        note = B/Washington/02/2019 NA
SEQUENCE: 217
MLPSTIQTLT LFLTSGGVLL SLYVSASLSY LLYSDILLKF SPTEITAPTM PLDCANASNV  60
QAVNRSATKG VTLLLPEPEW TYPRLSCPGS TFQKALLISP HRFGETKGNS APLIIREPFV  120
ACGPNECKHF ALTHYAAQPG GYYNGTRGDR NKLRHLISVK LGKIPTVENS IFHMAAWSGS  180
ACHDGKEWTY IGVDGPDNNA LLKVKYGEAY TDTYHSYANN ILRTQESACN CIGGNCYLMI  240
TDGSASGVSE CRFLKIREGR IIKEIFPTGR VKHTEECTCG FASNKTIECA CRDNRYTAKR  300
PFVKLNVETD TAEIRLMCTD TYLDTPRPND GSITGPCESD GDKGSGGIKG GFVHQRMKSK  360
IGRWYSRTMS KTERMGMGLY VKYGGDPWAD SDALTFSGVM VSMKEPGWYS FGFEIKDKKC  420
DVPCIGIEMV HDGGKETWHS AATAIYCLMG SGQLLWDTVT GVDMAL                466

SEQ ID NO: 218          moltype = AA  length = 466
FEATURE                 Location/Qualifiers
source                  1..466
                        mol_type = protein
                        note = Influenza B virus
                        organism = unidentified
REGION                  1..466
                        note = B/Austria/1359417/2021 NA
SEQUENCE: 218
MLPSTIQTLT LFLTSGGVLL SLYVSASLSY LLYSDILLKF SQTEITAPTM PLDCANASNV  60
QAVNRSATKG ATLLLPEPEW TYPRLSCPGS TFQKALLISP HRFGETKGNS APLIIREPFV  120
ACGPNECKHF ALTHYAAQPG GYYNGTRGDR NKLRHLISVK LGKIPTVENS IFHMAAWSGS  180
ACHDGKEWTY IGVDGPDNNA LLKVKYGEAY TDTYHSYANN ILRTQESACN CIGGNCYLMI  240
```

```
TDGSASGVSE CRFLKIREGR IIKEIFPTGR VKHTEECTCG FASNKTIECA CRDNRYTAKR  300
PFVKLNVETD TAEIRLMCTD TYLDTPRPND GSITGPCESD GDEGSGGIKG GFVHQRMKSK  360
IGRWYSRTMS KTERMGMGLY VKYGGDPWAD SDALVFSGVM ISMKEPGWYS FGFEIKDKKC  420
DVPCIGIEMV HDGGKETWHS AATAIYCLMG SGQLLWDTIT GVDMAL                 466

SEQ ID NO: 219         moltype = AA  length = 466
FEATURE                Location/Qualifiers
source                 1..466
                       mol_type = protein
                       note = Influenza B virus
                       organism = unidentified
REGION                 1..466
                       note = B/Beijing/184/1993 NA
SEQUENCE: 219
MLPSTIQTLT LFLTSGGVLL SLYVSASLSY LLYSDILLKF SPTEITAPTM PLDCANASNV  60
QAVNRSATKG VTLLLPEPEW TYPRLSCPGS TFQKALLISP HRFGETRGNS APLIIREPFI  120
ACGPKECKHF ALTHYAAQPG GYYNGTREDR NKLRHLISVK LGKIPTVENS IFHMAAWSGS  180
ACHDGREWTY IGVDGPDSNA LLKIKYGEAY TDTYHSYANN ILRTQESACN CIGGDCYLMI  240
TDGSASGTSK CRFLKIREGR IIKEIFPTGR VEHTEECTCG FASNKTIECA CRDNNYTAKR  300
PFVKLNVETD AAEIRLMCTE TYLDTPRPDD GSITGPCESN GDKGRGGIKG GFVHQRMASK  360
IGRWYSRTMS KTERMGMELY VKYDGDPWTD SDALALSGVM VSMEEPGWYS FGFEIKDKKC  420
DVPCIGIEMV HDGGKKTWHS AATAIYCLMG SGQLLWDTVT GVDMAL                 466

SEQ ID NO: 220         moltype = AA  length = 466
FEATURE                Location/Qualifiers
source                 1..466
                       mol_type = protein
                       note = Influenza B virus
                       organism = unidentified
REGION                 1..466
                       note = B/Sichuan/379/1999 NA
SEQUENCE: 220
MLPSTIQTLT LFLTSGGVLL SLYVSASLSY LLYSDILLKF SPTEITAPTM PLDCANASNV  60
QAVNRSATKG VTFLLPEPEW TYPRLSCPGS TFQKALLISP HRFGETKGNS APLIIREPFI  120
ACGPKECKHF ALTHYAAQPG GYYNGTREDR NKLRHLISVK LGKIPTVENS IFHMAAWSGS  180
ACHDGKEWTY IGVDGPDSNA LLKIKYGEAY TDTYHSYANN ILRTQESACN CIGGNCYLMI  240
TDGSASGISE CRFLKIREGR IIKEIFPTGR VKHTEECTCG FASNKTIECA CRDNSYTAKR  300
PFVKLNVETD TAEIRLMCTE TYLDTPRPDD GSITGPCESN GDKGSGGIKG GFVHQRMASK  360
IGRWYSRTMS KTKRMGMGLY VKYDGDPWTD SDALALSGVM VSMEEPGWYS FGFEIKDKKC  420
DVPCIGIEMV HDGGKETWHS AATAIYCLMG SGQLLWDTVT GVDMAL                 466

SEQ ID NO: 221         moltype = AA  length = 466
FEATURE                Location/Qualifiers
source                 1..466
                       mol_type = protein
                       note = Influenza B virus
                       organism = unidentified
REGION                 1..466
                       note = B/Shanghai/361/2002 NA
SEQUENCE: 221
MLPSTIQTLT LFLTSGGVLL SLYVSASLSY LLYSDILLKF STTEITAPTM PLDCANASNV  60
QAVNRSATKG VTLLLPEPEW TYPRLSCPGS TFQKALLISP HRFGETKGNS APLIIREPFI  120
ACGPKECKHF ALTHYAAQPG GYYNGTREDR NKLRHLISVK LGKIPTVENS IFHMAAWSGS  180
ACHDGKEWTY IGVDGPDSNA LLKIKYGEAY TDTYHSYANN ILRTQESACN CIGGNCYLMI  240
TDGSASGISE CRFLKIREGR IIKEIFPTGR VKHTEECTCG FASNKTIECA CRDNSYTAKR  300
PFVKLNVETD TAEIRLMCTE TYLDTPRPDD GSITGPCESN GNKGSGGIKG GFVHQRMASK  360
IGRWYSRTMS KTKRMGMGLY VKYDGDPWID SDALALSGVM VSMEEPGWYS FGFEIKDKKC  420
DVPCIGIEMV HDGGKETWHS AATAIYCLMG SGQLLWDTVT GVDMAL                 466

SEQ ID NO: 222         moltype = AA  length = 466
FEATURE                Location/Qualifiers
source                 1..466
                       mol_type = protein
                       note = Influenza B virus
                       organism = unidentified
REGION                 1..466
                       note = B/Florida/4/2006 NA
SEQUENCE: 222
MLPSTIQTLT LFLTSGGVLL SLYVSASLSY LLYSDILLKF SQTEITAPIM PLDCANASNV  60
QAVNRSAAKG VTLLLPEPEW TYPRLSCPGS TFQKALLISP HRFGETKGNS APLIIREPFI  120
ACGPTECKHF ALTHYAAQPG GYYNGTREDR NKLRHLISVK LGKIPTVENS IFHMAAWSGS  180
ACHDGKEWTY IGVDGPDSNA LLKIKYGEAY TDTYHSYAKN ILRTQESACN CIGGDCYLMI  240
TDGPASGISE CRFLKIREGR IIKEIFPTGR VKHTEECTCG FASNKTIECA CRDNSYTAKR  300
PFVKLNVETD TAEIRLMCTE TYLDTPRPND GSITGPCESD GDKGSGGIKG GFVHQRMASK  360
IGRWYSRTMS KTKRMGMGLY VKYDGDPWTD SEALALSGVM VSMEEPGWYS FGFEIKDKKC  420
DVPCIGIEMV HDGGKTTWHS AATAIYCLMG SGQLLWDTVT GVDMAL                 466

SEQ ID NO: 223         moltype = AA  length = 466
FEATURE                Location/Qualifiers
```

```
source                  1..466
                        mol_type = protein
                        note = Influenza B virus
                        organism = unidentified
REGION                  1..466
                        note = B/Wisconsin/1/2010 NA
SEQUENCE: 223
MLPSTIQTLT LFLTSGGVLL SLYVSASLSY LLYSDILLKF SRTEITAPIM PLDCANASNV  60
QAVNRSATKG VTLLLPEPEW TYPRLSCPGS TFQKALLISP HRFGETKGNS APLIIREPFI  120
ACGPKECKHF ALTHYAAQPG GYYNGTREDR NKLRHLISVK LGKIPTVENS IFHMAAWSGS  180
ACHDGREWTY IGVDGPDSNA LLKIKYGEAY TDTYHSYAKN ILRTQESACN CIGGDCYLMI  240
TDGPASGISE CRFLKIREGR IIKEIFPTGR VKHTEECTCG FASNKTIECA CRDNSYTAKR  300
PFVKLNVETD TAEIRLMCTE TYLDTPRPND GSITGPCESN GDKGSGGIKG GFVHQRMASK  360
IGRWYSRTMS KTKRMGMGLY VKYDGDPWTD SEALALSGVM VSMEEPGWYS FGFEIKDKKC  420
DVPCIGIEMV HDGGKTTWHS AATAIYCLMG SGQLLWDTVT GVNMTL                466

SEQ ID NO: 224          moltype = AA  length = 466
FEATURE                 Location/Qualifiers
source                  1..466
                        mol_type = protein
                        note = Influenza B virus
                        organism = unidentified
REGION                  1..466
                        note = B/Massachusetts/2/2012 NA
SEQUENCE: 224
MLPSTIQTLT LFLTSGGVLL SLYVSASLSY LLYSDILLKF SQTEITAPIM PLDCANASNV  60
QAVNHSAAKG VTLLLPEPEW TYPRLSCPGS TFQKALLISP HRFGEIKGNS APLIIREPFI  120
ACGPTECKHF ALTHYAAQPG GYYNGTREDR NKLRHLISVK LGKIPTVENS IFHMAAWSGS  180
ACHDGKEWTY IGVDGPDSNA LLKIKYGEAY TDTYHSYAKN ILRTQESACN CIGGDCYLMI  240
TDGPASGVSE CRFLKIREGR IIKEIFPTGR VKHTEECTCG FASNKTIECA CRDNRYTAKR  300
PFVKLNVETD TAEIRLMCTE TYLDTPRPND GSITGPCESD GDKGSGGIKG GFVHQRMASK  360
IGRWYSRTMS KTKRMGMGLY VKYDGDPWTD SEALALSGVM VSMEEPGWYS FGFEIKDKKC  420
DVPCIGIEMV HDGGKTTWHS AATAIYCLMG SGQLLWDTVT GVDMAL                466

SEQ ID NO: 225          moltype = AA  length = 466
FEATURE                 Location/Qualifiers
source                  1..466
                        mol_type = protein
                        note = Influenza B virus
                        organism = unidentified
REGION                  1..466
                        note = B/Phuket/3073/2013 NA
SEQUENCE: 225
MLPSTIQTLT LFLTSGGVLL SLYVSASLSY LLYSDILLKF SRTEVTAPIM PLDCANASNV  60
QAVNRSATKG VTPLLPEPEW TYPRLSCPGS TFQKALLISP HRFGETKGNS APLIIREPFI  120
ACGPKECKHF ALTHYAAQPG GYYNGTREDR NKLRHLISVK LGKIPTVENS IFHMAAWSGS  180
ACHDGREWTY IGVDGPDSNA LLKIKYGEAY TDTYHSYAKN ILRTQESACN CIGGDCYLMI  240
TDGPASGISE CRFLKIREGR IIKEIFPTGR VKHTEECTCG FASNKTIECA CRDNSYTAKR  300
PFVKLNVETD TAEIRLMCTK TYLDTPRPND GSITGPCESD GDEGSGGIKG GFVHQRMASK  360
IGRWYSRTMS KTKRMGMGLY VKYDGDPWTD SEALALSGVM VSMEEPGWYS FGFEIKDKKC  420
DVPCIGIEMV HDGGKTTWHS AATAIYCLMG SGQLLWDTVT GVNMTL                466

SEQ ID NO: 226          moltype = AA  length = 29
FEATURE                 Location/Qualifiers
source                  1..29
                        mol_type = protein
                        note = Influenza A virus
                        organism = unidentified
REGION                  1..29
                        note = A/Wisconsin/67/2022 (H1N1)pdm09 N1 NA Signal Peptide
SEQUENCE: 226
MNPNQKIITI GSVCMTIGTA NLILQIGNI                                   29

SEQ ID NO: 227          moltype = AA  length = 29
FEATURE                 Location/Qualifiers
source                  1..29
                        mol_type = protein
                        note = Influenza A virus
                        organism = unidentified
REGION                  1..29
                        note = A/Darwin/6/2021 (H3N2) N2 NA Signal Peptide
SEQUENCE: 227
MNPNQKIITI GSVSLTISTI CFFMQIAIL                                   29

SEQ ID NO: 228          moltype = AA  length = 31
FEATURE                 Location/Qualifiers
source                  1..31
                        mol_type = protein
                        note = Influenza B virus
```

```
                        organism = unidentified
REGION                  1..31
                        note = B/Austria/1359417/2021 B/Victoria lineage NA Signal
                         Peptide
SEQUENCE: 228
MLPSTIQTLT LFLTSGGVLL SLYVSASLSY L                                 31

SEQ ID NO: 229          moltype = AA  length = 31
FEATURE                 Location/Qualifiers
source                  1..31
                        mol_type = protein
                        note = Influenza B virus
                        organism = unidentified
REGION                  1..31
                        note = B/Phuket/3073/2013 B/Yamagata lineage NA Signal
                         Peptide
SEQUENCE: 229
MLPSTIQTLT LFLTSGGVLL SLYVSASLSY L                                 31

SEQ ID NO: 230          moltype = AA  length = 440
FEATURE                 Location/Qualifiers
source                  1..440
                        mol_type = protein
                        note = Influenza A virus
                        organism = unidentified
REGION                  1..440
                        note = A/Wisconsin/67/2022 (H1N1)pdm09 N1 NA without SP
SEQUENCE: 230
ISIWVSHSIQ IGNQSQIETC NKSVITYENN TWVNQTFVNI SNTNSAARQS VASVKLAGNS  60
SLCPVSGWAI YSKDNSVRIG SKGDVFVIRE PFISCSPLEC RTFFLTQGAL LNDKHSNGTI  120
KDRSPYRTLM SCPIGEVPSP YNSRFESVAW SASACHDGTN WLTIGISGPD SGAVAVLKYN  180
GIITDTIKSW RNKILRTQES ECACVNGSCF TIMTDGPSDG QASYKIFRIE KGKIIKSVEM  240
KAPNYHYEEC SCYPDSSEIT CVCRDNWHGS NRPWVSFNQN LEYQMGYICS GVFGDNPRPN  300
DKTGSCGPVL SNGANGVKGF SFKYGNGVWI GRTKSISSRK GFEMIWDPNG WTGTDNKFSK  360
KQDIVGINEW SGYSGSFVQH PELTGLNCIR PCFWVELIRG RPEENTIWTS GSSISFCGVD  420
SDIMGWSWPD GAELPFTIDN                                              440

SEQ ID NO: 231          moltype = AA  length = 440
FEATURE                 Location/Qualifiers
source                  1..440
                        mol_type = protein
                        note = Influenza A virus
                        organism = unidentified
REGION                  1..440
                        note = A/Darwin/6/2021 (H3N2) N2 NA without SP
SEQUENCE: 231
ITTVTLHFKQ YEFNSPPNNQ VMLCEPTIIE RNITEIVYLT NTTIEKEICP KPAEYRNWSK  60
PQCGITGFAP FSKDNSIRLS AGGDIWVTRE PYVSCDLDKC YQFALGQGTT LNNVHSNNTV  120
RDRTPYRTLL MNELGVPFHL GTKQVCIAWS SSSCHDGKAW LHVCITGDDK NATASFIYNG  180
RLVDSVVSWS NDILRTQESE CVCINGTCTV VMTDGNATGK ADTKILFIEE GKIVHTSKLS  240
GSAQHVEECS CYPRYPGVRC VCRDNWKGSN RPIIDINIKD HSIVSRYVCS GLVGDTPRKS  300
DSSSSSHCLN PNNEKGDHGV KGWAFDDGND VWMGRTINET SRLGYETFKV VEGWSNPKSK  360
LQINRQVIVD RGDRSGYSGI FSVEGKSCIN RCFYVELIRG RKEETEVLWT SNSIVVFCGT  420
SGTYGTGSWP DGANLSLMHI                                              440

SEQ ID NO: 232          moltype = AA  length = 435
FEATURE                 Location/Qualifiers
source                  1..435
                        mol_type = protein
                        note = Influenza B virus
                        organism = unidentified
REGION                  1..435
                        note = B/Austria/1359417/2021 B/Victoria lineage NA without
                         SP
SEQUENCE: 232
LYSDILLKFS QTEITAPTMP LDCANASNVQ AVNRSATKGA TLLLPEPEWT YPRLSCPGST  60
FQKALLISPH RFGETKGNSA PLIIREPFVA CGPNECKHFA LTHYAAQPGG YYNGTRGDRN  120
KLRHLISVKL GKIPTVENSI FHMAAWSGSA CHDGKEWTYI GVDGPDNNAL LKVKYGEAYT  180
DTYHSYANNI LRTQESACNC IGGNCYLMIT DGSASGVSEC RFLKIREGRI IKEIFPTGRV  240
KHTEECTCGF ASNKTIECAC RDNRYTAKRP FVKLNVETDT AEIRLMCTDT YLDTPRPNDG  300
SITGPCESDG DEGSGGIKGG FVHQRMKSKI GRWYSRTMSK TERMGMGLYV KYGGDPWADS  360
DALVFSGVMI SMKEPGWYSF GFEIKDKKCD VPCIGIEMVH DGGKETWHSA ATAIYCLMGS  420
GQLLWDTITG VDMAL                                                   435

SEQ ID NO: 233          moltype = AA  length = 435
FEATURE                 Location/Qualifiers
source                  1..435
                        mol_type = protein
                        note = Influenza B virus
```

-continued

```
                         organism = unidentified
REGION                   1..435
                         note = B/Phuket/3073/2013 B/Yamagata lineage NA without SP
SEQUENCE: 233
LYSDILLKFS RTEVTAPIMP LDCANASNVQ AVNRSATKGV TPLLPEPEWT YPRLSCPGST  60
FQKALLISPH RFGETKGNSA PLIIREPFIA CGPKECKHFA LTHYAAQPGG YYNGTREDRN  120
KLRHLISVKL GKIPTVENSI FHMAAWSGSA CHDGREWTYI GVDGPDSNAL LKIKYGEAYT  180
DTYHSYAKNI LRTQESACNC IGGDCYLMIT DGPASGISEC RFLKIREGRI IKEIFPTGRV  240
KHTEECTCGF ASNKTIECAC RDNSYTAKRP FVKLNVETDT AEIRLMCTKT YLDTPRPNDG  300
SITGPCESDG DEGSGGIKGG FVHQRMASKI GRWYSRTMSK TKRMGMGLYV KYDGDPWTDS  360
EALALSGVMV SMEEPGWYSF GFEIKDKKCD VPCIGIEMVH DGGKTTWHSA ATAIYCLMGS  420
GQLLWDTVTG VNMTL                                                 435
```

MUTANT INFLUENZA B/VICTORIA LINEAGE VIRUS HEMAGGLUTININ PROTEINS

RELATED APPLICATIONS

This application is a continuation of U.S. application Ser. No. 19/320,264, filed Sep. 5, 2025, which is a continuation of International Patent Application No. PCT/US2024/019210, filed Mar. 8, 2024, which claims the benefit under 35 U.S.C. § 119(e) of U.S. Provisional Application No. 63/489,707, filed Mar. 10, 2023, U.S. Provisional Application No. 63/518,923, filed Aug. 11, 2023, and U.S. Provisional Application No. 63/582,208, filed Sep. 12, 2023, the contents of each of which are incorporated by reference herein in their entirety.

REFERENCE TO AN ELECTRONIC SEQUENCE LISTING

The contents of the electronic sequence listing (M137870260WO00-SEQ-NTJ.xml; Size: 400,770 bytes; and Date of Creation: Mar. 8, 2024) are incorporated by reference herein in their entirety.

BACKGROUND

Respiratory diseases, encompassing a range of conditions affecting the gas exchange organs, pose significant health challenges globally. Among these, seasonal influenza, caused by influenza A and B viruses, is a common affliction with substantial health and economic impacts. The sudden onset of symptoms such as fever, cough, and muscle pain can lead to high levels of absenteeism and productivity losses.

In addition to influenza, other respiratory viruses, such as human coronaviruses and the human Respiratory Syncytial Virus (hRSV), contribute to the burden of respiratory illnesses. Certain strains of coronaviruses are commonly associated with mild to moderate upper respiratory tract infections. Some strains, such as Severe Acute Respiratory Syndrome Coronavirus 2 (SARS-CoV-2), have led to global health crises, as seen with the COVID-19 pandemic.

hRSV, a negative-sense, single-stranded RNA virus, presents another significant concern, particularly in children and older adults. In these populations, hRSV infection can progress to more severe conditions like bronchiolitis or pneumonia.

SUMMARY

Provided are compositions and methods for vaccination against seasonal influenza viruses, and optionally other respiratory viruses including hRSV and SARS-CoV-2. The compositions and methods are based, at least in part, on the finding that certain substitutions in influenza B virus (IBV) hemagglutinin (HA) proteins allows for stabilization of the HA proteins, and consequently improved cell surface expression and immunogenicity. Stabilization was also achieved in influenza A virus (IAV) HA proteins. Such influenza virus HA proteins allow for improved influenza vaccines, such as those containing RNAs (e.g., mRNAs) encoding the influenza virus HA proteins, or other compositions for vaccination (e.g., viral vector or protein-based vaccines).

Accordingly, some aspects relate to an influenza B/Victoria lineage virus hemagglutinin (HA) protein having an amino acid sequence comprising an amino acid substitution relative to a reference influenza B/Victoria lineage virus HA protein amino acid sequence, wherein the influenza B/Victoria lineage virus HA protein comprises one or more of (a)-(s):

(a) a tyrosine at position 381 and a valine at position 288;
(b) a cysteine at position 27 and a cysteine at position 349;
(c) a cysteine at position 295 and a cysteine at position 328;
(d) a cysteine at position 399 and a cysteine at position 473;
(e) a cysteine at position 422 and a cysteine at position 444;
(f) a cysteine at position 118 and a cysteine at position 216;
(g) a cysteine at position 237 and a cysteine at position 261;
(h) a cysteine at position 363 and a cysteine at position 480;
(i) a cysteine at position 364 and a cysteine at position 483;
(j) a cysteine at position 365 and a cysteine at position 476;
(k) a cysteine at position 366 and a cysteine at position 479;
(l) a cysteine at position 367 and a cysteine at position 483;
(m) a cysteine at position 435 and a cysteine at position 428;
(n) a cysteine at position 494 and a cysteine at position 483;
(o) a cysteine at position 494 and a cysteine at position 480;
(p) a proline at position 416, a proline at position 417, a proline at position 434, and a proline at position 433;
(q) a proline at position 434 and a proline at position 433;
® a proline at position 515, and a proline at position 516;
(s) a phenylalanine at position 473;

wherein the positions of (a)-(s) are numbered by alignment of the reference influenza B/Victoria lineage virus HA protein amino acid sequence to SEQ ID NO: 71.

In some embodiments, the influenza B/Victoria lineage virus HA protein comprises one or more of (a)-(s):

(a) H381Y and A288V substitutions;
(b) S27C and Y349C substitutions;
(c) I295C and K328C substitutions;
(d) S399C and H473C substitutions;
(e) L422C and D444C substitutions;
(f) K118C and L216C substitutions;
(g) V237C and D261C substitutions;
(h) G363C and K480C substitutions;
(i) A364C and K483C substitutions;
(j) I365C and A476C substitutions;
(k) A366C and R479C substitutions;
(l) G367C and K483C substitutions;
(m) E435C and A428C substitutions;
(n) N494C and K483C substitutions;
(o) N494C and K480C substitutions;
(p) E416P, L417P, N434P, and H433P substitutions;
(q) N434P and H433P substitutions;
(r) T515P and F516P substitutions; and
(s) an H473F substitution.

In some embodiments, the influenza B/Victoria lineage virus HA protein comprises tyrosine at position 381 and valine at position 288.

In some embodiments, the influenza B/Victoria lineage HA protein comprises H381Y and A288V substitutions.

In some embodiments, the influenza B/Victoria lineage HA protein further comprises one or more of (a)-(r):

(a) S27C and Y349C substitutions;
(b) I295C and K328C substitutions;
(c) S399C and H473C substitutions;
(d) L422C and D444C substitutions;
(e) K118C and L216C substitutions;
(f) V237C and D261C substitutions;
(g) G363C and K480C substitutions;
(h) A364C and K483C substitutions;
(i) I365C and A476C substitutions;
(j) A366C and R479C substitutions;
(k) G367C and K483C substitutions;
(l) E435C and A428C substitutions;
(m) N494C and K483C substitutions;
(n) N494C and K480C substitutions;
(o) E416P, L417P, N434P, and H433P substitutions;
(p) N434P and H433P substitutions;
(q) T515P and F516P substitutions;
(r) an H473F substitution.

In some embodiments, the influenza B/Victoria lineage virus HA protein comprises tyrosine at position 381, valine at position 288, cysteine at position 422, and cysteine at position 444.

In some embodiments, the influenza B/Victoria lineage virus HA protein comprises tyrosine at position 381, valine at position 288, cysteine at position 364, and cysteine at position 483.

In some embodiments, the influenza B/Victoria lineage virus HA protein comprises tyrosine at position 381, valine at position 288, cysteine at position 367, and cysteine at position 483.

In some embodiments, the influenza B/Victoria lineage virus HA protein comprises tyrosine at position 381, valine at position 288, cysteine at position 494, and cysteine at position 483.

In some embodiments, the influenza B/Victoria lineage virus HA protein comprises an amino acid sequence with at least 90% sequence identity to the amino acid sequence of SEQ ID NO: 71.

Some aspects relate to influenza B/Yamagata lineage virus hemagglutinin (HA) protein having an amino acid sequence comprising an amino acid substitution relative to a reference influenza B/Yamagata lineage virus HA protein amino acid sequence, wherein the influenza B/Yamagata lineage virus HA protein comprises one or more of (a)-(i):

(a) a cysteine at position 231 and a cysteine at position 273;
(b) a cysteine at position 295 and a cysteine at position 332;
(c) a cysteine at position 396 and a cysteine at position 510;
(d) a cysteine at position 239 and a cysteine at position 276;
(e) a cysteine at position 367 and a cysteine at position 401;
(f) a cysteine at position 363 and a cysteine at position 404;
(g) a cysteine at position 437 and a cysteine at position 429;
(h) a cysteine at position 451 and a cysteine at position 422; and
(i) a tyrosine at position 381 and a valine at position 290;

wherein the positions of (a)-(i) are numbered by alignment of the reference influenza B/Yamagata lineage virus HA protein amino acid sequence to SEQ ID NO: 70.

In some embodiments, the influenza B/Yamagata lineage virus HA protein comprises one or more of (a)-(i):

(a) A231C and G273C substitutions;
(b) K295C and I332C substitutions;
(c) A396C and L510C substitutions;
(d) V239C and V276C substitutions;
(e) I367C and S401C substitutions;
(f) F363C and E404C substitutions;
(g) E437C and G429C substitutions;
(h) D451C and K422C substitutions; and
(i) H381Y and A290V substitutions.

In some embodiments, the influenza B/Yamagata lineage virus HA protein comprises tyrosine at position 381 and valine substitution at position 290.

In some embodiments, the influenza B/Yamagata lineage virus HA protein comprises cysteine at position 239, cysteine at position 276, cysteine at position 451, and cysteine at position 422.

In some embodiments, the influenza B/Yamagata lineage virus HA protein comprises cysteine at position 367, cysteine at position 401, cysteine at position 451, and cysteine at position 422.

In some embodiments, the influenza B/Yamagata lineage virus HA protein comprises an amino acid sequence with at least 90% sequence identity to the amino acid sequence of SEQ ID NO: 70.

Some aspects relate to an influenza A virus (IAV) H1 hemagglutinin (HA) protein having an amino acid sequence comprising an amino acid substitution relative to a reference IAV H1 HA protein amino acid sequence, wherein the IAV H1 HA protein comprises one or more of (a)-(o):

(a) a cysteine at position 391 and a cysteine at position 37;
(b) a cysteine at position 395 and a cysteine at position 36;
(c) a cysteine at position 461 and a cysteine at position 348;
(d) a proline at position 404 and a proline at position 416;
(e) an isoleucine at position 395 and an isoleucine at position 447;
(f) a glycine at position 456 and an isoleucine at position 402;
(g) a cysteine at position 391, a cysteine at position 37, a proline at position 404, and a proline at position 416;
(h) a cysteine at position 391, a cysteine at position 37, an isoleucine at position 395, and an isoleucine at position 447;
(i) a cysteine at position 391, a cysteine at position 37, a glycine at position 456, and an isoleucine at position 402;
(j) a cysteine at position 395, a cysteine at position 36, a proline at position 404, and a proline at position 416;
(k) a cysteine at position 395, a cysteine at position 36, a glycine at position 456, and an isoleucine at position 402;
(l) a cysteine at position 461, a cysteine at position 348, a proline at position 404, and a proline at position 416;
(m) a cysteine at position 461, a cysteine at position 348, an isoleucine at position 395, and an isoleucine at position 447;
(n) a cysteine at position 461, a cysteine at position 348, a glycine at position 456, and an isoleucine at position 402; and
(o) a cysteine at position 391, a cysteine at position 37, a proline at position 404, a glycine at position 456, and an isoleucine at position 402;

wherein the positions of (a)-(o) are numbered by alignment of the reference IAV H1 HA protein amino acid sequence to SEQ ID NO: 83.

In some embodiments, the IAV H1 HA protein comprises one or more of (a)-(o):

(a) K391C and L37C substitutions;
(b) K395C and V36C substitutions;
(c) N461C and G348C substitutions;
(d) N404P and H416P substitutions;
(e) K395I and E447I substitutions;
(f) D456G and K402I substitutions;
(g) K391C, L37C, N404P, H416P substitutions;
(h) K391C, L37C, K395I, E447I substitutions;
(i) K391C, L37C, D456G, K402I substitutions;
(j) K395C, V36C, N404P, H416P substitutions;
(k) K395C, V36C, D456G, K402I substitutions;
(l) N461C, G348C, N404P, H416P substitutions;
(m) N461C, G348C, K395I, E447I substitutions;
(n) N461C, G348C, D456G, K402I substitutions; and
(o) K391C, L37C, N404P, H416P, D456G, K402I substitutions.

In some embodiments, the IAV H1 HA protein comprises proline at position 404, proline at position 416, cysteine at position 395, and cysteine at position 36.

In some embodiments, the IAV H1 HA protein comprises cysteine at position 456, isoleucine at position 402, cysteine at position 395, and cysteine at position 36.

In some embodiments, the IAV H1 HA protein comprises glycine at position 456, isoleucine at position 402, cysteine at position 395, and cysteine at position 36.

In some embodiments, the IAV H1 HA protein comprises proline at position 404, proline at position 416, cysteine at position 391, and cysteine at position 36.

In some embodiments, the IAV H1 HA protein comprises proline at position 404, proline at position 416, cysteine at position 391, cysteine at position 37, glycine at position 456, and isoleucine at position 402.

In some embodiments, the IAV H1 HA protein comprises an amino acid sequence with at least 90% sequence identity to the amino acid sequence of SEQ ID NO: 83.

Some aspects relate to an influenza A virus (IAV) H1 hemagglutinin (HA) protein having an amino acid sequence comprising an amino acid substitution relative to a reference IAV H1 HA protein amino acid sequence, wherein the IAV H1 HA protein comprises one or more of (a)-(t):

(a) a cysteine at position 410 and a cysteine at position 462;
(b) a cysteine at position 120 and a cysteine at position 419;
(c) a cysteine at position 391 and a cysteine at position 37;
(d) a cysteine at position 395 and a cysteine at position 36;
(e) a cysteine at position 406 and a cysteine at position 430;
(f) a cysteine at position 457 and a cysteine at position 346;
(g) a cysteine at position 461 and a cysteine at position 348;
(h) a proline at position 404 and a proline at position 419;
(i) a proline at position 404 and a proline at position 416;
(j) a proline at position 405 and a proline at position 406;
(k) a proline at position 415 and a proline at position 416;
(l) a tyrosine at position 25 and a glutamate at position 45;
(m) a tyrosine at position 370 and a tryptophan at position 497;
(n) a glycine at position 402, a glycine at position 405, and a glycine at position 407;
(o) an isoleucine at position 395 and an isoleucine at position 447;
(p) a glycine at position 456 and a glycine at position 402;
(q) a cysteine at position 442 and a cysteine at position 423;
(r) a glycine at position 391;
(s) a cysteine at position 410, a cysteine at position 462, a cysteine at position 457, and a cysteine at position 346; and
(t) a cysteine at position 391, a cysteine at position 37, a phenylalanine at position 370, and a phenylalanine at position 455;

wherein the positions of (a)-(t) are numbered by alignment of the reference IAV H1 HA protein amino acid sequence to SEQ ID NO: 95.

In some embodiments, the IAV H1 HA protein comprises one or more of (a)-(t):

(a) V410C and L462C substitutions;
(b) E120C and K419C substitutions;
(c) K391C and L37C substitutions;
(d) K395C and V36C substitutions;
(e) Q406C and D430C substitutions;
(f) S457C and L346C substitutions;
(g) N461C and G348C substitutions;
(h) N404P and K419P substitutions;
(i) N404P and H416P substitutions;
(j) T405P and Q406P substitutions;
(k) N415P and H416P substitutions;
(l) H25Y and H45E substitutions;
(m) H370Y and K497W substitutions;
(n) K402G, T405G, and F407G substitutions;
(o) K395I and E447I substitutions;
(p) D456G and K402I substitutions;
(q) L442C and N423C substitutions;
(r) a K391G substitution;
(s) V410C, L462C, S457C, L346C substitutions; and
(t) K391C, L37C, H370F, H455F substitutions.

In some embodiments, the IAV H1 HA protein comprises cysteine at position 391 and cysteine at position 37.

In some embodiments, the IAV H1 HA protein comprises cysteine at position 395 and cysteine at position 36.

In some embodiments, the IAV H1 HA protein comprises an amino acid sequence with at least 90% sequence identity to the amino acid sequence of SEQ ID NO: 95.

Some aspects relate to an influenza A virus (IAV) H3 hemagglutinin (HA) protein having an amino acid sequence comprising an amino acid substitution relative to a reference IAV H3 HA protein amino acid sequence, wherein the IAV H3 HA protein comprises one or more of (a) (j):

(a) a cysteine at position 40 and a cysteine at position 55;
(b) a cysteine at position 123 and a cysteine at position 421;
(c) a cysteine at position 260 and a cysteine at position 237;
(d) a cysteine at position 392 and a cysteine at position 46;
(e) a cysteine at position 411 and a cysteine at position 428;
(f) a proline at position 402, a proline at position 421, and a proline at position 414;
(g) a glycine at position 403;
(h) a glycine at position 408 and a glycine at position 409;
(i) an isoleucine at position 396; and
(j) an isoleucine at position 219 and a proline at position 504;

wherein the positions of (a)-(j) are numbered by alignment of the reference IAV H3 HA protein amino acid sequence to SEQ ID NO: 82.

In some embodiments, the IAV H3 HA protein comprises one or more of (a)-(j):

(a) T40C and A55C substitutions;
(b) S123C and R421C substitutions;
(c) L260C and P237C substitutions;
(d) Q392C and T46C substitutions;
(e) I411C and Y428C substitutions;
(f) G402P, R421P, and E414P substitutions;
(g) a K403G substitution;
(h) F408G and H409G substitutions;
(i) a K396I substitution; and
(j) T219I and H504P substitutions.

In some embodiments, the IAV H3 HA protein comprises proline at position 402, proline at position 421, and proline at position 414.

In some embodiments, wherein the IAV H3 HA protein comprises an amino acid sequence with at least 90% sequence identity to the amino acid sequence of SEQ ID NO: 82.

In some embodiments, the HA protein is a recombinant protein.

Some aspects relate to a nucleic acid encoding:
(a) the influenza B/Victoria lineage virus HA protein;
(b) the influenza B/Yamagata lineage virus HA protein;
(c) the IAV H1 HA protein; or
(d) the IAV H3 HA protein.

In some embodiments, the nucleic acid is a DNA, a messenger ribonucleic acid (mRNA), a circular ribonucleic acid (RNA), or a self-amplifying ribonucleic acid (saRNA).

Some aspects relate to a viral vector comprising:
(a) the influenza B/Victoria lineage virus HA protein, and/or a nucleic acid encoding the influenza B/Victoria lineage virus HA protein;
(b) the influenza B/Yamagata lineage virus HA protein, and/or a nucleic acid encoding the influenza B/Yamagata lineage virus HA protein;
(c) the IAV H1 HA protein, and/or a nucleic acid encoding the IAV H1 HA protein; and/or
(d) the IAV H3 HA protein, and/or a nucleic acid encoding the IAV H3 HA protein.

Some aspects relate to a vaccine comprising:
(a) the HA protein;
(b) the nucleic acid; or
(c) the viral vector.

In some embodiments, the nucleic acid is mRNA.

Some aspects relate to a messenger ribonucleic acid (mRNA) comprising an open reading frame (ORF) encoding an influenza B/Victoria lineage virus hemagglutinin (HA) protein having an amino acid sequence comprising an amino acid substitution relative to a reference influenza B/Victoria lineage virus HA protein amino acid sequence, wherein the influenza B/Victoria lineage virus HA protein comprises one or more of (a)-(s):
(a) a tyrosine at position 381 and a valine at position 288;
(b) a cysteine at position 27 and a cysteine at position 349;
(c) a cysteine at position 295 and a cysteine at position 328;
(d) a cysteine at position 399 and a cysteine at position 473;
(e) a cysteine at position 422 and a cysteine at position 444;
(f) a cysteine at position 118 and a cysteine at position 216;
(g) a cysteine at position 237 and a cysteine at position 261;
(h) a cysteine at position 363 and a cysteine at position 480;
(i) a cysteine at position 364 and a cysteine at position 483;
(j) a cysteine at position 365 and a cysteine at position 476;
(k) a cysteine at position 366 and a cysteine at position 479;
(l) a cysteine at position 367 and a cysteine at position 483;
(m) a cysteine at position 435 and a cysteine at position 428;
(n) a cysteine at position 494 and a cysteine at position 483;
(o) a cysteine substitution at position 494 and a cysteine at position 480;
(p) a proline at position 416, a proline at position 417, a proline at position 434, and a proline at position 433;
(q) a proline at position 434 and a proline at position 433;
(r) a proline at position 515, and a proline at position 516; and
(s) a phenylalanine at position 473;

wherein the positions of (a)-(s) are numbered by alignment of the reference influenza B/Victoria lineage virus HA protein amino acid sequence to SEQ ID NO: 71.

In some embodiments, the influenza B/Victoria lineage virus HA protein comprises tyrosine at position 381 and valine at position 288.

In some embodiments, the influenza B/Victoria lineage virus HA protein comprises tyrosine at position 381, valine at position 288, cysteine at position 422, and cysteine at position 444.

In some embodiments, the influenza B/Victoria lineage virus HA protein comprises tyrosine at position 381, valine at position 288, cysteine at position 364, and cysteine at position 483.

In some embodiments, the influenza B/Victoria lineage virus HA protein comprises tyrosine at position 381, valine at position 288, cysteine at position 367, and cysteine at position 483.

In some embodiments, the influenza B/Victoria lineage virus HA protein comprises tyrosine at position 381, valine at position 288, cysteine at position 494, and cysteine at position 483.

Some aspects relate to a messenger ribonucleic acid (mRNA) comprising an open reading frame (ORF) encoding an influenza B/Yamagata lineage virus hemagglutinin (HA) protein having an amino acid sequence comprising an amino acid substitution relative to a reference influenza B/Yamagata lineage virus HA protein amino acid sequence, wherein the influenza B/Yamagata lineage virus HA protein comprises one or more of (a)-(i):
(a) a cysteine at position 231 and a cysteine at position 273;
(b) a cysteine at position 295 and a cysteine at position 332;
(c) a cysteine at position 396 and a cysteine at position 510;
(d) a cysteine at position 239 and a cysteine at position 276;
(e) a cysteine at position 367 and a cysteine at position 401;
(f) a cysteine at position 363 and a cysteine at position 404;
(g) a cysteine at position 437 and a cysteine at position 429;
(h) a cysteine at position 451 and a cysteine at position 422; and
(i) a tyrosine at position 381 and a valine at position 290;

wherein the positions of (a)-(i) are numbered by alignment of the reference influenza B/Yamagata lineage virus HA protein amino acid sequence to SEQ ID NO: 70.

In some embodiments, the influenza B/Yamagata lineage virus HA protein comprises tyrosine at position 381 and valine at position 290.

In some embodiments, the influenza B/Yamagata lineage virus HA protein comprises cysteine at position 239, cysteine at position 276, cysteine at position 451, and cysteine at position 422.

In some embodiments, the influenza B/Yamagata lineage virus HA protein comprises cysteine at position 367, cysteine at position 401, cysteine at position 451, and cysteine at position 422.

Some aspects relate to a messenger ribonucleic acid (mRNA) comprising an open reading frame (ORF) encoding an influenza A virus (IAV) H1 hemagglutinin (HA) protein having an amino acid sequence comprising an amino acid substitution relative to a reference IAV H1 HA protein amino acid sequence, wherein the IAV H1 HA protein comprises one or more of (a)-(o):

(a) a cysteine at position 391 and a cysteine at position 37;
(b) a cysteine at position 395 and a cysteine at position 36;
(c) a cysteine at position 461 and a cysteine at position 348;
(d) a proline at position 404 and a proline at position 416;
(e) an isoleucine at position 395 and an isoleucine at position 447;
(f) a glycine at position 456 and an isoleucine at position 402;
(g) a cysteine at position 391, a cysteine at position 37, a proline at position 404, and a proline at position 416;
(h) a cysteine at position 391, a cysteine at position 37, an isoleucine at position 395, and an isoleucine at position 447;
(i) a cysteine at position 391, a cysteine at position 37, a glycine at position 456, and an isoleucine at position 402;
(j) a cysteine at position 395, a cysteine at position 36, a proline at position 404, and a proline at position 416;
(k) a cysteine at position 395, a cysteine at position 36, a glycine at position 456, and an isoleucine at position 402;
(l) a cysteine at position 461, a cysteine at position 348, a proline at position 404, and a proline at position 416;
(m) a cysteine at position 461, a cysteine at position 348, an isoleucine at position 395, and an isoleucine at position 447;
(n) a cysteine at position 461, a cysteine at position 348, a glycine at position 456, and an isoleucine at position 402; and
(o) a cysteine at position 391, a cysteine at position 37, a proline at position 404, a glycine at position 456, and an isoleucine at position 402;

wherein the positions of (a)-(o) are numbered by alignment of the reference IAV H1 HA protein amino acid sequence to SEQ ID NO: 83.

In some embodiments, the IAV H1 HA protein comprises proline at position 404, proline at position 416, cysteine at position 395, and cysteine at position 36.

In some embodiments, the IAV H1 HA protein comprises cysteine at position 456, isoleucine at position 402, cysteine at position 395, and cysteine at position 36.

In some embodiments, the IAV H1 HA protein comprises glycine at position 456, isoleucine at position 402, cysteine at position 395, and cysteine at position 36.

In some embodiments, the IAV H1 HA protein comprises proline at position 404, proline at position 416, cysteine at position 391, and cysteine at position 36.

In some embodiments, the IAV H1 HA protein comprises proline at position 404, proline at position 416, cysteine at position 391, cysteine at position 37, glycine at position 456, and isoleucine at position 402.

Some aspects relate to a messenger ribonucleic acid (mRNA) comprising an open reading frame (ORF) encoding an influenza A virus (IAV) H1 hemagglutinin (HA) protein having an amino acid sequence comprising an amino acid substitution relative to a reference IAV H1 HA protein amino acid sequence, wherein the IAV H1 HA protein comprises one or more of (a)-(t):

(a) a cysteine at position 410 and a cysteine at position 462;
(b) a cysteine at position 120 and a cysteine at position 419;
(c) a cysteine at position 391 and a cysteine at position 37;
(d) a cysteine at position 395 and a cysteine at position 36;
(e) a cysteine at position 406 and a cysteine at position 430;
(f) a cysteine at position 457 and a cysteine at position 346;
(g) a cysteine at position 461 and a cysteine at position 348;
(h) a proline at position 404 and a proline at position 419;
(i) a proline at position 404 and a proline at position 416;
(j) a proline at position 405 and a proline at position 406;
(k) a proline at position 415 and a proline at position 416;
(l) a tyrosine at position 25 and a glutamate at position 45;
(m) a tyrosine at position 370 and a tryptophan at position 497;
(n) a glycine at position 402, a glycine a position 405, and a glycine at position 407;
(o) an isoleucine at position 395 and an isoleucine at position 447;
(p) a glycine at position 456 and a glycine at position 402;
(q) a cysteine at position 442 and a cysteine at position 423;
(r) a glycine at position 391;
(s) a cysteine at position 410, a cysteine at position 462, a cysteine at position 457, and a cysteine at position 346; and
(t) a cysteine at position 391, a cysteine at position 37, a phenylalanine at position 370, and a phenylalanine at position 455;

wherein the positions of (a)-(t) are numbered by alignment of the reference IAV H1 HA protein amino acid sequence to SEQ ID NO: 95.

In some embodiments, the IAV H1 HA protein comprises cysteine at position 391 and cysteine at position 37.

In some embodiments, the IAV H1 HA protein comprises cysteine at position 395 and cysteine at position 36.

Some aspects relate to a messenger ribonucleic acid (mRNA) comprising an open reading frame (ORF) encoding an influenza A virus (IAV) H3 hemagglutinin (HA) protein having an amino acid sequence comprising an amino acid substitution relative to a reference IAV H3 HA protein amino acid sequence, wherein the IAV H3 HA protein comprises one or more of (a)-(j):

(a) a cysteine at position 40 and a cysteine at position 55;
(b) a cysteine at position 123 and a cysteine at position 421;
(c) a cysteine at position 260 and a cysteine at position 237;
(d) a cysteine at position 392 and a cysteine at position 46;

(e) a cysteine at position 411 and a cysteine at position 428;

(f) a proline at position 402, a proline at position 421, and a proline at position 414;

(g) a glycine at position 403;

(h) a glycine at position 408 and a glycine at position 409;

(i) an isoleucine at position 396; and (j) an isoleucine at position 219 and a proline at position 504;

wherein the positions of (a)-(j) are numbered by alignment of the reference IAV H3 HA protein amino acid sequence to SEQ ID NO: 82.

In some embodiments, the IAV H3 HA protein comprises proline at position 402, proline at position 421, and proline at position 414.

Some aspects relate to an mRNA vaccine comprising:

(a) the mRNA encoding the IAV H1 HA protein;

(b) the mRNA encoding the IAV H3 HA protein; and (c) the mRNA encoding the influenza B/Victoria lineage virus HA protein.

In some embodiments, the influenza B/Victoria lineage virus HA protein comprises tyrosine at position 381 and valine at position 288.

In some embodiments, the mRNA vaccine further comprises an additional mRNA encoding an additional IAV H3 HA protein.

In some embodiments, the mRNA vaccine further comprises two or more additional mRNAs, each independently encoding an additional IAV H3 HA protein.

In some embodiments, the mRNA vaccine further comprises the mRNA encoding influenza B/Yamagata lineage virus HA protein of the present disclosure.

In some embodiments, the influenza B/Yamagata lineage virus HA protein comprises tyrosine at position 381 and valine at position 290.

In some embodiments, the mRNA vaccine does not comprise an mRNA encoding an influenza B/Yamagata lineage virus HA protein.

In some embodiments, substantially equal masses of different mRNAs encoding different influenza virus HA proteins are present in the mRNA vaccine.

In some embodiments, the mRNA vaccine further comprises:

(i) a first additional mRNA encoding a first IAV neuraminidase (NA) protein of a first IAV NA subtype;

(ii) a second additional mRNA encoding a second IAV NA protein of a different IAV NA subtype than the first IAV NA subtype; and (iii) a third additional mRNA encoding an influenza B/Victoria lineage virus NA protein.

In some embodiments, the second IAV NA subtype is N2, wherein the mRNA vaccine further comprises an additional mRNA encoding an additional IAV N2 NA protein.

In some embodiments, the second IAV NA subtype is N2, wherein the mRNA vaccine further comprises two or more additional mRNAs each encoding an additional IAV N2 NA protein.

In some embodiments, the mRNA vaccine further comprises an additional mRNA encoding an influenza B/Yamagata lineage virus NA protein.

In some embodiments, the mRNA vaccine does not comprise an mRNA encoding an influenza B/Yamagata lineage virus NA protein.

In some embodiments, substantially equal masses of different mRNAs encoding different influenza virus NA proteins are present in the mRNA vaccine.

In some embodiments, substantially equal masses of (a) mRNAs encoding influenza virus HA proteins, and (b) mRNAs encoding influenza virus NA proteins are present in the mRNA vaccine.

In some embodiments, the mRNA vaccine comprises a 3:1 mass ratio of (a) mRNAs encoding influenza virus HA proteins, to (b) mRNAs encoding influenza virus NA proteins.

In some embodiments, the mRNA vaccine further comprises an mRNA encoding a full-length SARS-CoV-2 Spike (S) glycoprotein comprising one or more proline substitutions relative to SEQ ID NO: 78.

In some embodiments, further comprises an mRNA encoding a protein comprising one or more fragments of a SARS-CoV-2 Spike (S) glycoprotein.

In some embodiments, the one or more fragments comprises a fusion protein comprising (i) an N-terminal domain (NTD) of the SARS-CoV-2 S glycoprotein, (ii) a receptor-binding domain (RBD) of the SARS-CoV-2 S glycoprotein, and (iii) a transmembrane domain.

In some embodiments, the mRNA vaccine further comprises an mRNA encoding a fusion (F) glycoprotein of a human respiratory syncytial virus (hRSV), or a fragment of the hRSV F glycoprotein.

In some embodiments, the mRNA vaccine further comprises a lipid delivery vehicle in contact with the mRNA.

In some embodiments, the lipid delivery vehicle is a lipid nanoparticle comprising 20-60 mol % ionizable lipid, 5-25 mol % non-cationic lipid, 2-4 mol % PEG-modified lipid, and 25-55 mol % sterol.

In some embodiments, the ionizable lipid is a compound of Formula (IL*):

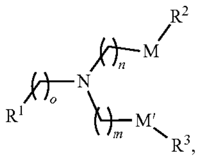

or a salt thereof, wherein:

$R^1$ is —OH, —$NR^N$—$C_{4-10}$ cycloalkenyl optionally substituted with one or more oxo or —$N(R^{N'}R^{N''})$;

$R^N$ is H or $C_{1-6}$ alkyl;

$R^{N'}$ is H or $C_{1-6}$ alkyl;

$R^{N''}$ is H or $C_{1-6}$ alkyl;

is 1, 2, 3, or 4;

n is 4, 5, 6, 7, or 8;

m is 4, 5, 6, 7, or 8;

M is —C(=O)—O—* or —O—C(=O)—*, wherein * indicates attachment to $R^2$;

M' is —C(=O)—O—* or —O—C(=O)—*, wherein * indicates attachment to $R^3$;

$R^2$ is

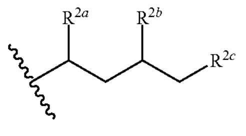

or —($C_{1-6}$ alkylene)-($C_{3-8}$ cycloalkyl)-$C_{1-6}$ alkyl;

$R^{2a}$ is —H or $C_{1-10}$ alkyl;

$R^{2b}$ is —H or $C_{1-10}$ alkyl;

$R^{2c}$ is $C_{1-8}$ alkyl or $C_{2-8}$ alkenyl;
$R^3$ is

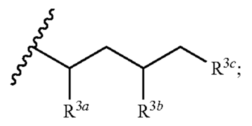

$R^{3a}$ is H or $C_{1-10}$ alkyl;
$R^{3b}$ is H or $C_{1-8}$ alkyl; and
$R^{3c}$ is $C_{1-10}$ alkyl or $C_{2-8}$ alkenyl.

In some embodiments, the ionizable lipid is

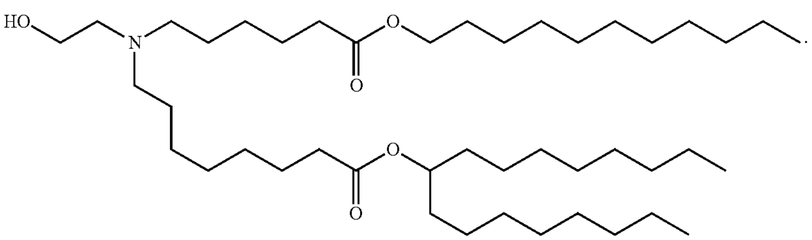

(I-25)

In some embodiments, the ionizable lipid is

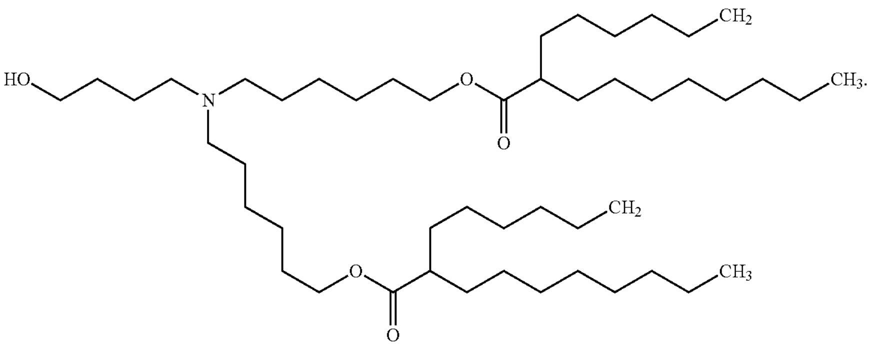

(IL**)

In some embodiments, 0.25 mol % to 1.0 mol % of the PEG-modified lipid is present in a core of the lipid nanoparticle.

In some embodiments, 2.0 mol % to 2.75 mol % of the PEG-modified lipid is not in the core of the lipid nanoparticle.

In some embodiments, the PEG-modified lipid is PEG-DMG or 134-hydroxy-3,6,9,12,15,18,21,24,27,30,33,36,39,42,45,48,51,54,57,60,63,66,69,72,75,78,81,84,87,90,93,96,99,102,105,108,111,114,117,120,123,126,129,132-tetratetracontaoxatetratriacontahectyl stearate.

In some embodiments, each mRNA comprises one or more chemically modified nucleotides.

In some embodiments, each mRNA comprises N1-methylpseudouridine.

In some embodiments, substantially all uracil nucleotides of each mRNA are modified to comprise N1-methylpseudouridine.

In some embodiments, each mRNA comprises 5-methylcytidine and 5-methyluridine.

In some embodiments, substantially all cytosine nucleotides of each mRNA are modified to comprise 5-methylcytidine, and substantially all uracil nucleotides of each mRNA are modified to comprise 5-methyluridine.

Some aspects relate to a method comprising administering the vaccine to a subject.

In some embodiments, the subject has not been vaccinated against an influenza virus for at least 6 months prior to administration of the vaccine.

BRIEF DESCRIPTION OF THE DRAWINGS

FIG. 10A), 5E04 (an H3 HA-specific antibody; FIG. 10B), and 2B06 (an H1 HA-specific antibody, FIG. 10C).

FIG. 12A shows in vitro surface expression levels of proteins expressed by mRNA encoding either wild-type or a mutant protein following staining with polyclonal sera antibodies or CR8059 (an influenza B virus HA-specific antibody). FIG. 12B shows the melting temperature of soluble proteins in PBS for wild-type and mutant proteins. FIG. 12C summarizes selection criteria for each candidate, with a star indicating the best performing mutant on the basis of polyclonal sera antibody binding, CR8059 antibody binding, melting temperature, and trimer formation.

FIG. 13A shows in vitro surface expression levels of proteins expressed by high doses of mRNA (0.5 μg mRNA) encoding either wild-type or a candidate protein following staining with polyclonal sera antibodies, CR8059 mAb (an influenza B virus HA-specific antibody), or mAb 042 (an influenza B virus HA head-specific antibody). FIG. 13B shows in vitro surface expression levels of proteins expressed by low doses of mRNA (0.1 μg mRNA) encoding either wild-type or a mutant protein following staining with polyclonal sera antibodies, CR8059 mAb, or mAb 042. FIG. 13C shows the melting temperature of soluble proteins in PBS for wild-type and mutant proteins.

FIG. 14A shows in vitro surface expression levels of proteins expressed by mRNA encoding either wild-type or a candidate protein following staining with polyclonal sera antibodies, 5E04 mAb (an influenza A virus H3 HA-specific antibody). FIG. 14B shows the melting temperature of soluble proteins in PBS for wild-type and mutant proteins. FIG. 14C summarizes selection criteria for each, with a star indicating the best performing mutant on the basis of polyclonal sera antibody binding, 5E04 binding, melting temperature, and trimer formation.

FIG. 16A shows in vitro surface expression levels of proteins expressed by mRNA encoding either wild-type or a mutant protein following staining with polyclonal sera antibodies, 2B06 mAb (an influenza A virus H1 HA-specific antibody). FIG. 16B shows the melting temperature of soluble proteins in PBS for wild-type and candidate proteins. FIG. 16C summarizes selection criteria for each mutant, with a star indicating the best performing mutant on the basis of polyclonal sera antibody binding, 2B06-binding, melting temperature, and trimer formation.

FIG. 17A shows local reactogenicity events for all participants (LEFT), young adults (18-49 years old; CENTER), or older adults (50-75 years old; RIGHT) receiving 8 study interventions (FLUBLOK®, 4×HA [50 μg], 4×HA/4×NA at 1:1 HA:NA [50, 100, or 150 μg], or 4×HA/4×NA at 3:1 HA:NA [25, 50 or 100 μg]). FIG. 17B shows systemic reactogenicity events for all participants (LEFT), young adults (18-49 years old; CENTER), or older adults (50-75 years old; RIGHT) receiving 8 study interventions (FLUBLOK®, 4×HA [50 μg], 4×HA/4×NA at 1:1 HA:NA [50, 100, or 150 μg], or 4×HA/4×NA at 3:1 HA:NA [25, 50 or 100 μg]). FIG. 17C shows HAI titers against H1N1, H3N2, B/Victoria and B/Yamagata HA proteins as fold-rise at Day 29 relative to Day 1, for participants treated with each study intervention, by administered dosage of HA components. FIG. 17D shows NAI titers against H1N1, H3N2, B/Victoria and B/Yamagata NA proteins as fold-rise at Day 29 relative to Day 1, for participants treated with each study intervention, by administered dosage of NA components. FIG. 17E shows elicited strain-specific hemagglutination and neuraminidase inhibition titers in all participants receiving FLUBLOK®, 4×HA (50 μg), or 4×HA/4×NA at 1:1 HA:NA (50 μg). FIG. 17F shows elicited strain-specific hemagglutination and neuraminidase inhibition titers for participants aged 50-75 years old and receiving FLUBLOK®, 4×HA (50 μg), or 4×HA/4×NA at 3:1 HA:NA (50 μg).

FIGS. 19A-19K show representative alignments of exemplary influenza virus HA protein sequences within IAV HA subtypes and IBV lineages (FIGS. 19A-19D), pairwise alignments demonstrating alignment to identify residues for substitution in other reference HA protein amino acid sequences (FIGS. 19E-19G), and pairwise alignments showing substitutions as present in modified HA protein amino acid sequences (FIGS. 19H-19K). FIG. 19A shows multiple alignment of influenza A/(H1N1)pdm09 HA proteins. FIG. 19B shows multiple alignment of influenza A/(H3N2) HA proteins. FIG. 19C shows multiple alignment of influenza B/Victoria lineage virus HA proteins. FIG. 19D shows multiple alignment of influenza B/Yamagata lineage virus HA proteins. FIG. 19E shows pairwise alignment of influenza B/Brisbane/60/2008 (B/Victoria lineage) virus and influenza B/Austria/1359417/2021 (B/Victoria lineage) virus HA protein amino acid sequence of SEQ ID NOs: 157 and 71, respectively, with highlighting indicating residues H381 and A288 of SEQ ID NO: 71 and corresponding residues (after alignment) H384 and A291 of SEQ ID NO: 157. FIG. 19F shows pairwise alignment of influenza A/Beijing/262/1995(H1N1) virus and influenza A/Wisconsin/67/2022(H1N1)pdm09 virus HA protein amino acid sequences of SEQ ID NOs: 123 and 83, respectively, with highlighting indicating residues L37 and K391 of SEQ ID NO: 83 and corresponding residues (after alignment) L37 and G390 of SEQ ID NO: 123. FIG. 19G shows pairwise alignment of influenza B/Austria/1359417/2021 virus HA protein with (SEQ ID NO: 71) and without (SEQ ID NO: 174) the signal peptide. FIG. 19H shows alignment of an IAV H1 HA protein comprising K391C and L37C substitutions, as present in SEQ ID NO: 94, relative to the influenza A/Wisconsin/67/2022(H1N1)pdm09 virus HA protein amino acid sequence of SEQ ID NO: 83. FIG. 19I shows alignment of an IAV H3 HA protein comprising G402P, R421P, and E414P substitutions, as present in SEQ ID NO: 91, relative to the influenza A/Darwin/6/2021(H3N2) virus HA protein amino acid sequence of SEQ ID NO: 82. FIG. 19J shows alignment of an influenza B/Victoria lineage HA protein comprising H381Y, A288V, N494C, and K483C substitutions, as present in SEQ ID NO: 87, relative to the influenza B/Austria/1359417/2021 virus HA protein amino acid sequence of SEQ ID NO: 71. FIG. 19K shows alignment of an influenza B/Yamagata lineage HA protein comprising V239C, V276C, D451C, and K422C substitutions, as present in SEQ ID NO: 85, relative to the influenza B/Phuket/1359417/2021 virus HA protein amino acid sequence of SEQ ID NO: 70.

DETAILED DESCRIPTION

Figure 1A:
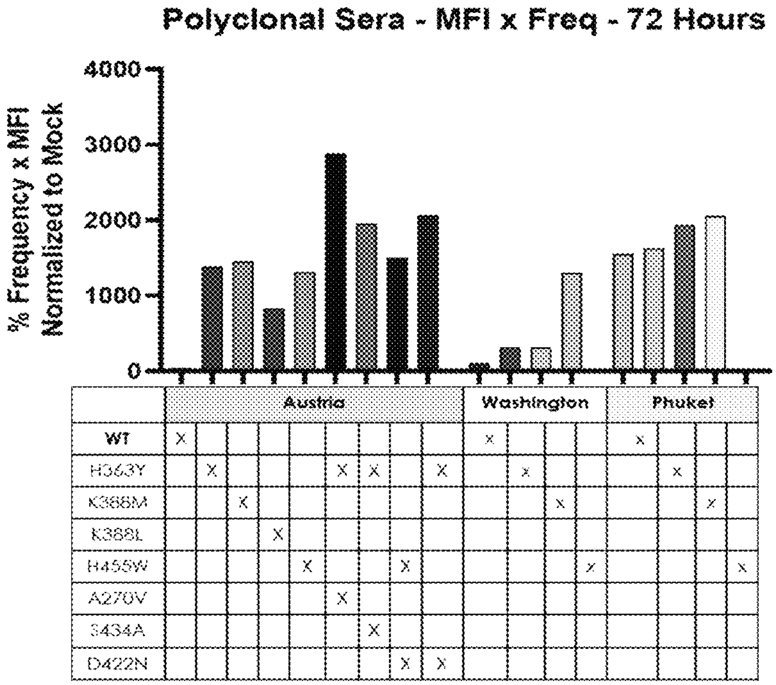
FIG. 1A is graph showing polyclonal sera antibody binding in vitro to protein expressed by mRNA encoding mutated influenza B virus hemagglutinin at 72 hours post-transfection into cells with transIT at 250 ng mRNA/$1\times10^6$ cells. Substitutions in FIG. 1A are numbered according to post-cleavage forms of the HA proteins.

Respiratory viruses are common agents of disease, having a significant impact on morbidity and mortality worldwide. Vaccines to respiratory viruses are designed to stimulate an immune response protective against the viruses. Various types of vaccines exist, including nucleic acid vaccines (e.g., DNA, and RNA such self-amplifying RNA or mRNA vaccines) that use the genetic instructions for antigenic polypeptide production to stimulate the immune response. Protein-based vaccines use an antigenic polypeptide or fragment thereof, either from inactivated viruses or purified subunits. Live attenuated vaccines use weakened live viruses comprising or encoding the antigenic polypeptide(s), while viral vector vaccines employ a virus to deliver the antigenic polypeptide(s) and/or nucleic acid(s) encoding the antigenic polypeptide(s) to cells. Mutations to stabilize the antigenic polypeptide(s) can enhance the effectiveness of these diverse types of vaccines, leading to improved immune responses and protection against the viruses. Some aspects relate to compositions and methods with improved vaccine efficacy, e.g., due to increased stability of the viral antigens. Preferred compositions comprise mRNA vaccines.

Seasonal Influenza Virus

Seasonal influenza is a contagious respiratory illness caused by influenza viruses, which can lead to annual epidemics with symptoms ranging from mild to severe, and potentially causing complications, particularly in high-risk groups. Without being bound by theory, influenza viruses are believed to spread through respiratory droplets and aerosols, but can also spread through contact with surfaces (fomites). Upon entering the respiratory tract, virions attach to cells via hemagglutinin (HA) proteins, which bind to sialic acid receptors on the cell surface. Virions then enter the cell, where they replicate and produce new virions that bud from the cell membrane. NA proteins on the virion surface cleave sialic acid from the cell surface, leading to release of free virions that may then infect other cells. This process continues until the immune system can clear the infection.

Influenza viruses belong to the Orthomyxoviridae family and are categorized into types A, B, C, and D. Among these, influenza A and B viruses are of significant concern for human health.

Influenza A viruses (IAVs) can be further classified based on two surface proteins, hemagglutinin (sometimes referred to as H or HA) and neuraminidase (sometimes referred to as N or NA). There are 18 known HA subtypes and 11 known N subtypes. However, only H1, H2, and H3, and N1 and N2 subtypes (e.g., A/(H1N1); A(H1N2); A(H2N2); and A(H3N2)) have caused widespread human disease. The genetic diversity of influenza A viruses, due to frequent mutation and reassortment, can result in novel strains with pandemic potential.

Influenza B viruses (IBVs) are not divided into subtypes, but can be broken down into lineages and strains within those lineages. Currently, two lineages circulate in humans: B/Yamagata (e.g., B/Yamagata/16/1988-like) and B/Victoria (e.g., B/Victoria/2/1987-like).

Non-exhaustive lists of A/(H1N1) subtype, A/(H3N2) subtype, B/Victoria lineage, and B/Yamagata lineage isolates are provided in Table IV-1.

A key challenge in influenza control through vaccination is rapid evolution of the viruses, which can alter their antigenic properties and result in evasion of pre-existing immunity (e.g., through infection with, or vaccination with, previously circulating strains). This necessitates regular updates to influenza vaccines to match currently circulating strains. Yet, stability deficiencies associated with vaccine antigens can limit the efficacy of such strain-matched vaccines. Thus, some aspects relate to compositions and methods that improve the stability of influenza virus antigenic polypeptides.

An influenza virus HA protein may comprise one or more mutations relative to a reference influenza virus HA protein. In the context of proteins having one or more mutations (e.g., substitutions), a "reference protein" (e.g., reference HA protein) refers to a protein into which a mutation is introduced to yield a protein having the mutation.

A reference HA protein may be an HA protein of an influenza virus isolate. An "influenza virus isolate" or "isolate of an influenza virus" refers to an influenza virus that has been obtained from an infected host and grown in cell culture. Amino acid sequences of proteins of a virus isolate (e.g., HA) may be determined by sequencing the isolate's genome segments (e.g., segment 4) and/or viral RNA from cells infected with the isolate. As used herein, a reference HA protein amino acid sequence of an influenza virus isolate is the HA protein amino acid sequence encoded by a consensus nucleotide sequence of segment 4 of the isolate. The skilled artisan will appreciate that a replicating virus (e.g., in cell culture) forms a population of virions, that each virion contains a genome that may have one or more mutations relative to a consensus nucleotide sequence (or set of consensus nucleotide sequences, for viruses with segmented genomes like influenza viruses), and that viral genomes may be defined in terms of that consensus nucleotide sequence (or set of consensus nucleotide sequences of genome segments, for segmented viral genomes). See, e.g., Domingo et al., *Gene.* 1985. 40(1):1-8; and Kuroda et al., *PLoS ONE.* 2010. 5(4):e10256. A reference HA protein amino acid sequence of an isolate will be understood not to encompass HA protein amino sequences that are not encoded by the consensus nucleotide sequence of genome segment 4 of the isolate, even if such other HA protein amino acid sequences may be encoded by a minority of genomes in a virion population of the isolate. A reference HA protein may be an engineered HA protein that is not encoded by a consensus nucleotide sequence of genome segment 4 of a naturally occurring influenza virus isolate.

The skilled artisan will appreciate that mutations may be applied to any B/Victoria lineage HA protein, B/Yamagata lineage HA protein, H1 HA protein, or H3 HA protein amino acid sequence that is extant at the time this specification is filed. The skilled artisan will also appreciate that the mutations may be applied to B/Victoria lineage HA protein, B/Yamagata lineage HA protein, H1 HA protein, or H3 HA protein amino acid sequences that do not yet exist at the time of filing this specification. Indeed, it is the continued evolution of influenza viruses that leads public health authorities to update the influenza virus isolates recommended for inclusion in seasonal vaccines each year. Thus, when a given influenza virus isolate is recommended for inclusion in a seasonal influenza vaccine, for instance, the skilled artisan could apply a mutation described below to the HA protein of that influenza virus isolate, to produce a mutated form of that recommended isolate's HA protein.

Recommendations for candidate vaccine viruses are typically made annually by the World Health Organization (WHO), following review of surveillance data and discussion of candidate vaccine viruses, which typically occurs early in the calendar year (e.g., February). World Health Organization. (2023 Feb. 24). Recommended composition of influenza virus vaccines for use in the 2023-2024 northern hemisphere influenza season: Questions and answers.

For example, the WHO recommended the following viruses for inclusion in vaccines to be used in the 2023-2024 northern hemisphere influenza season:

Egg-Based Vaccines:
- an A/Victoria/4897/2022(H1N1)pdm09-like virus;
- an A/Darwin/9/2021(H3N2)-like virus; and
- a B/Austria/1359417/2021 (B/Victoria lineage)-like virus.

Cell Culture- or Recombinant-Based Vaccines:
- an A/Wisconsin/67/2022(H1N1)pdm09-like virus;
- an A/Darwin/6/2021(H3N2)-like virus; and
- a B/Austria/1359417/2021 (B/Victoria lineage)-like virus. Id.

For quadrivalent vaccines of any (egg, cell culture-, or recombinant-based) type, the WHO recommended inclusion of a B/Phuket/3073/2013 (B/Yamagata lineage)-like virus as the B/Yamagata lineage component. Id. Regarding the term "-like virus", recommended vaccine viruses are representative of the antigenic group of viruses anticipated to circulate widely in the forthcoming influenza season, and that multiple candidate vaccine viruses may be available that possess HA proteins that are antigenically similar to the recommended vaccine viruses. Id. The term "-like virus" is included in recommendations to allow for use of other candidate vaccine viruses in manufacturing. Id.

Sequence information for influenza viruses recommended for inclusion in seasonal influenza vaccines (e.g., HA and NA protein amino acid sequences and corresponding genome segment nucleotide sequences) is typically available in publicly available databases, such as GenBank and GISAID.

The skilled artisan will appreciate that mutations described in the context of H1 HA proteins may be applied to extant or later-arising H1 HA proteins, mutations described in the context of H3 HA proteins may be applied to extant or later-arising H3 HA proteins, mutations described in the context of B/Victoria lineage HA proteins may be applied to extant or later-arising B/Victoria lineage HA proteins, and mutations described in the context of B/Yamagata lineage HA proteins may be applied to extant or later-arising B/Yamagata lineage HA proteins, as HA proteins within a given subtype or lineage are more similar to each other than to HA proteins of other subtypes or lineages.

At the time of filing of the instant specification, seasonal influenza vaccines are quadrivalent and intended to elicit immunity to an influenza A/(H1N1)pdm09 virus, an influenza A/(H3N2) virus, an influenza B/Victoria lineage virus, and an influenza B/Yamagata lineage virus. However, reassortment between influenza A viruses may result in the formation of novel IAVs that go on to predominate in the population, replacing the predominantly circulating influenza A/(H1N1)pdm09 and A/(H3N2) subtypes. The skilled artisan will appreciate that where mutations are disclosed in the context of H1 HAs of influenza A/(H1N1)pdm09 viruses (e.g., influenza A/Wisconsin/67/2022(H1N1)pdm09 and A/Sydney/5/2021(H1N1)pdm09 viruses), such mutations may also be applied to H1 HA proteins of other IAV subtypes containing H1 HAs (e.g., A/(H1N2). Mutations disclosed in the context of H3 HAs of influenza A/(H3N2) viruses (e.g., influenza A/Darwin/6/2021(H3N2) virus) may similarly be applied to H3 HA proteins of other IAV subtypes containing H3 HAs (e.g., A/(H3N8)).

Influenza virus HA proteins are discussed below in the section entitled "Influenza Virus HA Proteins". Those skilled in the art will appreciate that influenza virus proteins discussed therein are useful in multiple types of vaccine compositions. In some embodiments, the composition comprises one or more influenza virus proteins. In some embodiments, the composition comprises one or more nucleic acids (e.g., mRNAs) encoding one or more influenza virus proteins. These and other vaccine compositions are discussed below in the section entitled "Vaccine Compositions."

Thus, discussion of influenza virus proteins can also be applied to nucleic acids encoding said influenza virus proteins and vice versa unless otherwise clear from context. Thus, disclosure related to particular polypeptide mutations is also relevant to nucleic acids encoding those polypeptides with those mutations, unless otherwise clear from context. Likewise, disclosure related to mRNA encoding mutated influenza virus proteins may also be relevant to the mutated influenza virus proteins. Thus, when a composition comprising an mRNA encoding an influenza virus protein having a particular mutation is disclosed, the skilled artisan can infer that the influenza virus protein per se, and compositions comprising the influenza virus protein, are also disclosed. In some embodiments, an influenza virus protein is a recombinant protein. A "recombinant protein" refers to a protein that is produced in a heterologous organism that does not naturally produce the protein or a variant thereof. Non-limiting examples of organisms in which recombinant proteins may be produced include bacteria (e.g., *Escherichia coli*), yeast (e.g., *Saccharomyces cerevisiae*), and mammalian cells.

TABLE IV-1

Exemplary IAV and IBV isolates

| Subtype (IAV) or lineage (IBV) | Isolate | SEQ ID NO. of HA protein amino acid sequence | SEQ ID NO. of NA protein amino acid sequence |
|---|---|---|---|
| A/(H1N1) subtype | A/Beijing/262/1995 (H1N1) | 122 | 180 |
| | A/New Caledonia/20/1999 (H1N1) | 123 | 181 |
| | A/Solomon Islands/3/2006 (H1N1) | 124 | 182 |
| | A/Brisbane/59/2007 (H1N1) | 125 | 183 |
| | A/California/7/2009 (H1N1)pdm09 | 127 | 185 |
| | A/Michigan/45/2015 (H1N1)pdm09 | 128 | 186 |
| | A/Brisbane/02/2018 (H1N1)pdm09 | 129 | 187 |
| | A/Guangdong-Maonan/SWL1536/2019 (H1N1)pdm09 | 130 | 188 |
| | A/Hawaii/70/2019 (H1N1)pdm09 | 131 | 189 |
| | A/Victoria/2570/2019 (H1N1)pdm09 | 132 | 190 |
| | A/Wisconsin/588/2019 (H1N1)pdm09 | 133 | 191 |
| | A/Victoria/4897/2022 (H1N1)pdm09 | 134 | 192 |
| | A/Wisconsin/67/2022 (H1N1)pdm09 | 135 | 193 |
| A/(H3N2) subtype | A/Sydney/5/97 (H3N2) | 136 | 194 |
| | A/Moscow/10/1999 (H3N2) | 137 | 195 |
| | A/Fujian/411/2002 (H3N2) | 138 | 196 |
| | A/California/7/2004 (H3N2) | 139 | 197 |
| | A/Wisconsin/67/2005 (H3N2) | 140 | 198 |
| | A/Brisbane/10/2007 (H3N2) | 141 | 199 |
| | A/Perth/16/2009 (H3N2) | 142 | 200 |
| | A/Victoria/361/2011 (H3N2) | 143 | 201 |
| | A/Texas/50/2012 (H3N2) | 144 | 202 |
| | A/Switzerland/9715293/2013 (H3N2) | 145 | 203 |
| | A/Hong Kong/4801/2014 (H3N2) | 146 | 204 |
| | A/Singapore/INFIMH-16-0019/2016 (H3N2) | 147 | 205 |
| | A/Kansas/14/2017 (H3N2) | 148 | 206 |
| | A/Hong Kong/2671/2019 (H3N2) | 149 | 207 |
| | A/Hong Kong/45/2019 (H3N2) | 150 | 208 |
| | A/Cambodia/e0826360/2020 (H3N2) | 151 | 209 |
| | A/Darwin/9/2021 (H3N2) | 152 | 210 |
| | A/Darwin/6/2021 (H3N2) | 153 | 211 |
| B/Victoria lineage | B/Shangdong/7/1997 | 154 | 212 |
| | B/Hong Kong/330/2001 | 155 | 213 |
| | B/Malaysia/2506/2004 | 156 | 214 |
| | B/Brisbane/60/2008 | 157 | 215 |
| | B/Colorado/06/2017 | 158 | 216 |
| | B/Washington/02/2019 | 159 | 217 |
| | B/Austria/1359417/2021 | 160 | 218 |
| B/Yamagata lineage | B/Beijing/184/1993 | | 219 |
| | B/Sichuan/379/1999 | | 220 |
| | B/Shanghai/361/2002 | | 221 |
| | B/Florida/4/2006 | 164 | 222 |
| | B/Wisconsin/1/2010 | 165 | 223 |
| | B/Massachusetts/2/2012 | 166 | 224 |
| | B/Phuket/3073/2013 | 167 | 225 |

Influenza Virus HA Proteins

It was surprisingly discovered that influenza virus HA proteins having one or more mutations (such as a substitution) relative to a wild-type HA protein sequence exhibit increased stability, surface expression, and/or immunogenicity as compared to the wild-type influenza virus HA protein. Without being bound by theory, it is believed that such mutations in influenza virus HA proteins can stabilize the conformation of the HA proteins.

Mutations that may be applied to influenza virus HA proteins are described in Tables HA-1 to HA-5 below. For clarity, mutations are described using amino acid numbering corresponding to specific listed HA amino acid sequences (e.g., of recent vaccine strains A/Wisconsin/67/2022 (H1N1) pdm09 (SEQ ID NO: 83), A/Darwin/6/2021(H3N2) (SEQ ID NO: 82), B/Austria/1359417/2021 (B/Victoria lineage) (SEQ ID NO: 71), and B/Phuket/3073/2013 (B/Yamagata lineage) (SEQ ID NO: 70), and additional strain A/Sydney/5/2021(H1N1)pdm09 (SEQ ID NO: 95)). The person of ordinary skill in the art will appreciate that mutations disclosed in relation to a listed HA amino acid sequence may be applied to other HA amino acid sequences of that IAV HA subtype (e.g., H1, H3), or other HA amino acid sequences of that IBV lineage (i.e., B/Victoria or B/Yamagata lineage). To apply a mutation disclosed with numbering corresponding to a listed amino acid sequence (e.g., SEQ ID NO: 71) to a different reference HA protein, the skilled artisan may align that different reference HA protein's amino acid sequence to the listed amino acid sequence with which the mutation is numbered. For example, to apply an H381Y substitution numbered according to SEQ ID NO: 71 (the listed amino acid sequence), to a reference HA protein, the skilled artisan would align the reference HA protein amino acid sequence to SEQ ID NO: 71, and introduce a tyrosine (Y) at the residue of the reference HA protein that corresponds to H381 of SEQ ID NO: 71. An example of such an alignment is presented in FIG. 19E, the influenza B/Brisbane/60/2008 virus HA protein amino acid sequence of SEQ ID NO: 157, showing that residue H384 of SEQ ID NO: 157 aligns to residue H381 of SEQ ID NO: 71. Accordingly, to apply an H381Y substitution (or tyrosine substitution at position 381 generally) to SEQ ID NO: 157, the skilled artisan would replace residue 384 of SEQ ID NO: 157 with a tyrosine, because residue 384 of SEQ ID NO: 157 aligns to H381 of SEQ ID NO: 71. Another example is presented in FIG. 19F, showing alignment of the influenza A/Beijing/262/1995 (H1N1) virus HA protein amino acid sequence of SEQ ID NO: 123 to the influenza A/Wisconsin/62/2022(H1N1) pdm09 virus HA protein amino acid sequence. While both SEQ ID NOs: 123 and 83 contain an L37 residue, residue G390 of SEQ ID NO: 123 aligns to K391 of SEQ ID NO: 83. Thus, to apply a K391C substitution (numbered according to SEQ ID NO: 83) to the amino acid sequence of SEQ ID NO: 123, the skilled artisan would replace G390 of SEQ ID NO: 123 with a cysteine (C), because G390 aligns to K391 of SEQ ID NO: 83.

An Influenza virus HA protein may comprise one or more substitutions relative to a reference HA protein. For example, an influenza B/Victoria lineage virus HA protein having the amino acid sequence of SEQ ID NO: 77 comprises a tyrosine substitution and a valine substitution relative to the reference influenza B/Victoria lineage virus HA protein sequence of SEQ ID NO: 71. The skilled artisan will appreciate the substitutions disclosed in relation to a listed amino acid sequence (e.g., SEQ ID NO: 71) may be referred to in the form $X_1[\#]X_2$, where $X_1$ is the amino acid at position [#] in a listed amino acid sequence, and $X_2$ is the amino acid introduced by replacement of the $X_1$ at position [#]. For example, a tyrosine substitution at position 381 may also be referred to as an H381Y substitution, when using SEQ ID NO: 71 as a listed amino acid sequence, because the histidine (H) at position 381 of SEQ ID NO: 71 is replaced with a tyrosine (Y). Such a substitution may also be referred to as an "$X_2$ substitution at position [#]", meaning that a protein comprises an $X_2$ residue at position [#] (numbered by alignment to a listed sequence), regardless of whether the residue that was present at position [#] in the reference amino acid sequence was $X_1$, or a different residue other than $X_2$. The skilled artisan will understand that substitutions disclosed in the form $X_1[\#]X_2$ may also be applied to a reference amino acid sequence in the form of "$X_2$ substitution at position [#]" that is agnostic to the residue present in the reference amino acid sequence (numbered by alignment to a listed sequence). While the preceding paragraph uses SEQ ID NO: 71 (HA protein of influenza B/Austria/1359417/2021 (B/Victoria lineage) virus) as a reference HA protein amino acid sequence, a reference HA protein may be an HA protein of another influenza virus isolate, or an engineered HA protein that is not encoded by a genome of an isolate.

An influenza virus HA protein may comprise a specified residue at a specified position, with positions being numbered according to a listed amino acid sequence (e.g., SEQ ID NO: 71). As with determining the positions of substitutions numbered according to a listed amino acid sequence, the skilled artisan may align the HA protein sequence to the listed amino acid sequence, to determine whether the HA protein contains the specified residue at that position corresponding to the specified position of the listed amino acid sequence. For example, to determine whether an HA protein contains a tyrosine at position 381 and a valine at position 288, where the positions are numbered by alignment to SEQ ID NO: 71, the skilled artisan would align the amino acid sequence of the HA protein to SEQ ID NO: 71, determine whether the amino acid of the HA protein that aligns to residue 381 of SEQ ID NO: 71 is a tyrosine, and determine whether the amino acid of the HA protein that aligns to residue 288 of SEQ ID NO: 71 is a valine.

Unless otherwise clear from context, mutations in the instant specification are numbered according to full-length amino acid sequences of influenza virus HA proteins (e.g., SEQ ID NOs: 70, 71, 82, 83, and 95), each of which includes the signal peptide of the HA protein (i.e., residue 1 of each sequence is the methionine encoded by the start codon of an ORF encoding the HA protein). The person of ordinary skill will understand that other numbering schemes exist for reference to other forms or subunits of an HA protein, such as a post-signal peptide cleavage form (where residue 1 is the N-terminal amino acid after signal peptide cleavage). For instance, the skilled artisan will understand that reference to A270V+H363Y substitutions in influenza B/Austria/1359417/2021 virus HA protein would correspond to A288V+H381Y of SEQ ID NO: 71, because SEQ ID NO: 71 includes the signal peptide protein at its N-terminus, and after including that signal peptide, the A and H residues separated by 93 amino acids are found at positions 288 and 381 of SEQ ID NO: 71, respectively.

Some embodiments relate to HA proteins comprising one or more mutations selected from: (i) one or more introduced cysteines, where a disulfide bond is formed by at least one of the introduced cysteines; (ii) one or more proline or glycine substitutions in a B loop of the HA protein; (iii) one or more substitutions of a charged or polar cavity-lining residue with a hydrophobic residue; (iv) one or more substitutions of a pH-sensitive histidine in the HA protein; and/or (v) a mutation in, or removal of, a polybasic cleavage site of the HA protein.

In some embodiments, an HA protein comprises one or more substitutions of a pH-sensitive histidine in the HA protein and one or more substitutions of a charged or polar cavity-lining residue with a hydrophobic residue.

In some embodiments, an HA protein comprises an interprotomer disulfide bond formed by at least one introduced cysteine, and one or more proline substitutions in the B loop.

In some embodiments, an HA protein comprises an interprotomer disulfide bond formed by at least one introduced cysteine, and one or more substitutions of a charged or polar cavity-lining residue with a hydrophobic residue.

In some embodiments, an HA protein comprises an interprotomer disulfide bond formed by at least one introduced cysteine, one or more substitutions of a charged or polar cavity-lining residue with a hydrophobic residue, and one or more proline substitutions in the B loop.

In some embodiments, an HA protein comprises an interprotomer disulfide bond formed by at least one introduced cysteine, and an intraprotomer disulfide bond formed by at least one introduced cysteine, where the introduced cysteine(s) of the interpromoter disulfide bond are at different positions than the introduced cysteine(s) of the intraprotomer disulfide bond.

In some embodiments, an HA protein comprises an interprotomer disulfide bond formed by at least one introduced cysteine, and one or more substitutions of a pH-sensitive histidine in the HA protein and one or more substitutions of a charged or polar cavity-lining residue with a hydrophobic residue.

In some embodiments, an HA protein comprises one or more cysteine substitutions, such that a disulfide bond is formed between the introduced cysteines. In some embodiments, the disulfide bond is an interprotomer disulfide bond, which covalently links two protomers of an HA protein containing multiple protomers (e.g., three protomers). In some embodiments, the disulfide bond is an intraprotomer disulfide bond, which covalently links two residues of a single protomer of the HA protein. In some embodiments, the disulfide bond is in the head region (also referred to as the "globular head", "head", or HA1 subunit) of the HA protein. In some embodiments, the disulfide bond is in the stalk region (also referred to as the "stem", "stalk", or HA2 subunit) of the HA protein. Translation of an open reading frame encoding a full-length HA protein sequence produces a precursor HA0 polypeptide, which is then cleaved (e.g., by a serine protease) to produce an HA1 subunit (N-terminal to the cleavage site) and HA2 subunit (C-terminal to the cleavage site), which are connected by a disulfide bond. See, e.g., Wang et al., *J Virol.* 89(20):10602-10611. The positions of cleavage sites in IAV H1 HA, IAV H3 HA, influenza B/Victoria lineage virus HA, and influenza B/Yamagata lineage HA proteins are known in the art, allowing the skilled artisan to identify the residues of a given reference full-length HA protein sequence that correspond to HA1 and HA2 subunits of that reference HA protein.

In some embodiments, an HA protein comprises one or more proline substitutions in the B loop of the HA protein. In some embodiments, an HA protein comprises one or more glycine substitutions in the B loop of the HA protein. HA proteins comprise multiple subdomains, including a B loop, which enables the fusion of the viral envelope and endosomal membrane. Proline and glycine are among residues considered helix breakers, such that the introduction of proline or glycine residues can stabilize or destabilize proteins by altering their conformation (Lyu et al. 1990. *Science.* 250(4981), 669-673). In some embodiments, an HA protein comprises 2, 3, or 4 proline substitutions in the B loop. The location of the B loop in IAV H1 HA, IAV H3 HA, influenza B/Victoria lineage virus HA, and influenza B/Yamagata lineage HA proteins are known in the art, allowing the skilled artisan to identify the residues of a given reference full-length HA protein sequence that correspond to the B loop of that reference HA protein. See, e.g., Mair et al., *Biochim Biophys Acta.* 2014. 1838(4):1153-1168.

In some embodiments, an HA protein comprises one or more substitutions of a pH-sensitive histidine residue. The protonation state and charge of certain histidine residues of influenza virus HA proteins are sensitive to pH, such that histidine residues that are unprotonated at neutral pH may become protonated, and thus positively charged, as the pH of an endosome drops. Such protonation may result in a conformational change that allows the viral envelope to fuse with the endosomal membrane. For example, H5 HA1 residue His184 is located near positively charged residues in prefusion HA protein structures, and its protonation state acts as molecular switch triggering a conformational change in HA. See, e.g., Kampmann et al., *Structure.* 2006. 14(10): 1481-1487; Mair et al., *J Virol.* 2014. 88(22):13189-13200. Accordingly, replacement of one or more pH-sensitive histidines can inhibit or prevent a conformational change that occurs at low pH (e.g., transition to postfusion conformation), thereby stabilizing the HA protein.

In some embodiments, an HA protein comprises a substitution in, or removal of, a polybasic cleavage site. Cellular infection by influenza viruses involves cleavage of immature HA monomers at a cleavage site; differences in cleavage motifs of influenza viruses confer distinct tissue- and cell-specificity in which the viruses can replicate, resulting in different pathogenicity (Klenk et al. 1975. *Virology.* 68:426-439). Highly pathogenic avian influenza (HPAI) viruses typically possess polybasic HA cleavage sites (e.g., RKTR (SEQ ID NO: 120) or RKKR (SEQ ID NO: 121)), a feature which low pathogenic avian influenza (LPAI) viruses lack. In some embodiments, the mutation is a replacement of a polybasic cleavage site of an HPAI virus by a protease cleavage site of a LPAI virus. In some embodiments, the mutation is deletion of a polybasic cleavage site. In some embodiments, the mutation is deletion of an HPAI polybasic cleavage site. In some embodiments, the mutation is substitution of a polybasic cleavage site with an amino acid sequence that does not comprise a polybasic cleavage site. In some embodiments, the mutation is substitution of one or more arginine residues of an HPAI polybasic cleavage site with one or more non-basic residues (e.g. glycine and/or serine).

In some embodiments, an HA protein comprises one or more substitutions of a polar or charged cavity-lining residue with a hydrophobic residue. In some embodiments, a HA protein comprises one or more substitutions of a polar or charged cavity-lining residue with a glycine. Protein interiors may comprise tightly packed side chains which influence the stability of the protein, wherein larger cavities are less stable than narrow cavities (Bueno et al. *J Mol Bio.* 2006. 358(3):701-712). By replacing small cavity-lining residues with larger, hydrophobic residues, the stability of proteins can be increased by such cavity-filling mutations. Any suitable hydrophobic residue may be used in such a substitution, such as serine, alanine, valine, phenylalanine, histidine, leucine, methionine, valine, or tryptophan.

Influenza B Virus HA Proteins

Some embodiments relate to influenza B virus HA proteins. Influenza B virus HA proteins may comprise one or more mutations (e.g., substitutions) relative to an amino acid sequence of a reference influenza B virus HA protein. The reference IBV HA protein may be an HA protein of an IBV isolate. The reference IBV HA protein may be an engineered IBV HA protein. Non-limiting examples of mutations include (i) one or more introduced cysteines, where a disulfide bond is formed by at least one of the introduced cysteines; (ii) one or more proline or glycine substitutions in a B loop of the HA protein; (iii) one or more substitutions of a charged or polar cavity-lining residue with a hydrophobic residue; (iv) one or more substitutions of a pH-sensitive histidine in the HA protein; and/or (v) a mutation in, or removal of, a polybasic cleavage site of the HA protein.

B/Victoria Lineage HA Proteins

Some embodiments relate to influenza B/Victoria lineage virus HA proteins comprising an amino acid substitution relative to a reference influenza B/Victoria lineage virus HA protein. The reference influenza B/Victoria lineage virus HA protein may be an HA protein of an influenza B/Victoria lineage virus isolate. The reference influenza B/Victoria lineage virus HA protein may be an engineered influenza B/Victoria lineage virus HA protein. Non-limiting examples of influenza B/Victoria lineage virus isolates include B/Shangdong/7/1997, B/Hong Kong/330/2001, B/Malaysia/2506/2004, B/Brisbane/60/2008, B/Colorado/06/2017, B/Washington/02/2019, and B/Austria/1359417/2021. Representative amino acid sequences of influenza B/Victoria lineage virus HA proteins of previous seasonal influenza vaccines are provided as SEQ ID NOs: 154-160.

Those of ordinary skill in the art will appreciate that mutations disclosed in relation to a listed sequence, e.g., of influenza B/Austria/1359417/2021 virus HA, may be applied to HA proteins of other influenza B/Victoria lineage viruses or other reference influenza B/Victoria lineage virus HA proteins. For example, in applying an H381Y substitution to an influenza B/Victoria lineage virus HA protein, the skilled artisan would align the amino acid sequence of that reference HA protein to the B/Austria/1359417/2021 virus HA protein sequence of SEQ ID NO: 71, and introduce a Y (tyrosine) at the residue of the reference HA protein amino acid sequence that aligns to H381 (the histidine at position 381) of SEQ ID NO: 71.

Exemplary substitutions that may be present in influenza B/Victoria lineage HA proteins are provided below in Table HA-1. In the event a reference HA protein sequence (e.g. of an isolate) already includes a substitution mentioned in the table, then it will be appreciated that some embodiments will include the residues set forth at positions below without a substitution being made at that particular position. For example, if an isolate already contains a tyrosine at position 381, then embodiments comprising 381Y and 288V can be obtained with only a 288V substitution.

TABLE HA-1

| B/Victoria lineage HA substitutions (B/Austria/1359417/2021 (SEQ ID NO: 71) numbering) | |
|---|---|
| Substitution(s) | Mutation class |
| H381Y A288V | pH Switch / cavity filling |
| S27C Y349C | Intra-protomer DS (Head) |
| I295C K328C | Intra-protomer DS (Head) |
| S399C H473C | Intra-protomer DS (Stalk) |
| L422C D444C | Intra-protomer DS (Stalk) |
| K118C L216C | Inter-protomer DS (Head) |
| V237C D261C | Inter-protomer DS (Head) |
| G363C K480C | Inter-protomer DS (Stalk) |
| A364C K483C | Inter-protomer DS (Stalk) |
| I365C A476C | Inter-protomer DS (Stalk) |
| A366C R479C | Inter-protomer DS (Stalk) |
| G367C K483C | Inter-protomer DS (Stalk) |
| E435C A428C | Inter-protomer DS (Stalk) |
| N494C K483C | Inter-protomer DS (Stalk) |

TABLE HA-1-continued

| B/Victoria lineage HA substitutions (B/Austria/1359417/2021 (SEQ ID NO: 71) numbering) | |
|---|---|
| Substitution(s) | Mutation class |
| N494C K480C | Inter-protomer DS (Stalk) |
| E416P L417P N434P H433P | Prolines |
| N434P H433P | Prolines |
| T515P F516P | Prolines |
| H473F | pH Switch |

In preferred embodiments, the influenza B/Victoria lineage HA protein comprises a tyrosine substitution at position 381 and a valine substitution at position 288 (e.g., H381Y, A288V). These preferred substitutions can be combined with one or more additional substitutions set forth in the above table.

In some embodiments, the influenza B/Victoria lineage virus HA protein comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises H381Y and A288V substitutions relative to a reference influenza B/Victoria lineage virus HA protein, where the numbering of amino acids replaced in the reference HA protein corresponds to the numbering of SEQ ID NO: 71. An H381Y substitution is a replacement of a pH-sensitive histidine residue, and A290V is a cavity-filling substitution.

In some embodiments, the influenza B/Victoria lineage virus HA protein comprises a cysteine at position 27 and a cysteine at position 349, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 27 and a cysteine substitution at position 349 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises S27C and Y349C substitutions relative to a reference influenza B/Victoria lineage virus HA protein, where the numbering of amino acids replaced in the reference HA protein corresponds to the numbering of SEQ ID NO: 71. S27C and Y349C substitutions result in the formation of an intraprotomer disulfide bond in the head region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a cysteine at position 295 and a cysteine at position 328, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 295 and a cysteine substitution at position 328 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises I295C and K328C substitutions relative to a reference influenza B/Victoria lineage virus HA protein, where the numbering of amino acids replaced in the reference HA protein corresponds to the numbering of SEQ ID NO: 71. I295C and K328C substitutions result in the formation of an intraprotomer disulfide bond in the head region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a cysteine at position 399 and a cysteine at position 473, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 399 and a cysteine substitution at position 473 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises S399C and H473C substitutions relative to a reference influenza B/Victoria lineage virus HA protein, where the numbering of amino acids replaced in the reference HA protein corresponds to the numbering of SEQ ID NO: 71. S399C and H473C substitutions result in the formation of an intraprotomer disulfide bond in the stalk region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a cysteine at position 422 and a cysteine at position 444, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 422 and a cysteine substitution at position 444 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises L422C and D444C substitutions relative to a reference influenza B/Victoria lineage virus HA protein, where the numbering of amino acids replaced in the reference HA protein corresponds to the numbering of SEQ ID NO: 71. L422C and D444C substitutions result in the formation of an intraprotomer disulfide bond in the stalk region of the HA protein. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises a tyrosine at position 381, a valine at position 288, a cysteine at position 422, and a cysteine at position 444, where the positions are numbered by alignment of the amino acid sequence of the influenza B/Victoria lineage virus HA protein to SEQ ID NO: 71

In some embodiments, the influenza B/Victoria lineage virus HA protein comprises a cysteine at position 118 and a cysteine at position 216, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 118 and a cysteine substitution at position 216 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises K118C and L216C substitutions relative to a reference influenza B/Victoria lineage virus HA protein, where the numbering of amino acids replaced in the reference HA protein corresponds to the numbering of SEQ ID NO: 71. K118C and L216C substitutions result in the formation of an interprotomer disulfide bond in the head region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a cysteine at position 237 and a cysteine at position 261, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 237 and a cysteine substitution at position 261 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises V237C and D261C substitutions relative to a reference influenza B/Victoria lineage virus HA protein, where the numbering of amino acids replaced in the reference HA protein corresponds to the numbering of SEQ ID NO: 71. V237C and D261C substitutions result in the formation of an interprotomer disulfide bond in the head region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a cysteine at position 363 and a cysteine at position 480, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 363 and a cysteine substitution at position 480 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises G363C and K480C substitutions relative to a reference influenza B/Victoria lineage virus HA protein, where the numbering of amino acids replaced in the reference HA protein corresponds to the numbering of SEQ ID NO: 71. G363C and K480C substitutions result in the formation of an interprotomer disulfide bond in the stalk region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a cysteine at position 364 and a cysteine at position 483, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 364 and a cysteine substitution at position 483 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises A364C and K483C substitutions relative to a reference influenza B/Victoria lineage virus HA protein, where the numbering of amino acids replaced in the reference HA protein corresponds to the numbering of SEQ ID NO: 71. A364C and K483C substitutions result in the formation of an interprotomer disulfide bond in the stalk region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71. In some embodiments, the influenza B/Victoria lineage virus HA protein comprises a tyrosine at position 381, a valine at position 288, a cysteine at position 364 and a cysteine at position 483, where the positions are numbered by alignment of the amino acid sequence of the influenza B/Victoria lineage virus HA protein to SEQ ID NO: 71.

In some embodiments, the influenza B/Victoria lineage virus HA protein comprises a cysteine at position 365 and a cysteine at position 476, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 365 and a cysteine substitution at position 476 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises 1365C and A476C substitutions relative to a reference influenza B/Victoria lineage virus HA protein, where the numbering of amino acids replaced in the reference HA protein corresponds to the numbering of SEQ ID NO: 71. 1365C and A476C substitutions result in the formation of an interprotomer disulfide bond in the stalk region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a cysteine at position 366 and a cysteine at position 479, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 366 and a cysteine substitution at position 479 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises A366C and R479C substitutions relative to a reference influenza B/Victoria lineage virus HA protein, where the numbering of amino acids replaced in the reference HA protein corresponds to the numbering of SEQ ID NO: 71. A366C and R479C substitutions result in the formation of an interprotomer disulfide bond in the stalk region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a cysteine at position 367 and a cysteine at position 483, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 367 and a cysteine substitution at position 483 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises G367C and K483C substitutions relative to a reference influenza B/Victoria lineage virus HA protein, where the numbering of amino acids replaced in the reference HA protein corresponds to the numbering of SEQ ID NO: 71. G367C and K483C substitutions result in the formation of an interprotomer disulfide bond in the stalk region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71. In some embodiments, the influenza B/Victoria lineage virus HA protein comprises a tyrosine at position 381, a valine at position 288, a cysteine at position 367 and a cysteine at position 483, where the positions are numbered by alignment of the amino acid sequence of the influenza B/Victoria lineage virus HA protein to SEQ ID NO: 71.

In some embodiments, the influenza B/Victoria lineage virus HA protein comprises a cysteine at position 435 and a cysteine at position 428, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 435 and a cysteine substitution at position 428 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises E435C and A428C substitutions relative to a reference influenza B/Victoria lineage virus HA protein, where the numbering of amino acids replaced in the reference HA protein corresponds to the numbering of SEQ ID NO: 71. E435C and A428C substitutions result in the formation of an interprotomer disulfide bond in the stalk region of the HA protein. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a cysteine at position 494 and a cysteine at position 483, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 494 and a cysteine substitution at position 483 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises N494C and K483C substitutions relative to a reference influenza B/Victoria lineage virus HA protein, where the numbering of amino acids replaced in the reference HA protein corresponds to the numbering of SEQ ID NO: 71. N494C and K483C substitutions result in the formation of an interprotomer disulfide bond in the stalk region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71. In some embodiments, the influenza B/Victoria lineage virus HA protein comprises a tyrosine at position 381, a valine at position 288, a cysteine at position 494 and a cysteine at position 483, where the positions are numbered by alignment of the amino acid sequence of the influenza B/Victoria lineage virus HA protein to SEQ ID NO: 71.

In some embodiments, the influenza B/Victoria lineage virus HA protein comprises a cysteine at position 494 and a cysteine at position 480, where the positions are numbered by alignment of the amino acid sequence of the influenza B/Victoria lineage virus HA protein to SEQ ID NO: 71. In some embodiments, the influenza B/Victoria lineage virus HA protein comprises a cysteine substitution at position 494 and a cysteine substitution at position 480 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises N494C and K480C substitutions relative to a reference influenza B/Victoria lineage virus HA protein, where the numbering of amino acids replaced in the reference HA protein corresponds to the numbering of SEQ ID NO: 71. N494C and K480C substitutions result in the formation of an interprotomer disulfide bond in the stalk region of the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a proline at position 416, a proline at position 417, a proline at position 434, and a at position 433, where the positions are numbered by alignment of the amino acid sequence of the influenza B/Victoria lineage virus HA protein to SEQ ID NO: 71. In some embodiments, the influenza B/Victoria lineage virus HA protein comprises a proline substitution at position 416, a proline substitution at position 417, a proline substitution at position 434, and a substitution at position 433 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises E416P, L417P, N434P, and H433P substitutions relative to a reference influenza B/Victoria lineage virus HA protein, where the numbering of amino acids replaced in the reference HA protein corresponds to the numbering of SEQ ID NO: 71. Proline is a residue considered a helix breaker, and substitution of a residue in the B loop of an HA protein with proline (e.g., E416P, L417P, N434P, and H433P) can the protein by altering its conformation. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a proline at position 434 and a proline at position 433, where the positions are numbered by alignment of the amino acid sequence of the influenza B/Victoria lineage virus HA protein to SEQ ID NO: 71. In some embodiments, the influenza B/Victoria lineage virus HA protein comprises a proline substitution at position 434 and a proline substitution at position 433 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises N434P and H433P substitutions relative to a reference influenza B/Victoria lineage virus HA protein, where the numbering of amino acids replaced in the reference HA protein corresponds to the numbering of SEQ ID NO: 71. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a proline at position 515 and a proline at position 516, where the positions are numbered by alignment of the amino acid sequence of the influenza B/Victoria lineage virus HA protein to SEQ ID NO: 71. In some embodiments, the influenza B/Victoria lineage virus HA protein comprises a proline substitution at position 515 and a proline substitution at position 516 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises T515P and F516P substitutions relative to a reference influenza B/Victoria lineage virus HA protein, where the numbering of amino acids replaced in the reference HA protein corresponds to the numbering of SEQ ID NO: 71. Proline is a residue considered a helix breaker, and substitution of one or more residues in the B loop of an HA protein with proline (e.g., T515P and F516P) can the protein by altering its conformation. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

In some embodiments, the influenza B/Victoria lineage virus HA protein comprises a phenylalanine at position 473, where the positions are numbered by alignment of the amino acid sequence of the influenza B/Victoria lineage virus HA protein to SEQ ID NO: 71. In some embodiments, the influenza B/Victoria lineage virus HA protein comprises a phenylalanine substitution at position 473 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein comprises an H473F substitution relative to a reference influenza B/Victoria lineage virus HA protein, where the numbering of the amino acid replaced in the reference HA protein corresponds to the numbering of SEQ ID NO: 71. Substitution of a pH-sensitive histidine (e.g., H473) can inhibit or prevent the conformational change that occurs at low pH (e.g., during viral fusion), thereby stabilizing the HA protein. In some embodiments, the influenza B/Victoria lineage virus HA protein also comprises a tyrosine at position 381 and a valine at position 288, where the positions are numbered by alignment of the amino acid sequence of the influenza B/Victoria lineage virus HA protein to SEQ ID NO: 71. In some embodiments, the influenza B/Victoria lineage virus HA protein further comprises a tyrosine substitution at position 381 and a valine substitution at position 288 relative to a reference influenza B/Victoria lineage virus HA protein, where the positions are numbered by alignment of the amino acid sequence of the reference influenza B/Victoria lineage virus HA protein to SEQ ID NO: 71. In some embodiments, the influenza B/Victoria lineage virus HA protein further comprises H381Y and A288V substitutions relative to the reference HA protein, where the numbering of the amino acids replaced in the reference HA protein corresponds to the numbering of SEQ ID NO: 71.

Substitutions described in this subsection relating to B/Victoria lineage HA proteins may be combined. For example, any of the pairs of cysteine substitutions may be combined with one or more proline substitutions in the B loop and/or substitutions of pH-sensitive histidines. Pairs of cysteine substitutions that form different disulfide bonds (e.g., interprotomer versus intraprotomer bonds, head versus stalk region bonds) may also be combined. In some embodiments, the influenza B/Victoria lineage HA protein comprises one or more substitutions of a pH-sensitive histidine in the HA protein and one or more substitutions of a charged or polar cavity-lining residue with a hydrophobic residue.

In some embodiments, the influenza B/Victoria lineage HA protein comprises an amino acid sequence with at least 90%, at least 91%, at least 92%, at least 93%, at least 94%, at least 95%, at least 96%, at least 97%, at least 98%, or at least 99% sequence identity to the amino acid sequence of SEQ ID NO: 71. In some embodiments, the influenza B/Victoria lineage HA protein comprises an amino acid sequence with at least 90% sequence identity to the amino acid sequence of SEQ ID NO: 71.

B/Yamagata Lineage HA Proteins

Some embodiments relate to influenza B/Yamagata lineage virus HA proteins comprising an amino acid substitution relative to a reference influenza B/Yamagata lineage virus HA protein. The reference influenza B/Yamagata lineage virus HA protein may be an HA protein of an influenza B/Yamagata lineage virus isolate. The reference influenza B/Yamagata lineage virus HA protein may be an engineered influenza B/Yamagata lineage virus HA protein. Non-limiting examples of influenza B/Yamagata lineage virus isolates include B/Beijing/184/1993, B/Sichuan/379/1999, B/Shanghai/361/2002, B/Florida/4/2006, B/Wisconsin/1/2010, B/Massachusetts/2/2012, and B/Phuket/3073/2013. Representative amino acid sequences of influenza B/Yamagata lineage virus HA proteins of previous seasonal influenza vaccines are provided as SEQ ID NOs: 164-167.

Those of ordinary skill in the art will appreciate that mutations disclosed in relation to a listed sequence, e.g., of influenza B/Phuket/3073/2013 virus HA, may be applied to HA proteins of other influenza B/Yamagata lineage viruses or other reference influenza B/Victoria lineage virus HA proteins. For example, in applying an A231C substitution to another influenza B/Yamagata lineage virus HA protein, the skilled artisan would align the amino acid sequence of that reference HA protein to the influenza B/Phuket/3073/2013 virus HA protein sequence of SEQ ID NO: 70, and introduce a C at the residue of the reference HA protein amino acid sequence that aligns to A231 of SEQ ID NO: 70.

Exemplary substitutions that may be present in influenza B/Yamgata lineage HA proteins are provided below in Table HA-2. In the event a reference HA protein sequence (e.g. of an isolate) already includes a substitution mentioned in the table, then it will be appreciated that some embodiments will include the residues set forth at positions below without a substitution being made at that particular position. For example, if an isolate already contains a tyrosine at position 381, then embodiments comprising 381Y and 290V can be obtained with only a 290V substitution.

TABLE 2

| B/Yamagata lineage HA substitutions (B/Phuket/3073/2013 (SEQ ID NO: 70) numbering) | |
|---|---|
| Substitution(s) | Mutation class |
| A231C G273C | Intra-protomer DS (Head) |
| K295C I332C | Intra-protomer DS (Head) |
| A396C L510C | Intra-protomer DS (Stalk) |
| V239C V276C | Inter-protomer DS (Head) |
| I367C S401C | Inter-protomer DS (Stalk) |
| F363C E404C | Inter-protomer DS (Stalk) |
| E437C G429C | Inter-protomer DS (Stalk) |
| D451C K422C | Inter-protomer DS (Stalk) |
| H381Y A290V | pH Switch (H381Y) / Cavity Filling (A290V) |

In some embodiments, the influenza B/Yamagata lineage virus HA protein comprises a cysteine at position 231 and a cysteine at position 273, where the positions are numbered by alignment of the amino acid sequence of the influenza B/Yamagata lineage virus HA protein to SEQ ID NO: 70. In some embodiments, the influenza B/Yamagata lineage virus HA protein comprises a cysteine substitution at position 231 and a cysteine substitution at position 273 relative to a reference influenza B/Yamagata lineage virus HA protein, where the positions are numbered by alignment of the amino acid sequence of the reference influenza B/Yamagata lineage virus HA protein to SEQ ID NO: 70. In some embodiments, the influenza B/Yamagata lineage virus HA protein comprises A231C and G273C substitutions relative to a reference influenza B/Yamagata lineage virus HA protein, where the numbering of amino acids replaced in the reference HA protein corresponds to the numbering of SEQ ID NO: 70. A231C and G273C substitutions result in the formation of an intraprotomer disulfide bond in the head region of the HA protein.

In some embodiments, the influenza B/Yamagata lineage virus HA protein comprises a cysteine at position 295 and a cysteine at position 332, where the positions are numbered by alignment of the amino acid sequence of the influenza B/Yamagata lineage virus HA protein to SEQ ID NO: 70. In some embodiments, the influenza B/Yamagata lineage virus HA protein comprises a cysteine substitution at position 295 and a cysteine substitution at position 332 relative to a reference influenza B/Yamagata lineage virus HA protein, where the positions are numbered by alignment of the amino acid sequence of the reference influenza B/Yamagata lineage virus HA protein to SEQ ID NO: 70. In some embodiments, the influenza B/Yamagata lineage virus HA protein comprises K295C and I332C substitutions relative to a reference influenza B/Yamagata lineage virus HA protein, where the numbering of amino acids replaced in the reference HA protein corresponds to the numbering of SEQ ID NO: 70. K295C and I332C substitutions result in the formation of an intraprotomer disulfide bond in the head region of the HA protein.

In some embodiments, the influenza B/Yamagata lineage virus HA protein comprises a cysteine at position 396 and a cysteine at position 510, where the positions are numbered by alignment of the amino acid sequence of the influenza B/Yamagata lineage virus HA protein to SEQ ID NO: 70. In some embodiments, the influenza B/Yamagata lineage virus HA protein comprises a cysteine substitution at position 396 and a cysteine substitution at position 510 relative to a reference influenza B/Yamagata lineage virus HA protein, where the positions are numbered by alignment of the amino acid sequence of the reference influenza B/Yamagata lineage virus HA protein to SEQ ID NO: 70. In some embodiments, the influenza B/Yamagata lineage virus HA protein comprises A396C and L510C substitutions relative to a reference influenza B/Yamagata lineage virus HA protein, where the numbering of amino acids replaced in the reference HA protein corresponds to the numbering of SEQ ID NO: 70. A396C and L510C substitutions result in the formation of an intraprotomer disulfide bond in the stalk region of the HA protein.

In some embodiments, the influenza B/Yamagata lineage virus HA protein comprises a cysteine at position 239 and a cysteine at position 276, where the positions are numbered by alignment of the amino acid sequence of the influenza B/Yamagata lineage virus HA protein to SEQ ID NO: 70. In some embodiments, the influenza B/Yamagata lineage virus HA protein comprises a cysteine substitution at position 239 and a cysteine substitution at position 276 relative to a reference influenza B/Yamagata lineage virus HA protein, where the positions are numbered by alignment of the amino acid sequence of the reference influenza B/Yamagata lineage virus HA protein to SEQ ID NO: 70. In some embodiments, the influenza B/Yamagata lineage virus HA protein comprises V239C and V276C substitutions relative to a reference influenza B/Yamagata lineage virus HA protein, where the numbering of amino acids replaced in the reference HA protein corresponds to the numbering of SEQ ID NO: 70. V239C and V276C substitutions result in the formation of an interprotomer disulfide bond in the head region of the HA protein. In some embodiments, the influenza B/Yamagata lineage virus HA protein comprises a cysteine at position 239, a cysteine at position 276, a cysteine at position 451, and a cysteine at position 422, where the positions are numbered by alignment of the amino acid sequence of the influenza B/Yamagata lineage virus HA protein to SEQ ID NO: 70.

In some embodiments, the influenza B/Yamagata lineage virus HA protein comprises a cysteine at position 367 and a cysteine at position 401, where the positions are numbered by alignment of the amino acid sequence of the influenza B/Yamagata lineage virus HA protein to SEQ ID NO: 70. In some embodiments, the influenza B/Yamagata lineage virus HA protein comprises a cysteine substitution at position 367 and a cysteine substitution at position 401 relative to a reference influenza B/Yamagata lineage virus HA protein, where the positions are numbered by alignment of the amino acid sequence of the reference influenza B/Yamagata lineage virus HA protein to SEQ ID NO: 70. In some embodiments, the influenza B/Yamagata lineage virus HA protein comprises I367C and S401C substitutions relative to a reference influenza B/Yamagata lineage virus HA protein, where the numbering of amino acids replaced in the reference HA protein corresponds to the numbering of SEQ ID NO: 70. I367C and S401C substitutions result in the formation of an interprotomer disulfide bond in the stalk region of the HA protein. In some embodiments, the influenza B/Yamagata lineage virus HA protein comprises a cysteine at position 367, a cysteine at position 401, a cysteine at position 451, and a cysteine at position 422, where the positions are numbered by alignment of the amino acid sequence of the influenza B/Yamagata lineage virus HA protein to SEQ ID NO: 70.

In some embodiments, the influenza B/Yamagata lineage virus HA protein comprises a cysteine at position 363 and a cysteine at position 404, where the positions are numbered by alignment of the amino acid sequence of the influenza B/Yamagata lineage virus HA protein to SEQ ID NO: 70. In some embodiments, the influenza B/Yamagata lineage virus HA protein comprises a cysteine substitution at position 363 and a cysteine substitution at position 404 relative to a reference influenza B/Yamagata lineage virus HA protein, where the positions are numbered by alignment of the amino acid sequence of the reference influenza B/Yamagata lineage virus HA protein to SEQ ID NO: 70. In some embodiments, the influenza B/Yamagata lineage virus HA protein comprises F363C and E404C substitutions relative to a reference influenza B/Yamagata lineage virus HA protein, where the numbering of amino acids replaced in the reference HA protein corresponds to the numbering of SEQ ID NO: 70. F363C and E404C substitutions result in the formation of an interprotomer disulfide bond in the stalk region of the HA protein.

In some embodiments, the influenza B/Yamagata lineage virus HA protein comprises a cysteine at position 437 and a cysteine at position 429, where the positions are numbered by alignment of the amino acid sequence of the influenza B/Yamagata lineage virus HA protein to SEQ ID NO: 70. In some embodiments, the influenza B/Yamagata lineage virus HA protein comprises a cysteine substitution at position 437 and a cysteine substitution at position 429 relative to a reference influenza B/Yamagata lineage virus HA protein, where the positions are numbered by alignment of the amino acid sequence of the reference influenza B/Yamagata lineage virus HA protein to SEQ ID NO: 70. In some embodiments, the influenza B/Yamagata lineage virus HA protein comprises E437C and G429C substitutions relative to a reference influenza B/Yamagata lineage virus HA protein, where the numbering of amino acids replaced in the reference HA protein corresponds to the numbering of SEQ ID NO: 70. E437C and G429C substitutions result in the formation of an interprotomer disulfide bond in the stalk region of the HA protein.

In some embodiments, the influenza B/Yamagata lineage virus HA protein comprises a cysteine at position 451 and a cysteine at position 422, where the positions are numbered by alignment of the amino acid sequence of the influenza B/Yamagata lineage virus HA protein to SEQ ID NO: 70. In some embodiments, the influenza B/Yamagata lineage virus HA protein comprises a cysteine substitution at position 451 and a cysteine substitution at position 422 relative to a reference influenza B/Yamagata lineage virus HA protein, where the positions are numbered by alignment of the amino acid sequence of the reference influenza B/Yamagata lineage virus HA protein to SEQ ID NO: 70. In some embodiments, the influenza B/Yamagata lineage virus HA protein comprises D451C and K422C substitutions relative to a reference influenza B/Yamagata lineage virus HA protein, where the numbering of amino acids replaced in the reference HA protein corresponds to the numbering of SEQ ID NO: 70. D451C and K422C substitutions result in the formation of an interprotomer disulfide bond in the stalk region of the HA protein.

In some embodiments, the influenza B/Yamagata lineage virus HA protein comprises a tyrosine at position 381 and a valine at position 290, where the positions are numbered by alignment of the amino acid sequence of the influenza B/Yamagata lineage virus HA protein to SEQ ID NO: 70. In some embodiments, the influenza B/Yamagata lineage virus HA protein comprises a tyrosine substitution at position 381 and a valine substitution at position 290 relative to a reference influenza B/Yamagata lineage virus HA protein, where the positions are numbered by alignment of the amino acid sequence of the reference influenza B/Yamagata lineage virus HA protein to SEQ ID NO: 70. In some embodiments, the influenza B/Yamagata lineage virus HA protein comprises H381Y and A290V substitutions relative to a reference influenza B/Yamagata lineage virus HA protein, where the numbering of amino acids replaced in the reference HA protein corresponds to the numbering of SEQ ID NO: 70. H381Y is a pH-sensitive histidine residue replacement substitution, and A290V is a cavity-filling substitution.

Substitutions described in this subsection relating to B/Yamagata lineage HA proteins may be combined. For example, any of the pairs of cysteine substitutions may be combined with one or more substitutions of pH-sensitive histidines and/or cavity-filling substitutions. Pairs of cysteine substitutions that form different disulfide bonds (e.g., interprotomer v. intraprotomer bonds, head v. stalk region bonds) may also be combined. In some embodiments, the influenza B/Yamagata lineage HA protein comprises one or more substitutions of a pH-sensitive histidine in the HA protein and one or more substitutions of a charged or polar cavity-lining residue with a hydrophobic residue.

In some embodiments, the influenza B/Yamagata lineage virus HA protein comprises H381Y and A290V substitutions relative to a reference influenza B/Yamagata lineage virus HA protein, where the numbering of amino acids replaced in the reference HA protein corresponds to the numbering of SEQ ID NO: 70 in addition to one or more other substitutions described in this section.

In some embodiments, the influenza B/Yamagata lineage HA protein comprises an amino acid sequence with at least 90%, at least 91%, at least 92%, at least 93%, at least 94%, at least 95%, at least 96%, at least 97%, at least 98%, or at least 99% sequence identity to the amino acid sequence of SEQ ID NO: 70. In some embodiments, the influenza B/Yamagata lineage HA protein comprises an amino acid sequence with at least 90% sequence identity to the amino acid sequence of SEQ ID NO: 70.

Influenza a Virus HA Proteins

Some embodiments relate to influenza A virus HA proteins. Influenza A virus HA proteins may comprise one or more mutations (e.g., substitutions) relative to an amino acid sequence of an HA protein of an influenza A virus isolate.

H1 HA Proteins

Some embodiments relate to IAV H1 HA proteins comprising an amino acid substitution relative to a reference IAV H1 HA protein. The reference IAV H1 HA protein may be an HA protein of an isolate of an influenza A virus of an IAV subtype containing an H1 HA protein, such as an influenza A/(H1N1)pdm09 virus. H1 HA proteins are present, e.g., on influenza A viruses of the A/(H1N1)pdm09 subtype, but other IAV subtypes expressing H1 HA proteins have been identified (such as the H1N2 subtype endemic in pigs and occasionally observed in humans). Non-limiting examples of influenza A/(H1N1)pdm09 virus isolates (and related influenza A/(H1N1) virus isolates preceding the 2009 influenza A/(H1N1) virus pandemic) include A/Beijing/262/1995 (H1N1), A/New Caledonia/20/1999(H1N1), A/Solomon Islands/3/2006(H1N1), A/Brisbane/59/2007(H1N1), A/California/7/2009(H1N1)pdm09, A/Michigan/45/2015 (H1N1)pdm09, A/Brisbane/02/2018(H1N1)pdm09, A/Guangdong-Maonan/SWL1536/2019 (H1N1)pdm09, A/Hawaii/70/2019(H1N1)pdm09, (A/Victoria/2570/2019 (H1N1)pdm09, A/Wisconsin/588/2019(H1N1)pdm09, A/Victoria/4897/2022(H1N1)pdm09, and A/Wisconsin/67/2022(H1N1)pdm09. Representative amino acid sequences of influenza A/(H1N1)pdm09 virus HA proteins of previous seasonal influenza vaccines are provided as SEQ ID NOs: 122-135.

Those of ordinary skill in the art will appreciate that mutations disclosed in relation to a listed sequence, e.g., of influenza A/Wisconsin/67/2022(H1N1)pdm09 virus HA, may be applied to other IAV H1 HA proteins. For example, in applying a K391C substitution to another IAV H1 HA protein, the skilled artisan would align the amino acid sequence of that reference HA protein to the influenza A/Wisconsin/67/2022(H1N1)pdm09 virus HA protein sequence of SEQ ID NO: 83, and introduce a C at the residue of the reference HA protein amino acid sequence that aligns to K391 of SEQ ID NO: 83. Similarly, mutations disclosed in relation to a reference sequence of influenza A/Sydney/5/2021(H1N1)pdm09 virus HA may be applied to a different reference HA protein by alignment of the reference HA protein amino acid sequence to the amino acid sequence of SEQ ID NO: 95. Such alignment allows the skilled artisan to identify the residue in the reference HA protein amino acid sequence that corresponds to the mutated residue of the influenza A/Sydney/5/2021(H1N1)pdm09 virus HA protein (e.g., to identify the residue of the reference HA protein amino acid sequence that corresponds to V410 of the A/Sydney/5/2021(H1N1)pdm09 virus HA protein amino acid sequence, to determine where to introduce a C, in applying a V410C substitution).

Exemplary substitutions that may be present in IAV H1 HA proteins are provided below in Tables HA-3 and HA-4. In the event a reference HA protein sequence (e.g. of an isolate) already includes a substitution mentioned in the table, then it will be appreciated that some embodiments will include the residues set forth at positions below without a substitution being made at that particular position. For example, if an isolate already contains an isoleucine at position 395, then embodiments comprising 395I and 447I can be obtained with only a 447I substitution.

TABLE HA-3

| A/(H1N1) subtype HA substitutions (A/Wisconsin/67/2022 (H1N1)pdm09 (SEQ ID NO: 83) numbering) | |
|---|---|
| Substitution(s) | Mutation class |
| K391C L37C | Inter-protomer DS (Stalk) |
| K395C V36C | Inter-protomer DS (Stalk) |
| N461C G348C | Inter-protomer DS (Stalk) |
| N404P H416P | Proline (Pro) |
| K395I E447I | Hydrophobic Interaction (Hyd) |
| D456G K402I | Hydrophobic Interaction (Hyd) |
| K391C L37C N404P H416P | InterDS + Pro |
| K391C L37C K395I E447I | InterDS + Hyd |
| K391C L37C D456G K402I | InterDS + Hyd |
| K395C V36C N404P H416P | InterDS + Pro |
| K395C V36C D456G K402I | InterDS + Hyd |
| N461C G348C N404P H416P | InterDS + Pro |
| N461C G348C K395I E447I | InterDS + Hyd |
| N461C G348C D456G K402I | InterDS + Hyd |
| K391C L37C N404P H416P D456G K402I | InterDS + Pro + Hyd |

TABLE HA-4

| A/(H1N1) subtype HA substitutions (A/Sydney/5/2021(H1N1)pdm09 (SEQ ID NO: 95) numbering) | |
|---|---|
| Substitution(s) | Mutation class |
| V410C L462C | Intra-protomer DS |
| E120C K419C | Inter-protomer DS |
| K391C L37C | Inter-protomer DS |
| K395C V36C | Inter-protomer DS |
| Q406C D430C | Inter-protomer DS |
| S457C L346C | Inter-protomer DS |
| N461C G348C | Inter-protomer DS |
| N404P K419P | Proline |
| N404P H416P | Proline |
| T405P Q406P | Proline |
| N415P H416P | Proline |
| H25Y H45E | pH Switch |
| H370Y K497W | pH Switch |
| K402G T405G F407G | Glycine |
| K395I E447I | Cavity Filling |
| D456G K402I | Glycine(s) (D456G) / Cavity Filling (K402I) |
| L442C N423C | Inter-protomer DS |
| K391G | Glycine(s) |
| V410C L462C S457C L346C | Intra- and Inter-protomer DS |
| K391C L37C H370F H455F | Inter-protomer DS + pH Switch |

Some embodiments relate to IAV H1 HA proteins having one or more substitutions relative to a reference H1 HA protein, wherein the numbering of amino acids replaced in the reference IAV H1 HA protein corresponds to the numbering of SEQ ID NO: 83, which represents the HA protein of the influenza A/Wisconsin/67/2022(H1N1)pdm09 virus isolate.

In some embodiments, the IAV H1 HA protein comprises a cysteine at position 391 and a cysteine at position 37, where the positions are numbered by alignment of the amino acid sequence of the IAV H1 HA protein to SEQ ID NO: 83. In some embodiments, the IAV H1 HA protein comprises a cysteine substitution at position 391 and a cysteine substitution at position 37 relative to a reference IAV H1 HA protein, where the positions are numbered by alignment of the amino acid sequence of the reference IAV H1 HA protein to SEQ ID NO: 83. In some embodiments, the IAV H1 HA protein comprises K391C and L37C substitutions relative to a reference IAV H1 HA protein, where the numbering of amino acids replaced in the reference IAV H1 HA protein corresponds to the numbering of SEQ ID NO: 83. K391C and L37C substitutions result in the formation of an inter-protomer disulfide bond in the stalk region of the HA protein.

In some embodiments, the IAV H1 HA protein comprises a cysteine at position 395 and a cysteine at position 36, where the positions are numbered by alignment of the amino acid sequence of the IAV H1 HA protein to SEQ ID NO: 83. In some embodiments, the IAV H1 HA protein comprises a cysteine substitution at position 395 and a cysteine substitution at position 36 relative to a reference IAV H1 HA protein, where the positions are numbered by alignment of the amino acid sequence of the reference IAV H1 HA protein to SEQ ID NO: 83. In some embodiments, the IAV H1 HA protein comprises K395C and V36C substitutions relative to a reference IAV H1 HA protein, where the numbering of amino acids replaced in the reference IAV H1 HA protein corresponds to the numbering of SEQ ID NO: 83. K395C and V36C substitutions result in the formation of an interprotomer disulfide bond in the stalk region of the HA protein.

In some embodiments, the IAV H1 HA protein comprises a cysteine at position 461 and a cysteine at position 348, where the positions are numbered by alignment of the amino acid sequence of the IAV H1 HA protein to SEQ ID NO: 83. In some embodiments, the IAV H1 HA protein comprises a cysteine substitution at position 461 and a cysteine substitution at position 348 relative to a reference IAV H1 HA protein, where the positions are numbered by alignment of the amino acid sequence of the reference IAV H1 HA protein to SEQ ID NO: 83. In some embodiments, the IAV H1 HA protein comprises N461C and G348C substitutions relative to a reference IAV H1 HA protein, where the numbering of amino acids replaced in the reference IAV H1 HA protein corresponds to the numbering of SEQ ID NO: 83. N461C and G348C substitutions result in the formation of an interprotomer disulfide bond in the stalk region of the HA protein.

In some embodiments, the IAV H1 HA protein comprises a proline at position 404 and a proline at position 416, where the positions are numbered by alignment of the amino acid sequence of the IAV H1 HA protein to SEQ ID NO: 83. In some embodiments, the IAV H1 HA protein comprises a proline substitution at position 404 and a proline substitution at position 416 relative to a reference IAV H1 HA protein, where the positions are numbered by alignment of the amino acid sequence of the reference IAV H1 HA protein to SEQ ID NO: 83. In some embodiments, the IAV H1 HA protein comprises N404P and H416P substitutions relative to a reference IAV H1 HA protein, where the numbering of amino acids replaced in the reference IAV H1 HA protein corresponds to the numbering of SEQ ID NO: 83. N404P and H416P are proline substitutions in the B loop of the HA protein, stabilizing the HA protein by changing its conformation. In some embodiments, the IAV H1 HA protein comprises a proline at position 404, a proline at position 416, a cysteine at position 395, and a cysteine at position 36, where the positions are numbered by alignment of the amino acid sequence of the IAV H1 HA protein to SEQ ID NO: 83. In some embodiments, the IAV H1 HA protein comprises a proline at position 404, a proline at position 416, a cysteine at position 391, and a cysteine at position 36, where the positions are numbered by alignment of the amino acid sequence of the IAV H1 HA protein to SEQ ID NO: 83. In some embodiments, the IAV H1 HA protein comprises a proline at position 404, a proline at position 416, a cysteine at position 391, a cysteine at position 37, a glycine at position 456, and an isoleucine at position 402, where the positions are numbered by alignment of the amino acid sequence of the IAV H1 HA protein to SEQ ID NO: 83.

In some embodiments, the IAV H1 HA protein comprises a isoleucine at position 395 and a isoleucine at position 447, where the positions are numbered by alignment of the amino acid sequence of the IAV H1 HA protein to SEQ ID NO: 83. In some embodiments, the IAV H1 HA protein comprises a isoleucine substitution at position 395 and a isoleucine substitution at position 447 relative to a reference IAV H1 HA protein, where the positions are numbered by alignment of the amino acid sequence of the reference IAV H1 HA protein to SEQ ID NO: 83. In some embodiments, the IAV H1 HA protein comprises K395I and E447I substitutions relative to a reference IAV H1 HA protein, where the numbering of amino acids replaced in the reference IAV H1 HA protein corresponds to the numbering of SEQ ID NO: 83. K395I and E447I substitutions are replacements of charged lysine and glutamate residues with hydrophobic isoleucine residues.

In some embodiments, the IAV H1 HA protein comprises a glycine at position 456 and a isoleucine at position 402, where the positions are numbered by alignment of the amino acid sequence of the IAV H1 HA protein to SEQ ID NO: 83. In some embodiments, the IAV H1 HA protein comprises a glycine substitution at position 456 and a isoleucine substitution at position 402 relative to a reference IAV H1 HA protein, where the positions are numbered by alignment of the amino acid sequence of the reference IAV H1 HA protein to SEQ ID NO: 83. In some embodiments, the IAV H1 HA protein comprises D456G and K402I substitutions relative to a reference IAV H1 HA protein, where the numbering of amino acids replaced in the reference IAV H1 HA protein corresponds to the numbering of SEQ ID NO: 83. D456G and K402I substitutions are replacements of charged aspartate and lysine residues with uncharged glycine and uncharged, hydrophobic isoleucine residues. In some embodiments, the IAV H1 HA protein comprises a glycine at position 456, an isoleucine at position 402, a cysteine at position 395, and a cysteine at position 36, where the positions are numbered by alignment of the amino acid sequence of the IAV H1 HA protein to SEQ ID NO: 83.

In some embodiments, the amino acid substitution comprises a cysteine substitution at position 456 and a isoleucine substitution at position 402, where the positions are numbered by alignment of the amino acid sequence of the influenza B/Victoria lineage virus HA protein to SEQ ID NO: 83. In some embodiments, the IAV H1 HA protein comprises a cysteine substitution at position 456 and a isoleucine substitution at position 402, where the positions are numbered by alignment of the amino acid sequence of the IAV H1 HA protein to SEQ ID NO: 83. In some embodiments, the IAV H1 HA protein comprises D456C and K402I substitutions relative to a reference IAV H1 HA protein, where the numbering of amino acids replaced in the reference IAV H1 HA protein corresponds to the numbering of SEQ ID NO: 83. In some embodiments, the IAV H1 HA protein comprises a cysteine at position 456, an isoleucine at position 402, a cysteine at position 395, and a cysteine at position 36, where the positions are numbered by alignment of the amino acid sequence of the IAV H1 HA protein to SEQ ID NO: 83.

In some embodiments, the IAV H1 HA protein comprises an amino acid sequence with at least 90%, at least 91%, at least 92%, at least 93%, at least 94%, at least 95%, at least 96%, at least 97%, at least 98%, or at least 99% sequence identity to the amino acid sequence of SEQ ID NO: 83. In some embodiments, the IAV H1 HA protein comprises an amino acid sequence with at least 90% sequence identity to the amino acid sequence of SEQ ID NO: 83.

Some embodiments relate to IAV H1 HA proteins having one or more substitutions relative to a reference H1 HA protein, wherein the numbering of amino acids replaced in the reference IAV H1 HA protein corresponds to the numbering of SEQ ID NO: 95, which represents the HA protein of the influenza A/Sydney/5/2021(H1N1)pdm09 virus isolate.

In some embodiments, the IAV H1 HA protein comprises a cysteine at position 410 and a cysteine at position 462, where the positions are numbered by alignment of the amino acid sequence of the IAV H1 HA protein to SEQ ID NO: 95. In some embodiments, the IAV H1 HA protein comprises a cysteine substitution at position 410 and a cysteine substitution at position 462 relative to a reference IAV H1 HA protein, where the positions are numbered by alignment of the amino acid sequence of the reference IAV H1 HA protein to SEQ ID NO: 95. In some embodiments, the IAV H1 HA protein comprises V410C and L462C substitutions relative to a reference IAV H1 HA protein, where the numbering of amino acids replaced in the reference IAV H1 HA protein corresponds to the numbering of SEQ ID NO: 95. V410C and L462C substitutions result in the formation of an intraprotomer disulfide bond in the HA protein.

In some embodiments, the IAV H1 HA protein comprises a cysteine at position 120 and a cysteine at position 419, where the positions are numbered by alignment of the amino acid sequence of the IAV H1 HA protein to SEQ ID NO: 95. In some embodiments, the IAV H1 HA protein comprises a cysteine substitution at position 120 and a cysteine substitution at position 419 relative to a reference IAV H1 HA protein, where the positions are numbered by alignment of the amino acid sequence of the reference IAV H1 HA protein to SEQ ID NO: 95. In some embodiments, the IAV H1 HA protein comprises E120C and K419C substitutions relative to a reference IAV H1 HA protein, where the numbering of amino acids replaced in the reference IAV H1 HA protein corresponds to the numbering of SEQ ID NO: 95. E120C and K419C substitutions result in the formation of an interprotomer disulfide bond in the HA protein.

In some embodiments, the IAV H1 HA protein comprises a cysteine at position 391 and a cysteine at position 37, where the positions are numbered by alignment of the amino acid sequence of the IAV H1 HA protein to SEQ ID NO: 95. In some embodiments, the IAV H1 HA protein comprises a cysteine substitution at position 391 and a cysteine substitution at position 37 relative to a reference IAV H1 HA protein, where the positions are numbered by alignment of the amino acid sequence of the reference IAV H1 HA protein to SEQ ID NO: 95. In some embodiments, the IAV H1 HA protein comprises K391C and L37C substitutions relative to a reference IAV H1 HA protein, where the numbering of amino acids replaced in the reference IAV H1 HA protein corresponds to the numbering of SEQ ID NO: 95. K391C and L37C substitutions result in the formation of an interprotomer disulfide bond in the HA protein.

In some embodiments, the IAV H1 HA protein comprises a cysteine at position 395 and a cysteine at position 36, where the positions are numbered by alignment of the amino acid sequence of the IAV H1 HA protein to SEQ ID NO: 95. In some embodiments, the IAV H1 HA protein comprises a cysteine substitution at position 395 and a cysteine substitution at position 36 relative to a reference IAV H1 HA protein, where the positions are numbered by alignment of the amino acid sequence of the reference IAV H1 HA protein to SEQ ID NO: 95. In some embodiments, the IAV H1 HA protein comprises K395C and V36C substitutions relative to a reference IAV H1 HA protein, where the numbering of amino acids replaced in the reference IAV H1 HA protein corresponds to the numbering of SEQ ID NO: 95. K395C and V36C substitutions result in the formation of an interprotomer disulfide bond in the HA protein.

In some embodiments, the IAV H1 HA protein comprises a cysteine at position 406 and a cysteine at position 430, where the positions are numbered by alignment of the amino acid sequence of the IAV H1 HA protein to SEQ ID NO: 95. In some embodiments, the IAV H1 HA protein comprises a cysteine substitution at position 406 and a cysteine substitution at position 430 relative to a reference IAV H1 HA protein, where the positions are numbered by alignment of the amino acid sequence of the reference IAV H1 HA protein to SEQ ID NO: 95. In some embodiments, the IAV H1 HA protein comprises Q406C and D430C substitutions relative to a reference IAV H1 HA protein, where the numbering of amino acids replaced in the reference IAV H1 HA protein corresponds to the numbering of SEQ ID NO: 95. Q406C and D430C substitutions result in the formation of an interprotomer disulfide bond in the HA protein.

In some embodiments, the IAV H1 HA protein comprises a cysteine at position 457 and a cysteine at position 346, where the positions are numbered by alignment of the amino acid sequence of the IAV H1 HA protein to SEQ ID NO: 95. In some embodiments, the IAV H1 HA protein comprises a cysteine substitution at position 457 and a cysteine substitution at position 346 relative to a reference IAV H1 HA protein, where the positions are numbered by alignment of the amino acid sequence of the reference IAV H1 HA protein to SEQ ID NO: 95. In some embodiments, the IAV H1 HA protein comprises S457C and L346C substitutions relative to a reference IAV H1 HA protein, where the numbering of amino acids replaced in the reference IAV H1 HA protein corresponds to the numbering of SEQ ID NO: 95. S457C and L346C substitutions result in the formation of an interprotomer disulfide bond in the HA protein.

In some embodiments, the IAV H1 HA protein comprises a cysteine at position 461 and a cysteine at position 348, where the positions are numbered by alignment of the amino acid sequence of the IAV H1 HA protein to SEQ ID NO: 95. In some embodiments, the IAV H1 HA protein comprises a cysteine substitution at position 461 and a cysteine substitution at position 348 relative to a reference IAV H1 HA protein, where the positions are numbered by alignment of the amino acid sequence of the reference IAV H1 HA protein to SEQ ID NO: 95. In some embodiments, the IAV H1 HA protein comprises N461C and G348C substitutions relative to a reference IAV H1 HA protein, where the numbering of amino acids replaced in the reference IAV H1 HA protein corresponds to the numbering of SEQ ID NO: 95. N461C and G348C substitutions result in the formation of an interprotomer disulfide bond in the HA protein.

In some embodiments, the IAV H1 HA protein comprises a proline at position 404 and a proline at position 419, where the positions are numbered by alignment of the amino acid sequence of the IAV H1 HA protein to SEQ ID NO: 95. In some embodiments, the IAV H1 HA protein comprises a proline substitution at position 404 and a proline substitution at position 419 relative to a reference IAV H1 HA protein, where the positions are numbered by alignment of the amino acid sequence of the reference IAV H1 HA protein to SEQ ID NO: 95. In some embodiments, the IAV H1 HA protein comprises N404P and K419P substitutions relative to a reference IAV H1 HA protein, where the numbering of amino acids replaced in the reference IAV H1 HA protein corresponds to the numbering of SEQ ID NO: 95. N404P and K419P substitutions are proline substitutions in the B loop of the HA protein.

In some embodiments, the IAV H1 HA protein comprises a proline at position 404 and a proline at position 416, where the positions are numbered by alignment of the amino acid sequence of the IAV H1 HA protein to SEQ ID NO: 95. In some embodiments, the IAV H1 HA protein comprises a proline substitution at position 404 and a proline substitution at position 416 relative to a reference IAV H1 HA protein, where the positions are numbered by alignment of the amino acid sequence of the reference IAV H1 HA protein to SEQ ID NO: 95. In some embodiments, the IAV H1 HA protein comprises N404P and H416P substitutions relative to a reference IAV H1 HA protein, where the numbering of amino acids replaced in the reference IAV H1 HA protein corresponds to the numbering of SEQ ID NO: 95. N404P and H416P substitutions are proline substitutions in the B loop of the HA protein.

In some embodiments, the IAV H1 HA protein comprises a proline at position 405 and a proline at position 406, where the positions are numbered by alignment of the amino acid sequence of the IAV H1 HA protein to SEQ ID NO: 95. In some embodiments, the IAV H1 HA protein comprises a proline substitution at position 405 and a proline substitution at position 406 relative to a reference IAV H1 HA protein, where the positions are numbered by alignment of the amino acid sequence of the reference IAV H1 HA protein to SEQ ID NO: 95. In some embodiments, the IAV H1 HA protein comprises T405P and Q406P substitutions relative to a reference IAV H1 HA protein, where the numbering of amino acids replaced in the reference IAV H1 HA protein corresponds to the numbering of SEQ ID NO: 95. T405P and Q406P substitutions are proline substitutions in the B loop of the HA protein.

In some embodiments, the IAV H1 HA protein comprises a proline at position 415 and a proline at position 416, where the positions are numbered by alignment of the amino acid sequence of the IAV H1 HA protein to SEQ ID NO: 95. In some embodiments, the IAV H1 HA protein comprises a proline substitution at position 415 and a proline substitution at position 416 relative to a reference IAV H1 HA protein, where the positions are numbered by alignment of the amino acid sequence of the reference IAV H1 HA protein to SEQ ID NO: 95. In some embodiments, the IAV H1 HA protein comprises N415P and H416P substitutions relative to a reference IAV H1 HA protein, where the numbering of amino acids replaced in the reference IAV H1 HA protein corresponds to the numbering of SEQ ID NO: 95. N415P and H416P substitutions are proline substitutions in the B loop of the HA protein.

In some embodiments, the IAV H1 HA protein comprises a tyrosine at position 25 and a glutamic acid at position 45, where the positions are numbered by alignment of the amino acid sequence of the IAV H1 HA protein to SEQ ID NO: 95. In some embodiments, the IAV H1 HA protein comprises a tyrosine substitution at position 25 and a glutamic acid substitution at position 45 relative to a reference IAV H1 HA protein, where the positions are numbered by alignment of the amino acid sequence of the reference IAV H1 HA protein to SEQ ID NO: 95. In some embodiments, the IAV H1 HA protein comprises H25Y and H45E substitutions relative to a reference IAV H1 HA protein, where the numbering of amino acids replaced in the reference IAV H1 HA protein corresponds to the numbering of SEQ ID NO: 95. H25Y and H45E substitutions are replacements of pH-sensitive histidines.

In some embodiments, the IAV H1 HA protein comprises a tyrosine at position 370 and a tryptophan at position 497, where the positions are numbered by alignment of the amino acid sequence of the IAV H1 HA protein to SEQ ID NO: 95. In some embodiments, the IAV H1 HA protein comprises a tyrosine substitution at position 370 and a tryptophan substitution at position 497 relative to a reference IAV H1 HA protein, where the positions are numbered by alignment of the amino acid sequence of the reference IAV H1 HA protein to SEQ ID NO: 95. In some embodiments, the IAV H1 HA protein comprises H370Y and K497W substitutions relative to a reference IAV H1 HA protein, where the numbering of amino acids replaced in the reference IAV H1 HA protein corresponds to the numbering of SEQ ID NO: 95. An H370Y substitution is a replacement of a pH-sensitive histidine, and a K497W substitution is a cavity-filling substitution.

In some embodiments, the IAV H1 HA protein comprises a glycine at position 402, a glycine at position 405, and a glycine at position 407, where the positions are numbered by alignment of the amino acid sequence of the IAV H1 HA protein to SEQ ID NO: 95. In some embodiments, the IAV H1 HA protein comprises a glycine substitution at position 402, a glycine substitution at position 405, and a glycine substitution at position 407 relative to a reference IAV H1 HA protein, where the positions are numbered by alignment of the amino acid sequence of the reference IAV H1 HA protein to SEQ ID NO: 95. In some embodiments, the IAV H1 HA protein comprises K402G, T405G, and F407G substitutions relative to a reference IAV H1 HA protein, where the numbering of amino acids replaced in the reference IAV H1 HA protein corresponds to the numbering of SEQ ID NO: 95. K402G, T405G, and F407G substitutions are glycine substitutions in the B loop of the HA protein.

In some embodiments, the IAV H1 HA protein comprises a isoleucine at position 395 and a isoleucine at position 447, where the positions are numbered by alignment of the amino acid sequence of the IAV H1 HA protein to SEQ ID NO: 95. In some embodiments, the IAV H1 HA protein comprises a isoleucine substitution at position 395 and a isoleucine substitution at position 447 relative to a reference IAV H1 HA protein, where the positions are numbered by alignment of the amino acid sequence of the reference IAV H1 HA protein to SEQ ID NO: 95. In some embodiments, the IAV H1 HA protein comprises K395I and E447I substitutions relative to a reference IAV H1 HA protein, where the numbering of amino acids replaced in the reference IAV H1 HA protein corresponds to the numbering of SEQ ID NO: 95. K395I and E447I substitutions are cavity-filling substitutions In some embodiments, the IAV H1 HA protein comprises a glycine at position 456 and a isoleucine at position 402, where the positions are numbered by alignment of the amino acid sequence of the IAV H1 HA protein to SEQ ID NO: 95. In some embodiments, the IAV H1 HA protein comprises a glycine substitution at position 456 and a isoleucine substitution at position 402 relative to a reference IAV H1 HA protein, where the positions are numbered by alignment of the amino acid sequence of the reference IAV H1 HA protein to SEQ ID NO: 95. In some embodiments, the IAV H1 HA protein comprises D456G and K402I substitutions relative to a reference IAV H1 HA protein, where the numbering of amino acids replaced in the reference IAV H1 HA protein corresponds to the numbering of SEQ ID NO: 95. AD456G substitution is a glycine substitution in the B loop, and a K402I substitution is a cavity-filling substitution.

In some embodiments, the IAV H1 HA protein comprises a cysteine at position 442 and a cysteine at position 423, where the positions are numbered by alignment of the amino acid sequence of the IAV H1 HA protein to SEQ ID NO: 95. In some embodiments, the IAV H1 HA protein comprises a cysteine substitution at position 442 and a cysteine substitution at position 423 relative to a reference IAV H1 HA protein, where the positions are numbered by alignment of the amino acid sequence of the reference IAV H1 HA protein to SEQ ID NO: 95. In some embodiments, the IAV H1 HA protein comprises L442C and N423C substitutions relative to a reference IAV H1 HA protein, where the numbering of amino acids replaced in the reference IAV H1 HA protein corresponds to the numbering of SEQ ID NO: 95. L442C and N423C substitutions result in the formation of an interprotomer disulfide bond in the HA protein.

In some embodiments, the IAV H1 HA protein comprises a glycine at position 391, where the positions are numbered by alignment of the amino acid sequence of the IAV H1 HA protein to SEQ ID NO: 95. In some embodiments, the IAV H1 HA protein comprises a glycine substitution at position 391 relative to a reference IAV H1 HA protein, where the positions are numbered by alignment of the amino acid sequence of the reference IAV H1 HA protein to SEQ ID NO: 95. In some embodiments, the IAV H1 HA protein comprises a K391G substitution relative to a reference IAV H1 HA protein, where the numbering of amino acids replaced in the reference IAV H1 HA protein corresponds to the numbering of SEQ ID NO: 95. A K391G substitution is a glycine substitution in the B loop of the HA protein.

In some embodiments, the IAV H1 HA protein comprises an amino acid sequence with at least 90%, at least 91%, at least 92%, at least 93%, at least 94%, at least 95%, at least 96%, at least 97%, at least 98%, or at least 99% sequence identity to the amino acid sequence of SEQ ID NO: 95. In some embodiments, the IAV H1 HA protein comprises an amino acid sequence with at least 90% sequence identity to the amino acid sequence of SEQ ID NO: 95.

Substitutions described in this subsection relating to IAV H1 HA proteins may be combined. For example, any of the pairs of cysteine substitutions may be combined with one or more proline substitutions in the B loop, glycine substitutions in the B loop, substitutions of pH-sensitive histidines, and/or cavity-filling substitutions. Pairs of cysteine substitutions that form different disulfide bonds (e.g., interprotomer versus intraprotomer bonds, head versus stalk region bonds) may also be combined. Preferred combinations of substitutions are discussed below.

In some embodiments, the IAV H1 HA protein comprises an interprotomer disulfide bond formed by at least one introduced cysteine, and one or more proline substitutions in the B loop. In some embodiments, the IAV H1 HA protein comprises an interprotomer disulfide bond formed by at least one introduced cysteine, and one or more substitutions of a charged or polar cavity-lining residue with a hydrophobic residue. In some embodiments, the IAV H1 HA protein comprises an interprotomer disulfide bond formed by at least one introduced cysteine, one or more substitutions of a charged or polar cavity-lining residue with a hydrophobic residue, and one or more proline substitutions in the B loop.

In some embodiments, the IAV H1 HA protein comprises an interprotomer disulfide bond formed by at least one introduced cysteine, and an intraprotomer disulfide bond formed by at least one introduced cysteine, where the introduced cysteine(s) of the interpromoter disulfide bond are at different positions than the introduced cysteine(s) of the intraprotomer disulfide bond.

In some embodiments, the IAV H1 HA protein comprises an interprotomer disulfide bond formed by at least one introduced cysteine, and one or more substitutions of a pH-sensitive histidine in the HA protein and one or more substitutions of a charged or polar cavity-lining residue with a hydrophobic residue.

In some embodiments, the IAV H1 HA protein comprises a cysteine at position 391, a cysteine at position 37, a proline at position 404, and a proline at position 416, where the positions are numbered by alignment of the amino acid sequence of the IAV H1 HA protein to SEQ ID NO: 83. In some embodiments, the IAV H1 HA protein comprises a cysteine substitution at position 391, a cysteine substitution at position 37, a proline substitution at position 404, and a proline substitution at position 416 relative to a reference IAV H1 HA protein, where the positions are numbered by alignment of the amino acid sequence of the reference IAV H1 HA protein to SEQ ID NO: 83. In some embodiments, the IAV H1 HA protein comprises K391C, L37C, N404P, H416P substitutions relative to a reference IAV H1 HA protein, where the numbering of amino acids replaced in the reference IAV H1 HA protein corresponds to the numbering of SEQ ID NO: 83.

In some embodiments, the IAV H1 HA protein comprises a cysteine at position 391, a cysteine at position 37, a isoleucine at position 395, and a isoleucine at position 447, where the positions are numbered by alignment of the amino acid sequence of the IAV H1 HA protein to SEQ ID NO: 83. In some embodiments, the IAV H1 HA protein comprises a cysteine substitution at position 391, a cysteine substitution at position 37, a isoleucine substitution at position 395, and a isoleucine substitution at position 447 relative to a reference IAV H1 HA protein, where the positions are numbered by alignment of the amino acid sequence of the reference IAV H1 HA protein to SEQ ID NO: 83. In some embodiments, the IAV H1 HA protein comprises K391C, L37C, K395I, E447I substitutions relative to a reference IAV H1 HA protein, where the numbering of amino acids replaced in the reference IAV H1 HA protein corresponds to the numbering of SEQ ID NO: 83.

In some embodiments, the IAV H1 HA protein comprises a cysteine at position 391, a cysteine at position 37, a glycine at position 456, and a isoleucine at position 402, where the positions are numbered by alignment of the amino acid sequence of the IAV H1 HA protein to SEQ ID NO: 83. In some embodiments, the IAV H1 HA protein comprises a cysteine substitution at position 391, a cysteine substitution at position 37, a glycine substitution at position 456, and a isoleucine substitution at position 402 relative to a reference IAV H1 HA protein, where the positions are numbered by alignment of the amino acid sequence of the reference IAV H1 HA protein to SEQ ID NO: 83. In some embodiments, the IAV H1 HA protein comprises K391C, L37C, D456G, K402I substitutions relative to a reference IAV H1 HA protein, where the numbering of amino acids replaced in the reference IAV H1 HA protein corresponds to the numbering of SEQ ID NO: 83.

In some embodiments, the IAV H1 HA protein comprises a cysteine at position 395, a cysteine at position 36, a proline at position 404, and a proline at position 416, where the positions are numbered by alignment of the amino acid sequence of the IAV H1 HA protein to SEQ ID NO: 83. In some embodiments, the IAV H1 HA protein comprises a cysteine substitution at position 395, a cysteine substitution at position 36, a proline substitution at position 404, and a proline substitution at position 416 relative to a reference IAV H1 HA protein, where the positions are numbered by alignment of the amino acid sequence of the reference IAV H1 HA protein to SEQ ID NO: 83. In some embodiments, the IAV H1 HA protein comprises K395C, V36C, N404P, H416P substitutions relative to a reference IAV H1 HA protein, where the numbering of amino acids replaced in the reference IAV H1 HA protein corresponds to the numbering of SEQ ID NO: 83.

In some embodiments, the IAV H1 HA protein comprises a cysteine at position 395, a cysteine at position 36, a glycine at position 456, and a isoleucine at position 402, where the positions are numbered by alignment of the amino acid sequence of the IAV H1 HA protein to SEQ ID NO: 83. In some embodiments, the IAV H1 HA protein comprises a cysteine substitution at position 395, a cysteine substitution at position 36, a glycine substitution at position 456, and a isoleucine substitution at position 402 relative to a reference IAV H1 HA protein, where the positions are numbered by alignment of the amino acid sequence of the reference IAV H1 HA protein to SEQ ID NO: 83. In some embodiments, the IAV H1 HA protein comprises K395C, V36C, D456G, K402I substitutions relative to a reference IAV H1 HA protein, where the numbering of amino acids replaced in the reference IAV H1 HA protein corresponds to the numbering of SEQ ID NO: 83.

In some embodiments, the IAV H1 HA protein comprises a cysteine at position 461, a cysteine at position 348, a proline at position 404, and a proline at position 416, where the positions are numbered by alignment of the amino acid sequence of the IAV H1 HA protein to SEQ ID NO: 83. In some embodiments, the IAV H1 HA protein comprises a cysteine substitution at position 461, a cysteine substitution at position 348, a proline substitution at position 404, and a proline substitution at position 416 relative to a reference IAV H1 HA protein, where the positions are numbered by alignment of the amino acid sequence of the reference IAV H1 HA protein to SEQ ID NO: 83. In some embodiments, the IAV H1 HA protein comprises N461C, G348C, N404P, H416P substitutions relative to a reference IAV H1 HA protein, where the numbering of amino acids replaced in the reference IAV H1 HA protein corresponds to the numbering of SEQ ID NO: 83.

In some embodiments, the IAV H1 HA protein comprises a cysteine at position 461, a cysteine at position 348, a isoleucine at position 395, and a isoleucine at position 447, where the positions are numbered by alignment of the amino acid sequence of the IAV H1 HA protein to SEQ ID NO: 83. In some embodiments, the IAV H1 HA protein comprises a cysteine substitution at position 461, a cysteine substitution at position 348, a isoleucine substitution at position 395, and a isoleucine substitution at position 447 relative to a reference IAV H1 HA protein, where the positions are numbered by alignment of the amino acid sequence of the reference IAV H1 HA protein to SEQ ID NO: 83. In some embodiments, the IAV H1 HA protein comprises N461C, G348C, K395I, E447I substitutions relative to a reference IAV H1 HA protein, where the numbering of amino acids replaced in the reference IAV H1 HA protein corresponds to the numbering of SEQ ID NO: 83.

In some embodiments, the IAV H1 HA protein comprises a cysteine at position 461, a cysteine at position 348, a glycine at position 456, and a isoleucine at position 402, where the positions are numbered by alignment of the amino acid sequence of the IAV H1 HA protein to SEQ ID NO: 83. In some embodiments, the IAV H1 HA protein comprises a cysteine substitution at position 461, a cysteine substitution at position 348, a glycine substitution at position 456, and a isoleucine substitution at position 402 relative to a reference IAV H1 HA protein, where the positions are numbered by alignment of the amino acid sequence of the reference IAV H1 HA protein to SEQ ID NO: 83. In some embodiments, the IAV H1 HA protein comprises N461C, G348C, D456G, K402I substitutions relative to a reference IAV H1 HA protein, where the numbering of amino acids replaced in the reference IAV H1 HA protein corresponds to the numbering of SEQ ID NO: 83.

In some embodiments, the IAV H1 HA protein comprises a cysteine at position 391, a cysteine at position 37, a proline at position 404, a proline at position 416, a glycine at position 456, and a isoleucine at position 402, where the positions are numbered by alignment of the amino acid sequence of the IAV H1 HA protein to SEQ ID NO: 83. In some embodiments, the IAV H1 HA protein comprises a cysteine substitution at position 391, a cysteine substitution at position 37, a proline substitution at position 404, a proline substitution at position 416, a glycine substitution at position 456, and a isoleucine substitution at position 402 relative to a reference IAV H1 HA protein, where the positions are numbered by alignment of the amino acid sequence of the reference IAV H1 HA protein to SEQ ID NO: 83. In some embodiments, the IAV H1 HA protein comprises K391C, L37C, N404P, H416P, D456G, K402I substitutions relative to a reference IAV H1 HA protein, where the numbering of amino acids replaced in the reference IAV H1 HA protein corresponds to the numbering of SEQ ID NO: 83.

In some embodiments, the IAV H1 HA protein comprises a cysteine at position 410, a cysteine at position 462, a cysteine at position 457, and a cysteine at position 346, where the positions are numbered by alignment of the amino acid sequence of the IAV H1 HA protein to SEQ ID NO: 95. In some embodiments, the IAV H1 HA protein comprises a cysteine substitution at position 410, a cysteine substitution at position 462, a cysteine substitution at position 457, and a cysteine substitution at position 346 relative to a reference IAV H1 HA protein, where the positions are numbered by alignment of the amino acid sequence of the reference IAV H1 HA protein to SEQ ID NO: 95. In some embodiments, the IAV H1 HA protein comprises V410C, L462C, S457C, L346C substitutions relative to a reference IAV H1 HA protein, where the numbering of amino acids replaced in the reference IAV H1 HA protein corresponds to the numbering of SEQ ID NO: 95.

In some embodiments, the IAV H1 HA protein comprises a cysteine at position 391, a cysteine at position 37, a phenylalanine at position 370, and a phenylalanine at position 455, where the positions are numbered by alignment of the amino acid sequence of the IAV H1 HA protein to SEQ ID NO: 95. In some embodiments, the IAV H1 HA protein comprises a cysteine substitution at position 391, a cysteine substitution at position 37, a phenylalanine substitution at position 370, and a phenylalanine substitution at position 455 relative to a reference IAV H1 HA protein, where the positions are numbered by alignment of the amino acid sequence of the reference IAV H1 HA protein to SEQ ID NO: 95. In some embodiments, the IAV H1 HA protein comprises K391C, L37C, H370F, H455F substitutions relative to a reference IAV H1 HA protein, where the numbering of amino acids replaced in the reference IAV H1 HA protein corresponds to the numbering of SEQ ID NO: 95.

H3 HA Proteins

Some embodiments relate to IAV H3 HA proteins comprising an amino acid substitution relative to a reference IAV H3 HA protein. The reference IAV H3 HA protein may be an HA protein of an influenza A virus of an IAV subtype containing an H3 HA protein, such as an influenza A/(H3N2) virus. H3 HA proteins are present, e.g., on influenza A viruses of the H3N2 subtype, but other IAV subtypes expressing H3 HA proteins have been identified (such as the H3N8 subtype endemic in birds, horses, and dogs). Non-limiting examples of influenza A/(H3N2) virus isolates include A/Sydney/5/97(H3N2), A/Moscow/10/1999 (H3N2), A/Fujian/411/2002(H3N2), A/California/7/2004 (H3N2), A/Wisconsin/67/2005(H3N2), A/Brisbane/10/2007 (H3N2), A/Perth/16/2009(H3N2), A/Victoria/361/2011 (H3N2), A/Texas/50/2012(H3N2), A/Switzerland/9715293/2013(H3N2), A/Hong Kong/4801/2014(H3N2), A/Singapore/INFIMH-16-0019/2016(H3N2), A/Kansas/14/2017(H3N2), A/Hong Kong/2671/2019(H3N2), A/Hong Kong/45/2019(H3N2), A/Cambodia/e0826360/2020 (H3N2), A/Darwin/9/2021(H3N2), and A/Darwin/6/2021 (H3N2). Representative amino acid sequences of influenza A/(H3N2) virus HA proteins of previous seasonal influenza vaccines are provided as SEQ ID NOs: 136-153.

Those of ordinary skill in the art will appreciate that mutations disclosed in relation to a listed sequence, e.g., of influenza A/Darwin/6/2021(H3N2) virus HA, may be applied to HA proteins of other influenza A/(H3N2) viruses or other reference IAV H3 HA proteins. For example, in applying a T40C substitution to another IAV H3 HA protein, the skilled artisan would align the amino acid sequence of that reference HA protein to the influenza A/Darwin/6/2021 (H3N2) virus HA protein sequence of SEQ ID NO: 82 and introduce a C at the residue of the reference HA protein amino acid sequence that aligns to T40 of SEQ ID NO: 82.

Exemplary substitutions that may be present in IAV H1 HA proteins are provided below in Table HA-5. In the event a reference HA protein sequence (e.g. of an isolate) already includes a substitution mentioned in the table, then it will be appreciated that some embodiments will include the residues set forth at positions below without a substitution being made at that particular position. For example, if an isolate already contains an isoleucine at position 219, then embodiments comprising 219I and H504P can be obtained with only a 504P substitution.

TABLE HA-5

| A/(H3N2) subtype HA substitutions (A/Darwin/6/2021(H3N2) (SEQ ID NO: 82) numbering) | |
|---|---|
| Substitution(s) | Mutation class |
| T40C A55C | Intra-protomer DS (Head) |
| S123C R421C | Inter-protomer DS (Head) |
| L260C P237C | Inter-protomer DS (Head) |
| Q392C T46C | Inter-protomer DS (Stalk) |
| I411C Y428C | Inter-protomer DS (Stalk) |
| G402P R421P E414P | Proline(s) |
| K403G | Glycine(s) |
| F408G H409G | Glycine(s) |
| K396I | Cavity Filling |
| T219I H504P | Cavity Filling (T219I) / Proline (H504P) |

In some embodiments, the IAV H3 HA protein comprises a cysteine at position 40 and a cysteine at position 55, where the positions are numbered by alignment of the amino acid sequence of the IAV H3 HA protein to SEQ ID NO: 82. In some embodiments, the IAV H3 HA protein comprises a cysteine substitution at position 40 and a cysteine substitution at position 55 relative to a reference IAV H3 HA protein, where the positions are numbered by alignment of the amino acid sequence of the reference IAV H3 HA protein to SEQ ID NO: 82. In some embodiments, the IAV H3 HA protein comprises T40C and A55C substitutions relative to a reference IAV H3 HA protein, where the numbering of amino acids replaced in the reference IAV H3 HA protein corresponds to the numbering of SEQ ID NO: 82. T40C and A55C substitutions result in the formation of an intraprotomer disulfide bond in the head region of the HA protein.

In some embodiments, the IAV H3 HA protein comprises a cysteine at position 123 and a cysteine at position 421, where the positions are numbered by alignment of the amino acid sequence of the IAV H3 HA protein to SEQ ID NO: 82. In some embodiments, the IAV H3 HA protein comprises a cysteine substitution at position 123 and a cysteine substitution at position 421 relative to a reference IAV H3 HA protein, where the positions are numbered by alignment of the amino acid sequence of the reference IAV H3 HA protein to SEQ ID NO: 82. In some embodiments, the IAV H3 HA protein comprises S123C and R421C substitutions relative to a reference IAV H3 HA protein, where the numbering of amino acids replaced in the reference IAV H3 HA protein corresponds to the numbering of SEQ ID NO: 82. S123C and R421C substitutions result in the formation of an interprotomer disulfide bond in the head region of the HA protein.

In some embodiments, the IAV H3 HA protein comprises a cysteine at position 260 and a cysteine at position 237, where the positions are numbered by alignment of the amino acid sequence of the IAV H3 HA protein to SEQ ID NO: 82. In some embodiments, the IAV H3 HA protein comprises a cysteine substitution at position 260 and a cysteine substitution at position 237 relative to a reference IAV H3 HA protein, where the positions are numbered by alignment of the amino acid sequence of the reference IAV H3 HA protein to SEQ ID NO: 82. In some embodiments, the IAV H3 HA protein comprises L260C and P237C substitutions relative to a reference IAV H3 HA protein, where the numbering of amino acids replaced in the reference IAV H3 HA protein corresponds to the numbering of SEQ ID NO: 82. L260C and P237C substitutions result in the formation of an interprotomer disulfide bond in the head region of the HA protein.

In some embodiments, the IAV H3 HA protein comprises a cysteine at position 392 and a cysteine at position 46, where the positions are numbered by alignment of the amino acid sequence of the IAV H3 HA protein to SEQ ID NO: 82. In some embodiments, the IAV H3 HA protein comprises a cysteine substitution at position 392 and a cysteine substitution at position 46 relative to a reference IAV H3 HA protein, where the positions are numbered by alignment of the amino acid sequence of the reference IAV H3 HA protein to SEQ ID NO: 82. In some embodiments, the IAV H3 HA protein comprises Q392C and T46C substitutions relative to a reference IAV H3 HA protein, where the numbering of amino acids replaced in the reference IAV H3 HA protein corresponds to the numbering of SEQ ID NO: 82. Q392C and T46C substitutions result in the formation of an interprotomer disulfide bond in the stalk region of the HA protein.

In some embodiments, the IAV H3 HA protein comprises a cysteine at position 411 and a cysteine at position 428, where the positions are numbered by alignment of the amino acid sequence of the IAV H3 HA protein to SEQ ID NO: 82. In some embodiments, the IAV H3 HA protein comprises a cysteine substitution at position 411 and a cysteine substitution at position 428 relative to a reference IAV H3 HA protein, where the positions are numbered by alignment of the amino acid sequence of the reference IAV H3 HA protein to SEQ ID NO: 82. In some embodiments, the IAV H3 HA protein comprises I411C and Y428C substitutions relative to a reference IAV H3 HA protein, where the numbering of amino acids replaced in the reference IAV H3 HA protein corresponds to the numbering of SEQ ID NO: 82. I411C and Y428C substitutions result in the formation of an interprotomer disulfide bond in the stalk region of the HA protein.

In some embodiments, the IAV H3 HA protein comprises a proline at position 402, a proline at position 421, and a proline at position 414, where the positions are numbered by alignment of the amino acid sequence of the IAV H3 HA protein to SEQ ID NO: 82. In some embodiments, the IAV H3 HA protein comprises a proline substitution at position 402, a proline substitution at position 421, and a proline substitution at position 414 relative to a reference IAV H3 HA protein, where the positions are numbered by alignment of the amino acid sequence of the reference IAV H3 HA protein to SEQ ID NO: 82. In some embodiments, the IAV H3 HA protein comprises G402P, R421P, and E414P substitutions relative to a reference IAV H3 HA protein, where the numbering of amino acids replaced in the reference IAV H3 HA protein corresponds to the numbering of SEQ ID NO: 82. G402P, R421P, and E414P substitutions are proline substitutions in the B loop of the HA protein.

In some embodiments, the IAV H3 HA protein comprises a glycine at position 403, where the positions are numbered by alignment of the amino acid sequence of the IAV H3 HA protein to SEQ ID NO: 82. In some embodiments, the IAV H3 HA protein comprises a glycine substitution at position 403 relative to a reference IAV H3 HA protein, where the positions are numbered by alignment of the amino acid sequence of the reference IAV H3 HA protein to SEQ ID NO: 82. In some embodiments, the IAV H3 HA protein comprises a K403G substitution relative to a reference IAV H3 HA protein, where the numbering of amino acids replaced in the reference IAV H3 HA protein corresponds to the numbering of SEQ ID NO: 82. A K403G substitution is a glycine substitution in the B loop of the HA protein.

In some embodiments, the IAV H3 HA protein comprises a glycine at position 408 and a glycine at position 409, where the positions are numbered by alignment of the amino acid sequence of the IAV H3 HA protein to SEQ ID NO: 82. In some embodiments, the IAV H3 HA protein comprises a glycine substitution at position 408 and a glycine substitution at position 409 relative to a reference IAV H3 HA protein, where the positions are numbered by alignment of the amino acid sequence of the reference IAV H3 HA protein to SEQ ID NO: 82. In some embodiments, the IAV H3 HA protein comprises F408G and H409G substitutions relative to a reference IAV H3 HA protein, where the numbering of amino acids replaced in the reference IAV H3 HA protein corresponds to the numbering of SEQ ID NO: 82. F408G and H409G substitutions are glycine substitutions in the B loop of the HA protein.

In some embodiments, the IAV H3 HA protein comprises a isoleucine at position 396, where the positions are numbered by alignment of the amino acid sequence of the IAV H3 HA protein to SEQ ID NO: 82. In some embodiments, the IAV H3 HA protein comprises a isoleucine substitution at position 396 relative to a reference IAV H3 HA protein, where the positions are numbered by alignment of the amino acid sequence of the reference IAV H3 HA protein to SEQ ID NO: 82. In some embodiments, the IAV H3 HA protein comprises a K396I substitution relative to a reference IAV H3 HA protein, where the numbering of amino acids replaced in the reference IAV H3 HA protein corresponds to the numbering of SEQ ID NO: 82. A K396I substitution is a cavity-filling substitution.

In some embodiments, the IAV H3 HA protein comprises a isoleucine at position 219 and a proline at position 504, where the positions are numbered by alignment of the amino acid sequence of the IAV H3 HA protein to SEQ ID NO: 82. In some embodiments, the IAV H3 HA protein comprises a isoleucine substitution at position 219 and a proline substitution at position 504 relative to a reference IAV H3 HA protein, where the positions are numbered by alignment of the amino acid sequence of the reference IAV H3 HA protein to SEQ ID NO: 82. In some embodiments, the IAV H3 HA protein comprises T219I and H504P substitutions relative to a reference IAV H3 HA protein, where the numbering of amino acids replaced in the reference IAV H3 HA protein corresponds to the numbering of SEQ ID NO: 82. A T219I substitution is a cavity-filling substitution, and an H504P substitution is a proline substitution in the B loop of the HA protein.

Substitutions described in this subsection relating to IAV H3 HA proteins may be combined. For example, any of the pairs of cysteine substitutions may be combined with one or more proline substitutions in the B loop, glycine substitutions in the B loop, substitutions of pH-sensitive histidines, and/or cavity-filling substitutions. Pairs of cysteine substitutions that form different disulfide bonds (e.g., interprotomer v. intraprotomer bonds, head v. stalk region bonds) may also be combined. In some embodiments, the IAV H3 HA protein comprises one or more substitutions of a pH-sensitive histidine in the HA protein and one or more substitutions of a charged or polar cavity-lining residue with a hydrophobic residue.

In some embodiments, the IAV H3 HA protein comprises an amino acid sequence with at least 90%, at least 91%, at least 92%, at least 93%, at least 94%, at least 95%, at least 96%, at least 97%, at least 98%, or at least 99% sequence identity to the amino acid sequence of SEQ ID NO: 82. In some embodiments, the IAV H3 HA protein comprises an amino acid sequence with at least 90% sequence identity to the amino acid sequence of SEQ ID NO: 82.

Virus and Antigen Characterization

Influenza viruses and protein sequences thereof may be classified as belonging to a given IAV subtype or IBV lineage using any suitable classification method. Non-limiting examples of classification methods include sequence-based analyses (e.g., sequence comparison and phylogenetic tree building) and antigenic characterization (e.g., HAI assays, microneutralization assays, and immunofluorescence).

Sequence Analyses

Amino acid sequences of influenza virus antigens may be analyzed to classify them as belonging to a given IAV subtype or IBV lineage. For example, an HA amino acid sequence is classified into the H1 subtype, H3 subtype, B/Victoria lineage, B/Yamagata lineage on the basis of similarity to extant H1 HA, H3 HA, B/Victoria lineage HA, or B/Yamagata lineage HA amino sequences. As another example, an HA amino acid sequence may be fit into a phylogenetic tree of extant HA amino acid sequences, and classified as belonging to a given IAV subtype or IBV lineage according to its most likely place in the phylogenetic tree.

Nucleotide sequences of influenza virus genome segments may similarly be compared to extant genome segments to classify the influenza virus as belonging to a given IAV subtype or IBV lineage, on the basis of percentage identity to extant sequences of a given subtype or lineage. As another example, an influenza virus genome segment nucleotide sequence may be fit into a phylogenetic tree of extant genome segment nucleotide sequences, and classified as belonging to a given IAV subtype or IBV lineage according to its most likely place in the phylogenetic tree.

Antigenic Characterization

Serological methods such as the HAI test are useful for many epidemiological and immunological studies and for evaluation of the antibody response following vaccination. Serological methods are also useful in situations where identification of the virus is not feasible (e.g. after viral shedding has stopped). The HAI test is used to identify circulating influenza viruses that are antigenically similar to influenza viruses from previous seasons.

The hemagglutination inhibition (HAI) test is a classical laboratory procedure for the classification or subtyping of hemagglutinating viruses and further determining the antigenic characteristics of influenza viral isolates provided that the reference antisera used contain antibodies to currently circulating viruses (see, e.g., Pedersen J C *Methods Mol Biol.* 2014; 1161:11-25). The antisera used are based on antigen preparations derived from either the wild-type strain or a high-growth reassortant made using the wild-type strain or an antigenically equivalent strain. Effective hemagglutinin inhibition by sera or antibodies specific to H1 HA but not sera or antibodies specific to H3 HA, for example, indicates that an influenza virus expresses an HA belonging to the H1 subtype.

The microneutralization assay is a highly sensitive and specific assay for detecting virus-specific neutralizing antibodies to influenza viruses in human and animal sera, and in some embodiments, includes the detection of human antibodies to avian subtypes. Testing can be carried out quickly once a novel virus is identified and often before purified viral proteins become available for use in other assays. Neutralization of an influenza virus cells by sera or antibodies specific to H1 HA but not sera or antibodies specific to H3 HA, for example, indicates that an influenza virus expresses an HA belonging to the H1 subtype.

Immunofluorescence antibody (IFA) staining of virus-infected cells in original clinical specimens and field isolates is a rapid and sensitive method for diagnosing respiratory and other viral infections. In some embodiments, IFA staining is performed on isolates rather than original clinical specimens, as this allows any virus that is present to first be amplified, and if required used in other studies. Staining of influenza virus-infected cells by antibodies specific to H1 HA but not antibodies specific to H3 HA, for example, indicates that an influenza virus expresses an HA belonging to the H1 subtype.

Vaccine Compositions

Some aspects relate to compositions for use as vaccines against seasonal influenza viruses, and optionally other respiratory viruses (e.g., coronaviruses and/or respiratory syncytial viruses).

Some embodiments relate to compositions comprising nucleic acids (e.g., RNAs, (e.g., mRNAs)) encoding respiratory virus (e.g., influenza virus, RSV, SARS-CoV-2) antigens, where the nucleic acids encoding different antigens are present at certain ratios. A "ratio" of two nucleic acids (e.g., encoding proteins A and B) may refer to a molar ratio (the number of nucleic acid molecules encoding protein A, relative to the number of nucleic acid molecules encoding protein B), or a mass ratio (the mass of nucleic acids encoding protein A, relative to the mass of nucleic acids encoding protein B). Unless indicated otherwise or otherwise clear from context, reference to nucleic acids (e.g., RNAs (e.g., mRNAs)) being present at a "ratio" refers to a mass ratio of the nucleic acids.

Multivalent Vaccines

Some aspects relate to multivalent vaccines that comprise components to protect a subject against more than one influenza virus. Multivalent influenza vaccines can include three (trivalent), four (quadrivalent), five (pentavalent), or more (such as octavalent) components that each independently are designed to protect against one of a variety of influenza virus strains. For instance, a trivalent vaccine can include RNA(s) encoding an influenza A/(H1N1) virus protein, an influenza A/(H3N2) virus protein, and an influenza B/Victoria lineage virus protein. Some trivalent compositions comprise RNA(s) encoding two influenza A virus HA proteins and one influenza B virus HA proteins. Quadrivalent vaccines can include RNA(s) encoding three influenza A virus proteins (e.g., HA proteins) and one influenza B virus protein (e.g., HA protein). Some quadrivalent vaccines include mRNA encoding two influenza A virus proteins (e.g., HA proteins) and two influenza B virus proteins (e.g., HA proteins).

In some aspects, a multivalent vaccine comprises three mRNAs, a first encoding an influenza A/(H1N1) virus HA protein, a second encoding an influenza A/(H3N2) virus HA protein, and a third encoding an influenza B/Victoria lineage virus HA protein. In some embodiments, the mRNAs are present at a 1:1:1:1 mass ratio.

In some aspects, a multivalent vaccine comprises four mRNAs, a first encoding an influenza A/(H1N1) virus HA protein, a second encoding an influenza A/(H3N2) virus HA protein, a third encoding an influenza B/Victoria lineage virus HA protein, and a fourth encoding influenza B/Yamagata lineage virus HA protein. In some embodiments, the mRNAs are present at a 1:1:1:1 mass ratio.

In some aspects, a multivalent vaccine comprises eight mRNAs, a first encoding an IAV H1 HA protein, a second encoding an IAV H3 HA protein, a third encoding an influenza B/Victoria lineage virus HA protein, an influenza B/Yamagata lineage virus HA protein, a fifth encoding an IAV N1 NA protein, a sixth encoding an IAV N2 NA protein, a seventh encoding an influenza B/Victoria lineage virus NA protein, and an eighth encoding an influenza B/Yamagata lineage virus NA protein. In some embodiments, the mRNAs are present at a 1:1:1:1:1:1:1:1 mass ratio. In some embodiments, the mRNAs are present at a 3:3:3:3:1:1:1:1 mass ratio (i.e., the mRNAs encoding the HA proteins are present at 3 times the amount (by mass) of mRNAs encoding the NA proteins).

In some aspects, a multivalent vaccine comprises five mRNAs, a first encoding an IAV H1 HA protein, a second encoding a first IAV H3 HA protein, a third encoding a second IAV H3 HA protein, a fourth encoding an influenza B/Victoria lineage virus HA protein, and a fifth encoding an influenza B/Yamagata lineage HA protein. In some embodiments, the mRNAs are present at a 1:1:1:1:1 mass ratio.

In some aspects, a multivalent vaccine comprises four mRNAs, a first encoding an IAV H1 HA protein, a second encoding a first IAV H3 HA protein, a third encoding a second IAV H3 HA protein, and a fourth encoding an influenza B/Victoria lineage virus HA protein, where the vaccine does not comprise an mRNA encoding an influenza B/Yamagata lineage virus HA protein. In some embodiments, the mRNAs are present at a 1:1:1:1 mass ratio.

In some aspects, a multivalent vaccine comprises six mRNAs, a first encoding an IAV H1 HA protein, a second encoding a first IAV H3 HA protein, a third encoding a second IAV H3 HA protein, a fourth encoding a third IAV H3 HA protein, a fifth encoding an influenza B/Victoria lineage virus HA protein, and a sixth encoding an influenza B/Yamagata lineage HA protein. In some embodiments, the mRNAs are present at a 1:1:1:1:1:1 mass ratio.

In some aspects, a multivalent vaccine comprises five mRNAs, a first encoding an IAV H1 HA protein, a second encoding a first IAV H3 HA protein, a third encoding a second IAV H3 HA protein, a fourth encoding a third IAV H3 HA protein, and a fifth encoding an influenza B/Victoria lineage virus HA protein, where the vaccine does not comprise an mRNA encoding an influenza B/Yamagata lineage HA protein. In some embodiments, the mRNAs are present at a 1:1:1:1:1 mass ratio.

Some embodiments relate to multivalent vaccines comprising mRNAs encoding multiple H3 HA proteins derived from distinct influenza A/(H3N2) viruses. Separate H3 HA proteins may belong to different clades of the A/(H3N2) subtype. In some embodiments, each H3 HA protein encoded by an mRNA of a vaccine is derived from an influenza virus of a distinct clade within the A/(H3N2) subtype. In some embodiments, each H3 HA protein encoded by an mRNA of a vaccine differs from each other H3 HA protein encoded by other mRNAs of the vaccine by at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20 substitutions. Where two H3 HA proteins vary in length, the number of substitutions present between their amino acid sequences is calculated after aligning the amino acid sequences as discussed in the section entitled "Protein variants and alignment."

In some embodiments of multivalent vaccines, the influenza B/Victoria lineage virus HA protein is an influenza B/Victoria lineage virus HA protein described in the section entitled "B/Victoria lineage HA proteins." In some embodiments, the influenza B/Victoria lineage HA protein comprises an amino acid sequence with at least 90% sequence identity to the amino acid sequence of SEQ ID NO: 71.

In some embodiments of multivalent vaccines, the influenza B/Yamagata lineage virus HA protein is an influenza B/Yamagata lineage virus HA protein described in the section entitled "B/Yamagata lineage HA proteins." In some embodiments, the influenza B/Yamagata lineage HA protein comprises an amino acid sequence with at least 90% sequence identity to the amino acid sequence of SEQ ID NO: 70.

In some embodiments of multivalent vaccines, the IAV H1 HA protein is an IAV H1 HA protein described in the section entitled "H1 HA proteins." In some embodiments, the IAV H1 HA protein comprises an amino acid sequence with at least 90% sequence identity to the amino acid sequence of SEQ ID NO: 83. In some embodiments, the IAV H1 HA protein comprises an amino acid sequence with at least 90% sequence identity to the amino acid sequence of SEQ ID NO: 95.

In some embodiments of multivalent vaccines, the IAV H3 HA protein is an IAV H3 HA protein described in the section entitled "H3 HA proteins." Where a multivalent vaccine includes multiple H3 HA proteins (e.g., comprises multiple mRNAs encoding different H3 HA proteins), the different H3 HA proteins may each comprise the same substitutions, or different substitutions described in the section entitled "H3 HA proteins." In some embodiments, one or more H3 HA proteins does not comprise a substitution described in the section entitled "H3 HA proteins." In some embodiments, the IAV H3 HA protein comprises an amino acid sequence with at least 90% sequence identity to the amino acid sequence of SEQ ID NO: 82. In some embodiments, each IAV H3 HA protein comprises an amino acid sequence with at least 90% sequence identity to the amino acid sequence of SEQ ID NO: 82.

Combination Vaccines

Some embodiments of vaccines include combination vaccines. A "combination vaccine", as used herein, refers to a vaccine comprising one or more components for eliciting an immune response (i) to one or more influenza viruses, and (ii) to one or more viruses other than an influenza virus. As noted previously, discussion of combination vaccines comprising one or more RNAs (e.g., mRNAs) encoding proteins of different viruses may also be applied, inter alia, to combination vaccines comprising the same proteins (e.g., as isolated proteins or proteins present in viral vectors). The skilled artisan will appreciate that for combination vaccines comprising one or more RNAs (e.g., mRNAs) encoding two or more proteins, the two or more proteins may be encoded a single RNA, or different RNAs of the combination vaccine.

For example, a combination vaccine may include one or more RNAs, each encoding an antigen of a virus of a different family (e.g., a first antigen of an influenza virus (Orthomyxoviridae), and a second antigen of a coronavirus (Coronaviriade) or respiratory syncytial virus (Pneumoviridae)). In some embodiments, a composition includes one or more RNAs (e.g., mRNAs) encoding at least one influenza virus antigen, and at least one antigen of a different virus (e.g., a coronavirus or a virus from the Pneumoviridae family (e.g., respiratory syncytial virus (RSV)). In some embodiments, the different virus is SARS-CoV-2; that is, in some embodiments, a composition comprises one or more RNAs collectively encoding at least one influenza virus antigen, and at least one SARS-CoV-2 antigen. In some embodiments the different virus is human respiratory syncytial virus (hRSV); that is, in some embodiments, a composition comprises one or more RNAs collectively encoding at least one influenza virus antigen and at least one hRSV antigen. In some embodiments, a composition includes one or more RNAs collectively encoding at least one influenza virus antigen and at least one antigen of each of two different viruses (e.g. a coronavirus and an hRSV). In some embodiments, the different viruses are SARS-CoV-2 and hRSV; that is, in some embodiments, a composition comprises one or more RNAs collectively encoding at least one influenza virus antigen, at least one SARS-CoV-2 antigen, and at least one hRSV antigen.

With respect to the SARS-CoV-2 antigens of the combination vaccines, in some embodiments, the combination vaccine comprises 1, 2, 3, 4, 5, or 6 RNAs (e.g., mRNAs) encoding different coronavirus antigens, wherein each antigen comprises at least one mutation and/or at least one deletion relative to the amino acid sequence of SEQ ID NO: 78. In some embodiments, the combination vaccine comprises an RNA encoding a wild-type SARS-CoV-2 S protein antigen or the antigenic fragment thereof. In some embodiments, a combination vaccine includes an RNA encoding a fusion protein comprising at least two domains of a SARS-CoV-2 Spike (S) protein, and less than the full-length spike protein. In some embodiments, a combination vaccine comprises a first RNA encoding a first fusion protein comprising at least two domains of a SARS-CoV-2 Spike (S) protein and less than the full-length S protein, and a second RNA encoding a second fusion protein comprising at least two domains of a SARS-CoV-2 Spike (S) protein and less than the full-length S protein. In some embodiments, the two RNAs are present in the combination vaccine in a 1:1 ratio.

In some embodiments, the two RNAs are present in the combination vaccine in a 1:2, 1:3, 1:4, 1:5, 1:6, 1:7, 1:8, 1:9, or 1:10 ratio.

With respect to the antigens of viruses from the Pneumoviridae family, in some embodiments, the combination vaccine comprises 1, 2, 3, 4, 5, or 6 RNAs (e.g., mRNAs) encoding different antigens of viruses from the Pneumoviridae family (e.g., RSV) wherein each antigen comprises at least one mutation and/or at least one deletion relative to a reference Pneumoviridae family virus antigen. In some embodiments, the combination vaccine comprises an RNA encoding a wild-type hRSV F glycoprotein antigen or antigenic fragment thereof. In some embodiments, a combination vaccine includes an RNA encoding a hRSV F glycoprotein variant lacking a cytoplasmic tail. In some embodiments, a combination vaccine includes an RNA encoding a hRSV F glycoprotein variant lacking a cytoplasmic tail and further comprising one or more modifications relative to a wild-type hRSV F glycoprotein. In some embodiments, a combination vaccine comprises a first RNA encoding a first hRSV F glycoprotein variant lacking a cytoplasmic tail, and a second RNA encoding a second hRSV F glycoprotein variant lacking a cytoplasmic tail and further comprising one or more modifications relative to the wild-type hRSV F glycoprotein. In some embodiments, the two RNAs are present in the combination vaccine in a 1:1 ratio. In some embodiments, the two RNAs are present in the combination vaccine in a 1:2, 1:3, 1:4, 1:5, 1:6, 1:7, 1:8, 1:9, or 1:10 ratio.

In some embodiments, the combination vaccine comprises one or more RNAs (e.g., mRNAs) encoding influenza virus antigens (e.g., mRNA encoding HA antigens) and one or more RNAs (e.g., mRNAs) encoding antigens of at least one different respiratory virus (e.g., mRNA encoding a SARS-CoV-2 fusion protein or an hRSV F glycoprotein). In some embodiments, the ratio of RNAs encoding influenza virus antigens to RNAs encoding the at least one different respiratory virus antigen in the combination vaccine is 5:1, 4:1, 3:1, 2:1, or 1:1. In some embodiments, the ratio of RNAs encoding influenza virus antigens to RNAs encoding the at least one different respiratory virus antigen in the combination vaccine is 10:1. In some embodiments, the ratio of RNAs encoding influenza virus antigens to RNAs encoding the at least one different respiratory virus antigen in the combination vaccine is 15:1. In some embodiments, the ratio of RNAs encoding influenza virus antigens to RNAs encoding the at least one different respiratory virus antigen in the combination vaccine is 20:1. In some embodiments, the ratio of RNAs encoding influenza virus antigens to RNAs encoding the at least one different respiratory virus antigen in the combination vaccine is 25:1. In some embodiments, the ratio of RNAs encoding influenza virus antigens to RNAs encoding the at least one different respiratory virus antigen in the combination vaccine is 30:1.

In some embodiments, the combination vaccine comprises (i) one or more RNAs (e.g., mRNAs) encoding one or more influenza virus proteins, (ii) one or more RNAs (e.g., mRNAs) encoding one or more SARS-CoV-2 proteins, and (ii) one or more RNAs (e.g., mRNAs) encoding one or more hRSV proteins. In some embodiments, each of (i) RNA(s) encoding influenza virus protein(s), (ii) RNA(s) encoding SARS-CoV-2 protein(s), and (iii) RNA(s) encoding hRSV protein(s) are present in the combination vaccine in substantially equal masses. In some embodiments, the RNA(s) encoding influenza virus protein(s) are present in the combination vaccine at 3 times the mass of RNA(s) encoding SARS-CoV-2 protein(s), and 3 times the mass of RNA(s) encoding hRSV protein(s). In some embodiments, the RNA(s) encoding influenza virus protein(s) are present in the combination vaccine at 4 times the mass of RNA(s) encoding SARS-CoV-2 protein(s), and 4 times the mass of RNA(s) encoding hRSV protein(s). In some embodiments, the RNA(s) encoding influenza virus protein(s) are present in the combination vaccine at 5 times the mass of RNA(s) encoding SARS-CoV-2 protein(s), and 5 times the mass of RNA(s) encoding hRSV protein(s). In some embodiments, the RNA(s) encoding influenza virus protein(s) are present in the combination vaccine at 2 times the mass of RNA(s) encoding SARS-CoV-2 protein(s), and 4 times the mass of RNA(s) encoding hRSV protein(s). In some embodiments, the RNA(s) encoding influenza virus protein(s) are present in the combination vaccine at 4 times the mass of RNA(s) encoding SARS-CoV-2 protein(s), and 2 times the mass of RNA(s) encoding hRSV protein(s). In some embodiments, the RNA(s) encoding influenza virus protein(s) are present in the combination vaccine at 0.5 the mass of RNA(s) encoding SARS-CoV-2 protein(s), and 0.5 times the mass of RNA(s) encoding hRSV protein(s). In some embodiments, the mass ratio of (i) RNA(s) encoding influenza virus protein(s), to (ii) RNA(s) encoding SARS-CoV-2 protein(s), to (iii) RNA(s) encoding hRSV protein(s) in the combination vaccine is 4:1:1, 4:2:1, 4:3:2, 4:3:3, or 2:1:1.

In some embodiments, the combination vaccine comprises mRNA polynucleotide wherein each polynucleotide encodes a different respiratory virus antigenic polypeptide. In some embodiments, the first, second and third mRNA polynucleotides are present in the combination vaccine in a ratio of 1:1:1. In some embodiments, the combination vaccine comprises a ratio of mRNA polynucleotides encoding respiratory virus antigenic polypeptides of 4:1:1 from the first virus (e.g., influenza virus) to the second virus to the third virus. In some embodiments, the combination vaccine comprises a ratio of mRNA polynucleotides encoding respiratory virus antigenic polypeptides of 3:1:1 from the first virus (e.g., influenza virus) to the second virus to the third virus. In some embodiments, the combination vaccine comprises a ratio of mRNA polynucleotides encoding respiratory virus antigenic polypeptides of 5:1:1 from the first virus (e.g., influenza virus) to the second virus to the third virus. In some embodiments, the combination vaccine comprises a ratio of mRNA polynucleotides encoding respiratory virus antigenic polypeptides of 4:2:1 from the first virus (e.g., influenza virus) to the second virus to the third virus. In some embodiments, the combination vaccine comprises a ratio of mRNA polynucleotides encoding respiratory virus antigenic polypeptides of 1:2:1 from the first virus (e.g., influenza virus) to the second virus to the third virus. In some embodiments, the combination vaccine comprises a ratio of mRNA polynucleotides encoding respiratory virus antigenic polypeptides of 1:2:2 from the first virus (e.g., influenza virus) to the second virus to the third virus. In some embodiments, the combination vaccine comprises a ratio of mRNA polynucleotides encoding respiratory virus antigenic polypeptides of 8:2:2, 4:1:1, 4:2:2, 4:2:1, 4:3:2, 4:3:3, 4:3:2, or 4:2:2 from the first virus to the second virus to the third virus.

In some embodiments, each of the mRNA polynucleotides in the combination vaccine is complementary with and does not interfere with each other mRNA polynucleotide in the combination vaccine. That is, an antigen produced from administration of the combination vaccine do not significantly interfere with the immune response to any other of the antigens produced in response to the vaccine in such a way that would diminish the ability of the antigens to provoke a protective immune response in a subject. In some embodiments, the combination vaccine is additive with respect to neutralizing antibodies relative to each individual antigen in a vaccine.

Thus, compositions (e.g., RNA vaccines (e.g., mRNA vaccines)) may target one or more antigen(s) of the same strain/species, or one or more antigen(s) of different strains/species, e.g., antigens which induce immunity to organisms which are found in the same geographic areas where the risk of respiratory virus (e.g. influenza virus and/or coronavirus and/or respiratory syncytial virus) infection is high.

Combination vaccines comprising RNA (e.g., mRNA) polynucleotides encoding at least two respiratory virus antigenic polypeptides from at least two different respiratory virus families (e.g., influenza viruses of Orthomyxoviridae, respiratory syncytial virus of Pneumoviridae, and coronavirus of Coronaviridae) may be used for treating and/or preventing respiratory virus infections. In some embodiments, a combination vaccine comprises mRNA polynucleotides encoding antigens from the Orthomyxoviridae family (e.g., influenza virus antigens) and the Coronaviridae family (e.g., SARS-CoV-2). In some embodiments, a combination vaccine comprises mRNA polynucleotides encoding antigens from the Orthomyxoviridae family (e.g., influenza virus) and the Pneumoviridae family (e.g., human respiratory syncytial virus). In some embodiments, a composition comprises RNA (e.g., mRNA) polynucleotides encoding at least three respiratory antigenic polypeptides from at least three different respiratory viruses. In some embodiments, the three different viruses are from the Orthomyxoviridae (e.g., influenza virus), Coronaviridae (e.g., SARS-CoV-2) and Pneumoviridae families (e.g., human respiratory syncytial virus).

In some embodiments, one or more RNAs (e.g., mRNAs) encoding polypeptides from at least two different respiratory virus families are encapsulated in a single lipid nanoparticle. Some embodiments comprise one or more RNAs (e.g., mRNAs) encoding polypeptides from at least two different respiratory virus families, wherein the composition comprises lipid nanoparticles encapsulating one or more RNAs (e.g., mRNAs) encoding polypeptides from a single respiratory virus family.

In some embodiments, a combination vaccine comprises a combination of proteins or nucleic acids (e.g., RNAs (e.g., mRNAs)) collectively encoding the combination, the combination comprising: (i) an IAV H1 HA protein, (ii) an IAV H3 HA protein, (iii) an influenza B/Victoria lineage virus HA protein, and (iv) a SARS-CoV-2 S protein or fragment thereof.

In some embodiments, a combination vaccine comprises a combination of proteins or nucleic acids (e.g., RNAs (e.g., mRNAs) collectively encoding the combination, the combination comprising: (i) an IAV H1 HA protein, (ii) an IAV H3 HA protein, (iii) an influenza B/Victoria lineage virus HA protein, and (iv) an hRSV F protein or fragment thereof.

In some embodiments, a combination vaccine comprises a combination of proteins or nucleic acids (e.g., RNAs (e.g., mRNAs) collectively encoding the combination, the combination comprising: (i) an IAV H1 HA protein, (ii) an IAV H3 HA protein, (iii) an influenza B/Victoria lineage virus HA protein, (iv) a SARS-CoV-2 S protein or fragment thereof, and (v) an hRSV protein or fragment thereof.

In some embodiments, the combination comprises 2 IAV H3 HAs. In some embodiments, the combination comprises 3 IAV H3 HAs. In some embodiments, the combination comprises 4, 5, 6, 7, 8, 9, or 10 IAV H3 HAs.

In some embodiments, the combination further comprises an influenza B/Yamagata lineage HA protein. In some embodiments, the combination does not comprise an influenza B/Yamagata lineage HA protein.

In some embodiments, the combination further comprises: (i) an IAV N1 NA protein, (ii) an IAV N2 NA protein, and (iii) an influenza B/Victoria lineage NA protein. In some embodiments, the combination further comprises an influenza B/Yamagata lineage NA protein. In some embodiments, the combination does not comprise an influenza B/Yamagata lineage NA protein.

In some embodiments of combination vaccines, the influenza B/Victoria lineage virus HA protein is an influenza B/Victoria lineage virus HA protein described in the section entitled "B/Victoria lineage HA proteins." In some embodiments, the influenza B/Victoria lineage HA protein comprises an amino acid sequence with at least 90% sequence identity to the amino acid sequence of SEQ ID NO: 71.

In some embodiments of combination vaccines, the influenza B/Yamagata lineage virus HA protein is an influenza B/Yamagata lineage virus HA protein described in the section entitled "B/Yamagata lineage HA proteins." In some embodiments, the influenza B/Yamagata lineage HA protein comprises an amino acid sequence with at least 90% sequence identity to the amino acid sequence of SEQ ID NO: 70.

In some embodiments of combination vaccines, the IAV H1 HA protein is an IAV H1 HA protein described in the section entitled "H1 HA proteins." In some embodiments, the IAV H1 HA protein comprises an amino acid sequence with at least 90% sequence identity to the amino acid sequence of SEQ ID NO: 83. In some embodiments, the IAV H1 HA protein comprises an amino acid sequence with at least 90% sequence identity to the amino acid sequence of SEQ ID NO: 95.

In some embodiments of combination vaccines, the IAV H3 HA protein is an IAV H3 HA protein described in the section entitled "H3 HA proteins." Where a combination vaccine includes multiple H3 HA proteins (e.g., comprises multiple mRNAs encoding different H3 HA proteins), the different H3 HA proteins may each comprise the same substitutions, or different substitutions described in the section entitled "H3 HA proteins." In some embodiments, one or more H3 HA proteins does not comprise a substitution described in the section entitled "H3 HA proteins." In some embodiments, the IAV H3 HA protein comprises an amino acid sequence with at least 90% sequence identity to the amino acid sequence of SEQ ID NO: 82. In some embodiments, each IAV H3 HA protein comprises an amino acid sequence with at least 90% sequence identity to the amino acid sequence of SEQ ID NO: 82.

In some embodiments, the SARS-CoV-2 S protein or fragment thereof is a full-length S glycoprotein described in the "Coronaviruses" section below. In some embodiments, the SARS-CoV-2 S protein or fragment thereof is a protein comprising one or more fragments of the SARS-CoV-2 S glycoprotein, described in the "Coronaviruses" section below.

In some embodiments, the hRSV F protein or fragment thereof is an hRSV protein or fragment thereof described in the "Respiratory Syncytial Virus (hRSV)" section below.

Coronaviruses

Some embodiments of combination vaccines include coronavirus antigens or nucleic acids encoding coronavirus antigens. Coronaviruses are a family of enveloped, positive-sense, single-stranded RNA viruses that infect mammals and birds. Notable human coronaviruses that cause respiratory illnesses include 229E, NL63, OC43, HKU1, Middle East Respiratory Syndrome Coronavirus (MERS-CoV), and Severe Acute Respiratory Syndrome Coronavirus (SARS-CoV). Coronaviruses derive their name from the crown-like spikes on their surface, which are formed by the viral spike glycoprotein (S protein). The S protein binds to host receptors and mediates viral entry into cells. Other viral structural proteins include the envelope (E), membrane (M), and nucleocapsid (N) proteins. SARS-CoV-2 belongs to the betacoronavirus genus and is the causative agent of COVID-19. It has a size of 29.8-30 kb (see, e.g., Chan et al. 2000, supra; Kim et al. 2020 Cell, May 14; 181(4):914-921.e10.). The SARS-CoV-2 genome and is organized into specific genes encoding structural proteins and nonstructural proteins (Nsps). The order of the structural proteins in the genome is 5'-replicase (open reading frame (ORF)1/ab)-structural proteins [Spike (S)-Envelope I-Membrane (M)-Nucleocapsid (N)]-3'. The genome of coronaviruses includes a variable number of open reading frames that encode accessory proteins, nonstructural proteins, and structural proteins (Song et al. 2019 Viruses; 11(1): p. 59). Most of the antigenic epitopes are located in the structural proteins (Cui et al. 2019 Nat. Rev. Microbiol.; 17(3):181-192). Spike surface glycoprotein(S), a small envelope protein (E), matrix protein (M), and nucleocapsid protein (N) are four main structural proteins. Since S-protein contributes to cell tropism and virus entry and also it is capable to induce neutralizing antibodies (NAb) and protective immunity, it can be considered one of the most important targets in coronavirus vaccine development among all other structural proteins.

Variant viral strains of SARS-CoV-2 may emerge at times. These strains may emerge, for instance, seasonally. Thus, in exemplary aspects, the vaccines may be designed to combat seasonal coronavirus strains, and as such are vaccines for use in an upcoming or forthcoming Northern hemisphere season or Southern hemisphere season. Based on an understanding of circulating coronaviruses at a given point in time, the vaccines can be designed to combat such viruses as they are predicted to be those that will be circulating or prevalent in the upcoming or forthcoming virus season.

A preferred protein is the Spike (S) protein, which is on the surface of coronaviruses, including SARS-CoV-2. An example of a wild-type SARS-CoV-2 Spike protein is provided by the amino acid sequence of SEQ ID NO: 78. In some embodiments, the SARS-CoV-2 antigen is a full-length S protein. In some embodiments, the SARS-CoV-2 antigen comprises a full-length S protein with two or more proline substitutions. In some embodiments, the S protein comprises two proline substitutions at residues corresponding to K986V and V987P of SEQ ID NO: 78. In some embodiments, the S protein does not comprise a proline substitution.

In some embodiments, the SARS-CoV-2 antigen does not comprise a full-length S protein. For example, in some embodiments, the SARS-CoV-2 antigen comprises a receptor binding domain (RBD) of the S protein. In some embodiments, the SARS-CoV-2 antigen comprises a fusion protein comprising an RBD and an N-terminal domain (NTD) of the S protein. In some embodiments, the fusion protein comprises an RBD and an NTD of the S protein, and a transmembrane domain (TD). In some embodiments, the fusion protein comprises, in N-to-C-terminal order, the NTD-RBD-TD. In some embodiments, the RBD and NTD are linked through a linker. In some embodiments, the linker is a cleavable linker. In some embodiments, the linker is a non-cleavable linker. In some embodiments, the linker is a glycine-serine (GS) linker.

In some embodiments, the TD is a betacoronavirus TD. In some embodiments, the TD is a heterologous TD. In some embodiments the TD is a non-betacoronavirus TD. In some embodiments, the TD is an influenza virus hemagglutinin (HA) TD. In some embodiments, the TD is an influenza A virus H1 HA TD.

In some embodiments, the SARS-CoV-2 antigen comprises at least one mutation present in an S protein of a circulating SARS-CoV-2 isolate, as compared to the S protein amino acid sequence of SEQ ID NO: 78. In some embodiments, the SARS-CoV-2 antigen comprises at least 1, 2, 3, 4, 5, 6, 7, 8, 9, 10, 11, 12, 13, 14, 15, 16, 17, 18, 19, or 20 mutations present in a circulating SARS-CoV-2 S protein, as compared to SEQ ID NO: 78. In some embodiments, the SARS-CoV-2 antigen comprises an amino acid sequence with at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identity to SEQ ID NO: 78.

In some embodiments, the SARS-CoV-2 antigen comprises at least one mutation present in an RBD of an S protein of a circulating SARS-CoV-2 isolate, as compared to the S protein of SEQ ID NO: 78. In some embodiments, the SARS-CoV-2 Spike protein antigen comprises at least 1, 2, 3, 4, 5, 6, 7, 8, 9, 10, 11, 12, 13, 14, 15, 16, 17, 18, 19, or 20 RBD mutation(s) compared to SEQ ID NO: 78. In SEQ ID NO: 78, the RBD corresponds to amino acids 330-528, and so the skilled artisan will appreciate that "a mutation present in an RBD of an S protein" as compared to the S protein of SEQ ID NO: 78 refers to (i) a substitution at a position corresponding to any one of amino acids 330-528 of SEQ ID NO: 78, (ii) a deletion of any one or more of amino acids 330-528 of SEQ ID NO: 78, and/or (iii) an insertion of one or more amino acids at a position from amino acids 330-528 of SEQ ID NO: 78. In some embodiments, the SARS-CoV-2 antigen comprises an amino acid sequence with at least 80%, at least 81%, at least 82%, at least 83%, at least 84%, at least 85%, at least 86%, at least 87%, at least 88%, at least 89%, 90%, at least 91%, at least 92%, at least 93%, at least 94%, at least 95%, at least 96%, at least 97%, at least 98%, or at least 99% identity to SEQ ID NO: 60.

Mutations present in a SARS-CoV-2 antigen of a combination vaccine may be present on any circulating SARS-CoV-2 isolate. For example, at the time of filing the instant specification, isolates of the JN.1 variant are circulating. The SARS-CoV-2 sub-variant JN.1 (also known as BA.2.86.1.1), is a subvariant (sublineage) of the SARS-CoV-2 "Omicron" variant, and was first observed in August 2023; this variant is closely related to BA.2.86. The mutations observed in this variant are believed to provide high potential for immune evasion, particularly the L455F "FLip" mutation—a mutation also observed in XBB lineage variants (e.g., HK.3 and EG.5.1). Mutations observed in JN.1 include A31D, V238L, K1155R, N1708S, A1892T, V24F, R252K, T35I, ins16MPLF, R21T, S50L, Δ69-70, V127F, F157S, R158G, N211del, L212I, V213G, L216F, H245N, A264D, I332V, K356T, R403K, V445H, N450D, L452W, L455S, N481K, V483del, E484K, E554K, A570V, P621S, P681H, S939F, and P1143L.

Several sub-variants of the XBB variant have also been identified recently: HV.1, JD.1.1, HK.3, and EG.5. These sub-variants share several mutations, including T19I, L24S, del25/27, V83A, G142D, del144/144, H146Q, Q183E, V213E, G252V, G339H, R346T, L368I, S371F, S373P, S375F, T376A, D405N, R408S, K417N, N440K, V445P, G446S, F456L, N460K, S477N, T478K, E484A, F486P, F490S, Q498R, N501Y, Y505H, D614G, H655Y, N679K, P681H, N764K, D796Y, Q954H, and N969K; some variants include additional mutations, such as: Q52H, F157L, L452R, L455F, and A475V.

The skilled artisan will appreciate that SARS-CoV-2 antigens of combination vaccines may include mutations present in any SARS-CoV-2 S protein that is extant at the time the instant specification. The skilled artisan will also appreciate that SARS-CoV-2 S protein amino acid sequences that do not exist at the time of filing the instant specification may be analyzed for mutations relative to SEQ ID NO: 78, and those mutations may be applied to SARS-CoV-2 antigens of the combination vaccines.

In some embodiments, a combination vaccine comprises two or more coronavirus antigens or nucleic acids encoding two or more coronavirus antigens, such as SARS-CoV-2 antigens from different SARS-CoV-2 variant strains. In some embodiments, the composition comprises one or more RNAs collectively encoding two or more SARS-CoV-2 variant antigens.

Respiratory Syncytial Virus (RSV)

Some embodiments of combination vaccines include human respiratory syncytial virus antigens or nucleic acids encoding human respiratory syncytial virus antigens. Human respiratory syncytial virus (hRSV; also known as human orthopneumovirus) is a negative-sense, single-stranded ribonucleic acid (RNA) virus of the Pneumoviridae family. The virus is present in at least two antigenic subgroups, known as Group A and Group B.

The envelope of hRSV contains three surface glycoproteins: F, G, and SH. The G and F proteins are protective antigens and targets of neutralizing antibodies. The F protein, however, is more conserved across hRSV strains and types (A and B). hRSV F protein is a type I fusion glycoprotein that is well conserved between clinical isolates, including between the hRSV-A and hRSV-B antigenic subgroups. The F protein transitions between prefusion and more stable postfusion states, thereby facilitating entry into target cells. hRSV F glycoprotein is initially synthesized as an F0 precursor protein. hRSV F0 folds into a trimer, which is activated by furin cleavage into the mature prefusion protein comprising F1 and F2 subunits (Bolt, et al., Virus Res., 68:25, 2000). Although targets for neutralizing monoclonal antibodies exist on the postfusion conformation of F protein, the neutralizing Ab response primarily targets the F protein prefusion conformation in people naturally infected with hRSV (Magro M et al., *Proc Natl Acad Sci USA* 2012; 109(8):3089-94; Ngwuta J O et al., *Sci Transl Med* 2015; 7(309):309ra162). Consistent with this, hRSV F protein stabilized in the prefusion conformation produces a greater neutralizing immune response in animal models than that observed with hRSV F protein stabilized in the post fusion conformation (McLellan et al., Science, 342:592-598, 2013). Thus, stabilized prefusion hRSV F proteins are good candidates for inclusion in an hRSV vaccine. Other RSV proteins include the small hydrophobic (SH), matrix (M), nucleocapsid (N), phosphoprotein (P), polymerase (L) and nonstructural NS1/NS2 proteins. A preferred protein is the F glycoprotein, which present on the surface of hRSV, including wild-type hRSV and mutant strains, such as the hRSV F protein having an amino acid sequence of SEQ ID NO: 98.

hRSV commonly causes bronchiolitis. Most infected adults develop mild cold-like symptoms such as congestion, low-grade fever, and wheezing. Infants and small children may suffer more severe symptoms such as bronchiolitis and pneumonia. The disease may be transmitted among humans via contact with respiratory secretions.

Some embodiments relate to stabilized prefusion RSV F proteins that comprise mutations to prevent the transition of the protein into its post-fusion conformation. For example, in some embodiments, the stabilized prefusion RSV F protein comprises proline residue (e.g., an S215P substitution) and/or isoleucine (e.g., N67I substitution) substitutions. As an example, the DS-Cav1 variant, a stabilized prefusion RSV F protein, contains an additional disulfide bond (S155C/S290C) as well as two cavity-filling mutations (S190F/V207L). Another stabilized prefusion RSV F protein is PR-DM, which comprises one proline substitution (S215P) and one mutation in the F2 subunit (N67I).

In some embodiments, a stabilized prefusion hRSV F glycoprotein variant lacks a cytoplasmic tail. In some embodiments, the cytoplasmic tail comprises the C-terminal 20-30, 20-25, 15-30, 15-25, 15-20, 10-30, 10-25, 10-20, 10-15, 5-30, 5-25, 5-20, or 5-15 amino acids of the of the hRSV F glycoprotein variant. In some embodiments, the cytoplasmic tail comprises the C-terminal 25 amino acids (e.g., CKARSTPVTLSKDQLSGINNIAFSN (SEQ ID NO: 101)) of the hRSV F glycoprotein. In some embodiments, the cytoplasmic tail comprises the C-terminal 20 amino acids (e.g., TPVTLSKDQLSGINNIAFSN (SEQ ID NO: 102)) of the hRSV F glycoprotein. In some embodiments, the cytoplasmic tail comprises the C-terminal 15 amino acids (e.g., SKDQLSGINNIAFSN (SEQ ID NO: 103)) of the hRSV F glycoprotein. In some embodiments, the cytoplasmic tail comprises the C-terminal 10 amino acids (e.g., SGINNIAFSN (SEQ ID NO: 104)) of the hRSV F glycoprotein.

In some embodiments, a stabilized prefusion hRSV F glycoprotein variant lacks a cytoplasmic tail, wherein the RSV F glycoprotein variant has at least 80%, at least 85%, at least 90%, at least 95% identity to a wild-type hRSV F glycoprotein (e.g., a wild-type hRSV F glycoprotein comprising the sequence of SEQ ID NO: 98), and lacks a cytoplasmic tail. In some embodiments, stabilized prefusion hRSV F glycoprotein variant lacks a cytoplasmic tail, wherein the RSV F glycoprotein variant has at least 80%, at least 85%, at least 90%, at least 95% identity to the sequence of SEQ ID NO: 99. In some embodiments, stabilized prefusion hRSV F glycoprotein variant comprises the sequence of SEQ ID NO: 99.

In some embodiments, an hRSV F glycoprotein variant that lacks a cytoplasmic tail further comprises a modification, relative to the wild-type hRSV F glycoprotein (e.g., SEQ ID NO: 98), selected from the group consisting of: a P102X substitution, a substitution of amino acids 104-144 with a linker molecule, an A149X substitution, an S155X substitution, an S190X substitution, a V207X substitution, an S290X substitution, a L373X substitution, an I379X substitution, an M447X substitution, and a Y458X substitution, wherein X is any amino acid (e.g., A, R, N, D, C, E, Q, G, H, I, L, K, M, F, P, S, T, W, Y, or V) other than the amino acid replaced in the wild-the hRSV F glycoprotein amino acid sequence. In some embodiments, an hRSV F glycoprotein variant that lacks a cytoplasmic tail further comprises a modification, relative to the wild-type hRSV F glycoprotein, (SEQ ID NO: 98), selected from the group consisting of: a P102A substitution, a substitution of amino acids 104-144 with a linker molecule, an A149C substitution, an S155C substitution, an S190F substitution, a V207L substitution, an S290C substitution, a L373R substitution, an I379V substitution, an M447V substitution, and a Y458C substitution. In some embodiments, an hRSV F glycoprotein variant that lacks a cytoplasmic tail further comprises a P102A substitution. In some embodiments, an hRSV F glycoprotein variant that lacks a cytoplasmic tail further comprises a substitution of amino acids 104-144 with a linker molecule. In some embodiments, an hRSV F glycoprotein variant that lacks a cytoplasmic tail further comprises an A149C substitution. In some embodiments, an hRSV F glycoprotein variant that lacks a cytoplasmic tail further comprises an S155C substitution. In some embodiments, an hRSV F glycoprotein variant that lacks a cytoplasmic tail further comprises an S190F substitution. In some embodiments, an hRSV F glycoprotein variant that lacks a cytoplasmic tail further comprises a V207L substitution. In some embodiments, an hRSV F glycoprotein variant that lacks a cytoplasmic tail further comprises an S290C substitution. In some embodiments, an hRSV F glycoprotein variant that lacks a cytoplasmic tail further comprises an L373R substitution. In some embodiments, an hRSV F glycoprotein variant that lacks a cytoplasmic tail further comprises an I379V substitution. In some embodiments, an hRSV F glycoprotein variant that lacks a cytoplasmic tail further comprises an M447V substitution. In some embodiments, an hRSV F glycoprotein variant that lacks a cytoplasmic tail further comprises a Y458C substitution.

In some embodiments, an hRSV F glycoprotein variant that lacks a cytoplasmic tail further comprises the following modifications, relative to the wild-type hRSV F glycoprotein: a P102A substitution, a substitution of amino acids 104-144 with a linker molecule, an A149C substitution, an S155C substitution, an S190F substitution, a V207L substitution, an S290C substitution, a L373R substitution, an I379V substitution, an M447V substitution, and a Y458C substitution.

In some embodiments, an hRSV F glycoprotein comprises an amino acid sequence with at least 80%, at least 85%, at least 90%, at least 95%, at least 96%, at least 97%, at least 98%, or at least 99% identity to the amino acid sequence of SEQ ID NO: 99. In some embodiments, the hRSV F glycoprotein comprises the amino acid sequence of SEQ ID NO: 99. In some embodiments, the hRSV F glycoprotein consists of the amino acid sequence of SEQ ID NO: 99.

In some embodiments, the composition comprises an RNA having an ORF encoding an hRSV F glycoprotein, where the ORF comprises a nucleotide sequence with at least 70%, at least 75%, least 80%, at least 85%, at least 90%, at least 95%, at least 96%, at least 97%, at least 98%, or at least 99% identity to the nucleotide sequence of SEQ ID NO: 113. In some embodiments, the ORF comprises the nucleotide sequence of SEQ ID NO: 113.

In some embodiments, an hRSV F glycoprotein comprises an F1 subunit and an F2 subunit, the F1 subunit comprising at least 80%, at least 85%, at least 90%, at least 95%, at least 96%, at least 97%, at least 98%, or at least 99% identity to the amino acid sequence of SEQ ID NO: 106, and the F2 subunit comprising at least 80%, at least 85%, at least 90%, at least 95%, at least 96%, at least 97%, at least 98%, or at least 99% identity to the amino acid sequence of SEQ ID NO: 107. In some embodiments, the F1 subunit comprises the amino acid sequence of SEQ ID NO: 106, and the F2 subunit comprises the amino acid sequence of SEQ ID NO: 107. In some embodiments, the F1 subunit consists of the amino acid sequence of SEQ ID NO: 106, and the F2 subunit consists of the amino acid sequence of SEQ ID NO: 107. In some embodiments, the hRSV F glycoprotein comprises an amino acid sequence with at least 80%, at least 85%, at least 90%, at least 95%, at least 96%, at least 97%, at least 98%, or at least 99% identity to the amino acid sequence of SEQ ID NO: 108. In some embodiments, the hRSV F glycoprotein comprises the amino acid sequence of SEQ ID NO: 108. In some embodiments, the hRSV F glycoprotein consists of the amino acid sequence of SEQ ID NO: 108.

In some embodiments, an hRSV F glycoprotein comprises an F1 subunit and an F2 subunit, the F1 subunit comprising at least 80%, at least 85%, at least 90%, at least 95%, at least 96%, at least 97%, at least 98%, or at least 99% identity to the amino acid sequence of SEQ ID NO: 109, and the F2 subunit comprising at least 80%, at least 85%, at least 90%, at least 95%, at least 96%, at least 97%, at least 98%, or at least 99% identity to the amino acid sequence of SEQ ID NO: 110. In some embodiments, the F1 subunit comprises the amino acid sequence of SEQ ID NO: 109, and the F2 subunit comprises the amino acid sequence of SEQ ID NO: 110. In some embodiments, the F1 subunit comprises the amino acid sequence of SEQ ID NO: 109, and the F2 subunit comprises the amino acid sequence of SEQ ID NO: 110. In some embodiments, the F1 subunit consists of the amino acid sequence of SEQ ID NO: 109, and the F2 subunit consists of the amino acid sequence of SEQ ID NO: 110. In some embodiments, the hRSV F glycoprotein comprises an amino acid sequence with at least 80%, at least 85%, at least 90%, at least 95%, at least 96%, at least 97%, at least 98%, or at least 99% identity to the amino acid sequence of SEQ ID NO: 111. In some embodiments, the hRSV F glycoprotein comprises the amino acid sequence of SEQ ID NO: 111. In some embodiments, the hRSV F glycoprotein consists of the amino acid sequence of SEQ ID NO: 111.

In some embodiments, an hRSV F glycoprotein comprises an amino acid sequence with at least 80%, at least 85%, at least 90%, at least 95%, at least 96%, at least 97%, at least 98%, or at least 99% identity to the amino acid sequence of SEQ ID NO: 112.

Protein Variants and Alignment

Some embodiments relate to proteins having one or more mutations (e.g., substitutions) relative to a reference amino acid sequence and/or numbered according to a listed amino acid sequence.

Some embodiments relate to amino acid or nucleotide sequences having a specified percentage sequence identity to a comparator amino acid or nucleotide sequence, respectively. The term "identity" refers to a relationship between the sequences of two or more polypeptides (e.g. antigens) or polynucleotides (nucleic acids), as determined by comparing the sequences. Identity also refers to the degree of sequence relatedness between or among sequences as determined by the number of matches between strings of two or more amino acid residues or nucleic acid residues. "Percent (%) identity" or "percent (%) sequence identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity.

The percent sequence identity that a candidate sequence (e.g., as present in a claimed protein or nucleic acid) has to a comparator sequence (e.g., having a SEQ ID NO: specified herein) is calculated by (i) aligning the candidate sequence to the comparator sequence, (ii) determining the number of matching residues (amino acids or nucleotides) between the aligned candidate and comparator sequences, and (iii) dividing the number of matching residues by the length of the comparator sequence, including any gaps introduced into the comparator sequence when the two sequences are aligned.

For example, alignment of a candidate amino acid sequence of the influenza B/Brisbane/60/2008 virus HA protein amino acid sequence of SEQ ID NO: 157 to a comparator amino acid sequence of the influenza B/Austria/1359417/2021 virus HA protein amino acid sequence of SEQ ID NO: 71 reveals 572 matching residues (FIG. 19E). While SEQ ID NO: 71 is only 582 amino acids long, an internal gap three amino acids in length is introduced into SEQ ID NO: 71 in the alignment (FIG. 19E), making the denominator 585. Thus, candidate sequence SEQ ID NO: 157 has 572/585=97.8% sequence identity to comparator sequence SEQ ID NO: 71.

The skilled artisan will appreciate that to determine whether a candidate protein or nucleic acid comprises an amino acid sequence or nucleotide sequence with a given percentage sequence identity to a comparator sequence, the denominator (length of comparator sequence plus internal gaps) in calculating sequence identity need not include gaps shown at the ends of the comparator sequence in an alignment, as such gaps are added where a candidate sequence contains additional amino acids or nucleotides that extend beyond the portions that align to the N-terminal end and/or C-terminal end (amino acid sequences), or 5' end or 3' end (nucleotide sequences) of the comparator sequence. For example, alignment of the influenza B/Austria/1359417/2021 virus HA protein amino acid sequence of SEQ ID NO: 71, including the signal peptide, to its post-signal peptide cleavage form of SEQ ID NO: 174, results in a gap at the N-terminus of the comparator sequence, where the signal peptide is not present (FIG. 19F). A protein having the full-length amino acid sequence of SEQ ID NO: 71 would still comprise an amino acid sequence with 100% identity to SEQ ID NO: 174, because candidate sequence SEQ ID NO: 71 as aligned to comparator sequence SEQ ID NO: 174 contains 567 matches, and the number of amino acids in the comparator sequence of SEQ ID NO: 174 is 567 (567/567=100%).

Where an alignment between two sequences is contemplated, the first sequence (e.g., candidate sequence) is aligned to the second sequence (e.g., comparator sequence) using the Needleman-Wunsch algorithm for global alignment of the two sequences. Needleman & Wunsch, *J Mol Biol.* 1970. 48:443-453. Where two protein sequences are aligned, the Needleman-Wunsch algorithm uses a BLOSUM62 substitution scoring matrix, a Gap Open penalty of 10, a Gap Extend penalty of 0.5, and no End Gap penalties. Where two nucleotide sequences are aligned, the alignment uses an DNAFULL substitution scoring matrix, a Gap Open penalty of 10, a Gap Extend penalty of 0.5, and no End Gap penalties. The skilled artisan will appreciate that at the time of filing the instant specification, these parameters are the default parameters of the EMBOSS Needle pairwise comparison tool provided by European Bioinformatics Institute (see ebi.ac.uk). Other suitable alignment programs may be used to obtain a global alignment using these parameters, such as BLAST, or the Needleman-Wunsch algorithm may be implemented in a scripting language (e.g., Python).

Linkers and Cleavable Peptides

Some embodiments of proteins include a linker between at least one pair of portions of the protein. The linker may be, for example, a cleavable linker or protease-sensitive linker. In some embodiments, the linker is selected from the group consisting of F2A linker, P2A linker, T2A linker, E2A linker, and combinations thereof (see, e.g., WO 2017/127750). This family of self-cleaving peptide linkers, referred to as 2A peptides, has been described in the art (see, e.g., Kim, J. H. et al., *PLoS ONE* 2011; 6: e18556).

In some embodiments, the linker is an F2A linker. In some embodiments, the linker is a GS linker. GS linkers are polypeptide linkers that include glycine and serine amino acids repeats. They comprise flexible and hydrophilic residues and can be used to perform fusion of protein subunits without interfering in the folding and function of the protein domains, and without formation of secondary structures. In some embodiments, a protein comprises a GS linker that is 3 to 20 amino acids long. For example, the GS linker may have a length of (or have a length of at least) 3, 4, 5, 6, 7, 8, 9, 10, 11, 12, 13, 14, 15, 16, 17, 18, 19, or 20 amino acids. In some embodiments, a GS linker is (or is at least) 15 amino acids long (e.g., GGSGGSGGSGGSGGG (SEQ ID NO: 114)). In some embodiments, a GS linker is (or is at least) 8 amino acids long (e.g., GGGSGGGS (SEQ ID NO: 115)). In some embodiments, a GS linker is (or is at least) 7 amino acids long (e.g., GGGSGGG (SEQ ID NO: 116)). In some embodiments, a GS linker comprises the amino acid sequence GGGSGG (SEQ ID NO: 117). In some embodiments, a GS linker is (or is at least) 4 amino acid long (e.g., GGGS (SEQ ID NO: 118)). In some embodiments, the GS linker comprises (GGGS)n (SEQ ID NO: 118), where n is any integer from 1-5. In some embodiments, a GS linker is (or is at least) 4 amino acid long (e.g., GSGG (SEQ ID NO: 119)). In some embodiments, the GS linker comprises (GSGG)n (SEQ ID NO: 119), where n is any integer from 1-5. In some embodiments, a linker is a glycine linker, for example having a length of (or a length of at least) 3 amino acids (e.g., GGG). In some embodiments, a protein encoded by an RNA (e.g., mRNA) includes two or more linkers, which may be the same or different from each other. The skilled artisan will appreciate that other linkers may be suitable for use in proteins.

Signal Peptides

In some embodiments, a protein comprises a signal peptide. Signal peptides comprise the N-terminal 15-60 amino acids of proteins. In eukaryotes, the signal peptide of a nascent precursor protein (pre-protein) directs the ribosome to the rough endoplasmic reticulum (ER) membrane and initiates the transport of the growing peptide chain across it for processing. ER processing produces mature proteins, wherein the signal peptide is cleaved from precursor proteins, typically by an ER-resident signal peptidase of the host cell, or they remain uncleaved and function as a membrane anchor. A signal peptide may also facilitate the targeting of the protein to the cell membrane.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide has a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Signal peptides from heterologous genes (e.g., other than influenza virus HA, influenza virus NA, hRSV F, and SARS-CoV-2 S glycoproteins) may also be used in a protein.

The native signal peptide of a protein may be determined using any suitable method, such as a signal peptide prediction tool. Signal peptide prediction tools use bioinformatic algorithms, such as neural network, machine learning, and/or language model-based approaches, in combination with annotated protein databases (e.g., UniProt) to predict the signal peptide sequence within a given amino acid sequence. See, e.g., Teufel et al., *Nat Biotechnol.* 2022. 40(7):1023-1025 (SignalP 6.0)

Non-exhaustive examples of signal peptides of HA and NA proteins of influenza A/(H1N1) subtype, A/(H3N2) subtype, B/Victoria lineage, and B/Yamagata lineage isolates are provided in Table SP-1.

TABLE SP-1

Exemplary IAV and IBV HA and NA protein signal peptides

| Subtype (IAV) or lineage (IBV) | Isolate | HA protein signal peptide | NA protein signal peptide |
|---|---|---|---|
| A/(H1N1) subtype | A/Wisconsin/67/2022 (H1N1)pdm09 | MKAILVVMLYTFTTA NA (SEQ ID NO: 168) | MNPNQKIITIGSVCMTI GTANLILQIGNI (SEQ ID NO: 226) |
| A/(H3N2) subtype | A/Darwin/6/2021 (H3N2) | MKTIIALSNILCLVFA (SEQ ID NO: 169) | MNPNQKIITIGSVSLTIS TICFFMQIAIL (SEQ ID NO: 227) |
| B/Victoria lineage | B/Austria/1359417/2021 | MKAIIVLLMVVTSNA (SEQ ID NO: 170) | MLPSTIQTLTLFLTSGG VLLSLYVSASLSYL (SEQ ID NO: 228) |
| B/Yamagata lineage | B/Phuket/3073/2013 | MKAIIVLLMVVTSNA (SEQ ID NO: 171) | MLPSTIQTLTLFLTSGG VLLSLYVSASLSYL (SEQ ID NO: 229) |

Nucleic Acids

Provided are compositions comprising nucleic acids. In some embodiments, the nucleic acids comprise DNA. In some embodiments, the nucleic acids comprise RNA, such as self-amplifying RNA, circular RNA, or mRNA. Preferably, the nucleic acid comprises mRNA.

Except where otherwise noted, nucleic acid sequences set forth in the instant application may recite "T"s in a representative DNA sequence but where the sequence represents RNA, the "T"'s would be substituted for "U"s. Thus, any of the DNAs disclosed and identified by a particular sequence herein also discloses the corresponding RNA sequence where each "T" of the DNA sequence is substituted with "U.".

Messenger RNA (mRNA)

Messenger RNA (mRNA) is RNA that encodes a (at least one) protein or a fragment thereof and can be translated to produce the encoded protein or fragment in vitro, in vivo, in situ, or ex vivo. mRNA comprises an open reading frame (ORF) encoding the protein or fragment thereof. In some embodiments, the mRNA further comprises a 5' untranslated region (UTR), 3' UTR, a polyA tail, and/or a 5' cap analog.

The disclosed mRNA may encode a single protein or fragment or they may be polycistronic constructs, which encode more than one protein or fragment separately within the same mRNA molecule. Additionally or alternatively, the disclosed mRNA may encode a fusion protein or fragment thereof.

i. Open Reading Frame (ORF)

An open reading frame (ORF) is a continuous stretch of DNA or RNA beginning with a start codon (e.g., methionine (ATG or AUG)) and ending with a stop codon or codons (e.g., TAA, TAG, TGA, UAA, UAG, UGA, UGAUGA or UGAUAAUAG). For clarity: the stop codon itself is not considered a part of the ORF. An ORF typically encodes a protein or fragment thereof.

ii. Untranslated Regions (UTRs)

In some embodiments, mRNA comprises one or more regions or parts which act or function as an untranslated region. A 5' untranslated region" (5' UTR) is a region of an mRNA that is upstream (i.e., 5') from the start codon and does not encode a polypeptide. A 3' untranslated region" (3'UTR) is a region of an mRNA that is downstream (i.e., 3') from the stop codon and also does not encode a polypeptide The 5' UTR may start at the transcription start site and continues to the start codon but does not include the start codon. The 3' UTR may start immediately following the stop codon and continue until a transcriptional termination signal. A variety of 5' UTR and 3' UTR sequences are known. Exemplary UTR sequences include SEQ ID NOs: 1-35 (5' UTRs) and 36-44 (3' UTRs), which are shown in Tables S-1 (5' UTRs) and S-2 (3' UTRs) of the section "Exemplary Sequences". In some embodiments, the 5' UTR comprises a sequence provided in Table S-1 or a sequence with at least 80%, 85%, 90%, 95%, 96%, 97%, 98%, 99% or 100% identity to a 5' UTR sequence provided in Table S-1, or a variant or a fragment thereof. In some embodiments, the 3' UTR comprises a sequence provided in Table S-2 or a sequence with at least 80%, 85%, 90%, 95%, 96%, 97%, 98%, 99% or 100% identity to a 3' UTR sequence provided in Table S-2, or a variant or a fragment thereof.

Each RNA species in a multivalent RNA composition may comprise an IDR sequence that is not a sequence isomer of an IDR sequence of another RNA species in a multivalent RNA composition (e.g., the IDR sequence does not have the same number of adenosine nucleotides, the same number of cytosine nucleotides, the same number of guanine nucleotides, and the same number of uracil nucleotides (and consequently the same mass) as another IDR sequence in the composition, even if those sequences have different sequences).

Each RNA species in a multivalent RNA composition may comprise an IDR sequence having a mass that differs from the mass of IDR sequences of each other RNA species in a multivalent RNA composition. For example, the mass of each IDR sequence may differ from the mass of other IDR sequences by at least 9 Da, at least 25 Da, at least 25 Da, or at least 50 Da. Use of IDR sequences with distinct masses allows RNA fragments comprising different IDR sequences to be distinguished using mass-based analysis methods (e.g., mass spectrometry), which do not require reverse transcription, amplification, or sequencing of RNAs.

Each RNA species in an RNA composition may comprises an IDR sequence with a different length. For example, each IDR sequence may have a length independently selected from 0 to 25 nucleotides. The length of a nucleic acid influences the rate at which the nucleic acid traverses a chromatography column, and so the use of IDR sequences of different lengths on different RNA species allows RNA fragments having different IDR sequences to be distinguished using chromatography-based methods (e.g., LC-UV).

Combinations of features may be included in flanking regions and may be contained within other features. For example, the ORF may be flanked by a 5' UTR which may contain a strong Kozak translational initiation signal and/or a 3' UTR which may include an oligo (dT) sequence for templated addition of a poly-A tail. 5' UTR may comprise a first polynucleotide fragment and a second polynucleotide fragment from the same and/or different genes such as the 5' UTRs described in US 2010/0293625 and WO 2015/085318.

In some embodiments, a double, triple or quadruple UTR such as a 5' UTR or 3' UTR may be used. As used herein, a "double" UTR is one in which two copies of the same UTR are encoded either in series or substantially in series. For example, a double beta-globin 3' UTR may be used as described in US 2010/0129877.

For the purposes of the present disclosure, a UTR may also include one or more translation enhancer elements (TEE). As a non-limiting example, the TEE may include those described in US 2009/0226470, herein incorporated by reference, and those known in the art.

iii. PolyA Tail

In some embodiments, the mRNA contains a 3'-polyA tail. A polyA tail may contain 10 to 300 adenosine monophosphates. It can, in some instances, comprise up to about 400 adenine nucleotides. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine nucleotides. In some embodiments, a polyA tail contains 50 to 250 adenosine nucleotides. In some embodiments, a polyA tail has a length of about 50, about 100, about 150, about 200, about 250, about 300, about 350, or about 400 nucleotides. In some embodiments, a polyA tail has a length of 100 nucleotides.

In some embodiments, an mRNA may comprise two polyA sequences separated by an intervening nucleotide sequence. In some embodiments, the intervening nucleotide sequence comprises no more than 3, no more than two, no more than 1, or no adenosine nucleotides. In some embodiments, the intervening sequence comprises 3 adenosine nucleotides. In some embodiments, the intervening sequence is no more than 30, no more than 25, no more than 20, no more than 15, or no more than 10 nucleotides long. In some embodiments, the intervening sequence consists of 10 nucleotides. In some embodiments, the intervening sequence comprises the sequence of GCAUAUGACU. In some embodiments, the intervening sequence does not begin with an adenosine nucleotide, and does not end with an adenosine nucleotide. In some embodiments, the first polyA sequences comprises at least 15, at least 20, at least 25, or at least 30 consecutive adenosine nucleotides. In some embodiments, the second polyA sequences comprises at least 55, at least 60, at least 65, or at least 70 consecutive adenosine nucleotides. In some embodiments, the first polyA sequence comprises 30 consecutive adenosine nucleotides. In some embodiments, the second polyA sequence comprises 70 adenosine nucleotides.

iv. 5' Cap

In some embodiments, mRNA comprises a 5' end cap or a "5' terminal cap." A cap analog may be, for example, a dinucleotide cap, a trinucleotide cap, or a tetranucleotide cap. In some embodiments, a cap analog is a dinucleotide cap. In some embodiments, a cap analog is a trinucleotide cap. In some embodiments, a cap analog is a tetranucleotide cap.

5'-capping of polynucleotides may be completed concomitantly during an in vitro transcription reaction using, for example, the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, MA). 5'-capping of modified mRNA may be completed post-transcriptionally using, for example, a Vaccinia Virus Capping Enzyme to generate the "Cap 0" structure: m7G(5')ppp(5')G (New England BioLabs, Ipswich, MA). A Cap 1 structure may be generated using both Vaccinia Virus Capping Enzyme and a 2'-O methyl-transferase to generate: m7G(5')ppp(5')G-2'-O-methyl. A Cap 2 structure may be generated from the Cap 1 structure followed by the 2'-O-methylation of the 5'-antepenultimate nucleotide using a 2'-0 methyl-transferase. A Cap 3 structure may be generated from the Cap 2 structure followed by the 2'-O-methylation of the 5'-preantepenultimate nucleotide using a 2'-O methyl-transferase. Enzymes may be derived from a recombinant source. Other cap analogs, such as a 7 mG(5')ppp(5')NlmpNp cap, may be used.

Chemical Modifications

An mRNA may include nucleotides that are not chemically modified (i.e., unmodified nucleotides), nucleotides that are chemically modified, or both. Nucleotides that are not chemically modified are the standard ribonucleotides consisting of adenosine, guanosine, cytidine, and uridine.

Some embodiments of mRNAs comprise modified nucleosides and/or nucleotides. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside in combination with a phosphate group. Modifications to nucleotides or nucleosides can be at the sugar or nucleobase. Modified nucleotides may by synthesized by any useful method, such as, for example, chemically, enzymatically, or recombinantly.

In some embodiments, modified nucleobases in mRNA comprise N1-methyl-pseudouridine (m1ψ), N1-ethyl-pseudouridine (e1ψ), 5-methoxy-uridine (mo5U), 5-methyl-uridine (m5U), 5-methyl-cytidine (m5C), and/or pseudouridine (ψ). In some embodiments, modified nucleobases in mRNAs comprise 5-methoxymethyl uridine, 5-methylthio uridine, 1-methoxymethyl pseudouridine, 5-methyl cytidine, and/or 5-methoxy cytidine. In some embodiments, the mRNA includes a combination of at least two (e.g., 2, 3, 4 or more) of any of the aforementioned modified nucleobases, including but not limited to chemical modifications.

In some embodiments, a mRNA comprises 1-methyl-pseudouridine (mlv) substitutions at one or more or all uridine positions of the mRNA.

In some embodiments, a mRNA comprises 1-methyl-pseudouridine (m1ψ) substitutions at one or more or all uridine positions of the mRNA and 5-methyl cytidine substitutions at one or more or all cytidine positions of the mRNA.

In some embodiments, a mRNA comprises pseudouridine (ψ) substitutions at one or more or all uridine positions of the mRNA.

In some embodiments, a mRNA comprises pseudouridine (ψ) substitutions at one or more or all uridine positions of the mRNA and 5-methylcytidine substitutions at one or more or all cytidine positions of the mRNA.

In some embodiments, a mRNA comprises uridine at one or more or all uridine positions of the mRNA.

In some embodiments, a mRNA comprises 5-methyl-uridine and 5-methyl cytidine at one or more or all uridine and cytidine positions, respectively, of the mRNA.

In some embodiments, mRNAs are uniformly modified (e.g., fully modified, modified throughout the entire sequence) for a particular modification. For example, a mRNA can be uniformly modified with 1-methyl-pseudouridine, meaning that all uridine residues in the mRNA sequence are replaced with 1-methyl-pseudouridine. Similarly, a nucleic acid can be uniformly modified for any type of nucleoside residue present in the sequence by replacement with a modified residue such as those set forth above. In some embodiments, the ORF is uniformly modified for a particular modification, such as 1-methyl-pseudouridine. In some embodiments, the uniform modification does not include the mRNA cap. For instance, a cap with different modifications from the remainder of the mRNA can be added co-transcriptionally or post-transcriptionally to the mRNA.

Codon Optimization

In some embodiments, an ORF encoding a protein or fragment thereof is codon optimized. Codon optimization methods are known in the art. For example, an ORF of any one or more of the sequences listed below may be codon optimized. Codon optimization, in some embodiments, may be used to match codon frequencies in target and host organisms to ensure proper folding; bias GC content to increase RNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and RNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

In some embodiments, a codon optimized sequence shares less than 95%, less than 90%, less than 85%, less than 80%, or less than 75% sequence identity to a naturally-occurring or wild-type sequence open reading frame (e.g., a naturally-occurring or wild-type mRNA sequence encoding a protein or fragment thereof). In some embodiments, a codon optimized sequence shares between 65% and 85% sequence identity to a naturally-occurring or wild-type sequence (e.g., a naturally-occurring or wild-type RNA or DNA sequence encoding a protein or fragment thereof).

In some embodiments, a codon-optimized sequence encodes an antigen that is as immunogenic as, or more immunogenic than (e.g., at least 10%, at least 20%, at least 30%, at least 40%, at least 50%, at least 100%, or at least 200% more), than a protein or fragment thereof encoded by a non-codon-optimized sequence.

Self-Amplifying RNA

In some embodiments, an RNA is a self-amplifying RNA. A self-amplifying RNA is an RNA encoding one or more proteins that, individually or in conjunction, are capable of replicating the self-amplifying RNA. In some embodiments, the proteins encoded by the self-amplifying RNA are non-structural proteins nsP1, nsP2, nsP3, and nsP4, which form an RNA-dependent RNA polymerase (RdRp), or replicase, that is capable of replicating the self-amplifying RNA. By encoding proteins that are capable of replicating the RNA, a self-amplifying RNA is capable of self-amplification in a cell, provided that the cell can translate the RNA and produce the encoded protein(s). A self-amplifying RNA may be referred to as an RNA replicon.

When a self-amplifying RNA is translated, the one or more encoded viral non-structural proteins are translated. A "viral non-structural protein" is a protein encoded by a virus but that is not part of the virus particle. The viral non-structural proteins, in the context of self-amplifying RNA, replicate the nucleotide sequences encoding the desired protein from the self-amplifying RNA via the sub-genomic viral promoters. Such replication driven by the viral sub-genomic promoter using the viral non-structural proteins enhances the expression level of the encoded protein. In some embodiments, the viral non-structural proteins are from a single-strand positive-sense RNA viruses. In some embodiments, the viral non-structural proteins are from an Alphavirus, belonging to the Togaviridae family. In some embodiments, the alphavirus is Sindbis or Venezuelan equine encephalitis virus. In some embodiments, the viral non-structural protein is an RNA-dependent RNA polymerase (RdRp) polyprotein P1234 (also termed NSP1-4).

Upon translation, P1234 is rapidly cleaved into P123 and nsP4 by autoproteolytic activity originating from the nsP2 (proteinase) portion of the polyprotein. Alphaviral RNA synthesis occurs at the plasma membrane of a cell, where the nsPs, together with alphaviral RNA, form membrane invaginations (or "spherules"). These spherules contain dsRNA created by replication of "+" strand viral genomic RNA into "−" strand anti-genomic RNA. The "−" strand serves as a template from which additional "+" strand genomic RNA (synthesized from the 5' UTR) or a shorter subsequence of the genomic RNA (termed subgenomic RNA) is synthesized from the subgenomic viral promoter region located near the end of the nonstructural protein ORF. The "+" strand genomic RNA and the subgenomic RNA are exported out of the spherules into the cytoplasm where they are translated by endogenous ribosomes. The exported "+" strand genomic RNA can associate with nsPs and form additional spherules, thus resulting in exponential increase of replicon RNA.

The viral non-structural proteins facilitate the replication of the nucleotide sequences encoding the desired protein via the subgenomic viral promoters (also referred to as "subgenomic promoters" herein). A "subgenomic viral promoter" refers to a promoter the drives the transcription of subgenomic mRNAs. Typically, an mRNA is transcribed from genomic DNAs and episomal DNAs (e.g., plasmids). Some viruses may transcribe subgenomic mRNAs from a RNA replicon that is produced from its genomic RNA. Many positive-sense RNA viruses produce subgenomic mRNAs as one of the common infection techniques used by these viruses and generally transcribe late viral genes. Subgenomic viral promoters range from 20 nucleotide (Sindbis virus) to over 100 nucleotides (Beet necrotic yellow vein virus) and are usually found upstream of the transcription start. In some embodiments, the subgenomic viral promoter is 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 nucleotides long, or longer. Subgenomic viral promoters have been described in the art, e.g., in PCT Publication No. WO 2016/040359, and Wagner et al., *Nature Chemical Biology*, DOI: 10.1038/s41589-018-0146-9 (2018).

Circular RNA

In some embodiments, an RNA is a circular RNA. A circular RNA is an RNA with no 5' terminal nucleotide or 3' terminal nucleotide. Every nucleotide in a circular RNA is covalently bonded to both (1) a 5' adjacent nucleotide; and (2) a 3' adjacent nucleotide. In a circular RNA with a nucleotide sequence comprising every nucleotide of the circular RNA in 5'-to-3' order, the last nucleotide of the nucleotide sequence is covalently bonded to the first nucleotide of the nucleotide sequence.

A circular RNA may be a circular mRNA, comprising one or more 5' UTRs, an open reading frame, and one or more 3' UTRs. A circular RNA may comprise a polyA region, as described in the section entitled "PolyA Tails". The skilled artisan will appreciate that a polyA tail, when incorporated in a circular RNA, is referred to as a polyA region because a circular RNA does not have an end as a linear mRNA does.

A circular RNA may comprise an internal ribosome entry site (IRES). Inclusion of an IRES permits the translation of one or more open reading frames from a circular RNA, as circular RNAs do not comprise a 5' from which a ribosome may initiate translation as with capped linear mRNAs. The IRES element attracts a eukaryotic ribosomal translation initiation complex and promotes translation initiation. See, e.g., Kaufman et al., *Nucleic Acid Res.* 1991 19:4485-4490; Gurtu et al., *Biochem Biophys Res Commun.* 1996. 229:295-298; Rees et al., *BioTechniques.* 1996. 20:102-110; Kobayashi et al., *BioTechniques.* 1996. 21:399-402; and Mosser et al., *BioTechniques.* 1997. 22:150-161. A multitude of IRES sequences are available and include sequences derived from a wide variety of viruses, such as from leader sequences of picornaviruses such as the encephalomyocarditis virus (EMCV) UTR (Jang et al., *J Virol.* 1989. 63:1651-1660), the polio leader sequence, the hepatitis A virus leader, the hepatitis C virus IRES, human rhinovirus type 2 IRES (Dobrikova et al., *Proc Natl Acad Sci USA.* 2003. 100(25): 15125-15130), an IRES element from the foot and mouth disease virus (Ramesh et al., Nucleic Acid Res. 1996. 24:2697-2700), a giardiavirus IRES (Garlapati et al., *J Biol Chem.* 2004. 279(5):3389-3397). Additionally or alternatively, a circular RNA may comprise any of a variety of nonviral IRES sequences, such as IRES sequences from yeast, as well as the human angiotensin II type 1 receptor IRES (Martin et al., *Mol Cell Endocrinol.* (2003) 212:51-61), fibroblast growth factor IRESs (FGF-1 IRES and FGF-2 IRES, Martineau et al., *Mol Cell Biol.* 2004. 24(17):7622-7635), vascular endothelial growth factor (VEGF) IRES (Baranick et al., *Proc Natl Acad Sci USA.* 2008. 105(12): 4733-4738, Stein et al., *Mol Cell Biol.* 1998. 18(6):3112-3119, Bert et al., *RNA.* 2006. 12(6):1074-1083), and insulin-like growth factor II (IGF-II) IRES (Pedersen et al., *Biochem J.* 2002. 363 (Pt 1):37-44). These elements are commercially available in plasmids sold, e.g., by Clontech (Mountain View, CA), Invivogen (San Diego, CA), Addgene (Cambridge, MA) and GeneCopoeia (Rockville, MD). See also IRESite: The database of experimentally verified IRES structures. In some embodiments, a circular RNA comprises a coxsackievirus B3 (CVB3) IRES. See Gharbi et al., *PLoS One.* 2022. 17(10):e0274162. In some embodiments, a circular RNA comprises an EMCV IRES. In some embodiments, a circular RNA comprises a salivirus IRES. See Sweeney et al., *J Virol.* 2012. 86(3):1468-1486. In some embodiments, the salivirus IRES is present in or derived from Salivirus FHB (SaliFHB). See GenBank Accession No. KM023140.1.

Viral Vectors

Some aspects relate to viral vectors comprising or encoding influenza virus proteins. In some embodiments, the protein is comprised in a viral vector. In some embodiments, a viral vector comprises a nucleic acid encoding the protein.

Any suitable virus may be used as a viral vector. Non-limiting examples of viruses that may be used as viral vectors include retrovirus (e.g., lentivirus), adenovirus, adeno-associated virus (AAV), vesicular stomatitis virus (VSV), herpesvirus, Rous sarcoma virus, measles virus, poxvirus, gammavirus, alphavirus, murine stem cell virus, Moloney murine leukemia virus, and bovine leukemia virus. In some embodiments, the viral vector is a VSV vector. In some embodiments, the viral vector is a measles virus vector. In some embodiments, the viral vector is an adenovirus vector. These and other viral vectors suitable for expression of heterologous proteins (i.e., proteins not naturally expressed by a virus from which the viral vector is derived) are known in the art.

In some embodiments, a viral vector comprises an influenza B/Victoria lineage HA protein, or a nucleic acid encoding the influenza B/Victoria lineage HA protein. In some embodiments, the influenza B/Victoria lineage virus HA protein is an influenza B/Victoria lineage virus HA protein described in the section entitled "B/Victoria lineage HA proteins." In some embodiments, the influenza B/Victoria lineage HA protein comprises an amino acid sequence with at least 90% sequence identity to the amino acid sequence of SEQ ID NO: 71.

In some embodiments, a viral vector comprises an influenza B/Yamagata lineage HA protein, or a nucleic acid encoding the influenza B/Yamagata lineage HA protein. In some embodiments, the influenza B/Yamagata lineage virus HA protein is an influenza B/Yamagata lineage virus HA protein described in the section entitled "B/Yamagata lineage HA proteins." In some embodiments, the influenza B/Yamagata lineage HA protein comprises an amino acid sequence with at least 90% sequence identity to the amino acid sequence of SEQ ID NO: 70.

In some embodiments of viral vectors, a viral vector comprises an IAV H1 HA protein, or a nucleic acid encoding the IAV H1 HA protein. In some embodiments, the IAV H1 HA protein is an IAV H1 HA protein described in the section entitled "H1 HA proteins." In some embodiments, the IAV H1 HA protein comprises an amino acid sequence with at least 90% sequence identity to the amino acid sequence of SEQ ID NO: 83. In some embodiments, the IAV H1 HA protein comprises an amino acid sequence with at least 90% sequence identity to the amino acid sequence of SEQ ID NO: 95.

In some embodiments, a viral vector comprises an IAV H3 HA protein, or a nucleic acid encoding the IAV H3 HA protein. In some embodiments, IAV H3 HA protein is an IAV H3 HA protein described in the section entitled "H3 HA proteins." Where a combination or multivalent vaccine includes multiple H3 HA proteins (e.g., comprises multiple viral vectors comprising or encoding different H3 HA proteins), the different H3 HA proteins may each comprise the same substitutions, or different substitutions described in the section entitled "H3 HA proteins." In some embodiments, one or more H3 HA proteins does not comprise a substitution described in the section entitled "H3 HA proteins." In some embodiments, the IAV H3 HA protein comprises an amino acid sequence with at least 90% sequence identity to the amino acid sequence of SEQ ID NO: 82. In some embodiments, each IAV H3 HA protein comprises an amino acid sequence with at least 90% sequence identity to the amino acid sequence of SEQ ID NO: 82.

Nucleic Acid Production

In Vitro Transcription (IVT) of RNA cDNA encoding RNA polynucleotides may be transcribed using an in vitro transcription (IVT) system. In vitro transcription of RNA is known in the art and is described in International Publication WO 2014/152027, which is incorporated by reference herein to the extent it discloses IVT methods. In some embodiments, the RNA is prepared in accordance with any one or more of the methods described in WO 2018/053209 and WO 2019/036682, each of which is incorporated by reference herein to the extent it discloses RNA production methods.

In some embodiments, the RNA transcript is generated using a non-amplified, linearized DNA template in an in vitro transcription reaction to generate the RNA transcript. In some embodiments, the template DNA is isolated DNA. In some embodiments, the template DNA is cDNA. In some embodiments, the cDNA is formed by reverse transcription of an RNA polynucleotide, for example, but not limited to influenza virus mRNA. In some embodiments, cells, e.g., bacterial cells, e.g., *E. coli*, e.g., DH-1 cells are transfected with the plasmid DNA template. In some embodiments, the transfected cells are cultured to replicate the plasmid DNA which is then isolated and purified. In some embodiments, the DNA template includes a RNA polymerase promoter, e.g., a T7 promoter located 5' to and operably linked to the gene of interest.

In some embodiments, an in vitro transcription template encodes a 5' untranslated (UTR) region, contains an open reading frame, and encodes a 3' UTR and a poly(A) tail. The particular nucleic acid sequence composition and length of an in vitro transcription template will depend on the mRNA encoded by the template.

An in vitro transcription system typically comprises a transcription buffer, nucleotide triphosphates (NTPs), an RNase inhibitor, and a polymerase.

The NTPs may be manufactured in house, may be selected from a supplier, or may be synthesized. The NTPs may be selected from natural and unnatural NTPs, and may be selected from unmodified (e.g., ATP, GTP, UTP, CTP) or modified NTPs.

Any number of RNA polymerases or variants may be used to transcribe RNA. The polymerase may be selected from, but is not limited to, a phage RNA polymerase, e.g., a T7 RNA polymerase, a T3 RNA polymerase, a SP6 RNA polymerase, and/or mutant polymerases such as, but not limited to, polymerases able to incorporate modified nucleic acids and/or modified nucleotides, including chemically modified nucleic acids and/or nucleotides. Some embodiments exclude the use of DNase.

In some embodiments, the RNA transcript is capped via enzymatic capping. In some embodiments, the RNA comprises 5' terminal cap, for example, 7 mG(5')ppp(5') NlmpNp.

In some embodiments the RNA polymerase is a wild-type RNA polymerase. In some embodiments, the RNA polymerase is an RNA polymerase variant, such as those described in WO 2020/172239, incorporated herein by reference to the extent it describes RNA polymerase variants. RNA polymerase variants may include at least one amino acid substitution, relative to the wild-type (WT) RNA polymerase. A WT T7 RNA polymerase is represented by SEQ ID NO: 81. In some embodiments, the RNA polymerase is a variant RNA polymerase comprising the amino acid sequence of any one of SEQ ID NOs: 176-179.

Purification

Purification of the nucleic acids may include, but is not limited to, nucleic acid clean-up, quality assurance and quality control. Clean-up may be performed by methods known in the arts such as, but not limited to, AGENCOURT® beads (Beckman Coulter Genomics, Danvers, MA), poly-T beads, LNATM oligo-T capture probes (EXIQON® Inc, Vedbaek, Denmark); HPLC based purification methods such as, but not limited to, strong anion exchange HPLC, weak anion exchange HPLC, reverse phase HPLC (RP-HPLC), and hydrophobic interaction HPLC (HIC-HPLC); and/or tangential flow filtration. The term "purified" when used in relation to a nucleic acid such as a "purified nucleic acid" refers to one that is separated from at least one contaminant. A "contaminant" is any substance that makes another unfit, impure or inferior. Thus, a purified nucleic acid (e.g., DNA and RNA) is present in a form or setting different from that in which it is found in nature, or a form or setting different from that which existed prior to subjecting it to a treatment or purification method.

Lipid Compositions

In some embodiments, the nucleic acids are formulated as a lipid composition, such as a composition comprising a lipid nanoparticle, a liposome, and/or a lipoplex. In some embodiments, the lipid composition (e.g., lipid nanoparticle, liposome, and/or lipoplex) does not comprise protamine. In some embodiments, the lipid composition does comprise protamine. In some embodiments, nucleic acids are formulated as lipid nanoparticle (LNP) compositions. Lipid nanoparticles typically comprise ionizable lipid (e.g., ionizable amino lipid), non-cationic lipid (e.g., phospholipid), structural lipid (e.g., sterol), and PEG-modified lipid components along with the nucleic acid cargo of interest. The lipid nanoparticles can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2017/038426; PCT/US2014/027077; PCT/US2014/055394; PCT/US2016/52117; PCT/US2012/069610; PCT/US2017/027492; PCT/US2016/059575; PCT/US2016/069491; PCT/US2016/069493; and PCT/US2014/66242, all of which are incorporated by reference herein in their entirety.

In some embodiments, the lipid nanoparticle comprises a molar ratio of 20-60% ionizable lipid, 5-25% non-cationic lipid, 25-55% structural lipid, and 0.5-15% PEG-modified lipid.

In some embodiments, the lipid nanoparticle comprises a molar ratio of 20-60% ionizable lipid, 5-30% non-cationic lipid, 10-55% structural lipid, and 0.5-15% PEG-modified lipid.

In some embodiments, the lipid nanoparticle comprises 40-50 mol % ionizable lipid, optionally 45-50 mol %, for example, 45-46 mol %, 46-47 mol %, 47-48 mol %, 48-49 mol %, or 49-50 mol % for example about 45 mol %, 45.5 mol %, 46 mol %, 46.5 mol %, 47 mol %, 47.5 mol %, 48 mol %, 48.5 mol %, 49 mol %, or 49.5 mol %.

In some embodiments, the lipid nanoparticle comprises 20-60 mol % ionizable lipid. For example, the lipid nanoparticle may comprise 20-50 mol %, 20-40 mol %, 20-30 mol %, 30-60 mol %, 30-50 mol %, 30-40 mol %, 40-60 mol %, 40-50 mol %, or 50-60 mol % ionizable lipid. In some embodiments, the lipid nanoparticle comprises 20 mol %, 30 mol %, 40 mol %, 50 mol %, or 60 mol % ionizable lipid. In some embodiments, the lipid nanoparticle comprises 35 mol %, 36 mol %, 37 mol %, 38 mol %, 39 mol %, 40 mol %, 41 mol %, 42 mol %, 43 mol %, 44 mol %, 45 mol %, 46 mol %, 47 mol %, 48 mol %, 49 mol %, 50 mol %, 51 mol %, 52 mol %, 53 mol %, 54 mol %, or 55 mol % ionizable lipid.

In some embodiments, the lipid nanoparticle comprises 45-55 mole percent (mol %) ionizable lipid. For example, lipid nanoparticle may comprise 45, 46, 47, 48, 49, 50, 51, 52, 53, 54, or 55 mol % ionizable lipid.

Ionizable Lipids

In some embodiments, the ionizable lipid is a compound of Formula (IL*)

(IL*)

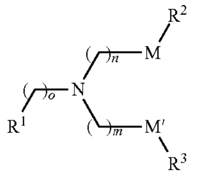

or a salt thereof, wherein:

$R^1$ is —OH, —$NR^N$—$C_{4-10}$ cycloalkenyl optionally substituted with one or more oxo or —$N(R^{N'}R^{N''})$;

$R^N$ is H or $C_{1-6}$ alkyl;

$R^{N'}$ is H or $C_{1-6}$ alkyl;

$R^{N''}$ is H or $C_{1-6}$ alkyl;

is 1, 2, 3, or 4;

n is 4, 5, 6, 7, or 8;

m is 4, 5, 6, 7, or 8;

M is —C(=O)—O—* or —O—C(=O)—*, wherein * indicates attachment to $R^2$;

M' is —C(=O)—O—* or —O—C(=O)—*, wherein * indicates attachment to $R^3$;

$R^2$ is

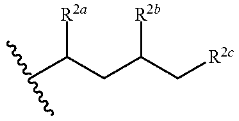

or —($C_{1-6}$ alkylene)-($C_{3-8}$ cycloalkyl)-$C_{1-6}$ alkyl;

$R^{2a}$ is —H or $C_{1-10}$ alkyl;

$R^{2b}$ is —H or $C_{1-10}$ alkyl;

$R^{2c}$ is $C_{1-8}$ alkyl or $C_{2-8}$ alkenyl;

$R^3$ is

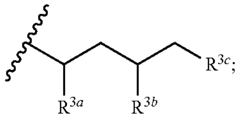

$R^{3a}$ is H or $C_{1-10}$ alkyl;

$R^{3b}$ is H or $C_{1-8}$ alkyl; and $R^{3c}$ is $C_{1-10}$ alkyl or $C_{2-8}$ alkenyl.

In some embodiments, the ionizable lipid is of Formula (IL**-I):

(IL**-I)

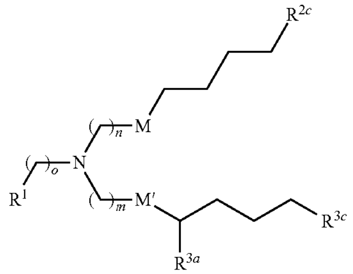

or a salt thereof, wherein:

$R^1$ is —OH;

o is 2, 3, or 4;

n is 4, 5, 6, 7, or 8;

M is —C(=O)—O—*, wherein * indicates attachment to $R^2$;

m is 6, 7, or 8;

M' is —C(=O)—O—*, wherein * indicates attachment to $R^3$;

$R^{2c}$ is $C_{4-8}$ alkyl;

$R^{3a}$ is $C_{7-10}$ alkyl; and $R^{3c}$ is $C_{3-5}$ alkyl.

In some embodiments, the ionizable lipid is of Formula (IL**-III):

(IL**-III)

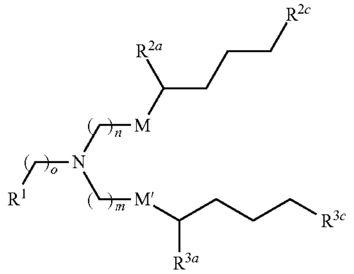

or a salt thereof, wherein:

$R^1$ is $NR^N$—$C_{4-10}$ cycloalkenyl optionally substituted with one or more oxo or —$N(R^{N'}R^{N''})$;

$R^N$ is H;

$R^{N'}$ is $C_{1-2}$ alkyl;

$R^{N''}$ is H;

o is 2, 3, or 4;

n is 6, 7, or 8;

M is —C(=O)—O—*, wherein * indicates attachment to $R^2$;

m is 6, 7, or 8;

M' is —C(═O)—O—*, wherein * indicates attachment to $R^3$;

$R^{2a}$ is $C_{7-10}$ alkyl;

$R^{2c}$ is $C_{4-6}$ alkyl;

$R^{3a}$ is $C_{1-3}$ alkyl; and $R^{3c}$ is $C_{4-6}$ alkyl.

In some embodiments, the ionizable lipid is of Formula (IL**-IV):

(IL**-IV)

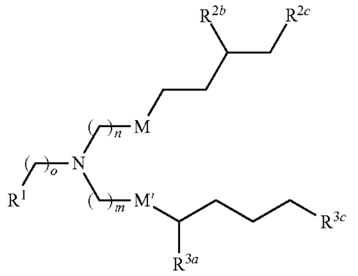

or a salt thereof, wherein:

$R^1$ is OH;

o is 2, 3, or 4;

n is 6, 7, or 8;

M is —C(═O)—O—*, wherein * indicates attachment to $R^2$;

m is 6, 7, or 8;

M' is —C(═O)—O—*, wherein * indicates attachment to $R^3$;

$R^{2b}$ is $C_{3-5}$ alkyl;

$R^{2c}$ is $C_{2-4}$ alkyl;

$R^{3a}$ is $C_{7-10}$ alkyl; and $R^{3c}$ is $C_{4-6}$ alkyl.

In some embodiments, the ionizable lipid is of Formula (IL*-I):

(IL*-Ia)

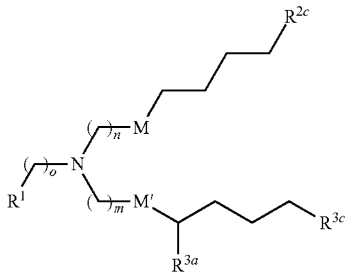

or a salt thereof, wherein:

$R^1$, o, m, n, M, M', $R^{2c}$, and $R^{3c}$ are as defined for variable IL*; and $R^{3a}$ is $C_{1-8}$ alkyl.

In some embodiments, ionizable lipid is of Formula (IL*-Ia):

(IL*-Ia)

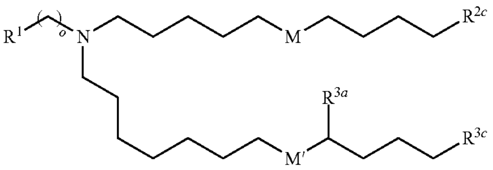

or a salt thereof, wherein:

$R^1$, o, m, n, M, M', $R^{2c}$, and $R^{3c}$ are as defined for Formula IL*; and $R^{3a}$ is $C_{1-8}$ alkyl.

In some embodiments, the ionizable lipid is of Formula (IL*-Ia'):

(IL*-Ia')

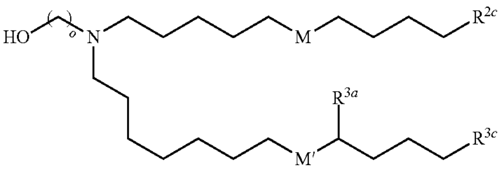

or a salt thereof, wherein:

o, M, M', $R^{2c}$ and $R^{3c}$ are as defined for variable IL*; and $R^{3a}$ is $C_{1-8}$ alkyl.

In some embodiments, the ionizable lipid is of Formula (IL*-Iia):

(IL*-Iia)

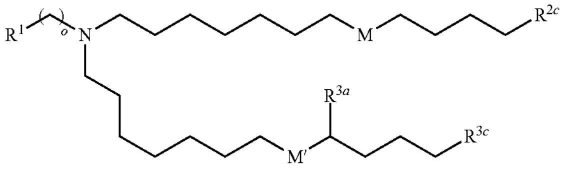

or a salt thereof, wherein:

$R^1$, o, m, n, M, M', $R^{2c}$, and $R^{3c}$ are as defined for Formula IL*; and $R^{3a}$ is $C_{1-8}$ alkyl.

In some embodiments, the ionizable lipid is of Formula (IL*-II'):

(IL*-II')

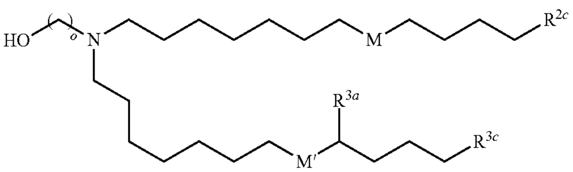

or a salt thereof, wherein:

o, M, M', $R^{2c}$ and $R^{3c}$ are as defined for variable IL*; and $R^{3a}$ is $C_{1-8}$ alkyl.

In some embodiments, the ionizable lipid is of Formula (IL*-III):

(IL*-III)

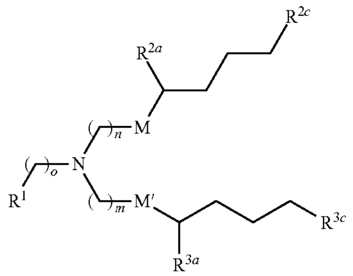

or a salt thereof, wherein:

$R^1$, o, m, n, M, M', $R^{2c}$, and $R^{3c}$ are as defined for variable IL*;

$R^{2a}$ is a $C_{1-8}$ alkyl; and $R^{3a}$ is $C_{1-8}$ alkyl.

In some embodiments, the ionizable lipid is of Formula (IL*-IIIa):

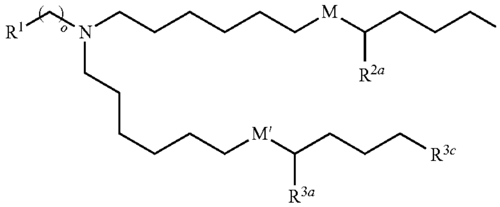

or a salt thereof, wherein:

$R^1$, o, m, n, M, M', $R^{2c}$, and $R^{3c}$ are as defined for variable IL*;

$R^{2b}$ is a $C_{1-8}$ alkyl; and $R^{3a}$ is $C_{1-8}$ alkyl.

In some embodiments, the ionizable lipid is of Formula (IL*-IIIa):

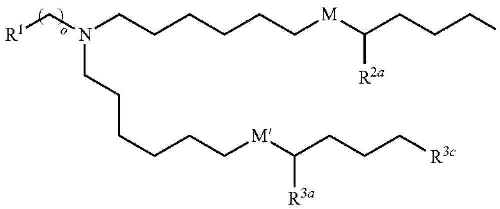

or a salt thereof, wherein:

$R^1$, o, M, M', $R^{2c}$, and $R^{3c}$ are as defined for variable IL*;

$R^{2a}$ is a $C_{1-8}$ alkyl; and $R^{3a}$ is $C_{1-8}$ alkyl.

In some embodiments, the ionizable lipid is of Formula (IL*-IIIa'):

(IL*-IIIa')

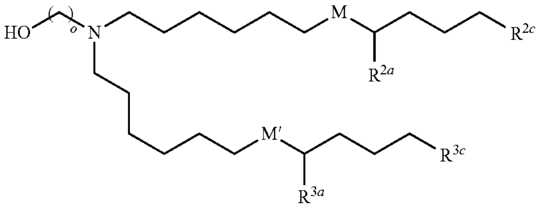

or a salt thereof, wherein:

$R^1$, o, M, M', $R^{2c}$, and $R^{3c}$ are as defined for variable IL*;

$R^{2a}$ is a $C_{1-8}$ alkyl; and $R^{3a}$ is $C_{1-8}$ alkyl.

In some embodiments, the ionizable lipid is of Formula (IL*-IIIb):

(IL*-IIIb)

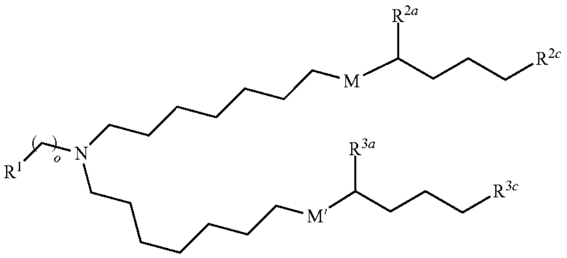

or a salt thereof, wherein:

$R^1$, o, M, M', $R^{2c}$, and $R^{3c}$ are as defined for variable IL*;

$R^{2a}$ is a $C_{1-8}$ alkyl; and $R^{3a}$ is $C_{1-8}$ alkyl.

In some embodiments, the ionizable lipid is of Formula (IL*-IIIb'):

(IL*-IIIb')

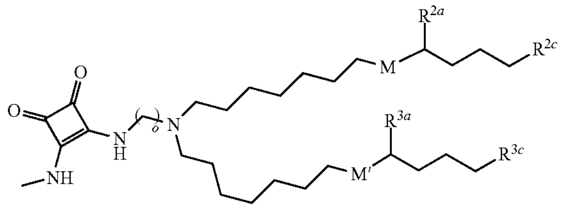

or a salt thereof, wherein:

$R^1$, o, M, M', $R^{2c}$, and $R^{3c}$ are as defined for variable IL*;

$R^{2a}$ is a $C_{1-8}$ alkyl; and $R^{3a}$ is $C_{1-8}$ alkyl.

In some embodiments, the ionizable lipid is of Formula (IL*-IV):

(IL*-IV)

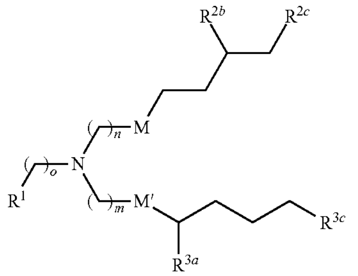

or a salt thereof, wherein:

$R^1$, o, m, n, M, M', $R^{2c}$, and $R^{3c}$ are as defined for variable IL*;

$R^{2b}$ is a $C_{1-8}$ alkyl; and $R^{3a}$ is $C_{1-8}$ alkyl.

In some embodiments, the ionizable lipid is of Formula (IL*-Iva):

(IL*-Iva)

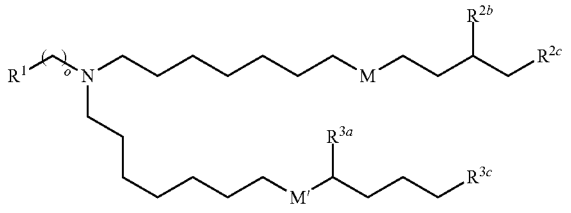

or a salt thereof, wherein:

$R^1$, o, m, n, M, M', $R^{2c}$, and $R^{3c}$ are as defined for variable IL*;

$R^{2b}$ is a $C_{1-8}$ alkyl; and $R^{3a}$ is $C_{1-8}$ alkyl.

In some embodiments, the ionizable lipid is of Formula (IL*-Iva'):

(IL*-Iva)

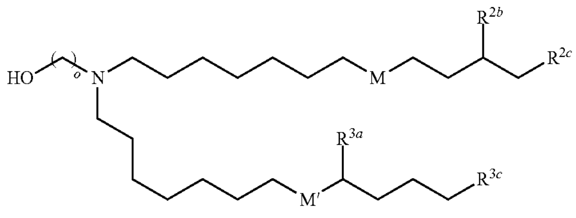

or a salt thereof, wherein:

o, M, M', $R^{2c}$, and $R^{3c}$ are as defined for variable IL*;

$R^{2a}$ is a $C_{1-8}$ alkyl; and $R^{3a}$ is $C_{1-8}$ alkyl.

Variables o, $R^1$, $R^N$, $R^{N'}$, $R^{N''}$ of Ionizable Lipid

In some embodiments of the ionizable lipid, o is 1.

In some embodiments of the ionizable lipid, o is 2.

In some embodiments of the ionizable lipid, o is 3.

In some embodiments of the ionizable lipid, o is 4.

In some embodiments of the ionizable lipid, $R^1$ is —OH.

In some embodiments of the ionizable lipid, $R^N$ is H.

In some embodiments of the ionizable lipid, $R^N$ is methyl.

In some embodiments of the ionizable lipid, $R^N$ is ethyl.

In some embodiments of the ionizable lipid, $R^1$ is —$NR^N$-cyclobutenyl, wherein the cyclobutenyl is optionally substituted with one or more oxo or —$N(R^{N'}R^{N''})$.

In some embodiments of the ionizable lipid, $R^{N'}$ is H.

In some embodiments of the ionizable lipid, $R^{N'}$ is methyl.

In some embodiments of the ionizable lipid, $R^{N'}$ is ethyl.

In some embodiments of the ionizable lipid, $R^{N''}$ is H.

In some embodiments of the ionizable lipid, $R^{N''}$ is methyl.

In some embodiments of the ionizable lipid, $R^{N''}$ is ethyl.

In some embodiments of the ionizable lipid, $R^{N'}$ is H and $R^{N''}$ is methyl.

In some embodiments of the ionizable lipid, $R^1$ is

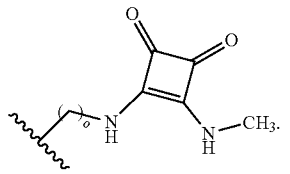

In some embodiments of the ionizable lipid, $R^1$ is

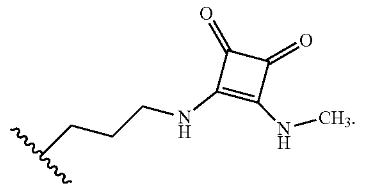 [SMILES: *CCCNc1c(NC)c(=O)c1=O]

Variables m and n of the Ionizable Lipid

In some embodiments of the ionizable lipid, m is 4.

In some embodiments of the ionizable lipid, m is 5.

In some embodiments of the ionizable lipid, m is 6.

In some embodiments of the ionizable lipid, m is 7.

In some embodiments of the ionizable lipid, m is 8.

In some embodiments of the ionizable lipid, m is 4.

In some embodiments of the ionizable lipid, n is 5.

In some embodiments of the ionizable lipid, n is 6.

In some embodiments of the ionizable lipid, n is 7.

In some embodiments of the ionizable lipid, n is 8.

In some embodiments of the ionizable lipid, n is 5 and m is 7.

In some embodiments of the ionizable lipid, n is 7 and m is 7.

In some embodiments of the ionizable lipid, m is 6 and n is 6.

Variables M and M' of Ionizable Lipid

In some embodiments of the ionizable lipid, M is —O—C(═O)—*, wherein * indicates attachment to $R^2$.

In some embodiments of the ionizable lipid, M is —C(—O)—O—* wherein * indicates attachment to $R^2$.

In some embodiments of the ionizable lipid, M' is —O—C(═O)—*, wherein * indicates attachment to $R^3$.

In some embodiments of the ionizable lipid, M' is —C(═O)—O—* wherein * indicates attachment to $R^3$.

In some embodiments of the ionizable lipid, M is —O—C(═O)—*, wherein * indicates attachment to $R^2$, and M' is —C(—O)—O—* wherein * indicates attachment to $R^3$ Variables $R^2$, $R^{2a}$, $R^{2b}$, $R^{2c}$ of Ionizable Lipid In some embodiments of the ionizable lipid, $R^2$ is

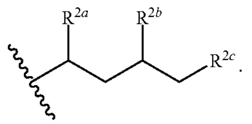

In some embodiments of the ionizable lipid, $R^{2a}$ is hydrogen.

In some embodiments of the ionizable lipid, $R^{2a}$ is methyl.

In some embodiments of the ionizable lipid, $R^{2a}$ is ethyl.

In some embodiments of the ionizable lipid, $R^{2a}$ is propyl.

In some embodiments of the ionizable lipid, $R^{2a}$ is butyl.

In some embodiments of the ionizable lipid, $R^{2a}$ is pentyl.

In some embodiments of the ionizable lipid, $R^{2a}$ is hexyl.

In some embodiments of the ionizable lipid, $R^{2a}$ is heptyl.

In some embodiments of the ionizable lipid, $R^{2a}$ is octyl.

In some embodiments of the ionizable lipid, $R^{2b}$ is hydrogen.

In some embodiments of the ionizable lipid, $R^{2b}$ is methyl.

In some embodiments of the ionizable lipid, $R^{2b}$ is ethyl.

In some embodiments of the ionizable lipid, $R^{2b}$ is propyl.

In some embodiments of the ionizable lipid, $R^{2b}$ is butyl.

In some embodiments of the ionizable lipid, $R^{2b}$ is pentyl.

In some embodiments of the ionizable lipid, $R^{2b}$ is hexyl.

In some embodiments of the ionizable lipid, $R^{2b}$ is heptyl.

In some embodiments of the ionizable lipid, $R^{2b}$ is octyl.

In some embodiments of the ionizable lipid, $R^{2a}$ is hydrogen and $R^{2b}$ is hydrogen.

In some embodiments of the ionizable lipid, $R^{2a}$ is hexyl and $R^{2b}$ is hydrogen.

In some embodiments of the ionizable lipid, $R^{2a}$ is octyl and $R^{2b}$ is hydrogen.

In some embodiments of the ionizable lipid, $R^{2a}$ is hydrogen and $R^{2b}$ is butyl.

In some embodiments of the ionizable lipid, $R^{2c}$ is methyl.

In some embodiments of the ionizable lipid, $R^{2c}$ is ethyl.

In some embodiments of the ionizable lipid, $R^{2c}$ is propyl.

In some embodiments of the ionizable lipid, $R^{2c}$ is butyl.

In some embodiments of the ionizable lipid, $R^{2c}$ is pentyl.

In some embodiments of the ionizable lipid, $R^{2c}$ is hexyl.

In some embodiments of the ionizable lipid, $R^{2c}$ is heptyl.

In some embodiments of the ionizable lipid, $R^{2c}$ is octyl.

In some embodiments of the ionizable lipid, $R^2$ is —($C_{1-6}$ alkylene)-($C_{3-8}$ cycloalkyl)-$C_{1-6}$ alkyl.

In some embodiments of the ionizable lipid, $R^2$ is —($C_{1-6}$ alkylene)-(cyclohexyl)-$C_{1-6}$ alkyl.

In some embodiments of the ionizable lipid, $R^2$ is —($C_{1-6}$ alkylene)-(cyclopentyl)-$C_{1-6}$ alkyl.

Variables $R^3$, $R^{3a}$, $R^{3b}$, and $R^{3c}$ of Ionizable Lipid

In some embodiments of the ionizable lipid, $R^3$ is

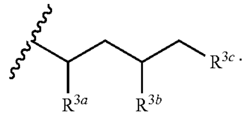

In some embodiments of the ionizable lipid, $R^{3a}$ is hydrogen.

In some embodiments of the ionizable lipid, $R^{3a}$ is methyl.

In some embodiments of the ionizable lipid, $R^{3a}$ is ethyl.

In some embodiments of the ionizable lipid, $R^{3a}$ is propyl.

In some embodiments of the ionizable lipid, $R^{3a}$ is butyl.

In some embodiments of the ionizable lipid, $R^{3a}$ is pentyl.

In some embodiments of the ionizable lipid, $R^{3a}$ is hexyl.

In some embodiments of the ionizable lipid, $R^{3a}$ is heptyl.

In some embodiments of the ionizable lipid, $R^{3a}$ is octyl.

In some embodiments of the ionizable lipid, $R^{3b}$ is hydrogen.

In some embodiments of the ionizable lipid, $R^{3b}$ is methyl.

In some embodiments of the ionizable lipid, $R^{3b}$ is ethyl.

In some embodiments of the ionizable lipid, $R^{3b}$ is propyl.

In some embodiments of the ionizable lipid, $R^{3b}$ is butyl.

In some embodiments of the ionizable lipid, $R^{3b}$ is pentyl.

In some embodiments of the ionizable lipid, $R^{3b}$ is hexyl.

In some embodiments of the ionizable lipid, $R^{3b}$ is heptyl.

In some embodiments of the ionizable lipid, $R^{3b}$ is octyl.

In some embodiments of the ionizable lipid, $R^{3a}$ is octyl and $R^{3b}$ is hydrogen.

In some embodiments of the ionizable lipid, $R^{3a}$ is ethyl and $R^{3b}$ is hydrogen.

In some embodiments of the ionizable lipid, $R^{3a}$ is hexyl and $R^{3b}$ is hydrogen.

In some embodiments of the ionizable lipid, $R^{3c}$ is methyl.

In some embodiments of the ionizable lipid, $R^{3c}$ is ethyl.

In some embodiments of the ionizable lipid, $R^{3c}$ is propyl.

In some embodiments of the ionizable lipid, $R^{3c}$ is butyl.

In some embodiments of the ionizable lipid, $R^{3c}$ is pentyl.

In some embodiments of the ionizable lipid, $R^{3c}$ is hexyl.

In some embodiments of the ionizable lipid, $R^{3c}$ is heptyl.

In some embodiments of the ionizable lipid, $R^{3c}$ is octyl.

It is understood that, for an ionizable lipid, variables o, $R^1$, $R^N$, $R^{N'}$, $R^{N'}$, m, n, M, M', $R^2$, $R^{2a}$, $R^{2b}$, $R^{2c}$, $R^3$, $R^{3a}$, $R^{3b}$, and $R^{3c}$ can each be, where applicable, selected from the groups described herein, and any group described herein for any of variables o, $R^1$, $R^N$, $R^{N'}$, $R^{N'}$, m, n, M, M', $R^2$, $R^{2a}$, $R^{2b}$, $R^{2c}$, $R^3$, $R^{3a}$, $R^{3b}$, and $R^{3c}$ can be combined, where applicable, with any group described herein for one or more of the remainder of variables o, $R^1$, $R^N$, $R^{N'}$, $R^{N'}$, m, n, M, M', $R^2$, $R^{2a}$, $R^{2b}$, $R^{2c}$, $R^3$, $R^{3a}$, $R^{3b}$, and $R^{3c}$.

In some embodiments, the ionizable lipid is a compound selected from:

(I-18)
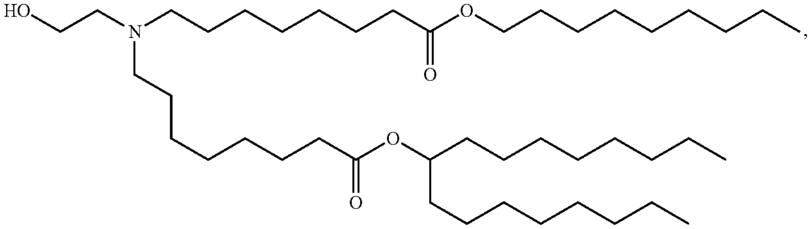
(I-25)
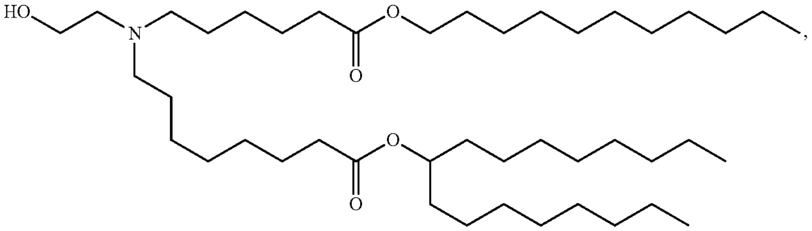
(I-301)
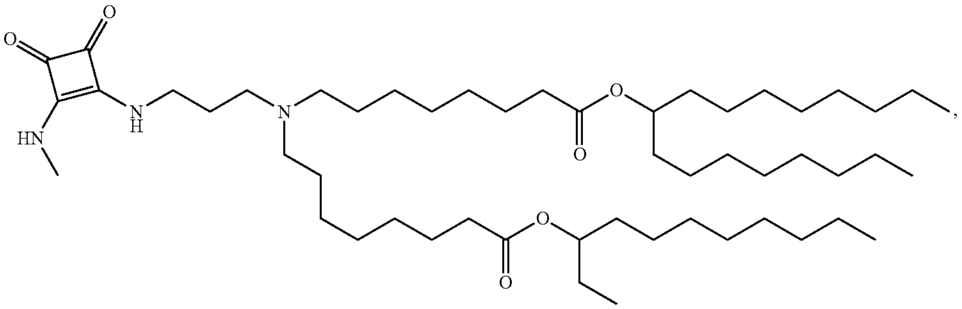
(II-6)
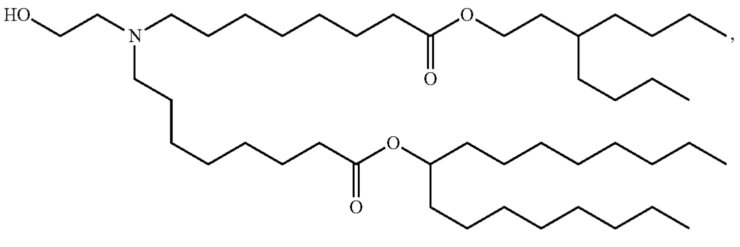
, and
(IL**)
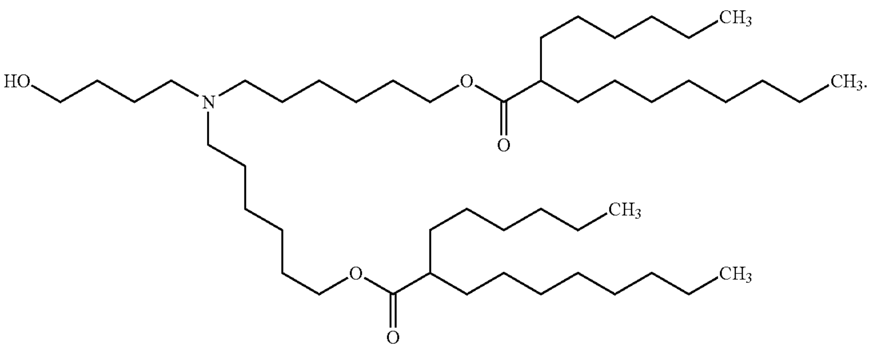

In some embodiments, the ionizable lipid is (I-18)

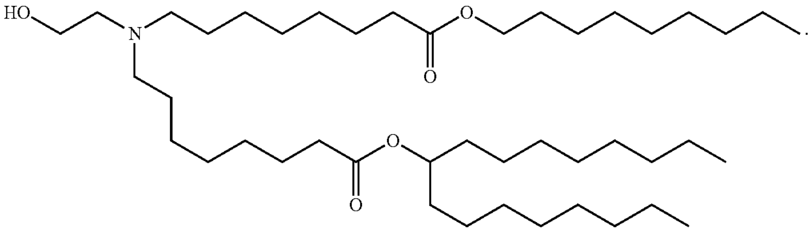

In some embodiments, the ionizable lipid is (I-25)

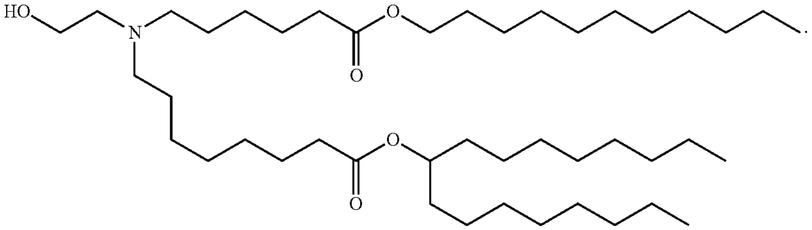

In some embodiments, the ionizable lipid is (I-301)

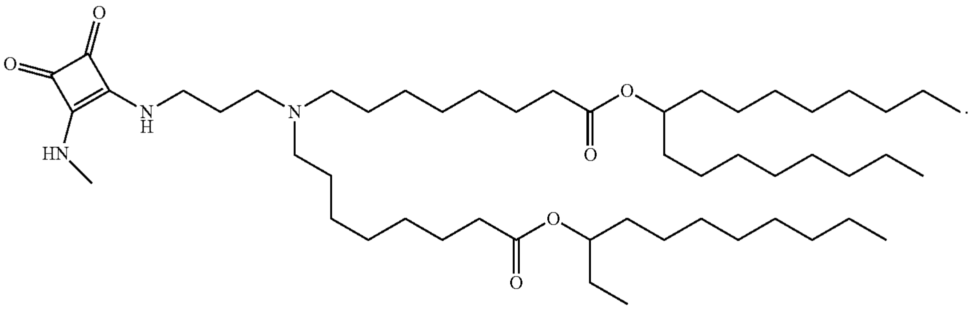

In some embodiments, the ionizable lipid is (II-6)

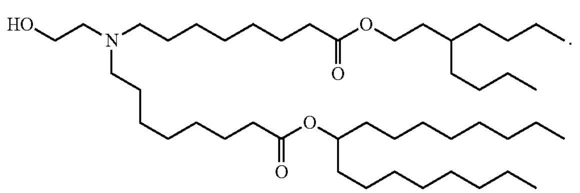

Without wishing to be bound by theory, it is understood that an ionizable lipid may have a positive or partial positive charge at physiological pH. Such lipids may be referred to as cationic or ionizable (amino) lipids. Lipids may also be zwitterionic, i.e., neutral molecules having both a positive and a negative charge.

Formula (AI)

In some embodiments, the ionizable amino lipid of a lipid nanoparticle is a compound of Formula (AI):

(AI)

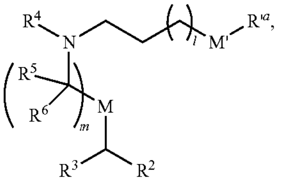

or its N-oxide, or a salt or isomer thereof, wherein $R'^{a}$ is $R'^{branched}$; wherein $R'^{branched}$ is:

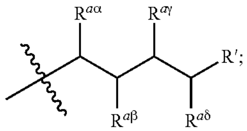

wherein

denotes a point of attachment;

wherein $R^{a\alpha}$, $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of —$(CH_2)_nOH$, wherein n is selected from the group consisting of 1, 2, 3, 4, and 5, and

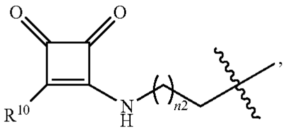

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some embodiments of the compounds of Formula (AI), $R'^{a}$ is $R'^{branched}$; $R'^{branched}$ is

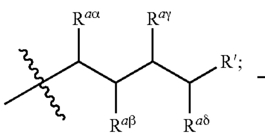 

denotes a point of attachment; $R^{a\alpha}$, $R^{a\beta}$, $R^{a\gamma}$, and $R^{a\delta}$ are each H; $R^2$ and $R^3$ are each $C_{1-14}$ alkyl; $R^4$ is —$(CH_2)_nOH$; n is 2; each $R^5$ is H; each $R^6$ is H; M and M' are each —C(O)O—; R' is a $C_{1-12}$ alkyl; l is 5; and m is 7.

In some embodiments of the compounds of Formula (AI), $R'^{a}$ is $R'^{branched}$; $R'^{branched}$ is

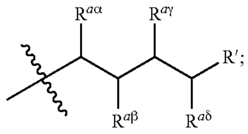 

denotes a point of attachment; $R^{a\alpha}$, $R^{a\beta}$, $R^{a\gamma}$, and $R^{a\delta}$ are each H; $R^2$ and $R^3$ are each $C_{1-14}$ alkyl; $R^4$ is —$(CH_2)_nOH$; n is 2; each $R^5$ is H; each $R^6$ is H; M and M' are each —C(O)O—; R' is a $C_{1-12}$ alkyl; l is 3; and m is 7.

In some embodiments of the compounds of Formula (AI), $R'^{a}$ is $R'^{branched}$; $R'^{branched}$ is

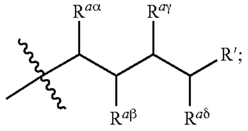 

denotes a point of attachment; $R^{a\alpha}$ is $C_{2-12}$ alkyl; $R^{a\beta}$, $R^{a\gamma}$, and $R^{a\delta}$ are each H; $R^2$ and $R^3$ are each $C_{1-14}$ alkyl; $R^4$ is

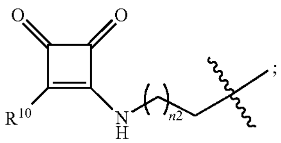

$R^{10}NH(C_{1-6}$ alkyl); n2 is 2; $R^5$ is H; each $R^6$ is H; M and M' are each —C(O)O—; R' is a $C_{1-12}$ alkyl; l is 5; and m is 7.

In some embodiments of the compounds of Formula (AI), $R'^{a}$ is $R'^{branched}$; $R'^{branched}$ is

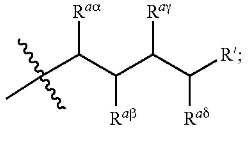 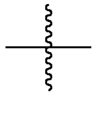

denotes a point of attachment; $R^{a\alpha}$, $R^{a\beta}$, and $R^{a\delta}$ are each H; $R^{a\gamma}$ is $C_{2-12}$ alkyl; $R^2$ and $R^3$ are each $C_{1-14}$ alkyl; $R^4$ is —$(CH_2)_nOH$; n is 2; each $R^5$ is H; each $R^6$ is H; M and M' are each —C(O)O—; R' is a $C_{1-12}$ alkyl; l is 5; and m is 7.

In some embodiments, the compound of Formula (AI) is selected from:

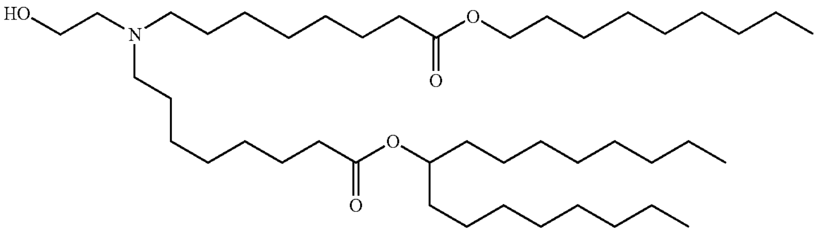
,
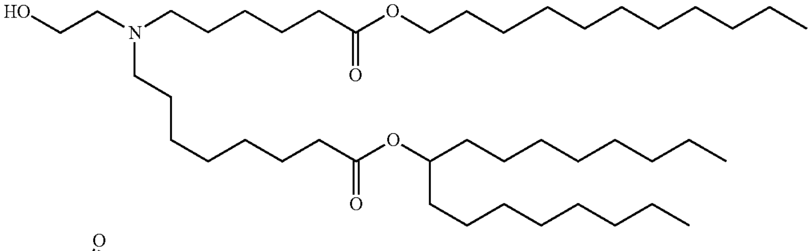
,
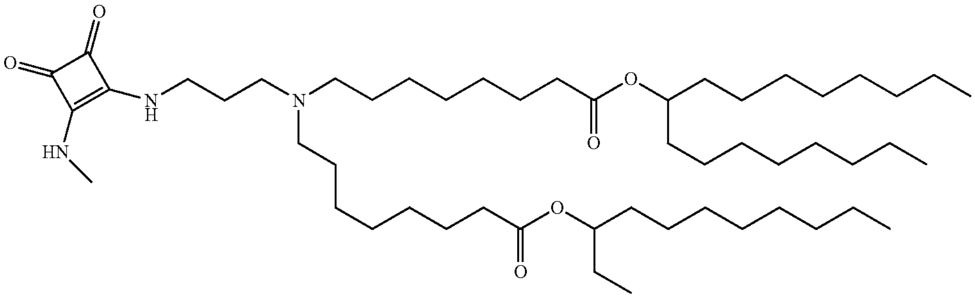
, and
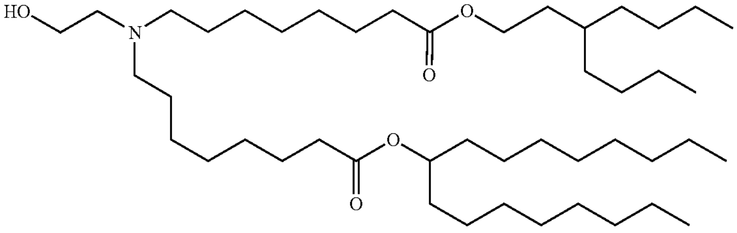
.

In some embodiments, the ionizable amino lipid of Formula (AI) is a compound of Formula (AIa):

(AIa)

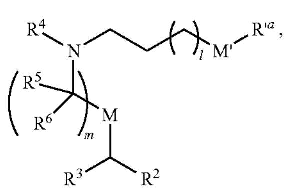

or its N-oxide, or a salt or isomer thereof, wherein $R'^{a}$ is $R'^{branched}$, wherein $R'^{branched}$ is:

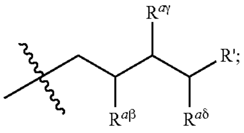

wherein

denotes a point of attachment;

wherein $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $-(CH_2)_nOH$ wherein n is selected from the group consisting of 1, 2, 3, 4, and 5, and

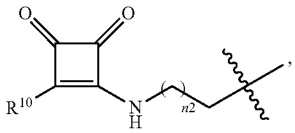
, wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some embodiments, the ionizable amino lipid of Formula (AI) is a compound of Formula (AIb):

(AIb)

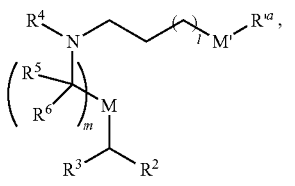

or its N-oxide, or a salt or isomer thereof, wherein $R'^{a}$ is $R'^{branched}$, wherein $R'^{branched}$ is:

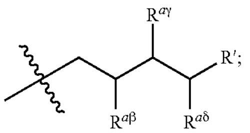

wherein

denotes a point of attachment;

wherein $R^{a\alpha}$, $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is $—(CH_2)_nOH$, wherein n is selected from the group consisting of 1, 2, 3, 4, and 5;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some embodiments of Formula (AI) or (AIb), $R'^{a}$ is $R'^{branched}$; $R'^{branched}$ is

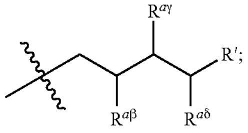 

denotes a point of attachment; $R^{a\beta}$, $R^{a\gamma}$, and $R^{a\delta}$ are each H; $R^2$ and $R^3$ are each $C_{1-14}$ alkyl; $R^4$ is $—(CH_2)_nOH$; n is 2; each $R^5$ is H; each $R^6$ is H; M and M' are each —C(O)O—; R' is a $C_{1-12}$ alkyl; l is 5; and m is 7.

In some embodiments of Formula (AI) or (AIb), $R'^{a}$ is $R'^{branched}$; $R'^{branched}$ is

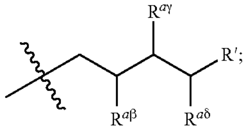 

denotes a point of attachment; $R^{a\beta}$, $R^{a\gamma}$, and $R^{a\delta}$ are each H; $R^2$ and $R^3$ are each $C_{1-14}$ alkyl; $R^4$ is $—(CH_2)_nOH$; n is 2; each $R^5$ is H; each $R^6$ is H; M and M' are each —C(O)O—; R' is a $C_{1-12}$ alkyl; l is 3; and m is 7.

In some embodiments of Formula (AI) or (AIb), $R'^{a}$ is $R'^{branched}$; $R'^{branched}$ is

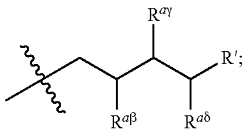 

denotes a point of attachment; $R^{a\beta}$ and $R^{a\delta}$ are each H; $R^{a\gamma}$ is $C_{2-12}$ alkyl; $R^2$ and $R^3$ are each $C_{1-14}$ alkyl; $R^4$ is $—(CH_2)_nOH$; n is 2; each $R^5$ is H; each $R^6$ is H; M and M' are each —C(O)O—; R' is a $C_{1-12}$ alkyl; l is 5; and m is 7.

In some embodiments, the ionizable amino lipid of Formula (AI) is a compound of Formula (AIc):

(AIc)

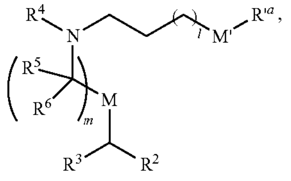

or its N-oxide, or a salt or isomer thereof, wherein $R'^{a}$ is $R'^{branched}$, wherein $R'^{branched}$ is:

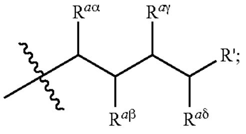

wherein

denotes a point of attachment;

wherein $R^{a\alpha}$, $R^{a\beta}$, $R^{a\gamma}$, and $R^{a\delta}$ are each independently selected from the group consisting of H, $C_{2-12}$ alkyl, and $C_{2-12}$ alkenyl;

$R^2$ and $R^3$ are each independently selected from the group consisting of $C_{1-14}$ alkyl and $C_{2-14}$ alkenyl;

$R^4$ is

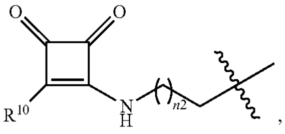

, wherein

denotes a point of attachment; wherein $R^{10}$ is $N(R)_2$; each R is independently selected from the group consisting of $C_{1-6}$ alkyl, $C_{2-3}$ alkenyl, and H; n2 is selected from the group consisting of 1, 2, 3, 4, 5, 6, 7, 8, 9, and 10;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are each independently selected from the group consisting of —C(O)O— and —OC(O)—;

R' is a $C_{1-12}$ alkyl or $C_{2-12}$ alkenyl;

l is selected from the group consisting of 1, 2, 3, 4, and 5; and m is selected from the group consisting of 5, 6, 7, 8, 9, 10, 11, 12, and 13.

In some embodiments, $R'^{a}$ is $R'^{branched}$, $R'^{branched}$ is

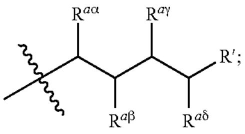

;

denotes a point of attachment; $R^{a\beta}$, $R^{a\gamma}$, and $R^{a\delta}$ are each H; $R^{a\delta}$ is $C_{2-12}$ alkyl; $R^2$ and $R^3$ are each $C_{1-14}$ alkyl; $R^4$ is

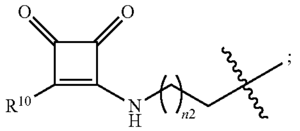

;

denotes a point of attachment; $R^{10}$ is $NH(C_{1-6}$ alkyl); n2 is 2; each $R^5$ is H; each $R^6$ is H; M and M' are each —C(O)O—; R' is a $C_{1-12}$ alkyl; l is 5; and m is 7.

In some embodiments, the compound of Formula (AIc) is:

Formula (AII)

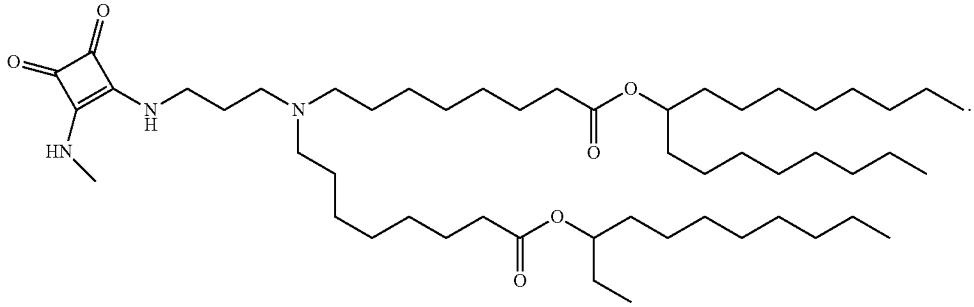

.

In some embodiments, the ionizable amino lipid is a compound of Formula (AII):

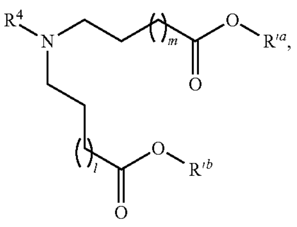

(AII)

or its N-oxide, or a salt or isomer thereof, wherein $R'^{a}$ is $R'^{branched}$ or R' cyclic, wherein $R'^{branched}$ is:

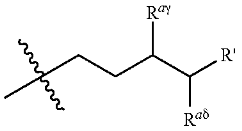

and R' cyclic is:

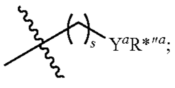

and $R'^{b}$ is:

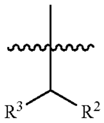

or

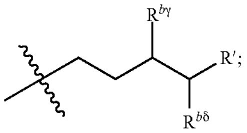

wherein

denotes a point of attachment;

$R^{a\gamma}$ and $R^{a\delta}$ are each independently selected from the group consisting of H, $C_{1-12}$ alkyl, and $C_{2-12}$ alkenyl, wherein at least one of $R^{a\gamma}$ and $R^{a\delta}$ is selected from the group consisting of $C_{1-12}$ alkyl and $C_{2-12}$ alkenyl;

$R^{b\gamma}$ and $R^{b\delta}$ are each independently selected from the group consisting of H, $C_{1-12}$ alkyl, and $C_{2-12}$ alkenyl, wherein at least one of $R^{b\gamma}$ and $R^{b\delta}$ is selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $—(CH_2)_nOH$ wherein n is selected from the group consisting of 1, 2, 3, 4, and 5, and

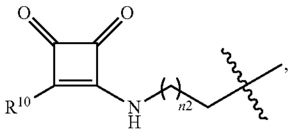

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-12}$ alkyl or $C_{2-12}$ alkenyl;

$Y^a$ is a $C_{3-6}$ carbocycle;

$R^{*\prime\prime a}$ is selected from the group consisting of $C_{1-15}$ alkyl and $C_{2-15}$ alkenyl; and s is 2 or 3;

m is selected from 1, 2, 3, 4, 5, 6, 7, 8, and 9;

l is selected from 1, 2, 3, 4, 5, 6, 7, 8, and 9.

In some embodiments, the ionizable amino lipid of Formula (AII) is a compound of Formula (AII-a):

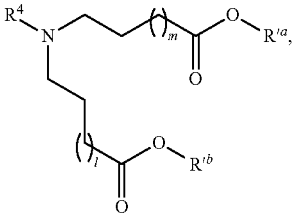

(AII-a)

or its N-oxide, or a salt or isomer thereof, wherein $R'^{a}$ is $R'^{branched}$ or R' cyclic, wherein $R'^{branched}$ is:

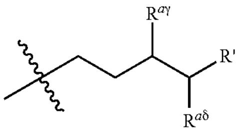

and $R'^{b}$ is:

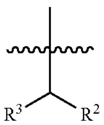

or

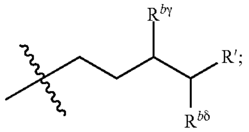

wherein

denotes a point of attachment;

$R^{a\gamma}$ and $R^{a\delta}$ are each independently selected from the group consisting of H, $C_{1-12}$ alkyl, and $C_{2-12}$ alkenyl, wherein at least one of $R^{a\gamma}$ and $R^{a\delta}$ is selected from the group consisting of $C_{1-12}$ alkyl and $C_{2-12}$ alkenyl;

$R^{b\gamma}$ and $R^{b\delta}$ are each independently selected from the group consisting of H, $C_{1-12}$ alkyl, and $C_{2-12}$ alkenyl, wherein at least one of $R^{b\gamma}$ and $R^{b\delta}$ is selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $—(CH_2)_nOH$ wherein n is selected from the group consisting of 1, 2, 3, 4, and 5, and

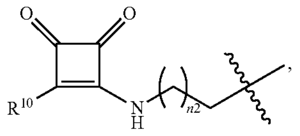

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some embodiments, the ionizable amino lipid of Formula (AII) is a compound of Formula (AII-b):

(AII-b)

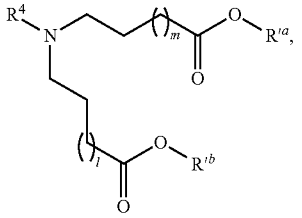

or its N-oxide, or a salt or isomer thereof, wherein $R'^{a}$ is $R'^{branched}$ or $R'^{cyclic}$; wherein $R'^{branched}$ is:

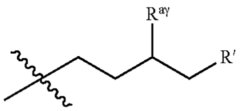

and $R'^{b}$ is:

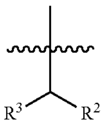

or

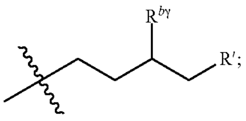

wherein

denotes a point of attachment;

$R^{a\gamma}$ and $R^{b\gamma}$ are each independently selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $-(CH_2)_nOH$ wherein n is selected from the group consisting of 1, 2, 3, 4, and 5, and

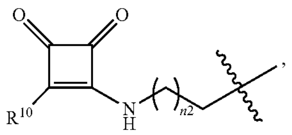

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some embodiments, the ionizable amino lipid of Formula (AII) is a compound of Formula (AII-c):

(AII-c)

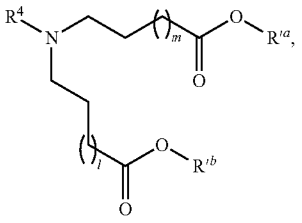

or its N-oxide, or a salt or isomer thereof, wherein $R'^{a}$ is $R'^{branched}$ or $R'^{cyclic}$; wherein $R'^{branched}$ is:

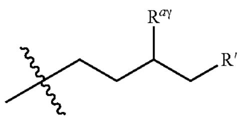

and $R'^{b}$ is:

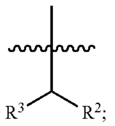

wherein

denotes a point of attachment;

wherein $R^{a\gamma}$ is selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is selected from the group consisting of $-(CH_2)_nOH$ wherein n is selected from the group consisting of 1, 2, 3, 4, and 5, and

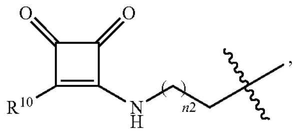

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

R' is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some embodiments, the ionizable amino lipid of Formula (AII) is a compound of Formula (AII-d):

(AII-d)

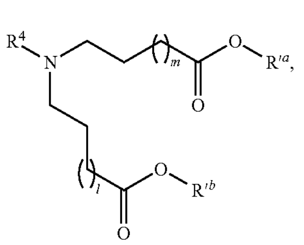

or its N-oxide, or a salt or isomer thereof, wherein $R'^{a}$ is $R'^{branched}$ or $R'^{cyclic}$; wherein $R'^{branched}$ is:

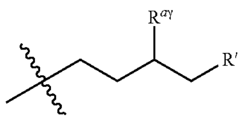

and $R'^{b}$ is:

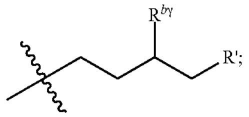

wherein

denotes a point of attachment;

wherein $R^{a\gamma}$ and $R^{b\gamma}$ are each independently selected from the group consisting of $C_{1-12}$ alkyl and $C_{2-12}$ alkenyl;

$R^4$ is selected from the group consisting of $-(CH_2)_nOH$ wherein n is selected from the group consisting of 1, 2, 3, 4, and 5, and

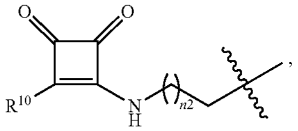

wherein

denotes a point of attachment; wherein $R^{10}$ is $N(R)_2$; each R is independently selected from the group consisting of $C_{1-6}$ alkyl, $C_{2-3}$ alkenyl, and H; and n2 is selected from the group consisting of 1, 2, 3, 4, 5, 6, 7, 8, 9, and 10;

each R' independently is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some embodiments, the ionizable amino lipid of Formula (AII) is a compound of Formula (AII-e):

(AII-e)

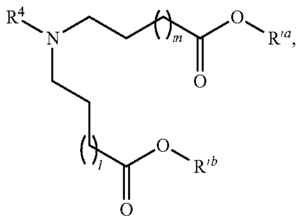

or its N-oxide, or a salt or isomer thereof, wherein $R'^{a}$ is $R'^{branched}$ or $R'^{cyclic}$; wherein $R'^{branched}$ is:

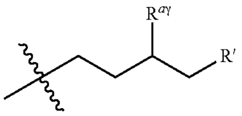

and $R'^{b}$ is:

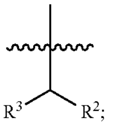

wherein

denotes a point of attachment;

wherein $R^{a\gamma}$ is selected from the group consisting of $C_{1-12}$ alkyl and $C_{2-12}$ alkenyl;

$R^2$ and $R^3$ are each independently selected from the group consisting of $C_{1-14}$ alkyl and $C_{2-14}$ alkenyl;

$R^4$ is $-(CH_2)_nOH$ wherein n is selected from the group consisting of 1, 2, 3, 4, and 5;

R' is a $C_{1-12}$ alkyl or $C_{2-12}$ alkenyl;

m is selected from 1, 2, 3, 4, 5, 6, 7, 8, and 9;

l is selected from 1, 2, 3, 4, 5, 6, 7, 8, and 9.

In some embodiments of the compound of Formula (AII), (AII-a), (AII-b), (AII-c), (AII-d), or (AII-e), m and l are each independently selected from 4, 5, and 6. In some embodiments of the compound of Formula (AII), (AII-a), (AII-b), (AII-c), (AII-d), or (AII-e), m and l are each 5.

In some embodiments of the compound of Formula (AII), (AII-a), (AII-b), (AII-c), (AII-d), or (AII-e), each R' independently is a $C_{1-12}$ alkyl. In some embodiments of the compound of Formula (AII), (AII-a), (AII-b), (AII-c), (AII-d), or (AII-e), each R' independently is a $C_{2-5}$ alkyl.

In some embodiments of the compound of Formula (AII), (AII-a), (AII-b), (AII-c), (AII-d), or (AII-e), $R'^{b}$ is:

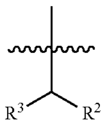

and $R^2$ and $R^3$ are each independently a $C_{1-14}$ alkyl. In some embodiments of the compound of Formula (AII), (AII-a), (AII-b), (AII-c), (AII-d), or (AII-e), $R'^{b}$ is:

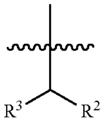

and $R^2$ and $R^3$ are each independently a $C_{6-10}$ alkyl. In some embodiments of the compound of Formula (AII), (AII-a), (AII-b), (AII-c), (AII-d), or (AII-e), $R'^{b}$ is:

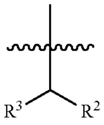

and $R^2$ and $R^3$ are each a $C_8$ alkyl.

In some embodiments of the compound of Formula (AII), (AII-a), (AII-b), (AII-c), (AII-d), or (AII-e), $R'^{branched}$ is:

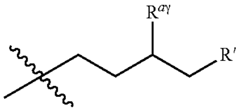

and $R'^{b}$ is:

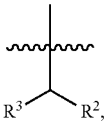

$R^{a\gamma}$ is a $C_{1-12}$ alkyl and $R^2$ and $R^3$ are each independently a $C_{6-10}$ alkyl. In some embodiments of the compound of Formula (AII), (AII-a), (AII-b), (AII-c), (AII-d), or (AII-e), $R'^{branched}$ is:

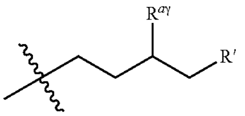

and $R'^{b}$ is:

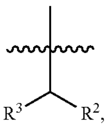

$R^{a\gamma}$ is a $C_{2-6}$ alkyl and $R^2$ and $R^3$ are each independently a $C_{6-10}$ alkyl.

In some embodiments of the compound of Formula (AII), (AII-a), (AII-b), (AII-c), (AII-d), or (AII-e), $R'^{branched}$ is:

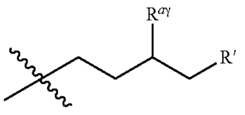

and $R'^{b}$ is:

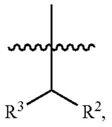

$R^{a\gamma}$ is a $C_{2-6}$ alkyl, and $R^2$ and $R^3$ are each a $C_8$ alkyl.

In some embodiments of the compound of Formula (AII), (AII-a), (AII-b), (AII-c), (AII-d), or (AII-e), $R'^{branched}$ is:

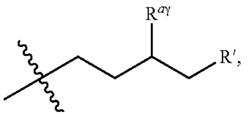

$R'^{b}$ is:

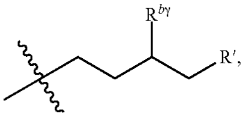

and $R^{a\gamma}$ and $R^{b\gamma}$ are each a $C_{1-12}$ alkyl. In some embodiments of the compound of Formula (AII), (AII-a), (AII-b), (AII-c), (AII-d), or (AII-e), $R'^{branched}$ is:

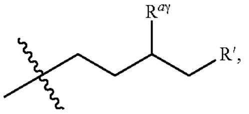

$R'^{b}$ is:

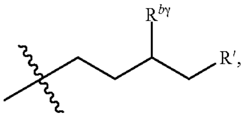

and $R^{a\gamma}$ and $R^{b\gamma}$ are each a $C_{2-6}$ alkyl.

In some embodiments of the compound of Formula (AII), (AII-a), (AII-b), (AII-c), (AII-d), or (AII-e), m and l are each independently selected from 4, 5, and 6 and each R' independently is a $C_{1-12}$ alkyl. In some embodiments of the compound of Formula (AII), (AII-a), (AII-b), (AII-c), (AII-d), or (AII-e), m and l are each 5 and each R' independently is a $C_{2-5}$ alkyl.

In some embodiments of the compound of (AII), (AII-a), (AII-b), (AII-c), (AII-d), or (AII-e), $R'^{branched}$ is:

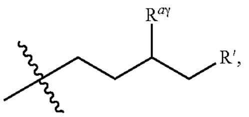

$R'^{b}$ is:

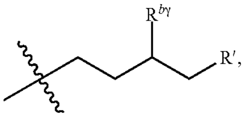

m and l are each independently selected from 4, 5, and 6, each R' independently is a $C_{1-12}$ alkyl, and $R^{a\gamma}$ and $R^{b\gamma}$ are each a $C_{1-12}$ alkyl. In some embodiments of the compound of Formula (AII), (AII-a), (AII-b), (AII-c), (AII-d), or (AII-e), $R'^{branched}$ is:

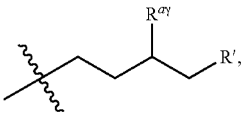

$R'^{b}$ is:

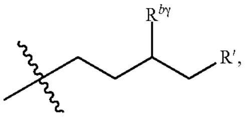

m and l are each 5, each R' independently is a $C_{2-5}$ alkyl, and $R^{a\gamma}$ and $R^{b\gamma}$ are each a $C_{2-6}$ alkyl.

In some embodiments of the compound of Formula (AII), (AII-a), (AII-b), (AII-c), (AII-d), or (AII-e), $R'^{branched}$ is:

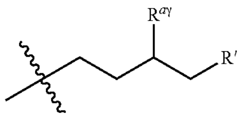

and $R'^{b}$ is:

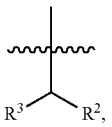

m and l are each independently selected from 4, 5, and 6, R' is a $C_{1-12}$ alkyl, $R^{a\gamma}$ is a $C_{1-12}$ alkyl and $R^2$ and $R^3$ are each independently a $C_{6-10}$ alkyl.

In some embodiments of the compound of Formula (AII), (AII-a), (AII-b), (AII-c), (AII-d), or (AII-e), $R'^{branched}$ is:

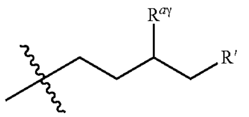

and $R'^{b}$ is:

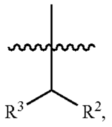

m and l are each 5, R' is a $C_{2-5}$ alkyl, $R^{a\gamma}$ is a $C_{2-6}$ alkyl, and $R^2$ and $R^3$ are each a $C_8$ alkyl.

In some embodiments of the compound of (AII), (AII-a), (AII-b), (AII-c), (AII-d), or (AII-e), $R^4$ is

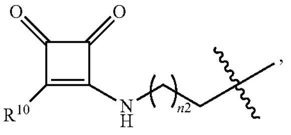

wherein $R^{10}$ is NH($C_{1-6}$ alkyl) and n2 is 2. In some embodiments of the compound of Formula (AII), (AII-a), (AII-b), (AII-c), (AII-d), or (AII-e), $R^4$ is

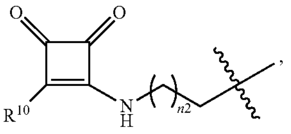

wherein $R^{10}$ is NH($CH_3$) and n2 is 2.

In some embodiments of the compound of Formula (AII), (AII-a), (AII-b), (AII-c), (AII-d), or (AII-e), $R'^{branched}$ is:

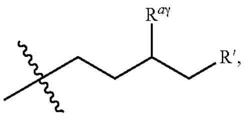

$R'^{b}$ is:

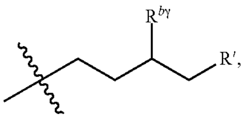

m and l are each independently selected from 4, 5, and 6, each R' independently is a $C_{1-12}$ alkyl, $R^{a\gamma}$ and $R^{b\gamma}$ are each a $C_{1-12}$ alkyl, and $R^4$ is

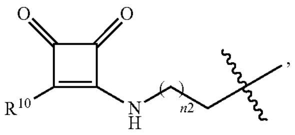

wherein $R^{10}$ is NH($C_{1-6}$ alkyl), and n2 is 2. In some embodiments of the compound of Formula (AII), (AII-a), (AII-b), (AII-c), (AII-d), or (AII-e), $R'^{branched}$ is:

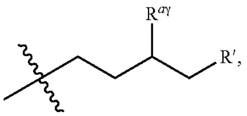

$R'^{b}$ is:

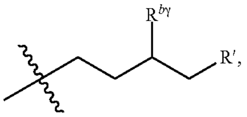

m and l are each 5, each R' independently is a $C_{2-5}$ alkyl, $R^{a\gamma}$ and $R^{b\gamma}$ are each a $C_{2-6}$ alkyl, and $R^4$ is

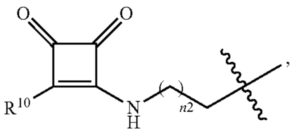

wherein $R^{10}$ is NH($CH_3$) and n2 is 2.

In some embodiments of the compound of Formula (AII), (AII-a), (AII-b), (AII-c), (AII-d), or (AII-e), $R'^{branched}$ is:

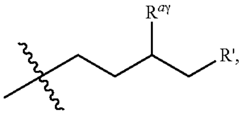

and $R'^{b}$ is:

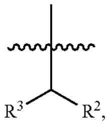

m and l are each independently selected from 4, 5, and 6, R' is a $C_{1-12}$ alkyl, $R^2$ and $R^3$ are each independently a $C_{6-10}$ alkyl, $R^{a\gamma}$ is a $C_{1-12}$ alkyl, and $R^4$ is

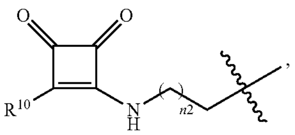

wherein $R^{10}$ is NH($C_{1-6}$ alkyl) and n2 is 2. In some embodiments of the compound of Formula (AII), (AII-a), (AII-b), (AII-c), (AII-d), or (AII-e), $R'^{branched}$ is:

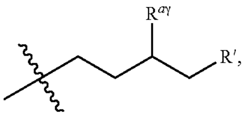

and $R'^b$ is:

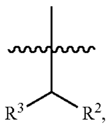

m and l are each 5, R' is a $C_{2-5}$ alkyl, $R^{a\gamma}$ is a $C_{2-6}$ alkyl, $R^2$ and $R^3$ are each a $C_8$ alkyl, and $R^4$ is

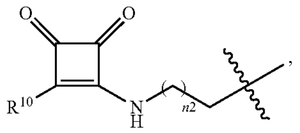

wherein $R^{10}$ is $NH(CH_3)$ and n2 is 2.

In some embodiments of the compound of Formula (AII), (AII-a), (AII-b), (AII-c), (AII-d), or (AII-e), $R^4$ is $-(CH_2)_nOH$ and n is 2, 3, or 4. In some embodiments of the compound of Formula (AII), (AII-a), (AII-b), (AII-c), (AII-d), or (AII-e), $R^4$ is $-(CH_2)_nOH$ and n is 2.

In some embodiments of the compound of Formula (AII), (AII-a), (AII-b), (AII-c), (AII-d), or (AII-e), $R'^{branched}$ is:

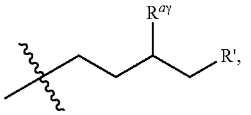

$R'^b$ is:

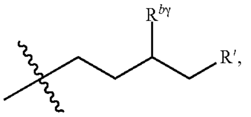

m and l are each independently selected from 4, 5, and 6, each R' independently is a $C_{1-12}$ alkyl, $R^{a\gamma}$ and $R^{b\gamma}$ are each a $C_{1-12}$ alkyl, $R^4$ is $-(CH_2)_nOH$, and n is 2, 3, or 4. In some embodiments of the compound of Formula (AII), (AII-a), (AII-b), (AII-c), (AII-d), or (AII-e), $R'^{branched}$ is:

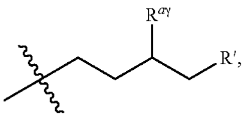

$R'^b$ is:

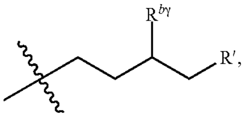

m and l are each 5, each R' independently is a $C_{2-5}$ alkyl, $R^{a\gamma}$ and $R^{b\gamma}$ are each a $C_{2-6}$ alkyl, $R^4$ is $-(CH_2)_nOH$, and n is 2.

In some embodiments, the ionizable amino lipid of Formula (AII) is a compound of Formula (AII-f):

(AII-f)

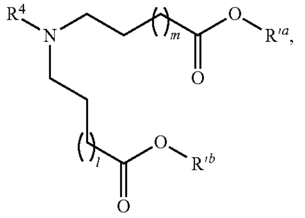

or its N-oxide, or a salt or isomer thereof, wherein $R'^a$ is $R'^{branched}$ or $R'^{cyclic}$; wherein $R'^{branched}$ is:

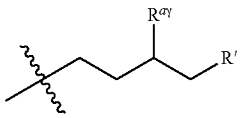

and $R'^b$ is:

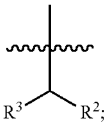

wherein

denotes a point of attachment;

$R^{a\gamma}$ is a $C_{1-12}$ alkyl;

$R^2$ and $R^3$ are each independently a $C_{1-14}$ alkyl;

$R^4$ is $-(CH_2)_nOH$ wherein n is selected from the group consisting of 1, 2, 3, 4, and 5;

R' is a $C_{1-12}$ alkyl;

m is selected from 4, 5, and 6; and l is selected from 4, 5, and 6.

In some embodiments of the compound of Formula (AII-f), m and l are each 5, and n is 2, 3, or 4.

In some embodiments of the compound of Formula (AII-f) R' is a $C_{2-5}$ alkyl, $R^{a\gamma}$ is a $C_{2-6}$ alkyl, and $R^2$ and $R^3$ are each a $C_{6-10}$ alkyl.

In some embodiments of the compound of Formula (AII-f), m and l are each 5, n is 2, 3, or 4, R' is a $C_{2-5}$ alkyl, $R^{a\gamma}$ is a $C_{2-6}$ alkyl, and $R^2$ and $R^3$ are each a $C_{6-10}$ alkyl.

In some embodiments, the ionizable amino lipid of Formula (AII) is a compound of Formula (AII-g):

(AII-g)

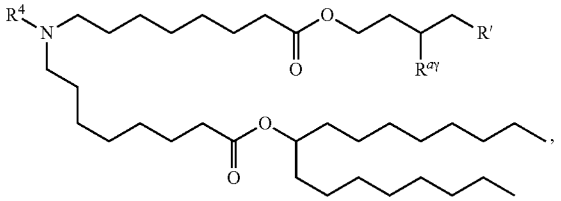

or its N-oxide, or a salt or isomer thereof; wherein $R^{a\gamma}$ is a $C_{2-6}$ alkyl;

R' is a $C_{2-5}$ alkyl; and $R^4$ is selected from the group consisting of $-(CH_2)_nOH$ wherein n is selected from the group consisting of 3, 4, and 5, and

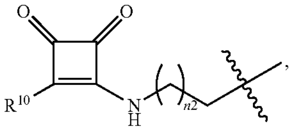

wherein

denotes a point of attachment, $R^{10}$ is $NH(C_{1-6}$ alkyl), and n2 is selected from the group consisting of 1, 2, and 3.

In some embodiments, the ionizable amino lipid of Formula (AII) is a compound of Formula (AII-h):

(AII-h)

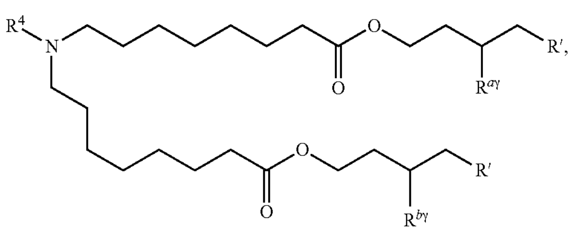

or its N-oxide, or a salt or isomer thereof; wherein $R^{a\gamma}$ and $R^{b\gamma}$ are each independently a $C_{2-6}$ alkyl;

each R' independently is a $C_{2-5}$ alkyl; and $R^4$ is selected from the group consisting of $-(CH_2)_nOH$ wherein n is selected from the group consisting of 3, 4, and 5, and

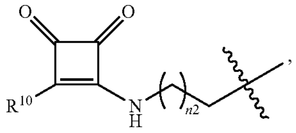

wherein

denotes a point of attachment, $R^{10}$ is $NH(C_{1-6}$ alkyl), and n2 is selected from the group consisting of 1, 2, and 3.

In some embodiments of the compound of Formula (AII-g) or (AII-h), $R^4$ is

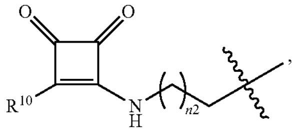

wherein $R^{10}$ is $NH(CH_3)$ and n2 is 2.

In some embodiments of the compound of Formula (AII-g) or (AII-h), $R^4$ is $-(CH_2)_2OH$.

Formula (AIII)

In some embodiments, the ionizable amino lipids of a lipid nanoparticle may be one or more of compounds of Formula (AIII):

(AIII)

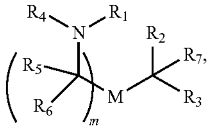

or their N-oxides, or salts or isomers thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of hydrogen, a $C_{3-6}$ carbocycle, $-(CH_2)_nQ$, $-(CH_2)_nCHQR$, —CHQR, $-CQ(R)_2$, and unsubstituted $C_{1-6}$ alkyl, where Q is selected from a carbocycle, heterocycle, —OR, $-O(CH_2)_nN(R)_2$, —C(O)OR, —OC(O)R, $-CX_3$, $-CX_2H$, $-CXH_2$, —CN, $-N(R)_2$, $-C(O)N(R)_2$, —N(R)C(O)R, $-N(R)S(O)_2R$, $-N(R)C(O)N(R)_2$, $-N(R)C(S)N(R)_2$, $-N(R)R_8$, $-N(R)S(O)_2R_8$, $-O(CH_2)_nOR$, $-N(R)C(=NR_9)N(R)_2$, $-N(R)C(=CHR_9)N(R)_2$, $-OC(O)N(R)_2$, —N(R)C(O)OR, —N(OR)C(O)R, $-N(OR)S(O)_2R$, —N(OR)C(O)OR, $-N(OR)C(O)N(R)_2$, $-N(OR)C(S)N(R)_2$, $-N(OR)C(=NR_9)N(R)_2$, $-N(OR)C(=CHR_9)N(R)_2$, $-C(=NR_9)N(R)_2$, $-C(=NR_9)R$, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —OC(O)-M"-C(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group, in which M" is a bond, $C_{1-13}$ alkyl or $C_{2-13}$ alkenyl;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and wherein when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

In some embodiments, another subset of compounds of Formula (AIII) includes those in which:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(═NR$_9$)N(R)$_2$, —N(R)C(═CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(═NR$_9$)N(R)$_2$, —N(OR)C(═CHR$_9$)N(R)$_2$, —C(═NR$_9$)N(R)$_2$, —C(═NR$_9$)R, —C(O)N(R)OR, and a 5- to 14-membered heterocycloalkyl having one or more heteroatoms selected from N, O, and S which is substituted with one or more substituents selected from oxo (═O), OH, amino, mono- or di-alkylamino, and $C_{1-3}$ alkyl, and each n is independently selected from 1, 2, 3, 4, and 5;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (AIII) includes those in which:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(═NR$_9$)N(R)$_2$, —N(R)C(═CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(═NR$_9$)N(R)$_2$, —N(OR)C(—CHR$_9$)N(R)$_2$, —C(═NR$_9$)R, —C(O)N(R)OR, and —C(═NR$_9$)N(R)$_2$, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (AIII) includes those in which:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —$N(R)C({=}NR_9)N(R)_2$, —$N(R)C({=}CHR_9)N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C({=}NR_9)N(R)_2$, —$N(OR)C({=}CHR_9)N(R)_2$, —$C({=}NR_9)R$, —C(O)N(R)OR, and —$C({=}NR_9)N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (AIII) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)_nCHQR$, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (AIII) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_nQ$, —$(CH_2)_nCHQR$, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In certain embodiments, a subset of compounds of Formula (AIII) includes those of Formula (AIII-A):

(AIII-A)

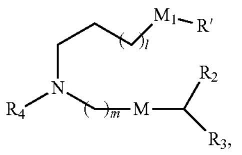

or its N-oxide, or a salt or isomer thereof, wherein l is selected from 1, 2, 3, 4, and 5; m is selected from 5, 6, 7, 8, and 9; $M_1$ is a bond or M'; $R_4$ is hydrogen, unsubstituted $C_{1-3}$ alkyl, or $—(CH_2)_nQ$, in which Q is —OH, $—NHC(S)N(R)_2$, $—NHC(O)N(R)_2$, —N(R)C(O)R, $—N(R)S(O)_2R$, $—N(R)R_8$, $—NHC(=NR_9)N(R)_2$, $—NHC(=CHR_9)N(R)_2$, $—OC(O)N(R)_2$, —N(R)C(O)OR, heteroaryl or heterocycloalkyl;

M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

For example, m is 5, 7, or 9. For example, Q is OH, $—NHC(S)N(R)_2$, or $—NHC(O)N(R)_2$. For example, Q is —N(R)C(O)R, or $—N(R)S(O)_2R$.

In certain embodiments, a subset of compounds of Formula (AIII) includes those of Formula (AIII-B):

(AIII-B)

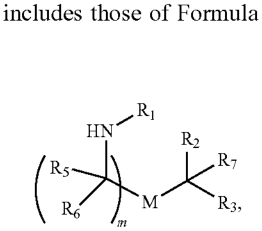

or its N-oxide, or a salt or isomer thereof in which all variables are as defined herein. For example, m is selected from 5, 6, 7, 8, and 9; $R^4$ is hydrogen, unsubstituted $C_{1-3}$ alkyl, or $—(CH_2)_nQ$, in which Q is H, $—NHC(S)N(R)_2$, $—NHC(O)N(R)_2$, —N(R)C(O)R, $—N(R)S(O)_2R$, $—N(R)R_8$, $—NHC(=NR_9)N(R)_2$, $—NHC(=CHR_9)N(R)_2$, $—OC(O)N(R)_2$, —N(R)C(O)OR, heteroaryl or heterocycloalkyl;

M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

For example, m is 5, 7, or 9. For example, Q is OH, $—NHC(S)N(R)_2$, or $—NHC(O)N(R)_2$. For example, Q is —N(R)C(O)R, or $—N(R)S(O)_2R$.

In certain embodiments, a subset of compounds of Formula (AIII) includes those of Formula (AIII-C):

(AIII-C)

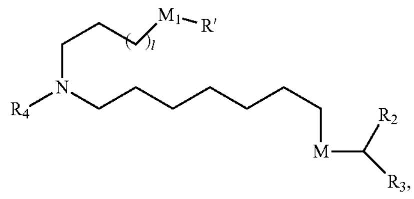

or its N-oxide, or a salt or isomer thereof, wherein l is selected from 1, 2, 3, 4, and 5; $M_1$ is a bond or M'; $R_4$ is hydrogen, unsubstituted $C_{1-3}$ alkyl, or $—(CH_2)_nQ$, in which n is 2, 3, or 4, and Q is OH, $—NHC(S)N(R)_2$, $—NHC(O)N(R)_2$, —N(R)C(O)R, $—N(R)S(O)_2R$, $—N(R)R_8$, $—NHC(=NR_9)N(R)_2$, $—NHC(=CHR_9)N(R)_2$, $—OC(O)N(R)_2$, —N(R)C(O)OR, heteroaryl or heterocycloalkyl;

M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, the compounds of Formula (AIII) are of Formula (AIII-D), (AIII-D)

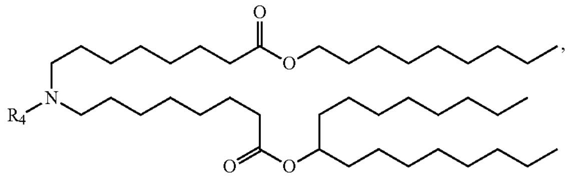

or their N-oxides, or salts or isomers thereof, wherein $R_4$ is as described in this Lipid Compositions section.

In another embodiment, the compounds of Formula (AIII) are of Formula (AIII-E), (AIII-E)

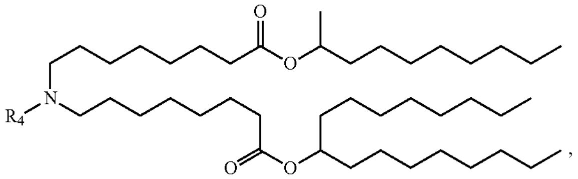

or their N-oxides, or salts or isomers thereof, wherein $R_4$ is as described in this in this Lipid Compositions section.

In another embodiment, the compounds of Formula (AIII) are of Formula (AIII-F) or (AIII-G):

(AIII-F)

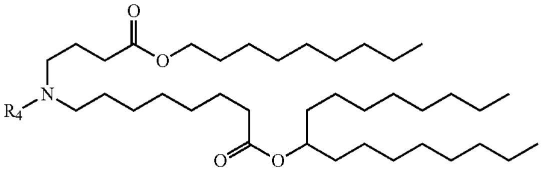

or (AIII-G)

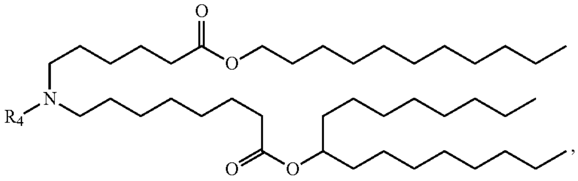

or their N-oxides, or salts or isomers thereof, wherein $R_4$ is as described in this in this Lipid Compositions section.

In another embodiment, the compounds of Formula (AIII) are of Formula (AIII-H):

(AIII-H)

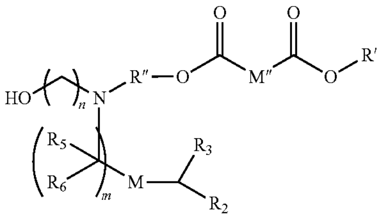

or their N-oxides, or salts or isomers thereof, wherein M is —C(O)O— or —OC(O)—, M" is $C_{1-6}$ alkyl or $C_{2-6}$ alkenyl, $R^2$ and $R^3$ are independently selected from the group consisting of $C_{5-14}$ alkyl and $C_{5-14}$ alkenyl, and n is selected from 2, 3, and 4.

In a further embodiment, the compounds of Formula (AIII) are of Formula (AIII-I):

(AIII-I)

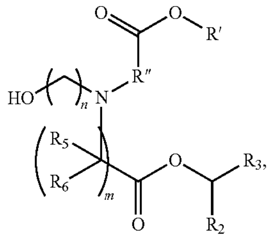

or their N-oxides, or salts or isomers thereof, wherein n is 2, 3, or 4; and m, R', R", and $R_2$ through $R_6$ are as described in this in this Lipid Compositions section. For example, each of $R_2$ and $R_3$ may be independently selected from the group consisting of $C_{5-14}$ alkyl and $C_{5-14}$ alkenyl.

In some embodiments, an ionizable amino lipid of comprises a compound having structure:

(Compound 1)

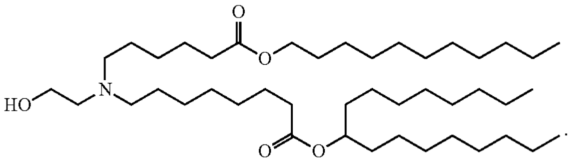

In some embodiments, an ionizable amino lipid comprises a compound having structure:

(Compound 2)

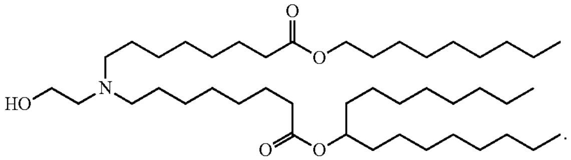

In a further embodiment, the compounds of Formula (AIII) are of Formula (AIII-J), (AIII-J)

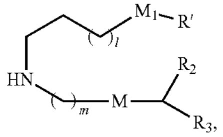

or their N-oxides, or salts or isomers thereof, wherein l is selected from 1, 2, 3, 4, and 5; m is selected from 5, 6, 7, 8, and 9; $M_1$ is a bond or M'; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, M" is $C_{1-6}$ alkyl (e.g., $C_{1-4}$ alkyl) or $C_{2-6}$ alkenyl (e.g. $C_{2-4}$ alkenyl). For example, $R_2$ and $R_3$ are independently selected from the group consisting of $C_{5-14}$ alkyl and $C_{5-14}$ alkenyl.

In some embodiments, the ionizable amino lipids are one or more of the compounds described in U.S. Application Nos. 62/220,091, 62/252,316, 62/253,433, 62/266,460, 62/333,557, 62/382,740, 62/393,940, 62/471,937, 62/471,949, 62/475,140, and 62/475,166, and PCT Application No. PCT/US2016/052352.

The central amine moiety of a lipid according to Formula (AIII), (AIII-A), (AIII-B), (AIII-C), (AIII-D), (AIII-E), (AIII-F), (AIII-G), (AIII-H), (AIII-I), or (AIII-J) may be protonated at a physiological pH. Thus, a lipid may have a positive or partial positive charge at physiological pH. Such amino lipids may be referred to as cationic lipids, ionizable lipids, cationic amino lipids, or ionizable amino lipids. Amino lipids may also be zwitterionic, i.e., neutral molecules having both a positive and a negative charge.

Formula (AIV)

In some embodiments, the ionizable amino lipids of a lipid nanoparticle may be one or more of compounds of formula (AIV), (AIV)

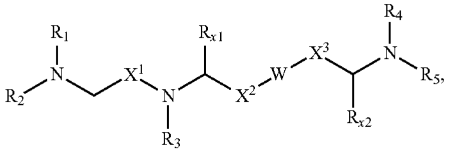

or salts or isomers thereof, wherein

W is

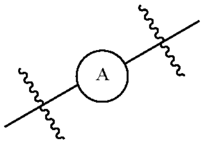

or

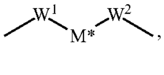, ring A is

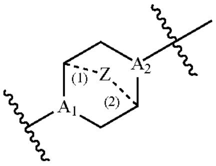

or

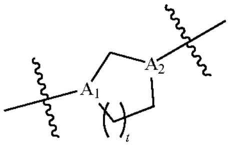

;

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

$R_{X1}$ and $R_{X2}$ are each independently H or $C_{1-3}$ alkyl;

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, $—S(O)_2—$, —C(O)S—, —SC(O)—, an aryl group, and a heteroaryl group;

M* is $C_1$-$C_6$ alkyl, $W^1$ and $W^2$ are each independently selected from the group consisting of —O— and $—N(R_6)—$;

each $R_6$ is independently selected from the group consisting of H and $C_{1-5}$ alkyl;

$X^1$, $X^2$, and $X^3$ are independently selected from the group consisting of a bond, $—CH_2—$, $—(CH_2)_2—$, —CHR—, —CHY—, —C(O)—, —C(O)O—, —OC(O)—, $—(CH_2)_n—C(O)—$, $—C(O)—(CH_2)_n—$, $—(CH_2)_n—C(O)O—$, $—OC(O)—(CH_2)_n—$, $—(CH_2)_n—OC(O)—$, $—C(O)O—(CH_2)_n—$, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H;

each R" is independently selected from the group consisting of $C_{3-12}$ alkyl, $C_{3-12}$ alkenyl and —R*MR'; and n is an integer from 1-6;

wherein when ring A is

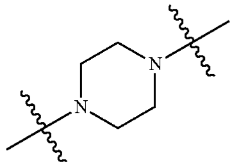, then i) at least one of $X^1$, $X^2$, and $X^3$ is not $—CH_2—$; and/or ii) at least one of $R_1$, $R_2$, $R_3$, $R_4$, and $R_5$ is —R"MR'.

In some embodiments, the compound is of any of formulae (AIVa)-(AIVh):

(AIVa)

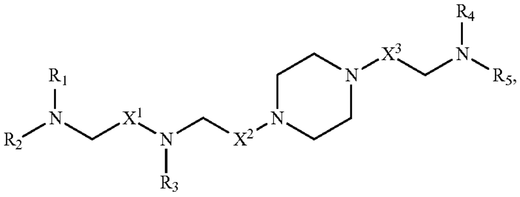

(AIVb)

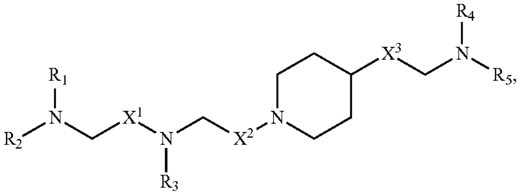

(AIVc)

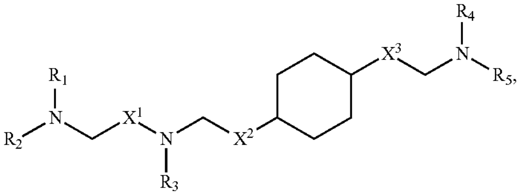

(AIVd)

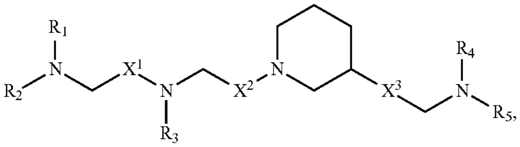

(AIVe)

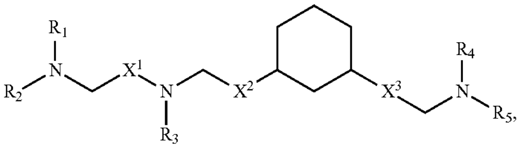

(AIVf)

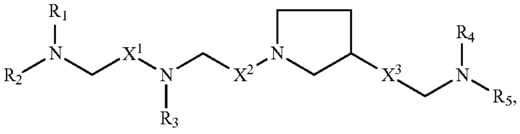

-continued (AIVg)

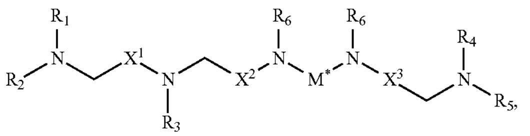

or (AIVh)

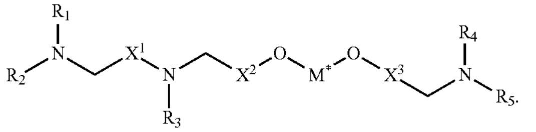

In some embodiments, the ionizable amino lipid is

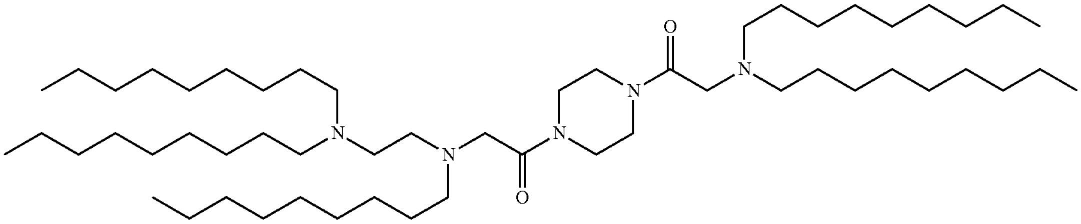

, or a salt thereof.

The central amine moiety of a lipid according to Formula (AIV), (AIVa), (AIVb), (AIVc), (AIVd), (AIVe), (AIVf), (AIVg), or (AIVh) may be protonated at a physiological pH. Thus, a lipid may have a positive or partial positive charge at physiological pH.

Formula (AV)

In some embodiments, the lipid nanoparticle comprises a lipid having the structure:

(AV)

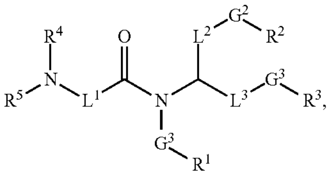

or a pharmaceutically acceptable salt, tautomer, or stereoisomer thereof, wherein:

$R^1$ is optionally substituted $C_1$-$C_{24}$ alkyl or optionally substituted $C_2$-$C_{24}$ alkenyl;

$R^2$ and $R^3$ are each independently optionally substituted $C_1$-$C_{36}$ alkyl;

$R^4$ and $R^5$ are each independently optionally substituted $C_1$-$C_6$ alkyl, or $R^4$ and $R^5$ join, along with the N to which they are attached, to form a heterocyclyl or heteroaryl;

$L^1$, $L^2$, and $L^3$ are each independently optionally substituted $C_1$-$C_{18}$ alkylene;

$G^1$ is a direct bond, $-(CH_2)_nO(C{=}O)-$, $-(CH_2)_n(C{=}O)O-$, or $-(C{=}O)-$;

$G^2$ and $G^3$ are each independently $-(C{=}O)O-$ or $-0(C{=}O)-$; and n is an integer greater than 0.

Formula (AVI)

In some embodiments, the lipid nanoparticle comprises a lipid having the structure:

(AVI)

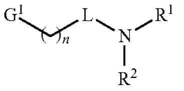

or a pharmaceutically acceptable salt, tautomer, or stereoisomer thereof, wherein:

$G^1$ is $-N(R^3)R^4$ or $-OR^5$;

$R^1$ is optionally substituted branched, saturated or unsaturated $C_{12}$-$C_{36}$ alkyl;

$R^2$ is optionally substituted branched or unbranched, saturated or unsaturated $C_{12}$-$C_{36}$ alkyl when L is $-C({=}O)-$; or $R^2$ is optionally substituted branched or unbranched, saturated or unsaturated $C_4$-$C_{36}$ alkyl when L is $C_6$-$C_{12}$ alkylene, $C_6$-$C_{12}$ alkenylene, or $C_2$-$C_6$ alkynylene;

$R^3$ and $R^4$ are each independently H, optionally substituted branched or unbranched, saturated or unsaturated $C_1$-$C_6$ alkyl; or $R^3$ and $R^4$ are each independently optionally substituted branched or unbranched, saturated or unsaturated $C_1$-$C_6$ alkyl when Lis $C_6$-$C_{12}$ alkylene, $C_6$-$C_{12}$ alkenylene, or $C_2$-$C_6$ alkynylene; or $R^3$ and $R^4$, together with the nitrogen to which they are attached, join to form a heterocyclyl;

$R^5$ is H or optionally substituted $C_1$-$C_6$ alkyl;

L is $-C({=}O)-$, $C_6$-$C_{12}$ alkylene, $C_6$-$C_{12}$ alkenylene, or $C_2$-$C_6$ alkynylene; and n is an integer from 1 to 12.

Formula (AVII)

In some embodiments, the lipid nanoparticle comprises a lipid having the structure:

(AVII)

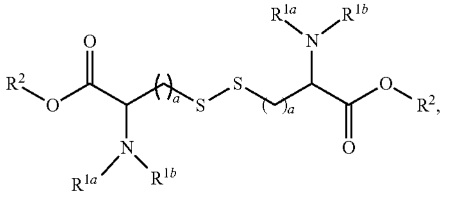

or a pharmaceutically acceptable salt thereof, wherein:

each $R^{1a}$ is independently hydrogen, $R^{1c}$, or $R^{1d}$, each $R^{1b}$ is independently $R^{1c}$ or $R^{1d}$, each $R^{1c}$ is independently $-[CH_2]_2C(O)X^1R^3$, each $R^{1d}$ Is independently $-C(O)R^4$;

each $R^2$ is independently $-[C(R^{2a})_2]_cR^{2b}$, each $R^{2a}$ is independently hydrogen or $C_1$-$C_6$ alkyl;

$R^{2b}$ is $-N(L_1\text{-}B)_2$; $-(OCH_2CH_2)_6OH$; or $-(OCH_2CH_2)_bOCH_3$;

each $R^3$ and $R^4$ is independently $C_6$-$C_{30}$ aliphatic;

each $L_3$ is independently $C_1$-$C_{10}$ alkylene;

each B is independently hydrogen or an ionizable nitrogen-containing group;

each $X^1$ is independently a covalent bond or O;

each a is independently an integer of 1-10;

each b is independently an integer of 1-10; and each c is independently an integer of 1-10.

Formula (AVIII)

In some embodiments, the lipid nanoparticle comprises a lipid having the structure:

(AVIII)

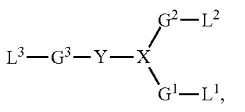

or a pharmaceutically acceptable salt, prodrug or stereoisomer thereof, wherein:

X is N, and Y is absent; or X is CR, and Y is NR;

$L^1$ is —O(C═O)$R^1$, —(C═O)O$R^1$, —C(═O)$R^1$, —O$R^1$, —S(O)$_x$$R^1$, —S—S$R^1$, —C(═O)S$R^1$, —SC(═O)$R^1$, —N$R^a$C(═O)$R^1$, —C(═O)N$R^b$$R^c$, —N$R^a$C(═O)N$R^b$$R^c$, —OC(═O)N$R^b$$R^c$, or —N$R^a$C(═O)O$R^1$;

$L^2$ is —O(C═O)$R^2$, —(C═O)O$R^2$, —C(═O)$R^2$, —O$R^2$, —S(O)$_x$$R^2$, —S—S$R^2$, —C(═O)S$R^2$, —SC(═O)$R^2$, —N$R^d$C(═O)$R^2$, —C(═O)N$R^e$$R^f$, —N$R^d$C(═O)N$R^e$$R^f$, —OC(═O)N$R^e$$R^f$; —N$R^d$C(═O)O$R^2$ or a direct bond to $R^2$;

$L^3$ is —O(C═O)$R^3$ or —(C═O)O$R^3$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_1$-$C_{24}$ heteroalkylene or $C_2$-$C_{24}$ heteroalkenylene when X is CR, and Y is NR; and $G^3$ is $C_1$-$C_{24}$ heteroalkylene or $C_2$-$C_{24}$ heteroalkenylene when X is N, and Y is absent;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

each R is independently H or $C_1$-$C_{12}$ alkyl;

$R^1$, $R^2$ and $R^3$ are each independently $C_1$-$C_{24}$ alkyl or $C_2$-$C_{24}$ alkenyl; and x is 0, 1 or 2, and wherein each alkyl, alkenyl, alkylene, alkenylene, heteroalkylene and heteroalkenylene is independently substituted or unsubstituted unless otherwise specified.

Formula (AIX)

In some embodiments, the lipid nanoparticle comprises a lipid having the structure:

(AIX)

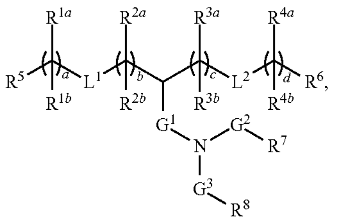

or a pharmaceutically acceptable salt, tautomer, prodrug or stereoisomer thereof, wherein:

$L^1$ and $L^2$ are each independently -0(C=0)0-, —(C=0)0-, —C(=0)-, -0-, —S(0)x-$_s$-S—S—, —C(=0)S—, —SC(=0)-, —N$R^a$C(=0)-, —C(=0)N$R^a$—, —N$R^a$C(=0)N$R^a$—, —OC(=0)N$R^a$—, —N$R^a$C(=0)0- or a direct bond;

$G^1$ is C, —$C_2$ alkylene, —(C=0)-, -0(C=0)-, —SC(=0)-, —N$R^a$C(=0)- or a direct bond;

$G^2$ is —C(0)-, —(CO)O—, —C(=0)S—, —C(=0)N$R^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent R and the carbon atom to which it is bound to form a carbon-carbon double bond;

$R^{4A}$ and $R^{4B}$ are, at each occurrence, independently either: (a) H or $C_1$-$C_{12}$ alkyl; or (b) $R^{4A}$ is H or $C_1$-$C_{12}$ alkyl, and $R^{4B}$ together with the carbon atom to which it is bound is taken together with an adjacent $R^{4B}$ and the carbon atom to which it is bound to form a carbon-carbon double bond;

$R^5$ and $R^6$ are each independently H or methyl;

$R^7$ is H or C, —$C_{20}$ alkyl;

$R^8$ is OH, —N($R^9$)(C=0)$R^{10}$, —(C=0)N$R^9$$R^{10}$, —N$R^9$$R^{10}$, —(C=0)OR"$^1$ or -0(C=0)R", provided that $G^3$ is $C_4$-$C_6$ alkylene when $R^8$ is —N$R^9$$R^{10}$, $R^9$ and $R^{10}$ are each independently H or $C_1$-$C_{12}$ alkyl;

R" is aralkyl;

a, b, c and d are each independently an integer from 1 to 24; and x is 0, 1 or 2, wherein each alkyl, alkylene and aralkyl is optionally substituted.

Formula (AX)

In some embodiments, the lipid nanoparticle comprises a lipid having the structure:

(AX)

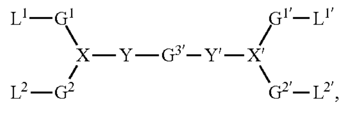

or a pharmaceutically acceptable salt, prodrug or stereoisomer thereof, wherein:

X and X' are each independently N or CR;

Y and Y' are each independently absent, —O(C═O)—, —(C═O)O— or NR, provided that:

a) Y is absent when X is N;

b) Y' is absent when X' is N;

c) Y is —O(C═O)—, —(C═O)O— or NR when X is CR; and d) Y' is —O(C═O)—, —(C═O)O— or NR when X' is CR, $L^1$ and $L^{1'}$ are each independently —O(C═O)R', —(C═O)OR', —C(═O)R', —$OR^1$, —$S(O)_zR'$, —S—$SR^1$, —C(═O)SR', —SC(═O)R', —$NR^a$C(═O)R', —C(═O)$NR^bR^c$, —$NR^a$C(═O)$NR^bR^c$, —OC(═O)$NR^bR^c$ or —$NR^a$C(═O)OR';

$L^2$ and $L^{2'}$ are each independently —O(C═O)$R^2$, —(C═O)$OR^2$, —C(═O)$R^2$, —$OR^2$, —$S(O)_zR^2$, —S—$SR^2$, —C(═O)$SR^2$, —SC(═O)$R^2$, —$NR^d$C(═O)$R^2$, —C(═O)$NR^eR^f$, —$NR^d$C(═O)$NR^eR^f$, —OC(═O)$NR^eR^f$; —$NR^d$C(═O)$OR^2$ or a direct bond to $R^2$;

$G^1$, $G^{1'}$, $G^2$ and $G^{2'}$ are each independently $C_2$-$C_{12}$ alkylene or $C_2$-$C_{12}$ alkenylene;

G is $C_2$-$C_{24}$ heteroalkylene or $C_2$-$C_{24}$ heteroalkenylene;

$R^a$, $R^b$, $R^d$ and $R^e$ are, at each occurrence, independently H, $C_1$-$C_{12}$ alkyl or $C_2$-$C_{12}$ alkenyl;

$R^c$ and $R^f$ are, at each occurrence, independently $C_1$-$C_{12}$ alkyl or $C_2$-$C_{12}$ alkenyl;

R is, at each occurrence, independently H or $C_1$-$C_{12}$ alkyl;

$R^1$ and $R^2$ are, at each occurrence, independently branched $C_6$-$C_{24}$ alkyl or branched $C_6$-$C_{24}$ alkenyl;

z is 0, 1 or 2, and wherein each alkyl, alkenyl, alkylene, alkenylene, heteroalkylene and heteroalkenylene is independently substituted or unsubstituted unless otherwise specified.

Formula (AXI)

In some embodiments, the lipid nanoparticle comprises a lipid having the structure:

(AXI)

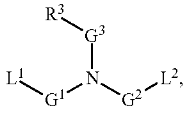

or a pharmaceutically acceptable salt, prodrug or stereoisomer thereof, wherein:

$L^1$ is —O(C═O)$R^1$, —(C═O)$OR^1$, —C(═O)$R^1$, —$OR^1$, —$S(O)_xR^1$, —S—$SR^1$, —C(═O)$SR^1$, —SC(═O)$R^1$, —$NR^a$C(═O)$R^1$, —C(═O)$NR^bR^c$, —$NR^a$C(═O)$NR^bR^c$, —OC(═O)$NR^bR^c$ or —$NR^a$C(═O)$OR^1$;

$L^2$ is —O(C═O)$R^2$, —(C═O)$OR^2$, —C(═O)$R^2$, —$OR^2$, —$S(O)_xR^2$, —S—$SR^2$, —C(═O)$SR^2$, —SC(═O)$R^2$, —$NR^d$C(═O)$R^2$, —C(═O)$NR^eR^f$, —$NR^d$C(═O)$NR^eR^f$, —OC(═O)$NR^eR^f$; —$NR^d$C(═O)$OR^2$ or a direct bond to $R^2$;

$G^1$ and $G^2$ are each independently $C_2$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene or $C_3$-$C_8$ cycloalkenylene;

$R^a$, $R^b$, $R^d$ and $R^e$ are each independently H or $C_1$-$C_{12}$ alkyl or $C_1$-$C_{12}$ alkenyl;

$R^c$ and $R^f$ are each independently $C_1$-$C_{12}$ alkyl or $C_2$-$C_{12}$ alkenyl;

$R^1$ and $R^2$ are each independently branched $C_6$-$C_{24}$ alkyl or branched $C_6$-$C_{24}$ alkenyl;

$R^3$ is —$N(R^4)R^5$;

$R^4$ is $C_1$-$C_{12}$ alkyl;

$R^5$ is substituted $C_1$-$C_{12}$ alkyl; and x is 0, 1 or 2, and wherein each alkyl, alkenyl, alkylene, alkenylene, cycloalkylene, cycloalkenylene, aryl and aralkyl is independently substituted or unsubstituted unless otherwise specified.

In some embodiments, the lipid nanoparticle comprises a lipid having the structure:

(AXIa)

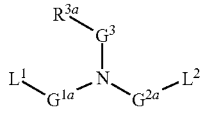

or (AXIb)

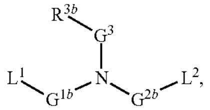

or a pharmaceutically acceptable salt, prodrug or stereoisomer thereof, wherein:

$L^1$ is —O(C═O)$R^1$, —(C═O)$OR^1$, —C(═O)$R^1$, —$OR^1$, —$S(O)_xR^1$, —S—$SR^1$, —C(═O)$SR^1$, —SC(═O)$R^1$, —$NR^a$C(═O)$R^1$, —C(═O)$NR^bR^c$, —$NR^a$C(═O)$NR^bR^c$, —OC(═O)$NR^bR^c$ or —$NR^a$C(═O)$OR^1$;

$L^2$ is —O(C═O)$R^2$, —(C═O)$OR^2$, —C(═O)$R^2$, —$OR^2$, —$S(O)_xR^2$, —S—$SR^2$, —C(═O)$SR^2$, —SC(═O)$R^2$, —$NR^d$C(═O)$R^2$, —C(═O)$NR^eR^f$, —$NR^d$C(═O)$NR^eR^f$,
—OC(═O)$NR^eR^f$; —$NR^d$C(═O)$OR^2$ or a direct bond to $R^2$;

$G^{1a}$ and $G^{2b}$ are each independently $C_2$-$C_{12}$ alkylene or $C_2$-$C_{12}$ alkenylene;

$G^{1b}$ and $G^{2b}$ are each independently $C_1$-$C_{12}$ alkylene or $C_2$-$C_{12}$ alkenylene;

$G^3$ is $C_1$-$C_{24}$ alkylene, $C_2$-$C_{24}$ alkenylene, $C_3$-$C_8$ cycloalkylene or $C_3$-$C_8$ cycloalkenylene;

$R^a$, $R^b$, $R^d$ and $R^e$ are each independently H or $C_1$-$C_{12}$ alkyl or $C_2$-$C_{12}$ alkenyl;

$R^c$ and $R^f$ are each independently $C_1$-$C_{12}$ alkyl or $C_2$-$C_{12}$ alkenyl;

$R^1$ and $R^2$ are each independently branched $C_6$-$C_{24}$ alkyl or branched $C_6$-$C_{24}$ alkenyl;

$R^{3a}$ is —C(═O)$N(R^{4a})R^{5a}$ or —C(═O)$OR^6$;

$R^{3b}$ is —$NR^{4b}$C(═O)$R^{5b}$;

$R^{4a}$ is $C_1$-$C_{12}$ alkyl;

$R^{4b}$ is H, $C_1$-$C_{12}$ alkyl or $C_2$-$C_{12}$ alkenyl;

$R^{5a}$ is H, $C_1$-$C_8$ alkyl or $C_2$-$C_8$ alkenyl;

$R^{5b}$ is $C_2$-$C_{12}$ alkyl or $C_2$-$C_{12}$ alkenyl when $R^{4b}$ is H; or $R^{5b}$ is $C_1$-$C_{12}$ alkyl or $C_2$-$C_{12}$ alkenyl when $R^{4b}$ is $C_1$-$C_{12}$ alkyl or $C_2$-$C_{12}$ alkenyl;

$R^6$ is H, aryl or aralkyl; and x is 0, 1 or 2, and wherein each alkyl, alkenyl, alkylene, alkenylene, cycloalkylene, cycloalkenylene, aryl and aralkyl is independently substituted or unsubstituted.

Formula (AXII)

In some embodiments, the lipid nanoparticle comprises a lipid having the structure:

(AXII)

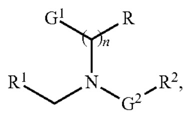

or a pharmaceutically acceptable salt, prodrug or stereoisomer thereof, wherein:

$G^1$ is —OH, —$R^3R^4$, —(C=0)$R^5$ or —$R^3$(C=0)$R^5$;

$G^2$ is —$CH_2$— or —(C=0)-;

R is, at each occurrence, independently H or OH;

$R^1$ and $R^2$ are each independently optionally substituted branched, saturated or unsaturated $C_{12}$-$C_{36}$ alkyl;

$R^3$ and $R^4$ are each independently H or optionally substituted straight or branched, saturated or unsaturated Ci-$C_6$ alkyl;

$R^5$ is optionally substituted straight or branched, saturated or unsaturated Ci-$C_6$ alkyl; and n is an integer from 2 to 6.

Formula (AXIII)

In some embodiments, the lipid nanoparticle comprises a lipid having the structure:

(AXIII)

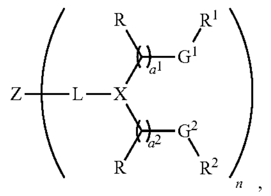

or a pharmaceutically acceptable salt, prodrug or stereoisomer thereof, wherein:

one of $G^1$ or $G^2$ is, at each occurrence, —O(C═O)—, —(C═O)O—, —C(═O)—, —O—, —S(O), —S—S—, —C(═O)S—, SC(═O)—, —N($R^a$)C(═O)—, —C(═O)N($R^a$)—, —N($R^a$)C(═O)N($R^a$)—, —OC(═O)N($R^a$)— or —N($R^a$)C(═O)O—, and the other of $G^1$ or $G^2$ is, at each occurrence, —O(C═O)—, —(C═O)O—, —C(═O)—, —O—, —S(O), —S—S—, —C(═O)S—, —SC(═O)—, —N($R^a$)C(═O)—, —C(═O)N($R^a$)—, —N($R^a$)C(═O)N($R^a$)—, —OC(═O)N($R^a$)— or —N($R^a$)C(═O)O— or a direct bond;

L is, at each occurrence, ~O(C═O)—, wherein ~ represents a covalent bond to X;

X is $CR^a$;

Z is alkyl, cycloalkyl or a monovalent moiety comprising at least one polar functional group when n is 1; or Z is alkylene, cycloalkylene or a polyvalent moiety comprising at least one polar functional group when n is greater than 1;

$R^a$ is, at each occurrence, independently H, $C_1$-$C_{12}$ alkyl, $C_1$-$C_{12}$ hydroxylalkyl, $C_1$-$C_{12}$ aminoalkyl, $C_1$-$C_{12}$ alkylaminylalkyl, $C_1$-$C_{12}$ alkoxyalkyl, $C_1$-$C_{12}$ alkoxycarbonyl, $C_1$-$C_{12}$ alkylcarbonyloxy, $C_1$-$C_{12}$ alkylcarbonyloxyalkyl or $C_1$-$C_{12}$ alkylcarbonyl;

R is, at each occurrence, independently either: (a) H or $C_1$-$C_{12}$ alkyl; or (b) R together with the carbon atom to which it is bound is taken together with an adjacent R and the carbon atom to which it is bound to form a carbon-carbon double bond;

$R^1$ and $R^2$ have, at each occurrence, the following structure, respectively:

$R^1$

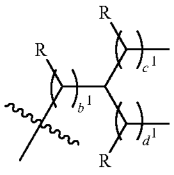

and $R^2$

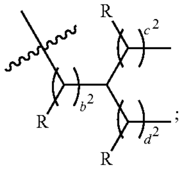

$a^1$ and $a^2$ are, at each occurrence, independently an integer from 3 to 12; $b^1$ and $b^2$ are, at each occurrence, independently 0 or 1;

$c^1$ and $c^2$ are, at each occurrence, independently an integer from 5 to 10; $d^1$ and $d^2$ are, at each occurrence, independently an integer from 5 to 10; y is, at each occurrence, independently an integer from 0 to 2; and n is an integer from 1 to 6, wherein each alkyl, alkylene, hydroxylalkyl, aminoalkyl, alkylaminylalkyl, alkoxyalkyl, alkoxycarbonyl, alkylcarbonyloxy, alkylcarbonyloxyalkyl and alkylcarbonyl is optionally substituted with one or more substituent.

Formula (AXIV)

In some embodiments, the lipid nanoparticle comprises a lipid having the structure:

(AXIV)

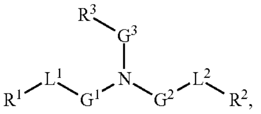

or a pharmaceutically acceptable salt, prodrug or stereoisomer thereof, wherein:

one of $L^1$ or $L^2$ is —O(C═O)—, —(C═O)O—, —C(═O)—, —O—, —$S(O)_x$—, —S—S—, —C(═O)S—, —SC(═O)—, —$R^a$C(═O)—, —C(═O)$R^a$—, $R^a$C(═O)$R^a$—, —OC(═O)$R^a$— or —$R^a$C(═O)O—, and the other of $L^1$ or $L^2$ is —O(C═O)—, —(C═O)O—, —C(═O)—, —O—, —$S(O)_x$—, —S—S—, —C(═O)S—, SC(═O)—, —$R^a$C(═O)—, —C(═O)$R^a$—, $R^a$C(═O)$R^a$—, —OC(═O)$R^a$— or —N$R^a$C(═O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, $OR^5$, CN, —C(═O)$OR^4$, —OC(═O)$R^4$ or —$R^5$C(═O)$R^4$;

$R^4$ is $C_1$-$C_{12}$ alkyl;

$R^5$ is H or $C_1$-$C_6$ alkyl; and x is 0, 1 or 2.

Formula (AXV)

In some embodiments, the lipid nanoparticle comprises a lipid having the structure:

(AXV)

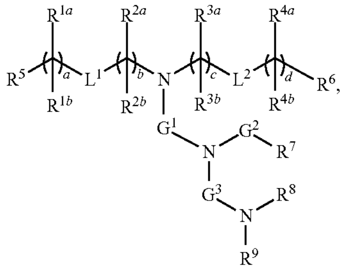

or a pharmaceutically acceptable salt, tautomer, prodrug or stereoisomer thereof, wherein:

$L^1$ and $L^2$ are each independently -0(C=0)-, —(C=0)0-, —C(=0)-, -0-, —$S(0)_x$—, —S—S—, —C(=0)S—, —SC(=0)-, —$R^a$C(=0)-, —C(=0)$R^a$—, —$R^a$C(=0)$R^a$—, —OC(=0)$R^a$—, —$R^a$C(=0)0- or a direct bond;

$G^1$ is $C_1$-$C_2$ alkylene, —(C=0)-, -0(C=0)-, —SC(=0)-, —$R^a$C(=0)- or a direct bond:

$G^2$ is —C(=0)-, —(C=0)0-, —C(=0)S—, —C(=0)N$R^a$— or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a): H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent R and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

Formula (AXVI)

In some embodiments, the lipid nanoparticle comprises a lipid having the structure:

(AXVI)

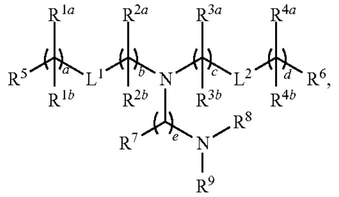

or a pharmaceutically acceptable salt, tautomer, prodrug or stereoisomer thereof, wherein:

$L^1$ and $L^2$ are each independently -0(C=0)-, —(C=0)0- or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl; $R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24; b and c are each independently an integer from 1 to 24; and e is 1 or 2, provided that:

at least one of $R^{1a}$, $R^{2a}$, $R^{3a}$ or $R^{4a}$ is $C_1$-$C_{12}$ alkyl, or at least one of $L^1$ or $L^2$ is -0(C=0)- or —(C=0)0-; and $R^{1a}$ and $R^{1b}$ are not isopropyl when a is 6 or n-butyl when a is 8.

Formula (AXVII)

In some embodiments, the lipid nanoparticle comprises a lipid having the structure:

(AXVII)

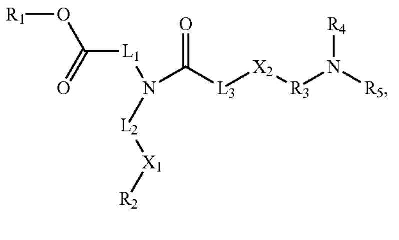

or a pharmaceutically acceptable salt thereof, wherein $R_1$ and $R_2$ are the same or different, each a linear or branched alkyl with 1-9 carbons, or as alkenyl or alkynyl with 2 to 11 carbon atoms, $L_1$ and $L_2$ are the same or different, each a linear alkyl having 5 to 18 carbon atoms, or form a heterocycle with N, $X_1$ is a bond, or is —CG-G-whereby L2-CO—O—$R_2$ is formed, $X_2$ is S or O, $L_3$ is a bond or a lower alkyl, or form a heterocycle with N, $R_3$ is a lower alkyl, and $R_4$ and $R_5$ are the same or different, each a lower alkyl.

Compounds ($A_1$)-($A_{11}$)

In some embodiments, the lipid nanoparticle comprises an ionizable lipid having the structure:

(A1)

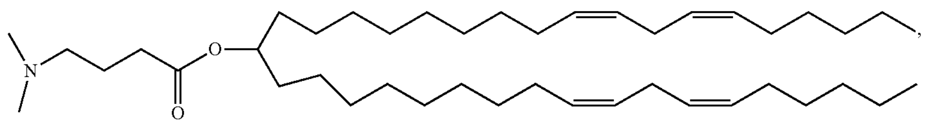

or a pharmaceutically acceptable salt thereof.

In some embodiments, the lipid nanoparticle comprises a lipid having the structure:

(A2)

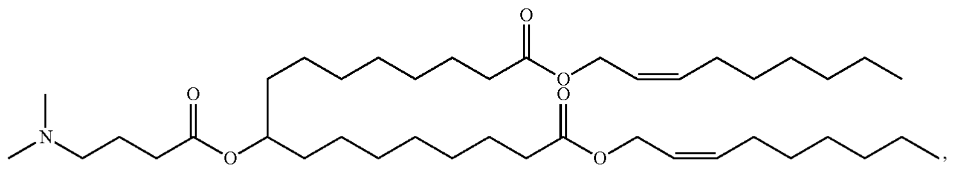

or a pharmaceutically acceptable salt thereof.

In some embodiments, the lipid nanoparticle comprises a lipid having the structure:

(A3)

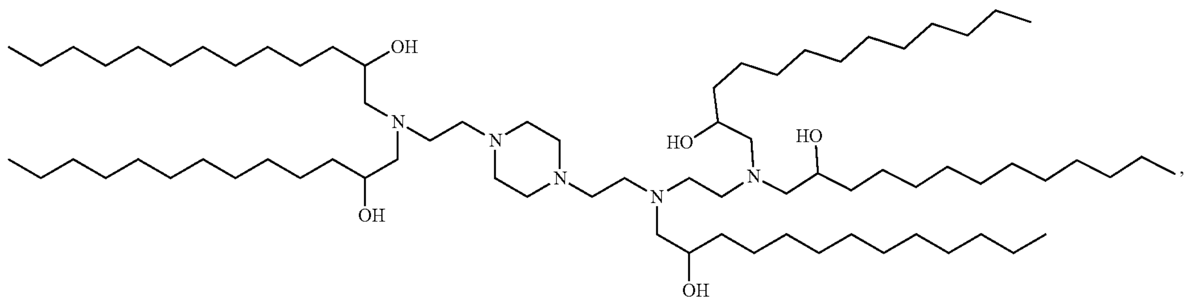

or a pharmaceutically acceptable salt thereof.

In some embodiments, the lipid nanoparticle comprises a lipid having the structure:

(A4)
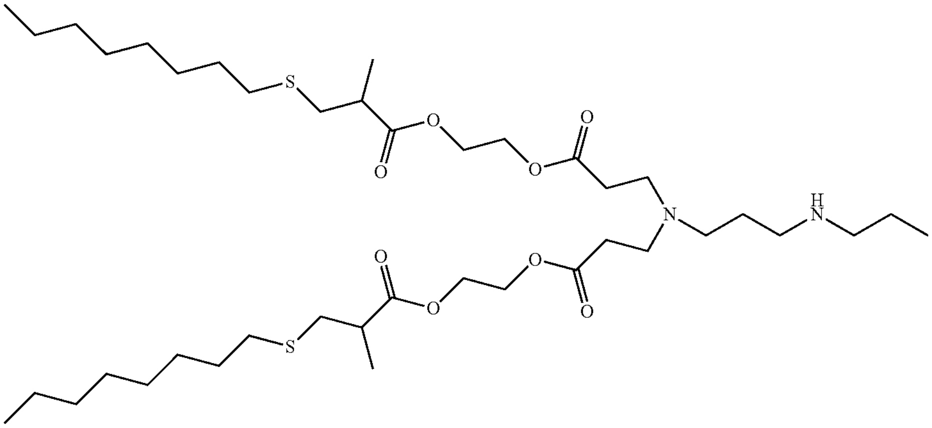
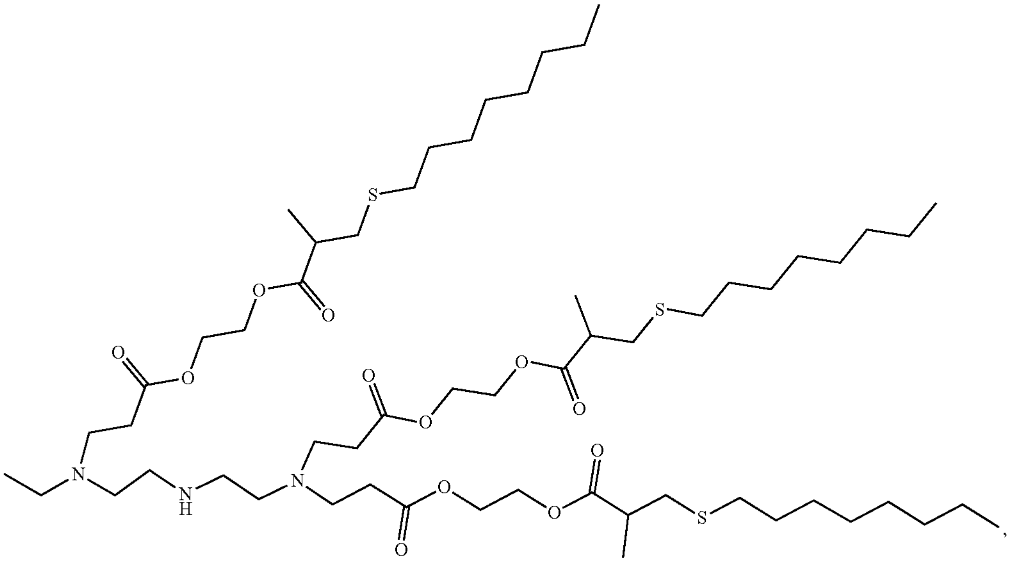
or a pharmaceutically acceptable salt thereof.
In some embodiments, the lipid nanoparticle comprises a lipid having the structure:
(A5)
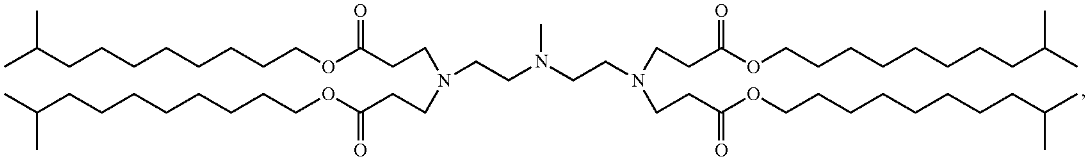
or a pharmaceutically acceptable salt thereof.
In some embodiments, the lipid nanoparticle comprises a lipid having the structure:

(A6)

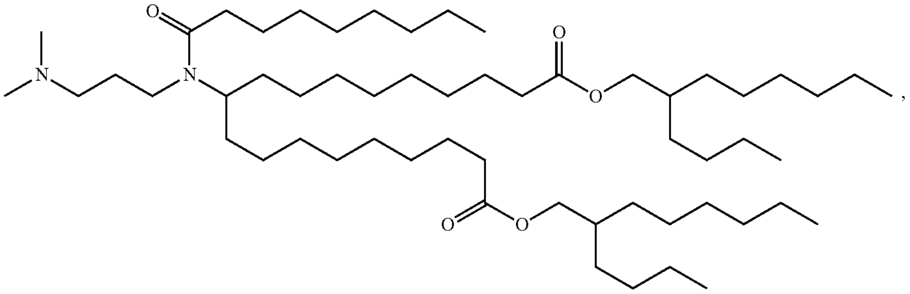

or a pharmaceutically acceptable salt thereof.

In some embodiments, the lipid nanoparticle comprises a lipid having the structure:

(A7)

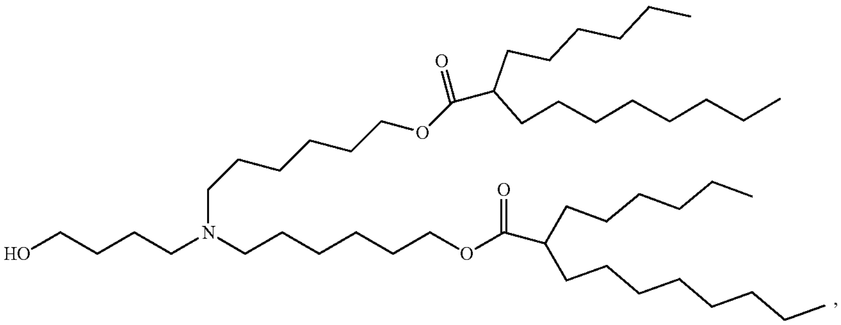

or a pharmaceutically acceptable salt thereof.

In some embodiments, the lipid nanoparticle comprises a lipid having the structure:

(A8)

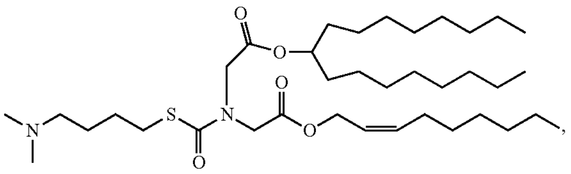

or a pharmaceutically acceptable salt thereof.

In some embodiments, the lipid nanoparticle comprises a lipid having the structure:

(A9)

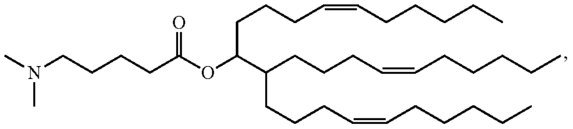

or a pharmaceutically acceptable salt thereof.

In some embodiments, the lipid nanoparticle comprises a lipid having the structure:

(A10)

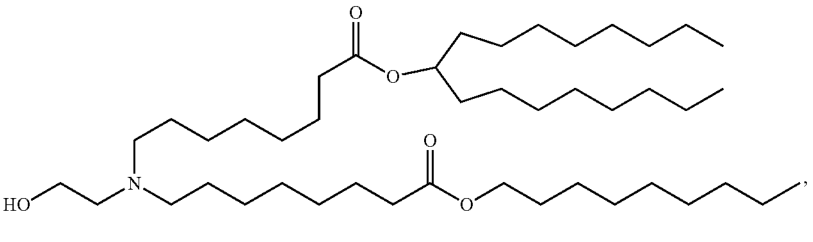

or a pharmaceutically acceptable salt thereof.

In some embodiments, the lipid nanoparticle comprises a lipid having the structure:

(A11)

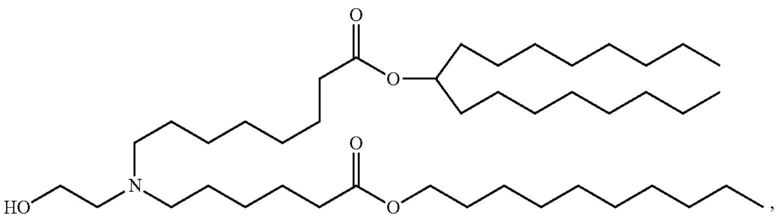

or a pharmaceutically acceptable salt thereof.

Non-Cationic Lipids

In certain embodiments, lipid nanoparticles comprise one or more non-cationic lipids. Non-cationic lipids may be phospholipids.

In some embodiments, the lipid nanoparticle comprises 5-25 mol % non-cationic lipid. For example, the lipid nanoparticle may comprise 5-20 mol %, 5-15 mol %, 5-10 mol %, 10-25 mol %, 10-20 mol %, 10-25 mol %, 15-25 mol %, 15-20 mol %, or 20-25 mol % non-cationic lipid. In some embodiments, the lipid nanoparticle comprises 5 mol %, 10 mol %, 15 mol %, 20 mol %, or 25 mol % non-cationic lipid.

In some embodiments, a non-cationic lipid comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPc), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, or mixtures thereof.

In some embodiments, the lipid nanoparticle comprises 5-15 mol %, 5-10 mol %, or 10-15 mol % DSPC. For example, the lipid nanoparticle may comprise 5, 6, 7, 8, 9, 10, 11, 12, 13, 14, or 15 mol % DSPC.

In certain embodiments, the lipid composition of the lipid nanoparticle compositions can comprise one or more phospholipids, for example, one or more saturated or (poly) unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, a phospholipid comprises 1,2-distearoyl-sn-glycero-3-phosphocholine (DSPC), 1,2-Distearoyl-sn-glycero-3-phosphoethanolamine (DSPE), 1,2-dioleoyl-sn-glycero-3-phosphoethanolamine 1,2-dilinoleoyl-sn-glycero-3-(DOPE), phosphocholine (DLPc), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, or mixtures thereof.

Formula (HI)

In certain embodiments, a phospholipid is an analog or variant of DSPC. In certain embodiments, a phospholipid is a compound of Formula (HI):

(HI)

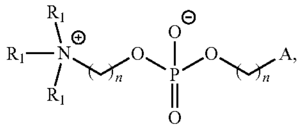

or a salt thereof, wherein:

each R1 is independently optionally substituted alkyl; or optionally two R1 are joined together with the intervening atoms to form optionally substituted monocyclic carbocyclyl or optionally substituted monocyclic heterocyclyl; or optionally three R1 are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

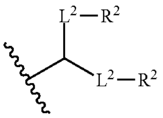

or

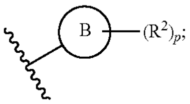

each instance of L2 is independently a bond or optionally substituted C1-6 alkylene, wherein one methylene unit of the optionally substituted C1-6 alkylene is optionally replaced with O, N(RN), S, C(O), C(O)N(RN), NRNC(O), C(O)O, OC(O), OC(O)O, OC(O)N(RN), —NRNC(O)O, or NRNC(O)N(RN);

each instance of R2 is independently optionally substituted C1-30 alkyl, optionally substituted C1-30 alkenyl, or optionally substituted C1-30 alkynyl; optionally wherein one or more methylene units of $R^2$ are independently replaced with optionally substituted carbocyclylene, optionally substituted heterocyclylene, optionally substituted arylene, optionally substituted heteroarylene, N(RN), O, S, C(O), C(O)N(RN), NRNC(O), NRNC(O)N(RN), C(O)O, OC(O), OC(O)O, OC(O)N(RN), NRNC(O)O, C(O)S, SC(O), C(=NRN), C(=NRN)N(RN), NRNC(=NRN), NRNC(=NRN)N(RN), C(S), C(S)N(RN), NRNC(S), NRNC(S)N(RN), S(O), OS(O), S(O)O, OS(O)O, OS(O)2, S(O)2O, OS(O)2O, N(RN)S(O), S(O)N(RN), N(RN)S(O)N(RN), OS(O)N(RN), N(RN)S(O)O, S(O)2, N(RN)S(O)2, S(O)2N(RN), N(RN)S(O)2N(RN), OS(O)2N(RN), or N(RN)S(O)2O;

each instance of RN is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound is not of the formula:

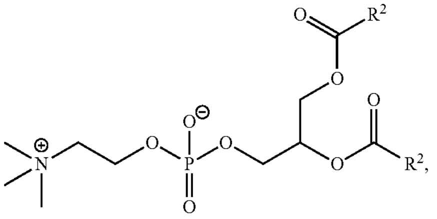

wherein each instance of R2 is independently unsubstituted alkyl, unsubstituted alkenyl, or unsubstituted alkynyl.

In some embodiments, the phospholipids may be one or more of the phospholipids described in PCT Application No. PCT/US2018/037922.

In some embodiments, the lipid nanoparticle comprises a molar ratio of 5-25% non-cationic lipid relative to the other lipid components. For example, the lipid nanoparticle may comprise a molar ratio of 5-30%, 5-15%, 5-10%, 10-25%, 10-20%, 10-25%, 15-25%, 15-20%, 20-25%, or 25-30% non-cationic lipid. In some embodiments, the lipid nanoparticle comprises a molar ratio of 5%, 10%, 15%, 20%, 25%, or 30% non-cationic lipid.

In some embodiments, the lipid nanoparticle comprises a molar ratio of 5-25% phospholipid relative to the other lipid components. For example, the lipid nanoparticle may comprise a molar ratio of 5-30%, 5-15%, 5-10%, 10-25%, 10-20%, 10-25%, 15-25%, 15-20%, 20-25%, or 25-30% phospholipid. In some embodiments, the lipid nanoparticle comprises a molar ratio of 5%, 10%, 15%, 20%, 25%, or 30% phospholipid lipid.

Structural Lipids

The lipid composition of a pharmaceutical composition can comprise one or more structural lipids. As used herein, the term "structural lipid" includes sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

In some embodiments, the structural lipids may be one or more of the structural lipids described in U.S. application Ser. No. 16/493,814.

In some embodiments, the lipid nanoparticle comprises a molar ratio of 25-55% structural lipid relative to the other lipid components. For example, the lipid nanoparticle may comprise a molar ratio of 10-55%, 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% structural lipid. In some embodiments, the lipid nanoparticle comprises a molar ratio of 10%, 15%, 20%, 25%, 30%, 35%, 40%, 45%, 50%, or 55% structural lipid.

In some embodiments, the lipid nanoparticle comprises 30-45 mol % sterol, optionally 35-40 mol %, for example, 30-31 mol %, 31-32 mol %, 32-33 mol %, 33-34 mol %, 35-35 mol %, 35-36 mol %, 36-37 mol %, 38-38 mol %, 38-39 mol %, or 39-40 mol %. In some embodiments, the lipid nanoparticle comprises 25-55 mol % sterol. For example, the lipid nanoparticle may comprise 25-50 mol %, 25-45 mol %, 25-40 mol %, 25-35 mol %, 25-30 mol %, 30-55 mol %, 30-50 mol %, 30-45 mol %, 30-40 mol %, 30-35 mol %, 35-55 mol %, 35-50 mol %, 35-45 mol %, 35-40 mol %, 40-55 mol %, 40-50 mol %, 40-45 mol %, 45-55 mol %, 45-50 mol %, or 50-55 mol % sterol. In some embodiments, the lipid nanoparticle comprises 25 mol %, 30 mol %, 35 mol %, 40 mol %, 45 mol %, 50 mol %, or 55 mol % sterol.

In some embodiments, the lipid nanoparticle comprises 35-40 mol % cholesterol. For example, the lipid nanoparticle may comprise 35, 35.5, 36, 36.5, 37, 37.5, 38, 38.5, 39, 39.5, or 40 mol % cholesterol.

Polyethylene Glycol (PEG)-Lipids

The lipid composition of a pharmaceutical composition can comprise one or more polyethylene glycol (PEG)-modified lipids.

As used herein, the term "PEG-lipid" or "PEG-modified lipid" refers to polyethylene glycol (PEG)-modified lipids. Non-limiting examples of PEG-modified lipids include PEG-modified phosphatidylethanolamine and phosphatidic acid, PEG-ceramide conjugates (e.g., PEG-CerC14 or PEG-CerC20), PEG-modified dialkylamines, and PEG-modified 1,2-diacyloxypropan-3-amines. Such lipids are also referred to as PEGylated lipids. For example, a PEG-modified lipid can be PEG-c-DOMG, PEG-DMG, PEG-DLPE, PEG-DMPE, PEG-DPPC, or a PEG-DSPE lipid.

some embodiments, a PEG moiety, for example an mPEG-$NH_2$, has a size of about 1000, 2000, 5000, 10,000, 15,000 or 20,000 daltons. In some embodiments, the PEG-modified lipid is $PEG_{2k}$-DMG.

In some embodiments, lipid nanoparticles can comprise a PEG-modified lipid which is a non-diffusible PEG. Non-limiting examples of non-diffusible PEGs include PEG-DSG and PEG-DSPE.

PEG-modified lipids are known in the art, such as those described in U.S. Pat. No. 8,158,601 and International Publ. No. WO 2015/130584 A2, which are incorporated herein by reference to the extent they describe PEG-modified lipids.

In general, some of the other lipid components (e.g., PEG-modified lipids) of various formulae may be synthesized as described International Patent Application No. PCT/US2016/000129, filed Dec. 10, 2016, entitled "Compositions and Methods for Delivery of Therapeutic Agents," which is incorporated by reference to the extent they disclose lipid components and production.

The lipid component of a lipid nanoparticle composition may include one or more molecules comprising polyethylene glycol, such as PEG or PEG-modified lipids. Such species may be alternately referred to as PEGylated lipids. A PEG-modified lipid is a lipid modified with polyethylene glycol. A PEG-modified lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG-modified lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

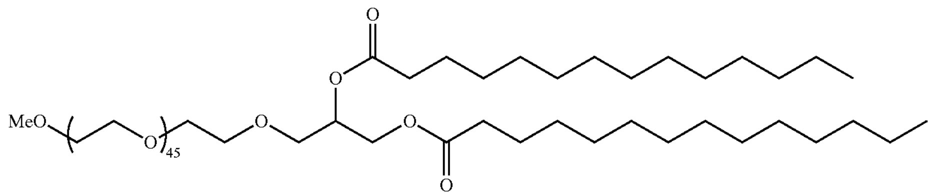

In some embodiments, the PEG-modified lipid includes, but not limited to 1,2-dimyristoyl-sn-glycerol methoxypolyethylene glycol (PEG-DMG), 1,2-distearoyl-sn-glycero-3-phosphoethanolamine-N-[amino (polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In some embodiments, the PEG-modified lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG, and/or PEG-DPG.

In some embodiments, the lipid moiety of the PEG-modified lipids includes those having lengths of from about $C_{14}$ to about $C_{22}$, preferably from about $C_{14}$ to about $C_{16}$. In some embodiments, PEG-modified lipids can be PEGylated lipids described in International Publication No. WO 2012/099755, which is herein incorporated by reference to the extent it discloses PEG-modified lipids. Any of these exemplary PEG-modified lipids may be modified to comprise a hydroxyl group on the PEG chain. In certain embodiments, the PEG-modified lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment.

Formula (PI)

In certain embodiments, a PEG-modified lipid is a compound of Formula (PI):

(PI)

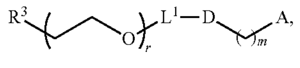

or salts thereof, wherein:

$R^3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, $N(R^N)$, S, C(O), $C(O)N(R^N)$, $NR^NC(O)$, C(O)O, OC(O), OC(O)O, $OC(O)N(R^N)$, $NR^NC(O)O$, or $NR^NC(O)N(R^N)$;

D is a moiety obtained by click chemistry or a moiety cleavable under physiological conditions;

m is 0, 1, 2, 3, 4, 5, 6, 7, 8, 9, or 10;

A is of the formula:

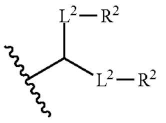

or

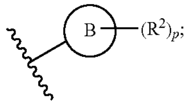

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$, $NR^NC(O)$, C(O)O, OC(O), OC(O)O, $OC(O)N(R^N)$, $NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$, C(O)O, OC(O), OC(O)O, $OC(O)N(R^N)$, $NR^NC(O)O$, C(O)S, SC(O), $C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $NR^NC(S)N(R^N)$, S(O), OS(O), S(O)O, OS(O)O, $OS(O)_2$, $S(O)_2O$, $OS(O)_2O$, $N(R^N)S(O)$, $S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (PI) is a PEG-OH lipid (i.e., $R^3$ is —$OR^O$, and $R^O$ is hydrogen). In certain embodiments, the compound of Formula (PI) is of Formula (PI-OH):

(PI-OH)

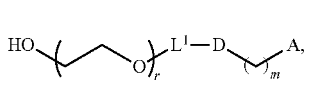

or a salt thereof.

Formula (PII)

In certain embodiments, a PEG-modified lipid is a PEGylated fatty acid. In certain embodiments, a PEG-modified lipid is a compound of Formula (PII). In some embodiments, compounds of Formula (PII) have the following formula:

(PII)

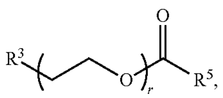

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$, C(O)O, OC(O), OC(O)O, $OC(O)N(R^N)$, $NR^NC(O)O$, C(O)S, SC(O), $C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $NR^NC(S)N(R^N)$, S(O), OS(O), S(O)O, OS(O)O, $OS(O)_2$, $S(O)_2O$, $OS(O)_2O$, $N(R^N)S(O)$, $S(O)N(R^N)$, $N(R^N)S(O)N(R^N)$, $OS(O)N(R^N)$, $N(R^N)S(O)O$, s $(O)_2$, n $(R^N)S(O)_2$, $S(O)_2N(R^N)$, $N(R^N)S(O)_2N(R^N)$, $OS(O)_2N(R^N)$, or $N(R^N)S(O)_2O$; and each instance of $R^N$ is independently hydrogen, optionally substituted alkyl, or a nitrogen protecting group.

In certain embodiments, the compound of Formula (PII) is of Formula (PII-OH):

(PII-OH)

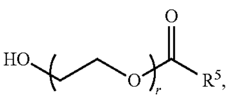

or a salt thereof. In some embodiments, r is 40-50.

In yet other embodiments the compound of Formula (PII) is:

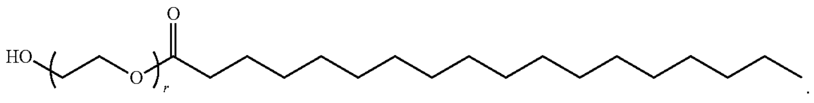

or a salt thereof.

In some embodiments, the compound of Formula (PII) is

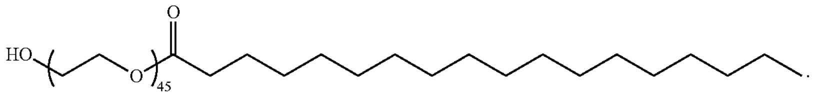

In some embodiments, the lipid composition of the pharmaceutical composition does not comprise a PEG-modified lipid.

In some embodiments, the PEG-modified lipids may be one or more of the PEG-modified lipids described in U.S. application Ser. No. 15/674,872.

In some embodiments, the lipid nanoparticle comprises a molar ratio of 0.5-15% PEG-modified lipid relative to the other lipid components. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15% PEG-modified lipid. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises 1-5% PEG-modified lipid, optionally 1-3 mol %, for example 1.5 to 2.5 mol %, 1-2 mol %, 2-3 mol %, 3-4 mol %, or 4-5 mol %. In some embodiments, the lipid nanoparticle comprises 0.5-15 mol % PEG-modified lipid. For example, the lipid nanoparticle may comprise 0.5-10 mol %, 0.5-5 mol %, 1-15 mol %, 1-10 mol %, 1-5 mol %, 2-15 mol %, 2-10 mol %, 2-5 mol %, 5-15 mol %, 5-10 mol %, or 10-15 mol %. In some embodiments, the lipid nanoparticle comprises 0.5 mol %, 1 mol %, 2 mol %, 3 mol %, 4 mol %, 5 mol %, 6 mol %, 7 mol %, 8 mol %, 9 mol %, 10 mol %, 11 mol %, 12 mol %, 13 mol %, 14 mol %, or 15 mol % PEG-modified lipid.

Some embodiments comprise adding PEG to a composition comprising an LNP encapsulating a nucleic acid (e.g., which already includes PEG in the amounts listed above). In embodiments comprise adding about 0.5 mo % or more PEG to an LNP composition, such as about 1 mol %, about 1.5 mol %, about 2 mol %, about 2.5 mol %, about 3 mol %, about 3.5 mol %, about 4 mol %, about 5 mol %, or more after formation of an LNP composition (e.g., which already contains PEG in amount listed elsewhere herein).

In some embodiments, a lipid nanoparticle comprises a first PEG-modified lipid in a core of the LNP, and a second PEG-modified lipid outside of the core of the LNP. The first and second PEG-modified lipids of the core and outside the core may the same PEG-modified lipids (i.e., have the same structure), or be different PEG-modified lipids (i.e., have different structures). In some embodiments, both PEG-modified lipids are 134-hydroxy-3,6,9,12,15,18,21,24,27,30,33,36,39,42,45,48,51,54,57,60,63,66,69,72,75,78,81,84,87,90,93,96,99,102,105,108,111,114,117,120,123,126,129,132-tetratetracontaoxatetratriacontahectyl stearate. In some embodiments, both PEG-modified lipids are PEG-DMG. In some embodiments, the first PEG-modified lipid is PEG-DMG and the second PEG-modified lipid is 134-hydroxy-3,6,9,12,15,18,21,24,27,30,33,36,39,42,45,48,51,54,57,60,63,66,69,72,75,78,81,84,87,90,93,96,99,102,105,108,111,114,117,120,123,126,129,132-tetratetracontaoxatetratriacontahectyl stearate. In some embodiments, the first PEG-modified lipid is 134-hydroxy-3,6,9,12,15,18,21,24,27,30,33,36,39,42,45,48,51,54,57,60,63,66,69,72,75,78,81,84,87,90,93,96,99,102,105,108,111,114,117,120,123,126,129,132-tetratetracontaoxatetratriacontahectyl stearate and the second PEG-modified lipid is PEG-DMG. In some embodiments, 0.25 mol % to 1.0 mol % (as a percentage of lipids in the LNP) of the first PEG-modified lipid is in the core of the lipid nanoparticle. In some embodiments, 0.25 mol % to 0.50 mol % of the first PEG-modified lipid is in the core of the lipid nanoparticle. In some embodiments, 0.25 mol %, 0.50 mol %, 0.75 mol %, or 1.0 mol % of the first PEG-modified lipid is in the core of the LNP. In some embodiments, 2.0 mol % to 2.75 mol % of the second PEG-modified lipid is outside the core of the LNP. In some embodiments, 2.0 mol %, 2.25 mol %, 2.5 mol %, or 2.75 mol % of the second PEG-modified lipid is outside the core of the LNP. In some embodiments, the LNP comprises 3.0 mol % PEG-modified lipids.

LNPs having certain amounts of a PEG-modified lipid in the core and certain amounts of a PEG-modified lipid outside of the core, and methods of producing the same, are disclosed in PCT Publication No. WO 2023/018773, which is incorporated by reference herein to the extent it discloses lipid nanoparticles and methods of producing lipid nanoparticles.

In some embodiments, the lipid nanoparticle comprises 20-60 mol % ionizable lipid, 5-25 mol % non-cationic lipid, 25-55 mol % sterol, and 0.5-15 mol % PEG-modified lipid.

In some embodiments, a LNP comprises an ionizable lipid of Compound (I-18), wherein the non-cationic lipid is DSPC, the structural lipid that is cholesterol, and the PEG-modified lipid is DMG-PEG. In some embodiments, a LNP comprises 20-60 mol % ionizable lipid of Compound (I-18), 5-25 mol % DSPC, 25-55 mol % cholesterol, and 2-4 mol % DMG-PEG.

In some embodiments, a LNP comprises an ionizable lipid of Compound (I-25), wherein the non-cationic lipid is DSPC, the structural lipid that is cholesterol, and the PEG-modified lipid is DMG-PEG. In some embodiments, a LNP comprises 20-60 mol % ionizable lipid of Compound (I-25), 5-25 mol % DSPC, 25-55 mol % cholesterol, and 2-4 mol % DMG-PEG.

In some embodiments, a LNP comprises an ionizable lipid of Compound (I-301), wherein the non-cationic lipid is DSPC, the structural lipid that is cholesterol, and the PEG-modified lipid is DMG-PEG. In some embodiments, a LNP comprises 20-60 mol % ionizable lipid of Compound (I-301), 5-25 mol % DSPC, 25-55 mol % cholesterol, and 2-4 mol % DMG-PEG.

In some embodiments, a LNP comprises an ionizable lipid of Compound (II-6), wherein the non-cationic lipid is DSPC, the structural lipid that is cholesterol, and the PEG-modified lipid is DMG-PEG. In some embodiments, a LNP comprises 20-60 mol % ionizable lipid of Compound (II-6), 5-25 mol % DSPC, 25-55 mol % cholesterol, and 2-4 mol % DMG-PEG.

In some embodiments, a LNP comprises an ionizable lipid of Compound (IL), wherein the non-cationic lipid is DSPC, the structural lipid that is cholesterol, and the PEG-modified lipid is DMG-PEG. In some embodiments, a LNP comprises 20-60 mol % ionizable lipid of Compound (IL), 5-25 mol % DSPC, 25-55 mol % cholesterol, and 2-4 mol % DMG-PEG.

In some embodiments, a LNP comprises an ionizable lipid of any of Formula (IL*), a phospholipid comprising DSPC, a structural lipid, and a PEG-modified lipid comprising PEG-DMG. In some embodiments, a LNP comprises 20-60 mol % ionizable lipid of Formula (IL*), 5-25 mol % phospholipid comprising DSPC, 25-55 mol % structural lipid, and 2-4 mol % PEG-modified lipid comprising DMG-PEG.

In some embodiments, a LNP comprises an ionizable lipid of any of Formula (IL*), a phospholipid comprising DSPC, a structural lipid, and a PEG-modified lipid comprising a compound having Formula (PII). In some embodiments, a LNP comprises 20-60 mol % ionizable lipid of Formula (IL*), 5-25 mol % phospholipid comprising DSPC, 25-55 mol % structural lipid, and 2-4 mol % PEG-modified lipid comprising a compound having Formula (PII).

In some embodiments, a LNP comprises an ionizable lipid of Formula (IL*), a phospholipid comprising a compound having Formula (HI), a structural lipid, and the PEG-modified lipid comprising a compound having Formula (PI) or (PII). In some embodiments, a LNP comprises 20-60 mol % ionizable lipid of Formula (IL*), 5-25 mol % phospholipid comprising a compound having Formula (HI), 25-55 mol % structural lipid, and 2-4 mol % PEG-modified lipid comprising a compound having Formula (PI) or (PII).

In some embodiments, a LNP comprises an ionizable lipid of Formula (IL*), a phospholipid comprising a compound having Formula (HI), a structural lipid, and the PEG-modified lipid comprising a compound having Formula (PI) or (PII). In some embodiments, a LNP comprises 20-60 mol % ionizable lipid of Formula (IL*), 5-25 mol % phospholipid comprising a compound having Formula (HI), 25-55 mol % structural lipid, and 2-4 mol % PEG-modified lipid modified lipid comprising a compound having Formula (PI) or (PII).

In some embodiments, a LNP comprises an ionizable lipid of Formula (IL*), a phospholipid having Formula (HI), a structural lipid, and a PEG-modified lipid comprising a compound having Formula (PII). In some embodiments, a LNP comprises 20-60 mol % ionizable lipid of Formula (IL*), 5-25 mol % phospholipid having Formula (HI), 25-55 mol % structural lipid, and 2-4 mol % PEG-modified lipid comprising a compound having Formula (PII).

In some embodiments, a LNP comprises an ionizable amino lipid of Compound 1, wherein the non-cationic lipid is DSPC, the structural lipid that is cholesterol, and the PEG-modified lipid is DMG-PEG. In some embodiments, a LNP comprises 20-60 mol % ionizable lipid of Compound 1, 5-25 mol % DSPC, 25-55 mol % cholesterol, and 2-4 mol % PEG-modified lipid DMG-PEG.

In some embodiments, a LNP comprises an ionizable amino lipid of Compound 2, wherein the non-cationic lipid is DSPC, the structural lipid that is cholesterol, and the PEG-modified lipid is DMG-PEG. In some embodiments, a LNP comprises 20-60 mol % ionizable lipid of Compound 2, 5-25 mol % DSPC, 25-55 mol % cholesterol, and 2-4 mol % PEG-modified lipid DMG-PEG.

In some embodiments, a LNP comprises an ionizable amino lipid of any of Formula (AIII), (AIV), or (AV), a phospholipid comprising DSPC, a structural lipid, and a PEG-modified lipid comprising PEG-DMG. In some embodiments, a LNP comprises 20-60 mol % ionizable lipid of any of Formula (AIII), (AIV), or (AV), 5-25 mol % DSPC, 25-55 mol % structural lipid, and 2-4 mol % PEG-modified lipid comprising DMG-PEG.

In some embodiments, a LNP comprises an ionizable amino lipid of any of Formula (AIII), (AIV), or (AV), a phospholipid comprising DSPC, a structural lipid, and a PEG-modified lipid comprising a compound having Formula (PII). In some embodiments, a LNP comprises 20-60 mol % ionizable lipid of any of Formula (AIII), (AIV), or (AV), 5-25 mol % DSPC, 25-55 mol % structural lipid, and 2-4 mol % PEG-modified lipid comprising a compound having Formula (PII).

In some embodiments, a LNP comprises an ionizable amino lipid of Formula (AIII), (AIV), or (AV), a phospholipid comprising a compound having Formula (HI), a structural lipid, and the PEG-modified lipid comprising a compound having Formula (PI) or (PII). In some embodiments, a LNP comprises 20-60 mol % ionizable lipid of Formula (AIII), (AIV), or (AV), 5-25 mol % phospholipid comprising a compound having Formula (HI), 25-55 mol % structural lipid, and 2-4 mol % PEG-modified lipid comprising a compound having Formula (PI) or (PII).

In some embodiments, a LNP comprises an ionizable amino lipid of Formula (AIII), (AIV), or (AV), a phospholipid comprising a compound having Formula (HI), a structural lipid, and the PEG-modified lipid comprising a compound having Formula (PI) or (PII). In some embodiments, a LNP comprises 20-60 mol % ionizable lipid of Formula (AIII), (AIV), or (AV), 5-25 mol % phospholipid comprising a compound having Formula (HI), 25-55 mol % structural lipid, and 2-4 mol % PEG-modified lipid comprising a compound having Formula (PI) or (PII).

In some embodiments, a LNP comprises an ionizable amino lipid of Formula (AIII), (AIV), or (AV), a phospholipid having Formula (HI), a structural lipid, and a PEG-modified lipid comprising a compound having Formula (PII). In some embodiments, a LNP comprises 20-60 mol % ionizable lipid of Formula (AIII), (AIV), or (AV), 5-25 mol % phospholipid having Formula (HI), 25-55 mol % structural lipid, and 2-4 mol % PEG-modified lipid comprising a compound having Formula (PII).

In some embodiments, the lipid nanoparticle comprises 49 mol % ionizable lipid, 10 mol % DSPC, 38.5 mol % cholesterol, and 2.5 mol % DMG-PEG.

In some embodiments, the lipid nanoparticle comprises 49 mol % ionizable lipid, 11 mol % DSPC, 38.5 mol % cholesterol, and 1.5 mol % DMG-PEG.

In some embodiments, the lipid nanoparticle comprises 48 mol % ionizable lipid, 11 mol % DSPC, 38.5 mol % cholesterol, and 2.5 mol % DMG-PEG.

In some embodiments, a LNP comprises an N:P ratio of from about 2:1 to about 30:1.

In some embodiments, a LNP comprises an N:P ratio of about 6:1.

In some embodiments, a LNP comprises an N:P ratio of about 3:1, 4:1, or 5:1.

In some embodiments, a LNP comprises a wt/wt ratio of the ionizable lipid component to the RNA of from about 10:1 to about 100:1.

In some embodiments, a LNP comprises a wt/wt ratio of the ionizable lipid component to the RNA of about 20:1.

In some embodiments, a LNP comprises a wt/wt ratio of the ionizable lipid component to the RNA of about 10:1.

Some embodiments comprise a composition having one or more LNPs having a diameter of about 150 nm or less, such as about 140 nm, 130 nm, 120 nm, 110 nm, 100 nm, 90 nm, 80 nm, 70 nm, 60 nm, 50 nm, 40 nm, 30 nm, or 20 nm or less. Some embodiments comprise a composition having a mean LNP diameter of about 150 nm or less, such as about 140 nm, 130 nm, 120 nm, 110 nm, 100 nm, 90 nm, 80 nm, 70 nm, 60 nm, 50 nm, 40 nm, 30 nm, or 20 nm or less. In some embodiments, the composition has a mean LNP diameter from about 30 nm to about 150 nm, or a mean diameter from about 60 nm to about 120 nm.

In some embodiments, an LNP further comprises one or more cargo molecules, including but not limited to nucleic acids (e.g., mRNA, plasmid DNA, DNA or RNA oligonucleotides, siRNA, shRNA, snRNA, snoRNA, lncRNA, etc.), small molecules, proteins and peptides.

Effective in vivo delivery of nucleic acids represents a continuing medical challenge. Exogenous nucleic acids (i.e., originating from outside of a cell or organism) are readily degraded in the body, e.g., by the immune system. Accordingly, effective delivery of nucleic acids to cells often requires the use of a particulate carrier (e.g., lipid nanoparticles). The particulate carrier should be formulated to have minimal particle aggregation, be relatively stable prior to intracellular delivery, effectively deliver nucleic acids intracellularly, and illicit no or minimal immune response. To achieve minimal particle aggregation and pre-delivery stability, many conventional particulate carriers have relied on the presence and/or concentration of certain components (e.g., PEG-modified lipid). However, it has been discovered that certain components may decrease the stability of encapsulated nucleic acids (e.g., mRNA molecules). The reduced stability may limit the broad applicability of the particulate carriers. As such, there remains a need for methods by which to improve the stability of nucleic acid (e.g., mRNA) encapsulated within lipid nanoparticles.

In some embodiments, a LNP comprises one or more ionizable molecules (e.g., amino lipids or ionizable lipids). The ionizable molecule may comprise a charged group and may have a certain pKa. In certain embodiments, the pKa of the ionizable molecule may be greater than or equal to about 6, greater than or equal to about 6.2, greater than or equal to about 6.5, greater than or equal to about 6.8, greater than or equal to about 7, greater than or equal to about 7.2, greater than or equal to about 7.5, greater than or equal to about 7.8, greater than or equal to about 8. In some embodiments, the pKa of the ionizable molecule may be less than or equal to about 10, less than or equal to about 9.8, less than or equal to about 9.5, less than or equal to about 9.2, less than or equal to about 9.0, less than or equal to about 8.8, or less than or equal to about 8.5. Combinations of the above referenced ranges are also possible (e.g., greater than or equal to 6 and less than or equal to about 8.5). Other ranges are also possible. In embodiments in which more than one type of ionizable molecule are present in a particle, each type of ionizable molecule may independently have a pKa in one or more of the ranges described above.

In general, an ionizable molecule comprises one or more charged groups. In some embodiments, an ionizable molecule may be positively charged or negatively charged. For instance, an ionizable molecule may be positively charged. For example, an ionizable molecule may comprise an amine group. As used herein, the term "ionizable molecule" has its ordinary meaning in the art and may refer to a molecule or matrix comprising one or more charged moiety. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule and/or matrix may be selected as desired.

In some cases, an ionizable molecule (e.g., an amino lipid or ionizable lipid) may include one or more precursor moieties that can be converted to charged moieties. For instance, the ionizable molecule may include a neutral moiety that can be hydrolyzed to form a charged moiety, such as those described above. As a non-limiting specific example, the molecule or matrix may include an amide, which can be hydrolyzed to form an amine, respectively. Those of ordinary skill in the art will be able to determine whether a given chemical moiety carries a formal electronic charge (for example, by inspection, pH titration, ionic conductivity measurements, etc.), and/or whether a given chemical moiety can be reacted (e.g., hydrolyzed) to form a chemical moiety that carries a formal electronic charge.

The ionizable molecule (e.g., amino lipid or ionizable lipid) may have any suitable molecular weight. In certain embodiments, the molecular weight of an ionizable molecule is less than or equal to about 2,500 g/mol, less than or equal to about 2,000 g/mol, less than or equal to about 1,500 g/mol, less than or equal to about 1,250 g/mol, less than or equal to about 1,000 g/mol, less than or equal to about 900 g/mol, less than or equal to about 800 g/mol, less than or equal to about 700 g/mol, less than or equal to about 600 g/mol, less than or equal to about 500 g/mol, less than or equal to about 400 g/mol, less than or equal to about 300 g/mol, less than or equal to about 200 g/mol, or less than or equal to about 100 g/mol. In some instances, the molecular weight of an ionizable molecule is greater than or equal to about 100 g/mol, greater than or equal to about 200 g/mol, greater than or equal to about 300 g/mol, greater than or equal to about 400 g/mol, greater than or equal to about 500 g/mol, greater than or equal to about 600 g/mol, greater than or equal to about 700 g/mol, greater than or equal to about 1000 g/mol, greater than or equal to about 1,250 g/mol, greater than or equal to about 1,500 g/mol, greater than or equal to about 1,750 g/mol, greater than or equal to about 2,000 g/mol, or greater than or equal to about 2,250 g/mol. Combinations of the above ranges (e.g., at least about 200 g/mol and less than or equal to about 2,500 g/mol) are also possible. In embodiments in which more than one type of ionizable molecules are present in a particle, each type of ionizable molecule may independently have a molecular weight in one or more of the ranges described above.

In some embodiments, the percentage (e.g., by weight, or by mole) of a single type of ionizable molecule (e.g., amino lipid or ionizable lipid) and/or of all the ionizable molecules within a particle may be greater than or equal to about 15%, greater than or equal to about 16%, greater than or equal to about 17%, greater than or equal to about 18%, greater than or equal to about 19%, greater than or equal to about 20%, greater than or equal to about 21%, greater than or equal to about 22%, greater than or equal to about 23%, greater than or equal to about 24%, greater than or equal to about 25%, greater than or equal to about 30%, greater than or equal to about 35%, greater than or equal to about 40%, greater than or equal to about 42%, greater than or equal to about 45%, greater than or equal to about 48%, greater than or equal to about 50%, greater than or equal to about 52%, greater than or equal to about 55%, greater than or equal to about 58%, greater than or equal to about 60%, greater than or equal to about 62%, greater than or equal to about 65%, or greater than or equal to about 68%. In some instances, the percentage (e.g., by weight, or by mole) may be less than or equal to about 70%, less than or equal to about 68%, less than or equal to about 65%, less than or equal to about 62%, less than or equal to about 60%, less than or equal to about 58%, less than or equal to about 55%, less than or equal to about 52%, less than or equal to about 50%, or less than or equal to about 48%. Combinations of the above referenced ranges are also possible (e.g., greater than or equal to 20% and less than or equal to about 60%, greater than or equal to 40% and less than or equal to about 55%, etc.). In embodiments in which more than one type of ionizable molecule is present in a particle, each type of ionizable molecule may independently have a percentage (e.g., by weight, or by mole) in one or more of the ranges described above. The percentage (e.g., by weight, or by mole) may be determined by extracting the ionizable molecule(s) from the dried particles using, e.g., organic solvents, and measuring the quantity of the agent using high pressure liquid chromatography (i.e., HPLC), liquid chromatography-mass spectrometry (LC-MS), nuclear magnetic resonance (NMR), or mass spectrometry (MS). Those of ordinary skill in the art would be "knowledgeable of techniques to determine the quantity of a component using the above-referenced techniques. For example, HPLC may be used to quantify the amount of a component, by, e.g., comparing the area under the curve of a HPLC chromatogram to a standard curve.

It should be understood that the terms "charged" or "charged moiety" does not refer to a "partial negative charge" or "partial positive charge" on a molecule. The terms "partial negative charge" and "partial positive charge" are given their ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way. In some embodiments, the composition comprises a liposome. A liposome is a lipid particle comprising lipids arranged into one or more concentric lipid bilayers around a central region. The central region of a liposome may comprise an aqueous solution, suspension, or other aqueous composition.

In some embodiments, the composition comprises a lipoplex. A lipoplex is a lipid particle comprising a cationic liposome and a nucleic acid (e.g., mRNA). Lipoplexes may be formed by contacting a liposome comprising a cationic lipid with a nucleic acid. A lipoplex may comprise multiple concentric lipid bilayers, each concentric bilayer separated by one or more nucleic acids. The central region of the lipoplex may comprise an aqueous solution, suspension, or other aqueous composition.

In some embodiments, the composition comprises a lipopolyplex. A lipopolyplex is a lipid particle comprising a lipid bilayer surrounding a complex of a cationic polymer and a nucleic acid (e.g., mRNA). See Midoux & Pichon, *Expert Rev Vaccines*. 2015. 14(2):221-234. A lipopolyplex may be formed by contacting a cationic liposome (e.g., liposome comprising a cationic lipid) with the complex of nucleic acid and cationic polymer. The central region of the lipopolyplex may comprise an aqueous solution, suspension, or other aqueous composition.

In some embodiments, the composition comprises a cationic nanoemulsion. A cationic nanoemulsion comprises a cationic lipid, hydrophilic surfactant, and hydrophobic surfactant.

A liposome, lipoplex, lipopolyplex, or cationic nanoemulsion may comprise a sterol. A liposome, lipoplex, lipopolyplex, or cationic nanoemulsion may comprise a neutral lipid. A liposome, lipoplex, lipopolyplex, or cationic nanoemulsion may comprise a PEG-modified lipid.

Stabilizing Compounds

Some embodiments of compositions are stabilized pharmaceutical compositions. Various non-viral delivery systems, including nanoparticle formulations, present attractive opportunities to overcome many challenges associated with RNA delivery. Lipid nanoparticles (LNPs) have drawn particular attention in recent years as various LNP formulations have shown promise in a variety of pharmaceutical applications. However, lipids have been shown to degrade nucleic acids, including mRNA, and lipid nanoparticle formulations undergo rapid loss of purity when stored as refrigerated liquids. Moreover, the storage stability of mRNA encapsulated within LNPs is lower than that of unencapsulated mRNA.

A class of compounds has been found to stabilize nucleic acids within a lipid carrier such as an LNP, an unexpected and unprecedented discovery which enables applications including extended refrigerated liquid shelf-life, extended in-use periods at room temperature, and extended in-use stability at physiological temperatures up to higher temperatures such as 40° C. Such stabilizing compounds solve a critical problem, as current manufacturing processes and formulations experience a 5-10% purity loss during LNP formation and processing that is typical with current large-scale LNP production.

In some embodiments, the stabilized pharmaceutical composition comprises a nucleic acid formulation comprising a nucleic acid and a stabilizing compound (e.g., a compound of Formula (I), of Formula (II), or a tautomer or solvate thereof). In some embodiments, the stabilized pharmaceutical composition comprises a nucleic acid formulation comprising a nucleic acid and a lipid, and a compound of Formula (I):

(I)

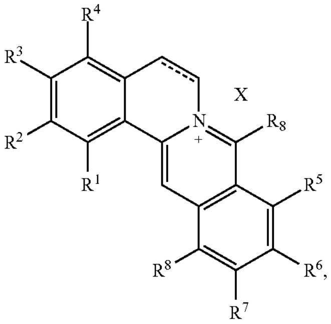

or a tautomer or solvate thereof, wherein:

$\overline{---}$ is a single bond or a double bond;

$R^1$ is H; $R^2$ is $OCH_3$, or together with $R^3$ is $OCH_2O$; $R^3$ is $OCH_3$, or together with $R^2$ is $OCH_2O$; $R^4$ is H; $R^5$ is H or $OCH_3$; $R^6$ is $OCH_3$; $R^7$ is H or $OCH_3$; $R^8$ is H; $R^9$ is H or $CH_3$; and X is a pharmaceutically acceptable anion, e.g., a halide such as chloride.

In some embodiments, the compound of Formula (I) has the structure of:

Formula (Ia)

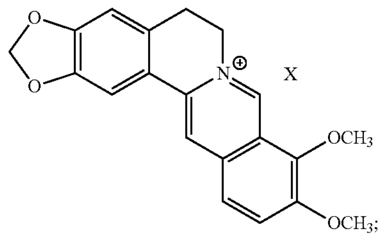

Formula (Ib)

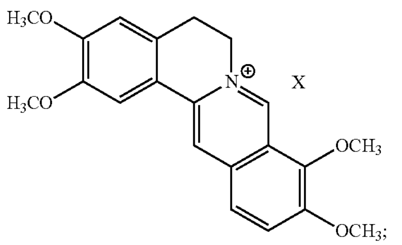

or

Formula (Ic)

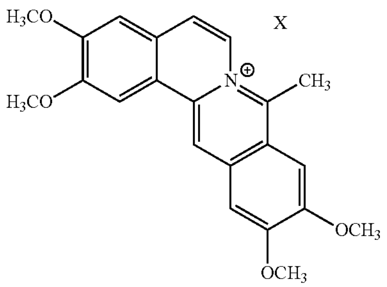

or a tautomer or solvate thereof.

In some embodiments, the stabilized pharmaceutical composition comprises a nucleic acid formulation comprising a nucleic acid and a lipid, and a compound of Formula (II):

(II)

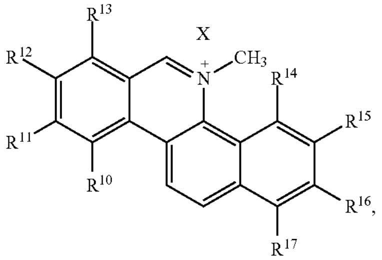

or a tautomer or solvate thereof, wherein:

$R^{10}$ is H; $R^{11}$ is H; $R^{12}$ together with $R^{13}$ is $OCH_2O$; $R^{14}$ is H; $R^{15}$ together with $R^{16}$ is $OCH_2O$; $R^{17}$ is H; and X is a pharmaceutically acceptable anion, e.g., a halide such as chloride.

In some embodiments, the compound of Formula (II) has the structure of:

Formula (IIa)

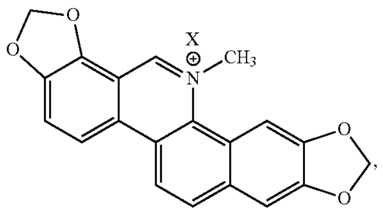

or a tautomer or solvate thereof.

Stabilizing compounds of Formulas (I), (Ia), (Ib), (Ic), (II), and (Iia) are described in International Application No. PCT/US2022/025967, which is incorporated by reference herein in its entirety.

In some embodiments, the nucleic acid formulation comprises lipid nanoparticles. In some embodiments, the nucleic acid is mRNA.

In some embodiments, the stabilizing compound ("the compound") has a purity of at least 70%, 80%, 90%, 95%, or 99%. In some embodiments, the compound contains fewer than 100 ppm of elemental metals. In some embodiments, the stabilized pharmaceutical composition ("the composition") comprises a pharmaceutically acceptable metal chelator, e.g., EDTA (ethylenediaminetetraacetic acid) or DTPA (diethylenetriaminepentaacetic acid).

In some embodiments, the composition is an aqueous solution. In some embodiments, the compound is present at a concentration between about 0.1 mM and about 10 mM in the aqueous solution. In some embodiments, the aqueous solution has a pH of or about 5 to 8, including pH of about 5, 5.5, 6, 6.5, 7, 7.5, or 8. In some embodiments, the aqueous solution does not comprise NaCl. In some embodiments, the aqueous solution comprises NaCl in a concentration of or about 150 mM. In some embodiments, the aqueous solution comprises a phosphate buffer, a tris buffer, an acetate buffer, a histidine buffer, or a citrate buffer.

In some embodiments, microbial growth in the composition is inhibited by the compound.

In some embodiments, the composition is characterized as having a mRNA purity level of greater than 60%, greater than 70%, greater than 80%, or greater than 90% main peak mRNA purity after at least thirty days of storage. In some embodiments, the composition comprises a mRNA purity level of greater than 50% main peak mRNA purity after at least six months of storage. In some embodiments, the storage is at room temperature.

In some embodiments, the composition comprises a lipid nanoparticle encapsulating a mRNA, and the composition comprises less than 50%, less than 60%, less than 70%, less than 80%, less than 90%, or less than 95% RNA fragments after at least thirty days of storage. In some embodiments, the storage temperature is greater than room temperature. In some embodiments, the storage temperature is about 4° C.

In some embodiments, the compound interacts with the nucleic acid comprised within a lipid nanostructure (e.g., a lipid nanoparticle, liposome, or lipoplex), e.g., via pi-pi stacking and/or by changing backbone helicity of the nucleic acid. In some embodiments, the compound intercalates with a nucleic acid. In some embodiments, the compound binds with a nucleic acid, e.g., reversible binding, and/or binding to the stranded regions of the nucleic acid. In some embodiments, the compound self-associates, binds to nucleic acid ribose contacts, and/or binds to nucleic acid base contacts. In some embodiments, the compound does not substantially bind to nucleic acid phosphate contacts. In some embodiments, the positive charge of the compound contributes to nucleic acid binding. In some embodiments, the interacts with the nucleic acid with a binding affinity defined by an equilibrium dissociation constant of less than 10-3 M (e.g., less than 10-4 M, less than 10-5 M, less than 10-5 M, less than 10-7 M, less than 10-8 M, or less than 10-9 M).

In some embodiments, the compound interacts with a nucleic acid and provides shielding from solvent, e.g., water. In some embodiments, the compound shields ribose from solvent more than the compound shields the phosphate groups of the nucleic acid. In some embodiments, the solvent exposure is measured by the solvent accessible surface area (SASA). In some embodiments, a stabilizing compound decreases the solvent accessible area of ribose to about 5-10 $nm^2$. In some embodiments, a stabilizing compound decreases the solvent accessible area of ribose to about 6-8 $nm^2$. In some embodiments, a stabilizing compound decreases the solvent accessible area of phosphate to about 9-12 $nm^2$. In some embodiments, a stabilizing compound decreases the solvent accessible area of phosphate to about 10-11 $nm^2$.

In some embodiments, a nucleic acid that is conformationally stabilized by the compound exhibits thermal unfolding temperatures (measured by circular dichroism or DSC, for example) that are higher than in the absence of the compound. In some embodiments, the compound confers increased stability, e.g., thermal stability, to the nucleic acid in a folded structure, e.g., relative to its unfolded or less folded or more linear form. In some embodiments, the compound causes compaction of the nucleic acid upon interaction with the nucleic acid. In some embodiments, the compound causes a decrease in the hydrodynamic radius of the nucleic acid molecule upon interaction with the nucleic acid. In some embodiments, a stabilizing compound causes compaction or a decrease in the hydrodynamic radius of a nucleic acid molecule by 5%, 10%, 15%, 20%, 25%, 30%, 35%, 40%, 45%, 50%, 55%, 60%, or more. In some embodiments, a stabilizing compound causes compaction or a decrease in the hydrodynamic radius of a nucleic acid molecule when the compound is in a concentration of 1 μM, 2 μM, 3 μM, 4 μM, 5 μM, 6 μM, 7 μM, 8 μM, 9 μM, 10 μM, 15 μM, 20 μM, 25 μM, 30 μM, 35 μM, 40 μM, 45 μM, 50 μM, 60 μM, 70 μM, 80 μM, 90 μM, or 100 μM.

Pharmaceutical Compositions

Provided are compositions comprising proteins or nucleic acids encoding proteins of interest. In some embodiments, the nucleic acids comprise DNA. In some embodiments, the nucleic acids comprise RNA, such as self-amplifying RNA, circular RNA, or mRNA. Preferably, the nucleic acid comprises mRNA. In some embodiments, the proteins are comprised in one or more viral vectors. In some embodiments, the proteins are encoded by one or more nucleic acids comprised in one or more viral vectors.

Compositions may not comprise antigens per se, but rather comprise nucleic acids, in particular mRNA(s), that encode antigens or antigenic sequences that, once delivered to a cell, tissue or subject, can be translated and ultimately produce an immune response. Delivery of nucleic acids, in particular mRNA(s), can be achieved by inclusion of nucleic acids in appropriate carriers or delivery vehicles (e.g., lipid nanoparticles) such that upon administration to cells, tissues or subjects, nucleic acid is taken up by cells which, in turn, express protein(s) encoded by the nucleic acids, e.g., mRNAs. Upon delivery and uptake by cells of the body, the mRNAs are translated in the cytosol and protein antigens are generated by the host cell machinery. The encoded protein antigen(s) are presented and elicit an adaptive humoral and cellular immune response.

Some embodiments of compositions (e.g., pharmaceutical compositions), methods, kits and reagents comprising mRNAs encoding influenza virus antigens and optionally other respiratory virus antigens are suitable for prevention or treatment of influenza virus in humans and other mammals, for example. Compositions (e.g., pharmaceutical compositions) can be used as therapeutic or prophylactic agents. They may be used in medicine to prevent and/or treat an influenza virus infection. In some embodiments, the compositions are used to treat and/or prevent influenza and also one or more additional respiratory infectious diseases, such as coronavirus and/or respiratory syncytial virus infection. Preferably, the composition is a vaccine, and more preferably the composition is an mRNA vaccine.

In some embodiments, a composition containing RNA can be administered to a subject (e.g., a mammalian subject, such as a human subject), and the RNA polynucleotides are translated in vivo to produce an antigenic polypeptide (antigen).

The term "pharmaceutical composition" refers to the combination of an active agent with a carrier, inert or active, making the composition especially suitable for therapeutic use in vivo or ex vivo. A "pharmaceutically acceptable carrier", after being administered to or upon a subject, does not cause undesirable physiological effects.

The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carriers include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences. In some embodiments, the pharmaceutical composition does not comprise protamine.

Compositions may be immunizing compositions (e.g., RNA vaccines (e.g., mRNA vaccines)), and used in methods, kits and reagents for prevention and/or treatment of respiratory virus (e.g., influenza virus) infection in humans and other mammals. Immunizing compositions can be used as therapeutic or prophylactic agents. In some embodiments, immunizing compositions are used to provide prophylactic protection from influenza virus infection. In some embodiments, immunizing compositions are used to treat an influenza virus infection. In some embodiments, embodiments, immunizing compositions are used in the priming of immune effector cells, for example, to activate peripheral blood mononuclear cells (PBMCs) ex vivo, which are then infused (re-infused) into a subject.

Pharmaceutical compositions may be in a form for administration intramuscularly, intranasally, subcutaneously, or intradermally. Preferably, the pharmaceutical compositions are in a form for administration intramuscularly.

Uses, Dosing, Administration

Provided are methods of administering a composition to a subject (e.g., a mammalian subject, preferably a human subject) in an effective amount to induce an antigen-specific immune response.

An "effective amount," "pharmaceutically effective amount," or "immunogenically effective amount" of a composition refers to a nontoxic but sufficient amount of an agent to provide the desired biological result. That result may be induction of an antibody response and/or T cell response to an antigen. An appropriate effective amount in any individual case may be determined by one of ordinary skill in the art using routine experimentation. Typically, an effective amount of a composition provides an induced or boosted immune response as a function of antigen production in the cells of the subject.

The effective amount (e.g., effective dose) of RNA in a composition may be as low as 5 μg, administered for example as a single dose. In some embodiments, the effective amount is a total dose of 5 μg-300 μg, for example, 5 μg-30 μg, 5 μg-25 μg, 5 μg-20 μg, 5 μg-15 μg, 5 μg -10 μg, 10 μg-30 μg, 10 μg-25 μg, 10 μg-20 μg, 10 μg-15 μg, 15 μg-30 μg, 15 μg-25 μg, 15 μg-20 μg, 20 μg-30 μg, 25 μg-30 μg, 25 μg-50 μg, 25 μg-150 μg, 25 μg-200 μg, 25 μg-250 μg, or 25 μg-300 μg. In some embodiments, the effective amount is 50 μg RNA. In some embodiments, the effective dose (e.g., effective amount) is at least 10 μg and less than 25 μg of RNA. In some embodiments, the effective dose (e.g., effective amount) is at least 5 μg and less than 25 μg of RNA. For example, the effective amount may be a total dose of 2.5 μg, 5 μg, 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 110 μg, 120 μg, 130 μg, 140 μg, 150 μg, 160 μg, 170 μg, 180 μg, 190 μg, 200 μg, 250 μg, or 300 μg. Any of the doses described above may be an effective amount for a booster dose; for example, in some embodiments, the booster dose is a total dose of 15 μg, 27.5 μg, 30 μg, 50 μg, 52.5 μg, 55 μg, or 60 μg RNA. In some embodiments, the booster dose is 50 μg RNA.

Any suitable method may be used to determine the ability of a composition to elicit an immune response (e.g., antigen-specific antibody production, antigen-specific CD8+ T cell activation or proliferation, and/or antigen-specific CD4+ T cell activation or proliferation). Antibody responses to an antigen may be measured, for example, by ELISA, HAI assay, or microneutralization assay of sera. T cell responses to an antigen may be measured, for example, by flow cytometry for analysis of cell subsets. In some embodiments, the effectiveness of a composition is determined using an animal model. Suitable animal models for influenza include mice, guinea pigs, ferrets, and swine. For example, a composition may be administered to an animal, after which blood, sera, peripheral blood mononuclear cells, lymph nodes, the spleen, and/or other organs of the animal may be analyzed for antibody and/or cellular responses. Viral challenge following administration of a composition may also be used to measure the efficacy of a composition. For example, a composition may be administered to an animal, after which the animal is inoculated with a virus, and the animal is monitored for signs of infection-related pathology (e.g., weight loss, respiratory defects, death) or viral replication (e.g., viral shedding, viremia). In some embodiments, the animal model is a mouse model. In some embodiments, the animal model is a ferret model. In some embodiments, the animal model is a guinea pig model. In some embodiments, a composition induces sterilizing immunity to a virus. A host with sterilizing immunity to a virus does not become infected (experience signs or symptoms of viral infection) following exposure to the virus.

In some embodiments, a composition is administered a single time. In some embodiments, a first composition is administered, and then a second composition is administered later. In some embodiments the two or more compositions are administered at least 1 week, at least 2 weeks, at least 3 weeks, at least 4 weeks, at least 5 weeks, at least 6 weeks, at least 7 week, and least 8 weeks, at least 3 months, at least 4 months, at least 5 months, at least 6 months, at least 7 months, at least 8 months, at least 9 months, at least 10 months, at least 11 months, or at least 12 months apart.

In some embodiments, a subject has not been vaccinated against an influenza virus for at least 2, at least 4, at least 6, at least 8, at least 10, or at least 12 months prior to administration of a composition. In some embodiments, a subject has not previously been vaccinated against an influenza virus comprising a reference influenza virus HA protein. In some embodiments, a subject has not previously been administered a composition comprising a reference HA protein or a nucleic acid encoding the reference HA protein.

Pharmaceutical compositions may be administered intramuscularly, intranasally, subcutaneously, or intradermally. Preferably, the pharmaceutical compositions are administered intramuscularly.

EXAMPLES

Example 1. Stabilizing Mutations: Influenza B Virus Hemagglutinin

Figure 1B:
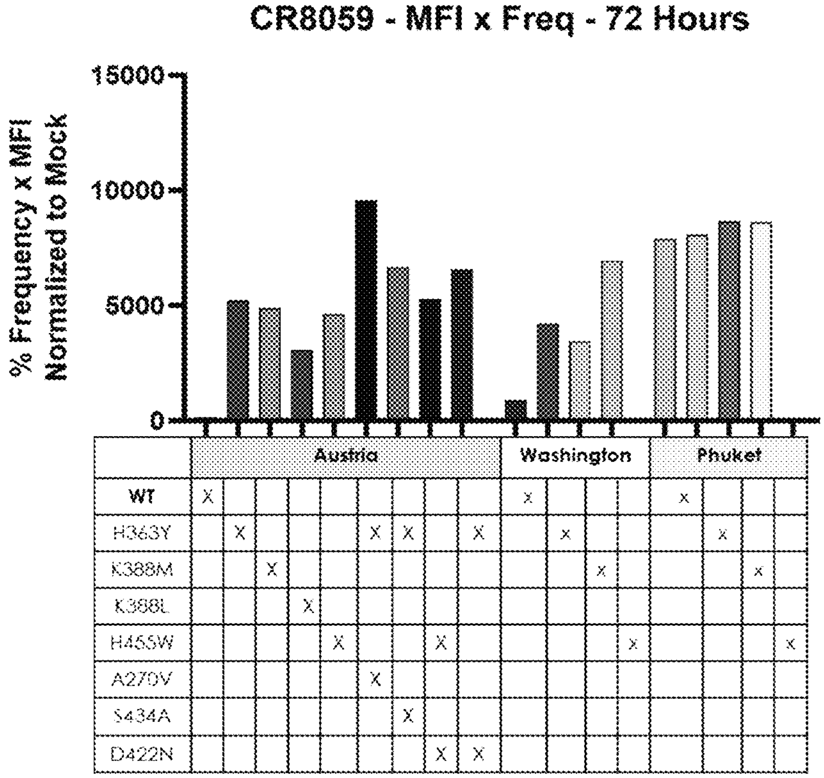
FIG. 1B is graph showing anti-hemagglutinin (CR8059) antibody binding in vitro to protein expressed by mRNA encoding mutated influenza B virus hemagglutinin at 72 hours post-transfection into cells with transIT at 250 ng mRNA/$1\times10^6$ cells. Substitutions in FIG. 1B are numbered according to post-cleavage forms of the HA proteins.
Figure 1C:
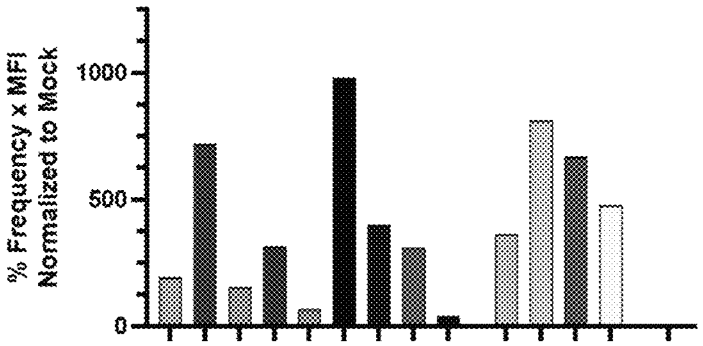
FIG. 1C is graph showing anti-hemagglutinin (CR8059) antibody binding in vitro to protein expressed by mRNA encoding mutated influenza B virus hemagglutinin at 72 hours post-transfection into cells with transIT at 100 ng mRNA/$1\times10^6$ cells. Substitutions in FIG. 1C are numbered according to post-cleavage forms of the HA proteins.
Figure 1D:
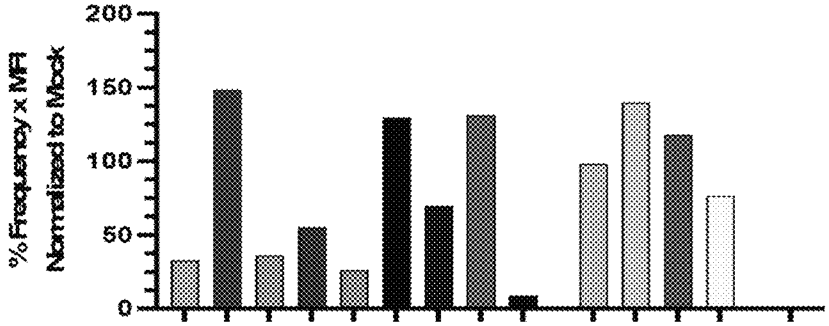
FIG. 1D is graph showing polyclonal sera antibody binding in vitro to protein expressed by mRNA encoding mutated influenza B virus hemagglutinin at 72 hours post-transfection into cells with transIT at 100 ng mRNA/$1\times10^6$ cells. Substitutions in FIG. 1D are numbered according to post-cleavage forms of the HA proteins.

In this Example, a variety of different stabilizing mutations were made to influenza B virus hemagglutinin (HA) antigens and the effects were tested. First, mRNA encoding influenza B virus HA antigens having stabilizing mutations was transfected (250 ng/1×$10^6$ cells). Expression levels were determined 72 hours later (FIGS. 1A-1B) and show that the stabilizing mutations are beneficial to in vitro expression in different influenza B virus HA backbones. CR8059 (an IBV HA strain-specific antibody) data is shown in FIG. 1A and polyclonal sera expression data is shown in FIG. 1B. The experiments were repeated for the B/Austria and B/Phuket strains using mRNA formulated in lipid nanoparticles without a transfection reagent (100 ng/1×$10^6$ cells). The expression data 72 hours after transfection is shown in FIGS. 1C-1D and further demonstrates that the stabilizing mutations increase expression above levels of the mock-transfected cells.

Figure 2A:
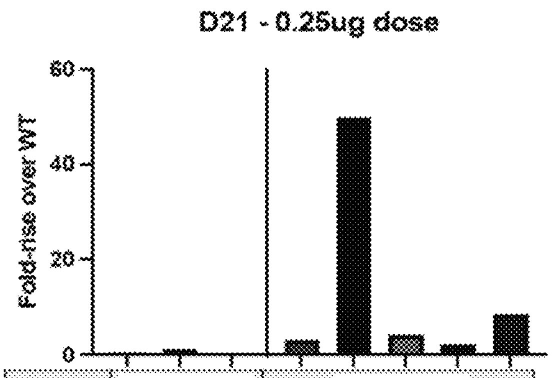
FIG. 2A is graph showing antibody binding titers (fold-rise over wild-type) resulting from injection of mRNA encoding mutated influenza B virus hemagglutinin in mice at 21 days post-injection with a 0.25 μg dose. Substitutions in FIG. 2A are numbered according to post-cleavage forms of the HA proteins.
Figure 2B:
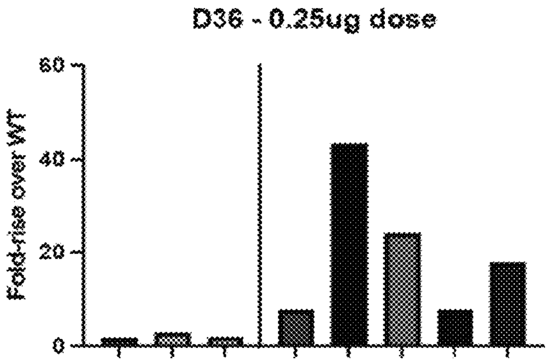
FIG. 2B is graph showing antibody binding titers (fold-rise over wild-type) result from injection of mRNA encoding mutated influenza B virus hemagglutinin in mice at 36 days post-injection with a 0.25 μg dose. Substitutions in FIG. 2B are numbered according to post-cleavage forms of the HA proteins.
Figure 3A:
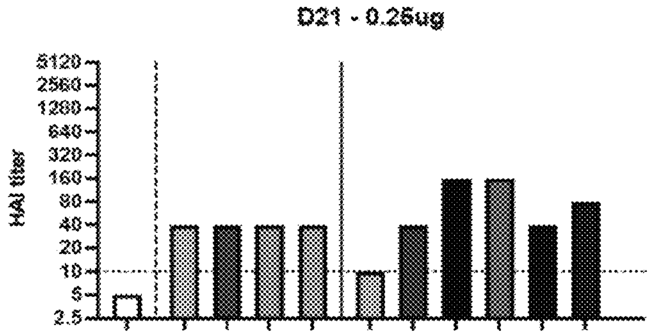
FIG. 3A is a graph showing HAI titers of sera collected from mice injected with 0.25 μg of mRNA encoding a mutated influenza B virus hemagglutinin protein at 21 days post-injection. Substitutions in FIG. 3A are numbered according to post-cleavage forms of the HA proteins.
Figure 3B:
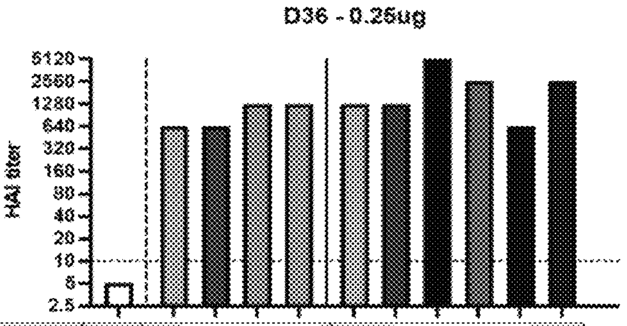
FIG. 3B is a graph showing HAI titers of sera collected from mice injected with 0.25 μg of mRNA encoding a mutated influenza B virus hemagglutinin protein at 36 days post-injection. Substitutions in FIG. 3B are numbered according to post-cleavage forms of the HA proteins.
Figure 4A:
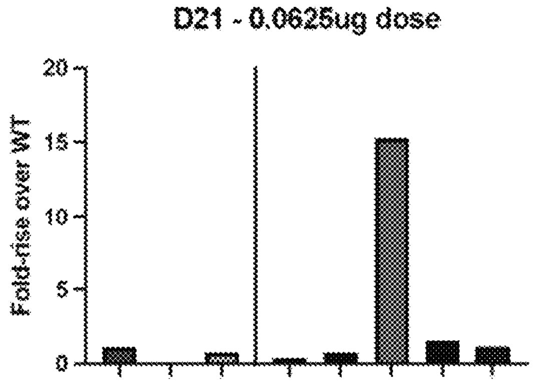
FIG. 4A is graph showing antibody binding titers from mice administered mRNA encoding a mutated B virus hemagglutinin protein at 21 days post-injection with a 0.0625 μg dose. Substitutions in FIG. 4A are numbered according to post-cleavage forms of the HA proteins.
Figure 4B:
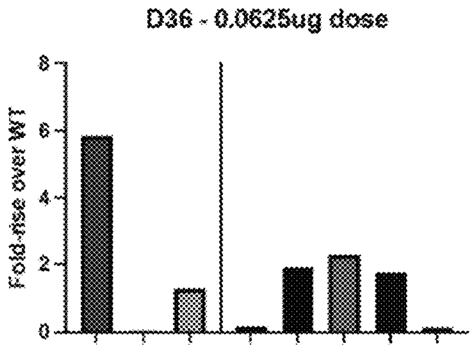
FIG. 4B is graph showing antibody binding titers from mice administered mRNA encoding a mutated IBV hemagglutinin protein at 36 days post-injection with a 0.0625 μg dose. Substitutions in FIG. 4B are numbered according to post-cleavage forms of the HA proteins.
Figure 5A:
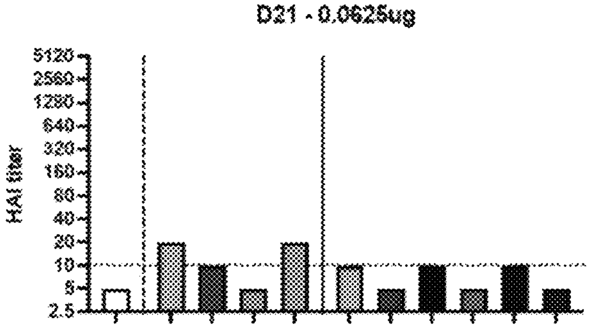
FIG. 5A is a graph showing HAI titers of sera collected from mice injected with 0.0625 μg of mRNA encoding a mutated influenza B virus hemagglutinin protein at 21 days post-injection. Substitutions in FIG. 5A are numbered according to post-cleavage forms of the HA proteins.
Figure 5B:
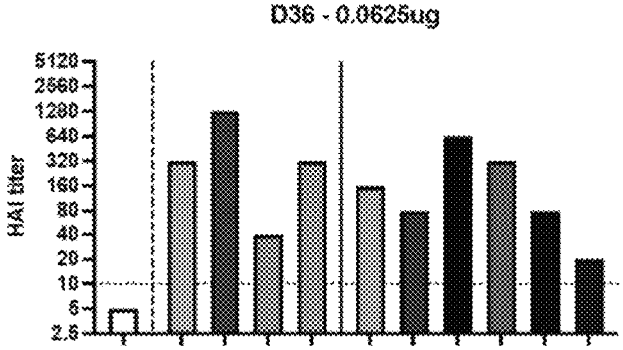
FIG. 5B is a graph showing an HAI titer of serum collected from mice injected with 0.0625 μg of mRNA encoding a mutated influenza B virus hemagglutinin protein at 36 days post-injection. Substitutions in FIG. 5B are numbered according to post-cleavage forms of the HA proteins.
Figure 6A:
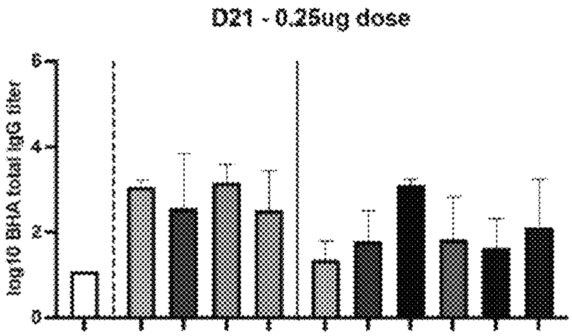
FIG. 6A is graph showing antibody binding titers from mice administered mRNA encoding a mutated IBV hemagglutinin protein, at 21 days post-injection with a 0.25 μg dose. Substitutions in FIG. 6A are numbered according to post-cleavage forms of the HA proteins.
Figure 6B:
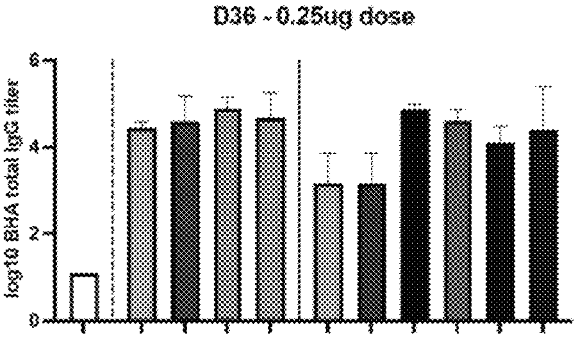
FIG. 6B is graph showing antibody binding titers from mice administered mRNA encoding a mutated IBV hemagglutinin protein encoded, at 36 days post-injection with a 0.25 μg dose. Substitutions in FIG. 6B are numbered according to post-cleavage forms of the HA proteins.
Figure 7A:
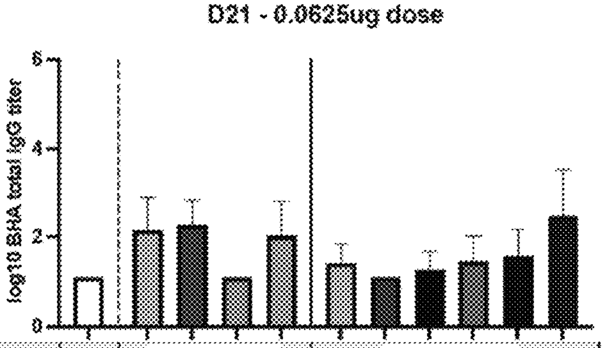
FIG. 7A is graph showing antibody binding titers from mice administered mRNA encoding a mutated IBV hemagglutinin protein, at 21 days post-injection with a 0.0625 μg dose. Substitutions in FIG. 7A are numbered according to post-cleavage forms of the HA proteins.
Figure 7B:
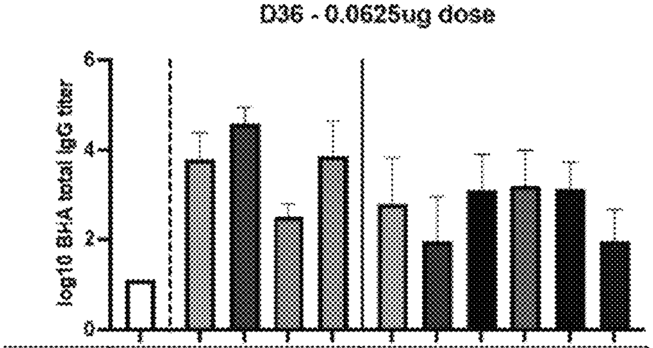
FIG. 7B is graph showing antibody binding titers from mice administered mRNA encoding a mutated B hemagglutinin protein, at 36 days post-injection with a 0.0625 μg dose. Substitutions in FIG. 7B are numbered according to post-cleavage forms of the HA proteins.

In an in vivo experiment, mice were administered mRNA encoding influenza B virus HA antigens having different stabilizing mutations at 0.25 μg/dose. Twenty-one and 36 days later, antibody-binding titers were measured by ELISA and normalized to wild-type mice. The data in FIG. 2A (Day 21) and FIG. 2B (Day 36) demonstrate that the combination of H381Y and A288V substitutions (numbered according to the full-length amino acid sequence of SEQ ID NO: 71 before signal peptide cleavage) had the greatest impact on binding titers. The ELISA titer data is provided in FIG. 6A (Day 21) and FIG. 6B (Day 36). HAI titers were measured in the same mice (FIG. 3A, Day 21; FIG. 3B, Day 36), and the combination of H381Y and A288V mutations was also found to have the greatest impact on HAI titer at Day 36. The antibody titer data for the 0.0625 μg dose is shown in FIGS. 4A-4B (ELISA data in FIGS. 7A-7B) and the HAI titers are shown in FIGS. 5A-5B. With respect to the HAI titers, the response to the 0.0625 μg dose was variable, although the H381Y and the H381Y+A288V mutations were found to induce the highest titers.

Figure 8:
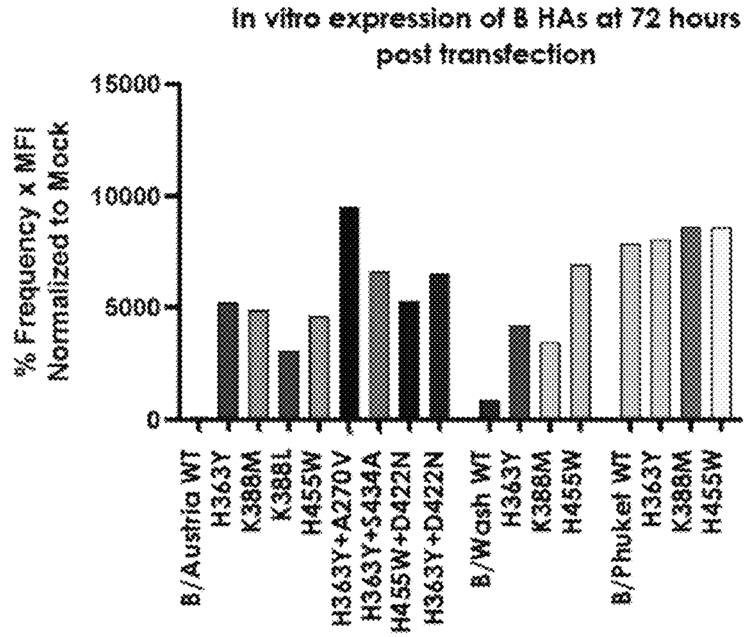
FIG. 8 shows in vitro expression data 72 hours after cells were transfected with mRNA encoding a mutated influenza B virus hemagglutinin protein (mutations to the protein are shown on the X-axis). Substitutions in FIG. 8 are numbered according to post-cleavage forms of the HA proteins.
Figure 9:
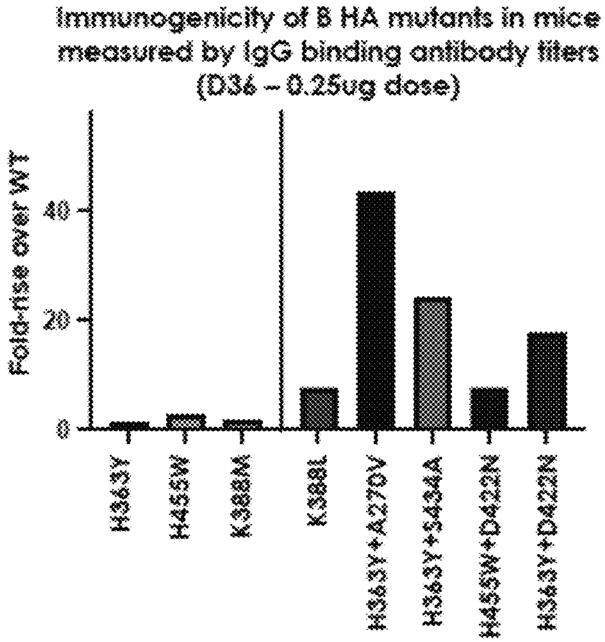
FIG. 9 shows IgG antibody binding titers in mice, 36 days after administration of a 0.25 μg dose of mRNA encoding a mutated influenza B virus hemagglutinin protein (mutations to the protein are shown on the X-axis). Substitutions in FIG. 9 are numbered according to post-cleavage forms of the HA proteins.

Further screening of the different mutations is shown in FIGS. 8 and 9, which depict the in vitro expression of different mutant influenza B virus HA antigens and immunogenicity (measured as IgG antibody binding titers on Day 36 after a 0.25 μg dose), respectively. Single point mutant influenza B virus HA proteins were found to have higher in vitro expression compared to wild-type and further improvements were observed for double mutants in the B/Austria (B/Victoria lineage) background. The single point mutations also improve expression for B/Washington HA and to a lesser extent B/Phuket HA proteins of the B/Yamagata lineage. In vivo, the double mutant, H381Y+A288V, showed the highest fold-rise over wild-type at a 0.25 ug dose.

Example 2. Effects of HA Stabilization on In Vitro Expression

Figure 10A:
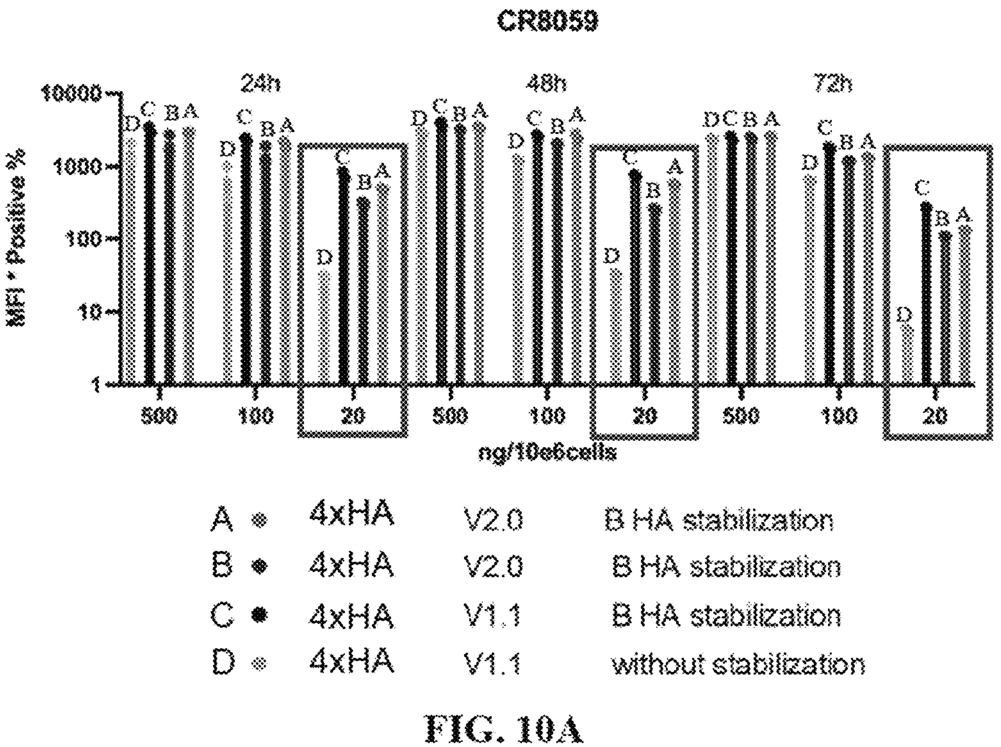
FIGS. 10A-10C are graphs showing show the effect of IBV HA stabilizing mutations on 4×HA in vitro expression. The graphs show expression levels following staining with CR8059 (a IBV HA-specific antibody.
Figure 10B:
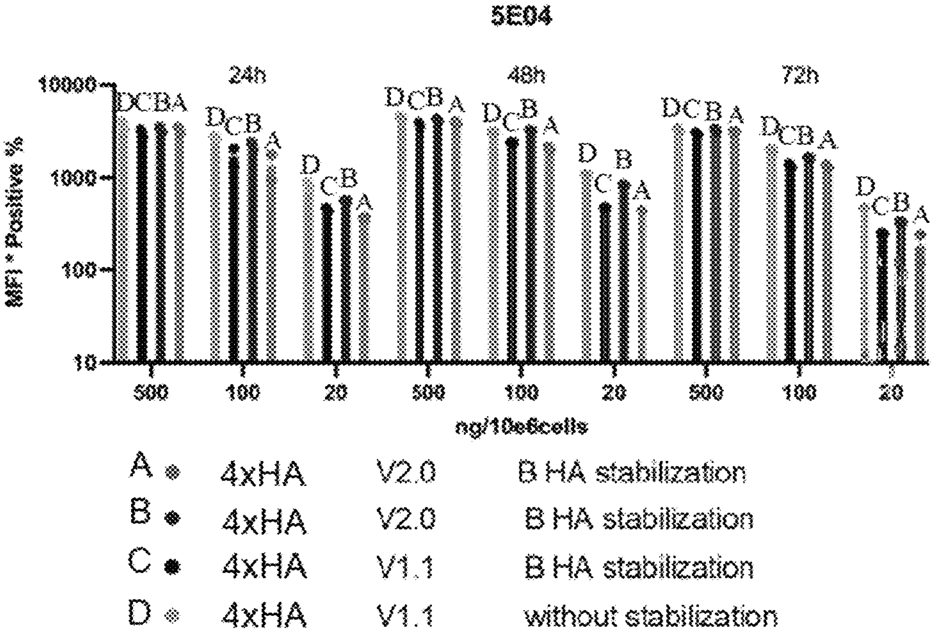
Figure 10C:
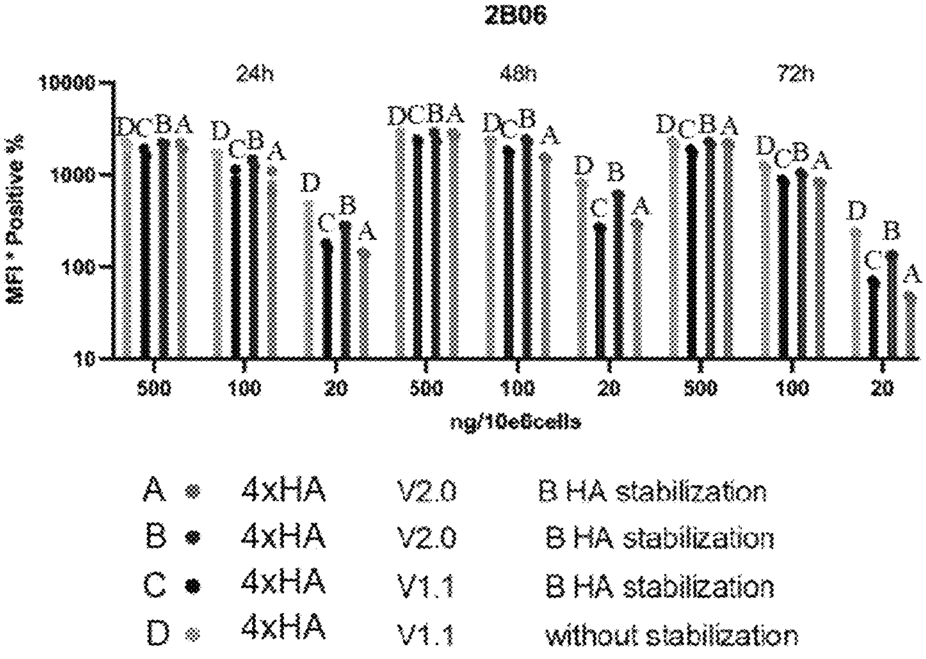

The effects of different stabilizing HA mutations on in vitro expression levels were examined. Expi293 cells were incubated with mRNA encoding four HA antigens:two HA antigens from influenza A viruses and two HA antigens from influenza B viruses. The HA antigens from influenza B viruses were either stabilized with at least one mutation, or not stabilized (wild-type HA). After incubation, the cells were stained with a IBV HA-specific antibody (CR8059), which showed that the stabilized constructs were more highly expressed at relatively lower dosage levels (FIG. 10A). Cells were also stained with an H3-specific antibody (5E04) (FIG. 10B) or an H1-specific antibody (2B06) (FIG. 10C). With respect to the A strain-specific antibodies, no differences in expression levels were noted with respect to the mutated and wild-type mRNA, demonstrating that the stabilized influenza B virus HA antigens did not affect the expression of the influenza A virus HA antigens.

Example 3. Combination Flu/SARS-CoV-2 Vaccine in Mice

The effects of administering a combination vaccine comprising mRNA encoding influenza virus HA antigens and a SARS-CoV-2 antigen were examined. The combination vaccine was created from a combination of:

"4×HA", an mRNA vaccine comprising four mRNAs encoding two HA antigens from influenza viruses (H1 and H3) and two HA antigens from influenza B viruses (H1 HA+H3 HA+B/Yamagata lineage HA+B/Victoria lineage HA at 1:1:1:1 ratio)

Figure 11A:
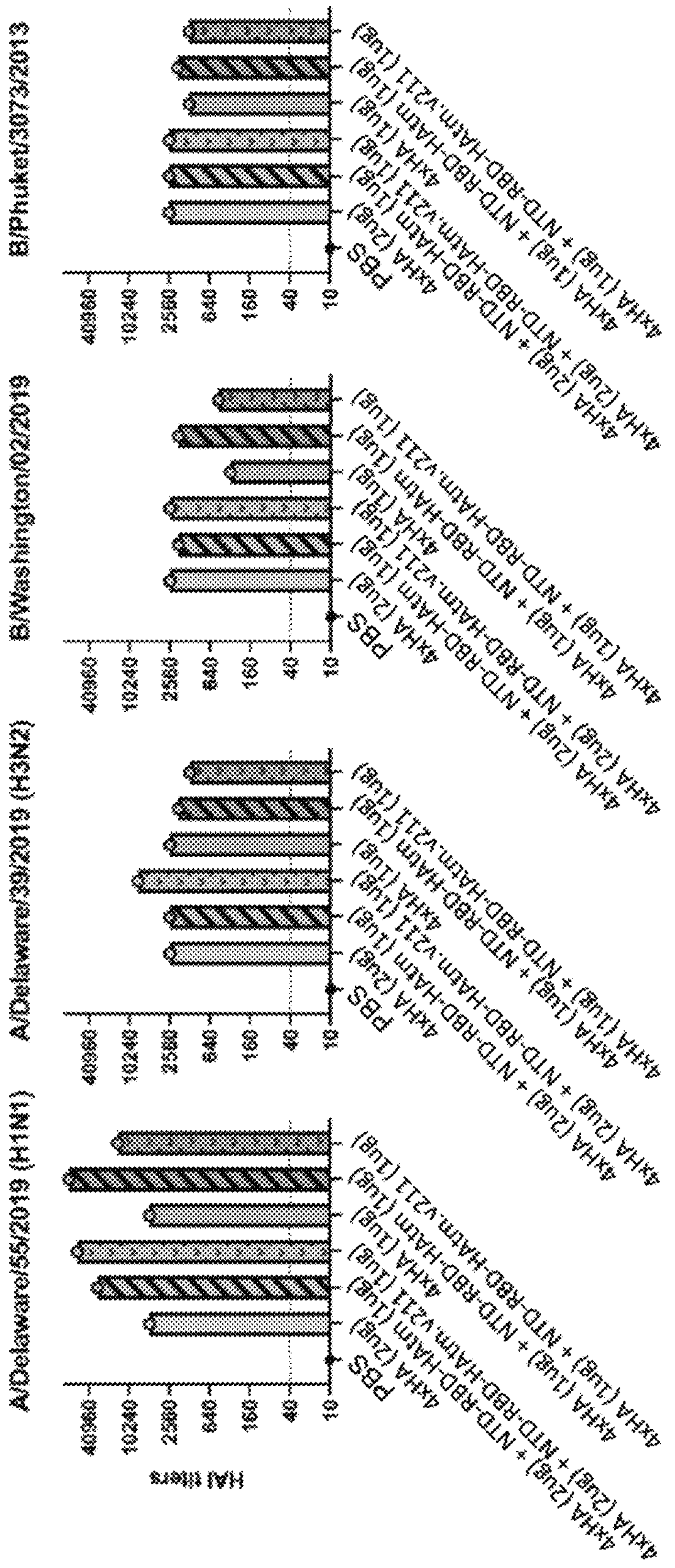
FIGS. 11A-11B show the HAI titers (FIG. 11A) and neutralizing antibody titers (FIG. 11B) present in samples from mice administered a flu vaccine (4×HA), a SARS-CoV-2 vaccine (NTD-RBD-HAtm), or a combination vaccine including mRNA encoding both influenza virus and coronavirus antigens (NTD-RBD-hAtm).
Figure 11B:
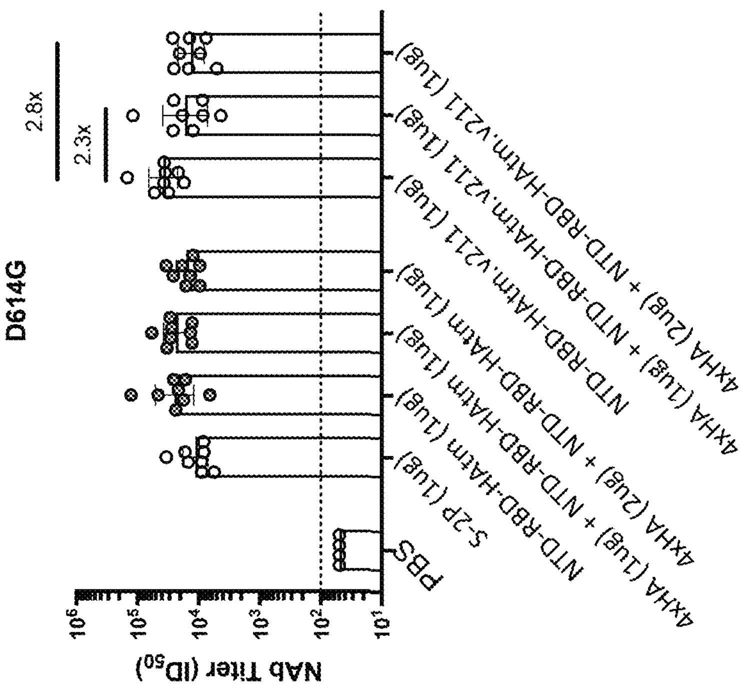

"NTD-RBD-HAtm", an mRNA vaccine comprising mRNA encoding a SARS-CoV-2 fusion protein comprising the receptor binding domain (RBD) and N-terminal domain (NTD) of the Spike protein, linked with an influenza virus HA transmembrane sequence The effects of the resulting combination vaccine, "4×HA/NTD-RBD-HAtm" (4×HA and NTD-RBD-HAtm mixed at a 1:1 or 2:1 ratio) were tested. BALB/c mice were administered the different vaccines in a prime-boost protocol and the resulting HAI titers and SARS-CoV-2 neutralization titers were measured. It was found that the inclusion of additional mRNA encoding a SARS-CoV-2 antigen did not impact the resulting HAI titers compared to the group administered the flu vaccine (4×HA) alone (FIG. 11A). In addition, SARS-CoV-2 neutralization titers were reduced relative to administration of NTD-RBd-HAtm by itself, but only to levels seen in mice administered mRNA encoding a SARS-CoV-2 protein having two stabilizing proline mutations (FIG. 11B).

Example 4. A Multi-Phase, Adaptive, Randomized, Observer-Blind, Placebo- and Active-Control Study to Evaluate the Safety, Reactogenicity, and Immunogenicity of mRNA-Based Influenza and SARS-CoV-2 Multi-Component Vaccines in Healthy Adults 4×HA/NTD-RBD-HAtm, a lipid-encapsulated mRNA-based prophylactic combination vaccine encoding influenza virus and SARS-CoV-2 antigens, is being developed. 4×HA/NTD-RBD-HAtm contains six mRNAs: four sequences encoding surface glycoprotein hemagglutinin (HA) of seasonal influenza viruses and two sequences encoding linked N terminal domain (NTD) and receptor-binding domain (RBD) of the SARS-CoV-2 spike protein. 4×HA/NTD-RBD-HAtm encodes the respective antigens also encoded by 4×HA (seasonal influenza) and NTD-RBD-HAtm (SARS-CoV-2 bivalent booster).

Study Vaccines: 4×HA/NTD-RBD-HAtm (4×HA/NTD-RBD-HAtm.1, 4×HA/NTD-RBD-HAtm.2, and 4×HA/NTD-RBD-HAtm.3)

As noted above, 4×HA/NTD-RBD-HAtm contains 6 mRNAs: 4 mRNAs that each encode a membrane-bound hemagglutinin (HA) of one of the 4 different influenza virus strains recommended by the WHO in an equivalent mass ratio (SEQ ID NOs: 64-67) and 2 sequences that encode the N-terminal domain (NTD) and receptor-binding domain (RBD) of the SARS-CoV-2 Spike glycoprotein of the original (Wuhan-Hu-1) and BA.4/BA.5 variants in an equivalent mass ratio (SEQ ID NOs: 68-69). The NTD and RBD sequences are linked together with a short flexible linker and a transmembrane domain anchors the protein to the cell membrane. The influenza virus HA proteins encoded by 4×HA/NTD-RBD-HAtm are also encoded by 4×HA (influenza) vaccine, and the SARS-CoV-2 fusion proteins are also encoded by the NTD-RBD-HAtm (SARS-CoV-2 bivalent) vaccine, except that the influenza B virus HA antigens encoded by 4×HA/NTD-RBD-HAtm vaccine contain stabilizing point mutations. The mRNAs in 4×HA/NTD-RBD-HAtm further comprise an updated sequence in the non-coding region.

Three 4×HA/NTD-RBD-HAtm vaccine compositions will be evaluated; each contain the same 6 mRNAs, but differ by the ratio of the combined mass of the 4 influenza virus mRNAs to the combined mass of the two SARS COV 2 mRNAs:

1. 4×HA/NTD-RBD-HAtm.1:5:1 combined influenza virus mRNA to combined SARS-CoV-2 mRNA mass ratio.
2. 4×HA/NTD-RBD-HAtm.2:10:1 combined influenza virus mRNA to combined SARs-CoV-2 mRNA mass ratio.
3. 4×HA/NTD-RBD-HAtm.3:20:1 combined influenza virus mRNA to combined SARS-CoV-2 mRNA mass ratio.

4×HA, NTD-RBD-HAtm, and S-2P will be used as controls. 4×HA is an LNP-encapsulated, mRNA-based, prophylactic vaccine containing 4 mRNAs that encode membrane-bound HA of the 4 different influenza virus strains recommended by the WHO in an equivalent mRNA mass ratio. NTD-RBD-HAtm is an LNP-encapsulated, mRNA-based prophylactic vaccine that encodes the RBD and NTD of the SARS-CoV-2 spike glycoprotein. The NTD and RBD sequences are linked together with a short flexible linker and a transmembrane domain anchors the protein to the cell membrane. S-2P.222 (Bivalent vaccine) is an LNP-encapsulated, mRNA-based prophylactic vaccine that contains 2 mRNAs that encode the full-length SARS-CoV-2 prefusion-stabilized spike glycoproteins of the original (Wuhan-Hu-1) and BA.4/BA.5 variants in an equivalent mass ratio. The lipid nanoparticle comprises 48% Compound 1, 2.5% PEG-DMG, 38.5% cholesterol, and 11% DSPC.

Cohorts and Duration

The trial will enroll approximately 1050 participants into 1 of 2 age cohorts: Cohort A for participants ≥65 to <80 years of age (approximately 550 participants) and Cohort B for participants ≥18 to <65 years of age (approximately 500 participants). In Cohort B, approximately 500 participants will be randomized (in equal allocation ratio) into the investigational vaccine arms with stratification by 2 age groups, ≥18 to <50 years and ≥50 to <65 years, and approximately 50% of the participants will be ≥50 to <65 years of age. The study intervention information, including dosages, is provided in Table E4-1 below.

All participants will have follow-up visits for 6 months after the study vaccination.

TABLE E4-1

Study Interventions and Dosages

| Cohort A Arms: (65-79 years) | Cohort B Arms: (18-64 years) | Intervention | Total mRNA Dose (μg) | Component mRNA Dose (μg) COVID | Flu |
|---|---|---|---|---|---|
| | B1 | 4xHA/NTD-RBD- | 15 | 2.5 | 12.5 |
| A2 | B2 | HAtm.1 (1:5) | 30 | 5 | 25 |
| A3 | | | 60 | 10 | 50 |
| A4 | B4 | 4xHA/NTD-RBD- | 27.5 | 2.5 | 25 |
| A5 | B5 | HAtm.2 (1:10) | 55 | 5 | 50 |
| A6 | B6 | 4xHA/NTD-RBD-HAtm.3 (1:20) | 52.5 | 2.5 | 50 |
| A7 | B7 | 4xHA.4 | 50 | — | 50 |
| A8 | B8 | NTD-RBD-HAtm (Wuhan-Hu-1 and BA.4/BA.5) | 5 | 5 | — |
| A9 | B9 | S-2P Bivalent (Wuhan-Hu-1 and BA.4/BA.5) | 50 | 50 | — |
| A10 | B10 | 4xHA | 50 | — | 50 |
| A11 | B11 | Fluaria | — | — | — |
| A12 | | Fluzone HD | — | — | — |

Objectives and Endpoints

The primary objective of this trial is to evaluate the safety and reactogenicity of the candidate vaccines across study arms.

The secondary objectives are to evaluate the humoral immune responses to vaccine-matched strains for influenza virus and SARS-CoV-2 across study vaccine arms at Day 29 and to evaluate the humoral immune responses to vaccine-matched strains for influenza virus and SARS-CoV-2 across study vaccine arms at all evaluable humoral immunogenicity time points. These will be evidenced by the following endpoints: GMT and GMFR at Day 29 compared to Day 1 by HAI assay for influenza and by PsVNA for SARS-CoV-2; influenza: percentage of participants with seroconversion, defined as a Day 29 titer ≥1:40 if baseline is <1:10 or a 4-fold or greater rise if baseline is ≥1:10 in anti-HA antibodies measured by HAI assay; SARS-CoV-2: percentage of participants with seroresponse, defined as a Day 29 titer ≥4-fold if baseline is ≥LLOQ or ≥4×LLOQ if baseline titer is <LLOQ in nAb titers measured by PsVNA; GMT and GMFR at all evaluable time points compared to Day 1 by HAI for influenza and PsVNA for SARS-CoV-2; influenza: percentage of participants with seroconversion; and SARS-CoV-2: percentage of participants with seroresponse.

The exploratory objectives are to evaluate the humoral immune responses to vaccine-mismatched strains for influenza virus and SARS-CoV-2 across study vaccine arms; to evaluate the humoral immune responses against vaccine-matched and vaccine-mismatched strains for influenza virus and SARS-CoV-2 across study vaccine arms; to evaluate the cellular immune responses against influenza virus and SARS-CoV-2 in a subset of participants; to further characterize the immune response to influenza virus and SARS-CoV-2 across study vaccine arms; and to assess the occurrence of clinical influenza and COVID-19 in study participants and characterize their immune response to infection and viral isolates. The exploratory objectives will be measured by the following endpoints: GMT and GMFR at all evaluable time points compared to Day 1 by HAI for influenza virus and PsVNA for SARS-CoV-2; influenza: percentage of participants with seroconversion; SARS-CoV-2: percentage of participants with seroresponse; GMT and GMFR at all evaluable time points compared to Day 1 by alternative methods, including, but not limited to: microneutralization assay for influenza virus or ligand-binding assay for SARS-CoV-2; frequency, magnitude, and phenotype of virus-specific T-cell and B-cell responses measured by flow cytometry or other methods; targeted repertoire analysis of B-cells and T-cells after vaccination; frequency, specificities, or other endpoints to be determined for the further characterization of immune responses; frequency of RT-PCR-confirmed clinical influenza and COVID-19; and assessment of immune responses to infection and viral isolates.

Example 5. Stabilizing Mutations for 4 Influenza Virus Strains

In this Example, several stabilizing mutations were made to hemagglutinin (HA) antigens of five influenza viruses: B/Austria/1359417/2021 HA (B/Victoria lineage), B/Phuket/3073/2013 (B/Yamagata lineage) HA, A/Darwin/6/2021 H3 HA, A/Wisconsin/67/2022 H1 HA, and A/Sydney H1 HA. Effects on expression, antibody binding, yield, and thermostability, as described in Example 1, were measured for each mutant HA. Briefly, plasmids encoding mRNAs encoding each candidate stabilized mutant HA were constructed and used to transfect cells. After 72 hours, surface expression levels were determined using flow cytometry on cell preparations stained with polyclonal sera antibodies, HA subtype-specific antigen antibodies, and/or HA subtype region-specific antibodies. Melting temperature, oligomerization profile, and yield were determined for soluble versions of each candidate protein using thermal shift assays, sodium dodecyl sulfate-polyacrylamide gel electrophoresis (SDS-PAGE), and AlphaLISA.

Figure 12A:
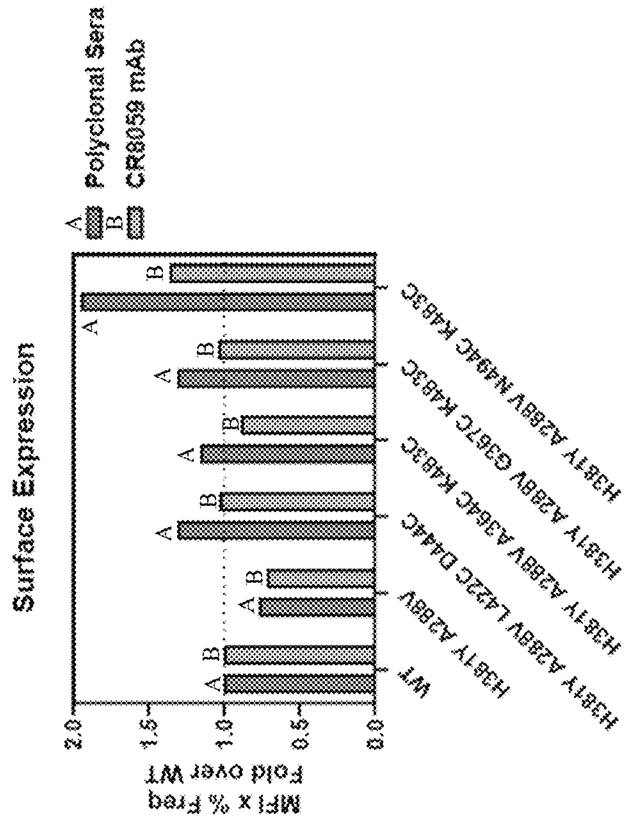
FIGS. 12A-12C show the effects of stabilizing mutant influenza B/Victoria lineage virus HA proteins comprising the following amino acid mutations relative to wild-type influenza B/Austria/1359417/2021 (B/Victoria lineage) virus HA protein amino acid sequence (SEQ ID NO: 71): (i) H381Y-A288V, (ii) H381Y-A288V-L422C-D444C, (iii) H381Y-A288V-A364C-K483C, (iv) H381Y-A288V-G367C-K483C, and (v) H381Y-288V-N494C-K483C.
Figure 12B:
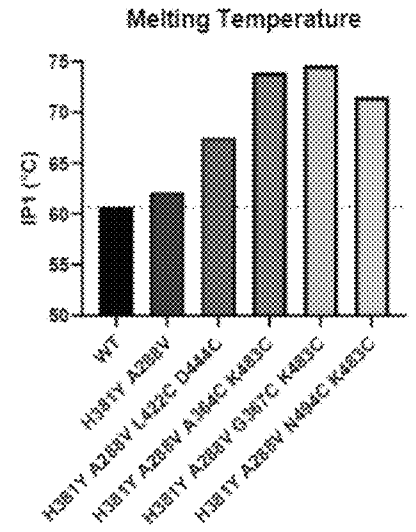
Figure 12C:
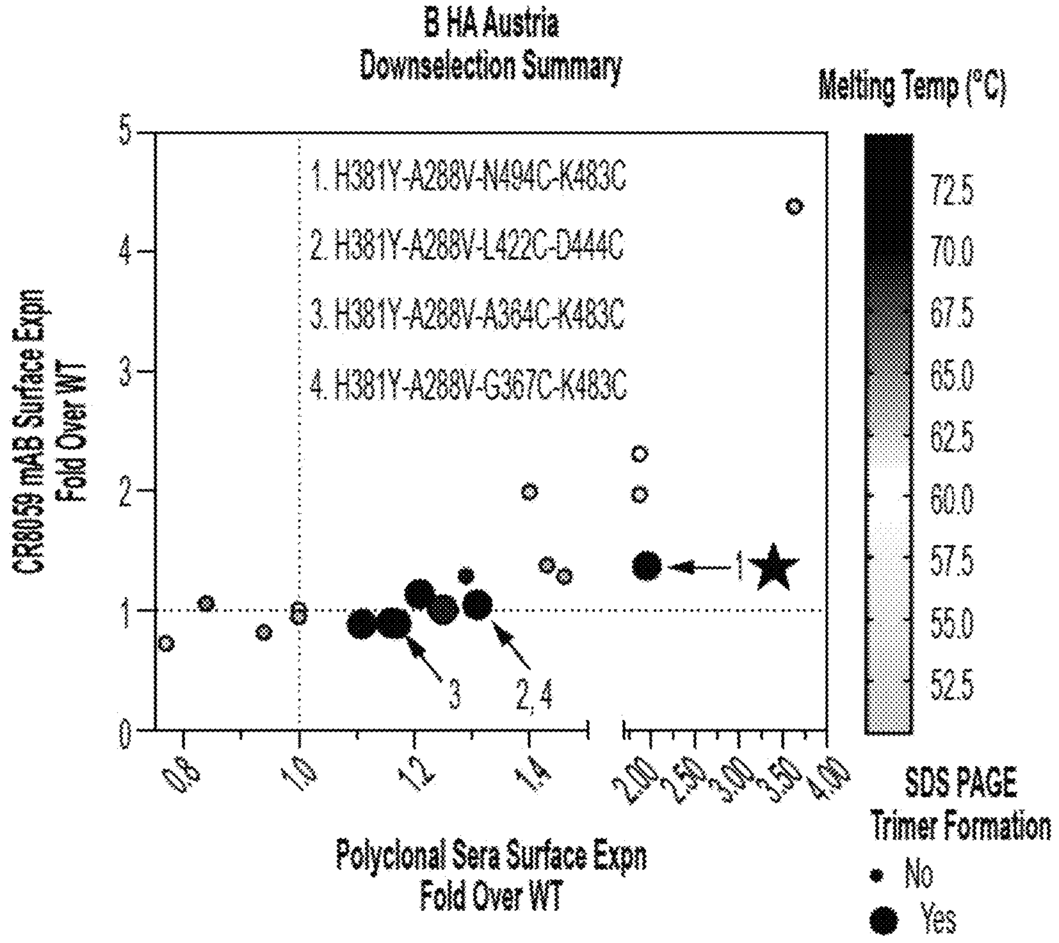
Figure 13A:
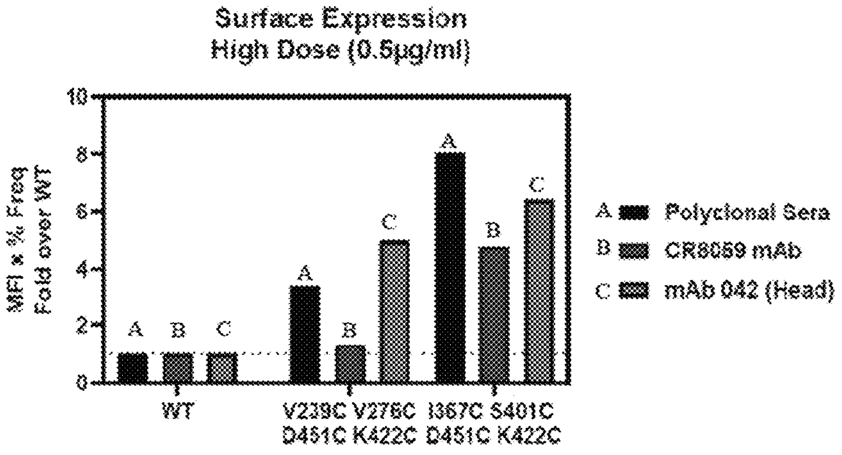
FIGS. 13A-13C show the effect of stabilizing mutant influenza B/Yamagata lineage virus HA proteins comprising the following amino acid mutations relative to wild-type influenza B/Phuket/3073/2013 (B/Yamagata lineage) virus HA protein amino acid sequence (SEQ ID NO: 70): (i) V239C-V276C-D451C-K422C, and (ii) I367C-S401C-D451C-K422C.
Figure 13B:
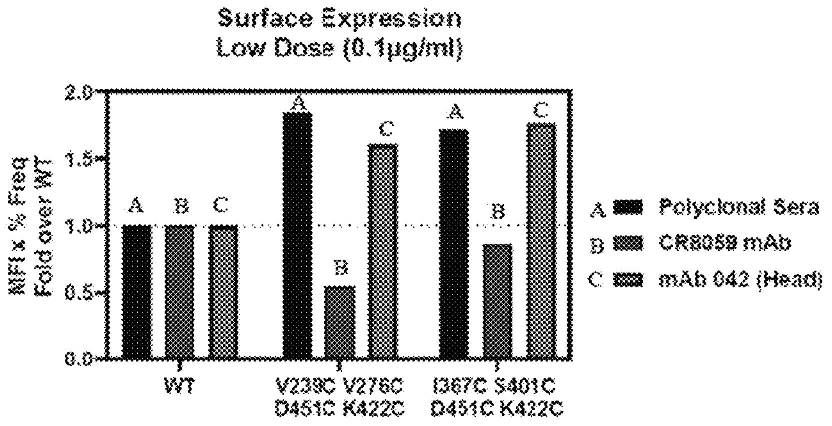

Based on surface expression and soluble protein metrics as described above, of nineteen B/Austria stabilizing mutant HA proteins (shown in Table E5-1), five candidate mutations (H381Y-A288V, H381Y-A288V-L422C-D444C, H381Y-A288V-A364C-K483C, H381Y-A288V-G367C-K483C, and H381Y-A288V-N494C-K483C relative to wild-type) were selected for further analysis. FIG. 12A shows surface expression of each mutation for each of the five B/Austria mutant HA proteins; relative to wild-type B/Austria HA, the H381Y-A288V-N494C-K483C mutant, a construct comprising an inter-protomer disulfide bond between stalk cysteines, showed beneficial surface expression based on polyclonal sera antibody and CR8059 antibody staining. FIG. 12B shows increased thermostability for four of the mutations relative to wild-type, including H381Y-A288V-N494C-K483C. As shown in FIG. 12C, the H381Y-A288V-N494C-K483C mutant HA had 2-fold surface expression as measured by polyclonal sera and +11° C. melting temperature over wild-type, and exhibited sustained formation of a trimer.

increased binding to polyclonal sera antibodies and mAb 042 antibodies when expressed in cells transfected with high doses of mRNA (0.5 μg/mL). Only the I367C-S401C-D451C-K422C mutant, a construct comprising two inter-protomer bonds between protomer stalks, also showed increased binding to CR8059 antibodies. Similar findings were made for proteins expressed in cells transfected with low doses of mRNA (0.1 μg/mL; FIG. 13B). However, thermostability assays showed an increased melting temperature for V239C-V276C-D451C-K422C, a construct

TABLE E5-1

B_Austria_HA Mutation Candidates

| Strain | Mutation | Construct Type | Surface Expression: Sera Freq * MFI/WT | Surface Expression: CR8059 Freq * MFI/WT | Soluble Protein: Melt Temp 1 (° C.) | Soluble Protein: Yield (mg) | Soluble Protein: Melt Temp 2 (° C.) |
|---|---|---|---|---|---|---|---|
| B_Austria_HA | Wild-type (WT) | NA | 1.00 | 1.00 | 60.41 | 0.92 | 60.7 |
| **B_Austria_HA** | **H381Y-A288V** | **pH Switch/ Cavity Filling** | **0.77** | **0.72** | **62.16** | **NA** | **NA** |
| B_Austria_HA | H381Y-A288V-S27C-Y349C | Intra-protomer DS (Head) | 0.94 | 0.81 | 63.41 | 0.73 | 64.25 |
| B_Austria_HA | H381Y-A288V-I295C-K328C | Intra-protomer DS (Head) | 1.40 | 1.98 | NA | 0.02 | 50.35 |
| B_Austria_HA | H381Y-A288V-S399C-H473C | Intra-protomer DS (Stalk) | 1.00 | 0.94 | 63.26 | 0.79 | 63.5 |
| **B_Austria_HA** | **H381Y-A288V-L422C-D444C** | **Intra-protomer DS (Stalk)** | **1.31** | **1.03** | **66.83** | **0.87** | **67.45** |
| B_Austria_HA | H381Y-A288V-K118C-L216C | Inter-protomer DS (Head) | 3.63 | 4.37 | 51.46 | 1.32 | 50.97 |
| B_Austria_HA | H381Y-A288V-V237C-D261C | Inter-protomer DS (Head) | 1.87 | 1.96 | NA | 0.17 | 55 |
| B_Austria_HA | H381Y-A288V-G363C-K480C | Inter-protomer DS (Stalk) | 1.17 | 0.88 | 70.69 | 0.67 | 71 |
| **B_Austria_HA** | **H381Y-A288V-A364C-K483C** | **Intra-protomer DS (Stalk)** | **1.16** | **0.89** | **72.75** | **0.68** | **73.92** |
| B_Austria_HA | H381Y-A288V-I365C-A476C | Inter-protomer DS (Stalk) | 1.11 | 0.88 | 71.78 | 0.71 | 72.03 |
| B_Austria_HA | H381Y-A288V-A366C-R479C | Inter-protomer DS (Stalk) | 1.25 | 1.00 | 68.56 | 0.82 | 68.84 |
| **B_Austria_HA** | **H381Y-A288V-G367C-K483C** | **Intra-protomer DS (Stalk)** | **1.31** | **1.04** | **73.51** | **0.61** | **74.61** |
| B_Austria_HA | H381Y-A288V-E435C-A428C | Inter-protomer DS (Stalk) | 1.21 | 1.13 | 70.37 | 0.90 | 70.59 |
| **B_Austria_HA** | **H381Y-A288V-N494C-K483C** | **Intra-protomer DS (Stalk)** | **1.95** | **1.36** | **71.01** | **0.26** | **71.51** |
| B_Austria_HA | H381Y-A288V-N494C-K480C | Inter-protomer DS (Stalk) | 1.29 | 1.28 | 67.33 | 0.20 | 69.11 |
| B_Austria_HA | H381Y-A288V-E416P-L417P-N434P-H433P | Proline Substitution | 1.43 | 1.37 | 63.31 | 0.79 | 64.07 |
| B_Austria_HA | H381Y-A288V-N434P-H433P | Proline Substitution | 0.84 | 1.05 | 65.24 | 0.99 | 65.17 |
| B_Austria_HA | H381Y-A288V-T515P-F516P | Proline Substitution | 1.87 | 2.30 | 59.29 | 0.35 | 59.49 |
| B_Austria_HA | H381Y-A288V-H473F | pH Switch/ Cavity Filling | 1.46 | 1.28 | 62.86 | 0.84 | 63.78 |

Figure 13C:
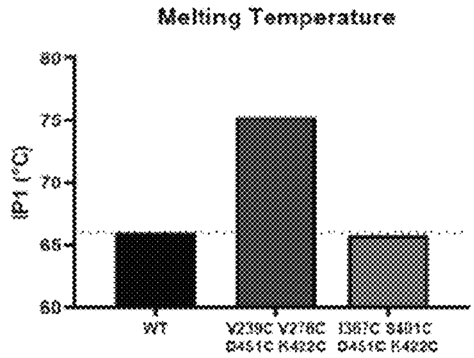

Bold = Candidates pursued in FIGS. 12A-C.
MFI = Mean Fluorescence Intensity;
WT = wild-type;
DS = introduced disulfide bond Based on surface expression and soluble protein metrics as described above, of nine B/Phuket stabilizing mutant HA proteins (shown in Table E5-2), three mutations (V239C-V276C, I367C-S401C, and D451C-K422C) relative to wild-type were combined and selected for further analysis. FIG. 13A shows surface expression of each of two B/Phuket mutant HA proteins: V239C-V276C-D451C-K422C and I367C-S401C-D451C-K422C. Both mutants showed comprising an inter-protomer disulfide bond between head cysteines, and an inter-protomer disulfide bond between stalk cysteines, while the melting temperature of the I367C-S401C-D451C-K422C mutant was similar to wild-type (FIG. 13C). The V239C-V276C-D451C-K422C mutant HA exhibited 3.4-fold higher surface expression as measured by polyclonal sera and +10° C. melting temperature over wild-type, and exhibited sustained formation of a trimer.

TABLE E5-2

B_Phuket_HA Mutation Candidates

| Strain | Mutation | Construct Type | Flow Cytometry (Surface Expresesion) Sera Freq * MFI/WT | CR8059 Freq * MFI/WT | Soluble Protein Melt Temp 1 (° C.) | Yield (mg) | Melt Temp 2 (° C.) |
|---|---|---|---|---|---|---|---|
| B_Phuket_HA | Wild-type (WT) | WT | 1.000 | 1.000 | 60.43 | 1.72 | 62.52 |
| B_Phuket_HA | A231C-G273C | Intra-protomer DS (Head) | 0.903 | 0.844 | 66.28 | 1.45 | 69.01 |
| B_Phuket_HA | K295C-1332C | Intra-protomer DS (Head) | 4.314 | 2.347 | 59.11 | 0.30 | 61.39 |
| B_Phuket_HA | A396C-L510C | Intra-protomer DS (Stalk) | 2.655 | 1.675 | 59.97 | 0.62 | 62.61 |
| **B_Phuket_HA** | **V239C-V276C** | **Inter-protomer DS (Head)** | **3.672** | **1.784** | **61.53** | **0.59** | **63.76** |
| **B_Phuket_HA** | **I367C-S401C** | **Inter-protomer DS (Stalk)** | **1.203** | **0.880** | **65.48** | **2.48** | **69.61** |
| B_Phuket_HA | F363C-E404C | Inter-protomer DS (Stalk) | 1.097 | 0.866 | 65.12 | 2.41 | 68.03 |
| B_Phuket_HA | E437C-G429C | Inter-protomer DS (Stalk) | 1.951 | 1.504 | 62.88 | 2.98 | 65.05 |
| **B_Phuket_HA** | **D451C-K422C** | **Inter-protomer DS (Stalk)** | **2.068** | **1.714** | **63.40** | **2.09** | **65.01** |
| B_Phuket_HA | H381Y-A290V | pH Switch/Cavity Filling | NA | NA | NA | 2.64 | 62.59 |

Figure 14A:
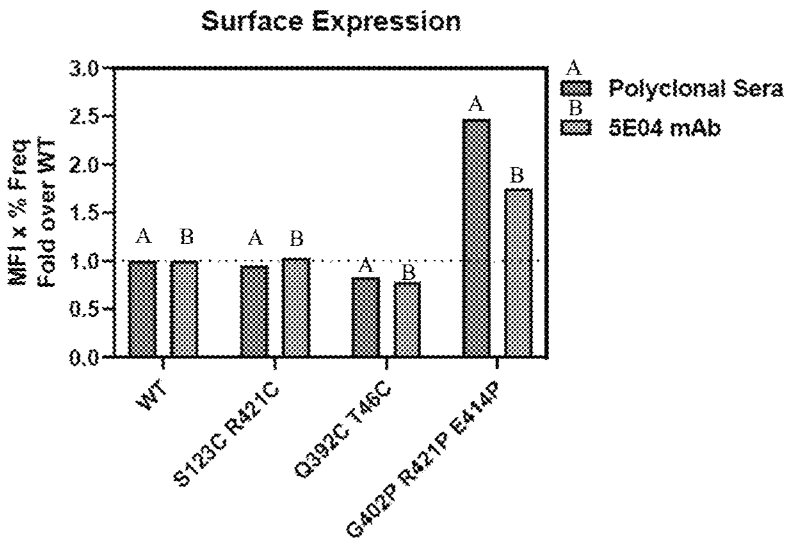
FIGS. 14A-14C show the effect of mutant stabilizing mutant IAV H3 HA proteins comprising the following amino acid mutations relative to wild-type influenza A/Darwin/6/2021(H3N2) virus HA protein amino acid sequence (SEQ ID NO: 82): (i) S123C-R421C, Q392C-T46C, and G402-R421P-E414P.
Figure 14B:
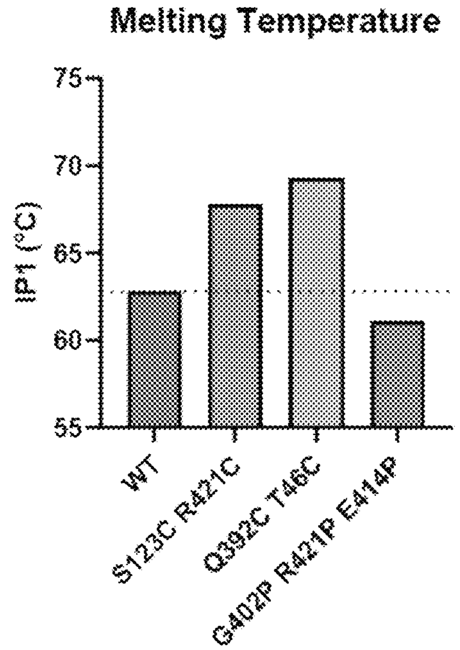
Figure 14C:
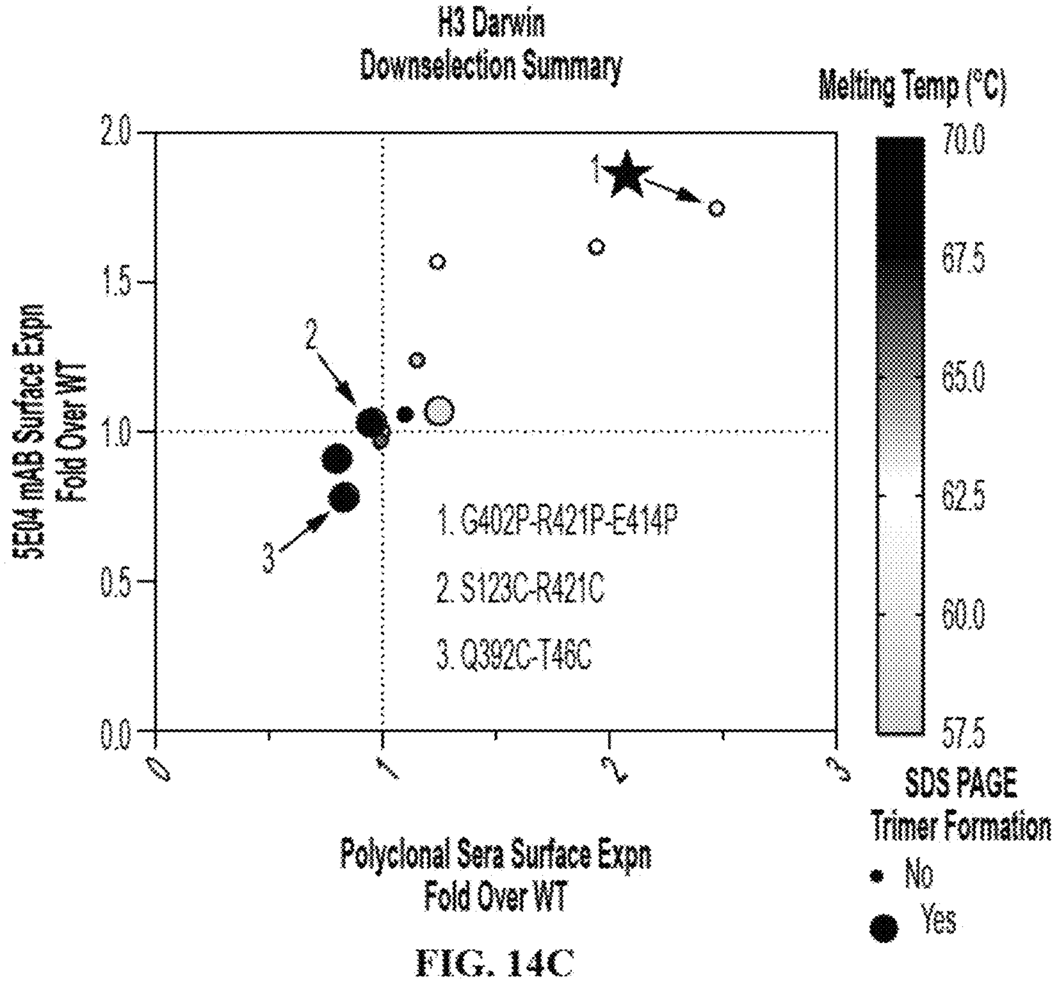

Bold = Candidates pursued in FIGS. 13A-C.
MFI = Mean Fluorescence Intensity;
WT = wild-type;
DS = introduced disulfide bond Based on surface expression and soluble protein metrics as described above, of nine A/Darwin stabilizing mutant H3 HA proteins (shown in Table E5-3), three candidate mutations (S123C-R241C, Q392C-T46C, and G402P-R421P-E414P) relative to wild-type were selected for further analysis. FIG. 14A shows surface expression of each mutation for each of the three A/Darwin mutant H3 HA proteins. Only the G402P-R421P-E414P mutant, a construct comprising proline substitution stabilizations, showed increased binding to both polyclonal sera antibodies and 5E04 antibodies. Melting temperatures of the S123C-R241C mutant and Q392C-T46C mutant, comprising interprotomer disulfide bonds between head cysteines and or stalk cysteines, respectively, were increased relative to wild-type (FIG. 14B). As shown in FIG. 14C, the G402P-R421P-E414P mutant H3 HA had 3-fold higher surface expression as measured by polyclonal sera and +1.7° C. melting temperature over wild-type.

TABLE E5-3

A_Darwin_H3 HA Mutation Candidates

| Strain | Mutation | Construct Type | Flow Cytometry (Surface Expression) Sera Freq * MFI/WT | 5E04 Freq * MFI/WT | Soluble Protein Melt Temp 1 (° C.) | Yield (mg) | Melt Temp 2 (° C.) |
|---|---|---|---|---|---|---|---|
| A_Darwin_H3 | Wild-type (WT) | WT | 1.00 | 1.00 | 60.8 | 0.88 | 62.8 |
| A_Darwin_H3 | T40C-A55C | Intra-protomer DS (Head) | 1.24 | 1.57 | 60.5 | 1.32 | 62.9 |
| **A_Darwin_H3** | **S123C-R421C** | **Inter-protomer DS (Head)** | **0.95** | **1.03** | **67.4** | **0.67** | **67.8** |
| A_Darwin_H3 | L260C-P237C | Inter-protomer DS (Head) | 0.80 | 0.91 | 67.4 | 0.20 | 70.0 |
| **A_Darwin_H3** | **Q392C-T46C** | **Inter-protomer DS (Stalk)** | **0.83** | **0.78** | **67.9** | **0.84** | **69.3** |
| A_Darwin_H3 | I411C-Y428C | Inter-protomer DS (Stalk) | 1.25 | 1.07 | 62.3 | 2.98 | 63.5 |
| **A_Darwin_H3** | **G402P-R421P-E414P** | **Proline Substitution** | **2.47** | **1.75** | **61.9** | **3.16** | **61.1** |
| A_Darwin_H3 | K403G | Glycine Substitution | 1.15 | 1.24 | 61.8 | 1.32 | 63.7 |
| A_Darwin_H3 | F408G-H409G | Glycine Substitution | 1.94 | 1.62 | 60.4 | 2.28 | 62.6 |

Figure 15:
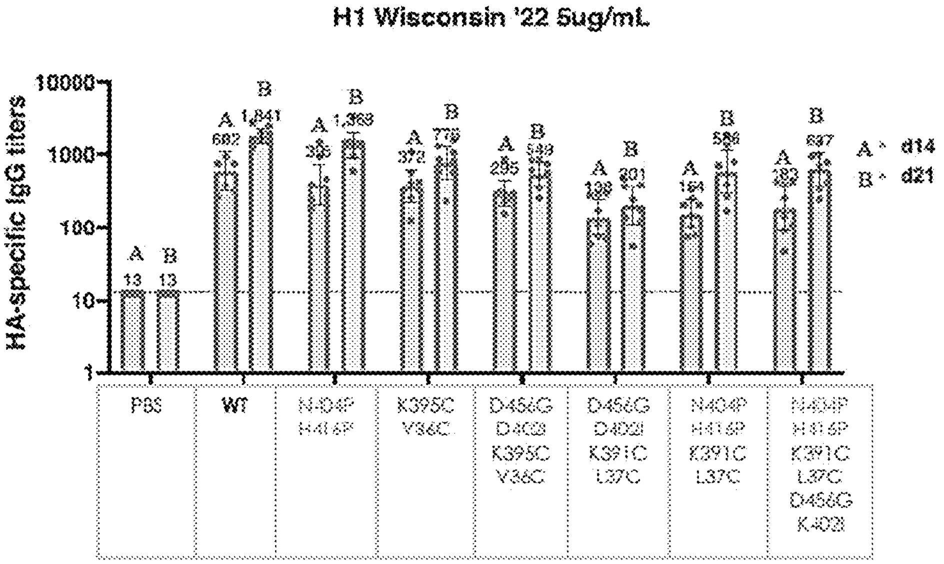
FIG. 15 shows HA-specific IgG titers of sera collected from mice injected with 5 μg/mL of mRNA encoding wild-type or mutant IAV H1 HA protein at 21 days post-injection. Candidate amino acid mutations included (i) N404P-H416P, (ii) K395C-V36C, (iii) D456C-D402I-K395C-V36C, (iv) D456C-D402I-K391C-L37C, (v) N404P-H416P-K391C-L37C, and (vi) N404P-H416-K391C-L37C-D456G-K402I relative to wild-type influenza A/Wisconsin/67/2022(H1N1)pdm09 virus HA protein amino acid sequence (SEQ ID NO: 83).

Bold = Candidates pursued in FIGS. 14A-C.
MFI = Mean Fluorescence Intensity;
WT = wild-type;
DS = introduced disulfide bond Based on surface expression and soluble protein metrics as described above, of sixteen A/Wisconsin stabilizing mutant H1 HA proteins (shown in Table E5-4), six candidate mutations and/or combinations of mutations (N404P-H416P, K395C-V36C, D456C-D402I-K395C-V36C, D456G-D402I-K395C-V36C, N404P-H416P-K391C-L37C, and N404P-H416P-K391C-L37C-D456G-K402I) relative to wild-type were selected for further analysis. FIG. 15 shows the results of an additional in vivo experiment, in which mice were administered mRNA encoding candidate stabilized mutant H1 HA proteins, as described in Example 1. HA-specific IgG titers were measured on Day 14 and Day 21. All candidate mutant H1 HA proteins elicited sera having similar binding titers relative to wild-type H1 HA.

TABLE E5-4

A_Wisconsin_H1 HA Mutation Candidates

| Strain | Mutation | Construct Type | Soluble Protein Sera Freq * MFI/WT | Soluble Protein 2B06 Freq * MFI/WT | Soluble Protein Melt Temp (° C.) |
|---|---|---|---|---|---|
| A_Wisconsin_H1 | Wild-type (WT) | WT | 1.000 | 1.000 | 61.11 |
| A_Wisconsin_H1 | V410C-L462C | Intra-protomer DS | 0.884 | 1.832 | 53.07 |
| A_Wisconsin_H1 | E120C-K419C | Inter-protomer DS | 1.267 | 2.662 | 58.85 |
| **A_Wisconsin_H1** | **K391C-L37C** | **Inter-protomer DS** | **1.005** | **1.103** | **74.27** |
| **A_Wisconsin_H1** | **K395C-V36C** | **Inter-protomer DS** | **1.095** | **1.373** | **73.51** |
| A_Wisconsin_H1 | Q406C-D430C | Inter-protomer DS | 1.228 | 2.822 | 58.20 |
| A_Wisconsin_H1 | S457C-L346C | Inter-protomer DS | 1.050 | 1.117 | 59.29 |
| A_Wisconsin_H1 | N461C-G348C | Inter-protomer DS | 1.072 | 1.014 | 65.86 |
| A_Wisconsin_H1 | N404P-K419P | Proline | 1.582 | 1.820 | 53.36 |
| **A_Wisconsin_H1** | **N404P-H416P** | **Proline** | **1.550** | **1.510** | **69.10** |
| A_Wisconsin_H1 | T405P-Q406P | Proline | 1.026 | 0.935 | 67.93 |
| A_Wisconsin_H1 | N415P-H416P | Proline | 1.319 | 3.194 | 54.79 |
| A_Wisconsin_H1 | H25Y-H45E | pH Switch/ Cavity Filling | 0.995 | 1.026 | 61.97 |
| A_Wisconsin_H1 | H370Y-K497W | pH Switch/ Cavity Filling | 1.337 | 1.217 | 60.51 |
| A_Wisconsin_H1 | K402G-T405G-F407G | Glycine Substitution | 1.152 | 1.467 | 64.34 |
| A_Wisconsin_H1 | K395I-E447I | Cavity Filling | 0.424 | 0.745 | 70.67 |
| **A_Wisconsin_H1** | **D456G-K402I** | **Cavity Filling (K4021)/Glycine (D456G)** | **1.179** | **1.201** | **65.95** |

Figure 16A:
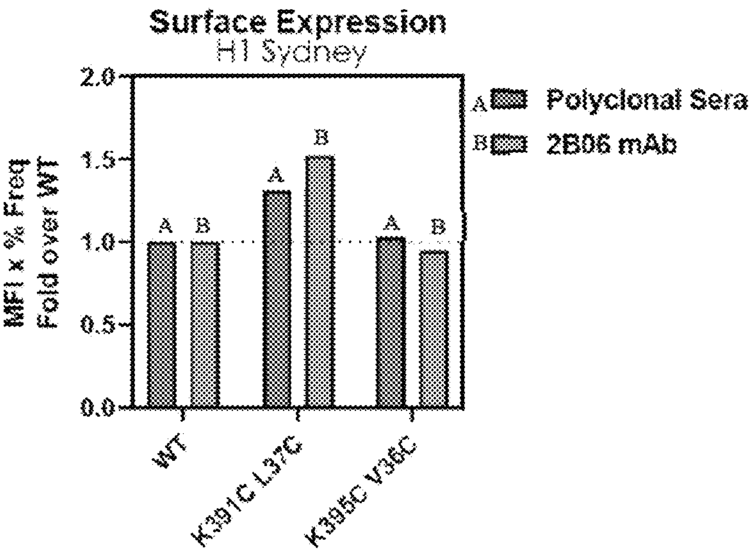
FIGS. 16A-16C show the effect of stabilizing mutant IAV H1 HA proteins comprising the following amino acid mutations relative to wild-type influenza A/Sydney/5/2021 (H1N1)pdm09 virus HA protein amino acid sequence (SEQ ID NO: 95): (i) K391C-L37C, and (ii) K395C-V36C.
Figure 16B:
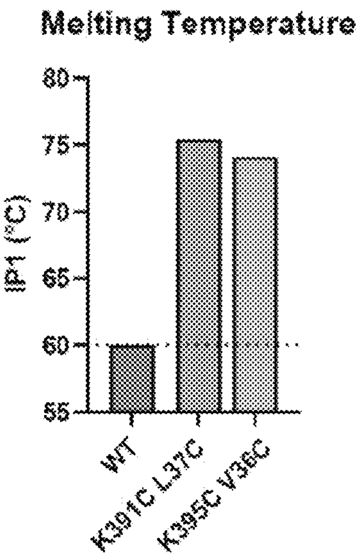
Figure 16C:
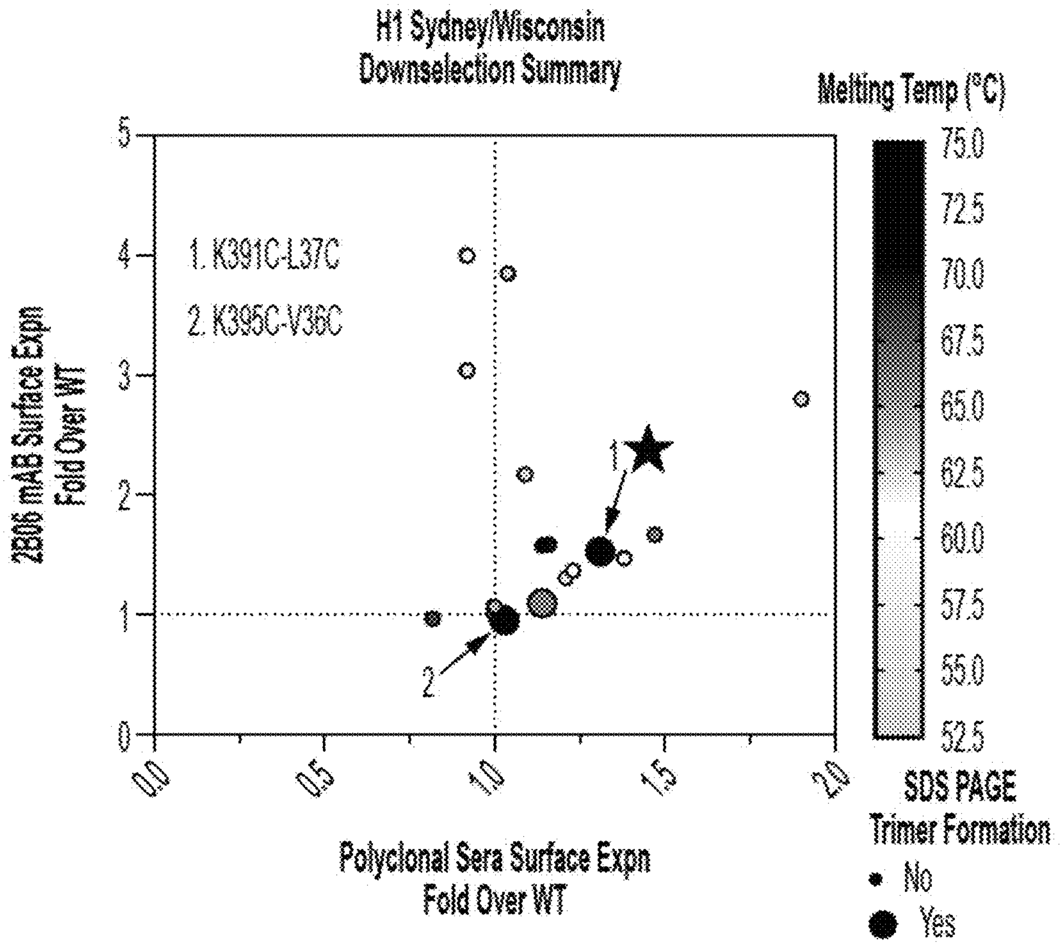

Bold = Top candidates pursued in FIG. 15.
MFI = Mean Fluorescence Intensity;
WT = wild-type;
DS = introduced disulfide bond Based on surface expression and soluble protein metrics as described above, of sixteen A/Sydney stabilizing mutant H1 HA proteins (shown in Table E5-5), two candidate mutations (K391C-L37C and K395C-V36C) relative to wild-type were selected for further analysis. FIG. 16A shows surface expression of each mutation for each of the two A/Sydney candidate mutant H1 HA proteins. The K391C-L37C mutant, a construct comprising an inter-protomer disulfide bond, showed increased binding to both polyclonal sera antibodies and 2B06 antibodies. Melting temperatures for both mutants were similarly increased relative to wild-type (FIG. 16B). Ultimately, the expression of each mutation for each of the two A/Sydney mutant H1 proteins. As shown in FIG. 16C, the K391C-L37C mutant H1 HA had 1.4-fold surface expression as measured by polyclonal sera and +15° C. melting temperature over wild-type, and exhibited sustained formation of a trimer.

TABLE E5-5

A_Sydney_H1 HA Mutation Candidates

| Strain | Mutation | Construct Type | Flow Cytometry (Surface Expression) Sera Freq * MFI/WT | Flow Cytometry (Surface Expression) 2B06 Freq * MFI/WT | Flow Cytometry (Surface Expression) Yield/ WT | Flow Cytometry (Surface Expression) Melt Temp - WT (° C.) | Soluble Protein Melt Temp 2 (° C.) |
|---|---|---|---|---|---|---|---|
| A_Sydney_H1 | Wild-type (WT) | WT | 1.00 | 1.00 | 1.00 | 61.53 | 60.7 |

TABLE E5-5-continued

| A_Sydney_H1 HA Mutation Candidates | | | | | | | | |
|---|---|---|---|---|---|---|---|---|
| | | | Flow Cytometry (Surface Expression) | | | | Soluble Protein |
| Strain | Mutation | Construct Type | Sera Freq * MFI/WT | 2B06 Freq * MFI/WT | Yield/ WT | Melt Temp - WT (° C.) | Melt Temp 2 (° C.) |
| A_Sydney_H1 | V410C L462C | Intra-protomer DS | 1.09 | 2.17 | 1.23 | 53.63 | NA |
| A_Sydney_H1 | E120C K419C | Inter-protomer DS | 0.92 | 4.00 | 2.29 | 59.32 | 64.25 |
| **A_Sydney_H1** | **K391C L37C** | **Inter-protomer DS** | **1.31** | **1.52** | **1.24** | **73.88** | **50.35** |
| **A_Sydney_H1** | **K395C V36C** | **Inter-protomer DS** | **1.03** | **0.95** | **1.72** | **73.07** | **63.5** |
| A_Sydney_H1 | Q406C D430C | Inter-protomer DS | 0.92 | 3.04 | 3.24 | 58.25 | 67.45 |
| A_Sydney_H1 | S457C L346C | Inter-protomer DS | 1.38 | 1.47 | 1.95 | 58.99 | 50.97 |
| A_Sydney_H1 | N461C G348C | Inter-protomer DS | 1.90 | 2.80 | 4.90 | 65.24 | 55 |
| A_Sydney_H1 | N404P K419P | Proline | 1.14 | 1.09 | 1.74 | 53.73 | 71 |
| A_Sydney_H1 | N404P H416P | Proline | 1.16 | 1.58 | 3.05 | 68.17 | 73.92 |
| A_Sydney_H1 | T405P Q406P | Proline | 0.82 | 0.96 | 1.06 | 66.77 | 72.03 |
| A_Sydney_H1 | N415P H416P | Proline | 1.04 | 3.85 | 2.89 | 55.41 | 68.84 |
| A_Sydney_H1 | H25Y H45E | pH Switch/ Cavity Filling | 1.21 | 1.30 | 1.14 | 58.87 | 74.61 |
| A_Sydney_H1 | H370Y K497W | pH Switch/ Cavity Filling | 1.23 | 1.36 | 3.38 | 58.58 | 70.59 |
| A_Sydney_H1 | K402G T405G F407G | Glycine Substitution | 1.00 | 1.06 | 1.23 | 62.57 | 71.51 |
| A_Sydney_H1 | K395I E447I | Cavity Filling | 1.14 | 1.57 | 0.31 | 70.60 | 69.11 |
| A_Sydney_H1 | D456G K402I | Cavity Filling (K402I)/ Glycine (D456G) | 1.47 | 1.66 | 1.04 | 66.22 | 64.07 |

Bold = Top candidates pursued in FIGS. 16A-C.
MFI = Mean Fluorescence Intensity;
WT = wild-type;
DS = introduced disulfide bond Example 6. A Phase 1, Randomized, Double-Blind, Active-Control Study to Evaluate the Safety, Reactogenicity, and Immunogenicity of Octovalent mRNA-Based Influenza Vaccines in Healthy Adults In this Phase 1 study, 4×HA/4×NA at 1:1 HA:NA and 4×HA/4×NA at 3:1 HA:NA, two octovalent lipid-encapsulated mRNA-based prophylactic combination vaccines encoding stabilized influenza virus glycoprotein hemagglutinin (HA) and neuraminidase (NA) antigens were evaluated for reactogenicity and safety. 4×HA/4×NA at 1:1 HA:NA contains 8 mRNAs: 4 mRNA sequences encoding stabilized mutant membrane-bound HA proteins (SEQ ID NOs: 85, 87, 91, and 94) and 4 mRNA sequences that encode NA proteins of the 4 different influenza viruses recommended by the WHO in an equivalent mass ratio. Substitutions present in each sequence are:

- SEQ ID NO: 85—Influenza B/Phuket/3073/2013 (B/Yamagata lineage) virus HA protein with V239C, V276C, D451C, and K422C substitutions relative to SEQ ID NO: 70;
- SEQ ID NO: 87—Influenza B/Austria/1359417/2021 (B/Victoria lineage) virus HA protein with H381Y, A288V, N494C, and K483C substitutions relative to SEQ ID NO: 71;
- SEQ ID NO: 91—Influenza A/Darwin/6/2021(H3N2) virus HA protein with G402P, R421P, and E414P substitutions relative to SEQ ID NO: 82; and
- SEQ ID NO: 94—Influenza A/Wisconsin/67/2022(H1N1) pdm09 HA protein with K391C and L37C substitutions relative to SEQ ID NO: 83.

The proteins encoded by 4×HA/4×NA at 1:1 HA:NA are also encoded by 4×HA/4×NA at 3:1 HA:NA, with the exception that 4×HA/4×NA at 3:1 HA:NA contains a 3:1 HA:NA ratio. 4×HA, and FLUBLOK®, a traditional seasonal flu vaccine, were used as controls. 4×HA is an LNP-encapsulated, mRNA-based, prophylactic vaccine containing 4 mRNAs that encode membrane-bound HA of the 4 different influenza viruses recommended by the WHO in an equivalent mRNA mass ratio. The lipid nanoparticle comprises 48% Compound 1, 2.5% PEG-DMG, 38.5% cholesterol, and 11% DSPC. FLUBLOK®, is an approved, quadrivalent recombinant full-length HA vaccine comprising HAs from A/West Virginia/30/2022 (A/Wisconsin/67/2022 pdm09-like (H1N1), virus)A/Darwin/6/2021(H3N2), B/Austria/1359417/2021 and B/Phuket/3073/2013, and a carrier comprising sodium chloride, monobasic sodium phosphate, dibasic sodium phosphate, and polysorbate.

Cohorts and Duration

The trial enrolled 572 participants into cohorts of 2 age groups, each cohort comprising 8 vaccination groups:

Cohort A for participants 18-49 years of age and Cohort B for participants 50-75 years of age (approximately 35 participants per vaccination group, per cohort). The study intervention information, including dosages, is provided in Table E6-1 below. All participants had follow-up visits for 6 months after the study vaccination.

TABLE E6-1

Study Interventions and Dosages

| Cohort A Arms (18-49 years) | Cohort B Arms (50-75 years) | Intervention | Total mRNA Dose (μg) | Component mRNA dose (μg) HA | NA |
|---|---|---|---|---|---|
| A1 | B1 | FLUBLOK ®, | — | — | — |
| A2 | B2 | 4xHA | 50 | 50 | — |
| A3 | B3 | 4xHA/4xNA at 3:1 HA:NA | 25 | 18.75 | 6.25 |
| A4 | B4 | 4xHA/4xNA at 1:1 HA:NA | 50 | 25 | 25 |
| A5 | B5 | 4xHA/4xNA at 3:1 HA:NA | 50 | 37.5 | 12.5 |
| A6 | B6 | 4xHA/4xNA at 1:1 HA:NA | 100 | 50 | 50 |
| A7 | B7 | 4xHA/4xNA at 3:1 HA:NA | 100 | 75 | 25 |
| A8 | B8 | 4xHA/4xNA at 1:1 HA:NA | 150 | 75 | 75 |

Objectives and Endpoints

Figure 17A:
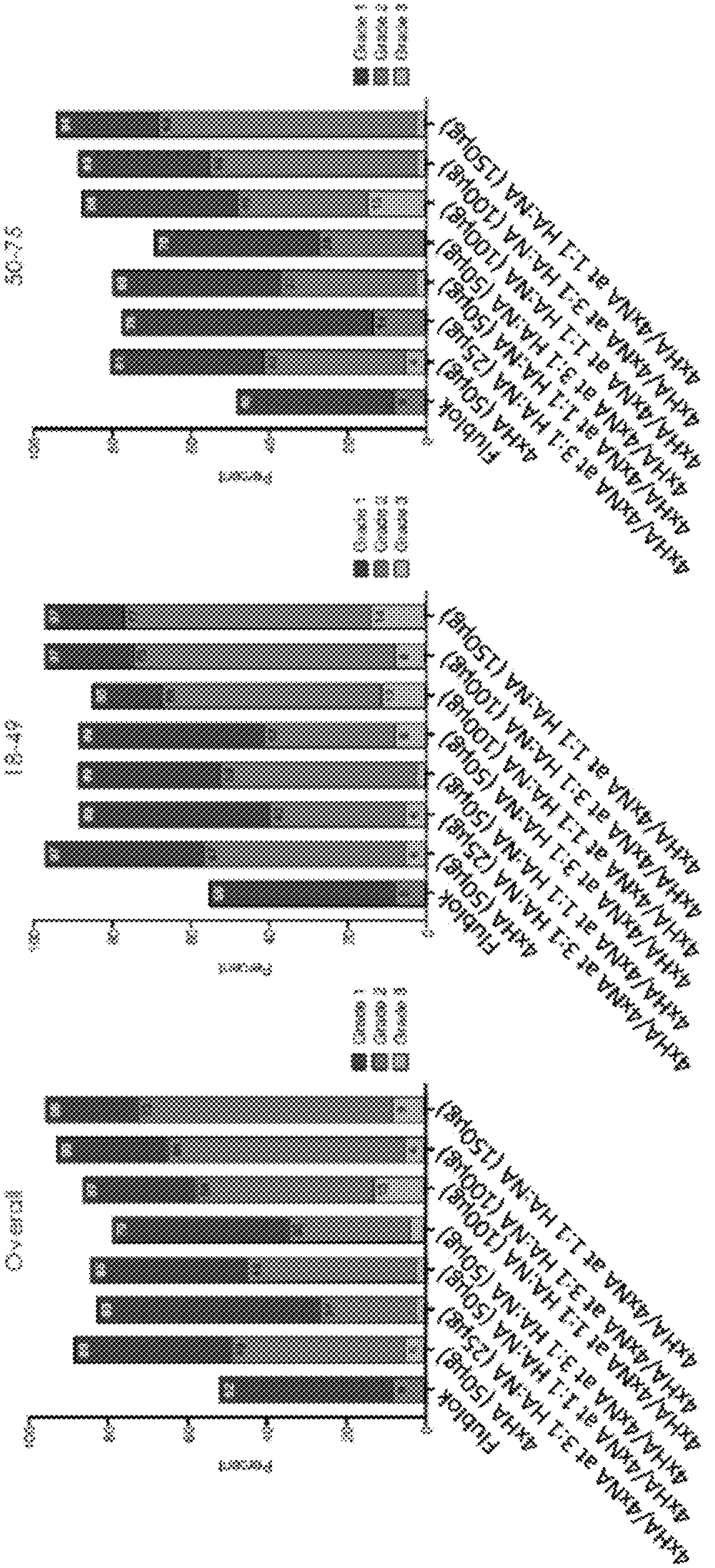
FIGS. 17A-17F show reactogenicity and immunogenicity data from the Phase 1 clinical trial described in Example 6.
Figure 17B:
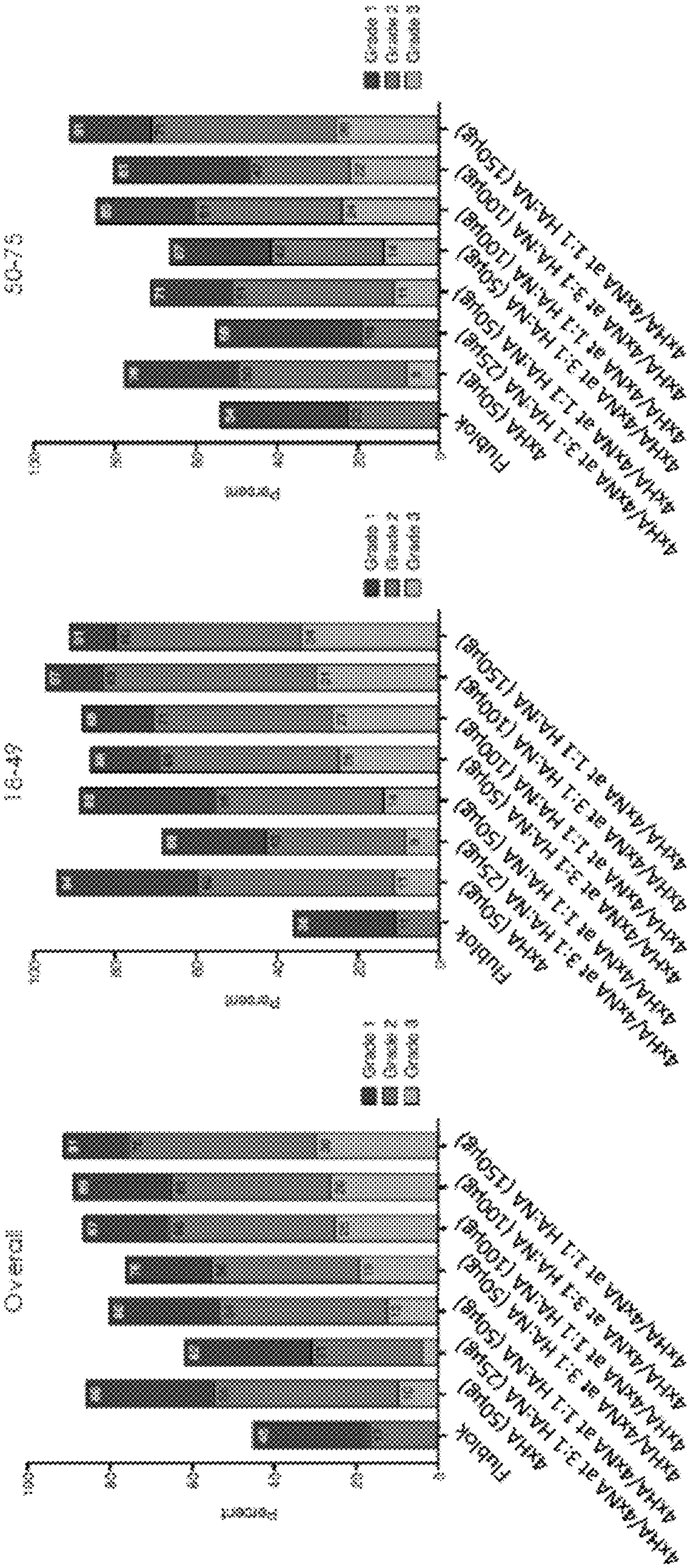

The primary objective of this trial was to evaluate the safety and reactogenicity of the candidate vaccines across study arms. As shown in FIG. 17A, 50 μg doses of 4×HA, 4×HA/4×NA at 1:1 HA:NA, and 4×HA/4×NA at 3:1 HA:NA elicited similar local reactions in all participants, regardless of composition. Importantly, introduction of NA-antigen encoding mRNA did not increase local reactogenicity. FIG. 17B shows similar systemic reactogenicity for participants to whom 50 μg doses of 4×HA/4×NA at 1:1 HA:NA and 4×HA was administered, while slightly higher systemic reactogenicity was observed in subjects treated with 50 μg doses of 4×HA/4×NA at 3:1 HA:NA. Higher doses of mRNA vaccines elicited higher rates of grade 2 and grade 3 local and systemic reactions.

Figure 17C:
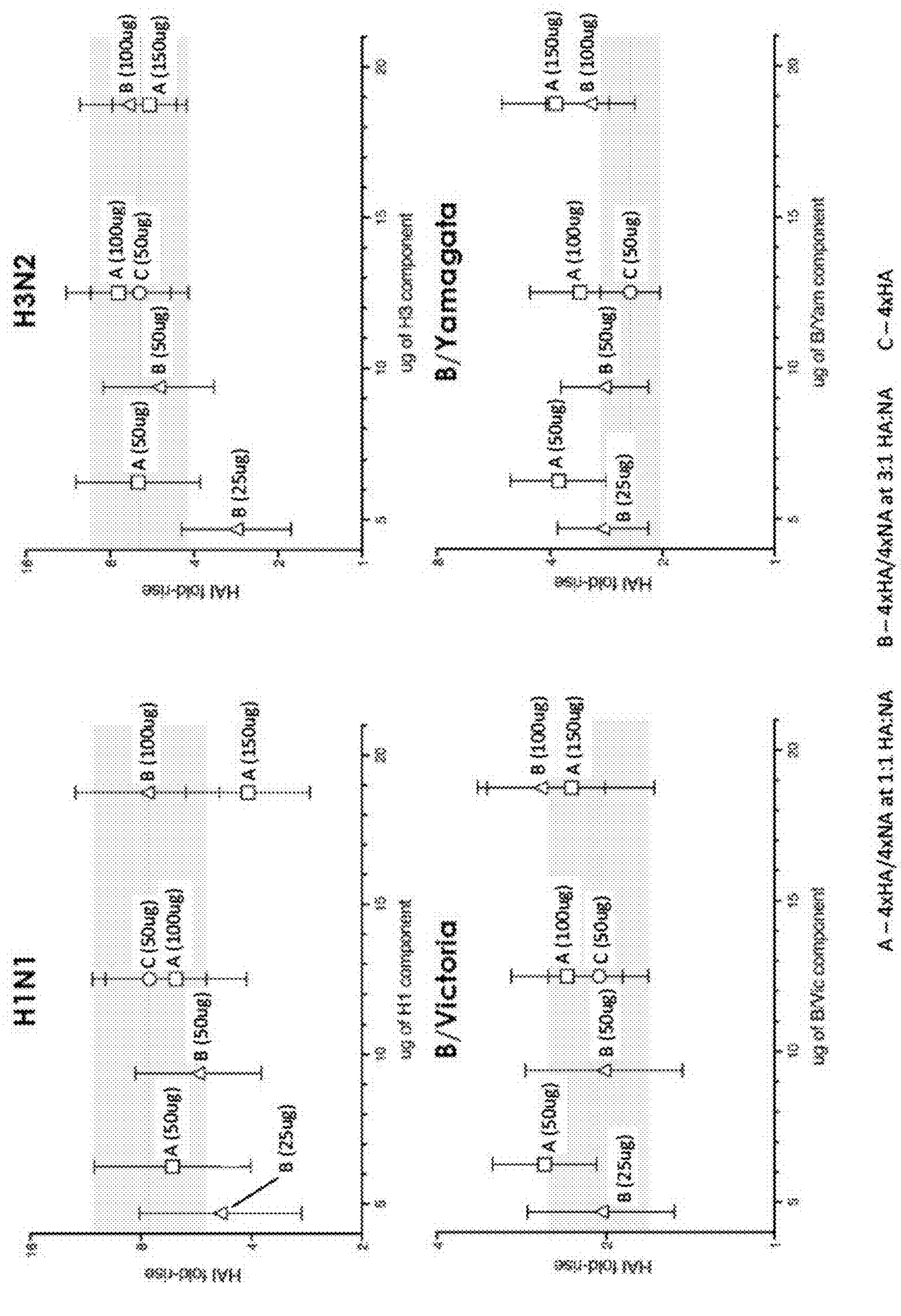
Figure 17D:
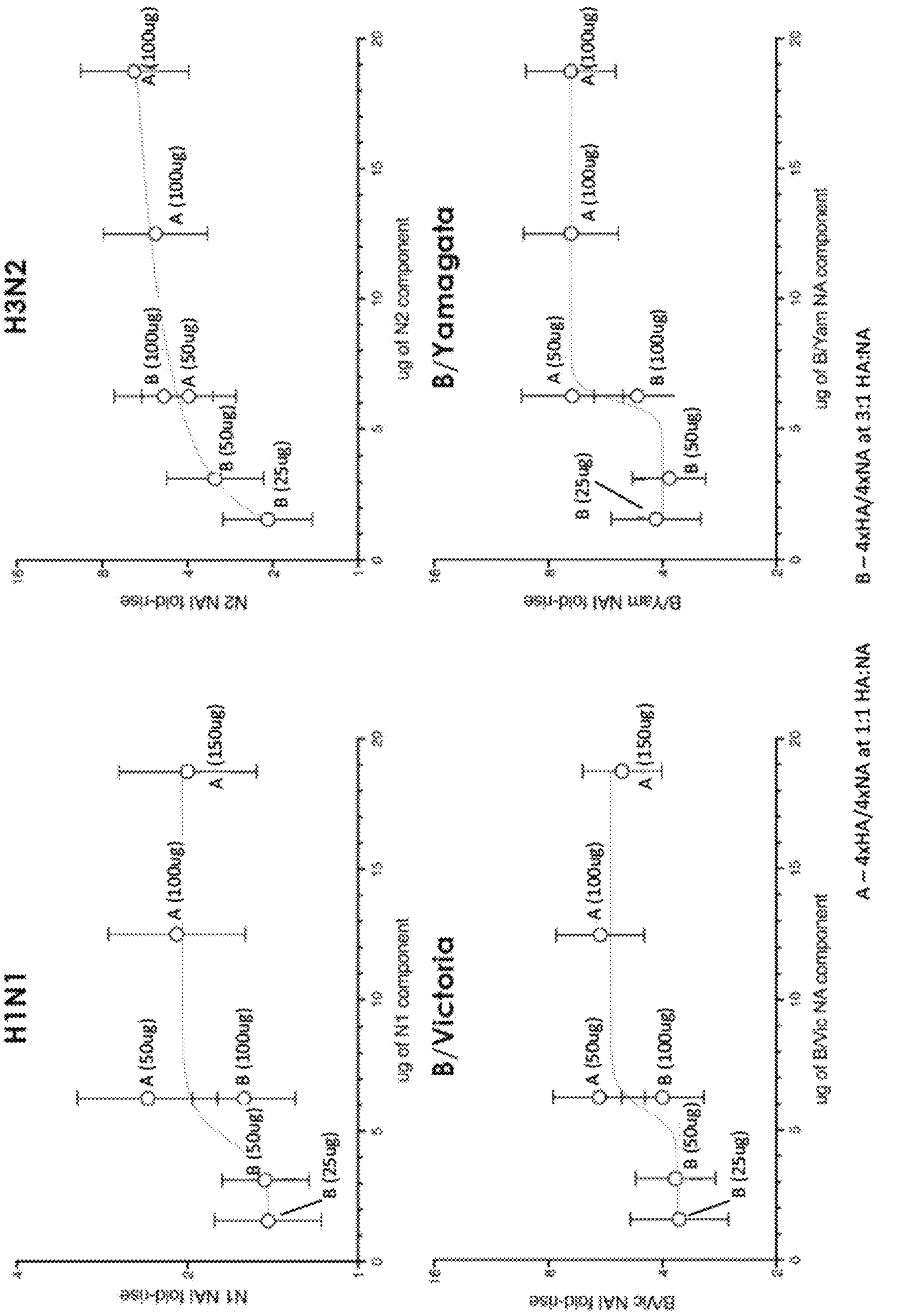
Figure 17E:
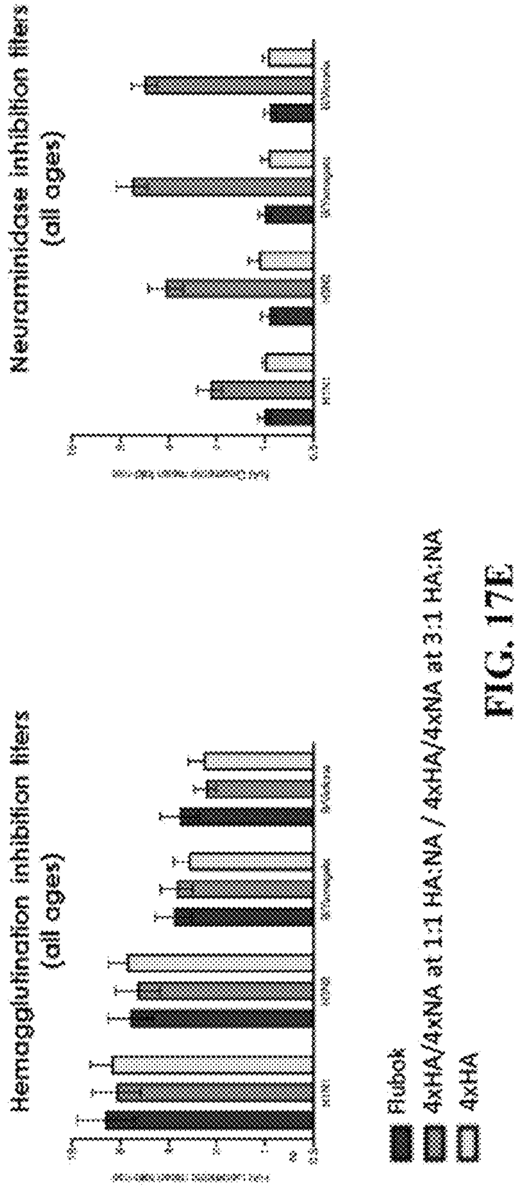
Figure 17F:
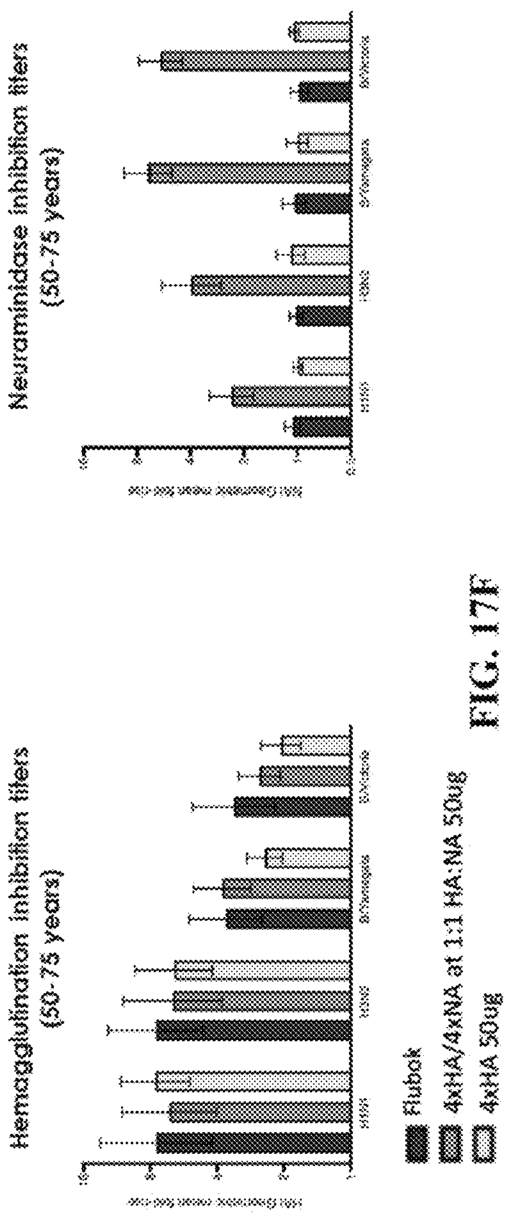

The secondary objectives of this trial were to evaluate the humoral immune responses to vaccine-matched strains for influenza viruses across study vaccine arms at Day 29. GMT and GMFR at Day 29 compared to Day 1 were assessed by HAI assay and NAI assay. In subjects aged 50-75 years at Day 29 compared to Day 1 by HAI assays. 4×HA/4×NA at 1:1 HA:NA at 50 μg elicited similar HAI fold-rises as 4×HA at 50 μg, despite including only half the dose of HA-encoding mRNAs (FIG. 17C). Similarly, FIG. 17D shows that, in subjects aged 50-75 years of age, for similar dose levels of NA-encoding mRNAs, 4×HA/4×NA at 1:1 HA:NA shows a trend for higher NAI titer rises than 4×HA/4×NA at 3:1 HA:NA (except for N2). Elicited HAI and NAI titers for FLUBLOK®, 4×HA/4×NA at 1:1 HA:NA/1030, and 4×HA were compared and 4×HA/4×NA at 1:1 HA:NA (50 μg) was found to elicit both HAI titers, similar to those induced by FLUBLOK®, and robust NAI titers (FIG. 17E). These findings held for subjects aged 50-75 (FIG. 17F).

Example 7. A Phase 2, Adaptive, Randomized, Observer-Blind, Placebo- and Active-Control Study to Evaluate the Safety and Immunogenicity of Octovalent mRNA-Based Influenza Vaccines Relative to a Quadrivalent mRNA-Based Influenza Vaccine in Healthy Adults As described in Example 6, 4×HA/4×NA at 1:1 HA:NA is an octovalent lipid-encapsulated mRNA-based prophylactic combination vaccines encoding stabilized influenza virus glycoprotein hemagglutinin (HA) and neuraminidase (NA) antigens. 4×HA/4×NA at 1:1 HA:NA contains 8 mRNAs: 4 mRNA sequences encoding stabilized mutant membrane-bound HA proteins (SEQ ID NOs: 85, 87, 91, and 94) and 4 mRNA sequences encoding wild-type or stabilized mutant membrane-bound NA proteins of the 4 different influenza viruses recommended by the WHO in an equivalent mass ratio. In this Phase 2 trial, the safety and immunogenicity of the two 4×HA/4×NA at 1:1 HA:NA formulations will be compared to 4×HA.

Cohorts and Duration

The trial will consist of two parts: Part A and Part B. The Part A trial will enroll approximately 900 older adult participants into 9 arms. Approximately 100 participants will be randomized (in equal allocation ratio) into investigational vaccine arms with stratification by 2 age groups, 18-49 years and 50-75 years. The study intervention information for Part A, including dosages, is provided in Table E7-1 below.

TABLE E7-1

Part A Interventions and Dosages

| Study Arms | Interventions | Total mRNA Dose (μg) | Component mRNA Dose (μg) HA | NA |
|---|---|---|---|---|
| A1 | 4xHA (4x HA mutant) | 50 | 50 | — |
| A2 | | 25 | 25 | — |
| A3 | 4xHA/4xNA at 1:1 HA:NA | 50 | 25 | 25 |
| A4 | (4x HA mutant; 4x mutated NA) | 75 | 32.5 | 32.5 |
| A5 | 4xHA/4xNA at 1:1 HA:NA | 25 | 12.5 | 12.5 |
| A6 | (4x HA mutant; 4x wild-type NA) | 50 | 24 | 25 |
| A7 | Fluzone HD (comparator) | — | — | — |
| A8 | FLUAD (comparator) | — | — | — |
| A9 | 4xHA (comparator) | 50 | 25 | — |

The Part B trial will enroll approximately 500 adult participants into 5 arms. Approximately 100 participants will be randomized (in equal allocation ratio) into the same 2 age groups. Study intervention information for Part B, including dosages, is provided in Table E7-2 below.

TABLE E7-2

Part B Interventions and Dosages

| Study Arms | Interventions | Total mRNA Dose (μg) | HA |
|---|---|---|---|
| B1 | 4xHA (4x HA mutant) | 2.5 | 50 |
| B2 | | 5 | 25 |
| B3 | | 10 | 25 |
| B4 | 4xHA (2xHA mutant- optimized B material from Example 4) | 50 | 50 |
| B5 | Fluarix | — | — |

All participants will have follow-up visits for 6 months after the study vaccination.

Objectives and Endpoints

The primary objective of this trial is to evaluate the safety and reactogenicity of the candidate vaccines across study arms.

The secondary objectives are to evaluate the humoral immune responses to vaccine-matched strains for influenza virus across study vaccine arms at Day 29. These will be evidenced by the following endpoints: GMT and GMFR at Day 29 compared to Day 1 by HAI assay and NAI assay;

percentage of participants with seroconversion, defined as a Day 29 titer ≥1:40 if baseline is <1:10 or a 4-fold or greater rise if baseline is ≥1:10 in anti-HA antibodies measured by HAI assay or in anti-NA antibodies measured by NAI assay; GMT and GMFR at all evaluable time points compared to Day 1 by HAI or NAI; and percentage of participants with seroconversion.

The exploratory objectives are to evaluate the humoral immune responses to vaccine-mismatched strains for influenza virus across study vaccine arms; to evaluate the humoral immune responses against vaccine-matched and vaccine-mismatched strains for influenza virus across study vaccine arms; to evaluate the cellular immune responses against influenza virus in a subset of participants; to further characterize the immune response to influenza virus across study vaccine arms; and to assess the occurrence of clinical influenza virus in study participants and characterize their immune response to infection and viral isolates. The exploratory objectives will be measured by the following endpoints: GMT and GMFR at all evaluable time points compared to Day 1 by HAI and NAI; percentage of participants with seroconversion; GMT and GMFR at all evaluable time points compared to Day 1 by alternative methods, including, but not limited to: microneutralization assay; frequency, magnitude, and phenotype of virus-specific T-cell and B-cell responses measured by flow cytometry or other methods; targeted repertoire analysis of B-cells and T-cells after vaccination; frequency, specificities, or other endpoints to be determined for the further characterization of immune responses; frequency of RT-PCR-confirmed clinical influenza; and assessment of immune responses to infection and viral isolates.

Example 8. A Phase 3, Randomized, Stratified, Observer-Blind, Active-Control Study to Evaluate the Immunogenicity, Reactogenicity and Safety of a Seasonal Influenza Vaccine in Adults 18 Years and Older As described in Example 6, the 4×HA vaccine comprises 4 mRNA sequences encoding stabilized mutant membrane-bound HA proteins (SEQ ID NOs: 85, 87, 91, and 94) of the four different influenza virus strains recommended by the WHO for 2022-2023 Northern Hemisphere cell- or recombinant-based vaccines was tested. In this Phase 3 trial, the immunogenicity, reactogenicity, and safety of the mRNA vaccine were compared to that of an influenza vaccine comparator (FLUARIX® Quadrivalent, which comprises 4 HAs of the 4 different influenza virus strains recommended by the WHO for 2022-2023 NH egg-based vaccines).

Treatment Groups and Dose Levels

Medically stable adults, aged 18 years and older, were screened and enrolled. Approximately 2400 participants were randomly assigned to treatment in this study in a 1:1: ratio to 1 of 2 treatment groups to receive either a single dose of mRNA-1010 or a single dose of a licensed seasonal influenza vaccine as an active comparator (FLUARIX® Quadrivalent) (Table E8-1 below).

TABLE E8-1

Treatment Groups and Dose Levels

| Treatment Group | Study Intervention | Total Dose (μg) | mRNA/Antigen HA (each) (μg) | No. of Participants |
|---|---|---|---|---|
| 1 | 4xHA (4x HA mutant) | 50 (of mRNA) | 12.5 (mRNA) | 1200 |
| 2 | FLUARIX ® Quadrivalent | 60 (of protein) | 15 (protein) | 1200 |

Objectives and Endpoints

The primary objectives of this trial were to evaluate the humoral immunogenicity of the mRNA vaccine relative to the influenza comparator vaccine against four vaccine-matched IAV and IBV strains at Day 29; and to evaluate the safety and reactogenicity of the mRNA vaccine. The humoral immunity was determined by the GMT at Day 29 (measured by HAI assay) and the proportion of participants reaching seroconversion at Day 29 (as measured by HAI assay).

The secondary objective was to further evaluate the humoral immunogenicity of the mRNA vaccine against four vaccine-matched IAV and IBV strains at Day 29. This was evidenced by the following endpoints: the proportion of participants with HAI titer ≥1:40 at Day 29 and the GMFR comparison between Day 29 and Day 1 (baseline) measured by HAI assay.

The exploratory objectives were to evaluate the humoral immunogenicity of the mRNA vaccine relative to that of the comparator vaccine against four vaccine-matched IAV and IBV strains at Day 181 (end of study) and to assess the occurrence of clinical influenza in study participants and characterize their immune responses to infection and viral isolates. These objectives were determined by measuring the GMT at Day 181 by HAI; determining the proportion of participants who reach seroconversion by Day 181 as measured by HAI; determining the GMT and GMFR of neutralizing antibodies by assays (e.g., microneutralization assays) or alternative methods against vaccine-matched or vaccine-mismatched strains on Day 29 compared to Day 1 (baseline); determining the GMT and GMFR of anti-HA antibodies as measured by HAI against vaccine-mismatched strains on Day 29 compared to Day 1 (baseline); and determining the frequency of RT-PCR-confirmed IL1 and assessment of immune responses in participants with RT-PCR-confirmed ILI.

Results

Figure 18A:
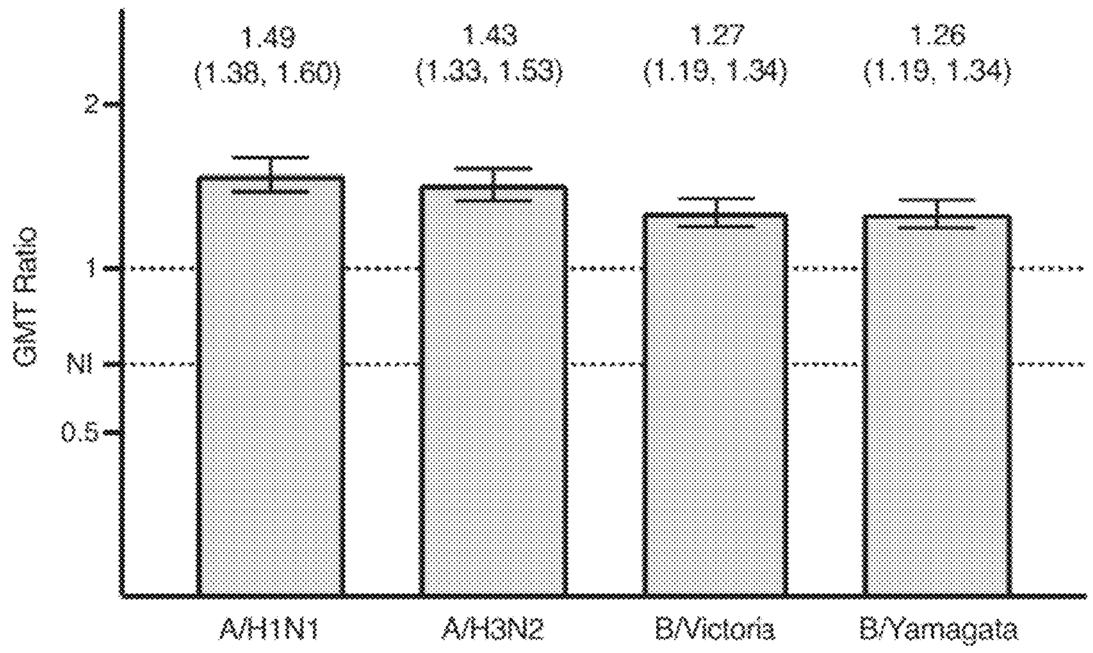
FIG. 18A shows the geometric mean titer (GMT) ratio against each of the four vaccine-matched strains in adults 18 years of age or older administered the 4×HA [50 μg] mRNA vaccine in which encoded HA proteins contained stabilizing substitutions (as present in SEQ ID NOs: 85, 87, 91, and 94).
Figure 18B:
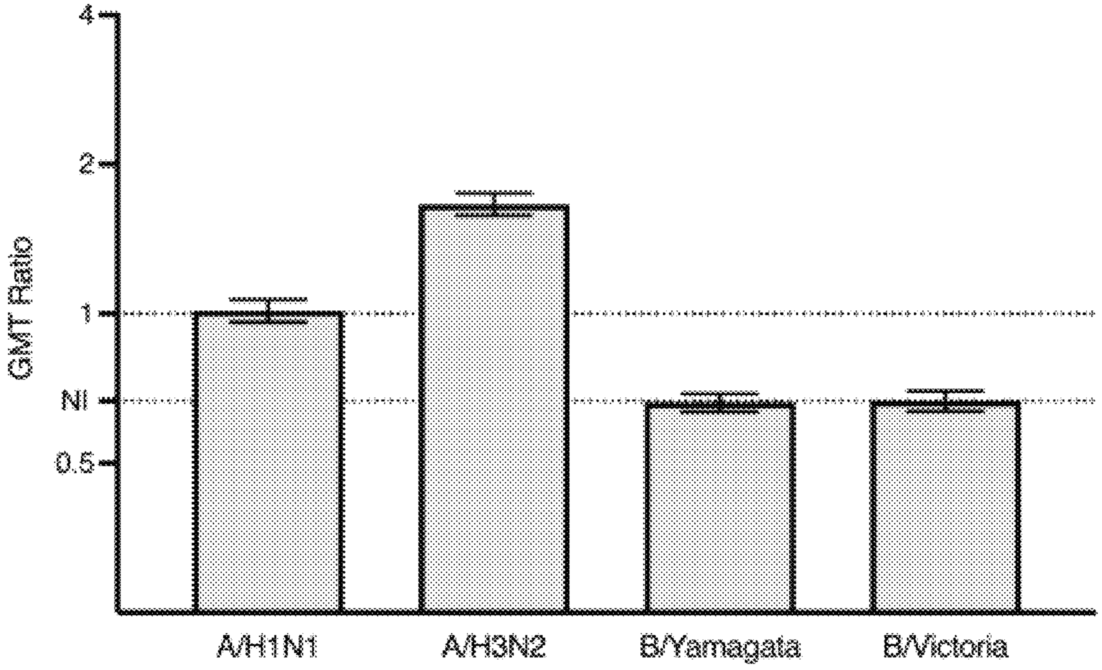
FIG. 18B shows GMT ratios against each of the four vaccine-matched strains in adults 18 years of age or older administered the 4×HA [50 μg] mRNA vaccine in a previous study, in which encoded HA proteins did not contain substitutions relative to wild-type amino acid sequences.

The mRNA vaccine was found to meet all primary immunogenicity endpoints, as measured by GMR and seroconversion rates. In particular, higher GMTs and seroconversion rates were observed for the mRNA vaccine for all four influenza virus strains (FIG. 18A). The increased titers against IBV HA proteins contrast with results of a previous study using mRNAs encoding non-mutant IBV HA proteins, where titers against both influenza B/Victoria lineage and influenza B/Yamagata lineage HA proteins were not superior to those elicited by comparator vaccines (FIG. 18B). Higher immunogenicity relative to the influenza vaccine comparator was consistently observed across all age groups, including adults of at least 65 years of age.

Example 9. A Phase 1/2, Randomized, Observer-blind, Active-Control Study to Evaluate the Safety, Reactogenicity, and Immunogenicity of mRNA-based Influenza Vaccines in Healthy Adults In this Phase 1/2 trial, the immunogenicity, reactogenicity, and safety of mRNA vaccines comprising 4 mRNAs each encoding one of: (i) an IAV H1 HA, (ii) an IAV H3 HA, (iii) an influenza B/Victoria lineage virus HA protein (with or without H381Y and A288V substitutions), and (iv) an influenza B/Yamagata lineage virus HA protein, were compared to that of comparator influenza vaccines (FLUARIX® Quadrivalent, which comprises 4 HAs of the 4 different influenza virus strains recommended by the WHO for 2022-2023 NH egg-based vaccines, and Fluzone high-dose).

Treatment Groups and Dose Levels

Subjects aged 18 to 80 were assigned to a treatment group in Table E9-1 below.

TABLE E9-1

| Interventions and Groups | | | | | |
|---|---|---|---|---|---|
| Group | Age | Number of Subjects | Vaccine Components | Dose | Dose (each mRNA/component) |
| A1 | 65 to <80 | 51 | Fluarix (comparator) | | |
| A2 | 65 to <80 | 50 | Fluzone high-dose (HD) (comparator) | Standard of care | Standard of care |
| A3 | 65 to <80 | 51 | 4xHA | 50 µg total mRNA | 12.5 µg each mRNA |
| A4 | 65 to <80 | 46 | 4xHA (H381Y-A288V) | 50 µg | 12.5 µg each mRNA |
| B1 | 50 to <65 | 25 | Fluarix (comparator) | Standard of care | Standard of care |
| B2 | 50 to <65 | 24 | 4xHA | 50 µg total mRNA | 12.5 µg each mRNA |
| B3 | 50 to <65 | 27 | 4xHA (H381Y-A288V) | 50 µg | 12.5 µg each mRNA |
| C1 | 18 to <50 | 24 | Fluarix (comparator) | Standard of care | Standard of care |
| C2 | 18 to <50 | 24 | 4xHA | 50 µg total mRNA | 12.5 µg each mRNA |
| C3 | 18 to <50 | 25 | 4xHA (H381Y-A288V) | 50 µg | 12.5 µg each mRNA |

Objectives and Endpoints

One objective of this trial was to evaluate humoral immune responses to vaccine-matched strains for influenza viruses at Day 29. This was evidenced by the following endpoints: GMT and GMFR at Day 29 compared to Day 1 by HAI assay, and percentage of participants with seroconversion, defined as a Day 29 titer greater than or equal to 1:40 if Baseline titer is less than 1:10, or a 4-fold or greater rise if Baseline titer is greater than or equal to 1:10, in anti-HA antibodies measured by HAI assay.

Results

The 4×HA mRNA vaccine in which the encoded influenza B/Victoria lineage HA protein included H381Y and A288V substitutions relative to SEQ ID NO: 71 elicited substantially higher anti-B/Victoria lineage HA antibody titers than each of the comparator mRNA vaccine (without H381Y and A288V substitutions), high-dose Fluzone, and Fluarix, as shown in Tables E9-2-E9-4:

TABLE E9-2

| Immunogenicity in subjects (Cohort A, 65 to <80 years) | | | | |
|---|---|---|---|---|
| | Fluarix (A1) N = 51 | Fluzone HD (A2) N = 50 | 4xHA (A3) N = 46 | 4xHA (H381Y-A288V) (A4) N = 49 |
| Day 1 GMT | 55.4 (41.3, 74.3) | 49.2 (35.8, 67.8) | 47.5 (34.7, 65.0) | 47.4 (35.2, 63.8) |
| Day 29 GMT | 100.7 (70.1, 144.8) | 106.3 (72.7, 155.3) | 89.3 (66.4, 120.2) | 150.5 (120.3, 188.4) |
| GMFR | 1.8 (1.3, 2.5) | 2.2 (1.6, 2.9) | 1.9 (1.5, 2.4) | 3.3 (2.4, 4.5) |
| SCR | 21.6 (11.3, 35.3) | 18.0 (8.6, 31.4) | 22.0 (11.5, 36.0) | 47.7 (32.5, 63.3) |

TABLE E9-3

| Immunogenicity in subjects (Cohort B, 50 to <65 years) | | | |
|---|---|---|---|
| | Fluarix (B1) N = 25 | 4xHA (B2) N = 24 | 4xHA (H381Y-A288V) (B3) N = 27 |
| Day 1 GMT | 45.9 (28.6, 73.8) | 54.0 (32.6, 89.7) | 39.0 (23.3, 65.2) |
| Day 29 GMT | 104.2 (67.7, 160.4) | 87.6 (58.8, 130.3) | 125.4 (79.4, 198.2) |
| GMFR | 2.3 (1.5, 3.4) | 1.6 (1.2, 2.2) | 3.2 (2.2, 4.7) |
| SCR | 32.0 (14.9, 53.5) | 8.7 (1.1, 28.0) | 40.7 (22.4, 61.2) |

TABLE E9-4

| Immunogenicity in subjects (Cohort C, 18 to <50 years) | | | |
|---|---|---|---|
| | Fluarix (C1) N = 24 | 4xHA (C2) N = 24 | 4xHA (H381Y-A288V) (C3) N = 25 |
| Day 1 GMT | 27.1 (19.1, 38.4) | 20.3 (13.6, 30.1) | 25.0 (18.3, 34.0) |
| Day 29 GMT | 72.3 (40.7, 128.5) | 40.6 (28.5, 57.7) | 54.2 (33.8, 87.0) |
| GMFR | 2.7 (1.7, 4.2) | 2.2 (1.6, 2.9) | 2.2 (1.5, 3.1) |
| SCR | 37.5 (18.8, 59.4) | 17.4 (5.0, 38.8) | 36.0 (18.0, 57.5) |

Data are shown as point estimate with 95% confidence interval in parentheses. GMT=geometric mean titer. GMFR=geometric mean fold rise. SCR=seroconversion rate. 95% CI is calculated based on the t-distribution of the log-transformed values for GM titer and GM fold rise values, respectively, then back transformed to the original scale for presentation.

Seroconversion at a participant level is defined as (a) a pre-vaccination HAI titer <1:10 and a post-vaccination titer >=1:40, or (b) a pre-vaccination HAI titer >=1:10 and a minimum 4-fold rise in post-vaccination HAI antibody titer.

Exemplary Sequences

| H1_Wisconsin_2019_WT_V2 | | |
|---|---|---|
| SEQ ID NO: 64 consists of from 5' end to 3' end: 5' UTR SEQ ID NO: 45, mRNA ORF SEQ ID NO: 46, and 3' UTR SEQ ID NO: 47. | | 64 |
| Chemistry | 1-methylpseudouridine | |
| Cap | 7mG(5')ppp(5')NlmpNp | |
| 5' UTR | AGGAAAUCGCAAAAUUUGCUCUUCGCGUUAGAUUUCUUUU<br>AGUUUUCUCGCAACUAGCAAGCUUUUUGUUCUCGCC | 45 |
| ORF of mRNA Construct (excluding the stop codon) | AUGAAGGCCAUCCUGGUCGUGAUGCUGUACACCUUCACCAC<br>CGCCAACGCCGACACCCUGUGCAUCGGCUACCACGCCAACA<br>ACAGCACCGACACCGUGGACACCGUGCUGGAGAAGAACGUG<br>ACCGUGACCCACAGCGUGAACCUGCUGGAGGACAAGCACAA<br>CGGCAAGCUGUGCAAGCUGAGGGGAGUGGCACCCCUGCACC<br>UGGGCAAGUGCAACAUCGCCGGCUGGAUCCUGGGCAACCCC<br>GAGUGCGAGAGCCUGAGCACAGCCCGGAGCUGGAGCUACAU<br>CGUGGAGACCAGCAACAGCGACAACGGCACCUGUUACCCCG<br>GCGACUUCAUCAACUACGAGGAGCUGCGGGAGCAGCUGAGC<br>AGCGUGAGCAGCUUCGAGCGGUUCGAGAUCUUCCCCAAGAC<br>CAGCAGCUGGCCCAACCACGACAGCGACAACGGCGUGACAG<br>CAGCCUGUCCACACGCCGGAGCCAAGAGCUUCUACAAGAAC<br>CUGAUCUGGCUGGUGAAGAAGGGCAAGAGCUACCCCAAGA<br>UCAACCAGACCUACAUCAACGACAAGGGCAAGGAGGUGCUG<br>GUGCUGUGGGGCAUCCACCACCCACCUACCAUCGCCGACCA<br>GCAGAGCCUGUACCAGAACGCCGACGCCUACGUGUUCGUGG<br>GCACCAGCCGGUACAGCAAGAAGUUCAAGCCAGAGAUCGCC<br>ACCCGGCCCAAGGUGAGAGACCAGGAGGGCCGGAUGAACUA<br>CUACUGGACCCUGGUGGAGCCCGGAGACAAGAUUACCUUCG<br>AGGCCACCGGCAACCUGGUGGCCCCUCGGUACGCCUUCACC<br>AUGGAACGGGACGCUGGCAGCGGCAUCAUCAUCAGCGACAC<br>UCCCGUGCACGACUGCAACACCACCUGCCAGACUCCCGAGG<br>GCGCUAUCAACACCAGCCUGCCCUUCCAGAACGUGCACCCC<br>AUCACCAUCGGCAAGUGCCCCAAGUACGUAAAGAGCACCAA<br>AUUGCGGCUGGCCACCGGACUCAGGAACGUGCCCAGCAUCC<br>AAAGCCGGGGCCUGUUUGGCGCAAUCGCCGGCUUCAUCGAG<br>GGCGGCUGGACUGGCAUGGUGGACGGCUGGUACGGCUACCA<br>CCACCAGAACGAACAGGGGAGCGGCUACGCAGCUGACCUGA<br>AGAGCACCCAGAACGCCAUCGACAAGAUCACCAACAAGGUG<br>AACAGCGUGAUCGAGAAGAUGAACACCCAGUUCACCGCCGU<br>GGGCAAGGAGUUCAACCACCUGGAGAAGCGGAUCGAGAACC<br>UGAACAAGAAGGUGGACGACGGCUUCCUGGACAUCUGGACC<br>UACAACGCCGAGCUGCUGGUUCUGCUGGAGAACGAGCGGAC<br>CCUGGACUAUCACGACAGCAACGUGAAGAACCUGUACGAGA<br>AGGUGCGGAACCAGCUGAAGAACAACGCCAAGGAGAUCGGC<br>AACGGCUGCUUCGAGUUCUACCACAAGUGCGACAACACCUG<br>CAUGGAGAGCGUGAAGAACGGCACCUACGACUACCCCAAGU<br>ACAGCGAGGAGGCCAAGCUGAACCGGGAGAAGAUCGACGGC<br>GUGAAGCUGGACAGCACCCGGAUCUACCAGAUCCUGGCCAU<br>CUACAGCACCGUGGCCAGCAGCCUGGUGCUGGUGGUGAGCC<br>UGGGCGCCAUCAGCUUCUGGAUGUGCAGCAACGGCAGCCUG<br>CAGUGCCGGAUCUGCAUC | 46 |

-continued

| | | |
|---|---|---|
| 3' UTR | UAAAGCUCCCCGGGGGCCUCGGUGGCCCUCCACCGAAGCAG<br>CCAUCAGCACCCCCAGCCCCUCCUCCCCUUCCUGCAGGUCAA<br>AGUGGUCUUUGAAUAAAGUCUGAGUGGGCGGC | 47 |
| Corresponding amino acid sequence | MKAILVVMLYTFTTANADTLCIGYHANNSTDTVDTVLEKNVTV<br>THSVNLLEDKHNGKLCKLRGVAPLHLGKCNIAGWILGNPECES<br>LSTARSWSYIVETSNSDNGTCYPGDFINYEELREQLSSVSSFE<br>RFEIFPKTSSWPNHDSDNGVTAACPHAGAKSFYKNLIWLVKKG<br>KSYPKINQTYINDKGKEVLVLWGIHHPPTIADQQSLYQNADAY<br>VFVGTSRYSKKFKPEIATRPKVRDQEGRMNYYWTLVEPGDKIT<br>FEATGNLVAPRYAFTMERDAGSGIIISDTPVHDCNTTCQTPEG<br>AINTSLPFQNVHPITIGKCPKYVKSTKLRLATGLRNVPSIQSR<br>GLFGAIAGFIEGGWTGMVDGWYGYHHQNEQGSGYAADLKSTQN<br>AIDKITNKVNSVIEKMNTQFTAVGKEFNHLEKRIENLNKKVDD<br>GFLDIWTYNAELLVLLENERTLDYHDSNVKNLYEKVRNQLKNN<br>AKEIGNGCFEFYHKCDNTCMESVKNGTYDYPKYSEEAKLNREK<br>IDGVKLDSTRIYQILAIYSTVASSLVLVVSLGAISFWMCSNGS<br>LQCRICI | 48 |
| PolyA tail | 100 nt | |

H3_A/Darwin/6/2021_G53D_V2

| | | |
|---|---|---|
| SEQ ID NO: 65 consists of from 5' end to 3' end: 5' UTR SEQ ID NO: 45, mRNA ORF SEQ ID NO: 49, and 3' UTR SEQ ID NO: 50. | | 65 |
| Chemistry | 1-methylpseudouridine | |
| Cap | 7mG(5')ppp(5')N1mpNp | |
| 5' UTR | AGGAAAUCGCAAAAUUUGCUCUUCGCGUUAGAUUUUUU<br>AGUUUUCUCGCAACUAGCAAGCUUUUUGUUCUCGCC | 45 |
| ORF of mRNA Construct (excluding the stop codon) | AUGAAGACCAUCAUCGCCCUGAGCAACAUCCUGUGCCUGGU<br>GUUCGCCCAGAAGAUCCCCGGCAACGAUAACAGCACCGCCA<br>CCCUGUGUCUGGGACACCACGCCGUGCCCAACGGCACCAUC<br>GUGAAGACUAUCACCAACGACCGGAUCGAGGUGACCAACGC<br>CACCGAGCUGGUGCAGAACAGCAGCAUCGGCGAGAUCUGCG<br>ACAGCCCUCACCAGAUCCUGGACGGCGGCAACUGCACCCUG<br>AUCGACGCACUGCUGGGCGACCCUCAGUGCGACGGCUUUCA<br>GAACAAGGAGUGGGACCUGUUCGUGGAGAGAUCGCGGGCC<br>AACAGCAACUGCUACCCCUACGACGUCCCCGACUACGCAAG<br>CCUGAGAAGCCUCGUGGCCUCAAGCGGCACCCUGGAGUUCA<br>AGAACGAGAGCUUCAACUGGACCGGCGUGAAGCAGAACGGC<br>ACCUCAAGCGCCUGCAUCCGGGGCUCCAGCAGCAGCUUCUU<br>CUCACGGCUGAACUGGCUGACCCACCUGAACAACAUCUACC<br>CCGCCCAGAACGUGACCAUGCCCAACAAGGAGCAGUUCGAC<br>AAGCUGUACAUCUGGGGAGUGCACCAUCCCGACACCGACAA<br>GAACCAGAUUAGCCUGUUCGCCCAGAGCAGCGGCCGGAUCA<br>CCGUGAGCACCAAGCGGAGCCAGCAGGCCGUGAUCCCCAAC<br>AUCGGCUCUCGGCCCAGAAUCCGGGACAUCCCCAGCCGGAU<br>CAGCAUCUACUGGACCAUUGUGAAGCCCGGCGACAUCCUGC<br>UGAUCAACUCCACCGGCAACCUGAUCGCCCCUCGGGGCUAU<br>UUCAAGAUCCGGAGCGGCAAGAGCAGCAUCAUGCGGAGCGA<br>CGCCCCUAUCGGCAAGUGCAAGAGCGAGUGCAUCACACCCA<br>ACGGAAGCAUCCCCAACGACAAGCCCUUCCAGAACGUGAAC<br>CGGAUAACCUACGGCGCCUGCCCUAGAUACGUGAAGCAGAG<br>CACCCUGAAGCUGGCCACCGGCAUGCGGAACGUGCCCGAGA<br>AGCAGACUCGGGGCAUCUUCGGCGCCAUCGCCGGCUUCAUC<br>GAGAACGGCUGGGAGGGCAUGGUGGACGGCUGGUACGGCU<br>UCCGGCACCAGAACUCUGAGGGCAGAGGACAGGCCGCAGAC<br>CUGAAGAGCACCCAGGCCGCCAUCGACCAGAUCAACGGCAA<br>GCUGAACCGGCUGAUCGGCAAGACCAACGAGAAGUUCCACC<br>AGAUCGAGAAGGAGUUCAGCGAGGUGGAGGGCAGGGUACA<br>GGACCUGGAGAAGUACGUGGAGGACACCAAGAUCGACCUG<br>UGGAGCUACAACGCCGAGCUGCUGGUAGCCCUGGAGAACCA<br>GCACACCAUCGACCUGACCGACAGCGAGAUGAACAAGCUGU<br>UCGAGAAGACCAAGAAGCAGCUGCGGGAGAACGCCGAGGAC<br>AUGGGCAACGGCUGCUUCAAGAUCUACCACAAGUGCGACAA<br>CGCCUGCAUCGGCAGCAUCCGGAACGAGACCUACGACCACA<br>ACGUGUACCGGGACGAGGCCCUGAACAACCGGUUCCAGAUC<br>AAGGGCGUGGAGCUGAAGAGCGGCUACAAGGACUGGAUCC<br>UGUGGAUCAGCUUCGCCAUGUCCUGCUUCCUGCUGUGCAUC<br>GCCCUGCUGGGUUUCAUCAUGUGGGCCUGCCAGAAGGGCAA<br>CAUCCGGUGCAACAUCUGCAUC | 49 |

-continued

| | | |
|---|---|---|
| 3' UTR | UAAAGCUCCCCGGGGGCCUCGGUGGCCCUCCGCAUCAGACC<br>AACGGCACACCCCCAGCCCCUCCUCCCCUUCCUGCAGGUCA<br>AGGAGUGGUCUUUGAAUAAAGUCUGAGUGGGCGGC | 50 |
| Corresponding amino acid sequence | MKTIIALSNILCLVFAQKIPGNDNSTATLCLGHHAVPNGTIVKTIT<br>NDRIEVTNATELVQNSSIGEICDSPHQILDGGNCTLIDALLGDPQC<br>DGFQNKEWDLFVERSRANSNCYPYDVPDYASLRSLVASSGTLEF<br>KNESFNWTGVKQNGTSSACIRGSSSSFFSRLNWLTHLNNIYPAQ<br>NVTMPNKEQFDKLYIWGVHHPDTDKNQISLFAQSSGRITVSTKR<br>SQQAVIPNiGSRPRIRDIPSRISIYWTIVKPGDILLINSTGNLI<br>APRGYFKIRSGKSSIMRSDAPIGKCKSECITPNGSIPNDKPFQN<br>VNRITYGACPRYVKQSTLKLATGMRNVPEKQTRGIFGAIAGFIE<br>NGWEGMVDGWYGFRHQNSEGRGQAADLKSTQAAIDQINGKLNRL<br>IGKTNEKFHQIEKEFSEVEGRVQDLEKYVEDTKIDLWSYNAELL<br>VALENQHTIDLTDSEMNKLFEKTKKQLRENAEDMGNGCFKIYHK<br>CDNACIGSIRNETYDHNVYRDEALNNRFQIKGVELKSGYKDWIL<br>WISFAMSCFLLCIALLGFIMWACQKGNIRCNICI | 51 |
| PolyA tail | 100 nt | |

B/Austria/1359417/2021 H363Y A270V HA_SEv4.5

| | | |
|---|---|---|
| SEQ ID NO: 66 consists of from 5' end to 3' end: 5' UTR SEQ ID NO: 45, mRNA ORF SEQ ID NO: 52, and 3' UTR SEQ ID NO: 53. | | 66 |
| Chemistry | 1-methylpseudouridine | |
| Cap | 7mG(5')ppp(5')NlmpNp | |
| 5' UTR | AGGAAAUCGCAAAAUUUGCUCUUCGCGUUAGAUUUCUUUU<br>AGUUUUCUCGCAACUAGCAAGCUUUUUGUUCUCGCC | 45 |
| ORF of mRNA Construct (excluding the stop codon) | AUGAAGGCUAUCAUCGUGCUGUUAAUGGUGGUGACCAGCA<br>ACGCCGACCGGAUCUGCACAGGCAUCACCUCUAGCAACAGC<br>CCUCACGUGGUCAAGACCGCCACACAGGGCGAGGUGAACGU<br>GACCGGCGUGAUUCCCCUGACCACCACCCCUACCAAGAGCC<br>ACUUCGCCAACCUGAAGGGAACCGAGACCCGGGGCAAGCUG<br>UGUCCAAAGUGCCUGAACUGUACCGACCUGGACGUGGCUCU<br>GGGCAGACCCAAGUGCACCGGCAAGAUCCCCAGCGCCCGGG<br>UGUCUAUCUUGCACGAAGUGCGGCCCGUGACUAGCGGUUGC<br>UUCCCCAUCAUGCACGACCGGACCAAGAUCAGACAGCUGCC<br>CAACCUGCUGCGGGGCUACGAGCACGUGCGGCUGUCCACCC<br>AUAACGUGAUCAACACCGAAGACGCACCCGGCGGCCCAUAC<br>GAGAUCGGCACCAGCGGCUCUUGCCUGAAUAUCACCAACGG<br>CAAGGGAUUCUUUGCUACCAUGGCCUGGGCCGUGCCAAAGA<br>ACAAGACUGCCACCAACCCUCUGACCAUCGAGGUGCCCUAC<br>AUCUGCACCGAGGAGGAGGACCAGAUCACCGUGUGGGGCUU<br>CCACAGCGACGACGAGACACAGAUGGCCAGACUGUACGGCG<br>ACAGCAAACCCCAGAAGUUCACCAGCAGCGCCAACGGCGUG<br>ACCACCCACUACGUGAGCCAGAUUGGCGGCUUCCCUAACCA<br>AACCGAGGACGGCGGCUUACCCCAGAGCGGCCGGAUCGUGG<br>UGGACUACAUGGUUCAGAAGAGCGGCAAGACCGGCACCAUC<br>ACCUACCAGCGGGGCAUCCUGUUACCACAGAAGGUGUGGUG<br>CGUGUCAGGGAAAUCAAAGGUCAUCAAGGGCUCCCUGCCAC<br>UGAUUGGCGAGGCCGACUGCCUGCACGAGAAGUACGGCGGC<br>CUGAACAAGAGCAAGCCCUACUACACCGGCGAGCACGCCAA<br>GGCAAUCGGCAACUGCCCCAUCUGGGUGAAGACACCCCUGA<br>AGCUGGCAAACGGCACCAAGUACCGGCCACCCGCCAAACUG<br>CUGAAGGAGCGGGGCUUCUUCGGCGCCAUUGCCGGCUUCCU<br>CGAAGGCGGUUGGGAGGGCAUGAUCGCAGGCUGGUACGGC<br>UACACUAGCCACGGCGCACACGGAGUAGCAGUGGCCGCCGA<br>CCUGAAGAGCACCCAGGAGGCCAUCAACAAGAUCACCAAGA<br>ACCUGAACAGCCUGAGCGAGCUGGAGGUGAAGAAUCUGCA<br>GAGGCUGUCUGGCGCUAUGGACGAGCUGCACAACGAGAUCC<br>UGGAGCUGGACGAGAAGGUGGACGACUUACGGGCCGACACC<br>AUCAGCAGCCAGAUCGAGCUGGCAGUGCUGCUGAGCAACGA<br>GGGCAUCAUCAACAGCGAGGACGAGCACCUGCUGGCCCUGG<br>AGCGGAAGCUGAAGAAGAUGCUGGGCCCUUCUGCCGUGGA<br>GAUCGGUAACGGCUGCUUCGAGACCAAGCACAAGUGCAACC<br>AGACCUGCCUGGAUCGGAUCGCAGCCGGCACCUUUGACGCC<br>GGGGAGUUCAGCCUGCCCACCUUCGACAGCUUGAACAUCAC<br>CGCCGCCAGCCUGAACGACGACGGCCUGGACAACCACACCA<br>UCCUGCUGUACUACUCUACAGCCGCUAGCAGCCUGGCCGUG<br>ACCCUGAUGAUCGCCAUCUUCGUGGUGUACAUGGUGAGCCG<br>GGACAACGUGAGCUGCAGCAUCUGCCUG | 52 |

-continued

| | | |
|---|---|---|
| 3' UTR | UAAAGCUCCCCGGGGGCCUCGGUGGCCCUCAACCUACGCCG<br>AAGACCACGCCCCCAGCCCCUCCUCCCCUUCCUGCAGGUCA<br>AGAGUGGUCUUUGAAUAAAGUCUGAGUGGGCGGC | 53 |
| Corresponding amino acid sequence | MKAIIVLLMVVTSNADRICTGITSSNSPHVVKTATQGEVNVTGVI<br>PLTTTPTKSHFANLKGTETRGKLCPKCLNCTDLDVALGRPKCTGK<br>IPSARVSILHEVRPVTSGCFPIMHDRTKIRQLPNLLRGYEHVRLS<br>THNVINTEDAPGGPYEIGTSGSCLNITNGKGFFATMAWAVPKNK<br>TATNPLTIEVPYICTEEEDQITVWGFHSDDETQMARLYGDSKPQ<br>KFTSSANGVTTHYVSQIGGFPNQTEDGGLPQSGRIVVDYMVQKS<br>GKTGTITYQRGILLPQKVWCVSGKSKVIKGSLPLIGEADCLHEK<br>YGGLNKSKPYYTGEHAKAIGNCPIWVKTPLKLANGTKYRPPAKL<br>LKERGFFGAIAGFLEGGWEGMIAGWYGYTSHGAHGVAVAADLK<br>STQEAINKITKNLNSLSELEVKNLQRLSGAMDELHNEILELDEK<br>VDDLRADTISSQIELAVLLSNEGIINSEDEHLLALERKLKKMLG<br>PSAVEIGNGCFETKHKCNQTCLDRIAAGTFDAGEFSLPTFDSLN<br>ITAASLNDDGLDNHTILLYYSTAASSLAVTLMIAIFVVYMVSRD<br>NVSCSICL | 54 |
| PolyA tail | 100 nt | |

B/Phuket/3073/2013 H363Y A270V HA

| | | |
|---|---|---|
| SEQ ID NO: 67 consists of from 5' end to 3' end: 5' UTR SEQ ID NO: 45, mRNA ORF SEQ ID NO: 55, and 3' UTR SEQ ID NO: 56. | | 67 |
| Chemistry | 1-methylpseudouridine | |
| Cap | 7mG(5')ppp(5')NlmpNp | |
| 5' UTR | AGGAAAUCGCAAAAUUUGCUCUUCGCGUUAGAUUUCUUUU<br>AGUUUUCUCGCAACUAGCAAGCUUUUUGUUCUCGCC | 45 |
| ORF of mRNA Construct (excluding the stop codon) | AUGAAGGCUAUCAUCGUGCUACUCAUGGUGGUAACCAGCA<br>ACGCCGACCGGAUCUGCACCGGCAUCACCAGCAGCAACAGC<br>CCGCACGUUGUGAAGACCGCCACCCAAGGCGAGGUGAACGU<br>GACCGGCGUGAUCCCACUGACCACCACUCCCACCAAGAGCU<br>ACUUCGCCAACCUGAAGGGCACUCGGACUCGGGGCAAGCUC<br>UGCCCCGACUGCCUGAACUGCACCGACCUGGACGUGGCUCU<br>GGGCAGACCCAUGUGCGUGGGGACCACCCCUUCUGCCAAGG<br>CCUCAAUCCUGCACGAGGUCAGGCCCGUGACCAGCGGGUGC<br>UUCCCCAUCAUGCACGACCGGACCAAGAUCAGACAGCUGCC<br>CAACCUGCUGCGGGGCUACGAGAAGAUCCGGCUGAGCACAC<br>AGAACGUGAUCGACGCCGAGAAGGCCCCUGGAGGUCCCUAC<br>CGGCUGGGCACCAGCGGAAGCUGCCCCAACGCCACGAGCAA<br>GAUCGGCUUCUUCGCCACCAUGGCCUGGGCUGUGCCCAAGG<br>ACAACUACAAGAACGCCACCAAUCCCCUGACCGUGGAGGUG<br>CCCUACAUUUGUACCGAGGGCGAGGACCAGAUCACCGUGUG<br>GGGCUUCCACAGCGACAACAAGACCCAAAUGAAGAGCCUGU<br>ACGGCGACAGCAAUCCCCAGAAGUUCACAAGCAGCGCCAAC<br>GGUGUGACCACCCACUACGUGAGCCAGAUUGGCGACUUCCC<br>CGACCAGACCGAGGACGGAGGGCUGCCGCAGAGUGGCCGGA<br>UCGUGGUGGACUACAUGAUGCAGAAGCCCGGCAAGACCGGC<br>ACCAUAGUGUAUCAGCGGGGCGUGCUGUUGCCUCAGAAAG<br>UUUGGUGUGUGAGCGGCAGGAGCAAGGUGAUCAAGGGCAG<br>CCUUCCCCUGAUCGGCGAGGCAGACUGCCUCCACGAGGAGU<br>ACGGCGGCCUGAACAAGAGCAAGCCCUACUACACCGGCAAG<br>CACGCCAAGGCAAUCGGGAACUGCCCCAUCUGGGUCAAGAC<br>CCCUCUGAAGCUGGCCAACGGCACCAAGUACCGGCCACCAG<br>CCAAGCUGCUGAAGGAGCGGGGCUUCUUUGGCGCCAUUGCC<br>GGCUUCCUCGAGGGAGGCUGGGAGGGCAUGAUCGCCGGCUG<br>GUACGGCUACACAAGCCACGGCGCACACGGAGUGGCUGUGG<br>CUGCCGACCUGAAGAGCACCCAGGAGGCCAUCAACAAGAUC<br>ACCAAGAAUCUGAACAGCCUGAGCGAGCUGGAGGUGAAGA<br>ACCUGCAGCGGCUGUCAGGCGCCAUGGACGAGCUGCACAAC<br>GAGAUCCUGGAGCUGGACGAGAAGGUGGACGACCUGCGUG<br>CCGACACCAUCAGCAGCCAGAUCGAGCUGGCCGUACUGCUG<br>AGCAACGAGGGCAUCAUCAACAGCGAGGACGAGCACCUGCU<br>GGCCCUGGAGCGGAAACUGAAGAAGAUGCUGGGACCCUCUG<br>CCGUGGACAUCGGCAACGGCUGCUUCGAGACUAAGCACAAG<br>UGCAACCAGACCUGCCUGGAUCGGAUCGCCGCCGGAACCUU<br>CAACGCCGGCGAGUUCAGCCUGCCCACCUUCGACAGCUUAA<br>ACAUCACCGCCGCCAGCCUGAACGACGACGGCCUGGACAAC<br>CACACCAUCCUGCUGUACUACAGCACUGCCGCCUCAAGCCU | 55 |

-continued

| | | |
|---|---|---|
| | GGCCGUGACCCUGAUGCUGGCCAUCUUCAUCGUGUACAUGG<br>UGAGCCGGGACAACGUGAGCUGCAGCAUCUGCCUG | |
| 3' UTR | UAAAGCUCCCCGGGGGCCUCGGUGGCCCUCAACGACCCUGC<br>CGCAGCAAACCCCCAGCCCCUCCUCCCCUUCCUGCAGGAUC<br>AGUGGUCUUUGAAUAAAGUCUGAGUGGGCGGC | 56 |
| Corresponding amino acid sequence | MKAIIVLLMVVTSNADRICTGITSSNSPHVVKTATQGEVNVTGVI<br>PLTTTPTKSYFANLKGTRTRGKLCPDCLNCTDLDVALGRPMCVG<br>TTPSAKASILHEVRPVTSGCFPIMHDRTKIRQLPNLLRGYEKIRL<br>STQNVIDAEKAPGGPYRLGTSGSCPNATSKIGFFATMAWAVPKD<br>NYKNATNPLTVEVPYICTEGEDQITVWGFHSDNKTQMKSLYGD<br>SNPQKFTSSANGVTTHYVSQIGDFPDQTEDGGLPQSGRIVVDYM<br>MQKPGKTGTIVYQRGVLLPQKVWCVSGRSKVIKGSLPLIGEADC<br>LHEEYGGLNKSKPYYTGKHAKAIGNCPIWVKTPLKLANGTKYR<br>PPAKLLKERGFFGAIAGFLEGGWEGMIAGWYGYTSHGAHGVAVA<br>ADLKSTQEAINKITKNLNSLSELEVKNLQRLSGAMDELHNEILE<br>LDEKVDDLRADTISSQIELAVLLSNEGIINSEDEHLLALERKLK<br>KMLGPSAVDIGNGCFETKHKCNQTCLDRIAAGTFNAGEFSLPTF<br>DSLNITAASLNDDGLDNHTILLYYSTAASSLAVTLMLAIFIVYM<br>VSRDNVSCSICL | 57 |
| PolyA tail | 100 nt | |

NTD-RBD-HATM vV2

| | | |
|---|---|---|
| SEQ ID NO: 68 consists of from 5' end to 3' end: 5' UTR SEQ ID NO: 45, mRNA ORF SEQ ID NO: 58, and 3' UTR SEQ ID NO: 59. | | 68 |
| Chemistry | 1-methylpseudouridine | |
| Cap | 7mG(5')ppp(5')N1mpNp | |
| 5' UTR | AGGAAAUCGCAAAAUUUGCUCUUCGCGUUAGAUUUCUUUU<br>AGUUUUCUCGCAACUAGCAAGCUUUUUGUUCUCGCC | 45 |
| ORF of mRNA Construct (excluding the stop codon) | AUGUUCGUGUUCCUGGUGCUGCUGCCCCUGGUGAGCAGCCA<br>GUGCGUGAACCUGACCACCCGGACCCAGCUGCCACCAGCCU<br>ACACCAACAGCUUCACCCGGGGCGUCUACUACCCCGACAAG<br>GUGUUCCGGAGCAGCGUCCUGCACAGCACCCAGGACCUGUU<br>CCUGCCCUUCUUCAGCAACGUGACCUGGUUCCACGCCAUCC<br>ACGUGAGCGGCACCAACGGCACCAAGCGGUUCGACAACCCC<br>GUGCUGCCCUUCAACGACGGCGUGUACUUCGCCAGCACCGA<br>GAAGAGCAACAUCAUCCGGGGCUGGAUCUUCGGCACCACCC<br>UGGACAGCAAGACCCAGAGCCUGCUGAUCGUGAAUAACGCC<br>ACCAACGUGGUGAUCAAGGUGUGCGAGUUCCAGUUCUGCA<br>ACGACCCCUUCCUGGGCGUGUACUACCACAAGAACAACAAG<br>AGCUGGAUGGAGAGCGAGUUCCGGGUGUACAGCAGCGCCA<br>ACAACUGCACCUUCGAGUACGUGAGCCAGCCCUUCCUGAUG<br>GACCUGGAGGGCAAGCAGGGCAACUUCAAGAACCUGCGGGA<br>GUUCGUGUUCAAGAACAUCGACGGCUACUUCAAGAUCUACA<br>GCAAGCACACCCCAAUCAACCUGGUGCGGGAUCUGCCCCAG<br>GGCUUCUCAGCCCUGGAGCCCCUGGUGGACCUGCCCAUCGG<br>CAUCAACAUCACCCGGUUCCAGACCCUGCUGGCCCUGCACC<br>GGAGCUACCUGACCCCAGGCGACAGCAGCAGCGGGUGGACA<br>GCAGGCGCGGCUGCUUACUACGUGGGCUACCUGCAGCCCCG<br>GACCUUCCUGCUGAAGUACAACGAGAACGGCACCAUCACCG<br>ACGCCGUGGACGGAGGCGGAUCGGGAGGCGGACCCAACAUC<br>ACCAACCUGUGCCCCUUCGGCGAGGUGUUCAACGCCACCCG<br>GUUCGCCAGCGUGUACGCCUGGAACCGGAAGCGGAUCAGCA<br>ACUGCGUGGCCGACUACAGCGUGCUGUACAACAGCGCCAGC<br>UUCAGCACCUUCAAGUGCUACGGCGUGAGCCCCACCAAGCU<br>GAACGACCUGUGCUUCACCAACGUGUACGCCGACAGCUUCG<br>UGAUCCGUGGCGACGAGGUGCGGCAGAUCGCACCCGGCCAG<br>ACAGGCAAGAUCGCCGACUACAACUACAAGCUGCCCGACGA<br>CUUCACCGGCUGCGUGAUCGCCUGGAACAGCAACAACCUCG<br>ACAGCAAGGUGGGCGGCAACUACAACUACCUGUACCGGCUG<br>UUCCGGAAGAGCAACCUGAAGCCCUUCGAGCGGGACAUCAG<br>CACCGAGAUCUACCAAGCCGGCUCCACCCCUUGCAACGGCG<br>UGGAGGGCUUCAACUGCUACUUCCCUCUGCAGAGCUACGGC<br>UUCCAGCCCACCAACGGCGUGGGCUACCAGCCCUACCGGGU<br>GGUGGUGCUGAGCUUCGAGCUGCUGCACGCCCCAGCCACCG<br>UGUGUGGCCCCAAGUCUGGCGGAGGCAGCAUCCUGGCCAUC<br>UACAGCACCGUGGCCAGCAGCCUGGUGCUGCUGGUGAGCCU<br>GGGCGCCAUCAGCUUC | 58 |
| 3' UTR | UAAAGCUCCCCGGGGGCCUCGGUGGCCUAGCUUCUUGCCCC<br>UUGGGCCUCCCCCCAGCCCCUCCUCCCCUUCCUGCACCUGUA<br>CUUCCGUGGUCUUUGAAUAAAGUCUGAGUGGGCGGC | 59 |

-continued

| | | |
|---|---|---|
| Corresponding amino acid sequence | MFVFLVLLPLVSSQCVNLTTRTQLPPAYTNSFTRGVYYPDKVFR<br>SSVLHSTQDLFLPFFSNVTWFHAIHVSGTNGTKRFDNPVLPFNDG<br>VYFASTEKSNIIRGWIFGTTLDSKTQSLLIVNNATNVVIKVCEFQF<br>CNDPFLGVYYHKNNKSWMESEFRVYSSANNCTFEYVSQPFLMD<br>LEGKQGNFKNLREFVFKNIDGYFKIYSKHTPINLVRDLPQGFSAL<br>EPLVDLPIGINITRFQTLLALHRSYLTPGDSSSGWTAGAAAYYVG<br>YLQPRTFLLKYNENGTITDAVDGGGSGGGPNITNLCPFGEVFNA<br>TRFASVYAWNRKRISNCVADYSVLYNSASFSTFKCYGVSPTKLN<br>DLCFTNVYADSFVIRGDEVRQIAPGQTGKIADYNYKLPDDFTGC<br>VIAWNSNNLDSKVGGNYNYLYRLFRKSNLKPFERDISTEIYQAG<br>STPCNGVEGFNCYFPLQSYGFQPTNGVGYQPYRVVVLSFELLHA<br>PATVCGPKSGGGSILAIYSTVASSLVLLVSLGAISF | 60 |
| PolyA tail | 100 nt | |

BA.4.BA.5-NTD-RBD-HATM

| | | |
|---|---|---|
| SEQ ID NO: 69 consists of from 5' end to 3' end: 5' UTR SEQ ID NO: 45, mRNA ORF SEQ ID NO: 61, and 3' UTR SEQ ID NO: 62. | | 69 |
| Chemistry | 1-methylpseudouridine | |
| Cap | 7mG(5')ppp(5')NlmpNp | |
| 5' UTR | AGGAAAUCGCAAAAUUUGCUCUUCGCGUUAGAUUUCUUUU<br>AGUUUUCUCGCAACUAGCAAGCUUUUUGUUCUCGCC | 45 |
| ORF of mRNA Construct (excluding the stop codon) | AUGUUCGUGUUCCUGGUGCUGCUGCCCCUGGUGAGCAGCCA<br>GUGCGUGAACCUGAUCACCCGGACCCAGAGCUACACCAACA<br>GCUUCACCCGGGGCGUCUACUACCCCGACAAGGUGUUCCGG<br>AGCAGCGUCCUGCACAGCACCCAGGACCUGUUCCUGCCCUU<br>CUUCAGCAACGUGACCUGGUUCCACGCCAUCAGCGGCACCA<br>ACGGCACCAAGCGGUUCGACAACCCCGUGCUGCCCUUCAAC<br>GACGGCGUGUACUUCGCCAGCACCGAGAAGAGCAACAUCAU<br>CCGGGGCUGGAUCUUCGGCACCACCCUGGACAGCAAGACCC<br>AGAGCCUGCUGAUCGUGAAUAACGCCACCAACGUGGUGAUC<br>AAGGUGUGCGAGUUCCAGUUCUGCAACGACCCCUUCCUGGA<br>CGUGUACUACCACAAGAACAACAAGAGCUGGAUGGAGAGC<br>GAGUUCCGGGUGUACAGCAGCGCCAACAACUGCACCUUCGA<br>GUACGUGAGCCAGCCCUUCCUGAUGGACCUGGAGGGCAAGC<br>AGGGCAACUUCAAGAACCUGCGGGAGUUCGUGUUCAAGAA<br>CAUCGACGGCUACUUCAAGAUCUACAGCAAGCACACCCCAA<br>UCAACCUGGGCCGGGAUCUGCCCCAGGGCUUCUCAGCCCUG<br>GAGCCCCUGGUGGACCUGCCCAUCGGCAUCAACAUCACCCG<br>GUUCCAGACCCUGCUGGCCCUGCACCGGAGCUACCUGACCC<br>CAGGCGACAGCAGCAGCGGGUGGACAGCAGGCGCGGCUGCU<br>UACUACGUGGGCUACCUGCAGCCCCGGACCUUCCUGCUGAA<br>GUACAACGAGAACGGCACCAUCACCGACGCCGUGGACGGCG<br>GAGGCUCUGGAGGCGGCCCCAACAUCACCAACCUGUGCCCC<br>UUCGACGAGGUGUUCAACGCCACCCGGUUCGCCAGCGUGUA<br>CGCCUGGAACCGGAAGCGGAUCAGCAACUGCGUGGCCGACU<br>ACAGCGUGCUGUACAACUUCGCCCCAUUCUUCGCCUUCAAG<br>UGCUACGGCGUGAGCCCCACCAAGCUGAACGACCUGUGCUU<br>CACCAACGUGUACGCCGACAGCUUCGUGAUCCGUGGCAACG<br>AGGUGAGCCAGAUCGCACCCGGCCAGACAGGCAACAUCGCC<br>GACUACAACUACAAGCUGCCCGACGACUUCACCGGCUGCGU<br>GAUCGCCUGGAACAGCAACAAGCUCGACAGCAAGGUGGGCG<br>GCAACUACAACUACCGGUACCGGCUGUUCCGGAAGAGCAAC<br>CUGAAGCCCUUCGAGCGGGACAUCAGCACCGAGAUCUACCA<br>AGCCGGCAACAAGCCUUGCAACGGCGUGGCCGGCGUGAACU<br>GCUACUUCCCUCUGCAGAGCUACGGCUUCCGGCCCACCUAC<br>GGCGUGGGCCACCAGCCCUACCGGGUGGUGGUGCUGAGCUU<br>CGAGCUGCUGCACGCCCCAGCCACCGUGUGUGGCCCCAAGA<br>GCGGCGGCGGCAGCAUCCUGGCCAUCUACAGCACCGUGGCC<br>AGCAGCCUGGUGCUGCUGGUGAGCCUGGGCGCCAUCAGCUU<br>U | 61 |
| 3' UTR | UAAAGCUCCCCGGGGGCCUCGGUGGCCUAGCUUCUUGCCCC<br>UUGGGCCUCCCCCCAGCCCCUCCUCCCCUUCCUGCAUUUGCC<br>UGUGAGCAGUGGUCUUUGAAUAAAGUCUGAGUGGGCGGC | 62 |
| Corresponding amino acid sequence | MFVFLVLLPLVSSQCVNLITRTQSYTNSFTRGVYYPDKVFRSSVL<br>HSTQDLFLPFFSNVTWFHAISGTNGTKRFDNPVLPFNDGVYFAST<br>EKSNIIRGWIFGTTLDSKTQSLLIVNNATNVVIKVCEFQFCNDPFL<br>DVYYHKNNKSWMESEFRVYSSANNCTFEYVSQPFLMDLEGKQ<br>GNFKNLREFVFKNIDGYFKIYSKHTPINLGRDLPQGFSALEPLVD<br>LPIGINITRFQTLLALHRSYLTPGDSSSGWTAGAAAYYVGYLQPR<br>TFLLKYNENGTITDAVDGGGSGGGPNITNLCPFDEVFNATRFAS<br>VYAWNRKRISNCVADYSVLYNFAPFFAFKCYGVSPTKLNDLCF | 63 |

-continued

| | |
|---|---|
| | TNVYADSFVIRGNEVSQIAPGQTGNIADYNYKLPDDFTGCVIAW<br>NSNKLDSKVGGNYNYRYRLFRKSNLKPFERDISTEIYQAGNKPC<br>NGVAGVNCYFPLQSYGFRPTYGVGHQPYRVVVLSFELLHAPAT<br>VCGPKSGGGSILAIYSTVASSLVLLVSLGAISF |
| PolyA tail | 100 nt |

Additional Influenza Virus Sequences (mutation(s) relative to wild-type sequence are bolded and underlined)

| Name | Sequence | SEQ ID NO: |
|---|---|---|
| B/Phuket/ 3073/2013 (B/Yamagata lineage) HA: wild-type | MKAIIVLLMVVTSNADRICTGITSSNSPHVVKTATQGEVNVTGVIPLTTTPTKSY<br>FANLKGTRTRGKLCPDCLNCTDLDVALGRPMCVGTTPSAKASILHEVRPVTSG<br>CFPIMHDRTKIRQLPNLLRGYEKIRLSTQNVIDAEKAPGGPYRLGTSGSCPNATS<br>KIGFFATMAWAVPKDNYKNATNPLTVEVPYICTEGEDQITVWGFHSDNKTQM<br>KSLYGDSNPQKFTSSANGVTTHYVSQIGDFPDQTEDGGLPQSGRIVVDYMMQK<br>PGKTGTIVYQRGVLLPQKVWCASGRSKVIKGSLPLIGEADCLHEEYGGLNKSK<br>PYYTGKHAKAIGNCPIWVKTPLKLANGTKYRPPAKLLKERGFFGAIAGFLEGG<br>WEGMIAGWHGYTSHGAHGVAVAADLKSTQEAINKITKNLNSLSELEVKNLQR<br>LSGAMDELHNEILELDEKVDDLRADTISSQIELAVLLSNEGIINSEDEHLLALER<br>KLKKMLGPSAVDIGNGCFETKHKCNQTCLDRIAAGTFNAGEFSLPTFDSLNITA<br>ASLNDDGLDNHTILLYYSTAASSLAVTLMLAIFIVYMVSRDNVSCSICL | 70 |
| B/Austria/ 1359417/ 2021 (B/Victoria lineage) HA: wild-type | MKAIIVLLMVVTSNADRICTGITSSNSPHVVKTATQGEVNVTGVIPLTTTPTKSH<br>FANLKGTETRGKLCPKCLNCTDLDVALGRPKCTGKIPSARVSILHEVRPVTSGC<br>FPIMHDRTKIRQLPNLLRGYEHVRLSTHNVINTEDAPGGPYEIGTSGSCLNITNG<br>KGFFATMAWAVPKNKTATNPLTIEVPYICTEEEDQITVWGFHSDDETQMARLY<br>GDSKPQKFTSSANGVTTHYVSQIGGFPNQTEDGGLPQSGRIVVDYMVQKSGKT<br>GTITYQRGILLPQKVWCASGKSKVIKGSLPLIGEADCLHEKYGGLNKSKPYYTG<br>EHAKAIGNCPIWVKTPLKLANGTKYRPPAKLLKERGFFGAIAGFLEGGWEGMI<br>AGWHGYTSHGAHGVAVAADLKSTQEAINKITKNLNSLSELEVKNLQRLSGAM<br>DELHNEILELDEKVDDLRADTISSQIELAVLLSNEGIINSEDEHLLALERKLKKM<br>LGPSAVEIGNGCFETKHKCNQTCLDRIAAGTFDAGEFSLPTFDSLNITAASLND<br>DGLDNHTILLYYSTAASSLAVTLMIAIFVVYMVSRDNVSCSICL | 71 |
| A/Darwin/ 6/2021 (H3N2) HA: wild-type | MKTIIALSNILCLVFAQKIPGNDNSTATLCLGHHAVPNGTIVKTITNDRIEVTNA<br>TELVQNSSIGEICGSPHQILDGGNCTLIDALLGDPQCDGFQNKEWDLFVERSRA<br>NSNCYPYDVPDYASLRSLVASSGTLEFKNESFNWTGVKQNGTSSACIRGSSSSF<br>FSRLNWLTSLNnIYPAQNVTMPNKEQFDKLYIWGVHHPDTDKNQISLFAQSSG<br>RITVSTKRSQQAVIPNIGSRPRIRGIPSRISIYWTIVKPGDILLINSTGNLIAPRGYF<br>KIRSGKSSIMRSDAPIGKCKSECITPNGSIPNDKPFQNVNRITYGACPRYVKQSTL<br>KLATGMRNVPEKQTRGIFGAIAGFIENGWEGMVDGWYGFRHQNSEGRGQAA<br>DLKSTQAAIDQINGKLNRLIGKTNEKFHQIEKEFSEVEGRVQDLEKYVEDTKID<br>LWSYNAELLVALENQHTIDLTDSEMNKLFEKTKKQLRENAEDMGNGCFKIYH<br>KCDNACIGSIRNETYDHNVYRDEALNNRFQIKGVELKSGYKDWILWISFAMSC<br>FLLCIALLGFIMWACQKGNIRCNICI | 82 |
| A/ Wisconsin/ 67/2022 (H1N1) HA: wild-type | MKAILVVMLYTFTTANADTLCIGYHANNSTDTVDTVLEKNVTVTHSVNLLED<br>KHNGKLCKLRGVAPLHLGQCNIAGWILGNPECESLSTARSWSYIVETSNSDNG<br>TCYPGDFINYEELREQLSSVSSFERFEIFPKTSSWPNHDSDNGVTAACSHAGARS<br>FYKNLIWLVKKGKSYPKINQTYINDKGKEVLVLWGIHHPPTITDQESLYQNAD<br>AYVFVGTSRYSKKFKPEIATRPKVRDQAGRMNYYWTLVEPGDKITFEATGNL<br>VAPRYAFTMEKEAGSGIIISDTPVHDCNATCQTPEGAINTSLPFQNVHPITIGKCP<br>KYVRSTKLRLATGLRNVPSIQSRGLFGAIAGFIEGGWTGMVDGWYGYHHQND<br>QGSGYAADLKSTQNAIDKITNKVNSVIEKMNTQFTAVGKEFNHLEKRIENLNK<br>KVDDGFLDVWTYNAELLVLLENERTLDYHDSNVKNLYEKVRHQLKNNAKEI<br>GNGCFEFYHKCDNTCMESVKNGTYDYPKYSEEAKLNREKIDGVKLDSTRIYQI<br>LAIYSTVASSLVLVVSLGAISFWMCSNGSLQCRICI | 83 |
| A/Sydney/ 5/2021 (H1N1) HA: wild-type | MKAILVVMLYTFTTANADTLCIGYHANNSTDTVDTVLEKNVTVTHSVNLLED<br>KHNGKLCKLRGVAPLHLGQCNIAGWILGNPECESLSTARSWSYIVETSNSDNG<br>TCYPGNFINYEELREQLSSVSSFERFEIFPKTSSWPNHDSDNGVTAACPHAGAKS<br>FYKNLIWLVKKGKSYPKINQTYINDKGKEVLVLWGIHHPPTITDQESLYQNAD<br>AYVFVGTSRYSKKFKPEIAARPKVRDRAGRMNYYWTLVEPGDKITFEATGNL<br>VAPRYAFTMEKDAGSGIIISDTPVHDCNTTCQTPEGAINTSLPFQNVHPITIGKCP<br>KYVRSTKLRLATGLRNVPSIQSRGLFGAIAGFIEGGWTGMVDGWYGYHHQNE<br>QGSGYAADLKSTQNAIDKITNKVNSVIEKMNTQFTAVGKEFNHLEKRIENLNK<br>KVDDGFLDIWTYNAELLVLLENERTLDYHDSNVKNLYEKVRNQLKNNAKEIG<br>NGCFEFYHKCDNTCMESVKNGTYDYPKYSEEAKLNREKIDGVKLDSTRIYQIL<br>AIYSTVASSLVLVVSLGAISFWMCSNGSLQCRICI | 95 |
| B_Phuket_ HA: Q267L | MKAIIVLLMVVTSNADRICTGITSSNSPHVVKTATQGEVNVTGVIPLTTTPTKSY<br>FANLKGTRTRGKLCPDCLNCTDLDVALGRPMCVGTTPSAKASILHEVRPVTSG<br>CFPIMHDRTKIRQLPNLLRGYEKIRLSTQNVIDAEKAPGGPYRLGTSGSCPNATS | 72 |

-continued

| Name | Sequence | SEQ ID NO: |
|---|---|---|
| | KIGFFATMAWAVPKDNYKNATNPLTVEVPYICTEGEDQITVWGFHSDNKTQM<br>KSLYGDSNPQKFTSSANGVTTHYVSQIGDFPDQTEDGGLPQSGRIVVDYMMLK<br>PGKTGTIVYQRGVLLPQKVWCASGRSKVIKGSLPLIGEADCLHEEYGGLNKSK<br>PYYTGKHAKAIGNCPIWVKTPLKLANGTKYRPPAKLLKERGFFGAIAGFLEGG<br>WEGMIAGWHGYTSHGAHGVAVAADLKSTQEAINKITKNLNSLSELEVKNLQR<br>LSGAMDELHNEILELDEKVDDLRADTISSQIELAVLLSNEGIINSEDEHLLALER<br>KLKKMLGPSAVDIGNGCFETKHKCNQTCLDRIAAGTFNAGEFSLPTFDSLNITA<br>ASLNDDGLDNHTILLYYSTAASSLAVTLMLAIFIVYMVSRDNVSCSICL | |
| B_Phuket_<br>HA: G273A | MKAIIVLLMVVTSNADRICTGITSSNSPHVVKTATQGEVNVTGVIPLTTTPTKSY<br>FANLKGTRTRGKLCPDCLNCTDLDVALGRPMCVGTTPSAKASILHEVRPVTSG<br>CFPIMHDRTKIRQLPNLLRGYEKIRLSTQNVIDAEKAPGGPYRLGTSGSCPNATS<br>KIGFFATMAWAVPKDNYKNATNPLTVEVPYICTEGEDQITVWGFHSDNKTQM<br>KSLYGDSNPQKFTSSANGVTTHYVSQIGDFPDQTEDGGLPQSGRIVVDYMMQK<br>PGKT**A**TIVYQRGVLLPQKVWCASGRSKVIKGSLPLIGEADCLHEEYGGLNKSK<br>PYYTGKHAKAIGNCPIWVKTPLKLANGTKYRPPAKLLKERGFFGAIAGFLEGG<br>WEGMIAGWHGYTSHGAHGVAVAADLKSTQEAINKITKNLNSLSELEVKNLQR<br>LSGAMDELHNEILELDEKVDDLRADTISSQIELAVLLSNEGIINSEDEHLLALER<br>KLKKMLGPSAVDIGNGCFETKHKCNQTCLDRIAAGTFNAGEFSLPTFDSLNITA<br>ASLNDDGLDNHTILLYYSTAASSLAVTLMLAIFIVYMVSRDNVSCSICL | 73 |
| B_Phuket_<br>HA: H435L | MKAIIVLLMVVTSNADRICTGITSSNSPHVVKTATQGEVNVTGVIPLTTTPTKSY<br>FANLKGTRTRGKLCPDCLNCTDLDVALGRPMCVGTTPSAKASILHEVRPVTSG<br>CFPIMHDRTKIRQLPNLLRGYEKIRLSTQNVIDAEKAPGGPYRLGTSGSCPNATS<br>KIGFFATMAWAVPKDNYKNATNPLTVEVPYICTEGEDQITVWGFHSDNKTQM<br>KSLYGDSNPQKFTSSANGVTTHYVSQIGDFPDQTEDGGLPQSGRIVVDYMMQK<br>PGKTGTIVYQRGVLLPQKVWCASGRSKVIKGSLPLIGEADCLHEEYGGLNKSK<br>PYYTGKHAKAIGNCPIWVKTPLKLANGTKYRPPAKLLKERGFFGAIAGFLEGG<br>WEGMIAGWHGYTSHGAHGVAVAADLKSTQEAINKITKNLNSLSELEVKNLQR<br>LSGAMDEL**L**NEILELDEKVDDLRADTISSQIELAVLLSNEGIINSEDEHLLALER<br>KLKKMLGPSAVDIGNGCFETKHKCNQTCLDRIAAGTFNAGEFSLPTFDSLNITA<br>ASLNDDGLDNHTILLYYSTAASSLAVTLMLAIFIVYMVSRDNVSCSICL | 74 |
| B_Phuket_<br>HA:<br>Q267L-<br>G273A-<br>H435L | MKAIIVLLMVVTSNADRICTGITSSNSPHVVKTATQGEVNVTGVIPLTTTPTKSY<br>FANLKGTRTRGKLCPDCLNCTDLDVALGRPMCVGTTPSAKASILHEVRPVTSG<br>CFPIMHDRTKIRQLPNLLRGYEKIRLSTQNVIDAEKAPGGPYRLGTSGSCPNATS<br>KIGFFATMAWAVPKDNYKNATNPLTVEVPYICTEGEDQITVWGFHSDNKTQM<br>KSLYGDSNPQKFTSSANGVTTHYVSQIGDFPDQTEDGGLPQSGRIVVDYMM**L**K<br>PGKT**A**TIVYQRGVLLPQKVWCASGRSKVIKGSLPLIGEADCLHEEYGGLNKSK<br>PYYTGKHAKAIGNCPIWVKTPLKLANGTKYRPPAKLLKERGFFGAIAGFLEGG<br>WEGMIAGWHGYTSHGAHGVAVAADLKSTQEAINKITKNLNSLSELEVKNLQR<br>LSGAMDEL**L**NEILELDEKVDDLRADTISSQIELAVLLSNEGIINSEDEHLLALER<br>KLKKMLGPSAVDIGNGCFETKHKCNQTCLDRIAAGTFNAGEFSLPTFDSLNITA<br>ASLNDDGLDNHTILLYYSTAASSLAVTLMLAIFIVYMVSRDNVSCSICL | 75 |
| B_Phuket_<br>HA:<br>V239C-<br>V276C-<br>D451C-<br>K422C | MKAIIVLLMVVTSNADRICTGITSSNSPHVVKTATQGEVNVTGVIPLTTTPTKSY<br>FANLKGTRTRGKLCPDCLNCTDLDVALGRPMCVGTTPSAKASILHEVRPVTSG<br>CFPIMHDRTKIRQLPNLLRGYEKIRLSTQNVIDAEKAPGGPYRLGTSGSCPNATS<br>KIGFFATMAWAVPKDNYKNATNPLTVEVPYICTEGEDQITVWGFHSDNKTQM<br>KSLYGDSNPQKFTSSANGVTTHY**C**SQIGDFPDQTEDGGLPQSGRIVVDYMMQK<br>PGKTGTI**C**YQRGVLLPQKVWCASGRSKVIKGSLPLIGEADCLHEEYGGLNKSK<br>PYYTGKHAKAIGNCPIWVKTPLKLANGTKYRPPAKLLKERGFFGAIAGFLEGG<br>WEGMIAGWHGYTSHGAHGVAVAADLKSTQEAINKITKNLNSLSELEV**C**NLQR<br>LSGAMDELHNEILELDEKVDDLRA**C**TISSQIELAVLLSNEGIINSEDEHLLALER<br>KLKKMLGPSAVDIGNGCFETKHKCNQTCLDRIAAGTFNAGEFSLPTFDSLNITA<br>ASLNDDGLDNHTILLYYSTAASSLAVTLMLAIFIVYMVSRDNVSCSICL | 85 |
| B_Phuket_<br>HA: 1367C-<br>S401C-<br>D451C-<br>K422C | MKAIIVLLMVVTSNADRICTGITSSNSPHVVKTATQGEVNVTGVIPLTTTPTKSY<br>FANLKGTRTRGKLCPDCLNCTDLDVALGRPMCVGTTPSAKASILHEVRPVTSG<br>CFPIMHDRTKIRQLPNLLRGYEKIRLSTQNVIDAEKAPGGPYRLGTSGSCPNATS<br>KIGFFATMAWAVPKDNYKNATNPLTVEVPYICTEGEDQITVWGFHSDNKTQM<br>KSLYGDSNPQKFTSSANGVTTHYVSQIGDFPDQTEDGGLPQSGRIVVDYMMQK<br>PGKTGTIVYQRGVLLPQKVWCASGRSKVIKGSLPLIGEADCLHEEYGGLNKSK<br>PYYTGKHAKAIGNCPIWVKTPLKLANGTKYRPPAKLLKERGFFGA**C**AGFLEGG<br>WEGMIAGWHGYTSHGAHGVAVAADLK**C**TQEAINKITKNLNSLSELEV**C**NLQR<br>LSGAMDELHNEILELDEKVDDLRA**C**TISSQIELAVLLSNEGIINSEDEHLLALER<br>KLKKMLGPSAVDIGNGCFETKHKCNQTCLDRIAAGTFNAGEFSLPTFDSLNITA<br>ASLNDDGLDNHTILLYYSTAASSLAVTLMLAIFIVYMVSRDNVSCSICL | 86 |
| B_Austria__<br>HA: H383Y | MKAIIVLLMVVTSNADRICTGITSSNSPHVVKTATQGEVNVTGVIPLTTTPTKSH<br>FANLKGTETRGKLCPKCLNCTDLDVALGRPKCTGKIPSARVSILHEVRPVTSGC<br>FPIMHDRTKIRQLPNLLRGYEHVRLSTHNVINTEDAPGGPYEIGTSGSCLNITNG<br>KGFFATMAWAVPKNKTATNPLTIEVPYICTEEEDQITVWGFHSDDETQMARLY<br>GDSKPQKFTSSANGVTTHYVSQIGGFPNQTEDGGLPQSGRIVVDYMVQKSGKT<br>GTITYQRGILLPQKVWCASGKSKVIKGSLPLIGEADCLHEKYGGLNKSKPYYTG<br>EHAKAIGNCPIWVKTPLKLANGTKYRPPAKLLKERGFFGAIAGFLEGGWEGMI | 76 |

-continued

| Name | Sequence | SEQ ID NO: |
|---|---|---|
| | AGWYGYTSHGAHGVAVAADLKSTQEAINKITKNLNSLSELEVKNLQRLSGAM DELHNEILELDEKVDDLRADTISSQIELAVLLSNEGIINSEDEHLLALERKLKKM LGPSAVEIGNGCFETKHKCNQTCLDRIAAGTFDAGEFSLPTFDSLNITAASLND DGLDNHTILLYYSTAASSLAVTLMIAIFVVYMVSRDNVSCSICL | |
| B_Austria_ HA: A290V | MKAIIVLLMVVTSNADRICTGITSSNSPHVVKTATQGEVNVTGVIPLTTTPTKSH FANLKGTETRGKLCPKCLNCTDLDVALGRPKCTGKIPSARVSILHEVRPVTSGC FPIMHDRTKIRQLPNLLRGYEHVRLSTHNVINTEDAPGGPYEIGTSGSCLNITNG KGFFATMAWAVPKNKTATNPLTIEVPYICTEEEDQITVWGFHSDDETQMARLY GDSKPQKFTSSANGVTTHYVSQIGGFPNQTEDGGLPQSGRIVVDYMVQKSGKT GTITYQRGILLPQKVWCVSGKSKVIKGSLPLIGEADCLHEKYGGLNKSKPYYTG EHAKAIGNCPIWVKTPLKLANGTKYRPPAKLLKERGFFGAIAGFLEGGWEGMI AGWYGYTSHGAHGVAVAADLKSTQEAINKITKNLNSLSELEVKNLQRLSGAM DELHNEILELDEKVDDLRADTISSQIELAVLLSNEGIINSEDEHLLALERKLKKM LGPSAVEIGNGCFETKHKCNQTCLDRIAAGTFDAGEFSLPTFDSLNITAASLND DGLDNHTILLYYSTAASSLAVTLMIAIFVVYMVSRDNVSCSICL | 77 |
| B_Austria_ HA: H381Y- A288V- N494C- K483C | MKAIIVLLMVVTSNADRICTGITSSNSPHVVKTATQGEVNVTGVIPLTTTPTKSH FANLKGTETRGKLCPKCLNCTDLDVALGRPKCTGKIPSARVSILHEVRPVTSGC FPIMHDRTKIRQLPNLLRGYEHVRLSTHNVINTEDAPGGPYEIGTSGSCLNITNG KGFFATMAWAVPKNKTATNPLTIEVPYICTEEEDQITVWGFHSDDETQMARLY GDSKPQKFTSSANGVTTHYVSQIGGFPNQTEDGGLPQSGRIVVDYMVQKSGKT GTITYQRGILLPQKVWCVSGKSKVIKGSLPLIGEADCLHEKYGGLNKSKPYYTG EHAKAIGNCPIWVKTPLKLANGTKYRPPAKLLKERGFFGAIAGFLEGGWEGMI AGWYGYTSHGAHGVAVAADLKSTQEAINKITKNLNSLSELEVKNLQRLSGAM DELHNEILELDEKVDDLRADTISSQIELAVLLSNEGIINSEDEHLLALERKLKCM LGPSAVEIGCGCFETKHKCNQTCLDRIAAGTFDAGEFSLPTFDSLNITAASLND DGLDNHTILLYYSTAASSLAVTLMIAIFVVYMVSRDNVSCSICL | 87 |
| B_Austria_ HA: H381Y- A288V- L422C- D444C | MKAIIVLLMVVTSNADRICTGITSSNSPHVVKTATQGEVNVTGVIPLTTTPTKSH FANLKGTETRGKLCPKCLNCTDLDVALGRPKCTGKIPSARVSILHEVRPVTSGC FPIMHDRTKIRQLPNLLRGYEHVRLSTHNVINTEDAPGGPYEIGTSGSCLNITNG KGFFATMAWAVPKNKTATNPLTIEVPYICTEEEDQITVWGFHSDDETQMARLY GDSKPQKFTSSANGVTTHYVSQIGGFPNQTEDGGLPQSGRIVVDYMVQKSGKT GTITYQRGILLPQKVWCVSGKSKVIKGSLPLIGEADCLHEKYGGLNKSKPYYTG EHAKAIGNCPIWVKTPLKLANGTKYRPPAKLLKERGFFGAIAGFLEGGWEGMI AGWYGYTSHGAHGVAVAADLKSTQEAINKITKNLNSLSELEVKNCQRLSGAM DELHNEILELDEKVCDLRADTISSQIELAVLLSNEGIINSEDEHLLALERKLKKM LGPSAVEIGNGCFETKHKCNQTCLDRIAAGTFDAGEFSLPTFDSLNITAASLND DGLDNHTILLYYSTAASSLAVTLMIAIFVVYMVSRDNVSCSICL | 88 |
| B_Austria_ HA: H381Y- A288V- A364C- K483C | MKAIIVLLMVVTSNADRICTGITSSNSPHVVKTATQGEVNVTGVIPLTTTPTKSH FANLKGTETRGKLCPKCLNCTDLDVALGRPKCTGKIPSARVSILHEVRPVTSGC FPIMHDRTKIRQLPNLLRGYEHVRLSTHNVINTEDAPGGPYEIGTSGSCLNITNG KGFFATMAWAVPKNKTATNPLTIEVPYICTEEEDQITVWGFHSDDETQMARLY GDSKPQKFTSSANGVTTHYVSQIGGFPNQTEDGGLPQSGRIVVDYMVQKSGKT GTITYQRGILLPQKVWCVSGKSKVIKGSLPLIGEADCLHEKYGGLNKSKPYYTG EHAKAIGNCPIWVKTPLKLANGTKYRPPAKLLKERGFFGCIAGFLEGGWEGMI AGWYGYTSHGAHGVAVAADLKSTQEAINKITKNLNSLSELEVKNLQRLSGAM DELHNEILELDEKVDDLRADTISSQIELAVLLSNEGIINSEDEHLLALERKLKCM LGPSAVEIGNGCFETKHKCNQTCLDRIAAGTFDAGEFSLPTFDSLNITAASLND DGLDNHTILLYYSTAASSLAVTLMIAIFVVYMVSRDNVSCSICL | 89 |
| B_Austria_ HA: H381Y- A288V- G367C- K483C | MKAIIVLLMVVTSNADRICTGITSSNSPHVVKTATQGEVNVTGVIPLTTTPTKSH FANLKGTETRGKLCPKCLNCTDLDVALGRPKCTGKIPSARVSILHEVRPVTSGC FPIMHDRTKIRQLPNLLRGYEHVRLSTHNVINTEDAPGGPYEIGTSGSCLNITNG KGFFATMAWAVPKNKTATNPLTIEVPYICTEEEDQITVWGFHSDDETQMARLY GDSKPQKFTSSANGVTTHYVSQIGGFPNQTEDGGLPQSGRIVVDYMVQKSGKT GTITYQRGILLPQKVWCVSGKSKVIKGSLPLIGEADCLHEKYGGLNKSKPYYTG EHAKAIGNCPIWVKTPLKLANGTKYRPPAKLLKERGFFGAIACFLEGGWEGMI AGWYGYTSHGAHGVAVAADLKSTQEAINKITKNLNSLSELEVKNLQRLSGAM DELHNEILELDEKVDDLRADTISSQIELAVLLSNEGIINSEDEHLLALERKLKCM LGPSAVEIGNGCFETKHKCNQTCLDRIAAGTFDAGEFSLPTFDSLNITAASLND DGLDNHTILLYYSTAASSLAVTLMIAIFVVYMVSRDNVSCSICL | 90 |
| A_Darwin_ H3 HA: G402P- R421P- E414P | MKTIIALSNILCLVFAQKIPGNDNSTATLCLGHHAVPNGTIVKTITNDRIEVTNA TELVQNSSIGEICGSPHQILDGGNCTLIDALLGDPQCDGFQNKEWDLFVERSRA NSNCYPYDVPDYASLRSLVASSGTLEFKNESFNWTGVKQNGTSSACIRGSSSSF FSRLNWLTSLNNIYPAQNVTMPNKEQFDKLYIWGVHHPDTDKNQISLFAQSSG RITVSTKRSQQAVIPNIGSRPRIRGIPSRISIYWTIVKPGDILLINSTGNLIAPRGYF KIRSGKSSIMRSDAPIGKCKSECITPNGSIPNDKPFQNVNRITYGACPRYVKQSTL KLATGMRNVPEKQTRGIFGAIAGFIENGWEGMVDGWYGFRHQNSEGRGQAA DLKSTQAAIDQINGKLNRLIPKTNEKFHQIEKPFSEVEGPVQDLEKYVEDTKIDL WSYNAELLVALENQHTIDLTDSEMNKLFEKTKKQLRENAEDMGNGCFKIYHK CDNACIGSIRNETYDHNVYRDEALNNRFQIKGVELKSGYKDWILWISFAMSCF LLCIALLGFIMWACQKGNIRCNICI | 91 |

-continued

| Name | Sequence | SEQ ID NO: |
|---|---|---|
| A_Darwin_<br>H3 HA:<br>S123C-<br>R421C | MKTIIALSNILCLVFAQKIPGNDNSTATLCLGHHAVPNGTIVKTITNDRIEVTNA<br>TELVQNSSIGEICGSPHQILDGGNCTLIDALLGDPQCDGFQNKEWDLFVERSRA<br>NSNCYPYDVPDYACLRSLVASSGTLEFKNESFNWTGVKQNGTSSACIRGSSSSF<br>FSRLNWLTSLNNIYPAQNVTMPNKEQFDKLYIWGVHHPDTDKNQISLFAQSSG<br>RITVSTKRSQQAVIPNIGSRPRIRGIPSRISIYWTIVKPGDILLINSTGNLIAPRGYF<br>KIRSGKSSIMRSDAPIGKCKSECITPNGSIPNDKPFQNVNRITYGACPRYVKQSTL<br>KLATGMRNVPEKQTRGIFGAIAGFIENGWEGMVDGWYGFRHQNSEGRGQAA<br>DLKSTQAAIDQINGKLNRLIGKTNEKFHQIEKEFSEVEGCVQDLEKYVEDTKID<br>LWSYNAELLVALENQHTIDLTDSEMNKLFEKTKKQLRENAEDMGNGCFKIYH<br>KCDNACIGSIRNETYDHNVYRDEALNNRFQIKGVELKSGYKDWILWISFAMSC<br>FLLCIALLGFIMWACQKGNIRCNICI | 92 |
| A_Darwin_<br>H3 HA:<br>Q392C-<br>T46C | MKTIIALSNILCLVFAQKIPGNDNSTATLCLGHHAVPNGTIVKTICNDRIEVTNA<br>TELVQNSSIGEICGSPHQILDGGNCTLIDALLGDPQCDGFQNKEWDLFVERSRA<br>NSNCYPYDVPDYASLRSLVASSGTLEFKNESFNWTGVKQNGTSSACIRGSSSSF<br>FSRLNWLTSLNnIYPAQNVTMPNKEQFDKLYIWGVHHPDTDKNQISLFAQSSG<br>RITVSTKRSQQAVIPNIGSRPRIRGIPSRISIYWTIVKPGDILLINSTGNLIAPRGYF<br>KIRSGKSSIMRSDAPIGKCKSECITPNGSIPNDKPFQNVNRITYGACPRYVKQSTL<br>KLATGMRNVPEKQTRGIFGAIAGFIENGWEGMVDGWYGFRHQNSEGRGQAA<br>DLKSTQAAIDCINGKLNRLIGKTNEKFHQIEKEFSEVEGRVQDLEKYVEDTKID<br>LWSYNAELLVALENQHTIDLTDSEMNKLFEKTKKQLRENAEDMGNGCFKIYH<br>KCDNACIGSIRNETYDHNVYRDEALNNRFQIKGVELKSGYKDWILWISFAMSC<br>FLLCIALLGFIMWACQKGNIRCNICI | 93 |
| A_Wisconsin_<br>H1 HA:<br>K391C-<br>L37C | MKAILVVMLYTFTTANADTLCIGYHANNSTDTVDTVCEKNVTVTHSVNLLED<br>KHNGKLCKLRGVAPLHLGQCNIAGWILGNPECESLSTARSWSYIVETSNSDNG<br>TCYPGDFINYEELREQLSSVSSFERFEIFPKTSSWPNHDSDNGVTAACSHAGARS<br>FYKNLIWLVKKGKSyPKINQTYINDKGKEVLVLWGIHHPPTITDQESLYQNADA<br>YVFVGTSRYSKKFKPEIATRPKVRDQAGRMNYYWTLVEPGDKITFEATGNLV<br>APRYAFTMEKEAGSGIIISDTPVHDCNATCQTPEGAINTSLPFQNVHPITIGKCPK<br>YVRSTKLRLATGLRNVPSIQSRGLFGAIAGFIEGGWTGMVDGWYGYHHQNDQ<br>GSGYAADLKSTQNAIDCITNKVNSVIEKMNTQFTAVGKEFNHLEKRIENLNKK<br>VDDGFLDVWTYNAELLVLLENERTLDYHDSNVKNLYEKVRHQLKNNAKEIG<br>NGCFEFYHKCDNTCMESVKNGTYDYPKYSEEAKLNREKIDGVKLDSTRIYQIL<br>AIYSTVASSLVLVVSLGAISFWMCSNGSLQCRICI | 94 |
| A_Wisconsin_<br>H1 HA:<br>K395C-<br>V36C | MKAILVVMLYTFTTANADTLCIGYHANNSTDTVDTCLEKNVTVTHSVNLLED<br>KHNGKLCKLRGVAPLHLGQCNIAGWILGNPECESLSTARSWSYIVETSNSDNG<br>TCYPGDFINYEELREQLSSVSSFERFEIFPKTSSWPNHDSDNGVTAACSHAGARS<br>FYKNLIWLVKKGKSYPKINQTYINDKGKEVLVLWGIHHPPTITDQESLYQNAD<br>AYVFVGTSRYSKKFKPEIATRPKVRDQAGRMNYYWTLVEPGDKITFEATGNL<br>VAPRYAFTMEKEAGSGIIISDTPVHDCNATCQTPEGAINTSLPFQNVHPITIGKCP<br>KYVRSTKLRLATGLRNVPSIQSRGLFGAIAGFIEGGWTGMVDGWYGYHHQND<br>QGSGYAADLKSTQNAIDKITNCVNSVIEKMNTQFTAVGKEFNHLEKRIENLNK<br>KVDDGFLDVWTYNAELLVLLENERTLDYHDSNVKNLYEKVRHQLKNNAKEI<br>GNGCFEFYHKCDNTCMESVKNGTYDYPKYSEEAKLNREKIDGVKLDSTRIYQI<br>LAIYSTVASSLVLVVSLGAISFWMCSNGSLQCRICI | 84 |
| A_Sydney_<br>H1 HA:<br>K391C-<br>L37C | MKAILVVMLYTFTTANADTLCIGYHANNSTDTVDTVCEKNVTVTHSVNLLED<br>KHNGKLCKLRGVAPLHLGQCNIAGWILGNPECESLSTARSWSYIVETSNSDNG<br>TCYPGNFINYEELREQLSSVSSFERFEIFPKTSSWPNHDSDNGVTAACPHAGAKS<br>FYKNLIWLVKKGKSYPKINQTYINDKGKEVLVLWGIHHPPTITDQESLYQNAD<br>AYVFVGTSRYSKKFKPEIAARPKVRDRAGRMNYYWTLVEPGDKITFEATGNL<br>VAPRYAFTMEKDAGSGIIISDTPVHDCNTTCQTPEGAINTSLPFQNVHPITIGKCP<br>KYVRSTKLRLATGLRNVPSIQSRGLFGAIAGFIEGGWTGMVDGWYGYHHQNE<br>QGSGYAADLKSTQNAIDCITNKVNSVIEKMNTQFTAVGKEFNHLEKRIENLNK<br>KVDDGFLDIWTYNAELLVLLENERTLDYHDSNVKNLYEKVRNQLKNNAKEIG<br>NGCFEFYHKCDNTCMESVKNGTYDYPKYSEEAKLNREKIDGVKLDSTRIYQIL<br>AIYSTVASSLVLVVSLGAISFWMCSNGSLQCRICI | 96 |
| A_Sydney_<br>H1 HA:<br>K395C-<br>V36C | MKAILVVMLYTFTTANADTLCIGYHANNSTDTVDTCLEKNVTVTHSVNLLED<br>KHNGKLCKLRGVAPLHLGQCNIAGWILGNPECESLSTARSWSYIVETSNSDNG<br>TCYPGNFINYEELREQLSSVSSFERFEIFPKTSSWPNHDSDNGVTAACPHAGAKS<br>FYKNLIWLVKKGKSYPKINQTYINDKGKEVLVLWGIHHPPTITDQESLYQNAD<br>AYVFVGTSRYSKKFKPEIAARPKVRDRAGRMNYYWTLVEPGDKITFEATGNL<br>VAPRYAFTMEKDAGSGIIISDTPVHDCNTTCQTPEGAINTSLPFQNVHPITIGKCP<br>KYVRSTKLRLATGLRNVPSIQSRGLFGAIAGFIEGGWTGMVDGWYGYHHQNE<br>QGSGYAADLKSTQNAIDKITNCVNSVIEKMNTQFTAVGKEFNHLEKRIENLNK<br>KVDDGFLDIWTYNAELLVLLENERTLDYHDSNVKNLYEKVRNQLKNNAKEIG<br>NGCFEFYHKCDNTCMESVKNGTYDYPKYSEEAKLNREKIDGVKLDSTRIYQIL<br>AIYSTVASSLVLVVSLGAISFWMCSNGSLQCRICI | 97 |

Wild-Type Wuhan-Hu-1; USA-WA1/2020 Isolate

| | | |
|---|---|---|
| Wild-Type Wuhan-Hu-1; USA-WA1/2020 isolate | MFVFLVLLPLVSSQCVNLTTRTQLPPAYTNSFTRGVYYPDKVERSSVLHSTQDLFLPFFSN<br>VTWFHAIHVSGTNGTKRFDNPVLPENDGVYFASTEKSNIIRGWIFGTTLDSKTQSLLIVNN<br>ATNVVIKVCEFQFCNDPFLGVYYHKNNKSWMESEFRVYSSANNCTFEYVSQPFLMDLEGKQ<br>GNFKNLREFVFKNIDGYFKIYSKHTPINLVRDLPQGFSALEPLVDLPIGINITRFQTLLAL<br>HRSYLTPGDSSSGWTAGAAAYYVGYLQPRTFLLKYNENGTITDAVDCALDPLSETKCTLKS<br>FTVEKGIYQTSNFRVQPTESIVRFPNITNLCPFGEVFNATRFASVYAWNRKRISNCVADYS<br>VLYNSASFSTFKCYGVSPTKLNDLCFTNVYADSFVIRGDEVRQIAPGQTGKIADYNYKLPD<br>DFTGCVIAWNSNNLDSKVGGNYNYLYRLFRKSNLKPFERDISTEIYQAGSTPCNGVEGENC<br>YFPLQSYGFQPTNGVGYQPYRVVVLSFELLHAPATVCGPKKSTNLVKNKCVNFNFNGLTGT<br>GVLTESNKKFLPFQQFGRDIADTTDAVRDPQTLEILDITPCSFGGVSVITPGTNTSNQVAV<br>LYQDVNCTEVPVAIHADQLTPTWRVYSTGSNVFQTRAGCLIGAEHVNNSYECDIPIGAGIC<br>ASYQTQTNSPRRARSVASQSIIAYTMSLGAENSVAYSNNSIAIPTNFTISVTTEILPVSMT<br>KTSVDCTMYICGDSTECSNLLLQYGSFCTQLNRALTGIAVEQDKNTQEVFAQVKQIYKTPP<br>IKDFGGFNFSQILPDPSKPSKRSFIEDLLFNKVTLADAGFIKQYGDCLGDIAARDLICAQK<br>FNGLTVLPPLLTDEMIAQYTSALLAGTITSGWTFGAGAALQIPFAMQMAYRFNGIGVTQNV<br>LYENQKLIANQFNSAIGKIQDSLSSTASALGKLQDVVNQNAQALNTLVKQLSSNFGAISSV<br>LNDILSRLDKVEAEVQIDRLITGRLQSLQTYVTQQLIRAAEIRASANLAATKMSECVLGQS<br>KRVDFCGKGYHLMSFPQSAPHGVVFLHVTYVPAQEKNFTTAPAICHDGKAHFPREGVFVSN<br>GTHWFVTQRNFYEPQIITTDNTFVSGNCDVVIGIVNNTVYDPLQPELDSFKEELDKYFKNH<br>TSPDVDLGDISGINASVVNIQKEIDRLNEVAKNLNESLIDLQELGKYEQYIKWPWYIWLGF<br>IAGLIAIVMVTIMLCCMTSCCSCLKGCCSCGSCCKFDEDDSEPVLKGVKLHYT | SEQ ID NO: 78 |

Respiratory Syncytial Virus F Glycoprotein and SARS-CoV-2 Spike Glycoprotein

| | | |
|---|---|---|
| Wild-Type RSVF Glycoprotein | MELLIHRSSAIFLTLAINTLYLTSSQNITEEFYQSTCSAVSRGYFSALRTGWYTSVITIELSN<br>IKETKCNGTDTKVKLIKQELDKYKNAVTELQLLMQNTPAANNRARREAPQYMNYTINTTKNLN<br>VSISKKRKRRFLGFLLGVGSAIASGIAVSKVLHLEGEVNKIKNALLSTNKAVVSLSNGVSVLT<br>SKVLDLKNYINNQLLPIVNQQSCRISNIETVIEFQQKNSRLLEITREFSVNAGVTTPLSTYML<br>TNSELLSLINDMPITNDQKKLMSSNVQIVRQQSYSIMSIIKEEVLAYVVQLPIYGVIDTPCWK<br>LHTSPLCTTNIKEGSNICLTRTDRGWYCDNAGSVSFFPQADTCKVQSNRVFCDTMNSLTLPSE<br>VSLCNTDIFNSKYDCKIMTSKTDISSSVITSLGAIVSCYGKTKCTASNKNRGIIKTESNGCDY<br>VSNKGVDTVSVGNTLYYVNKLEGKNLYVKGEPIINYYDPLVFPSDEFDASISQVNEKINQSLA<br>FIRRSDELLHNVNTGKSTTNIMITAIIIVIIVVLLSLIAIGLLLYCKAKNTPVTLSKDQLSGI<br>NNIAFSK | SEQ ID NO: 98 |
| Prefusion RSV F Glycoprotein | MELLILKANAITTILTAVTFCFASGQNITEEFYQSTCSAVSKGYLSALRTGWYTSVITIELSN<br>IKENKCNGTDAKVKLIKQELDKYKNAVTELQLLMQSTPATGSGSAICSGVAVCKVLHLEGEVN<br>KIKSALLSTNKAVVSLSNGVSVLTFKVLDLKNYIDKQLLPILNKQSCSISNIETVIEFQQKNN<br>RLLEITREFSVNAGVTTPVSTYMLTNSELLSLINDMPITNDQKKLMSNNVQIVRQQSYSIMCI<br>IKEEVLAYVVQLPLYGVIDTPCWKLHTSPLCTTNTKEGSNICLTRTDRGWYCDNAGSVSFFPQ<br>AETCKVQSNRVFCDTMNSRTLPSEVNLCNVDIFNPKYDCKIMTSKTDVSSSVITSLGAIVSCY<br>GKTKCTASNKNRGIIKTFSNGCDYVSNKGVDTVSVGNTLYCVNKQEGKSLYVKGEPIINFYDP<br>LVFPSDEFDASISQVNEKINQSLAFIRKSDELLHNVNAGKSTTNIMITTIIIVIIVILLSLIA<br>VGLLLY | SEQ ID NO: 99 |
| Prefusion RSV F Glycoprotein ORF (not including stop codon) | ATGGAGCTGCTGATCCTGAAGGCCAACGCCATCACGACCATCCTGACCGCCGTGACCTTCTGC<br>TTCGCCAGCGGGCAGAACATCACCGAGGAGTTCTACCAGTCCACCTGCTCCGCCGTGAGCAAG<br>GGCTACCTGTCTGCCCTGAGAACCGGCTGGTACACCAGCGTGATCACCATCGAGCTGTCCAAC<br>ATCAAGGAGAACAAGTGCAACGGCACCGACGCCAAGGTGAAGCTGATCAAGCAGGAGCTGGAC<br>AAGTACAAGAACGCAGTGACCGAGCTGCAGCTGCTGATGCAGAGCACACCAGCCACCGGTAGC<br>GGGTCCGCCATTTGCTCCGGCGTGGCCGTGTGCAAGGTGCTGCACCTGGAGGGCGAGGTGAAC<br>AAGATCAAGAGCGCCCTGCTCTCCACCAACAAGGCCGTGGTGAGCCTGAGCAACGGGGTGAGC<br>GTGCTGACCTTCAAGGTGCTGGACCTGAAGAACTACATCGACAAGCAGCTGCTGCCTATCCTG<br>AACAAGCAGAGCTGCAGCATCAGCAACATCGAGACCGTGATCGAGTTCCAGCAGAAGAACAAC<br>CGGCTGCTGGAGATCACCAGGGAGTTCAGCGTGAACGCAGGGGTGACCACACCCGTGTCCACC<br>TACATGCTGACCAACTCCGAGCTGCTGAGCCTGATCAACGATATGCCCATCACCAACGACCAG<br>AAGAAGCTGATGAGCAACAACGTGCAGATCGTGCGGCAGCAGTCCTACTCCATCATGTGCATC<br>ATCAAGGAGGAGGTGCTGGCCTACGTGGTGCAGCTGCCCCTGTACGGCGTGATCGACACCCCT<br>TGCTGGAAGCTGCACACCAGCCCTCTGTGCACCACCAACACGAAGGAGGGCAGCAATATCTGC<br>CTGACCCGGACCGACAGGGGCTGGTACTGCGACAACGCCGGCAGCGTGTCCTTCTTTCCCCAG<br>GCCGAGACCTGCAAGGTGCAGTCCAACAGGGTGTTCTGCGACACCATGAACTCTCGCACCCTG<br>CCCAGCGAGGTGAACCTGTGCAACGTGGACATCTTCAACCCCAAGTACGACTGCAAGATCATG<br>ACCTCCAAGACCGACGTGTCCTCTAGCGTTATCACCTCCCTGGGCGCCATCGTGAGCTGCTAC<br>GGCAAGACCAAGTGCACCGCCAGCAACAAGAACAGGGGCATCATCAAGACCTTCAGCAACGGG<br>TGCGACTACGTGTCCAACAAGGGCGTGGACACCGTGTCCGTGGGCAACACCCTGTACTGCGTG<br>AACAAGCAGGAGGGCAAGAGCCTGTACGTGAAGGGCGAGCCCATCATCAACTTCTACGACCCT<br>CTGGTGTTCCCCAGCGACGAGTTCGACGCCAGCATCTCCCAGGTGAACGAGAAGATCAACCAG<br>AGCCTGGCCTTCATCCGCAAGAGCGACGAGCTGCTGCACAACGTGAACGCCGGCAAGAGCACC<br>ACAAACATCATGATCACCACCATCATCATCGTGATAATCGTGATCCTGCTGTCCCTGATCGCT<br>GTGGGCCTGCTGCTGTAC | SEQ ID NO: 113 |
| RSV F C-terminal 25 amino acids | CKARSTPVTLSKDQLSGINNIAFSN | SEQ ID NO: 100 |

-continued

| | | |
|---|---|---|
| RSV F C-<br>terminal 20<br>amino acids | TPVTLSKDQLSGINNIAFSN | SEQ ID<br>NO: 101 |
| RSV-F C-<br>terminal 15<br>amino acids | SKDQLSGINNIAFSN | SEQ ID<br>NO: 102 |
| RSV-F C-<br>terminal 10<br>amino acids | SGINNIAFSN | SEQ ID<br>NO: 103 |
| Wild-type<br>SARS-CoV-2 S<br>protein | MFVFLVLLPLVSSQCVNLTTRTQLPPAYTNSFTRGVYYPDKVFRSSVLHSTQDLFLPFFSNVT<br>WFHAIHVSGTNGTKRFDNPVLPENDGVYFASTEKSNIIRGWIFGTTLDSKTQSLLIVNNATNV<br>VIKVCEFQFCNDPFLGVYYHKNNKSWMESEFRVYSSANNCTFEYVSQPFLMDLEGKQGNEKNL<br>REFVFKNIDGYFKIYSKHTPINLVRDLPQGFSALEPLVDLPIGINITRFQTLLALHRSYLTPG<br>DSSSGWTAGAAAYYVGYLQPRTFLLKYNENGTITDAVDCALDPLSETKCTLKSFTVEKGIYQT<br>SNFRVQPTESIVRFPNITNLCPFGEVENATRFASVYAWNRKRISNCVADYSVLYNSASFSTEK<br>CYGVSPTKLNDLCFTNVYADSFVIRGDEVRQIAPGQTGKIADYNYKLPDDFTGCVIAWNSNNL<br>DSKVGGNYNYLYRLFRKSNLKPFERDISTEIYQAGSTPCNGVEGENCYFPLQSYGFQPTNGVG<br>YQPYRVVVLSFELLHAPATVCGPKKSTNLVKNKCVNFNFNGLTGTGVLTESNKKFLPFQQFGR<br>DIADTTDAVRDPQTLEILDITPCSFGGVSVITPGTNTSNQVAVLYQDVNCTEVPVAIHADQLT<br>PTWRVYSTGSNVFQTRAGCLIGAEHVNNSYECDIPIGAGICASYQTQTNSPRRARSVASQSII<br>AYTMSLGAENSVAYSNNSIAIPTNFTISVTTEILPVSMTKTSVDCTMYICGDSTECSNLLLQY<br>GSFCTQLNRALTGIAVEQDKNTQEVFAQVKQIYKTPPIKDFGGFNFSQILPDPSKPSKRSFIE<br>DLLFNKVTLADAGFIKQYGDCLGDIAARDLICAQKFNGLTVLPPLLTDEMIAQYTSALLAGTI<br>TSGWTFGAGAALQIPFAMQMAYRFNGIGVTQNVLYENQKLIANQFNSAIGKIQDSLSSTASAL<br>GKLQDVVNQNAQALNTLVKQLSSNFGAISSVLNDILSRLDKVEAEVQIDRLITGRLQSLQTYV<br>TQQLIRAAEIRASANLAATKMSECVLGQSKRVDFCGKGYHLMSFPQSAPHGVVFLHVTYVPAQ<br>EKNFTTAPAICHDGKAHFPREGVFVSNGTHWFVTQRNFYEPQIITTDNTFVSGNCDVVIGIVN<br>NTVYDPLQPELDSFKEELDKYFKNHTSPDVDLGDISGINASVVNIQKEIDRLNEVAKNLNESL<br>IDLQELGKYEQYIKWPWYIWLGFIAGLIAIVMVTIMLCCMTSCCSCLKGCCSCGSCCKFDEDD<br>SEPVLKGVKLHYT | NO: 104<br>SEQ ID |
| Prefusion<br>SARS-CoV-2 S<br>protein | MFVFLVLLPLVSSQCVNLTTRTQLPPAYTNSFTRGVYYPDKVFRSSVLHSTQDLFLPFFSNVT<br>WFHAIHVSGTNGTKRFDNPVLPFNDGVYFASTEKSNIIRGWIFGTTLDSKTQSLLIVNNATNV<br>VIKVCEFQFCNDPFLGVYYHKNNKSWMESEFRVYSSANNCTFEYVSQPFLMDLEGKQGNEKNL<br>REFVFKNIDGYFKIYSKHTPINLVRDLPQGFSALEPLVDLPIGINITRFQTLLALHRSYLTPG<br>DSSSGWTAGAAAYYVGYLQPRTFLLKYNENGTITDAVDCALDPLSETKCTLKSFTVEKGIYQT<br>SNFRVQPTESIVRFPNITNLCPFGEVENATRFASVYAWNRKRISNCVADYSVLYNSASFSTEK<br>CYGVSPTKLNDLCFTNVYADSFVIRGDEVRQIAPGQTGKIADYNYKLPDDFTGCVIAWNSNNL<br>DSKVGGNYNYLYRLFRKSNLKPFERDISTEIYQAGSTPCNGVEGENCYFPLQSYGFQPTNGVG<br>YQPYRVVVLSFELLHAPATVCGPKKSTNLVKNKCVNFNFNGLTGTGVLTESNKKFLPFQQFGR<br>DIADTTDAVRDPQTLEILDITPCSFGGVSVITPGTNTSNQVAVLYQDVNCTEVPVAIHADQLT<br>PTWRVYSTGSNVFQTRAGCLIGAEHVNNSYECDIPIGAGICASYQTQTNSPRRARSVASQSII<br>AYTMSLGAENSVAYSNNSIAIPTNFTISVTTEILPVSMTKTSVDCTMYICGDSTECSNLLLQY<br>GSFCTQLNRALTGIAVEQDKNTQEVFAQVKQIYKTPPIKDFGGFNFSQILPDPSKPSKRSFIE<br>DLLFNKVTLADAGFIKQYGDCLGDIAARDLICAQKFNGLTVLPPLLTDEMIAQYTSALLAGTI<br>TSGWTFGAGAALQIPFAMQMAYRFNGIGVTQNVLYENQKLIANQFNSAIGKIQDSLSSTASAL<br>GKLQDVVNQNAQALNTLVKQLSSNFGAISSVLNDILSRLDPPEAEVQIDRLITGRLQSLQTYV<br>TQQLIRAAEIRASANLAATKMSECVLGQSKRVDFCGKGYHLMSFPQSAPHGVVFLHVTYVPAQ<br>EKNFTTAPAICHDGKAHFPREGVFVSNGTHWFVTQRNFYEPQIITTDNTFVSGNCDVVIGIVN<br>NTVYDPLQPELDSFKEELDKYFKNHTSPDVDLGDISGINASVVNIQKEIDRLNEVAKNLNESL<br>IDLQELGKYEQYIKWPWYIWLGFIAGLIAIVMVTIMLCCMTSCCSCLKGCCSCGSCCKFDEDD<br>SEPVLKGVKLHYT | SEQ ID<br>NO: 105 |

It should be understood that any of the mRNA sequences may include a 5' UTR and/or a 3' UTR. The UTR sequences may be selected from the following sequences, or other known UTR sequences may be used. It should also be understood that any of the mRNA constructs may further comprise a poly(A) tail and/or cap (e.g., 7 mG(5')ppp(5') NlmpNp). Further, while many of the mRNAs and encoded antigen sequences include a signal peptide and/or a peptide tag (e.g., C-terminal His tag), it should be understood that the indicated signal peptide and/or peptide tag may be substituted for a different signal peptide and/or peptide tag, or the signal peptide and/or peptide tag may be omitted.

5' UTR:

(SEQ ID NO: 1)

GGGAAAUAAGAGAGAAAAGAAGAGUAAGAAGAAAUAUAAGAG

CCACC

-continued

5' UTR:

(SEQ ID NO: 2)

GGGAAAUAAGAGAGAAAAGAAGAGUAAGAAGAAAUAUAAGACC

CCGGCGCCGCCACC

3' UTR:

(SEQ ID NO: 3)

UGAUAAUAGGCUGGAGCCUCGGUGGCCAUGCUUCUUGCCCCUU

GGGCCUCCCCCCAGCCCCUCCUCCCCUUCCUGCACCCGUACCC

CCGUGGUCUUUGAAUAAAGUCUGAGUGGGCGGC

-continued

3' UTR:

(SEQ ID NO: 4)
UGAUAAUAGGCUGGAGCCUCGGUGGCCUAGCUUCUUGCCCCUU
GGGCCUCCCCCCAGCCCCUCCUCCCCUUCCUGCACCCGUACCC
CCGUGGUCUUUGAAUAAAGUCUGAGUGGGCGGC

TABLE S-1

| 5' UTR sequences | |
|---|---|
| SEQ ID NO: | Sequence |
| 5 | GGAAAUCGCAAAAUUUGCUCUUCGCGUUAGAUUUCUUUUAGUUUUCUCGCAACUAGCAAG<br>CUUUUUGUUCUCGCC |
| 6 | GGAAAUCCCCACAACCGCCUCAUAUCCAGGCUCAAGAAUAGAGCUCAGUGUUUUGUUGUU<br>UAAUCAUUCCGACGUGUUUUGCGAUAUUCGCGCAAAGCAGCCAGUCGCGCGCUUGCUUUU<br>AAGUAGAGUUGUUUUUCCACCCGUUUGCCAGGCAUCUUUAAUUUAACAUAUUUUUAUUUU<br>UCAGGCUAACCUACGCCGCCACC |
| 7 | GGAAAUAAGAGAGAAAAGAAGAGUAAGAAGAAAUAUAAGAUCUCCCUGAGCUUCAGGGAG<br>CCCCGGCGCCGCCACC |
| 8 | GGAAACCCCCCACCCCCGUAAGAGAGAAAAGAAGAGUAAGAAGAAAUAUAAGAUCUCCCU<br>GAGCUUCAGGGAGCCCCGGCGCCGCCACC |
| 9 | GGAGAACUUCCGCUUCCGUUGGCGCAAGCGCUUUCAUUUUUUCUGCUACCGUGACUAAG |
| 10 | GGAAAUAAGAGAGAAAAGAAGAGUAAGAAGAAAUAUAAGAGCCACC |
| 11 | GGAAAUAAGAGAGAAAAGAAGAGUAAGAAGAAAUAUAAGA<u>CCCCGGCGCC</u>GCCACC |
| 12 | GGAAAUCGCAAAAUUUGCUCUUCGCGUUAGAUUUCUUUUAGUUUUCUCGCAACUAGCAAG<br>CUUUUUGUUCUCGCCGCCGCC |
| 13 | GGAAAUCGCAAAAUUUUCUUUUCGCGUUAGAUUUCUUUUAGUUUUCUUUCAACUAGCAAG<br>CUUUUUGUUCUCGCCGCCGCC |
| 14 | G G A A A U C G C A A A A $(N_2)_x$ $(N_3)_x$ C U $(N_4)_x$ $(N_5)_x$ C G C G U<br>U A G A U U U C U U U U A G U U U U C U N N C A A C U A G C<br>A A G C U U U U U G U U C U C G C C ($N_8$ C C )x<br>$(N_2)_x$ is a uracil and x is an integer from 0 to 5, e.g., wherein x = 3 or 4;<br>$(N_3)_x$ is a guanine and x is an integer from 0 to 1;<br>$(N_4)_x$ is a cytosine and x is an integer from 0 to 1;<br>$(N_5)_x$ is a uracil and x is an integer from 0 to 5, e.g., wherein x = 2 or 3;<br>$N_6$ is a uracil or cytosine;<br>$N_7$ is a uracil or guanine;<br>$N_8$ is adenine or guanine and x is an integer from 0 to 1. |
| 15 | GGAAAAUUUUAGCCUGGAACGUUAGAUAACUGUCCUGUUGUCUUUAUAUACUUGGUCCCC<br>AAGUAGUUUGUCUUCCAAA |
| 16 | GGAAACUUUAUUUAGUGUUACUUUAUUUUCUGUUUAUUUGUGUUUCUUCAGUGGGUUUGU<br>UCUAAUUUCCUUGGCCGCC |
| 17 | GGAAAAUCUGUAUUAGGUUGGCGUGUUCUUUGGUCGGUUGUUAGUAUUGUUGUUGAUUCG<br>UUUGUGGUCGGUUGCCGCC |
| 18 | GGAAAAUUAUUAACAUCUUGGUAUUCUCGAUAACCAUUCGUUGGAUUUUAUUGUAUUCGU<br>AGUUUGGGUUCCUGCCGCC |
| 19 | GGAAAUUAUUAUUAUUUCUAGCUACAAUUUAUCAUUGUAUUAUUUUAGCUAUUCAUCAUU<br>AUUUACUUGGUGAUCAACA |
| 20 | GGAAAUAGGUUGUUAACCAAGUUCAAGCCUAAUAAGCUUGGAUUCUGGUGACUUGCUUCA<br>CCGUUGGCGGGCACCGAUC |
| 21 | GGAAAUCGUAGAGAGUCGUACUUAGUACAUAUCGACUAUCGGUGGACACCAUCAAGAUUA<br>UAAACCAGGCCAGA |
| 22 | GGAAACCCGCCCAAGCGACCCCAACAUAUCAGCAGUUGCCCAAUCCCAACUCCCAACACA<br>AUCCCCAAGCAACGCCGCC |
| 23 | GGAAAGCGAUUGAAGGCGUCUUUUCAACUACUCGAUUAAGGUUGGGUAUCGUCGUGGGAC<br>UUGGAAAUUUGUUGUUUCC |

TABLE S-1-continued

| 5' UTR sequences | |
|---|---|
| SEQ ID NO: | Sequence |
| 24 | GGAAACUAAUCGAAAUAAAAGAGCCCCGUACUCUUUUAUUUCUAUUAGGUUAGGAGCCUU AGCAUUUGUAUCUUAGGUA |
| 25 | GGAAAUGUGAUUUCCAGCAACUUCUUUUGAAUAUAUUGAAUUCCUAAUUCAAAGCGAACA AAUCUACAAGCCAUAUACC |
| 26 | GGAAAUCGUAGAGAGUCGUACUUACGUGGUCGCCAUUGCAUAGCGCGAAAGCAACAGG AACAAGAACGCGCC |
| 27 | GGAAAUCGUAGAGAGUCGUACUUAGAAUAAACAGAGUCGGGUCGACUUGUCUCUGAUACU ACGACGUCACAAUC |
| 28 | GGAAAAUUUGCCUUCGGAGUUGCGUAUCCUGAACUGCCCAGCCUCCUGAUAUACAACUGU UCCGCUUAUUCGGGCCGCC |
| 29 | GGAAAUCUGAGCAGGAAUCCUUUGUGCAUUGAAGACUUUAGAUUCCUCUCUGCGGUAGAC GUGCACUUAUAAGUAUUUG |
| 30 | GGAAAGCGAUUGAAGGCGUCUUUUCAACUACUCGAUUAAGGUUGGGUAUCGUCGUGGGAC UUGGAAAUUUGUUGCCACC |
| 31 | GGAAAUUUUUUUUUGAUAUUAUAAGAGUUUUUUUUUGAUAUUAAGAAAAUUUUUUUUUGA UAUUAGAAGAGUAAGAAGAAAUAUAAGACCCCGGCGCCGCCACC |
| 32 | GGAAAUAAGAGAGAAAAGAAGAGUAAGAAGAAAUAUAAGAGCCAAAAAAAAAAAAACC |
| 33 | GGAAAUCUCCCUGAGCUUCAGGGAGUAAGAGAGAAAAGAAGAGUAAGAAGAAAUAUAAGA CCCCGGCGCCGCCACC |
| 34 | GCCRCC, wherein R = A or G |
| 35 | GGACUCACUAUUUGUUUUCGCGCCCAGUUGCAAAAA |

TABLE S-2

| 3' UTR sequences (stop cassette is italicized; miR binding sites are boldened) | |
|---|---|
| SEQ ID NO: | |
| 36 | *UAAAGCUCCCCGGGG*GCCUCGGUGGCCUAGCUUCUUGCCCCUUGGGCCUCCCCCCAGCC CCUCCUCCCCUUCCUGCACCCGUACCCCCGUGGUCUUUGAAUAAAGUCUGAGUGGGGGC |
| 37 | UAAGUCUAAGCUGGAGCCUCCUGAGAGACCUGUGUGAACUAUUGAGAAGAUCGGAACAG CUCCUUACUCUGAGGAAGUUGGUACCCCCGUGGUCUUUGAAUAAAGUCUGAGUGGGCGGC |
| 38 | *UAAAGCUCCCCGGGG***CAAACACCAUUGUCACACUCCA**GCCUCGGUGGCCUAGCUUCUUG CCCCUUGGGCC**CAAACACCAUUGUCACACUCCA**UCCCCCCAGCCCCUCCUCCCCUUCCUGCA CCCGUACCCCC**CAAACACCAUUGUCACACUCCA**GUGGUCUUUGAAUAAAGUCUGAGUGGGCG GC (miR122 binding sites boldened) |
| 39 | *UAAAGCUCCCCGGGG***UCCAUAAAGUAGGAAACACUACA**GCUGGAGCCUCGGUGGCCUAG CUUCUUGCCCCUUGGGCC**CAAACACCAUUGUCACACUCCA**UCCCCCCAGCCCCUCCUCCCCU UCCUGCACCCGUACCCCCGUGGUCUUUGAAUAAAGUCUGAGUGGGGGC (miR-142-3p and miR122 binding sites boldened) |
| 40 | *UAAAGCUCCCCGGGG*GCCUCGGUGGCCUAGCUUCUUGCCCCUUGGGCCUCCCCCCAGCC CCUCCUCCCCUUCCUGCACCCGUACCCCC**CAAACACCAUUGUCACACUCCA**GUGGUCUUUGA AUAAAGUCUGAGUGGGCGGC (miR122 binding site boldened) |
| 41 | *UAAGCCCCUCCGGGG***CAAACACCAUUGUCACACUCCA**GCCUCGGUGGCCUAGCUUCUUG CCCCUUGGGCC**CAAACACCAUUGUCACACUCCA**UCCCCCCAGCCCCUCCUCCCCUUCCUGCA CCCGUACCCCC**CAAACACCAUUGUCACACUCCA**GUGGUCUUUGAAUAAAGUCUGAGUGGGCG GC (miR122 binding sites boldened) |

TABLE S-2-continued

| 3' UTR sequences (stop cassette is italicized; miR binding sites are boldened) | |
|---|---|
| SEQ ID NO: | |
| 42 | *UAAGCCCCUCCGGGG***UCCAUAAAGUAGGAAACACUACA**GCCUCGGUGGCCUAGCUUCUU GCCCCUUGGGCC**UCCAUAAAGUAGGAAACACUACA**UCCCCCCAGCCCCUCCUCCCCUUCCUG CACCCGUACCCCCGCAUUAUUACUCACGGUACGAGUGGUCUUUGAAUAAAGUCUGAGUGGG CGGC (miR-142-3p and miR-126-3p binding sites boldened) |
| 43 | *UAAGCCCCUCCGGGG***UCCAUAAAGUAGGAAACACUACA**GCUGGAGCCUCGGUGGCCUAG CUUCUUGCCCCUUGGGCC**CAAACACCAUUGUCACACUCCA**UCCCCCCAGCCCCUCCUCCCCU UCCUGCACCCGUACCCCCGUGGUCUUUGAAUAAAGUCUGAGUGGGGGGC (miR-142-3p and miR122 binding sites boldened) |
| 44 | *UAAGCCCCUCCGGGG*GCCUCGGUGGCCUAGCUUCUUGCCCCUUGGGCCUCCCCCCAGCC CCUCCUCCCCUUCCUGCACCCGUACCCCC**CAAACACCAUUGUCACACUCCA**GUGGUCUUUGA AUAAAGUCUGAGUGGGCGGC (miR122 binding site boldened) |

EQUIVALENTS

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between and including the upper and lower ends of the range are specifically contemplated and described herein.

ENUMERATED EMBODIMENTS

1. A messenger ribonucleic acid (mRNA) vaccine comprising a first mRNA encoding a stabilized prefusion hemagglutinin (HA) antigen of a first influenza B virus, wherein the HA antigen comprises at least one stabilizing substitution in a non-surface-exposed region of the HA antigen.

2. The mRNA vaccine of Embodiment 1, wherein the HA antigen of the first influenza B virus comprises two stabilizing mutations.

3. The mRNA vaccine of any one of the preceding Embodiments, wherein the HA antigen of the first influenza B virus comprises three stabilizing mutations.

4. The mRNA vaccine of any one of the preceding Embodiments, wherein the stabilizing substitution comprises a substitution at an amino acid position selected from the group consisting of: Q267, A288, G273, H381, K388, D422, S434, H435, and H455; wherein the amino acid position is determined by alignment to, and/or using the amino acid numbering of SEQ ID NO: 70 or 71.

5. The mRNA vaccine of Embodiment 4, wherein the stabilizing substitution is selected from the group consisting of: Q267L, A288V, G273A, H381Y, K388M, K388L, D422N, S434A, H435L, and H455W; wherein the amino acid position is determined by alignment to, and/or using the amino acid numbering of SEQ ID NO: 70 or 71.

6. The mRNA vaccine of Embodiment 4 or 5, wherein the HA antigen comprises an H381Y substitution.

7. The mRNA vaccine of Embodiment 4 or 5, wherein the HA antigen comprises an A288V substitution.

8. The mRNA vaccine of any one of Embodiments 4-7, wherein the HA antigen comprises an H381Y substitution and an A288V substitution.

9. The mRNA vaccine of Embodiment 4 or 5, wherein the HA antigen comprises a Q267L substitution.

10. The mRNA vaccine of Embodiment 4 or 5, wherein the HA antigen comprises a G273A substitution.

11. The mRNA vaccine of Embodiment 4 or 5, wherein the HA antigen comprises an H435L substitution.

12. The mRNA vaccine of any one of Embodiments 9-11, wherein the HA antigen comprises Q267L, G273A, and H435L substitutions.

13. The mRNA of any one of the preceding Embodiments, wherein the HA antigen comprises an H381Y substitution.

14. The mRNA of any one of the preceding Embodiments, wherein the HA antigen comprises a A288V substitution.

15. The mRNA of any one of the preceding Embodiments, wherein the HA antigen comprises V239C, V276C, D451C, and K422C substitutions.

16. The mRNA of any one of the preceding Embodiments, wherein the HA antigen comprises I367C, S401C, D451C, and K422C substitutions.

17. The mRNA of any one of the preceding Embodiments, wherein the HA antigen comprises H381Y, A288V, N494C, and K483C substitutions.

18. The mRNA of any one of the preceding Embodiments, wherein the HA antigen comprises H381Y, A288V, L422C, and D444C substitutions.

19. The mRNA of any one of the preceding Embodiments, wherein the HA antigen comprises H381Y, A288V, A364C, and K483C substitutions.

20. The mRNA of any one of the preceding Embodiments, wherein the HA antigen comprises H381Y, A288V, G367C, and K483C substitutions.

21. The mRNA vaccine of any one of the preceding Embodiments, wherein the substitution is relative to SEQ ID NO: 70.

22. The mRNA vaccine of any one of the preceding Embodiments, wherein the substitution is relative to SEQ ID NO: 71.

23. The mRNA vaccine of any one of Embodiments 1-5, wherein the HA antigen comprises an amino acid sequence that has at least 90%, at least 95%, or at least 98% identity to a sequence selected from the group consisting of SEQ ID NOs: 48, 51, 54, 57, 72-77, and 85-90.

24. The mRNA vaccine of Embodiment 23, wherein the HA antigen comprises an amino acid sequence selected from the group consisting of SEQ ID NOs: 48, 51, 54, 57, 72-77, and 85-90.

25. The mRNA vaccine of any one of Embodiments 23-24, wherein the mRNA comprises an open reading frame (ORF) that comprises a sequence that has at least 90%, at least 95%, or at least 98% identity to a sequence selected from the group consisting of SEQ ID NOs: 46, 49, 52, and 55.

26. The mRNA vaccine of any one of Embodiments 23-25, wherein the mRNA comprises an ORF that comprises a sequence selected from the group consisting of SEQ ID NOs: 46, 49, 52, and 55.

27. The mRNA vaccine of any one of Embodiments 23-26, wherein the mRNA comprises a sequence that has at least 90%, at least 95%, or at least 98% identity to a sequence selected from the group consisting of SEQ ID NOs: 64-67.

28. The mRNA vaccine of any one of Embodiments 23-24, wherein the mRNA comprises a sequence a sequence selected from the group consisting of SEQ ID NOs: 64-67.

29. The mRNA vaccine of any one of the preceding Embodiments, further comprising a second mRNA encoding an HA antigen of a second influenza B virus.

30. The mRNA vaccine of Embodiment 29, wherein the HA antigen of the second influenza B virus comprises 1, 2, or 3 stabilizing substitutions and wherein the first and second influenza B viruses are different from one another.

31. The mRNA vaccine of Embodiment 30, wherein the HA antigen comprises the substitutions of any one of Embodiments 4-20.

32. The mRNA vaccine of Embodiment 30 or 31, wherein the stabilizing substitutions of the HA antigen of the first influenza B virus are the same as the stabilizing substitutions of the HA antigen of the second influenza B virus.

33. The mRNA vaccine of Embodiment 30 or 31, wherein the stabilizing substitutions of the HA antigen of the first influenza B virus are different from the stabilizing substitutions of the HA antigen of the second influenza B virus.

34. The mRNA vaccine of any one of the preceding Embodiments, further comprising 1-4 mRNA molecules, each encoding an HA antigen of a different influenza A virus.

35. The mRNA vaccine of Embodiment 34, wherein the vaccine comprises 2 mRNA molecules, each encoding an HA antigen of a different influenza A virus.

36. The mRNA vaccine of Embodiment 34 or 35, wherein one HA antigen is an H1 HA antigen, and one HA antigen is an H3 HA antigen.

37. The mRNA vaccine of Embodiment 36, wherein the H1 HA antigen comprises:

(i) a K391C substitution and an L37C substitution; and/or (ii) a K395C substitution and a V36C substitution, wherein the amino acid position is determined by alignment to, and/or using the amino acid numbering of SEQ ID NO: 83 or 95.

38. The mRNA vaccine of Embodiment 36 or 37, wherein the H3 HA antigen comprises:

(i) a Q392C substitution and a T46C substitution;

(ii) an S123C substitution and an R421C substitution; and/or (iii) a G402P substitution, an R421P substitution, and/or an E414P substitution, wherein the amino acid position is determined by alignment to, and/or using the amino acid numbering of SEQ ID NO: 82.

39. The mRNA vaccine of any one of Embodiments 36-38, wherein the H1 HA antigen comprises an amino acid sequence with at least 95% or at least 98% sequence identity to any one of SEQ ID NOs: 84, 96, or 97.

40. The mRNA vaccine of any one of Embodiments 36-38, wherein the H3 HA antigen comprises an amino acid sequence with at least 95% or at least 98% sequence identity to any one of SEQ ID NOs: 91-93.

41. The mRNA vaccine of any one of the preceding Embodiments, further comprising an mRNA encoding a first SARS-CoV-2 antigen.

42. The mRNA vaccine of Embodiment 41, further comprising an mRNA encoding a second SARS-CoV-2 antigen and wherein the first SARS-CoV-2 antigen is from wild-type SARS-CoV-2 and the second SARS-CoV-2 antigen is from a variant of the SARS-CoV-2 virus.

43. The mRNA vaccine of Embodiment 41 or 42, wherein the first SARS-CoV-2 antigen and, optionally, the second SARS-CoV-2 antigen each comprise a receptor binding domain (RBD) of a SARS-CoV-2 spike protein, a N-terminal domain (NTD), and an influenza virus hemagglutinin transmembrane (HATM) domain joined by linkers (NTD-RBD-HATM).

44. The mRNA vaccine of Embodiment 43, wherein a ratio of mRNAs encoding influenza virus antigens to mRNAs encoding SARS-CoV-2 antigens in the mRNA vaccine is 5:1, 10:1, or 20:1, optionally wherein the ratio is a molar ratio or a mass ratio.

45. The mRNA vaccine of any one of the preceding Embodiments, further comprising an mRNA encoding a human respiratory syncytial virus (hRSV) F glycoprotein.

46. The mRNA vaccine of Embodiment 45, wherein the hRSV F glycoprotein lacks a cytoplasmic tail.

47. The mRNA vaccine of Embodiment 45 or 46, wherein the hRSV F glycoprotein comprises an amino acid sequence with at least 95% to SEQ ID NO: 99.

48. The mRNA vaccine of any one of Embodiments 45-47, wherein the ratio of mRNAs encoding influenza virus antigens to mRNAs encoding hRSV F glycoproteins is 5:1, 10:1, or 20:1, optionally wherein the ratio is a molar ratio or a mass ratio.

49. The mRNA vaccine of any one of the preceding Embodiments, wherein each mRNA comprises a 5' untranslated region (UTR), a 3' UTR, and a polyA tail.

50. The mRNA vaccine of Embodiment 49, wherein the 5' UTR comprises a sequence having at least 95% identity to a sequence selected from SEQ ID NOs: 1, 2, and 5-35.

51. The mRNA vaccine of Embodiment 50, wherein the 5' UTR comprises a sequence selected from SEQ ID NOs: 1, 2, and 5-35.

52. The mRNA vaccine of any one of Embodiments 49-51, wherein the 3' UTR comprises a sequence having at least 95% identity to a sequence selected from SEQ ID NOs: 3, 4, and 36-44.

53. The mRNA vaccine of Embodiment 52, wherein the 3' UTR comprises a sequence selected from SEQ ID NOs: 3, 4, and 36-44.

54. The mRNA vaccine of any one of the preceding Embodiments, wherein each mRNA comprises a 5' tetranucleotide cap.

55. The mRNA vaccine of any one of the preceding Embodiments, wherein each mRNA comprises a chemical modification.

56. The mRNA vaccine of Embodiment 55, wherein the chemical modification is 1-methylpseudouridine.

57. The mRNA vaccine of any one of the preceding Embodiments further comprising a lipid nanoparticle.

58. The mRNA vaccine of Embodiment 57, wherein the lipid nanoparticle comprises an ionizable amino lipid, a sterol, a neutral lipid, and a polyethylene glycol (PEG)-modified lipid.

59. The mRNA vaccine of Embodiment 57 or 58, wherein the lipid nanoparticle comprises 40-55 mol % ionizable amino lipid, 30-45 mol % sterol, 5-15 mol % neutral lipid, and 1-5 mol % PEG-modified lipid.

60. The mRNA vaccine of any one of Embodiments 57-59, wherein the lipid nanoparticle comprises 40-50 mol % ionizable amino lipid, 35-45 mol % sterol, 10-15 mol % neutral lipid, and 2-4 mol % PEG-modified lipid.

61. The mRNA vaccine of any one of Embodiments 57-60, wherein the lipid nanoparticle comprises 45 mol %, 46 mol %, 47 mol %, 48 mol %, 49 mol %, or 50 mol % ionizable amino lipid.

62. The mRNA vaccine of any one of Embodiments 57-61, wherein the ionizable amino lipid has the structure of Compound 1:

(c) the third mRNA encoding the HA antigen of the first influenza A virus having at least 95% or at least 98% identity to SEQ ID NO: 48;

(d) the fourth mRNA encoding the HA antigen of the second influenza A virus having at least 95% or 98% identity to SEQ ID NO: 51;

(e) the fifth mRNA encoding a first SARS-CoV-2 antigen having at least 95% or at least 98% identity to SEQ ID NO: 60; and/or (f) the sixth mRNA encoding a second SARS-CoV antigen having at least 95% or at least 98% identity to SEQ ID NO: 63.

68. The mRNA vaccine of Embodiment 67, wherein:

(a) the first mRNA encodes the HA antigen of the first influenza B virus comprising SEQ ID NO: 54;

(b) the second mRNA encoding the HA antigen of the second influenza B virus comprising SEQ ID NO: 57;

(c) the third mRNA encoding the HA antigen of the first influenza A virus comprising SEQ ID NO: 48;

(d) the fourth mRNA encoding the HA antigen of the second influenza A virus comprising SEQ ID NO: 51;

(e) the fifth mRNA encoding a first SARS-CoV-2 antigen comprising SEQ ID NO: 60; and/or (f) the sixth mRNA encoding a second SARS-CoV antigen comprising SEQ ID NO: 63.

69. The mRNA vaccine of any one of Embodiments 66-68, wherein:

(a) the first mRNA comprises an open reading frame (ORF) comprising a sequence having at least 90%, at least 95%, or at least 98% identity to SEQ ID NO: 52;

(Compound 1)

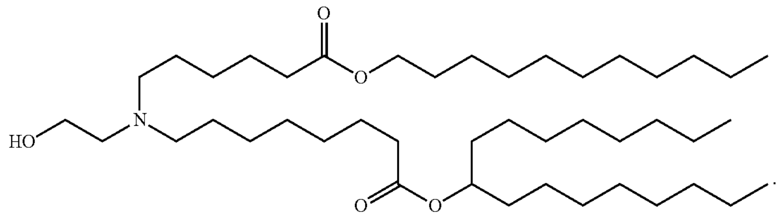

63. The mRNA vaccine of any one of Embodiments 57-62, wherein the sterol is cholesterol.

64. The mRNA vaccine of any one of Embodiments 57-63, wherein the neutral lipid is 1,2 distearoyl-sn-glycero-3-phosphocholine (DSPC).

65. The mRNA vaccine of any one of Embodiments 57-64, wherein the PEG-modified lipid is 1,2 dimyristoyl-sn-glycerol, methoxypolyethyleneglycol (PEG2000 DMG).

66. A messenger ribonucleic acid (mRNA) vaccine comprising a first mRNA encoding a stabilized prefusion hemagglutinin (HA) antigen of a first influenza B virus, a second mRNA encoding a stabilized prefusion HA antigen of a second influenza B virus, a third mRNA encoding an HA antigen of a first influenza A virus, a fourth mRNA encoding an HA antigen of a second influenza A virus, a fifth mRNA encoding a first SARS-CoV-2 antigen, and a sixth mRNA encoding a second SARS-CoV-2 antigen.

67. The mRNA vaccine of Embodiment 66, wherein:

(a) the first mRNA encodes the HA antigen of the first influenza B virus having at least 95% or at least 98% identity to SEQ ID NO: 54;

(b) the second mRNA encoding the HA antigen of the second influenza B virus having at least 95% or at least 98% identify to SEQ ID NO: 57;

(b) the second mRNA comprises an ORF comprising a sequence having at least 90%, at least 95%, or at least 98% identity to SEQ ID NO: 55;

(c) the third mRNA comprises an ORF comprising a sequence having at least 90%, at least 95%, or at least 98% identity to SEQ ID NO: 46;

(d) the fourth mRNA comprises an ORF comprising a sequence having at least 90%, at least 95%, or at least 98% identity to SEQ ID NO: 49;

(e) the fifth mRNA comprises an ORF comprising a sequence having at least 90%, at least 95%, or at least 98% identity to SEQ ID NO: 58; and/or (f) the sixth mRNA comprises an ORF comprising a sequence having at least 90%, at least 95%, or at least 98% identity to SEQ ID NO: 61.

70. The mRNA vaccine of Embodiment 69, wherein:

(a) the first mRNA comprises an ORF comprising SEQ ID NO: 52;

(b) the second mRNA comprises an ORF comprising SEQ ID NO: 55;

(c) the third mRNA comprises an ORF comprising SEQ ID NO: 46;

(d) the fourth mRNA comprises an ORF comprising SEQ ID NO: 49;

(e) the fifth mRNA comprises an ORF comprising SEQ ID NO: 58; and/or (f) the sixth mRNA comprises an ORF comprising SEQ ID NO: 61.

71. The mRNA vaccine of any one of Embodiments 66-70, wherein:

(a) the first mRNA comprises a sequence having at least 90%, at least 95%, or at least 98% identity to SEQ ID NO: 66;

(b) the second mRNA comprises a sequence having at least 90%, at least 95%, or at least 98% identity to SEQ ID NO: 67;

(c) the third mRNA comprises a sequence having at least 90%, at least 95%, or at least 98% identity to SEQ ID NO: 64;

(d) the fourth mRNA comprises a sequence having at least 90%, at least 95%, or at least 98% identity to SEQ ID NO: 65;

(e) the fifth mRNA comprises a sequence having at least 90%, at least 95%, or at least 98% identity to SEQ ID NO: 68; and/or (f) the sixth mRNA comprises a sequence having at least 90%, at least 95%, or at least 98% identity to SEQ ID NO: 69.

72. The mRNA vaccine of Embodiment 71, wherein:

(a) the first mRNA comprises SEQ ID NO: 66;

(b) the second mRNA comprises SEQ ID NO: 67;

(c) the third mRNA comprises SEQ ID NO: 64;

(d) the fourth mRNA comprises SEQ ID NO: 65;

(e) the fifth mRNA comprises SEQ ID NO: 68; and/or (f) the sixth mRNA comprises SEQ ID NO: 69.

73. The mRNA vaccine of any one of Embodiments 66-72, wherein a ratio of the first mRNA to the second mRNA to the third mRNA to the fourth mRNA is 1:1:1:1, optionally wherein the ratio is a molar ratio or a mass ratio.

74. The mRNA vaccine of any one of Embodiments 66-73, wherein a ratio of the fifth mRNA to the sixth mRNA is 1:1, optionally wherein the ratio is a molar ratio or a mass ratio.

75. The mRNA vaccine of any one of Embodiments 66-74, wherein the ratio of the (first mRNA, second mRNA, third mRNA, and fourth mRNA) to the (fifth mRNA and sixth mRNA) is 5:1, optionally wherein the ratio is a molar ratio or a mass ratio.

76. The mRNA vaccine of any one of Embodiments 66-74, wherein the ratio of the (first mRNA, second mRNA, third mRNA, and fourth mRNA) to the (fifth mRNA and sixth mRNA) is 10:1, optionally wherein the ratio is a molar ratio or a mass ratio.

77. The mRNA vaccine of any one of Embodiments 66-74, wherein the ratio of the (first mRNA, second mRNA, third mRNA, and fourth mRNA) to the (fifth mRNA and sixth mRNA) is 20:1, optionally wherein the ratio is a molar ratio or a mass ratio.

78. The mRNA vaccine of any one of Embodiments 66-77, comprising 10 μg-100 μg total mRNA.

79. The mRNA vaccine of Embodiment 78, comprising 15 μg total mRNA.

80 The mRNA vaccine of Embodiment 78, comprising 27.5 μg total mRNA.

81. The mRNA vaccine of Embodiment 78, comprising 30 μg total mRNA.

82. The mRNA vaccine of Embodiment 78, comprising 52.5 μg total mRNA.

83. The mRNA vaccine of Embodiment 78, comprising 55 μg total mRNA.

84. The mRNA vaccine of Embodiment 78, comprising 60 μg total mRNA.

85 The mRNA vaccine of any one of Embodiments 66-84, wherein each mRNA comprises a 5' untranslated region (UTR), a 3' UTR, and a polyA tail.

86. The mRNA vaccine of any one of Embodiments 66-85, wherein each mRNA comprises a 5' tetranucleotide cap.

87. The mRNA vaccine of any one of Embodiments 66-86, wherein each mRNA comprises a chemical modification.

88. The mRNA vaccine of Embodiment 87, wherein the chemical modification is 1-methylpseudouridine.

89. The mRNA vaccine of any one of Embodiments 66-88, further comprising a lipid nanoparticle.

90. The mRNA vaccine of Embodiment 89, wherein the lipid nanoparticle comprises an ionizable amino lipid, a sterol, a neutral lipid, and a polyethylene glycol (PEG)-modified lipid.

91. The mRNA vaccine of Embodiment 89 or 90, wherein the lipid nanoparticle comprises 40-55 mol % ionizable amino lipid, 30-45 mol % sterol, 5-15 mol % neutral lipid, and 1-5 mol % PEG-modified lipid.

92. The mRNA vaccine of any one of Embodiments 89-91, wherein the lipid nanoparticle comprises 40-50 mol % ionizable amino lipid, 35-45 mol % sterol, 10-15 mol % neutral lipid, and 2-4 mol % PEG-modified lipid.

93. The mRNA vaccine of any one of Embodiments 89-92, wherein the lipid nanoparticle comprises 45 mol %, 46 mol %, 47 mol %, 48 mol %, 49 mol %, or 50 mol % ionizable amino lipid.

94. The mRNA vaccine of any one of Embodiments 89-93, wherein the ionizable amino lipid has the structure of Compound 1:

(Compound 1)

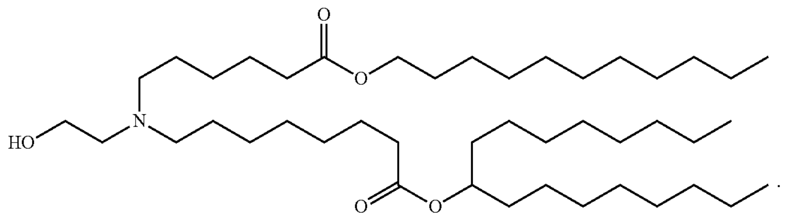

95. The mRNA vaccine of any one of Embodiments 89-94, wherein the sterol is cholesterol.

96. The mRNA vaccine of any one of Embodiments 89-95, wherein the neutral lipid is 1,2 distearoyl-sn-glycero-3-phosphocholine (DSPC).

97. The mRNA vaccine of any one of Embodiments 89-96, wherein the PEG-modified lipid is 1,2 dimyristoyl-sn-glycerol, methoxypolyethyleneglycol (PEG2000 DMG).

98. A method comprising administering to a subject in need thereof the mRNA vaccine of any one of the preceding Embodiments.

99. A composition comprising a lipid delivery vehicle and a messenger ribonucleic acid (mRNA) comprising an open reading frame (ORF) encoding a hemagglutinin (HA) protein of an influenza virus, wherein the hemagglutinin protein comprises one or more mutations selected from the group consisting of:

(i) one or more introduced cysteines, wherein the HA protein comprises a disulfide bond formed by at least one of the one or more introduced cysteines;

(ii) a proline or glycine substitution in a B loop of the HA protein;

(iii) one or more substitutions of a cavity-lining residue with a larger hydrophobic residue;

(iv) one or more substitutions of a pH-sensitive histidine in the HA protein, and (v) removal of a polybasic cleavage site.

100. The composition of Embodiment 99, wherein one or more introduced cysteines are present in a stalk region of the HA protein.

101. The composition of Embodiment 99, wherein one or more introduced cysteines are present in a head region of the HA protein.

102. The composition of any one of Embodiments 99-101, wherein two or more protomers of the HA protein are connected by a disulfide bond comprising the introduced cysteines.

103. The composition of any one of Embodiments 99-102, wherein the introduced cysteines are present at one or more of positions 36, 37, 46, 123, 239, 276, 364, 367, 391, 392, 395, 401, 422, 444, 451, 483, 494 relative to a reference influenza virus HA amino acid sequence, wherein the numbering of amino acids is according to any one of SEQ ID NOs: 70, 71, 82, 83, and 95.

104. The composition of any one of Embodiments 99-103, wherein the HA protein comprises one or more proline substitutions in the B loop.

105. The composition of any one of Embodiments 99-104, wherein the HA protein comprises one or more glycine substitutions in the B loop.

106. The composition of any one of Embodiments 99-105, wherein the proline or glycine substitutions are present at one or more of positions 402, 404, 405, 406, 414, 415, 416, 419, or 421 relative to a reference influenza virus HA amino acid sequence, wherein the numbering of amino acids is according to any one of SEQ ID NOs: 70, 71, 82, 83, and 95.

107. The composition of any one of Embodiments 99-106, wherein one or more of the cavity-lining residues are selected from serine, alanine, and valine.

108. The composition of any one of Embodiments 99-107, wherein one of more the larger hydrophobic residues are selected from phenylalanine, histidine, leucine, methionine, valine, and tryptophan.

109. The composition of any one of Embodiments 99-108, wherein the pH-sensitive histidine is uncharged at neutral pH in a reference influenza virus HA protein.

110. The composition of any one of Embodiments 99-109, wherein the pH-sensitive histidine is present at position 381, relative to a reference influenza virus HA amino acid sequence, wherein the numbering of amino acids is according to any one of SEQ ID NOs: 70, 71, 82, 83, and 95.

111. The composition of any one of Embodiments 99-110, wherein one or more arginines of the polybasic cleavage site are substituted with a non-basic residue that is not lysine or histidine.

112. The composition of any one of Embodiments 99-111, wherein the HA protein does not comprise a polybasic cleavage site of a highly pathogenic avian influenza (HPAI) virus.

113. The composition of any one of Embodiments 99-112, wherein the HA protein comprises an amino acid sequence with at least 90% sequence identity to any one of SEQ ID NOs: 84-94, 96, and 97.

114. A messenger ribonucleic acid (mRNA) vaccine comprising an mRNA polynucleotide comprising an open reading frame (ORF) encoding an influenza B/Victoria lineage virus hemagglutinin (HA) antigen comprising H381Y, A288V, N494C, and K483C mutations relative to a wild-type influenza B/Victoria lineage HA protein.

115. The mRNA vaccine of Embodiment 114, wherein the influenza B/Victoria lineage virus HA antigen comprises an amino acid sequence that has at least 90%, at least 95%, or at least 98% identity to SEQ ID NO: 87.

116. A messenger ribonucleic acid (mRNA) vaccine comprising an mRNA polynucleotide comprising an open reading frame (ORF) encoding an influenza B/Yamagata lineage virus hemagglutinin (HA) antigen comprising V239C, V276C, D451C, and K422C mutations relative to a wild-type influenza B/Yamagata lineage HA protein.

117. The mRNA vaccine of Embodiment 116, wherein the influenza B/Yamagata lineage virus HA antigen comprises an amino acid sequence that has at least 90%, at least 95%, or at least 98% identity to SEQ ID NO: 85.

118. The mRNA vaccine of any one of Embodiments 114-117, further comprising an mRNA encoding an influenza A virus (IAV) H1 HA antigen comprising K391C and L37C mutations relative to a wild-type influenza A/(H1N1) virus HA protein.

119. The mRNA vaccine of Embodiment 118, wherein the IAV H1 HA antigen comprises an amino acid sequence that has at least 90%, at least 95%, or at least 98% identity to SEQ ID NO: 94.

120. The mRNA vaccine of any one of Embodiments 114-119, further comprising an mRNA encoding an influenza A virus (IAV) H3 HA antigen comprising G402P, R421P, E414P mutations relative to a wild-type influenza A/(H3N2) virus HA protein.

121. The mRNA vaccine of Embodiment 120, wherein the IAV H3 HA antigen comprises an amino acid sequence that has at least 90%, at least 95%, or at least 98% identity to SEQ ID NO: 91.

122. The mRNA vaccine of any one of Embodiments 114-121, further comprising an mRNA encoding a SARS-CoV-2 antigen.

123. The mRNA vaccine of Embodiment 122, wherein the SARS-CoV-2 antigen comprises a receptor binding domain (RBD) of a SARS-CoV-2 Spike (S) protein, a N-terminal domain (NTD), and an influenza virus hemagglutinin transmembrane (HATM) domain joined by linkers (NTD-RBD-HATM).

124. The mRNA vaccine of any one of Embodiments 114-123, further comprising an mRNA encoding a human respiratory syncytial virus (hRSV) F glycoprotein.

125. The mRNA vaccine of Embodiment 124, wherein the hRSV F glycoprotein lacks a cytoplasmic tail.

126. The mRNA vaccine of Embodiment 125, wherein the hRSV F glycoprotein comprises an amino acid sequence with at least 95% to SEQ ID NO: 99.

127. The mRNA vaccine of any one of Embodiments 114-126, wherein each mRNA comprises a chemical modification.

128. The mRNA vaccine of Embodiment 127, wherein the chemical modification is N1-methylpseudouridine.

129. The mRNA vaccine of any one of Embodiments 114-128, further comprising a lipid nanoparticle.

130. The mRNA vaccine of Embodiment 129, wherein the lipid nanoparticle comprises an ionizable amino lipid, a sterol, a neutral lipid, and a polyethylene glycol (PEG)-modified lipid.

131. The mRNA vaccine of Embodiment 130, wherein the ionizable amino lipid has the structure of Compound 1:

(Compound 1)

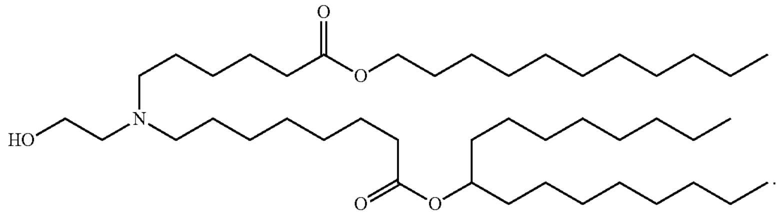

132. A method comprising administering the mRNA vaccine of any one of Embodiments 114-131 to a subject in need thereof.

What is claimed is:

1. A mutant influenza B/Victoria lineage virus hemagglutinin (HA) protein having an amino acid sequence comprising an amino acid substitution relative to a reference influenza B/Victoria lineage virus HA protein amino acid sequence, wherein the amino acid sequence of the mutant influenza B/Victoria lineage virus HA protein comprises one or more of (a)-(s):

(a) a tyrosine at position 381 and a valine at position 288;
(b) a cysteine at position 27 and a cysteine at position 349;
(c) a cysteine at position 295 and a cysteine at position 328;
(d) a cysteine at position 399 and a cysteine at position 473;
(e) a cysteine at position 422 and a cysteine at position 444;
(f) a cysteine at position 118 and a cysteine at position 216;
(g) a cysteine at position 237 and a cysteine at position 261;
(h) a cysteine at position 363 and a cysteine at position 480;
(i) a cysteine at position 364 and a cysteine at position 483;
(j) a cysteine at position 365 and a cysteine at position 476;
(k) a cysteine at position 366 and a cysteine at position 479;
(l) a cysteine at position 367 and a cysteine at position 483;
(m) a cysteine at position 435 and a cysteine at position 428;
(n) a cysteine at position 494 and a cysteine at position 483;
(o) a cysteine at position 494 and a cysteine at position 480;
(p) a proline at position 416, a proline at position 417, a proline at position 434, and a proline at position 433;
(q) a proline at position 434 and a proline at position 433;
(r) a proline at position 515, and a proline at position 516;
(s) a phenylalanine at position 473;

wherein the positions of (a)-(s) are numbered by alignment to SEQ ID NO: 71.

2. The mutant influenza B/Victoria lineage virus HA protein of claim 1, wherein the amino acid sequence of the mutant influenza B/Victoria lineage virus HA protein comprises one or more of substitutions (a)-(s) relative to the reference influenza B/Victoria lineage virus HA protein amino acid sequence:

(a) H381Y and A288V substitutions;
(b) S27C and Y349C substitutions;
(c) I295C and K328C substitutions;
(d) S399C and H473C substitutions;
(e) L422C and D444C substitutions;
(f) K118C and L216C substitutions;
(g) V237C and D261C substitutions;
(h) G363C and K480C substitutions;
(i) A364C and K483C substitutions;
(j) I365C and A476C substitutions;
(k) A366C and R479C substitutions;
(l) G367C and K483C substitutions;
(m) E435C and A428C substitutions;
(n) N494C and K483C substitutions;
(o) N494C and K480C substitutions;
(p) E416P, L417P, N434P, and H433P substitutions;
(q) N434P and H433P substitutions;
(r) T515P and F516P substitutions; and
(s) an H473F substitution, wherein the positions of (a)-(s) are numbered by alignment to SEQ ID NO: 71.

3. The mutant influenza B/Victoria lineage virus HA protein of claim 1, wherein the amino acid sequence of the mutant influenza B/Victoria lineage virus HA protein comprises tyrosine at position 381 and valine at position 288.

4. The mutant influenza B/Victoria lineage virus HA protein of claim 2, wherein the amino acid sequence of the mutant influenza B/Victoria lineage HA protein comprises H381Y and A288V substitutions relative to the reference influenza B/Victoria lineage virus HA protein amino acid sequence.

5. The mutant influenza B/Victoria lineage virus HA protein of claim 4, wherein the amino acid sequence of the mutant influenza B/Victoria lineage virus HA protein further comprises one or more of substitutions (a)-(r) relative to the reference influenza B/Victoria lineage virus HA protein amino acid sequence:

(a) S27C and Y349C substitutions;
(b) I295C and K328C substitutions;
(c) S399C and H473C substitutions;
(d) L422C and D444C substitutions;
(e) K118C and L216C substitutions;
(f) V237C and D261C substitutions;
(g) G363C and K480C substitutions;
(h) A364C and K483C substitutions;
(i) I365C and A476C substitutions;
(j) A366C and R479C substitutions;
(k) G367C and K483C substitutions;
(l) E435C and A428C substitutions;
(m) N494C and K483C substitutions;
(n) N494C and K480C substitutions;
(o) E416P, L417P, N434P, and H433P substitutions;
(p) N434P and H433P substitutions;
(q) T515P and F516P substitutions;
(r) an H473F substitution, wherein the positions of (a)-(r) are numbered by alignment to SEQ ID NO: 71.

6. The mutant influenza B/Victoria lineage virus HA protein of claim 1, wherein the amino acid sequence of the mutant influenza B/Victoria lineage virus HA protein comprises (a) tyrosine at position 381, (b) valine at position 288, and (c) cysteine at position 422 and cysteine at position 444, cysteine at position 364 and cysteine at position 483, cysteine at position 367 and cysteine at position 483, or cysteine at position 494 and cysteine at position 483.

7. The mutant influenza B/Victoria lineage virus HA protein of claim 1, wherein the mutant influenza B/Victoria lineage virus HA protein comprises an amino acid sequence with at least 90% sequence identity to the amino acid sequence of SEQ ID NO: 71.

8. A pharmaceutical composition comprising the mutant influenza B/Victoria lineage virus hemagglutinin (HA) protein of claim 1 and a pharmaceutically acceptable carrier.

9. The pharmaceutical composition of claim 8, wherein the composition is formulated for intramuscular, intranasal, subcutaneous, or intradermal administration.

* * * * *